US012264156B2

United States Patent
Amantini et al.

(10) Patent No.: US 12,264,156 B2
(45) Date of Patent: Apr. 1, 2025

(54) COMPOUNDS AND PHARMACEUTICAL COMPOSITIONS THEREOF FOR THE TREATMENT OF DISEASES

(71) Applicant: GALAPAGOS NV, Mechelen (BE)

(72) Inventors: David Amantini, Romainville (FR); Reginald Christophe Xavier Brys, Mechelen (BE); Denis Bucher, Rheinfelden (CH); Steve Irma Joel De Vos, Mechelen (BE); Nicolas Desroy, Romainville (FR); Agnès Marie Joncour, Romainville (FR); Christophe Peixoto, Romainville (FR); Taoues Temal-Laïb, Romainville (FR); Amynata Tirera, Romainville (FR)

(73) Assignee: GALAPAGOS NV, Mechelen (BE)

( * ) Notice: Subject to any disclaimer, the term of this patent is extended or adjusted under 35 U.S.C. 154(b) by 973 days.

(21) Appl. No.: 17/252,146

(22) PCT Filed: May 29, 2019

(86) PCT No.: PCT/EP2019/063956
§ 371 (c)(1),
(2) Date: Dec. 14, 2020

(87) PCT Pub. No.: WO2019/238424
PCT Pub. Date: Dec. 19, 2019

(65) Prior Publication Data
US 2022/0402911 A1    Dec. 22, 2022

(30) Foreign Application Priority Data

Jun. 15, 2018 (GB) .................................. 1809836
Oct. 25, 2018 (GB) .................................. 1817344

(51) Int. Cl.
C07D 471/04    (2006.01)
A61P 1/00    (2006.01)
A61P 17/06    (2006.01)
A61P 19/02    (2006.01)

(52) U.S. Cl.
CPC .............. *C07D 471/04* (2013.01); *A61P 1/00* (2018.01); *A61P 17/06* (2018.01); *A61P 19/02* (2018.01)

(58) Field of Classification Search
CPC .................................................. C07D 471/04
See application file for complete search history.

(56) References Cited

U.S. PATENT DOCUMENTS

2012/0010188 A1   1/2012  Nilsson et al.
2016/0122341 A1   5/2016  Vakalopoulos et al.

FOREIGN PATENT DOCUMENTS

| CN | 105339368 A | 2/2016 |
|---|---|---|
| CN | 106496222 A | 3/2017 |
| WO | 2022/031928 A1 | 2/2022 |
| WO | 2024062360 A1 | 3/2024 |
| WO | 2024141444 A1 | 7/2024 |

OTHER PUBLICATIONS

Darling "Nuts and bolts of the salt-inducible kinases (SIKs)" Biochemical Journal (2021) 478 1377-1397.*
Desroy "Salt-Inducible Kinases: an Emerging Target Class With Broad Therapeutic Potential" 2023 Medicinal Chemistry Reviews, vol. 58, pp. 209-231.*
Chen "Salt-Inducible Kinase 2: An Oncogenic Signal Transmitter and Potential Target for Cancer Therapy." Front. Oncol. 2019 9:18, 1-6.*
Achuthan "A systematic review of the pharmacological approaches against snoring: can we count on the chickens that have hatched?" Sleep Breath (2015) 19:1035-1042.*
Ashour Ahmed A. et al., "SIK2 is a centrosome kinase required for bipolar mitotic spindle formation that provides a potential target for therapy in ovarian cancer," Cancer Cell, 2010, vol. 18, pp. 109-121.
Charoenfuprasert S. et al., "Identification of salt-inducible kinase 3 as a novel tumor antigen associated with tumorigenesis of ovarian cancer," Oncogene, 2011, vol. 30, pp. 3570-3584.

(Continued)

*Primary Examiner* — David K O'Dell
(74) *Attorney, Agent, or Firm* — ArentFox Schiff LLP

(57) ABSTRACT

The present invention discloses compounds according to Formula I:

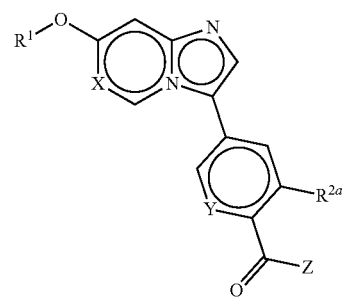

wherein $R^1$, $R^{2a}$, X, Y, and Z are as defined herein.
The present invention relates to compounds, methods for their production, pharmaceutical compositions comprising the same, and methods of treatment using the same, for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases by administering the compound of the invention.

20 Claims, 1 Drawing Sheet

(56) References Cited

OTHER PUBLICATIONS

Clark K. et al., "Phosphorylation of CRTC3 by the salt-inducible kinases controls the interconversion of classically activated and regulatory macrophages," Proc. Natl. Acad. Sci. U. S. A., 2012, vol. 109, pp. 16986-16991.
Darling N.J. et al., "Inhibition of SIK2 and SIK3 during differentiation enhances the anti-inflammatory phenotype of macrophages," Biochem. J., 2017, vol. 474, pp. 521-537.
Katoh Y. et al., "Salt-inducible kinase (SIK) isoforms: their involvement in steroidogenesis and adipogenesis," Mol. Cell. Endocrinol., 2004, vol. 217, pp. 109-112.
Kumagai A. et al., "A Potent Inhibitor of SIK2, 3, 3', 7-Trihydroxy-4'-Methoxyflavon (4'-O-Methylfisetin), Promotes Melanogenesis in B16F10 Melanoma Cells. PLoS ONE 6", 2011, pp. 1-10.
Liu J.Z. et al.,"Dense genotyping of immune-related disease regions identifies nine new risk loci for primary sclerosing cholangitis," Nat. Genet., 2013, vol. 45, pp. 670-675.
Nixon M. et al., "Skeletal muscle salt inducible kinase 1 promotes insulin resistance in obesity," Mol. Metab., 2016, vol. 5, pp. 34-46.
Ozanne J. et al., "The clinically approved drugs dasatinib and bosutinib induce anti-inflammatory macrophages by inhibiting the salt-inducible kinases," Biochem. J., 2015, vol. 465, pp. 271-279.
Sasaki T. et al., "SIK2 Is a Key Regulator for Neuronal Survival after Ischemia via TORC1-CREB," Neuron, 2011, vol. 69, pp. 106-119.
Sina C. et al.,"G Protein-Coupled Receptor 43 Is Essential for Neutrophil Recruitment during Intestinal Inflammation," J. Immunol., 2009, vol. 183, pp. 7514-7522.
Sundberg T.B. et al., "Small-molecule screening identifies inhibition of salt-inducible kinases as a therapeutic strategy to enhance immunoregulatory functions of dendritic cells," Proc. Natl. Acad. Sci. U. S. A., 2014, vol. 111, pp. 12468-12473.
Wein M.N. et al., "SIKs control osteocyte responses to parathyroid hormone," Nat. Commun., 2016, vol. 7, pp. 1-19.
Wirtz S. et al., "Chemically induced mouse models of intestinal inflammation," Nat. Protoc., 2007, vol. 2, pp. 541-546.
Yu J. et al., "Salt-inducible kinase 1 is involved in high glucose-induced mesangial cell proliferation mediated by the ALK5 signaling pathway," Int. J. Mol. Med., 2013, vol. 32, pp. 151-157.
Bush K.A. et al., "Reduction of joint inflammation and bone erosion in rat adjuvant arthritis by treatment with interleukin-17 receptor IgG1 Fc fusion protein," Arthritis Rheum., 2002, vol. 46, pp. 802-805.
Jou I.M. et al., "Thrombospondin 1 as an effective gene therapeutic strategy in collagen-induced arthritis," Arthritis Rheum., 2005, vol. 52, pp. 339-344.
Nishida, K. et.al., "Histone deacetylase inhibitor suppression of autoantibody-mediated arthritis in mice via regulation of p16INK4a and p21WAF1/Cip1 expression," Arthritis Rheum., 2004, vol. 50, pp. 3365-3376.
Rizzo H.L. et al., "IL-23-Mediated Psoriasis-Like Epidermal Hyperplasia Is Dependent on IL-17A," J. Immunol., 2011, vol. 186, pp. 1495-1502.
Salvemini D. et al., "Amelioration of joint disease in a rat model of collagen-induced arthritis by M40403, a superoxide dismutase mimetic," Arthritis Rheum., 2001, vol. 44, pp. 2909-2921.
Sherlock J.P. et al., "IL-23 induces spondyloarthropathy by acting on ROR-yt+ CD3+CD4-CD8-entheseal resident T cells," Nat. Med., 2012, vol. 18, pp. 1069-1076.
Sims N.A. et al., "Targeting osteoclasts with zoledronic acid prevents bone destruction in collagen-induced arthritis," Arthritis Rheum., 2004, vol. 50, pp. 2338-2346.
Van der Fits L. et al., "Imiquimod-Induced Psoriasis-Like Skin Inflammation in Mice Is Mediated via the IL-23/IL-17 Axis.," J. Immunol., 2009, vol. 182, pp. 5836-5845.
Yokogawa M. et al., "Epicutaneous Application of Toll-like Receptor 7 Agonists Leads to Systemic Autoimmunity in Wild-Type Mice: A New Model of Systemic Lupus Erythematosus," Arthritis Rheumatol., 2014, vol. 66, pp. 694-706.

Argilés J.M. et al., "Catabolic proinflammatory cytokines," Curr. Opin. Clin. Nutr. Metab. Care, 1998, vol. 1, pp. 245-251.
Ashcroft T. et al., "Simple method of estimating severity of pulmonary fibrosis on a numerical scale," J. Clin. Pathol., 1988, vol. 41, pp. 467-470.
Dempster D.W. et al., "Standardized nomenclature, symbols, and units for bone histomorphometry: a 2012 update of the report of the ASBMR Histomorphometry Nomenclature Committee," J. Bone Miner. Res. Off. J. Am. Soc. Bone Miner. Res. 2013, vol. 28, pp. 1-16.
Devos F.C. et al., "Forced expiration measurements in mouse models of obstructive and restrictive lung diseases," Respir. Res., 2017, vol. 18, pp. 1-14.
Favaudon V. et al., "Ultrahigh dose-rate FLASH irradiation increases the differential response between normal and tumor tissue in mice," Sci. Transl. Med. 2014, vol. 6, pp. 1-10.
Glasson S.S. et al., "The surgical destabilization of the medial meniscus (DMM) model of osteoarthritis in the 129/SvEv mouse," Osteoarthritis Cartilage, 2007, vol. 15, pp. 1061-1069.
Khachigian L.M., "Collagen antibody-induced arthritis," Nat. Protoc., 2006, vol. 1, pp. 2512-2516.
Li M. et al., "Topical vitamin D3 and low-calcemic analogs induce thymic stromal lymphopoietin in mouse keratinocytes and trigger an atopic dermatitis," Proc. Natl. Acad. Sci. U. S. A., 2006, vol. 103, pp. 11736-11741.
Lin H-S. et al., "Anti-rheumatic activities of histone deacetylase (HDAC) inhibitors in vivo in collagen-induced arthritis in rodents," Br. J. Pharmacol., 2007, vol. 150, pp. 862-872.
Lindebo Holm T. et al., "Pharmacological Evaluation of the SCID T Cell Transfer Model of Colitis: As a Model of Crohn's Disease," Int. J. Inflamm. 2012, Article ID No. 412178, pp. 1-11.
Matsuse T. et al., "ICAM-1 mediates lung leukocyte recruitment but not pulmonary fibrosis in a murine model of pleomycin-induced lung injury," Eur. Respir. J., 1999, vol. 13, pp. 71-77.
Maxwell J.R. et al., "Differential Roles for Interleukin-23 and Interleukin-17 in Intestinal Immunoregulation," Immunity, 2015, vol. 43, pp. 739-750.
MD Biosciences Inc., "Monoclonal Antibody Induced Arthritis: a shorter, more synchronized alternative to the classic CIA model," BioTechniques, 2008, vol. 44, pp. 279-280.
Miller R.E. et al., "Therapeutic effects of an anti-ADAMTS-5 antibody on joint damage and mechanical allodynia in a murine model of osteoarthritis," Osteoarthritis Cartilage, 2016, vol. 24, pp. 299-306.
Nandakumar K.S. et al., "Collagen Type II-Specific Monoclonal Antibody-Induced Arthritis in Mice," Am. J. Pathol., 2003, vol. 163, pp. 1827-1837.
Rall L.C. et al., "Rheumatoid cachexia: metabolic abnormalities, mechanisms and interventions," Rheumatology, 2004, vol. 43, pp. 1219-1223.
Shelton D.L. et al., "Nerve growth factor mediates hyperalgesia and cachexia in auto-immune arthritis," Pain, 2005, vol. 116, pp. 8-16.
Walsmith J. et al., "Tumor necrosis factor-alpha production is associated with less body cell mass in women with rheumatoid arthritis," J. Rheumatol., 2004, vol. 31, pp. 23-29.
Yao C. et al., "Prostaglandin E2 promotes Th1 differentiation via synergistic amplification of IL-12 signalling by cAMP and PI3-kinase," Nat. Commun., 2013, vol. 4, pp. 1-13.
International Search Report and Written Opinion issued in PCT/EP2019/063956, dated Aug. 19, 2019, pp. 1-10.
Xi Jian-Bei et al., "Structure-based design and synthesis of imidazo[1,2-a]pyridine derivatives as novel and potent Nek2 inhibitors within vitroandin vivoantitumor activities," European Journal of Medicinal Chemistry, 2017, vol. 126, pp. 1083-1106.
Sekioka R. et al., "Discovery of novel scaffolds for [gamma]-secretase modulators without an arylimidazole moiety," Bioorganic & Medicinal Chemistry, 2018, vol. 26, No. 2, pp. 435-442.
Xiaohui H. et al., "Identification of potent and selective RIPK2 inhibitors for the treatment of inflammatory diseases," ACS Medicinal Chemistry Letters, 2017, vol. 8, No. 10, pp. 1048-1053.

(56) References Cited

OTHER PUBLICATIONS

Öster L. et al., 2024. "The structures of salt inducible kinase 3 in complex with pharmacological inhibitors reveal determinants for binding and selectivity," JBC 107201. https://doi.org/10.1016/j.jbc.2024.107201.

Peixoto C. et al., 2024. "Discovery of Clinical Candidate GLPG3970: A Potent and Selective Dual SIK2/SIK3 Inhibitor for the Treatment of Autoimmune and Inflammatory Diseases," J. Med. Chem. https://doi.org/10.1021/acs.jmedchem.3c02246.

* cited by examiner

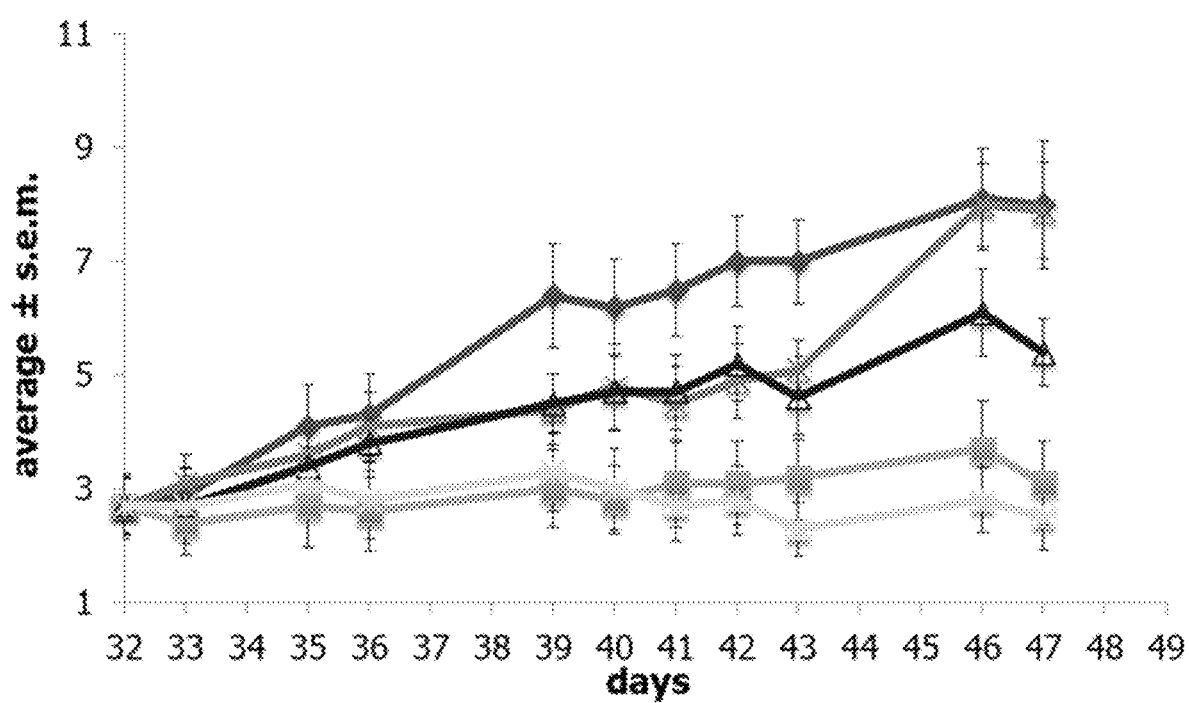

COMPOUNDS AND PHARMACEUTICAL COMPOSITIONS THEREOF FOR THE TREATMENT OF DISEASES

CROSS-REFERENCE TO RELATED APPLICATIONS

This application is a National Stage Entry of PCT/EP2019/063956, filed May 29, 2019, which claims foreign priority to GB Patent Application Nos. 1809836.8, filed on Jun. 15, 2018, and 1817344.3, filed on Oct. 25, 2018, the disclosures of which are hereby incorporated by reference in their entireties.

FIELD OF THE INVENTION

The present invention relates to compounds, methods for the production of the compounds of the invention, pharmaceutical compositions comprising the compounds of the invention, uses and methods for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases by administering the compounds of the invention. In particular, the compounds of the invention may inhibit Salt-Inducible Kinases ("SIK" kinases).

BACKGROUND OF THE INVENTION

Protein kinases belong to a large family of structurally related enzymes which are responsible for the control of a wide variety of cellular signal transduction processes. In particular, they have been shown to be key regulators in cellular functions including for example proliferation, metabolism, and apoptosis.

Consequently, defective control of protein phosphorylation which leads to uncontrolled signaling is involved in a number of diseases, including for example, inflammation, allergies, cancer, autoimmune diseases, CNS disorders, and angiogenesis.

In healthy individuals inflammation is self-limiting, and resolution is controlled by the release of anti-inflammatory mediators and cytokines, such as interleukin-10 (IL-10), produced by "suppressive" or "regulatory" cells, which are produced as part of a negative feedback loop.

Indeed, in the normal process of inflammation in the body, an initial pro-inflammatory response is followed by a pro-resolution response which turns the inflammation off after the insult has been resolved, leading to the reduction of pro-inflammatory cytokines such as TNFα and IL-12, coupled with increased levels of anti-inflammatory cytokines such as IL-10 and TGF-β, resulting in the generation of a so-called tolerogenic environment.

Adenosine Monophosphate-activated Protein Kinases (AMPK) belong to the protein kinase family, which comprises Salt-Inducible Kinases (SIKs), a family of serine/threonine kinases widely expressed in the body, and involved in particular in cellular energy homeostasis. Three SIK isoforms have been identified, named SIK1 (also referred as SNF1-Like Kinase (SNF1LK) or Myocardial Snf1-like Kinase (MSK)), SIK2 (SNF1LK2 or KIAA0781) and SIK3 (KIAA0999) (Katoh et al. 2004).

The SIKs play a number of roles in different cell types. They have been found to phosphorylate a number of substrates including CREB-responsive transcriptional co-activator (CRTC) proteins and Histone de-acetylase (HDAC) proteins, thereby regulating the transcription of a number of different genes. One of the roles of CRTC signalling relates to control the phenotype of macrophages, in particular polarisation of macrophages through phosphorylation of CRTC3 as measured by decreased proinflammatory cytokine IL-12 secretion and concomitant increased pro-resolution cytokine IL-10 secretion (Clark et al. 2012; Ozanne et al. 2015).

SIK1 has recently been shown to be involved in skeletal muscle sensitivity in obese mice, and may be an interesting target to prevent type II diabetes (Nixon et al. 2016), and diabetic nephropathy (Yu et al. 2013).

The regulation of ALK5 by SIK1 (Yu et al. 2013) and the identification of the SIK2 gene as a risk locus for primary sclerosing cholangitis (Liu et al. 2013) suggest a role for SIK proteins in fibrotic diseases.

SIK2 and SIK3 have recently been identified to play a role in inflammation through the secretion of high levels of anti-inflammatory cytokines, in particular Interleukin-10 (IL-10) and very low levels of pro-inflammatory cytokines such as TNFα (Darling et al. 2017).

A role for SIK2 in T helper (Th)1 cell differentiation has recently been described through the regulation of IFNγ and IL-12 signaling, suggesting SIK2 may be an interesting target for inflammatory diseases (Yao et al. 2013).

Recently, it has also been shown that like PTH, small molecule SIK inhibitors cause decreased phosphorylation and increased nuclear translocation of HDAC4/5 and CRTC2. Treatment with the small molecule SIK inhibitor YKL-05-099 increased bone formation and bone mass in mice (Wein et al. 2016), confirming the relevance of SIK inhibition in the treatment of bone turnover diseases.

Furthermore, it was shown that inhibition of SIK2 after oxygen-glucose deprivation enhances neuron survival (Sasaki et al. 2011) or promotes melanogenesis in melanoma cells (Kumagai et al. 2011). In this context, since therapeutic strategies are needed to modulate the stress cellular response, such as during ischaemia and post reperfusion of tissue, in the chronic phase of cardiac remodelling, in diabetes and neurodegenerative conditions, the rapid activation or degradation of the SIK proteins, following multiple kinds of stresses, makes them interesting targets in inflammatory, cardiac or metabolic diseases and neurodegenerative disorders. SIK inhibition might also have application in cosmetology or pigmentation-related diseases to induce melanogenesis.

The regulation of ALK5 by SIK1 (Yu et al. 2013) and the identification of the SIK2 gene as a risk locus for primary sclerosing cholangitis (Liu et al. 2013) suggest a role for SIK proteins in fibrotic diseases.

Besides the pivotal function in cellular energy homeostasis, the SIK proteins have also been involved in the regulation of the cell cycle. Higher expression of SIK2 significantly correlated with poor survival in patients with high-grade serous ovarian cancers (Ashour Ahmed et al. 2010), moreover, expression of SIK3 was elevated in ovarian cancers, particularly in the serous subtype and at later stages (Charoenfuprasert et al. 2011). Therefore SIK inhibition may be useful in the treatment of cancer.

Despite great advances over the past two decades in the treatments of patients affected by autoimmune disorders, based on antibodies targeting pro-inflammatory cytokines such as anti-TNFα, a significant proportion of patients do not respond to these therapies or experience serious adverse events such as opportunistic infections. Therefore a large unmet medical need still exists for the treatment of these diseases, and new agents for the prophylaxis and/or treatment of the above mentioned diseases are required.

BRIEF DESCRIPTION OF THE DRAWINGS

FIG. 1 refers to Example 4.2 and shows the evolution of the clinical score in the CIA mouse model for the vehicle (filled diamonds), Enbrel® (filled squares), Cpd 88 dosed at 10 mg/kg b.i.d. (crosses), Cpd 88 dosed at 30 mg/kg b.i.d. (triangles) and Cpd 88 dosed at 60 mg/kg b.i.d. (asterisks)

SUMMARY OF THE INVENTION

The present invention is based on the identification of novel compounds, and their use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases. In particular, the compounds of the invention may be SIK inhibitors, and more particularly SIK1, SIK2 and/or SIK3 inhibitors. The present invention also provides methods for the production of these compounds, pharmaceutical compositions comprising these compounds and methods for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases by administering the compounds of the invention.

Accordingly, in a first aspect of the invention, the compounds of the invention are provided having a Formula I.

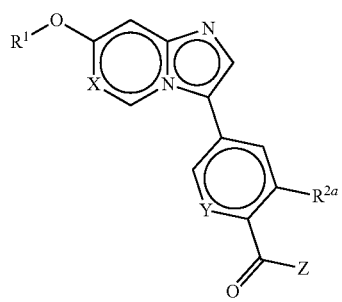

I wherein,
X is N or CH;
Y is N or $CR^{2b}$;

Z is
—$NHR^{3a}$,
N-linked 4-7 membered heterocycloalkyl further comprising zero, one, or two additional heteroatoms independently selected from N, O, and S, optionally substituted with one or more independently selected $R^{15}$ groups, or
—$NR^{3b}$—, wherein the N atom and $R^{2a}$ together with the atoms onto which they are attached form a fused 5-6 membered heterocycloalkenyl comprising one or two double bonds;

$R^1$ is
$C_{1-8}$ alkyl optionally substituted with one or more independently selected $R^4$ groups,
phenyl,
$C_{3-8}$ monocyclic or bridged polycyclic cycloalkyl optionally substituted with one or more independently selected $R^5$ groups,
4-8 membered monocyclic, spirocyclic, or bridged polycyclic heterocycloalkyl comprising one, two, or three heteroatoms independently selected from N, O, and S, which heterocycloalkyl is optionally substituted with one or more independently selected $C_{1-4}$ alkyl optionally substituted with one or more independently selected —CN or —C(=O)—$C_{1-4}$ alkoxy, or
5-6 membered monocyclic heteroaryl comprising one, two, or three heteroatoms independently selected from N, O, and S;

$R^{2a}$ and $R^{2b}$ are independently selected from
halo,
$C_{1-4}$ alkyl,
$C_{1-4}$ alkoxy optionally substituted with one or more independently selected halo or $C_{1-4}$ alkoxy, and
—$NR^{6a}R^{6b}$;

$R^{3a}$ is
$C_{1-6}$ alkyl optionally substituted with one or more independently selected halo or —CN, or
$C_{3-7}$ cycloalkyl optionally substituted with one or more independently selected halo or —OH;

$R^{3b}$ is selected from H, $C_{3-7}$ cycloalkyl and $C_{1-6}$ alkyl optionally substituted with one or more independently selected halo or —CN;

each $R^4$ is independently selected from
halo,
—OH,
—CN,
phenyl,
—C(=O)OH,
—O—C(=O)—$C_{1-4}$ alkyl,
—O—S(=O)$_2$—$C_{1-4}$ alkyl,
$C_{1-4}$ alkoxy optionally substituted with one or more independently selected
—OH,
$C_{1-4}$ alkoxy,
4-8 membered monocyclic heterocycloalkyl comprising one, two, or three heteroatoms independently selected from N, O, and S, which heterocycloalkyl is optionally substituted with one or more independently selected $C_{1-4}$ alkyl, or
—$NR^{7a}R^{7b}$, wherein each $R^{7a}$ and $R^{7b}$ is independently selected from H and $C_{1-4}$ alkyl,
$C_{3-7}$ cycloalkyl optionally substituted with one or more independently selected halo, —C(=O)—$C_{1-4}$ alkoxy, —$NR^{8a}R^{8b}$, or $C_{1-4}$ alkyl optionally substituted with one or more independently selected
—$NR^{9a}R^{9b}$, 5-6 membered monocyclic heterocycloalkyl comprising one or two N atoms fused to a 5-6 membered monocyclic heteroaryl comprising one, two, or three heteroatoms independently selected from N, O, and S, which heteroaryl is optionally substituted with one or more independently selected $C_{1-4}$ alkyl, 5-6 membered monocyclic heteroaryl comprising one, two, or three heteroatoms independently selected from N, O, and S, which heteroaryl is optionally substituted with one or more independently selected $C_{1-4}$ alkyl or $C_{3-7}$ cycloalkyl, 4-11 membered monocyclic, spirocyclic, or bridged polycyclic heterocycloalkyl comprising one, two, or three heteroatoms independently selected from N, O, and S, which heterocycloalkyl is optionally substituted with one or more independently selected $R^{10}$, —$NR^{11a}R^{11b}$, —C(=O)—$C_{1-4}$ alkoxy, and —C(=O)—$NR^{12a}R^{12b}$;

each R is selected from halo,

—CN, and

—$NR^{13a}R^{13b}$;

each $R^{6a}$ and $R^{6b}$ is independently selected from H and $C_{1-4}$ alkyl;

each $R^{10}$ is selected from

—OH, phenyl,

=NH, halo, oxo,

—CN,

—C(=O)H,

—C(=O)$NH_2$,

—C(=O)OH,

—$NR^{14a}R^{14b}$, $C_{1-4}$ alkyl optionally substituted with one or more independently selected halo, —CN, —OH, —C(=O)—$C_{1-4}$ alkoxy, or $C_{1-4}$ alkoxy, $C_{3-7}$ cycloalkyl, 4-6 membered monocyclic heterocycloalkyl comprising one, two, or three heteroatoms independently selected from N, O, and S, —C(=O)—$C_{1-4}$ alkyl, —S(=O)$_2$—$C_{1-4}$ alkyl, and —C(=O)—$C_{1-6}$ alkoxy;

each $R^{11a}$, $R^{11b}$ is independently selected from

H, phenyl, $C_{1-4}$ alkyl optionally substituted with one or more independently selected halo, —OH, —CN, or $C_{1-4}$ alkoxy, $C_{3-7}$ cycloalkyl, —C(=O)—$C_{1-4}$ alkoxy, —C(=O)—$C_{1-4}$ alkyl optionally substituted with one or more independently selected halo, and 5-6 membered monocyclic heteroaryl comprising one, two, or three heteroatoms independently selected from N, O, and S;

each $R^{8a}$, $R^{8b}$, $R^{9a}$, $R^{9b}$, $R^{12a}$, $R^{12b}$ $R^{13a}$, and $R^{13b}$ is independently selected from H and $C_{1-4}$ alkyl;

each $R^{14a}$ and $R^{14b}$ is independently selected from H, $C_{1-4}$ alkyl, and —S(=O)$_2$—$C_{1-4}$ alkyl; and each $R^{15}$ is independently selected from —OH, —CN, and $C_{1-4}$ alkyl optionally substituted with one or more independently selected halo or —CN.

In a particular aspect, the compounds of the invention are provided for use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases.

Furthermore, it has also been unexpectedly demonstrated that the compounds of the invention exhibit potency against SIK, particularly SIK1, SIK2 and/or SIK3, more particularly SIK2 and/or SIK3, which may result in a tolerogenic therapy (i.e. reduction of pro-inflammatory cytokines such as TNFα and IL-12, coupled with increased levels of anti-inflammatory cytokines such as IL-10 and TGF-β).

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the treatment of inflammatory diseases, autoinflammatory diseases, autoimmune diseases, proliferative diseases, fibrotic diseases, transplantation rejection, diseases involving impairment of cartilage turnover, congenital cartilage malformation, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Alkyl' means straight or branched aliphatic hydrocarbon having the specified number of carbon atoms. Particular alkyl groups have 1 to 6 carbon atoms or 1 to 4 carbon atoms. Branched means that one or more alkyl groups such as methyl, ethyl or propyl is attached to a linear alkyl chain. Particular alkyl groups are methyl (—$CH_3$), ethyl (—$CH_2$—$CH_3$), n-propyl (—$CH_2$—$CH_2$—$CH_3$), isopropyl (—CH($CH_3$)$_2$), n-butyl (—$CH_2$—$CH_2$—$CH_2$—$CH_3$), tert-butyl (—C($CH_3$)$_3$), sec-butyl (—CH($CH_3$)—$CH_2CH_3$), isobutyl (—$CH_2$—CH($CH_3$)$_2$), n-pentyl (—$CH_2$—$CH_2$—$CH_2$—$CH_2$—$CH_3$), n-hexyl (—$CH_2$—$CH_2$—$CH_2$—$CH_2$—$CH_2$—$CH_3$), and 1,2-dimethylbutyl (—$CHCH_3$)—C($CH_3$)H—$CH_2$—$CH_3$). Particular alkyl groups have between 1 and 4 carbon atoms.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═$CH_2$), n-propenyl (—$CH_2$CH═$CH_2$), isopropenyl (—C($CH_3$)═$CH_2$) and the like.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—$CH_2$—), ethylene (—$CH_2$—$CH_2$—), or —CH($CH_3$)— and the like.

'Alkynylene' refers to divalent alkyne radical groups having the number of carbon atoms and the number of triple bonds specified, in particular 2 to 6 carbon atoms and more particularly 2 to 4 carbon atoms which can be straight-chained or branched. This term is exemplified by groups such as —C≡C—, —$CH_2$—C≡C—, and —C($CH_3$)H—C≡CH—.

'Alkoxy' refers to the group O-alkyl, where the alkyl group has the number of carbon atoms specified. In particular the term refers to the group —O—$C_{1-6}$ alkyl. Particular alkoxy groups are methoxy, ethoxy, n-propoxy, isopropoxy, n-butoxy, tert-butoxy, isobutoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Amino' refers to the radical —$NH_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or fused polycyclic, with the number of ring atoms specified. Specifically, the term includes groups that include from 6 to 10 ring members. Particular aryl groups include phenyl, and naphthyl.

'Cycloalkyl' refers to a non-aromatic hydrocarbyl ring structure, monocyclic, fused polycyclic, bridged polycyclic, or spirocyclic, with the number of ring atoms specified. A cycloalkyl may have from 3 to 12 carbon atoms, in particular from 3 to 10, and more particularly from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

As used herein, term 'polycyclic' refers to chemical groups featuring several closed rings of atoms. In particular it refers to groups featuring two, three or four rings of atoms, more particularly two or three rings of atoms, most particularly two rings of atoms.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or fused polycyclic, that includes one or more heteroatoms independently selected from O, N and S and the number of ring atoms specified. In particular, the aromatic ring structure may have from 5 to 9 ring members. The heteroaryl group can be, for example, a five membered or six membered monocyclic ring or a fused bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In particular, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered monocyclic heteroaryl groups include but are not limited to pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered monocyclic heteroaryl groups include but are not limited to pyridinyl, pyrazinyl, pyridazinyl, pyrimidinyl and triazinyl.

Particular examples of bicyclic heteroaryl groups containing a five membered ring fused to another five-membered ring include but are not limited to imidazothiazolyl and imidazoimidazolyl.

Particular examples of bicyclic heteroaryl groups containing a six membered ring fused to a five membered ring include but are not limited to benzofuranyl, benzothiophenyl, benzoimidazolyl, benzoxazolyl, benzisoxazolyl, benzothiazolyl, benzisothiazolyl, isobenzofuranyl, indolyl, isoindolyl, indolizinyl, purinyl (e.g. adenine, guanine), indazolyl, pyrazolopyrimidinyl, triazolopyrimidinyl, and pyrazolopyridinyl groups.

Particular examples of bicyclic heteroaryl groups containing two fused six membered rings include but are not limited to quinolinyl, isoquinolinyl, pyridopyridinyl, quinoxalinyl, quinazolinyl, cinnolinyl, phthalazinyl, naphthyridinyl, and pteridinyl groups. Particular heteroaryl groups are those derived from thiophenyl, pyrrolyl, benzothiophenyl, benzofuranyl, indolyl, pyridinyl, quinolinyl, imidazolyl, oxazolyl and pyrazinyl.

Examples of representative heteroaryls include the following:

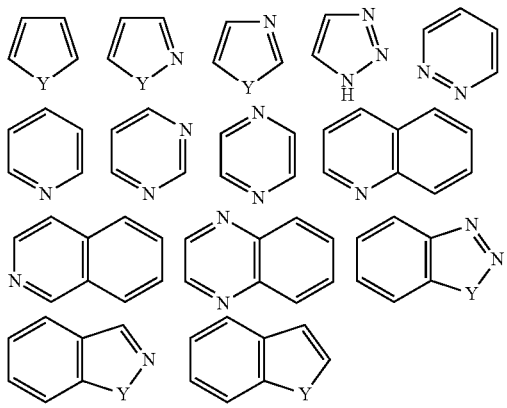

wherein each Y is selected from >C=O, NH, O and S.

'Heterocycloalkyl' means a non-aromatic fully saturated ring structure, monocyclic, fused polycyclic, spirocyclic, or bridged polycyclic, that includes one or more heteroatoms independently selected from O, N and S and the number of ring atoms specified. The heterocycloalkyl ring structure may have from 4 to 12 ring members, in particular from 4 to 10 ring members and more particularly from 4 to 7 ring members. Each ring may contain up to four heteroatoms typically selected from nitrogen, sulphur and oxygen. Typically the heterocycloalkyl ring will contain up to 4 heteroatoms, more typically up to 3 heteroatoms, more usually up to 2, for example a single heteroatom. Examples of heterocyclic rings include, but are not limited to azetidinyl, oxetanyl, thietanyl, pyrrolidinyl (e.g. 1-pyrrolidinyl, 2-pyrrolidinyl and 3-pyrrolidinyl), tetrahydrofuranyl (e.g. 1-tetrahydrofuranyl, 2-tetrahydrofuranyl and 3-tetrahydrofuranyl), tetrahydrothiophenyl (e.g. 1-tetrahydrothiophenyl, 2-tetrahydrothiophenyl and 3-tetrahydrothiophenyl), piperidinyl (e.g. 1-piperidinyl, 2-piperidinyl, 3-piperidinyl and 4-piperidinyl), tetrahydropyranyl (e.g. 4-tetrahydropyranyl), tetrahydrothiopyranyl (e.g. 4-tetrahydrothiopyranyl), morpholinyl, thiomorpholinyl, dioxanyl, or piperazinyl.

As used herein, the term 'heterocycloalkenyl' means a 'heterocycloalkyl', which comprises at least one double bond. Particular examples of heterocycloalkenyl groups are shown in the following illustrative examples:

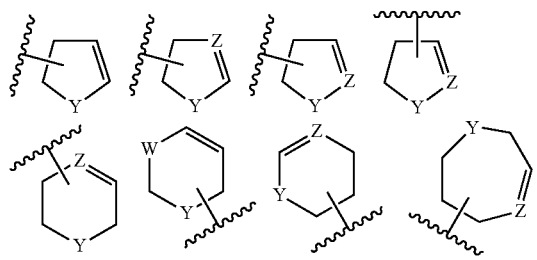

wherein each W is selected from $CH_2$, NH, O and S; each Y is selected from NH, O, C(=O), $SO_2$, and S; and each Z is selected from N or CH.

Particular examples of monocyclic rings are shown in the following illustrative examples:

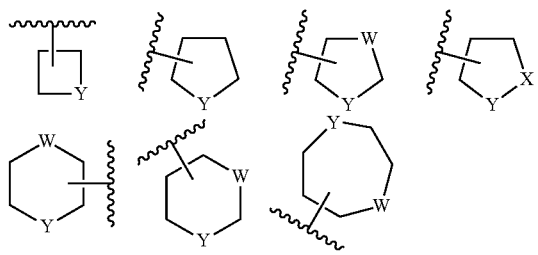

wherein each W and Y is independently selected from —$CH_2$—, —NH—, —O— and —S—.

Particular examples of fused bicyclic rings are shown in the following illustrative examples:

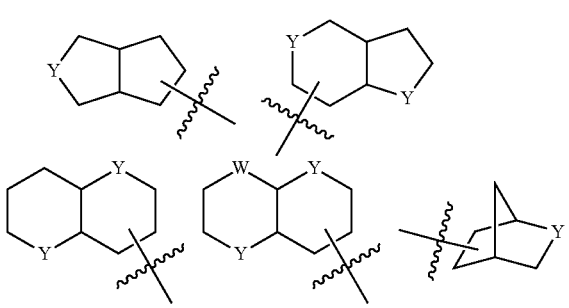

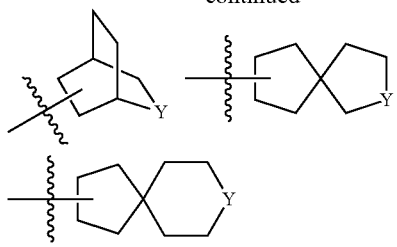

wherein each W and Y is independently selected from —CH$_2$—, —NH—, —O— and —S—.

Particular examples of bridged bicyclic rings are shown in the following illustrative examples:

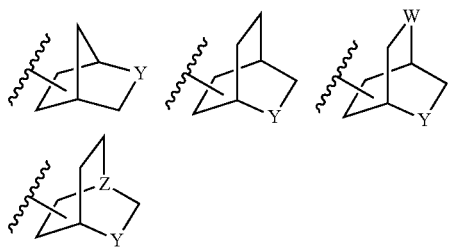

wherein each W and Y is independently selected from —CH$_2$—, —NH—, —O— and —S—.

Particular examples of spirocyclic rings are shown in the following illustrative examples:

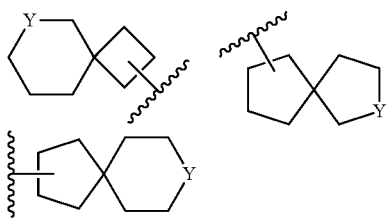

wherein each Y is selected from —CH$_2$—, —NH—, —O— and —S—.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as —SO$_3$H.

'Thiol' refers to the group —SH.

As used herein, term 'substituted with one or more' refers to one to four substituents. In particular, it refers to one to three substituents. More particularly, it refers to one or two substituents. Most particularly, it refers to one substituent.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, EtOH, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein the term 'inflammatory disease(s)' refers to the group of conditions including, rheumatoid arthritis, osteoarthritis, juvenile idiopathic arthritis, psoriasis, psoriatic arthritis, ankylosing spondylitis, allergic airway disease (e.g. asthma, rhinitis), chronic obstructive pulmonary disease (COPD), inflammatory bowel diseases (e.g. Crohn's disease, ulcerative colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma), chronic obstructive pulmonary disease (COPD) and inflammatory bowel diseases. More particularly the term refers to rheumatoid arthritis, chronic obstructive pulmonary disease (COPD) and inflammatory bowel diseases As used herein the term 'autoinflammatory diseases(s)' refers to the group of diseases including Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease.

As used herein the term 'autoimmune disease(s)' refers to the group of diseases including obstructive airways disease, including conditions such as COPD, asthma (e.g. intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, autoimmune liver diseases (e.g. autoimmune hepatitis, primary sclerosing cholangitis, and primary biliary cirrhosis), Sjögren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly the term refers to COPD, asthma, systemic lupus erythematosis, type I diabetes mellitus and inflammatory bowel disease.

As used herein the term 'proliferative disease(s)' refers to conditions such as cancer (e.g. uterine leiomyosarcoma or prostate cancer), myeloproliferative disorders (e.g. polycythemia vera, essential thrombocytosis and myelofibrosis), leukemia (e.g. acute myeloid leukemia, acute and chronic lymphoblastic leukemia), multiple myeloma, psoriasis, restenosis, scleroderma or fibrosis. In particular the term refers to cancer, leukemia, multiple myeloma and psoriasis As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types (such as but not limited to, melanoma, lymphoma, leukemia, fibrosarcoma, rhabdomyosarcoma, and mastocytoma) and types of tissue carcinoma (such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, and uterine leiomyosarcoma). In particular, the term 'cancer' refers to acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-cell lymphoma, embryonal tumors, endometrial cancer, ependymoblastoma, ependymoma, esophageal cancer, Ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hypopharyngeal cancer, intraocular melanoma, islet cell tumors (endocrine pancreas), Kaposi sarcoma, kidney cancer, Langerhans cell histiocytosis, laryngeal cancer, leukemia, hairy cell leukemia, liver cancer, non-small cell lung cancer, small cell lung cancer, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, myeloid leukemia, multiple myeloma, nasopharyngeal cancer, neuroblastoma, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, Sezary syndrome, skin cancer, small cell lung cancer, small intestine cancer, soft tissue sarcoma, squamous cell carcinoma, stomach (gastric) cancer, supratentorial primitive neuroectodermal tumors, testicular cancer, throat cancer, thymoma and thymic carcinoma, thyroid cancer, urethral cancer, uterine cancer, uterine sarcoma, vaginal cancer, vulvar cancer, and Wilms tumor.

As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukemia (AML), and acute lymphoblastic leukemia (ALL) and chronic lymphoblastic leukemia (CLL).

As used herein the term 'fibrotic disease(s)' refers to diseases characterized by excessive scarring due to excessive production, deposition, and contraction of extracellular matrix, and that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract. In particular, the term fibrotic diseases refers to idiopathic pulmonary fibrosis (IPF); cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak syndrome, tuberous sclerosis, neurofibromatosis, metabolic storage diseases, familial interstitial lung disease); radiation induced fibrosis; chronic obstructive pulmonary disease; scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; diabetic nephropathy, focal segmental glomerular sclerosis; IgA nephropathy; hypertension; Alport syndrome; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Dupuytren disease, keloids, cutaneous fibrosis; cutaneous scleroderma; systemic sclerosis, spinal cord injury/fibrosis; myelofibrosis; Duchenne muscular dystrophy (DMD) associated musculoskeletal fibrosis, vascular restenosis; atherosclerosis; arteriosclerosis; Wegener's granulomatosis; Peyronie's disease, or chronic lymphocytic. More particularly, the term 'fibrotic diseases' refers to idiopathic pulmonary fibrosis (IPF), Dupuytren disease, nonalcoholic steatohepatitis (NASH), systemic sclerosis, renal fibrosis, and cutaneous fibrosis.

As used herein the term 'transplantation rejection' refers to the acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases.

As used herein the term 'diseases involving impairment of cartilage turnover' includes conditions such as osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

As used herein the term 'congenital cartilage malformation(s)' includes conditions such as hereditary chondrolysis, chondrodysplasias and pseudochondrodysplasias, in particular, but without limitation, microtia, anotia, metaphyseal chondrodysplasia, and related disorders.

As used herein the term 'diseases involving impairment of bone turnover' includes conditions such as osteoporosis (including postmenopausal osteoporosis, male osteoporosis, glucocorticosteroid induced osteoporosis and juvenile osteoporosis), osteoporosis caused through neoplastic bone marrow disorders, osteopenia, hormone deficiency (vitamin D deficiency, male and female hypogonadism), hormone excess (hyperprolactinaemia, excess glucocorticoid, hyperthyroidism, hyperparathyroidism), Paget's disease, osteoarthritis, renal bone disease, osteogenesis imperfecta, hypophosphatasia.

As used herein the term 'disease(s) associated with hypersecretion of IL-6' includes conditions such as Castleman's disease, multiple myeloma, psoriasis, Kaposi's sarcoma and/or mesangial proliferative glomerulonephritis.

As used herein the term 'disease(s) associated with hypersecretion of of TNFα, interferons, IL-12 and/or IL-23' includes conditions such as systemic and cutaneous lupus erythematosis, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease.

As used herein, the term 'respiratory disease(s)' refers to diseases affecting the organs that are involved in breathing, such as the nose, throat, larynx, eustachian tubes, trachea, bronchi, lungs, related muscles (e.g., diaphram and intercostals), and nerves. In particular, examples of respiratory diseases include asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation, cystic fibrosis, and hypoxia.

As used herein the term 'endocrine and/or metabolic disease(s)' refers to the group of conditions involving the body's over- or under-production of certain hormones, while metabolic disorders affect the body's ability to process certain nutrients and vitamins. Endocrine disorders include hypothyroidism, congenital adrenal hyperplasia, diseases of the parathyroid gland, diabetes mellitus, diseases of the adrenal glands (including Cushing's syndrome and Addison's disease), and ovarian dysfunction (including polycystic ovary syndrome), among others. Some examples of metabolic disorders include cystic fibrosis, phenylketonuria (PKU), diabetes, hyperlipidemia, gout, and rickets. A particular example of metabolic disorders is obesity and/or type II diabetes.

As used herein the term 'cardiovascular disease(s)' refers to diseases affecting the heart or blood vessels or both. In particular, cardiovascular disease includes arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; vasoconstriction (including that associated with migraines); vascular abnormality, inflammation, or insufficiency limited to a single organ or tissue. More particularly, cardiovascular disease refers to atherosclerosis.

As used herein the term 'dermatological disease(s)' refers to a skin disorder. In particular, dermatological disorders include proliferative or inflammatory disorders of the skin such as atopic dermatitis, bullous disorders, collagenoses, psoriasis, psoriatic lesions, dermatitis, contact dermatitis, eczema, vitiligo, pruritus, scleroderma, wound healing, scarring, hypertrophic scarring, keloids, Kawasaki disease, rosacea, Sjögren-Larsson syndrome, or urticaria.

As used herein the term 'abnormal angiogenesis associated disease(s)' refers to diseases caused by the dysregulation of the processes mediating angiogenesis. In particular, abnormal angiogenesis associated disease refers to atherosclerosis, hypertension, tumor growth, inflammation, rheumatoid arthritis, wet-form macular degeneration, choroidal neovascularization, retinal neovascularization, and diabetic retinopathy.

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgaard 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters.

Particular such prodrugs are the $C_{1-8}$ alkyl, $C_{2-8}$ alkenyl, $C_{6-10}$ optionally substituted aryl, and ($C_{6-10}$ aryl)-($C_{1-4}$ alkyl) esters of the compounds of the invention.

The present disclosure includes all isotopic forms of the compounds of the invention provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exists as a mixture of mass numbers.

The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2H$ or D), carbon-11 ($^{11}C$), carbon-13 ($^{13}C$), carbon-14 ($^{14}C$), nitrogen-13 ($^{13}N$), nitrogen-15 ($^{15}N$), oxygen-15 ($^{15}O$), oxygen-17 ($^{17}O$), oxygen-18 ($^{18}O$), phosphorus-32 ($^{32}P$), sulphur-35 ($^{35}S$), chlorine-36 ($^{36}Cl$), chlorine-37 ($^{37}Cl$), fluorine-18 ($^{18}F$) iodine-123 ($^{123}I$), iodine-125 ($^{125}I$) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Unnatural variant isotopic forms which incorporate deuterium i.e. $^2H$ or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}C$, $^{18}F$, $^{15}O$ and $^{13}N$, and would be useful in Positron Emission Topography (PET) studies for examining substrate receptor occupancy.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

THE INVENTION

The present invention is based on the identification of novel compounds, and their use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases. In particular, the compounds of the invention may be SIK inhibitors, more particularly SIK1, SIK2 and/or SIK3 inhibitors.

The present invention also provides methods for the production of these compounds, pharmaceutical compositions comprising these compounds and methods for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases by administering the compounds of the invention.

Accordingly, in a first aspect of the invention, the compounds of the invention are provided having Formula I:

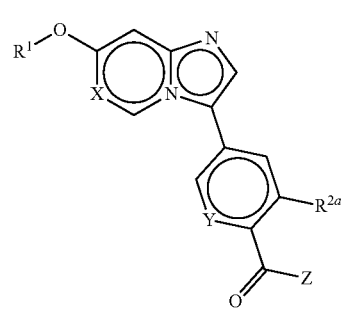

wherein,
X is N or CH;
Y is N or $CR^{2b}$;
Z is
—$NHR^{3a}$,
N-linked 4-7 membered heterocycloalkyl further comprising zero, one, or two additional heteroatoms independently selected from N, O, and S, optionally substituted with one or more independently selected $R^{15}$ groups, or
—$NR^{3b}$—, wherein the N atom and $R^{2a}$ together with the atoms onto which they are attached form a fused 5-6 membered heterocycloalkenyl comprising one or two double bonds;
$R^1$ is
$C_{1-8}$ alkyl optionally substituted with one or more independently selected $R^4$ groups,
phenyl,
$C_{3-8}$ monocyclic or bridged polycyclic cycloalkyl optionally substituted with one or more independently selected $R^5$ groups,
4-8 membered monocyclic, spirocyclic, or bridged polycyclic heterocycloalkyl comprising one, two, or three heteroatoms independently selected from N, O, and S, which heterocycloalkyl is optionally substituted with one or more independently selected $C_{1-4}$ alkyl optionally substituted with one or more independently selected —CN or —C(═O)—$C_{1-4}$ alkoxy, or
5-6 membered monocyclic heteroaryl comprising one, two, or three heteroatoms independently selected from N, O, and S;
$R^{2a}$ and $R^{2b}$ are independently selected from
halo,
$C_{1-4}$ alkyl,
$C_{1-4}$ alkoxy optionally substituted with one or more independently selected halo or $C_{1-4}$ alkoxy, and
—$NR^{6a}R^{6b}$;
$R^{3a}$ is
$C_{1-6}$ alkyl optionally substituted with one or more independently selected halo or —CN, or
$C_{3-7}$ cycloalkyl optionally substituted with one or more independently selected halo or —OH;
$R^{3b}$ is selected from H, $C_{3-7}$ cycloalkyl and $C_{1-6}$ alkyl optionally substituted with one or more independently selected halo or —CN;
each $R^4$ is independently selected from
halo,
—OH,
—CN,
phenyl,
—C(═O)OH, —O—C(=O)—$C_{1-4}$ alkyl,
—O—S(=O)$_2$—$C_{1-4}$ alkyl,
$C_{1-4}$ alkoxy optionally substituted with one or more independently selected
—OH,
$C_{1-4}$ alkoxy,
4-8 membered monocyclic heterocycloalkyl comprising one, two, or three heteroatoms independently selected from N, O, and S, which heterocycloalkyl is optionally substituted with one or more independently selected $C_{1-4}$ alkyl, or
—NR$^{7a}$R$^{7b}$, wherein each R$^{7a}$ and R$^{7b}$ is independently selected from H and $C_{1-4}$ alkyl,
$C_{3-7}$ cycloalkyl optionally substituted with one or more independently selected halo, —C(=O)—$C_{1-4}$ alkoxy, —NR$^{8a}$R$^{8b}$, or $C_{1-4}$ alkyl optionally substituted with one or more independently selected —NR$^{9a}$R$^{9b}$,
5-6 membered monocyclic heterocycloalkyl comprising one or two N atoms fused to a 5-6 membered monocyclic heteroaryl comprising one, two, or three heteroatoms independently selected from N, O, and S, which heteroaryl is optionally substituted with one or more independently selected $C_{1-4}$ alkyl,
5-6 membered monocyclic heteroaryl comprising one, two, or three heteroatoms independently selected from N, O, and S, which heteroaryl is optionally substituted with one or more independently selected $C_{1-4}$ alkyl or $C_{3-7}$ cycloalkyl,
4-11 membered monocyclic, spirocyclic, or bridged polycyclic heterocycloalkyl comprising one, two, or three heteroatoms independently selected from N, O, and S, which heterocycloalkyl is optionally substituted with one or more independently selected R$^{10}$,
—NR$^{11a}$R$^{11b}$,
—C(=O)—$C_{1-4}$ alkoxy, and
—C(=O)—NR$^{12a}$R$^{12b}$;
each R$^5$ is selected from
halo,
—CN, and
—NR$^{13a}$R$^{13b}$;
each R$^{6a}$ and R$^{6b}$ is independently selected from H and $C_{1-4}$ alkyl;
each R$^{10}$ is selected from
—OH,
phenyl,
=NH,
halo,
oxo,
—CN,
—C(=O)H,
—C(=O)NH$_2$,
—C(=O)OH,
—NR$^{14a}$R$^{14b}$,
$C_{1-4}$ alkyl optionally substituted with one or more independently selected halo, —CN, —OH, —C(=O)—$C_{1-4}$ alkoxy, or $C_{1-4}$ alkoxy,
$C_{3-7}$ cycloalkyl,
4-6 membered monocyclic heterocycloalkyl comprising one, two, or three heteroatoms independently selected from N, O, and S,
—C(=O)—$C_{1-4}$ alkyl,
—S(=O)$_2$—$C_{1-4}$ alkyl, and
—C(=O)—$C_{1-6}$ alkoxy;
each R$^{11a}$, R$^{11b}$ is independently selected from
H,
phenyl,
$C_{1-4}$ alkyl optionally substituted with one or more independently selected halo, —OH, —CN, or $C_{1-4}$ alkoxy,
$C_{3-7}$ cycloalkyl,
—C(=O)—$C_{1-4}$ alkoxy,
—C(=O)—$C_{1-4}$ alkyl optionally substituted with one or more independently selected halo, and
5-6 membered monocyclic heteroaryl comprising one, two, or three heteroatoms independently selected from N, O, and S;
each R$^{8a}$, R$^{8b}$, R$^{9a}$, R$^{9b}$, R$^{12a}$, R$^{12b}$ R$^{13a}$, and R$^{13b}$ is independently selected from H and $C_{1-4}$ alkyl;
each R$^{14a}$ and R$^{14b}$ is independently selected from H, $C_{1-4}$ alkyl, and —S(=O)$_2$—$C_{1-4}$ alkyl; and
each R$^{15}$ is independently selected from —OH, —CN, and $C_{1-4}$ alkyl optionally substituted with one or more independently selected halo or —CN.

In one embodiment, the compound of the invention is according to Formula I, wherein
Z is
—NHR$^{3a}$, or
—NR$^{3b}$—, wherein the N atom and R$^{2a}$ together with the atoms onto which they are attached form a fused 5-6 membered heterocycloalkenyl comprising one or two double bonds;
R$^1$ is
$C_{1-8}$ alkyl optionally substituted with one or more independently selected R$^4$ groups,
phenyl,
$C_{3-8}$ monocyclic or bridged polycyclic cycloalkyl optionally substituted with one or more independently selected R$^5$ groups,
4-8 membered monocyclic or spirocyclic heterocycloalkyl comprising one, two, or three heteroatoms independently selected from N, O, and S, which heterocycloalkyl is optionally substituted with one or more independently selected $C_{1-4}$ alkyl, or
5-6 membered monocyclic heteroaryl comprising one, two, or three heteroatoms independently selected from N, O, and S;
R$^{3a}$ is
$C_{1-6}$ alkyl optionally substituted with one or more independently selected halo or —CN, or
$C_{3-7}$ cycloalkyl;
each R$^4$ is independently selected from:
halo,
—OH,
—CN,
phenyl,
$C_{1-4}$ alkoxy optionally substituted with one or more independently selected —OH, $C_{1-4}$ alkoxy, or —NR$^{7a}$R$^{7b}$, wherein each R$^{7a}$ and R$^{7b}$ is independently selected from H and $C_{1-4}$ alkyl,
$C_{3-7}$ cycloalkyl optionally substituted with one or more independently selected halo, —C(=O)—$C_{1-4}$ alkoxy, —NR$^{8a}$R$^{8b}$, or $C_{1-4}$ alkyl optionally substituted with one or more independently selected —NR$^{9a}$R$^{9b}$,
5-6 membered monocyclic heteroaryl comprising one, two, or three heteroatoms independently selected from N, O, and S, which heteroaryl is optionally substituted with one or more independently selected $C_{1-4}$ alkyl or $C_{3-7}$ cycloalkyl,
4-8 membered monocyclic or bridged polycyclic heterocycloalkyl comprising one, two, or three heteroatoms independently selected from N, O, and S, which heterocycloalkyl is optionally substituted with one or more independently selected $R^{10}$,
—$NR^{11a}R^{11b}$, and
—C(=O)—$NR^{12a}R^{12b}$;

each $R^{10}$ is selected from
halo,
oxo,
—CN,
—C(=O)H,
—$NR^{14a}R^{14b}$,
$C_{1-4}$ alkyl optionally substituted with one or more independently selected halo or $C_{1-4}$ alkoxy,
$C_{3-7}$ cycloalkyl,
—C(=O)—$C_{1-4}$ alkyl,
—S(=O)$_2$—$C_{1-4}$ alkyl, and
—C(=O)—$C_{1-6}$ alkoxy;

each $R^{11a}$, $R^{11b}$ is independently selected from
H,
phenyl,
$C_{1-4}$ alkyl optionally substituted with one or more independently selected halo, —OH, —CN, or $C_{1-4}$ alkoxy,
$C_{3-7}$ cycloalkyl,
—C(=O)—$C_{1-4}$ alkyl, and
5-6 membered monocyclic heteroaryl comprising one, two, or three heteroatoms independently selected from N, O, and S; and each $R^{14a}$, and $R^{14b}$ is independently selected from H and $C_{1-4}$ alkyl.

In one embodiment, the compound of the invention is according to Formula I, wherein X is N.

In one embodiment, the compound of the invention is according to Formula I, wherein X is CH.

In one embodiment, the compound of the invention is according to Formula I, wherein $R^{2a}$ is halo. In a particular embodiment, $R^{2a}$ is F, Cl, or Br. In a more particular embodiment, $R^{2a}$ is F.

In one embodiment, the compound of the invention is according to Formula I, wherein $R^{2a}$ is $C_{1-4}$ alkyl. In a particular embodiment, $R^{2a}$ is —CH$_3$, —CH$_2$CH$_3$, or —CH(CH$_3$)$_2$. In a more particular embodiment, $R^{2a}$ is —CH$_3$.

In one embodiment, the compound of the invention is according to Formula I, wherein $R^{2a}$ is $C_{1-4}$ alkoxy. In a particular embodiment, $R^{2a}$ is —O—CH$_3$, —O—CH$_2$CH$_3$, or —O—CH(CH$_3$)$_2$. In a more particular embodiment, $R^{2a}$ is —O—CH$_3$ or —O—CH$_2$CH$_3$. In a most particular embodiment, $R^{2a}$ is —O—CH$_3$.

In one embodiment, the compound of the invention is according to Formula I, wherein $R^{2a}$ is $C_{1-4}$ alkoxy substituted with one or more independently selected halo or $C_{1-4}$ alkoxy. In a particular embodiment, $R^{2a}$ is —O—CH$_3$, —O—CH$_2$CH$_3$, or —O—CH(CH$_3$)$_2$, each of which is substituted with one or more independently selected halo or $C_{1-4}$ alkoxy. In another particular embodiment, $R^{2a}$ is $C_{1-4}$ alkoxy substituted with one, two, or three independently selected halo or $C_{1-4}$ alkoxy. In yet another particular embodiment, $R^{2a}$ is $C_{1-4}$ alkoxy substituted with one or more independently selected F, Cl, Br, —O—CH$_3$, —O—CH$_2$CH$_3$, or —O—CH(CH$_3$)$_2$. In a more particular embodiment, $R^{2a}$ is —O—CH$_3$, —O—CH$_2$CH$_3$, or —O—CH(CH$_3$)$_2$, each of which is substituted with one, two, or three independently selected halo or $C_{1-4}$ alkoxy. In another more particular embodiment, $R^{2a}$ is $C_{1-4}$ alkoxy substituted with one, two, or three independently selected F, Cl, Br, —O—CH$_3$, —O—CH$_2$CH$_3$, or —O—CH(CH$_3$)$_2$. In a further more particular embodiment, $R^{2a}$ is —O—CH$_3$, substituted with one, two, or three independently selected halo. In another further more particular embodiment, $R^{2a}$ is —O—CH$_2$CH$_3$, substituted with one, two, or three independently selected halo or $C_{1-4}$ alkoxy. In a most particular embodiment, $R^{2a}$ is —O—CHF$_2$ or —O—CH$_2$CH$_2$—O—CH$_2$CH$_3$.

In one embodiment, the compound of the invention is according to Formula I, wherein $R^{2a}$ is —$NR^{6a}R^{6b}$, and $R^{6a}$ and $R^{6b}$ are independently selected from H and $C_{1-4}$ alkyl. In a particular embodiment, $R^{6a}$ and $R^{6b}$ are both H. In another particular embodiment, one of $R^{6a}$ and $R^{6b}$ is H, and the other is $C_{1-4}$ alkyl. In yet another particular embodiment, $R^{6a}$ and $R^{6b}$ are both $C_{1-4}$ alkyl. In a more particular embodiment, one of $R^{6a}$ and $R^{6b}$ is H, and the other is —CH$_3$, —CH$_2$CH$_3$, or —CH(CH$_3$)$_2$. In another more particular embodiment, $R^{6a}$ and $R^{6b}$ are independently —CH$_3$, —CH$_2$CH$_3$, or —CH(CH$_3$)$_2$. In a most particular embodiment, one of $R^{6a}$ and $R^{6b}$ is H, and the other is —CH$_3$.

In one embodiment, the compound of the invention is according to Formula I, wherein Z is —$NR^{3b}$— wherein the N atom and $R^{2a}$ together with the atoms onto which they are attached form a fused 5-6 membered heterocycloalkenyl comprising one or two double bonds, and $R^{3b}$ is as previously described. In a particular embodiment, Z is —$NR^{3b}$—, wherein the N atom and $R^{2a}$ together with the atoms onto which they are attached form a fused 3-pyrroline, 1,2-dihydropyridine, or 1,2,3,6-tetrahydropyridine. In a more particular embodiment, Z is —$NR^{3b}$—, wherein the N atom and $R^{2a}$ together with the atoms onto which they are attached form a fused 1,2,3,6-tetrahydropyridine.

In one embodiment, the compound of the invention is according to Formula IIa, IIb, or IIc:

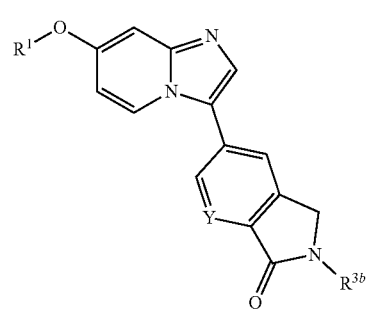

IIa

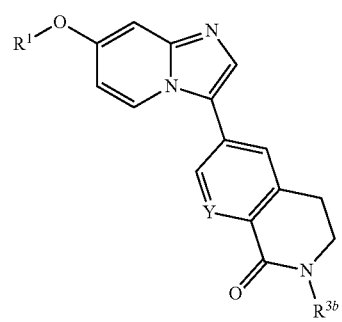

IIb

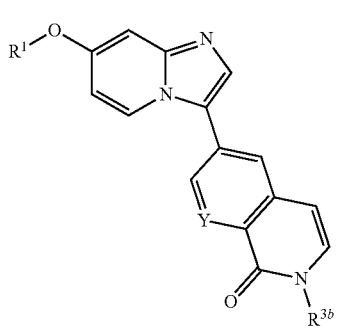

IIc wherein $R^1$, $R^{3b}$, and Y are as described above.

In one embodiment, the compound of the invention is according to any one of Formulae I-IIc, wherein $R^{3b}$ is H.

In one embodiment, the compound of the invention is according to any one of Formulae I-IIc, wherein $R^{3b}$ is $C_{3-7}$ cycloalkyl. In a particular embodiment, $R^{3b}$ is cyclopropyl, cyclobutyl, or cyclopentyl. In a more particular embodiment, $R^{3b}$ is cyclopropyl.

In one embodiment, the compound of the invention is according to any one of Formulae I-IIc, wherein $R^{3b}$ is $C_{1-6}$ alkyl. In a particular embodiment, $R^{3b}$ is —$CH_3$, —$CH_2CH_3$, —$CH_2CH_2CH_3$, —$CH(CH_3)_2$, or —$C(CH_3)_3$. In a more particular embodiment, $R^{3b}$ is —$CH_2CH_3$.

In one embodiment, the compound of the invention is according to any one of Formulae I-IIc, wherein $R^{3b}$ is $C_{1-6}$ alkyl substituted with one or more independently selected halo or —CN. In a particular embodiment, $R^{3b}$ is —$CH_3$, —$CH_2CH_3$, —$CH_2CH_2CH_3$, —$CH(CH_3)_2$, or —$C(CH_3)_3$, each of which is substituted with one or more independently selected halo or —CN. In another particular embodiment, $R^{3b}$ is $C_{1-6}$ alkyl substituted with one, two, or three independently selected halo or —CN. In yet another particular embodiment, $R^{3b}$ is $C_{1-6}$ alkyl substituted with one or more independently selected F, Cl, or —CN. In a more particular embodiment, $R^{3b}$ is —$CH_3$, —$CH_2CH_3$, —$CH_2CH_2CH_3$, —$CH(CH_3)_2$, or —$C(CH_3)_3$, each of which is substituted with one, two, or three independently selected halo or —CN. In another more particular embodiment, $R^{3b}$ is $C_{1-6}$ alkyl substituted with one, two, or three independently selected F, Cl, or —CN. In yet another more particular embodiment, $R^{3b}$ is —$CH_3$, —$CH_2CH_3$, —$CH_2CH_2CH_3$, —$CH(CH_3)_2$, or —$C(CH_3)_3$, each of which is substituted with one or more independently selected F, Cl, or —CN. In a further more particular embodiment, $R^{3b}$ is —$CH_3$, —$CH_2CH_3$, —$CH_2CH_2CH_3$, —$CH(CH_3)_2$, or —$C(CH_3)_3$, each of which is substituted with one, two, or three independently selected F, Cl, or —CN. In another further more particular embodiment, $R^{3b}$ is —$CH_3$, —$CH_2CH_3$, —$CH_2CH_2CH_3$, —$CH(CH_3)_2$, or —$C(CH_3)_3$, each of which is substituted with one or more F or —CN. In yet another further more particular embodiment, $R^{3b}$ is $C_{1-6}$ alkyl substituted with one, two, or three independently selected F or —CN. In a most particular embodiment, $R^{3b}$ is —$CH_2CH_3$ substituted with one, two, or three F. In another most particular embodiment, $R^{3b}$ is —$CH_2$—CN. In a further most particular embodiment, $R^{3b}$ is —$CH_2CF_3$.

In one embodiment, the compound of the invention is according to Formula I, wherein Z is N-linked 4-7 membered heterocycloalkyl further comprising zero, one, or two additional heteroatoms independently selected from N, O, and S. In a particular embodiment, Z is azetidinyl, pyrrolidinyl, piperidinyl, morpholinyl, thiomorpholinyl, or piperazinyl. In a more particular embodiment, Z is azetidinyl.

In one embodiment, the compound of the invention is according to Formula I, wherein Z is N-linked 4-7 membered heterocycloalkyl further comprising zero, one, or two additional heteroatoms independently selected from N, O, and S, substituted with one or more independently selected $R^{15}$ groups. In a particular embodiment, Z is azetidinyl, pyrrolidinyl, piperidinyl, morpholinyl, thiomorpholinyl, or piperazinyl, each of which is substituted with one or more independently selected $R^{15}$ groups. In another particular embodiment, Z is N-linked 4-7 membered heterocycloalkyl further comprising zero, one, or two additional heteroatoms independently selected from N, O, and S, substituted with one, two, or three independently selected $R^{15}$ groups. In a more particular embodiment, Z is azetidinyl substituted with one or more independently selected $R^{15}$ groups. In another more particular embodiment, Z is azetidinyl, pyrrolidinyl, piperidinyl, morpholinyl, thiomorpholinyl, or piperazinyl, each of which is substituted with one, two, or three independently selected $R^{15}$ groups. In yet another more particular embodiment, Z is N-linked 4-7 membered heterocycloalkyl further comprising zero, one, or two additional heteroatoms independently selected from N, O, and S, substituted with one or two independently selected $R^{15}$ group. In a further more particular embodiment, Z is azetidinyl substituted with one, two, or three independently selected $R^{15}$ groups. In another further more particular embodiment, Z is azetidinyl, pyrrolidinyl, piperidinyl, morpholinyl, thiomorpholinyl, or piperazinyl, each of which is substituted with one or two independently selected $R^{15}$ groups. In a most particular embodiment, Z is azetidinyl substituted with one or two independently selected $R^{15}$ groups.

In one embodiment, the compound of the invention is according to Formula I, wherein Z is N-linked 4-7 membered heterocycloalkyl further comprising zero, one, or two additional heteroatoms independently selected from N, O, and S, substituted with one or more independently selected $R^{15}$ groups, and $R^{15}$ is —OH, —CN, or $C_{1-4}$ alkyl. In a particular embodiment, $R^{15}$ is —OH, —CN, —$CH_3$, —$CH_2CH_3$, or —$CH(CH_3)_2$. In a more particular embodiment, $R^{15}$ is —OH or —CN.

In one embodiment, the compound of the invention is according to Formula I, wherein Z is N-linked 4-7 membered heterocycloalkyl further comprising zero, one, or two additional heteroatoms independently selected from N, O, and S, substituted with one or more independently selected $R^{15}$ groups, and $R^{15}$ is $C_{1-4}$ alkyl substituted with one or more independently selected halo or —CN. In a particular embodiment, $R^{15}$ is —$CH_3$, —$CH_2CH_3$, or —$CH(CH_3)_2$, each of which is substituted with one or more independently selected halo or —CN. In another particular embodiment, $R^{15}$ is $C_{1-4}$ alkyl substituted with one, two, or three independently selected halo or —CN. In yet another particular embodiment, $R^{15}$ is $C_{1-4}$ alkyl substituted with one or more F, Cl, Br, or —CN. In a more particular embodiment, $R^{15}$ is —$CH_3$ substituted with one or more independently selected halo or —CN. In another more particular embodiment, $R^{15}$ is —$CH_3$, —$CH_2CH_3$, or —$CH(CH_3)_2$, each of which is substituted with one, two, or three independently selected halo or —CN. In yet another more particular embodiment, $R^{15}$ is —$CH_3$, —$CH_2CH_3$, or —$CH(CH_3)_2$, each of which is substituted with one or more independently selected F, Cl, Br, or —CN. In yet another more particular embodiment, $R^{15}$ is $C_{1-4}$ alkyl substituted with one, two, or three independently selected F, Cl, Br, or —CN. In a further more particular embodiment, $R^{15}$ is —$CH_3$ substituted with one, two, or three independently selected halo or —CN. In another further more particular embodiment, $R^{15}$ is —$CH_3$ substituted with one or more, two, or three independently selected F, Cl, Br, or —CN. In a most particular embodiment, $R^{15}$ is —$CH_3$ substituted with one, two, or three independently selected F or —CN.

In one embodiment, the compound of the invention is according to Formula I, wherein Z is —$NHR^{3a}$, and $R^{3a}$ is $C_{1-6}$ alkyl. In a particular embodiment, $R^{3a}$ is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, or —$CH(CH_3)CH(CH_3)_2$. In a more particular embodiment, $R^{3a}$ is —$CH_3$, —$CH_2CH_3$, —$CH_2CH_2CH_3$, —$CH(CH_3)_2$, or —$CH_2CH(CH_3)_2$. In a most particular embodiment, $R^{3a}$ is —$CH_2CH_3$.

In one embodiment, the compound of the invention is according to Formula I, wherein Z is —$NHR^{3a}$ and $R^{3a}$ is $C_{1-6}$ alkyl substituted with one or more independently selected halo or —CN. In a particular embodiment, $R^{3a}$ is —$CH_3$, —$CH_2CH_3$, —$CH_2CH_2CH_3$, —$CH(CH_3)_2$, or —$C(CH_3)_3$, each of which is substituted with one or more independently selected halo or —CN. In another particular embodiment, $R^{3a}$ is $C_{1-6}$ alkyl substituted with one, two, or three independently selected halo or —CN. In yet another particular embodiment, $R^{3a}$ is $C_{1-6}$ alkyl substituted with one or more independently selected F, Cl, or —CN. In a more particular embodiment, $R^{3a}$ is —$CH_3$, —$CH_2CH_3$, —$CH_2CH_2CH_3$, —$CH(CH_3)_2$, or —$C(CH_3)_3$, each of which is substituted with one, two, or three independently selected halo or —CN. In another more particular embodiment, $R^{3a}$ is $C_{1-6}$ alkyl substituted with one, two, or three independently selected F, Cl, or —CN. In yet another more particular embodiment, $R^{3a}$ is —$CH_3$, —$CH_2CH_3$, —$CH_2CH_2CH_3$, —$CH(CH_3)_2$, or —$C(CH_3)_3$, each of which is substituted with one or more independently selected F, Cl, or —CN. In a further more particular embodiment, $R^{3a}$ is —$CH_3$, —$CH_2CH_3$, —$CH_2CH_2CH_3$, —$CH(CH_3)_2$, or —$C(CH_3)_3$, each of which is substituted with one, two, or three independently selected F, Cl, or —CN. In another further more particular embodiment, $R^{3a}$ is —$CH_3$, —$CH_2CH_3$, —$CH_2CH_2CH_3$, —$CH(CH_3)_2$, or —$C(CH_3)_3$, each of which is substituted with one or more F or —CN. In yet another further more particular embodiment, $R^{3a}$ is $C_{1-6}$ alkyl substituted with one, two, or three independently selected F or —CN. In a most particular embodiment, $R^{3a}$ is —$CH_2CH_3$ substituted with one, two, or three F. In another most particular embodiment, $R^{3a}$ is —$CH_2$—CN. In a further most particular embodiment, $R^{3a}$ is —$CH_2CF_3$.

In one embodiment, the compound of the invention is according to Formula I, wherein Z is —$NHR^{3a}$ and $R^{3a}$ is $C_{3-7}$ cycloalkyl. In a particular embodiment, $R^{3a}$ is cyclopropyl, cyclobutyl, or cyclopentyl. In a more particular embodiment, $R^{3a}$ is cyclopropyl.

In one embodiment, the compound of the invention is according to Formula I, wherein Z is —$NHR^{3a}$ and $R^{3a}$ is $C_{3-7}$ cycloalkyl substituted with one or more independently selected halo or —OH. In a particular embodiment, $R^{3a}$ is cyclopropyl, cyclobutyl, or cyclopentyl, each of which is substituted with one or more independently selected halo or —OH. In another particular embodiment, $R^{3a}$ is $C_{3-7}$ cycloalkyl substituted with one, two, or three independently selected halo or —OH. In yet another particular embodiment, $R^{3a}$ is $C_{3-7}$ cycloalkyl substituted with one or more independently selected F, Cl, or —OH. In a more particular embodiment, $R^{3a}$ is cyclopropyl, cyclobutyl, or cyclopentyl, each of which is substituted with one or more independently selected halo or —OH. In another more particular embodiment, $R^{3a}$ is $C_{3-7}$ cycloalkyl substituted with one, two, or three independently selected F, Cl, or —OH. In yet another more particular embodiment, $R^{3a}$ is cyclopropyl, cyclobutyl, or cyclopentyl, each of which is substituted with one or more independently selected F, Cl, or —OH. In a further more particular embodiment, $R^{3a}$ is cyclopropyl, cyclobutyl, or cyclopentyl, each of which is substituted with one, two, or three independently selected F, Cl, or —OH. In another further more particular embodiment, $R^{3a}$ is cyclopropyl, cyclobutyl, or cyclopentyl, each of which is substituted with one or more F or —OH. In yet another further more particular embodiment, $R^{3a}$ is $C_{3-7}$ cycloalkyl substituted with one, two, or three independently selected F or —OH. In a most particular embodiment, $R^{3a}$ is

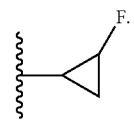

In a further most particular embodiment, $R^{3a}$ is

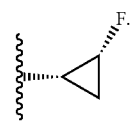

In one embodiment, the compound of the invention is according to any one of Formulae I-IIc, wherein Y is N.

In one embodiment, the compound of the invention is according to any one of Formulae I-IIc, wherein Y is $CR^{2b}$ and $R^{2b}$ is halo. In a particular embodiment, $R^{2b}$ is F, Cl, or Br. In a more particular embodiment, $R^{2b}$ is F.

In one embodiment, the compound of the invention is according to any one of Formulae I-IIc, wherein Y is $CR^{2b}$ and $R^{2b}$ is $C_{1-4}$ alkyl. In a particular embodiment, $R^{2b}$ is —$CH_3$, —$CH_2CH_3$, or —$CH(CH_3)_2$.

In a more particular embodiment, $R^{2b}$ is —$CH_3$.

In one embodiment, the compound of the invention is according to any one of Formulae I-IIc, wherein Y is $CR^{2b}$ and $R^{2b}$ is $C_{1-4}$ alkoxy. In a particular embodiment, $R^{2b}$ is —O—$CH_3$, —O—$CH_2CH_3$, or —O—$CH(CH_3)_2$. In a more particular embodiment, $R^{2b}$ is —O—$CH_3$ or —O—$CH_2CH_3$. In a most particular embodiment, $R^{2b}$ is —O—$CH_3$.

In one embodiment, the compound of the invention is according to any one of Formulae I-IIc, wherein Y is $CR^{2b}$ and $R^{2b}$ is $C_{1-4}$ alkoxy substituted with one or more independently selected halo or $C_{1-4}$ alkoxy. In a particular embodiment, $R^{2b}$ is —O—$CH_3$, —O—$CH_2CH_3$, or —O—$CH(CH_3)_2$, each of which is substituted with one or more independently selected halo or $C_{1-4}$ alkoxy. In another particular embodiment, $R^{2b}$ is $C_{1-4}$ alkoxy substituted with one, two, or three independently selected halo or $C_{1-4}$ alkoxy. In yet another particular embodiment, $R^{2b}$ is $C_{1-4}$ alkoxy substituted with one or more independently selected F, Cl, Br, —O—$CH_3$, —O—$CH_2CH_3$, or —O—$CH(CH_3)_2$. In a more particular embodiment, $R^{2b}$ is —O—$CH_3$, —O—$CH_2CH_3$, or —O—$CH(CH_3)_2$, each of which is substituted with one, two, or three independently selected halo or $C_{1-4}$ alkoxy. In another more particular embodiment, $R^{2b}$ is $C_{1-4}$ alkoxy substituted with one, two, or three independently selected F, Cl, Br, —O—$CH_3$, —O—$CH_2CH_3$, or —O—$CH(CH_3)_2$. In a further more particular embodiment, R²ᵇ is —O—CH₃, substituted with one, two, or three independently selected halo. In another further more particular embodiment, R²ᵇ is —O—CH₂CH₃, substituted with one, two, or three independently selected halo or C₁₋₄ alkoxy. In a most particular embodiment, R²ᵇ is —O—CHF₂ or —O—CH₂CH₂—O—CH₂CH₃.

In one embodiment, the compound of the invention is according to any one of Formulae I-IIc, wherein Y is CR²ᵇ, R²ᵇ is —NR⁶ᵃR⁶ᵇ, and R⁶ᵃ and R⁶ᵇ are independently selected from H and C₁₋₄ alkyl. In a particular embodiment, R⁶ᵃ and R⁶ᵇ are both H. In another particular embodiment, one of R⁶ᵃ and R⁶ᵇ is H, and the other is C₁₋₄ alkyl. In yet another particular embodiment, R⁶ᵃ and R⁶ᵇ are both C₁₋₄ alkyl. In a more particular embodiment, one of R⁶ᵃ and R⁶ᵇ is H, and the other is —CH₃, —CH₂CH₃, or —CH(CH₃)₂. In another more particular embodiment, R⁶ᵃ and R⁶ᵇ are —CH₃, —CH₂CH₃, or —CH(CH₃)₂. In a most particular embodiment, one of R⁶ᵃ and R⁶ᵇ is H, and the other is —CH₃.

In one embodiment, the compound of the invention is according to Formula IIIa, IIIb, or IIIc:

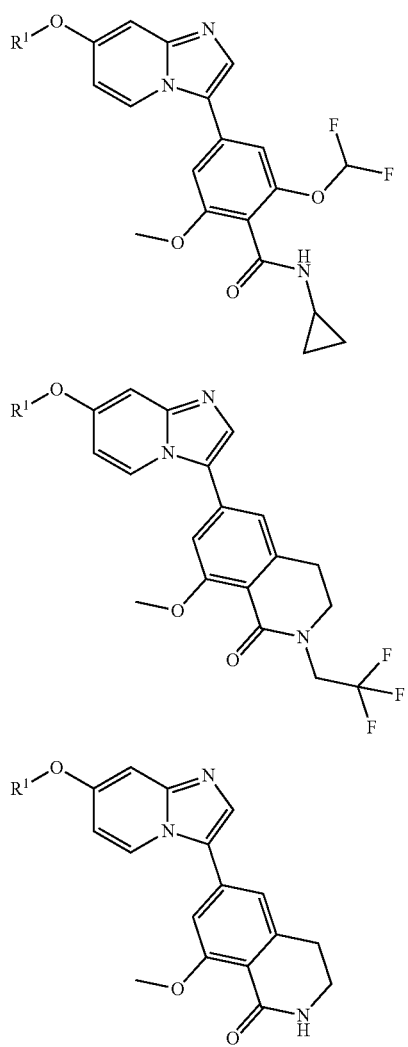

IIIa

IIIb

IIIc wherein R¹ is as described above.

In one embodiment, the compound of the invention is according to any one of Formulae I-IIIc, wherein R¹ is C₁₋₈ alkyl. In a particular embodiment, R¹ is —CH₃, —CH₂CH₃, —CH₂CH₂CH₃, —CH(CH₃)₂, —CH₂CH₂CH₂CH₃, —CH₂CH(CH₃)₂, —CH(CH₃)CH₂CH₃, —C(CH₃)₃, —CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₃)CH(CH₃)₂, —CH₂C(CH₃)₃, —CH₂CH₂CH₂CH₂CH₂CH₃, —CH(CH₃)CH₂CH₂CH₂CH₃, —CH₂CH(CH₃)CH₂CH₂CH₃, —CH₂CH₂CH(CH₃)CH₂CH₃, —CH₂CH₂CH₂CH(CH₃)₂, —CH(CH₂CH₃)CH₂CH₂CH₃, —CH(CH₂CH₃)₂, —CH(CH₃)CH(CH₃) CH₂CH₃, —CH(CH₃)CH₂CH(CH₃)₂, —CH₂CH₂CH₂CH₂CH₂CH₂CH₃, —CH₂CH₂CH₂CH₂CH (CH₃)₂, —CH(CH₃)CH₂CH₂CH(CH₃)₂, —CH₂CH(CH₃) CH₂CH(CH₃)₂, —CH₂CH₂CH(CH₃)CH(CH₃)₂, —CH₂CH₂C(CH₃)₂CH₂CH₃, —CH₂CH(CH₃)CH(CH₃) CH₂CH₃, or —CH(CH₃)CH₂CH(CH₃)CH₂CH₃. In a more particular embodiment, R¹ is —CH₃, —CH₂CH₃, —CH₂CH₂CH₃, —CH(CH₃)₂, —CH₂CH₂CH₂CH₃, —CH₂CH(CH₃)₂, —CH(CH₃)CH₂CH₃, —C(CH₃)₃, —CH₂CH₂CH(CH₃)₂, —CH₂C(CH₃)₃, or —CH₂CH₂CH₂CH(CH₃)₂. In a most particular embodiment, R¹ is —CH₃, —CH₂CH₃, or —CH₂C(CH₃)₃.

In one embodiment, the compound of the invention is according to any one of Formulae I-IIIc, wherein R¹ is C₁₋₈ alkyl substituted with one or more independently selected R⁴ groups. In a particular embodiment, R¹ is —CH₃, —CH₂CH₃, —CH₂CH₂CH₃, —CH(CH₃)₂, —CH₂CH₂CH₂CH₃, —CH₂CH(CH₃)₂, —CH(CH₃) CH₂CH₃, —C(CH₃)₃, —CH₂CH₂CH₂CH₂CH₃, —CH (CH₃)CH₂CH₂CH₃, —CH₂CH(CH₃)CH₂CH₃, —CH₂CH₂CH(CH₃)₂, —CH(CH₂CH₃)₂, —CH(CH₃)CH (CH₃)₂, —CH₂C(CH₃)₃, —CH₂CH₂CH₂CH₂CH₂CH₃, —CH(CH₃)CH₂CH₂CH₂CH₃, —CH₂CH(CH₃) CH₂CH₂CH₃, —CH₂CH₂CH(CH₃)CH₂CH₃, —CH₂CH₂CH₂CH(CH₃)₂, —CH(CH₂CH₃)CH₂CH₂CH₃, —CH(CH₂CH₃)₂, —CH(CH₃)CH(CH₃)CH₂CH₃, —CH(CH₃)CH₂CH(CH₃)₂, —CH₂CH₂CH₂CH₂CH₂CH₂CH₃, —CH₂CH₂CH₂CH₂CH (CH₃)₂, —CH(CH₃)CH₂CH₂CH(CH₃)₂, —CH₂CH(CH₃) CH₂CH(CH₃)₂, —CH₂CH₂CH(CH₃)CH(CH₃)₂, —CH₂CH₂C(CH₃)₂CH₂CH₃, —CH₂CH(CH₃)CH(CH₃) CH₂CH₃, or —CH(CH₃)CH₂CH(CH₃)CH₂CH₃, each of which is substituted with one or more independently selected R⁴ groups. In another particular embodiment, R¹ is C₁₋₈ alkyl substituted with one, two, or three independently selected R⁴ groups. In a more particular embodiment, R¹ is —CH₃, —CH₂CH₃, —CH₂CH₂CH₃, —CH(CH₃)₂, —CH₂CH₂CH₂CH₃, —CH₂CH(CH₃)₂, —CH(CH₃) CH₂CH₃, —C(CH₃)₃, —CH₂CH₂CH(CH₃)₂, —CH₂C (CH₃)₃, or —CH₂CH₂CH₂CH(CH₃)₂, each of which is substituted with one or more independently selected R⁴ groups. In another more particular embodiment, R¹ is —CH₃, —CH₂CH₃, —CH₂CH₂CH₃, —CH(CH₃)₂, —CH₂CH₂CH₂CH₃, —CH₂CH(CH₃)₂, —CH(CH₃) CH₂CH₃, —C(CH₃)₃, —CH₂CH₂CH₂CH₃, —CH (CH₃)CH₂CH₂CH₃, —CH₂CH(CH₃)CH₂CH₃, —CH₂CH₂CH(CH₃)₂, —CH(CH₂CH₃)₂, —CH(CH₃)CH (CH₃)₂, —CH₂C(CH₃)₃, —CH₂CH₂CH₂CH₂CH₂CH₃, —CH(CH₃)CH₂CH₂CH₂CH₃, —CH₂CH(CH₃) CH₂CH₂CH₃, —CH₂CH₂CH(CH₃)CH₂CH₃, —CH₂CH₂CH₂CH(CH₃)₂, —CH(CH₂CH₃)CH₂CH₂CH₃, —CH(CH₂CH₃)₂, —CH(CH₃)CH(CH₃)CH₂CH₃, —CH(CH₃)CH₂CH(CH₃)₂, —CH₂CH₂CH₂CH₂CH₂CH₂CH₃, —CH₂CH₂CH₂CH₂CH (CH₃)₂, —CH(CH₃)CH₂CH₂CH(CH₃)₂, —CH₂CH(CH₃)

CH₂CH(CH₃)₂, —CH₂CH₂CH(CH₃)CH(CH₃)₂, —CH₂CH₂C(CH₃)₂CH₂CH₃, —CH₂CH(CH₃)CH(CH₃)CH₂CH₃, or —CH(CH₃)CH₂CH(CH₃)CH₂CH₃, each of which is substituted with one, two, or three independently selected $R^4$ groups. In yet another more particular embodiment, $R^1$ is $C_{1-8}$ alkyl substituted with one $R^4$ group. In a further more particular embodiment, $R^1$ is —CH₃, —CH₂CH₃, —CH₂CH₂CH₃, —CH(CH₃)₂, —CH₂CH₂CH₂CH₃, —CH₂CH(CH₃)₂, —CH(CH₃)CH₂CH₃, —C(CH₃)₃, —CH₂CH₂CH(CH₃)₂, —CH₂C(CH₃)₃, or —CH₂CH₂CH₂CH(CH₃)₂, each of which is substituted with one, two, or three independently selected $R^4$ groups. In another further more particular embodiment, $R^1$ is —CH₃, —CH₂CH₃, —CH₂CH₂CH₃, —CH(CH₃)₂, —CH₂CH₂CH₂CH₃, —CH₂CH(CH₃)₂, —CH(CH₃)CH₂CH₃, —C(CH₃)₃, —CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₂CH₃)₂, —CH(CH₃)CH(CH₃)₂, —CH₂C(CH₃)₃, —CH₂CH₂CH₂CH₂CH₂CH₃, —CH(CH₃)CH₂CH₂CH₂CH₃, —CH₂CH(CH₃)CH₂CH₂CH₃, —CH₂CH₂CH(CH₃)CH₂CH₃, —CH₂CH₂CH₂CH(CH₃)₂, —CH(CH₂CH₃)CH₂CH₂CH₃, —CH₂CH(CH₂CH₃)₂, —CH(CH₃)CH(CH₃)CH₂CH₃, —CH(CH₂CH₃)CH(CH₃)₂, —CH₂CH₂CH₂CH₂CH₂CH₂CH₃, —CH₂CH₂CH₂CH₂CH(CH₃)₂, —CH(CH₃)CH₂CH₂CH(CH₃)₂, —CH₂CH(CH₃)CH₂CH(CH₃)₂, —CH₂CH₂C(CH₃)₂CH₂CH₃, —CH₂CH(CH₃)CH(CH₃)CH₂CH₃, or —CH(CH₃)CH₂CH(CH₃)CH₂CH₃, each of which is substituted with one $R^4$ group. In a most particular embodiment, $R^1$ is —CH₃, —CH₂CH₃, —CH₂CH₂CH₃, —CH(CH₃)₂, —CH₂CH₂CH₂CH₃, —CH₂CH(CH₃)₂, —CH(CH₃)CH₂CH₃, —C(CH₃)₃, —CH₂CH₂CH(CH₃)₂, —CH₂C(CH₃)₃, or —CH₂CH₂CH₂CH(CH₃)₂, each of which is substituted with one $R^4$ group.

In one embodiment, the compound of the invention is according to any one of Formulae I-IIIc, wherein $R^1$ is phenyl.

In one embodiment, the compound of the invention is according to any one of Formulae I-IIIc, wherein $R^1$ is $C_{3-8}$ monocyclic or bridged polycyclic cycloalkyl. In a particular embodiment, $R^1$ is cyclopropyl, cyclobutyl, cyclopentyl, cyclohexyl, bicyclo[2.1.1]hexanyl, bicyclo[2.2.1]heptanyl, or bicyclo[2.2.2]octanyl. In a more particular embodiment, $R^1$ is cyclobutyl, cyclopentyl, cyclohexyl, or bicyclo[2.2.1]heptanyl.

In one embodiment, the compound of the invention is according to any one of Formulae I-IIIc, wherein $R^1$ is $C_{3-8}$ monocyclic or bridged polycyclic cycloalkyl substituted with one or more independently selected $R^{15}$ groups. In a particular embodiment, $R^1$ is cyclopropyl, cyclobutyl, cyclopentyl, cyclohexyl, bicyclo[2.1.1]hexanyl, bicyclo[2.2.1]heptanyl, or bicyclo[2.2.2]octanyl, each of which is substituted with one or more independently selected R groups. In another particular embodiment, $R^1$ is $C_{3-8}$ monocyclic or bridged polycyclic cycloalkyl substituted with one, two, or three independently selected $R^5$ groups. In a more particular embodiment, $R^1$ is cyclobutyl, cyclopentyl, or cyclohexyl, each of which is substituted with one or more independently selected $R^5$ groups. In another more particular embodiment, $R^1$ is cyclopropyl, cyclobutyl, cyclopentyl, cyclohexyl, bicyclo[2.1.1]hexanyl, bicyclo[2.2.1]heptanyl, or bicyclo[2.2.2]octanyl, each of which is substituted with one, two, or three independently selected $R^{15}$ groups.

In yet another more particular embodiment, $R^1$ is $C_{3-8}$ monocyclic or bridged polycyclic cycloalkyl substituted with one $R^5$ group. In a further more particular embodiment, $R^1$ is cyclobutyl, cyclopentyl, or cyclohexyl, each of which is substituted with one, two, or three independently selected $R^5$ groups. In another further more particular embodiment, $R^1$ is cyclopropyl, cyclobutyl, cyclopentyl, cyclohexyl, bicyclo[2.1.1]hexanyl, bicyclo[2.2.1]heptanyl, or bicyclo[2.2.2]octanyl, each of which is substituted with one $R^5$ group. In a most particular embodiment, $R^1$ is cyclobutyl, cyclopentyl, or cyclohexyl, each of which is substituted with one $R^5$ group.

In one embodiment, the compound of the invention is according to any one of Formulae I-IIIc, wherein $R^1$ is 4-8 membered monocyclic, spirocyclic, or bridged polycyclic heterocycloalkyl comprising one, two, or three heteroatoms independently selected from N, O, and S. In a particular embodiment, $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, 6-thiaspiro[3.4]octanyl, 7-azabicyclo[2.2.1]heptanyl, 2-azabicyclo[2.2.1]heptanyl, 7-oxabicyclo[2.2.1]heptanyl, 2-oxabicyclo[2.2.1]heptanyl, 7-thiabicyclo[2.2.1]heptanyl, 2-thiabicyclo[2.2.1]heptanyl, quinuclidinyl, 1,4-diazabicyclo[2.2.2]octanyl, 2-azabicyclo[2.2.2]octanyl, 2-oxabicyclo[2.2.2]octanyl, 2-thiabicyclo[2.2.2]octanyl, 8-azabicyclo[3.2.1]octanyl, 3,8-diazabicyclo[3.2.1]octanyl, 3-oxa-8-azabicyclo[3.2.1]octanyl, 3-thia-8-azabicyclo[3.2.1]octanyl, 8-oxabicyclo[3.2.1]octanyl, or 8-thiabicyclo[3.2.1]octanyl. In a more particular embodiment, $R^1$ is oxetanyl, tetrahydrofuranyl, tetrahydropyranyl, 2-oxaspiro[3.3]heptanyl, or 8-azabicyclo[3.2.1]octanyl.

In one embodiment, the compound of the invention is according to any one of Formulae I-IIIc, wherein $R^1$ is 4-8 membered monocyclic or spirocyclic heterocycloalkyl comprising one, two, or three heteroatoms independently selected from N, O, and S. In a particular embodiment, $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, or 6-thiaspiro[3.4]octanyl. In a more particular embodiment, $R^1$ is oxetanyl, tetrahydrofuranyl, tetrahydropyranyl, or 2-oxaspiro[3.3]heptanyl.

In one embodiment, the compound of the invention is according to any one of Formulae I-IIIc, wherein $R^1$ is 4-8 membered monocyclic, spirocyclic, or bridged polycyclic heterocycloalkyl comprising one, two, or three heteroatoms independently selected from N, O, and S, which heterocycloalkyl is substituted with one or more independently selected $C_{1-4}$ alkyl optionally substituted with one or more independently selected —CN or —C(=O)—$C_{1-4}$ alkoxy. In a particular embodiment, $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, 6-thiaspiro[3.4]octanyl, 7-azabicyclo[2.2.1]heptanyl, 2-azabicyclo[2.2.1]heptanyl, 7-oxabicyclo[2.2.1]heptanyl, 2-oxabicyclo[2.2.1]heptanyl, 7-thiabicyclo[2.2.1]heptanyl, 2-thiabicyclo[2.2.1]heptanyl, quinuclidinyl, 1,4-diazabicyclo[2.2.2]octanyl, 2-azabicyclo[2.2.2]octanyl, 2-oxabicyclo[2.2.2]octanyl, 2-thiabicyclo[2.2.2]octanyl, 8-azabicyclo[3.2.1]octanyl, 3,8-diazabicyclo[3.2.1]octanyl, 3-oxa-8-azabicyclo[3.2.1]octanyl, 3-thia-8-azabicyclo[3.2.1]octanyl, 8-oxabicyclo[3.2.1]octanyl, or 8-thiabicyclo[3.2.1]octanyl, each of which is substituted with one, two, or three independently selected $C_{1-4}$ alkyl optionally substituted with one or more independently selected —CN or —C(=O)—$C_{1-4}$ alkoxy. In a more particular embodiment, $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, 6-thiaspiro[3.4]octanyl, 7-azabicyclo[2.2.1]heptanyl, 2-azabicyclo[2.2.1]heptanyl, 7-oxabicyclo[2.2.1]heptanyl, 2-oxabicyclo[2.2.1]heptanyl, 7-thiabicyclo[2.2.1]heptanyl, 2-thiabicyclo[2.2.1]heptanyl, quinuclidinyl, 1,4-diazabicyclo[2.2.2]octanyl, 2-azabicyclo[2.2.2]octanyl, 2-oxabicyclo[2.2.2]octanyl, 2-thiabicyclo[2.2.2]octanyl, 8-azabicyclo[3.2.1]octanyl, 3,8-diazabicyclo[3.2.1]octanyl, 3-oxa-8-azabicyclo[3.2.1]octanyl, 3-thia-8-azabicyclo[3.2.1]octanyl, 8-oxabicyclo[3.2.1]octanyl, or 8-thiabicyclo[3.2.1]octanyl, each of which is substituted with one, two, or three independently selected —CH$_3$, —CH$_2$CH$_3$, or —CH(CH$_3$)$_2$, each of which is optionally substituted with one, two, or three independently selected —CN, —C(=O)—O—CH$_3$, —C(=O)—O—CH$_2$CH$_3$, or —C(=O)—O—CH(CH$_3$)$_2$. In another more particular embodiment, $R^1$ is azetidinyl, pyrrolidinyl, piperidinyl, or 8-azabicyclo[3.2.1]octanyl, each of which is substituted with one, two, or three independently selected $C_{1-4}$ alkyl optionally substituted with one or more independently selected —CN or —C(=O)—$C_{1-4}$ alkoxy. In a further more particular embodiment, $R^1$ is azetidinyl, pyrrolidinyl, piperidinyl, or 8-azabicyclo[3.2.1]octanyl, each of which is substituted with one, two, or three independently selected —CH$_3$, —CH$_2$CH$_3$, or —CH(CH$_3$)$_2$, each of which is optionally substituted with one, two, or three independently selected —CN, —C(=O)—O—CH$_3$, —C(=O)—O—CH$_2$CH$_3$, or —C(=O)—O—CH(CH$_3$)$_2$. In another further more particular embodiment, $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, 6-thiaspiro[3.4]octanyl, 7-azabicyclo[2.2.1]heptanyl, 2-azabicyclo[2.2.1]heptanyl, 7-oxabicyclo[2.2.1]heptanyl, 2-oxabicyclo[2.2.1]heptanyl, 7-thiabicyclo[2.2.1]heptanyl, 2-thiabicyclo[2.2.1]heptanyl, quinuclidinyl, 1,4-diazabicyclo[2.2.2]octanyl, 2-azabicyclo[2.2.2]octanyl, 2-oxabicyclo[2.2.2]octanyl, 2-thiabicyclo[2.2.2]octanyl, 8-azabicyclo[3.2.1]octanyl, 3,8-diazabicyclo[3.2.1]octanyl, 3-oxa-8-azabicyclo[3.2.1]octanyl, 3-thia-8-azabicyclo[3.2.1]octanyl, 8-oxabicyclo[3.2.1]octanyl, or 8-thiabicyclo[3.2.1]octanyl, each of which is substituted with one, two, or three independently selected —CH$_3$, —CH$_2$—CH$_2$—CN, or —CH$_2$—C(=O)—O—CH$_2$CH$_3$. In a most particular embodiment, $R^1$ is azetidinyl, pyrrolidinyl, piperidinyl, or 8-azabicyclo[3.2.1]octanyl, each of which is substituted with one —CH$_3$, —CH$_2$—CH$_2$—CN, or —CH$_2$—C(=O)—O—CH$_2$CH$_3$.

In one embodiment, the compound of the invention is according to any one of Formulae I-IIIc, wherein $R^1$ is 4-8 membered monocyclic or spirocyclic heterocycloalkyl comprising one, two, or three heteroatoms independently selected from N, O, and S, which heterocycloalkyl is substituted with one or more independently selected $C_{1-4}$ alkyl. In a particular embodiment, $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, or 6-thiaspiro[3.4]octanyl, each of which is substituted with one, two, or three independently selected $C_{1-4}$ alkyl. In a more particular embodiment, $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, or 6-thiaspiro[3.4]octanyl, each of which is substituted with one, two, or three independently selected —CH$_3$, —CH$_2$CH$_3$, or —CH(CH$_3$)$_2$. In another more particular embodiment, $R^1$ is azetidinyl, pyrrolidinyl, or piperidinyl, each of which is substituted with one, two, or three independently selected $C_{1-4}$ alkyl. In a further more particular embodiment, $R^1$ is azetidinyl, pyrrolidinyl, or piperidinyl, each of which is substituted with one, two, or three independently selected —CH$_3$, —CH$_2$CH$_3$, or —CH(CH$_3$)$_2$. In another further more particular embodiment, $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro

[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, or 6-thiaspiro[3.4]octanyl, each of which is substituted with one, two, or three —CH$_3$. In a most particular embodiment, R$^1$ is azetidinyl, pyrrolidinyl, or piperidinyl, each of which is substituted with one —CH$_3$.

In one embodiment, the compound of the invention is according to any one of Formulae I-IIIc, wherein R$^1$ is 5-6 membered monocyclic heteroaryl comprising one, two, or three heteroatoms independently selected from N, O, and S. In a particular embodiment, R$^1$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl. In a more particular embodiment, R$^1$ is pyridinyl, pyrazinyl, pyridazinyl, or pyrimidinyl. In a most particular embodiment, R$^1$ is pyridinyl.

In one embodiment, the compound of the invention is according to any one of Formulae I-IIIc, wherein R$^5$ is halo or —CN. In a particular embodiment, R$^5$ is F, Cl, Br, or —CN. In a more particular embodiment, R$^5$ is F or —CN.

In one embodiment, the compound of the invention is according to any one of Formulae I-IIIc, wherein R is —NR$^{13a}$R$^{13b}$, and each R$^{13a}$ and R$^{13b}$ are as previously described. In a particular embodiment, R$^{13a}$ and R$^{13b}$ are both H. In another particular embodiment, one of R$^{13a}$ and R$^{13b}$ is H, and the other is C$_{1-4}$ alkyl. In yet another particular embodiment, R$^{13a}$ and R$^{13b}$ are both C$_{1-4}$ alkyl. In a more particular embodiment, one of R$^{13a}$ and R$^{13b}$ is H, and the other is —CH$_3$, —CH$_2$CH$_3$, or —CH(CH$_3$)$_2$. In another more particular embodiment, each R$^{13a}$ and R$^{13b}$ is independently —CH$_3$, —CH$_2$CH$_3$, or —CH(CH$_3$)$_2$. In a most particular embodiment, R is —NH—CH$_3$.

In one embodiment, the compound of the invention is according to Formula IVa, IVb, IVc, IVd, IVe, or IVf:

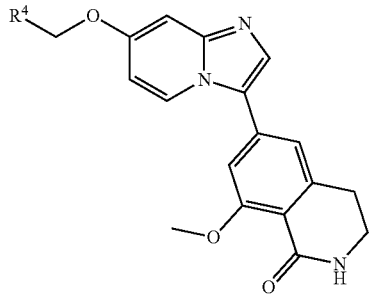

IVa

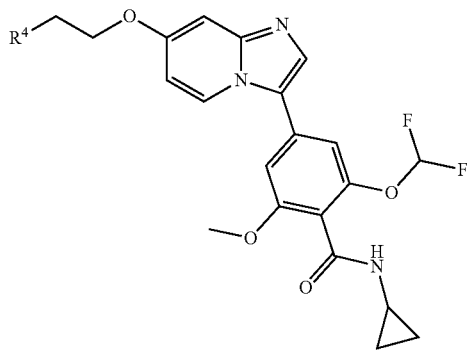

IVb

IVc

IVd

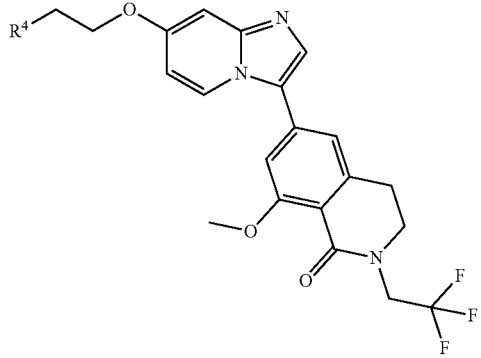

IVe

IVf

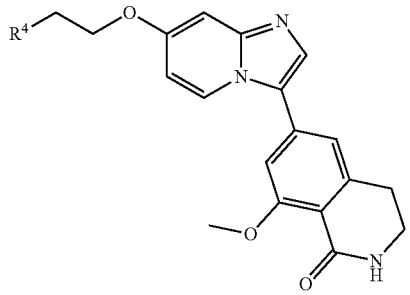

wherein R$^4$ is as described above.

In one embodiment, the compound of the invention is according to any one of Formulae I-IVf, wherein R$^4$ is halo, —OH, —CN, phenyl, or —C(═O)OH. In a particular embodiment, R$^4$ is F, Cl, Br, —OH, —CN, phenyl, or —C(═O)OH. In a more particular embodiment, R$^4$ is F, —OH, —CN, phenyl, or —C(═O)OH.

In one embodiment, the compound of the invention is according to any one of Formulae I-IVf, wherein R$^4$ is halo, —OH, —CN, or phenyl. In a particular embodiment, R$^4$ is F, Cl, Br, —OH, —CN, or phenyl. In a more particular embodiment, R$^4$ is F, —OH, —CN, or phenyl.

In one embodiment, the compound of the invention is according to any one of Formulae I-IVf, wherein $R^4$ is —O—C(=O)—$C_{1-4}$ alkyl. In a particular embodiment, $R^4$ is —O—C(=O)—$CH_3$, —O—C(=O)—$CH_2CH_3$, or —O—C(=O)—$CH(CH_3)_2$. In a more particular embodiment, $R^4$ is —O—C(=O)—$CH_3$.

In one embodiment, the compound of the invention is according to any one of Formulae I-IVf, wherein $R^4$ is —O—S(=O)$_2$—$C_{1-4}$ alkyl. In a particular embodiment, $R^4$ is —O—S(=O)$_2$—$CH_3$, —O—S(=O)$_2$—$CH_2CH_3$, or —O—S(=O)$_2$—$CH(CH_3)_2$. In a more particular embodiment, $R^4$ is —O—S(=O)$_2$—$CH_3$.

In one embodiment, the compound of the invention is according to any one of Formulae I-IVf, wherein $R^4$ is $C_{1-4}$ alkoxy. In a particular embodiment, $R^4$ is —O—$CH_3$, —O—$CH_2CH_3$, or —O—$CH(CH_3)_2$. In a more particular embodiment, $R^4$ is —O—$CH_3$ or —O—$CH_2CH_3$.

In one embodiment, the compound of the invention is according to any one of Formulae I-IVf, wherein $R^4$ is $C_{1-4}$ alkoxy substituted with one or more independently selected 4-8 membered monocyclic heterocycloalkyl comprising one, two, or three heteroatoms independently selected from N, O, and S, which heterocycloalkyl is optionally substituted with one or more independently selected $C_{1-4}$ alkyl. In a particular embodiment, $R^4$ is —O—$CH_3$, —O—$CH_2CH_3$, or —O—$CH(CH_3)_2$, each of which is substituted with one or more independently selected 4-8 membered monocyclic heterocycloalkyl comprising one, two, or three heteroatoms independently selected from N, O, and S, which heterocycloalkyl is optionally substituted with one or more independently selected $C_{1-4}$ alkyl. In another particular embodiment, $R^4$ is $C_{1-4}$ alkoxy substituted with one 4-8 membered monocyclic heterocycloalkyl comprising one, two, or three heteroatoms independently selected from N, O, and S, which heterocycloalkyl is optionally substituted with one or more independently selected $C_{1-4}$ alkyl. In yet another particular embodiment, $R^4$ is $C_{1-4}$ alkoxy substituted with one or more independently selected azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, or piperazinyl, each of which is optionally substituted with one, two, or three —$CH_3$, —$CH_2CH_3$, or —$CH(CH_3)_2$. In a more particular embodiment, $R^4$ is —O—$CH_2CH_3$ substituted with one or more independently selected 4-8 membered monocyclic heterocycloalkyl comprising one, two, or three heteroatoms independently selected from N, O, and S, which heterocycloalkyl is optionally substituted with one or more independently selected $C_{1-4}$ alkyl. In another more particular embodiment, $R^4$ is —O—$CH_3$, —O—$CH_2CH_3$, or —O—$CH(CH_3)_2$, each of which is substituted with one 4-8 membered monocyclic heterocycloalkyl comprising one, two, or three heteroatoms independently selected from N, O, and S, which heterocycloalkyl is optionally substituted with one or more independently selected $C_{1-4}$ alkyl. In yet another more particular embodiment, $R^4$ is —O—$CH_3$, —O—$CH_2CH_3$, or —O—$CH(CH_3)_2$, each of which is substituted with one or more independently selected azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, or piperazinyl, each of which is optionally substituted with one, two, or three —$CH_3$, —$CH_2CH_3$, or —$CH(CH_3)_2$. In yet another more particular embodiment, $R^4$ is $C_{1-4}$ alkoxy substituted with one or more independently selected piperidinyl, morpholinyl, or piperazinyl, each of which is optionally substituted with one —$CH(CH_3)_2$. In yet another more particular embodiment, $R^4$ is —O—$CH_2CH_3$ substituted with one 4-8 membered monocyclic heterocycloalkyl comprising one, two, or three heteroatoms independently selected from N, O, and S, which heterocycloalkyl is optionally substituted with one or more independently selected $C_{1-4}$ alkyl. In another further more particular embodiment, $R^4$ is —O—$CH_2CH_3$ substituted with one or more independently selected azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, or piperazinyl, each of which is optionally substituted with one, two, or three —$CH_3$, —$CH_2CH_3$, or —$CH(CH_3)_2$. In yet another further more particular embodiment, $R^4$ is $C_{1-4}$ alkoxy substituted with one piperidinyl, morpholinyl, or piperazinyl, each of which is optionally substituted with one —$CH(CH_3)_2$. In yet another further more particular embodiment, $R^4$ is —O—$CH_3$, —O—$CH_2CH_3$, or —O—$CH(CH_3)_2$, each of which is substituted with one azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, or piperazinyl, each of which is optionally substituted with one, two, or three —$CH_3$, —$CH_2CH_3$, or —$CH(CH_3)_2$. In yet another further more particular embodiment, $R^4$ is —O—$CH_3$, —O—$CH_2CH_3$, or —O—$CH(CH_3)_2$, each of which is substituted with one or more independently selected piperidinyl, morpholinyl, or piperazinyl, each of which is optionally substituted with one —$CH(CH_3)_2$. In an even further more particular embodiment, $R^4$ is —O—$CH_2CH_3$ substituted with one azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, or piperazinyl, each of which is optionally substituted with one, two, or three —$CH_3$, —$CH_2CH_3$, or —$CH(CH_3)_2$. In another even further more particular embodiment, $R^4$ is —O—$CH_2CH_3$ substituted with one or more independently selected piperidinyl, morpholinyl, or piperazinyl, each of which is optionally substituted with one —$CH(CH_3)_2$. In yet another even further more particular embodiment, $R^4$ is —O—$CH_3$, —O—$CH_2CH_3$, or —O—$CH(CH_3)_2$, each of which is substituted with one piperidinyl, morpholinyl, or piperazinyl, each of which is optionally substituted with one —$CH(CH_3)_2$. In a most particular embodiment, $R^4$ is —O—$CH_2CH_3$ substituted with one piperidinyl, morpholinyl, or piperazinyl, each of which is optionally substituted with one —$CH(CH_3)_2$.

In one embodiment, the compound of the invention is according to any one of Formulae I-IVf, wherein $R^4$ is $C_{1-4}$ alkoxy substituted with one or more independently selected —OH, $C_{1-4}$ alkoxy, or —$NR^{7a}R^{7b}$, wherein each $R^{7a}$ and $R^{7b}$ is independently selected from H and $C_{1-4}$ alkyl. In a particular embodiment, $R^4$ is —O—$CH_3$, —O—$CH_2CH_3$, or —O—$CH(CH_3)_2$, each of which is substituted with one or more independently selected —OH, $C_{1-4}$ alkoxy, or —$NR^{7a}R^{7b}$, wherein each $R^{7a}$ and $R^{7b}$ is independently selected from H and $C_{1-4}$ alkyl. In another particular embodiment, $R^4$ is $C_{1-4}$ alkoxy substituted with one, two or three independently selected —OH, $C_{1-4}$ alkoxy, or —$NR^{7a}R^{7b}$, wherein each $R^{7a}$ and $R^{7b}$ is independently selected from H and $C_{1-4}$ alkyl. In yet another particular embodiment, $R^4$ is $C_{1-4}$ alkoxy substituted with one or more independently selected —OH, —O—CH$_3$, —O—CH$_2$CH$_3$, —O—CH(CH$_3$)$_2$, —NH$_2$, —NH—CH$_3$, —NH—CH$_2$CH$_3$, —NH—CH(CH$_3$)$_2$, —N(CH$_3$)$_2$, —N(CH$_3$)—CH$_2$CH$_3$, —N(CH$_3$)—CH(CH$_3$)$_2$, —N(CH$_2$CH$_3$)$_2$, —N(CH$_2$CH$_3$)—CH(CH$_3$)$_2$, or —N(CH(CH$_3$)$_2$)$_2$. In a more particular embodiment, $R^4$ is —O—CH$_2$CH$_3$ substituted with one or more independently selected —OH, $C_{1-4}$ alkoxy, or —NR$^{7a}$R$^{7b}$, wherein each $R^{7a}$ and $R^{7b}$ is independently selected from H and $C_{1-4}$ alkyl. In another more particular embodiment, $R^4$ is —O—CH$_3$, —O—CH$_2$CH$_3$, or —O—CH(CH$_3$)$_2$, each of which is substituted with one, two or three independently selected —OH, $C_{1-4}$ alkoxy, or —NR$^{7a}$R$^{7b}$, wherein each $R^{7a}$ and $R^{7b}$ is independently selected from H and $C_{1-4}$ alkyl. In yet another more particular embodiment, $R^4$ is —O—CH$_3$, —O—CH$_2$CH$_3$, or —O—CH(CH$_3$)$_2$, each of which is substituted with one or more independently selected —OH, —O—CH$_3$, —O—CH$_2$CH$_3$, —O—CH(CH$_3$)$_2$, —NH$_2$, —NH—CH$_3$, —NH—CH$_2$CH$_3$, —NH—CH(CH$_3$)$_2$, —N(CH$_3$)$_2$, —N(CH$_3$)—CH$_2$CH$_3$, —N(CH$_3$)—CH(CH$_3$)$_2$, —N(CH$_2$CH$_3$)$_2$, —N(CH$_2$CH$_3$)—CH(CH$_3$)$_2$, or —N(CH(CH$_3$)$_2$)$_2$. In yet another more particular embodiment, $R^4$ is $C_{1-4}$ alkoxy substituted with one —OH, $C_{1-4}$ alkoxy, or —NR$^{7a}$R$^{7b}$, wherein each $R^{7a}$ and $R^{7b}$ is independently selected from H and $C_{1-4}$ alkyl. In yet another more particular embodiment, $R^4$ is $C_{1-4}$ alkoxy substituted with one, two or three independently selected —OH, —O—CH$_3$, —O—CH$_2$CH$_3$, —O—CH(CH$_3$)$_2$, —NH$_2$, —NH—CH$_3$, —NH—CH$_2$CH$_3$, —NH—CH(CH$_3$)$_2$, —N(CH$_3$)$_2$, —N(CH$_3$)—CH$_2$CH$_3$, —N(CH$_3$)—CH(CH$_3$)$_2$, —N(CH$_2$CH$_3$)$_2$, —N(CH$_2$CH$_3$)—CH(CH$_3$)$_2$, or —N(CH(CH$_3$)$_2$)$_2$. In yet another more particular embodiment, $R^4$ is $C_{1-4}$ alkoxy substituted with one or more independently selected —OH, —O—CH$_3$, or —N(CH$_3$)$_2$. In a further more particular embodiment, $R^4$ is —O—CH$_2$CH$_3$ substituted with one, two, or three independently selected —OH, $C_{1-4}$ alkoxy, or —NR$^{7a}$R$^{7b}$, wherein each $R^{7a}$ and $R^{7b}$ is independently selected from H and $C_{1-4}$ alkyl. In another further more particular embodiment, $R^4$ is —O—CH$_2$CH$_3$ substituted with one or more independently selected —OH, —O—CH$_3$, —O—CH$_2$CH$_3$, —O—CH(CH$_3$)$_2$, —NH$_2$, —NH—CH$_3$, —NH—CH$_2$CH$_3$, —NH—CH(CH$_3$)$_2$, —N(CH$_3$)$_2$, —N(CH$_3$)—CH$_2$CH$_3$, —N(CH$_3$)—CH(CH$_3$)$_2$, —N(CH$_2$CH$_3$)$_2$, —N(CH$_2$CH$_3$)—CH(CH$_3$)$_2$, or —N(CH(CH$_3$)$_2$)$_2$. In another further more particular embodiment, $R^4$ is —O—CH$_3$, —O—CH$_2$CH$_3$, or —O—CH(CH$_3$)$_2$, each of which is substituted with one —OH, $C_{1-4}$ alkoxy, or —NR$^{7a}$R$^{7b}$, wherein each $R^{7a}$ and $R^{7b}$ is independently selected from H and $C_{1-4}$ alkyl. In another further more particular embodiment, $R^4$ is —O—CH$_3$, —O—CH$_2$CH$_3$, or —O—CH(CH$_3$)$_2$, each of which is substituted with one, two, or three independently selected —OH, —O—CH$_3$, —O—CH$_2$CH$_3$, —O—CH(CH$_3$)$_2$, —NH$_2$, —NH—CH$_3$, —NH—CH$_2$CH$_3$, —NH—CH(CH$_3$)$_2$, —N(CH$_3$)$_2$, —N(CH$_3$)—CH$_2$CH$_3$, —N(CH$_3$)—CH(CH$_3$)$_2$, —N(CH$_2$CH$_3$)$_2$, —N(CH$_2$CH$_3$)—CH(CH$_3$)$_2$, or —N(CH(CH$_3$)$_2$)$_2$. In another further more particular embodiment, $R^4$ is —O—CH$_3$, —O—CH$_2$CH$_3$, or —O—CH(CH$_3$)$_2$, each of which is substituted with one or more —OH, —O—CH$_3$, or —N(CH$_3$)$_2$. In another further more particular embodiment, $R^4$ is $C_{1-4}$ alkoxy substituted with one —OH, —O—CH$_3$, —O—CH$_2$CH$_3$, —O—CH(CH$_3$)$_2$, —NH$_2$, —NH—CH$_3$, —NH—CH$_2$CH$_3$, —NH—CH(CH$_3$)$_2$, —N(CH$_3$)$_2$, —N(CH$_3$)—CH$_2$CH$_3$, —N(CH$_3$)—CH(CH$_3$)$_2$, —N(CH$_2$CH$_3$)$_2$, —N(CH$_2$CH$_3$)—CH(CH$_3$)$_2$, or —N(CH(CH$_3$)$_2$)$_2$. In another further more particular embodiment, $R^4$ is $C_{1-4}$ alkoxy substituted with one, two, or three —OH, —O—CH$_3$, or —N(CH$_3$)$_2$. In an even further more particular embodiment, $R^4$ is —O—CH$_2$CH$_3$ substituted with one —OH, $C_{1-4}$ alkoxy, or —NR$^{7a}$R$^{7b}$, wherein each $R^{7a}$ and $R^{7b}$ is independently selected from H and $C_{1-4}$ alkyl. In another even further more particular embodiment, $R^4$ is —O—CH$_2$CH$_3$ substituted with one, two, or three —OH, —O—CH$_3$, —O—CH$_2$CH$_3$, —O—CH(CH$_3$)$_2$, —NH$_2$, —NH—CH$_3$, —NH—CH$_2$CH$_3$, —NH—CH(CH$_3$)$_2$, —N(CH$_3$)$_2$, —N(CH$_3$)—CH$_2$CH$_3$, —N(CH$_3$)—CH(CH$_3$)$_2$, —N(CH$_2$CH$_3$)$_2$, —N(CH$_2$CH$_3$)—CH(CH$_3$)$_2$, or —N(CH(CH$_3$)$_2$)$_2$. In yet another even further more particular embodiment, $R^4$ is —O—CH$_2$CH$_3$ substituted with one or more —OH, —O—CH$_3$, or —N(CH$_3$)$_2$. In yet another even further more particular embodiment, $R^4$ is —O—CH$_3$, —O—CH$_2$CH$_3$, or —O—CH(CH$_3$)$_2$, each of which is substituted with one —OH, —O—CH$_3$, —O—CH$_2$CH$_3$, —O—CH(CH$_3$)$_2$, —NH$_2$, —NH—CH$_3$, —NH—CH$_2$CH$_3$, —NH—CH(CH$_3$)$_2$, —N(CH$_3$)$_2$, —N(CH$_3$)—CH$_2$CH$_3$, —N(CH$_3$)—CH(CH$_3$)$_2$, —N(CH$_2$CH$_3$)$_2$, —N(CH$_2$CH$_3$)—CH(CH$_3$)$_2$, or —N(CH(CH$_3$)$_2$)$_2$. In yet another even further more particular embodiment, $R^4$ is —O—CH$_3$, —O—CH$_2$CH$_3$, or —O—CH(CH$_3$)$_2$, each of which is substituted with one, two, or three —OH, —O—CH$_3$, or —N(CH$_3$)$_2$. In a furthest more particular embodiment, $R^4$ is —O—CH$_2$CH$_3$ substituted with one —OH, —O—CH$_3$, —O—CH$_2$CH$_3$, —O—CH(CH$_3$)$_2$, —NH$_2$, —NH—CH$_3$, —NH—CH$_2$CH$_3$, —NH—CH(CH$_3$)$_2$, —N(CH$_3$)$_2$, —N(CH$_3$)—CH$_2$CH$_3$, —N(CH$_3$)—CH(CH$_3$)$_2$, —N(CH$_2$CH$_3$)$_2$, —N(CH$_2$CH$_3$)—CH(CH$_3$)$_2$, or —N(CH(CH$_3$)$_2$)$_2$. In another furthest more particular embodiment, $R^4$ is —O—CH$_2$CH$_3$ substituted with one, two, or three —OH, —O—CH$_3$, or —N(CH$_3$)$_2$. In yet another furthest more particular embodiment, $R^4$ is —O—CH$_3$, —O—CH$_2$CH$_3$, or —O—CH(CH$_3$)$_2$, each of which is substituted with one —OH, —O—CH$_3$, or —N(CH$_3$)$_2$. In a most particular embodiment, $R^4$ is —O—CH$_2$CH$_3$ substituted with one —OH, —O—CH$_3$, or —N(CH$_3$)$_2$.

In one embodiment, the compound of the invention is according to any one of Formulae I-IVf, wherein $R^4$ is $C_{3-7}$ cycloalkyl. In a particular embodiment, $R^4$ is cyclopropyl, cyclobutyl, cyclopentyl, or cyclohexyl.

In one embodiment, the compound of the invention is according to any one of Formulae I-IVf, wherein $R^4$ is $C_{3-7}$ cycloalkyl substituted with one or more independently selected halo, —C(=O)—$C_{1-4}$ alkoxy, —NR$^{8a}$R$^{8b}$, or $C_{1-4}$ alkyl optionally substituted with one or more independently selected —NR$^{9a}$R$^{9b}$. In a particular embodiment, $R^4$ is cyclopropyl, cyclobutyl, cyclopentyl, or cyclohexyl, each of which is substituted with one or more independently selected halo, —C(=O)—$C_{1-4}$ alkoxy, —NR$^{8a}$R$^{8b}$, or $C_{1-4}$ alkyl optionally substituted with one or more independently selected —NR$^{9a}$R$^{9b}$. In another particular embodiment, $R^4$ is $C_{3-7}$ cycloalkyl substituted with one, two, or three independently selected halo, —C(=O)—$C_{1-4}$ alkoxy, —NR$^{8a}$R$^{8b}$, or $C_{1-4}$ alkyl optionally substituted with one or more independently selected —NR$^{9a}$R$^{9b}$. In yet another particular embodiment, $R^4$ is $C_{3-7}$ cycloalkyl substituted with one or more independently selected F, Cl, Br, —C(=O)—O—CH$_3$, —C(=O)—O—CH$_2$CH$_3$, —C(=O)—O—CH(CH$_3$)$_2$, —NR$^{8a}$R$^{8b}$, —CH$_3$ optionally substituted with one —NR$^{9a}$R$^{9b}$, —CH$_2$CH$_3$ optionally substituted with one —NR$^{9a}$R$^{9b}$, or —CH(CH$_3$)$_2$ optionally substituted with one —NR$^{9a}$R$^{9b}$. In a more particular embodiment, $R^4$ is cyclopropyl, cyclobutyl, cyclopentyl, or cyclohexyl, each of which is substituted with one, two, or three independently selected halo, —C(=O)—$C_{1-4}$ alkoxy, —NR$^{8a}$R$^{8b}$, or C$_{1-4}$ alkyl optionally substituted with one or more independently selected —NR$^{9a}$R$^{9b}$. In another more particular embodiment, R$^4$ is cyclopropyl, cyclobutyl, cyclopentyl, or cyclohexyl, each of which is substituted with one or more independently selected F, Cl, Br, —C(=O)—O—CH$_3$, —C(=O)—O—CH$_2$CH$_3$, —C(=O)—O—CH(CH$_3$)$_2$, —NR$^{8a}$R$^{8b}$, —CH$_3$ optionally substituted with one —NR$^{9a}$R$^{9b}$, —CH$_2$CH$_3$ optionally substituted with one —NR$^{9a}$R$^{9b}$, or —CH(CH$_3$)$_2$ optionally substituted with one —NR$^{9a}$R$^{9b}$. In yet another more particular embodiment, R$^4$ is C$_{3-7}$ cycloalkyl substituted with one, two, or three independently selected F, Cl, Br, —C(=O)—O—CH$_3$, —C(=O)—O—CH$_2$CH$_3$, —C(=O)—O—CH(CH$_3$)$_2$, —NR$^{8a}$R$^{8b}$, —CH$_3$ optionally substituted with one —NR$^{9a}$R$^{9b}$, —CH$_2$CH$_3$ optionally substituted with one —NR$^{9a}$R$^{9b}$, or —CH(CH$_3$)$_2$ optionally substituted with one —NR$^{9a}$R$^{9b}$. In yet another more particular embodiment, R$^4$ is C$_{3-7}$ cycloalkyl substituted with one or more independently selected F, —C(=O)—O—CH$_3$, —NR$^{8a}$R$^{8b}$, —CH$_3$, or —CH$_2$—NR$^{9a}$R$^{9b}$. In a further more particular embodiment, R$^4$ is cyclopropyl, cyclobutyl, cyclopentyl, or cyclohexyl, each of which is substituted with one, two, or three independently selected F, Cl, Br, —C(=O)—O—CH$_3$, —C(=O)—O—CH$_2$CH$_3$, —C(=O)—O—CH(CH$_3$)$_2$, —NR$^{8a}$R$^{8b}$, —CH$_3$ optionally substituted with one —NR$^{9a}$R$^{9b}$, —CH$_2$CH$_3$ optionally substituted with one —NR$^{9a}$R$^{9b}$, or —CH(CH$_3$)$_2$ optionally substituted with one —NR$^{9a}$R$^{9b}$. In yet another further more particular embodiment, R$^4$ is cyclopropyl, cyclobutyl, cyclopentyl, or cyclohexyl, each of which is substituted with one or more independently selected F, —C(=O)—O—CH$_3$, —NR$^{8a}$R$^{8b}$, —CH$_3$, or —CH$_2$—NR$^{9a}$R$^{9b}$. In yet another further more particular embodiment, R$^4$ is C$_{3-7}$ cycloalkyl substituted with one, two, or three independently selected F, —C(=O)—O—CH$_3$, —NR$^{8a}$R$^{8b}$, —CH$_3$, or —CH$_2$—NR$^{9a}$R$^{9b}$. In an even further more particular embodiment, R$^4$ is cyclopropyl, cyclobutyl, cyclopentyl, or cyclohexyl, each of which is substituted with one, two, or three independently selected F, —C(=O)—O—CH$_3$, —NR$^{8a}$R$^{8b}$, —CH$_3$, or —CH$_2$—NR$^{9a}$R$^{9b}$. In a most particular embodiment, R$^4$ is cyclopropyl, cyclobutyl, cyclopentyl, or cyclohexyl, each of which is substituted with one, two or three F. In another most particular embodiment, R$^4$ is cyclopropyl, cyclobutyl, cyclopentyl, or cyclohexyl, each of which is substituted with one —C(=O)—O—CH$_3$, —NR$^{8a}$R$^{8b}$, —CH$_3$, or —CH$_2$—NR$^{9a}$R$^{9b}$.

In one embodiment, the compound of the invention is according to any one of Formulae I-IVf, wherein R$^4$ is C$_{3-7}$ cycloalkyl substituted with —NR$^{8a}$R$^{8b}$, and R$^{8a}$ and R$^{8b}$ are as previously described. In a particular embodiment, R$^{8a}$ and R$^{8b}$ are both H. In another particular embodiment, one of R$^{8a}$ and R$^{8b}$ is H, and the other is C$_{1-4}$ alkyl. In yet another particular embodiment, R$^{8a}$ and R$^{8b}$ are both C$_{1-4}$ alkyl. In a more particular embodiment, one of R$^{8a}$ and R$^{8b}$ is H, and the other is —CH$_3$, —CH$_2$CH$_3$, or —CH(CH$_3$)$_2$. In another more particular embodiment, R$^{8a}$ and R$^{8b}$ are independently —CH$_3$, —CH$_2$CH$_3$, or —CH(CH$_3$)$_2$.

In one embodiment, the compound of the invention is according to any one of Formulae I-IVf, wherein R$^4$ is C$_{3-7}$ cycloalkyl substituted with one or more independently selected C$_{1-4}$ alkyl substituted with one or more independently selected —NR$^{9a}$R$^{9b}$, and R$^{9a}$ and R$^{9b}$ are as previously described. In a particular embodiment, R$^{9a}$ and R$^{9b}$ are both H. In another particular embodiment, one of R$^{9a}$ and R$^{9b}$ is H, and the other is C$_{1-4}$ alkyl. In yet another particular embodiment, R$^{9a}$ and R$^{9b}$ are both C$_{1-4}$ alkyl. In a more particular embodiment, one of R$^{9a}$ and R$^{9b}$ is H, and the other is —CH$_3$, —CH$_2$CH$_3$, or —CH(CH$_3$)$_2$. In another more particular embodiment, R$^{9a}$ and R$^{9b}$ are independently —CH$_3$, —CH$_2$CH$_3$, or —CH(CH$_3$)$_2$.

In one embodiment, the compound of the invention is according to any one of Formulae I-IVf, wherein R$^4$ is 5-6 membered monocyclic heterocycloalkyl comprising one or two N atoms fused to a 5-6 membered monocyclic heteroaryl comprising one, two, or three heteroatoms independently selected from N, O, and S. In a particular embodiment, R$^4$ is pyrrolidinyl, piperidinyl, or piperazinyl, each of which is fused to a 5-6 membered monocyclic heteroaryl comprising one, two, or three heteroatoms independently selected from N, O, and S. In another particular embodiment, R$^4$ is 5-6 membered monocyclic heterocycloalkyl comprising one or two N atoms fused to a pyrrole, furane, thiophene, imidazole, furazane, oxazole, oxadiazole, isoxazole, thiazole, isothiazole, pyrazole, triazole, pyridine, pyrazine, pyridazine, or pyrimidine. In a more particular embodiment, R$^4$ is pyrrolidinyl, piperidinyl, or piperazinyl, each of which is fused to a pyrrole, furane, thiophene, imidazole, furazane, oxazole, oxadiazole, isoxazole, thiazole, isothiazole, pyrazole, triazole, pyridine, pyrazine, pyridazine, or pyrimidine. In a most particular embodiment, R$^4$ is 1H,2H,3H,4H-pyrrolo[1,2-a]pyrazinyl, 5H,6H,7H,8H-imidazo[1,2-a]pyrazinyl, 5H,6H,7H,8H-[1,2,4]triazolo[1,5-a]pyrazinyl, 5,6,7,8-tetrahydro-1,6-naphthyridinyl, or 5H,6H,7H,8H-pyrido[4,3-d]pyrimidinyl.

In one embodiment, the compound of the invention is according to any one of Formulae I-IVf, wherein R$^4$ is 5-6 membered monocyclic heterocycloalkyl comprising one or two N atoms fused to a 5-6 membered monocyclic heteroaryl comprising one, two, or three heteroatoms independently selected from N, O, and S, which heteroaryl is substituted with one or more independently selected C$_{1-4}$ alkyl. In a particular embodiment, R$^4$ is pyrrolidinyl, piperidinyl, or piperazinyl, each of which is fused to a 5-6 membered monocyclic heteroaryl comprising one, two, or three heteroatoms independently selected from N, O, and S, which heteroaryl is substituted with one or more independently selected C$_{1-4}$ alkyl. In another particular embodiment, R$^4$ is 5-6 membered monocyclic heterocycloalkyl comprising one or two N atoms fused to a pyrrole, furane, thiophene, imidazole, furazane, oxazole, oxadiazole, isoxazole, thiazole, isothiazole, pyrazole, triazole, pyridine, pyrazine, pyridazine, or pyrimidine, each of which is substituted with one, two, or three independently selected —CH$_3$, —CH$_2$CH$_3$, or —CH(CH$_3$)$_2$. In a more particular embodiment, R$^4$ is pyrrolidinyl, piperidinyl, or piperazinyl, each of which is fused to a pyrrole, furane, thiophene, imidazole, furazane, oxazole, oxadiazole, isoxazole, thiazole, isothiazole, pyrazole, triazole, pyridine, pyrazine, pyridazine, or pyrimidine, each of which is substituted with one, two, or three independently selected —CH$_3$, —CH$_2$CH$_3$, or —CH(CH$_3$)$_2$. In a most particular embodiment, R$^4$ is piperidinyl fused to an imidazole substituted with one —CH$_3$.

In one embodiment, the compound of the invention is according to any one of Formulae I-IVf, wherein R$^4$ is 5-6 membered monocyclic heteroaryl comprising one, two, or three heteroatoms independently selected from N, O, and S. In a particular embodiment, R$^4$ is pyrrolyl, imidazolyl, pyrazolyl, triazolyl, oxazolyl, thiazolyl, isoxazolyl, isothiazolyl, oxadiazolyl, thiadiazolyl, pyridinyl, pyridazinyl, pyrimidinyl, or pyrazinyl. In a more particular embodiment, R$^4$ is thiazolyl, oxazolyl, pyridinyl, pyridazinyl, or pyrimidinyl.

In one embodiment, the compound of the invention is according to any one of Formulae I-IVf, wherein R$^4$ is 5-6 membered monocyclic heteroaryl comprising one, two, or three heteroatoms independently selected from N, O, and S, which heteroaryl is substituted with one or more independently selected $C_{1-4}$ alkyl or $C_{3-7}$ cycloalkyl. In a particular embodiment, $R^4$ is pyrrolyl, imidazolyl, pyrazolyl, triazolyl, oxazolyl, thiazolyl, isoxazolyl, isothiazolyl, oxadiazolyl, thiadiazolyl, pyridinyl, pyridazinyl, pyrimidinyl, or pyrazinyl, each of which is substituted with one or more independently selected $C_{1-4}$ alkyl or $C_{3-7}$ cycloalkyl. In another particular embodiment, $R^4$ is 5-6 membered monocyclic heteroaryl comprising one, two, or three heteroatoms independently selected from N, O, and S, which heteroaryl is substituted with one, two, or three independently selected $C_{1-4}$ alkyl or $C_{3-7}$ cycloalkyl. In yet another particular embodiment, $R^4$ is 5-6 membered monocyclic heteroaryl comprising one, two, or three heteroatoms independently selected from N, O, and S, which heteroaryl is substituted with one or more independently selected —$CH_3$, —$CH_2CH_3$, —$CH(CH_3)_2$, cyclopropyl, cyclobutyl, cyclopentyl, or cyclohexyl. In a more particular embodiment, $R^4$ is imidazolyl, pyrazolyl, triazolyl, thiazolyl, or oxadiazolyl, each of which is substituted with one or more independently selected $C_{1-4}$ alkyl or $C_{3-7}$ cycloalkyl. In another more particular embodiment, $R^4$ is pyrrolyl, imidazolyl, pyrazolyl, triazolyl, oxazolyl, thiazolyl, isoxazolyl, isothiazolyl, oxadiazolyl, thiadiazolyl, pyridinyl, pyridazinyl, pyrimidinyl, or pyrazinyl, each of which is substituted with one, two, or three independently selected $C_{1-4}$ alkyl or $C_{3-7}$ cycloalkyl. In an even more particular embodiment, $R^4$ is imidazolyl, pyrazolyl, triazolyl, thiazolyl, or oxadiazolyl, each of which is substituted with one, two, or three independently selected $C_{1-4}$ alkyl or $C_{3-7}$ cycloalkyl. In another even more particular embodiment, $R^4$ is pyrrolyl, imidazolyl, pyrazolyl, triazolyl, oxazolyl, thiazolyl, isoxazolyl, isothiazolyl, oxadiazolyl, thiadiazolyl, pyridinyl, pyridazinyl, pyrimidinyl, or pyrazinyl, each of which is substituted with one, two, or three independently selected —$CH_3$, —$CH_2CH_3$, —$CH(CH_3)_2$, cyclopropyl, cyclobutyl, cyclopentyl, or cyclohexyl. In a most particular embodiment, $R^4$ is imidazolyl, pyrazolyl, triazolyl, thiazolyl, or oxadiazolyl, each of which is substituted with one or two independently selected —$CH_3$, —$CH_2CH_3$, —$CH(CH_3)_2$, or cyclopropyl.

In one embodiment, the compound of the invention is according to any one of Formulae I-IVf, wherein $R^4$ is 4-11 membered monocyclic, spirocyclic, or bridged polycyclic heterocycloalkyl comprising one, two, or three heteroatoms independently selected from N, O, and S. In a particular embodiment, $R^4$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, oxazolidinyl, thiazolidinyl, morpholinyl, thiomorpholinyl, dioxanyl, piperazinyl, 1-oxaspiro[3.3]heptanyl, 2-oxaspiro[3.3]heptanyl, 1-thiaspiro[3.3]heptanyl, 2-thiaspiro[3.3]heptanyl, 1-azaspiro[3.3]heptanyl, 1-oxa-6-azaspiro[3.3]heptanyl, 1-thia-6-azaspiro[3.3]heptanyl, 2-azaspiro[3.3]heptanyl, 2-oxa-6-azaspiro[3.3]heptanyl, 2-thia-6-azaspiro[3.3]heptanyl, 6-oxa-1-azaspiro[3.3]heptanyl, 6-thia-1-azaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-thiaspiro[3.4]octanyl, 2-thiaspiro[3.4]octanyl, 5-thiaspiro[3.4]octanyl, 6-thiaspiro[3.4]octanyl, 1-azaspiro[3.4]octanyl, 1-oxa-6-azaspiro[3.4]octanyl, 1-thia-6-azaspiro[3.4]octanyl, 2-azaspiro[3.4]octanyl, 2-oxa-5-azaspiro[3.4]octanyl, 2-oxa-6-azaspiro[3.4]octanyl, 2-thia-5-azaspiro[3.4]octanyl, 2-thia-6-azaspiro[3.4]octanyl, 5-azaspiro[3.4]octanyl, 6-azaspiro[3.4]octanyl, 1-oxa-6-azaspiro[3.5]nonanyl, 1-thia-6-azaspiro[3.5]nonanyl, 2,8-dioxa-5-azaspiro[3.5] nonanyl, 2-oxa-6-azaspiro[3.5]nonanyl, 2-oxa-8-thia-5-azaspiro[3.5]nonanyl, 2-thia-6-azaspiro[3.5]nonanyl, 5-oxa-8-azaspiro[3.5]nonanyl, 5-thia-8-azaspiro[3.5]nonanyl, 8-oxa-5-azaspiro[3.5]nonanyl, 8-thia-5-azaspiro[3.5] nonanyl, 1-azaspiro[4.5]decanyl, 1-oxa-7-azaspiro[4.5]decanyl, 1-oxa-8-azaspiro[4.5]decanyl, 1-thia-7-azaspiro[4.5]decanyl, 1-thia-8-azaspiro[4.5]decanyl, 2-azaspiro[4.5] decanyl, 2-oxa-6-azaspiro[4.5]decanyl, 2-oxa-7-azaspiro[4.5]decanyl, 2-oxa-8-azaspiro[4.5]decanyl, 2-thia-6-azaspiro[4.5]decanyl, 2-thia-7-azaspiro[4.5]decanyl, 2-thia-8-azaspiro[4.5]decanyl, 6-azaspiro[4.5]decanyl, 6-oxa-2-azaspiro[4.5]decanyl, 6-oxa-9-azaspiro[4.5]decanyl, 6-thia-2-azaspiro[4.5]decanyl, 6-thia-9-azaspiro[4.5]decanyl, 7-azaspiro[4.5]decanyl, 7-oxa-1-azaspiro[4.5]decanyl, 7-oxa-2-azaspiro[4.5]decanyl, 7-thia-1-azaspiro[4.5]decanyl, 7-thia-2-azaspiro[4.5]decanyl, 8-azaspiro[4.5]decanyl, 8-oxa-1-azaspiro[4.5]decanyl, 8-oxa-2-azaspiro[4.5]decanyl, 8-thia-1-azaspiro[4.5]decanyl, 8-thia-2-azaspiro[4.5] decanyl, 9-oxa-6-azaspiro[4.5]decanyl, 9-thia-6-azaspiro [4.5]decanyl, 2-oxabicyclo[2.1.1]hexanyl, 5-oxabicyclo [2.1.1]hexanyl, 2-azabicyclo[2.1.1]hexanyl, 5-azabicyclo [2.1.1]hexanyl, 2-thiabicyclo[2.1.1]hexanyl, 5-thiabicyclo [2.1.1]hexanyl, 2-oxabicyclo[2.2.1]heptanyl, 7-oxabicyclo [2.2.1]heptanyl, 2-oxabicyclo[3.1.1]heptanyl, 3-oxabicyclo [3.1.1]heptanyl, 6-oxabicyclo[3.1.1]heptanyl, 2-azabicyclo [2.2.1]heptanyl, 7-azabicyclo[2.2.1]heptanyl, 2-azabicyclo [3.1.1]heptanyl, 3-azabicyclo[3.1.1]heptanyl, 6-azabicyclo [3.1.1]heptanyl, 2-thiabicyclo[2.2.1]heptanyl, 7-thiabicyclo [2.2.1]heptanyl, 2-thiabicyclo[3.1.1]heptanyl, 3-thiabicyclo [3.1.1]heptanyl, 6-thiabicyclo[3.1.1]heptanyl, 2-oxabicyclo [3.2.1]octanyl, 3-oxabicyclo[3.2.1]octanyl, 6-oxabicyclo [3.2.1]octanyl, 8-oxabicyclo[3.2.1]octanyl, 2-azabicyclo [3.2.1]octanyl, 3-azabicyclo[3.2.1]octanyl, 6-azabicyclo [3.2.1]octanyl, 8-azabicyclo[3.2.1]octanyl, 2-thiabicyclo [3.2.1]octanyl, 3-thiabicyclo[3.2.1]octanyl, 6-thiabicyclo [3.2.1]octanyl, 8-thiabicyclo[3.2.1]octanyl, 2-oxa-5-azabicyclo[2.2.1]heptanyl, 3-oxa-6-azabicyclo[3.1.1] heptanyl, 6-oxa-3-azabicyclo[3.1.1]heptanyl, 2-oxa-6-azabicyclo[3.2.1]octanyl, 3-oxa-6-azabicyclo[3.2.1]octanyl, 3-oxa-8-azabicyclo[3.2.1]octanyl, 8-oxa-2-azabicyclo [3.2.1]octanyl, 8-oxa-3-azabicyclo[3.2.1]octanyl, 8-oxa-6-azabicyclo[3.2.1]octanyl, 2-thia-5-azabicyclo[2.2.1]heptanyl, 3-thia-6-azabicyclo[3.1.1]heptanyl, 6-thia-3-azabicyclo [3.1.1]heptanyl, 2-thia-6-azabicyclo[3.2.1]octanyl, 3-thia-6-azabicyclo[3.2.1]octanyl, 3-thia-8-azabicyclo[3.2.1]octanyl, 8-thia-2-azabicyclo[3.2.1]octanyl, 8-thia-3-azabicyclo [3.2.1]octanyl, or 8-thia-6-azabicyclo[3.2.1]octanyl. In a more particular embodiment, $R^4$ is azetidinyl, oxetanyl, pyrrolidinyl, tetrahydrofuranyl, piperidinyl, tetrahydropyranyl, morpholinyl, dioxanyl, 1-azaspiro[3.3]heptanyl, 2-azaspiro[3.3]heptanyl, 2-oxa-6-azaspiro[3.3]heptanyl, 6-oxa-1-azaspiro[3.3]heptanyl, 2-oxa-6-azaspiro[3.4]octanyl, 2,8-dioxa-5-azaspiro[3.5]nonanyl, 2-oxa-6-azaspiro [3.5]nonanyl, 8-oxa-5-azaspiro[3.5]nonanyl, 2-oxa-5-azabicyclo[2.2.1]heptanyl, 3-oxa-8-azabicyclo[3.2.1]octanyl, or 8-oxa-3-azabicyclo[3.2.1]octanyl.

In one embodiment, the compound of the invention is according to any one of Formulae I-IVf, wherein $R^4$ is 4-8 membered monocyclic or bridged polycyclic heterocycloalkyl comprising one, two, or three heteroatoms independently selected from N, O, and S. In a particular embodiment, $R^4$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, oxazolidinyl, thiazolidinyl, morpholinyl, thiomorpholinyl, dioxanyl, piperazinyl, 2-oxabicyclo[2.1.1]hexanyl, 5-oxabicyclo[2.1.1]hexanyl, 2-azabicyclo[2.1.1]hexanyl, 5-azabicyclo[2.1.1]hexanyl, 2-thiabicyclo[2.1.1]hexanyl, 5-thiabicyclo[2.1.1]hexanyl, 2-oxabicyclo[2.2.1]heptanyl, 7-oxabicyclo[2.2.1]heptanyl, 2-oxabicyclo[3.1.1]heptanyl, 3-oxabicyclo[3.1.1]heptanyl, 6-oxabicyclo[3.1.1]heptanyl, 2-oxabicyclo[2.2.1]heptanyl, 7-azabicyclo[2.2.1]heptanyl, 2-azabicyclo[3.1.1]heptanyl, 3-azabicyclo[3.1.1]heptanyl, 6-azabicyclo[3.1.1]heptanyl, 2-thiabicyclo[2.2.1]heptanyl, 7-thiabicyclo[2.2.1]heptanyl, 2-thiabicyclo[3.1.1]heptanyl, 3-thiabicyclo[3.1.1]heptanyl, 6-thiabicyclo[3.1.1]heptanyl, 2-oxabicyclo[3.2.1]octanyl, 3-oxabicyclo[3.2.1]octanyl, 6-oxabicyclo[3.2.1]octanyl, 8-oxabicyclo[3.2.1]octanyl, 2-azabicyclo[3.2.1]octanyl, 3-azabicyclo[3.2.1]octanyl, 6-azabicyclo[3.2.1]octanyl, 8-azabicyclo[3.2.1]octanyl, 2-thiabicyclo[3.2.1]octanyl, 3-thiabicyclo[3.2.1]octanyl, 6-thiabicyclo[3.2.1]octanyl, 8-thiabicyclo[3.2.1]octanyl, 2-oxa-5-azabicyclo[2.2.1]heptanyl, 3-oxa-6-azabicyclo[3.1.1]heptanyl, 6-oxa-3-azabicyclo[3.1.1]heptanyl, 2-oxa-6-azabicyclo[3.2.1]octanyl, 3-oxa-6-azabicyclo[3.2.1]octanyl, 3-oxa-8-azabicyclo[3.2.1]octanyl, 8-oxa-2-azabicyclo[3.2.1]octanyl, 8-oxa-3-azabicyclo[3.2.1]octanyl, 8-oxa-6-azabicyclo[3.2.1]octanyl, 2-thia-5-azabicyclo[2.2.1]heptanyl, 3-thia-6-azabicyclo[3.1.1]heptanyl, 6-thia-3-azabicyclo[3.1.1]heptanyl, 2-thia-6-azabicyclo[3.2.1]octanyl, 3-thia-6-azabicyclo[3.2.1]octanyl, 3-thia-8-azabicyclo[3.2.1]octanyl, 8-thia-2-azabicyclo[3.2.1]octanyl, 8-thia-3-azabicyclo[3.2.1]octanyl, or 8-thia-6-azabicyclo[3.2.1]octanyl. In a more particular embodiment, $R^4$ is azetidinyl, oxetanyl, pyrrolidinyl, tetrahydrofuranyl, piperidinyl, tetrahydropyranyl, morpholinyl, dioxanyl, 2-oxa-5-azabicyclo[2.2.1]heptanyl, 3-oxa-8-azabicyclo[3.2.1]octanyl, or 8-oxa-3-azabicyclo[3.2.1]octanyl.

In one embodiment, the compound of the invention is according to any one of Formulae I-IVf, wherein $R^4$ is 4-11 membered monocyclic, spirocyclic, or bridged polycyclic heterocycloalkyl comprising one, two, or three heteroatoms independently selected from N, O, and S, which heterocycloalkyl is substituted with one or more independently selected $R^{10}$. In a particular embodiment, $R^4$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, oxazolidinyl, thiazolidinyl, morpholinyl, thiomorpholinyl, dioxanyl, piperazinyl, 1-azaspiro[3.3]heptanyl, 1-oxa-6-azaspiro[3.3]heptanyl, 1-thia-6-azaspiro[3.3]heptanyl, 2-azaspiro[3.3]heptanyl, 2-oxa-6-azaspiro[3.3]heptanyl, 2-thia-6-azaspiro[3.3]heptanyl, 6-oxa-1-azaspiro[3.3]heptanyl, 6-thia-1-azaspiro[3.3]heptanyl, 1-azaspiro[3.4]octanyl, 1-oxa-6-azaspiro[3.4]octanyl, 1-thia-6-azaspiro[3.4]octanyl, 2-azaspiro[3.4]octanyl, 2-oxa-5-azaspiro[3.4]octanyl, 2-oxa-6-azaspiro[3.4]octanyl, 2-thia-5-azaspiro[3.4]octanyl, 2-thia-6-azaspiro[3.4]octanyl, 5-azaspiro[3.4]octanyl, 6-azaspiro[3.4]octanyl, 1-oxa-6-azaspiro[3.5]nonanyl, 1-thia-6-azaspiro[3.5]nonanyl, 2,8-dioxa-5-azaspiro[3.5]nonanyl, 2-oxa-6-azaspiro[3.5]nonanyl, 2-oxa-8-thia-5-azaspiro[3.5]nonanyl, 2-thia-6-azaspiro[3.5]nonanyl, 5-oxa-8-azaspiro[3.5]nonanyl, 5-thia-8-azaspiro[3.5]nonanyl, 8-oxa-5-azaspiro[3.5]nonanyl, 8-thia-5-azaspiro[3.5]nonanyl, 1-azaspiro[4.5]decanyl, 1-oxa-3,8-diazaspiro[4.5]decanyl, 1-oxa-7-azaspiro[4.5]decanyl, 1-oxa-8-azaspiro[4.5]decanyl, 1-thia-3,8-diazaspiro[4.5]decanyl, 1-thia-7-azaspiro[4.5]decanyl, 1-thia-8-azaspiro[4.5]decanyl, 2-azaspiro[4.5]decanyl, 2-oxa-6-azaspiro[4.5]decanyl, 2-oxa-7-azaspiro[4.5]decanyl, 2-oxa-8-azaspiro[4.5]decanyl, 2-thia-6-azaspiro[4.5]decanyl, 2-thia-7-azaspiro[4.5]decanyl, 2-thia-8-azaspiro[4.5]decanyl, 6-azaspiro[4.5]decanyl, 6-oxa-2-azaspiro[4.5]decanyl, 6-oxa-9-azaspiro[4.5]decanyl, 6-thia-2-azaspiro[4.5]decanyl, 6-thia-9-azaspiro[4.5]decanyl, 7-azaspiro[4.5]decanyl, 7-oxa-1-azaspiro[4.5]decanyl, 7-oxa-2-azaspiro[4.5]decanyl, 7-thia-1-azaspiro[4.5]decanyl, 7-thia-2-azaspiro[4.5]decanyl, 8-azaspiro[4.5]decanyl, 8-oxa-1-azaspiro[4.5]decanyl, 8-oxa-2-azaspiro[4.5]decanyl, 8-thia-1-azaspiro[4.5]decanyl, 8-thia-2-azaspiro[4.5]decanyl, 9-oxa-6-azaspiro[4.5]decanyl, 9-thia-6-azaspiro[4.5]decanyl, 2-oxabicyclo[2.1.1]hexanyl, 5-oxabicyclo[2.1.1]hexanyl, 2-azabicyclo[2.1.1]hexanyl, 5-azabicyclo[2.1.1]hexanyl, 2-thiabicyclo[2.1.1]hexanyl, 5-thiabicyclo[2.1.1]hexanyl, 2-oxabicyclo[2.2.1]heptanyl, 7-oxabicyclo[2.2.1]heptanyl, 2-oxabicyclo[3.1.1]heptanyl, 3-oxabicyclo[3.1.1]heptanyl, 6-oxabicyclo[3.1.1]heptanyl, 2-oxabicyclo[2.2.1]heptanyl, 7-azabicyclo[2.2.1]heptanyl, 2-azabicyclo[3.1.1]heptanyl, 3-azabicyclo[3.1.1]heptanyl, 6-azabicyclo[3.1.1]heptanyl, 2-thiabicyclo[2.2.1]heptanyl, 7-thiabicyclo[2.2.1]heptanyl, 2-thiabicyclo[3.1.1]heptanyl, 3-thiabicyclo[3.1.1]heptanyl, 6-thiabicyclo[3.1.1]heptanyl, 2-oxabicyclo[3.2.1]octanyl, 3-oxabicyclo[3.2.1]octanyl, 6-oxabicyclo[3.2.1]octanyl, 8-oxabicyclo[3.2.1]octanyl, 2-azabicyclo[3.2.1]octanyl, 3-azabicyclo[3.2.1]octanyl, 6-azabicyclo[3.2.1]octanyl, 8-azabicyclo[3.2.1]octanyl, 2-thiabicyclo[3.2.1]octanyl, 3-thiabicyclo[3.2.1]octanyl, 6-thiabicyclo[3.2.1]octanyl, 8-thiabicyclo[3.2.1]octanyl, 2-oxa-5-azabicyclo[2.2.1]heptanyl, 3-oxa-6-azabicyclo[3.1.1]heptanyl, 6-oxa-3-azabicyclo[3.1.1]heptanyl, 2-oxa-6-azabicyclo[3.2.1]octanyl, 3-oxa-6-azabicyclo[3.2.1]octanyl, 3-oxa-8-azabicyclo[3.2.1]octanyl, 8-oxa-2-azabicyclo[3.2.1]octanyl, 8-oxa-3-azabicyclo[3.2.1]octanyl, 8-oxa-6-azabicyclo[3.2.1]octanyl, 2-thia-5-azabicyclo[2.2.1]heptanyl, 3-thia-6-azabicyclo[3.1.1]heptanyl, 6-thia-3-azabicyclo[3.1.1]heptanyl, 2-thia-6-azabicyclo[3.2.1]octanyl, 3-thia-6-azabicyclo[3.2.1]octanyl, 3-thia-8-azabicyclo[3.2.1]octanyl, 8-thia-2-azabicyclo[3.2.1]octanyl, 8-thia-3-azabicyclo[3.2.1]octanyl, or 8-thia-6-azabicyclo[3.2.1]octanyl, each of which is substituted with one or more independently selected $R^{10}$. In another particular embodiment, $R^4$ is 4-11 membered monocyclic or bridged polycyclic heterocycloalkyl comprising one, two, or three heteroatoms independently selected from N, O, and S, which heterocycloalkyl is substituted with one, two, or three independently selected $R^{10}$. In a more particular embodiment, $R^4$ is azetidinyl, oxetanyl, pyrrolidinyl, tetrahydrofuranyl, piperidinyl, oxazolidinyl, morpholinyl, thiomorpholinyl, piperazinyl, 1-thia-6-azaspiro[3.3]heptanyl, 2-azaspiro[3.3]heptanyl, or 1-oxa-3,8-diazaspiro[4.5]decanyl, each of which is substituted with one or more independently selected $R^{10}$. In another more particular embodiment, $R^4$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, oxazolidinyl, thiazolidinyl, morpholinyl, thiomorpholinyl, dioxanyl, piperazinyl, 1-azaspiro[3.3]heptanyl, 1-oxa-6-azaspiro[3.3]heptanyl, 1-thia-6-azaspiro[3.3]heptanyl, 2-azaspiro[3.3]heptanyl, 2-oxa-6-azaspiro[3.3]heptanyl, 2-thia-6-azaspiro[3.3]heptanyl, 6-oxa-1-azaspiro[3.3]heptanyl, 6-thia-1-azaspiro[3.3]heptanyl, 1-azaspiro[3.4]octanyl, 1-oxa-6-azaspiro[3.4]octanyl, 1-thia-6-azaspiro[3.4]octanyl, 2-azaspiro[3.4]octanyl, 2-oxa-5-azaspiro[3.4]octanyl, 2-oxa-6-azaspiro[3.4]octanyl, 2-thia-5-azaspiro[3.4]octanyl, 2-thia-6-azaspiro[3.4]octanyl, 5-azaspiro[3.4]octanyl, 6-azaspiro[3.4]octanyl, 1-oxa-6-azaspiro[3.5]nonanyl, 1-thia-6-azaspiro[3.5]nonanyl, 2,8-dioxa-5-azaspiro[3.5]nonanyl, 2-oxa-6-azaspiro[3.5]nonanyl, 2-oxa-8-thia-5-azaspiro[3.5]nonanyl, 2-thia-6-azaspiro[3.5]nonanyl, 5-oxa-8-azaspiro[3.5]nonanyl, 5-thia-8-azaspiro[3.5]nonanyl, 8-oxa-5-azaspiro[3.5]nonanyl, 8-thia-5-azaspiro[3.5]nonanyl, 1-azaspiro[4.5]decanyl, 1-oxa-3,8-diazaspiro[4.5]decanyl, 1-oxa-7-azaspiro[4.5]decanyl, 1-oxa-8-azaspiro[4.5]decanyl, 1-thia-3,8-diazaspiro

[4.5]decanyl, 1-thia-7-azaspiro[4.5]decanyl, 1-thia-8-azaspiro[4.5]decanyl, 2-azaspiro[4.5]decanyl, 2-oxa-6-azaspiro[4.5]decanyl, 2-oxa-7-azaspiro[4.5]decanyl, 2-oxa-8-azaspiro[4.5]decanyl, 2-thia-6-azaspiro[4.5]decanyl, 2-thia-7-azaspiro[4.5]decanyl, 2-thia-8-azaspiro[4.5]decanyl, 6-azaspiro[4.5]decanyl, 6-oxa-2-azaspiro[4.5]decanyl, 6-oxa-9-azaspiro[4.5]decanyl, 6-thia-2-azaspiro[4.5]decanyl, 6-thia-9-azaspiro[4.5]decanyl, 7-azaspiro[4.5]decanyl, 7-oxa-1-azaspiro[4.5]decanyl, 7-oxa-2-azaspiro[4.5]decanyl, 7-thia-1-azaspiro[4.5]decanyl, 7-thia-2-azaspiro[4.5]decanyl, 8-azaspiro[4.5]decanyl, 8-oxa-1-azaspiro[4.5]decanyl, 8-oxa-2-azaspiro[4.5]decanyl, 8-thia-1-azaspiro[4.5]decanyl, 8-thia-2-azaspiro[4.5]decanyl, 9-oxa-6-azaspiro[4.5]decanyl, 9-thia-6-azaspiro[4.5]decanyl, 2-oxabicyclo[2.1.1]hexanyl, 5-oxabicyclo[2.1.1]hexanyl, 2-azabicyclo[2.1.1]hexanyl, 5-azabicyclo[2.1.1]hexanyl, 2-thiabicyclo[2.1.1]hexanyl, 5-thiabicyclo[2.1.1]hexanyl, 2-oxabicyclo[2.2.1]heptanyl, 7-oxabicyclo[2.2.1]heptanyl, 2-oxabicyclo[3.1.1]heptanyl, 3-oxabicyclo[3.1.1]heptanyl, 6-oxabicyclo[3.1.1]heptanyl, 2-azabicyclo[2.2.1]heptanyl, 7-azabicyclo[2.2.1]heptanyl, 2-azabicyclo[3.1.1]heptanyl, 3-azabicyclo[3.1.1]heptanyl, 6-azabicyclo[3.1.1]heptanyl, 2-thiabicyclo[2.2.1]heptanyl, 7-thiabicyclo[2.2.1]heptanyl, 2-thiabicyclo[3.1.1]heptanyl, 3-thiabicyclo[3.1.1]heptanyl, 6-thiabicyclo[3.1.1]heptanyl, 2-oxabicyclo[3.2.1]octanyl, 3-oxabicyclo[3.2.1]octanyl, 6-oxabicyclo[3.2.1]octanyl, 8-oxabicyclo[3.2.1]octanyl, 2-azabicyclo[3.2.1]octanyl, 3-azabicyclo[3.2.1]octanyl, 6-azabicyclo[3.2.1]octanyl, 8-azabicyclo[3.2.1]octanyl, 2-thiabicyclo[3.2.1]octanyl, 3-thiabicyclo[3.2.1]octanyl, 6-thiabicyclo[3.2.1]octanyl, 8-thiabicyclo[3.2.1]octanyl, 2-oxa-5-azabicyclo[2.2.1]heptanyl, 3-oxa-6-azabicyclo[3.1.1]heptanyl, 6-oxa-3-azabicyclo[3.1.1]heptanyl, 2-oxa-6-azabicyclo[3.2.1]octanyl, 3-oxa-6-azabicyclo[3.2.1]octanyl, 3-oxa-8-azabicyclo[3.2.1]octanyl, 8-oxa-2-azabicyclo[3.2.1]octanyl, 8-oxa-3-azabicyclo[3.2.1]octanyl, 8-oxa-6-azabicyclo[3.2.1]octanyl, 2-thia-5-azabicyclo[2.2.1]heptanyl, 3-thia-6-azabicyclo[3.1.1]heptanyl, 6-thia-3-azabicyclo[3.1.1]heptanyl, 2-thia-6-azabicyclo[3.2.1]octanyl, 3-thia-6-azabicyclo[3.2.1]octanyl, 3-thia-8-azabicyclo[3.2.1]octanyl, 8-thia-2-azabicyclo[3.2.1]octanyl, 8-thia-3-azabicyclo[3.2.1]octanyl, or 8-thia-6-azabicyclo[3.2.1]octanyl, each of which is substituted with one, two, or three independently selected $R^{10}$. In a most particular embodiment, $R^4$ is azetidinyl, oxetanyl, pyrrolidinyl, tetrahydrofuranyl, piperidinyl, oxazolidinyl, morpholinyl, thiomorpholinyl, piperazinyl, 1-thia-6-azaspiro[3.3]heptanyl, 2-azaspiro[3.3]heptanyl, or 1-oxa-3,8-diazaspiro[4.5]decanyl, each of which is substituted with one, two, or three independently selected $R^{10}$.

In one embodiment, the compound of the invention is according to any one of Formulae I-IVf, wherein $R^4$ is 4-8 membered monocyclic or bridged polycyclic heterocycloalkyl comprising one, two, or three heteroatoms independently selected from N, O, and S, which heterocycloalkyl is substituted with one or more independently selected $R^{10}$. In a particular embodiment, $R^4$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, oxazolidinyl, thiazolidinyl, morpholinyl, thiomorpholinyl, dioxanyl, piperazinyl, 2-oxabicyclo[2.1.1]hexanyl, 5-oxabicyclo[2.1.1]hexanyl, 2-azabicyclo[2.1.1]hexanyl, 5-azabicyclo[2.1.1]hexanyl, 2-thiabicyclo[2.1.1]hexanyl, 5-thiabicyclo[2.1.1]hexanyl, 2-oxabicyclo[2.2.1]heptanyl, 7-oxabicyclo[2.2.1]heptanyl, 2-oxabicyclo[3.1.1]heptanyl, 3-oxabicyclo[3.1.1]heptanyl, 6-oxabicyclo[3.1.1]heptanyl, 2-azabicyclo[2.2.1]heptanyl, 7-azabicyclo[2.2.1]heptanyl, 2-azabicyclo[3.1.1]heptanyl, 3-azabicyclo[3.1.1]heptanyl, 6-azabicyclo[3.1.1]heptanyl, 2-thiabicyclo[2.2.1]heptanyl, 7-thiabicyclo[2.2.1]heptanyl, 2-thiabicyclo[3.1.1]heptanyl, 3-thiabicyclo[3.1.1]heptanyl, 6-thiabicyclo[3.1.1]heptanyl, 2-oxabicyclo[3.2.1]octanyl, 3-oxabicyclo[3.2.1]octanyl, 6-oxabicyclo[3.2.1]octanyl, 8-oxabicyclo[3.2.1]octanyl, 2-azabicyclo[3.2.1]octanyl, 3-azabicyclo[3.2.1]octanyl, 6-azabicyclo[3.2.1]octanyl, 8-azabicyclo[3.2.1]octanyl, 2-thiabicyclo[3.2.1]octanyl, 3-thiabicyclo[3.2.1]octanyl, 6-thiabicyclo[3.2.1]octanyl, 8-thiabicyclo[3.2.1]octanyl, 2-oxa-5-azabicyclo[2.2.1]heptanyl, 3-oxa-6-azabicyclo[3.1.1]heptanyl, 6-oxa-3-azabicyclo[3.1.1]heptanyl, 2-oxa-6-azabicyclo[3.2.1]octanyl, 3-oxa-6-azabicyclo[3.2.1]octanyl, 3-oxa-8-azabicyclo[3.2.1]octanyl, 8-oxa-2-azabicyclo[3.2.1]octanyl, 8-oxa-3-azabicyclo[3.2.1]octanyl, 8-oxa-6-azabicyclo[3.2.1]octanyl, 2-thia-5-azabicyclo[2.2.1]heptanyl, 3-thia-6-azabicyclo[3.1.1]heptanyl, 6-thia-3-azabicyclo[3.1.1]heptanyl, 2-thia-6-azabicyclo[3.2.1]octanyl, 3-thia-6-azabicyclo[3.2.1]octanyl, 3-thia-8-azabicyclo[3.2.1]octanyl, 8-thia-2-azabicyclo[3.2.1]octanyl, 8-thia-3-azabicyclo[3.2.1]octanyl, or 8-thia-6-azabicyclo[3.2.1]octanyl, each of which is substituted with one, two, or three independently selected $R^{10}$. In another particular embodiment, $R^4$ is 4-8 membered monocyclic or bridged polycyclic heterocycloalkyl comprising one, two, or three heteroatoms independently selected from N, O, and S, which heterocycloalkyl is substituted with one, two, or three independently selected $R^{10}$. In a more particular embodiment, $R^4$ is azetidinyl, oxetanyl, pyrrolidinyl, tetrahydrofuranyl, piperidinyl, oxazolidinyl, morpholinyl, thiomorpholinyl, piperazinyl, each of which is substituted with one or more independently selected $R^{10}$. In another more particular embodiment, $R^4$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, oxazolidinyl, thiazolidinyl, morpholinyl, thiomorpholinyl, dioxanyl, piperazinyl, 2-oxabicyclo[2.1.1]hexanyl, 5-oxabicyclo[2.1.1]hexanyl, 2-azabicyclo[2.1.1]hexanyl, 5-azabicyclo[2.1.1]hexanyl, 2-thiabicyclo[2.1.1]hexanyl, 5-thiabicyclo[2.1.1]hexanyl, 2-oxabicyclo[2.2.1]heptanyl, 7-oxabicyclo[2.2.1]heptanyl, 2-oxabicyclo[3.1.1]heptanyl, 3-oxabicyclo[3.1.1]heptanyl, 6-oxabicyclo[3.1.1]heptanyl, 2-azabicyclo[2.2.1]heptanyl, 7-azabicyclo[2.2.1]heptanyl, 2-azabicyclo[3.1.1]heptanyl, 3-azabicyclo[3.1.1]heptanyl, 6-azabicyclo[3.1.1]heptanyl, 2-thiabicyclo[2.2.1]heptanyl, 7-thiabicyclo[2.2.1]heptanyl, 2-thiabicyclo[3.1.1]heptanyl, 3-thiabicyclo[3.1.1]heptanyl, 6-thiabicyclo[3.1.1]heptanyl, 2-oxabicyclo[3.2.1]octanyl, 3-oxabicyclo[3.2.1]octanyl, 6-oxabicyclo[3.2.1]octanyl, 8-oxabicyclo[3.2.1]octanyl, 2-azabicyclo[3.2.1]octanyl, 3-azabicyclo[3.2.1]octanyl, 6-azabicyclo[3.2.1]octanyl, 8-azabicyclo[3.2.1]octanyl, 2-thiabicyclo[3.2.1]octanyl, 3-thiabicyclo[3.2.1]octanyl, 6-thiabicyclo[3.2.1]octanyl, 8-thiabicyclo[3.2.1]octanyl, 2-oxa-5-azabicyclo[2.2.1]heptanyl, 3-oxa-6-azabicyclo[3.1.1]heptanyl, 6-oxa-3-azabicyclo[3.1.1]heptanyl, 2-oxa-6-azabicyclo[3.2.1]octanyl, 3-oxa-6-azabicyclo[3.2.1]octanyl, 3-oxa-8-azabicyclo[3.2.1]octanyl, 8-oxa-2-azabicyclo[3.2.1]octanyl, 8-oxa-3-azabicyclo[3.2.1]octanyl, 8-oxa-6-azabicyclo[3.2.1]octanyl, 2-thia-5-azabicyclo[2.2.1]heptanyl, 3-thia-6-azabicyclo[3.1.1]heptanyl, 6-thia-3-azabicyclo[3.1.1]heptanyl, 2-thia-6-azabicyclo[3.2.1]octanyl, 3-thia-6-azabicyclo[3.2.1]octanyl, 3-thia-8-azabicyclo[3.2.1]octanyl, 8-thia-2-azabicyclo[3.2.1]octanyl, 8-thia-3-azabicyclo[3.2.1]octanyl, or 8-thia-6-azabicyclo[3.2.1]octanyl, each of which is substituted with one, two, or three independently selected $R^{10}$. In a most particular embodiment, $R^4$ is azetidinyl, oxetanyl, pyrrolidinyl, tetrahydrofuranyl, piperidinyl, oxazolidinyl, morpholinyl, thiomorpholinyl, or piperazinyl, each of which is substituted with one, two, or three independently selected $R^{10}$.

In one embodiment, the compound of the invention is according to any one of Formulae I-IVf, wherein $R^4$ is 4-11 membered monocyclic, spirocyclic, or bridged polycyclic heterocycloalkyl comprising one, two, or three heteroatoms independently selected from N, O, and S, which heterocycloalkyl is substituted with one or more independently selected $R^{10}$, and $R^{10}$ is as previously described. In a particular embodiment, $R^{10}$ is —OH, phenyl, =NH, halo, oxo, —CN, —C(=O)H, —C(=O)NH$_2$, —C(=O)OH, —NR$^{14a}$R$^{14b}$, $C_{1-4}$ alkyl optionally substituted with one or more independently selected halo, —CN, —OH, —C(=O)—$C_{1-4}$ alkoxy, or $C_{1-4}$ alkoxy, $C_{3-7}$ cycloalkyl, 4-6 membered monocyclic heterocycloalkyl comprising one, two, or three heteroatoms independently selected from N, O, and S, —C(=O)—$C_{1-4}$ alkyl, —S(=O)$_2$—$C_{1-4}$ alkyl, or —C(=O)—$C_{1-6}$ alkoxy. In a more particular embodiment, $R^{10}$ is —OH, phenyl, =NH, F, Cl, Br, oxo, —CN, —C(=O)H, —C(=O)NH$_2$, —C(=O)OH, —NR$^{14a}$R$^{14b}$, —CH$_3$, —CH$_2$CH$_3$, —CH(CH$_3$)$_2$, —CHF$_2$, —CF$_3$, —CH$_2$—CHF$_2$, —CH$_2$—CF$_3$, —CH$_2$—CN, —CH$_2$—CH$_2$—CN, —CH(CH$_3$)—CN, —C(CH$_3$)$_2$—CN, —CH(CH$_3$)—CH$_2$—CN, —CH$_2$—C(CH$_3$)$_2$—CN, —CH$_2$—OH, —CH$_2$—CH$_2$—OH, —CH(CH$_3$)—OH, —C(CH$_3$)$_2$—OH, —CH(CH$_3$)—CH$_2$—OH, —CH$_2$—C(CH$_3$)$_2$—OH, —CH$_2$—C(=O)—O—CH$_3$, —CH$_2$—C(=O)—O—CH$_2$—CH$_3$, —CH$_2$—CH$_2$—C(=O)—O—CH$_3$, —CH$_2$—CH$_2$—C(=O)—O—CH$_2$—CH$_3$, —CH(CH$_3$)—C(=O)—O—CH$_3$, —CH(CH$_3$)—C(=O)—O—CH$_2$—CH$_3$, —C(CH$_3$)$_2$—C(=O)—O—CH$_3$, —C(CH$_3$)$_2$—C(=O)—O—CH$_2$—CH$_3$, —CH(CH$_3$)—CH$_2$—C(=O)—O—CH$_3$, —CH(CH$_3$)—CH$_2$—C(=O)—O—CH$_2$—CH$_3$, —CH$_2$—CH(CH$_3$)—C(=O)—O—CH$_3$, —CH$_2$—CH(CH$_3$)—C(=O)—O—CH$_2$—CH$_3$, —CH$_2$—C(CH$_3$)$_2$—C(=O)—O—CH$_3$, —CH$_2$—C(CH$_3$)$_2$—C(=O)—O—CH$_2$—CH$_3$, —CH$_2$—O—CH$_3$, —CH$_2$CH$_2$—O—CH$_3$, cyclopropyl, cyclobutyl, cyclopentyl, cyclohexyl, azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, —C(=O)—CH$_3$, —C(=O)—CH$_2$CH$_3$, —C(=O)—CH(CH$_3$)$_2$, —S(=O)$_2$—CH$_3$, —S(=O)$_2$—CH$_2$CH$_3$, —S(=O)$_2$—CH(CH$_3$)$_2$, —C(=O)—O—CH$_3$, —C(=O)—O—CH$_2$CH$_3$, —C(=O)—O—CH(CH$_3$)$_2$, or —C(=O)—O—C(CH$_3$)$_3$. In a most particular embodiment, $R^{10}$ is —OH, phenyl, =NH, F, oxo, —CN, —C(=O)H, —NR$^{14a}$R$^{14b}$, —CH$_3$, —CH$_2$CH$_3$, —CH(CH$_3$)$_2$, —CF$_3$, —CH$_2$—CHF$_2$, —CH$_2$—CF$_3$, —CH$_2$—CN, —CH$_2$—CH$_2$—CN, —CH$_2$—OH, —CH$_2$—CH$_2$—OH, —CH$_2$—C(CH$_3$)$_2$—OH, —CH$_2$—C(=O)—O—CH$_2$—CH$_3$, —CH$_2$—O—CH$_3$, cyclopropyl, oxetanyl, —C(=O)—CH$_3$, —S(=O)$_2$—CH$_3$, —C(=O)—O—CH$_3$, —C(=O)—O—CH$_2$CH$_3$, or —C(=O)—O—C(CH$_3$)$_3$.

In one embodiment, the compound of the invention is according to any one of Formulae I-IVf, wherein $R^4$ is 4-8 membered monocyclic or bridged polycyclic heterocycloalkyl comprising one, two, or three heteroatoms independently selected from N, O, and S, which heterocycloalkyl is substituted with one or more independently selected $R^{10}$, and $R^{10}$ is as previously described. In a particular embodiment, $R^{10}$ is halo, oxo, —CN, —C(=O)H, —NR$^{14a}$R$^{14b}$, $C_{1-4}$ alkyl optionally substituted with one or more independently selected halo or $C_{1-4}$ alkoxy, $C_{3-7}$ cycloalkyl, —C(=O)—$C_{1-4}$ alkyl, —S(=O)$_2$—$C_{1-4}$ alkyl, or —C(=O)—$C_{1-6}$ alkoxy. In a more particular embodiment, $R^{10}$ is F, Cl, Br, oxo, —CN, —C(=O)H, —NR$^{14a}$R$^{14b}$, —CH$_3$, —CH$_2$CH$_3$, —CH(CH$_3$)$_2$, —CHF$_2$, —CF$_3$, —CH$_2$—CHF$_2$, —CH$_2$—CF$_3$, —CH$_2$—O—CH$_3$, —CH$_2$CH$_2$—O—CH$_3$, cyclopropyl, cyclobutyl, cyclopentyl, cyclohexyl, —C(=O)—CH$_3$, —C(=O)—CH$_2$CH$_3$, —C(=O)—CH(CH$_3$)$_2$, —S(=O)$_2$—CH$_3$, —S(=O)$_2$—CH$_2$CH$_3$, —S(=O)$_2$—CH(CH$_3$)$_2$, —C(=O)—O—CH$_3$, —C(=O)—O—CH$_2$CH$_3$, —C(=O)—O—CH(CH$_3$)$_2$, or —C(=O)—O—C(CH$_3$)$_3$. In a most particular embodiment, $R^{10}$ is F, oxo, —CN, —C(=O)H, —NR$^{14a}$R$^{14b}$, —CH$_3$, —CH$_2$CH$_3$, —CH(CH$_3$)$_2$, —CF$_3$, —CH$_2$—CHF$_2$, —CH$_2$—CF$_3$, —CH$_2$—O—CH$_3$, cyclopropyl, —C(=O)—CH$_3$, —S(=O)$_2$—CH$_3$, —C(=O)—O—CH$_3$, or —C(=O)—O—C(CH$_3$)$_3$.

In one embodiment, the compound of the invention is according to any one of Formulae I-IVf, wherein $R^4$ is 4-11 membered monocyclic, spirocyclic, or bridged polycyclic heterocycloalkyl comprising one, two, or three heteroatoms independently selected from N, O, and S, which heterocycloalkyl is substituted with one or more independently selected $R^{10}$, $R^{10}$ is —NR$^{14a}$R$^{14b}$, and R$^{14a}$ and R$^{14b}$ are as previously described. In a particular embodiment, R$^{14a}$ and R$^{14b}$ are both H. In another particular embodiment, one of R$^{14a}$ and R$^{14b}$ is H, and the other is $C_{1-4}$ alkyl or —S(=O)$_2$—$C_{1-4}$ alkyl. In yet another particular embodiment, R$^{14a}$ and R$^{14b}$ are independently $C_{1-4}$ alkyl or —S(=O)$_2$—$C_{1-4}$ alkyl. In a more particular embodiment, one of R$^{14a}$ and R$^{14b}$ is H, and the other is —CH$_3$, —CH$_2$CH$_3$, —CH(CH$_3$)$_2$, or —S(=O)$_2$—CH$_3$. In another more particular embodiment, R$^{14a}$ and R$^{14b}$ are independently —CH$_3$, —CH$_2$CH$_3$, —CH(CH$_3$)$_2$, or —S(=O)$_2$—CH$_3$.

In one embodiment, the compound of the invention is according to any one of Formulae I-IVf, wherein $R^4$ is 4-8 membered monocyclic or bridged polycyclic heterocycloalkyl comprising one, two, or three heteroatoms independently selected from N, O, and S, which heterocycloalkyl is substituted with one or more independently selected $R^{10}$, $R^{10}$ is —NR$^{14a}$R$^{14b}$, and R$^{14a}$ and R$^{14b}$ are as previously described. In a particular embodiment, R$^{14a}$ and R$^{14b}$ are both H. In another particular embodiment, one of R$^{14a}$ and R$^{14b}$ is H, and the other is $C_{1-4}$ alkyl. In yet another particular embodiment, R$^{14a}$ and R$^{14b}$ are both $C_{1-4}$ alkyl. In a more particular embodiment, one of R$^{14a}$ and R$^{14b}$ is H, and the other is —CH$_3$, —CH$_2$CH$_3$, or —CH(CH$_3$)$_2$. In another more particular embodiment, R$^{14a}$ and R$^{14b}$ are independently —CH$_3$, —CH$_2$CH$_3$, or —CH(CH$_3$)$_2$.

In one embodiment, the compound of the invention is according to any one of Formulae I-IVf, wherein $R^4$ is —NR$^{11a}$R$^{11b}$, and R$^{11a}$ and R$^{11b}$ are as previously described. In a particular embodiment, R$^{11a}$ is H. In another particular embodiment, R$^{11a}$ is $C_{1-4}$ alkyl optionally substituted with one or more independently selected halo, —OH, —CN, or $C_{1-4}$ alkoxy. In a more particular embodiment, R$^{11a}$ is —CH$_3$, —CH$_2$CH$_3$, —CH(CH$_3$)$_2$, or —CH$_2$CHF$_2$. In a most particular embodiment, R$^{11a}$ is —CH$_3$.

In one embodiment, the compound of the invention is according to any one of Formulae I-IVf, wherein $R^4$ is —NR$^{11a}$R$^{11b}$, R$^{11a}$ is as previously described, and R$^{11b}$ is H or phenyl. In a most particular embodiment, $R^4$ is —NH$_2$.

In one embodiment, the compound of the invention is according to any one of Formulae I-IVf, wherein $R^4$ is —NR$^{11a}$R$^{11b}$, R$^{11a}$ is as previously described, and R$^{11b}$ is $C_{1-4}$ alkyl. In a particular embodiment, R$^{11b}$ is —CH$_3$, —CH$_2$CH$_3$, or —CH(CH$_3$)$_2$. In a more particular embodiment, $R^4$ is —NH—CH$_3$, —N(CH$_3$)$_2$, —NH—CH$_2$CH$_3$, —N(CH$_2$CH$_3$)$_2$, —N(CH(CH$_3$)$_2$)$_2$, or —N(CH$_3$)—CH$_2$CHF$_2$.

In one embodiment, the compound of the invention is according to any one of Formulae I-IVf, wherein $R^4$ is —NR$^{11a}$R$^{11b}$, R$^{11a}$ is as previously described, and R$^{11b}$ is C$_{1-4}$ alkyl substituted with one or more independently selected halo, —OH, —CN, or C$_{1-4}$ alkoxy. In a particular embodiment, R$^{11b}$ is —CH$_3$, —CH$_2$CH$_3$, or —CH(CH$_3$)$_2$, each of which is substituted with one or more independently selected halo, —OH, —CN, or C$_{1-4}$ alkoxy. In another particular embodiment, R$^{11b}$ is C$_{1-4}$ alkyl substituted with one, two, or three independently selected halo, —OH, —CN, or C$_{1-4}$ alkoxy. In yet another particular embodiment, R$^{11b}$ is C$_{1-4}$ alkyl substituted with one or more independently selected halo, —OH, —CN, —O—CH$_3$, —O—CH$_2$CH$_3$, or —O—CH(CH$_3$)$_2$. In a more particular embodiment, R$^{11b}$ is —CH$_3$, or —CH$_2$CH$_3$, each of which is substituted with one F, —OH, —CN, or —O—CH$_3$. In a most particular embodiment, R$^{11b}$ is —CH$_2$—CN, —CH$_2$CH$_2$—OH, or —CH$_2$CH$_2$—O—CH$_3$.

In one embodiment, the compound of the invention is according to any one of Formulae I-IVf, wherein R$^4$ is —NR$^{11a}$R$^{11b}$, R$^{11a}$ is as previously described, and R$^{11b}$ is C$_{3-7}$ cycloalkyl. In a particular embodiment, R$^{11b}$ is cyclopropyl, cyclobutyl, cyclopentyl, or cyclohexyl. In a more particular embodiment, R$^{11b}$ is cyclopropyl.

In one embodiment, the compound of the invention is according to any one of Formulae I-IVf, wherein R$^4$ is —NR$^{11a}$R$^{11b}$, R$^{11a}$ is as previously described, and R$^{11b}$ is —C(=O)—C$_{1-4}$ alkoxy. In a particular embodiment, R$^{11b}$ is —C(=O)—O—CH$_3$, —C(=O)—O—CH$_2$CH$_3$, or —C(=O)—O—CH(CH$_3$)$_2$. In a more particular embodiment, R$^{11b}$ is —C(=O)—O—CH$_3$.

In one embodiment, the compound of the invention is according to any one of Formulae I-IVf, wherein R$^4$ is —NR$^{11a}$R$^{11b}$, R$^{11a}$ is as previously described, and R$^{11b}$ is —C(=O)—C$_{1-4}$ alkyl. In a particular embodiment, R$^{11b}$ is —C(=O)—CH$_3$, —C(=O)—CH$_2$CH$_3$, or —C(=O)—CH(CH$_3$)$_2$. In a more particular embodiment, R$^{11b}$ is —C(=O)—CH$_3$.

In one embodiment, the compound of the invention is according to any one of Formulae I-IVf, wherein R$^4$ is —NR$^{11a}$R$^{11b}$, R$^{11a}$ is as previously described, and R$^{11b}$ is —C(=O)—C$_{1-4}$ alkyl substituted with one or more independently selected halo. In a particular embodiment, R$^{11b}$ is —C(=O)—CH$_3$, —C(=O)—CH$_2$CH$_3$, or —C(=O)—CH(CH$_3$)$_2$, each of which is substituted with one, two, or three F, Cl, or Br. In a more particular embodiment, R$^{11b}$ is —C(=O)—CH$_3$ substituted with one, two, or three F. In a most particular embodiment, R$^{11b}$ is —C(=O)—CHF$_2$.

In one embodiment, the compound of the invention is according to any one of Formulae I-IVf, wherein R$^4$ is —NR$^{11a}$R$^{11b}$, R$^{11a}$ is as previously described, and R$^{11b}$ is 5-6 membered monocyclic heteroaryl comprising one, two, or three heteroatoms independently selected from N, O, and S. In a particular embodiment, R$^{11b}$ is pyrrolyl, furanyl, thiophenyl, pyrazolyl, isoxazolyl, isothiazolyl, imidazolyl, oxazolyl, thiazolyl, triazolyl, furazanyl, thiadiazolyl, oxadiazolyl, tetrazolyl, oxatriazolyl, thiatriazolyl, pyridinyl, pyrazinyl, pyridazinyl, or pyrimidinyl. In a more particular embodiment, R$^{11b}$ is pyridinyl, pyridazinyl, or pyrimidinyl.

In one embodiment, the compound of the invention is according to any one of Formulae I-IVf, wherein R$^4$ is —C(=O)—C$_{1-4}$ alkoxy. In a particular embodiment, R$^4$ is —C(=O)—O—CH$_3$, —C(=O)—O—CH$_2$CH$_3$, or —C(=O)—O—CH(CH$_3$)$_2$. In a more particular embodiment, R$^4$ is —C(=O)—O—CH$_2$CH$_3$.

In one embodiment, the compound of the invention is according to any one of Formulae I-IVf, wherein R$^4$ is —C(=O)—NR$^{12a}$R$^{12b}$, and each R$^{12a}$ and R$^{12b}$ are as previously described. In a particular embodiment, R$^{12a}$ and R$^{12b}$ are both H. In another particular embodiment, one of R$^{12a}$ and R$^{12b}$ is H, and the other is C$_{1-4}$ alkyl. In yet another particular embodiment, R$^{12a}$ and R$^{12b}$ are both C$_{1-4}$ alkyl. In a more particular embodiment, one of R$^{12a}$ and R$^{12b}$ is H, and the other is —CH$_3$, —CH$_2$CH$_3$, or —CH(CH$_3$)$_2$. In another more particular embodiment, each R$^{12a}$ and R$^{12b}$ is independently —CH$_3$, —CH$_2$CH$_3$, or —CH(CH$_3$)$_2$. In a most particular embodiment, R$^{12a}$ and R$^{12b}$ are —CH$_3$.

In one embodiment, the compound of the invention is according to Formula I, wherein the compound is selected from:

N-cyclopropyl-2-(difluoromethoxy)-6-methoxy-4-(7-tetrahydropyran-4-yloxyimidazo[1,2-a]pyridin-3-yl)benzamide, N-cyclopropyl-2-(difluoromethoxy)-6-methoxy-4-[7-[(1-methyl-3-piperidyl)oxy]imidazo[1,2-a]pyridin-3-yl]benzamide, N-cyclopropyl-2-(difluoromethoxy)-6-methoxy-4-[7-(2-methoxy-2-methyl-propoxy)imidazo[1,2-a]pyridin-3-yl]benzamide, 2,6-dimethoxy-4-(7-tetrahydropyran-4-yloxyimidazo[1,2-a]pyridin-3-yl)-N-(2,2,2-trifluoroethyl)benzamide, 2,6-dimethoxy-4-[7-[(1-methyl-3-piperidyl)oxy]imidazo[1,2-a]pyridin-3-yl]-N-(2,2,2-trifluoroethyl)benzamide, N-cyclopropyl-2-(difluoromethoxy)-4-[7-[2-(dimethylamino)ethoxy]imidazo[1,2-a]pyridin-3-yl]-6-methoxybenzamide, N-cyclopropyl-2-(difluoromethoxy)-6-methoxy-4-[7-[(1-methyl-4-piperidyl)oxy]imidazo[1,2-a]pyridin-3-yl]benzamide, N-cyclopropyl-2-(difluoromethoxy)-6-methoxy-4-[7-(2-morpholinoethoxy)imidazo[1,2-a]pyridin-3-yl]benzamide, N-cyclopropyl-2-(difluoromethoxy)-6-methoxy-4-[7-[2-(4-methylpiperazin-1-yl)ethoxy]imidazo[1,2-a]pyridin-3-yl]benzamide, N-cyclopropyl-2-(difluoromethoxy)-6-methoxy-4-[7-[2-(1-piperidyl)ethoxy]imidazo[1,2-a]pyridin-3-yl]benzamide, N-cyclopropyl-2-(difluoromethoxy)-6-methoxy-4-[7-(2-methyl-2-morpholino-propoxy)imidazo[1,2-a]pyridin-3-yl]benzamide, N-cyclopropyl-2-(difluoromethoxy)-6-methoxy-4-[7-(1-methyl-2-morpholino-ethoxy)imidazo[1,2-a]pyridin-3-yl]benzamide, N-cyclopropyl-2-(difluoromethoxy)-4-[7-[3-(dimethylamino)propoxy]imidazo[1,2-a]pyridin-3-yl]-6-methoxybenzamide, N-cyclopropyl-2-(difluoromethoxy)-6-methoxy-4-[7-[(1-methylazetidin-3-yl)methoxy]imidazo[1,2-a]pyridin-3-yl]benzamide, N-cyclopropyl-2-(difluoromethoxy)-6-methoxy-4-[7-(1-methylpyrrolidin-3-yl)oxyimidazo[1,2-a]pyridin-3-yl]benzamide, N-cyclopropyl-2-(difluoromethoxy)-6-methoxy-4-[7-[3-(1-piperidyl)propoxy]imidazo[1,2-a]pyridin-3-yl]benzamide, N-cyclopropyl-2-(difluoromethoxy)-6-methoxy-4-[7-[2-(1-methylpyrrolidin-2-yl)ethoxy]imidazo[1,2-a]pyridin-3-yl]benzamide, 6-[7-[2-(dimethylamino)ethoxy]imidazo[1,2-a]pyridin-3-yl]-8-methoxy-2-(2,2,2-trifluoroethyl)-3,4-dihydroisoquinolin-1-one, N-cyclopropyl-2-(difluoromethoxy)-6-methoxy-4-[7-[(3-methylimidazol-4-yl)methoxy]imidazo[1,2-a]pyridin-3-yl]benzamide, N-cyclopropyl-2-(difluoromethoxy)-6-methoxy-4-[7-(2-pyrrolidin-1-ylethoxy)imidazo[1,2-a]pyridin-3-yl]benzamide, N-cyclopropyl-2-(difluoromethoxy)-6-methoxy-4-[7-(3-morpholinopropoxy)imidazo[1,2-a]pyridin-3-yl]benzamide, N-cyclopropyl-2-(difluoromethoxy)-4-[7-[2-(1,1-dioxo-1,4-thiazinan-4-yl)ethoxy]imidazo[1,2-a]pyridin-3-yl]-6-methoxy-benzamide, N-cyclopropyl-2-(difluoromethoxy)-6-methoxy-4-[7-[(1-methyl-2-piperidyl)methoxy]imidazo[1,2-a]pyridin-3-yl]benzamide, N-cyclopropyl-2-(difluoromethoxy)-6-methoxy-4-[7-[2-(1-methyl-2-piperidyl)ethoxy]imidazo[1,2-a]pyridin-3-yl]benzamide, N-cyclopropyl-2-(difluoromethoxy)-6-methoxy-4-[7-[(1-methyl-4-piperidyl)methoxy]imidazo[1,2-a]pyridin-3-yl]benzamide, N-cyclopropyl-2-(difluoromethoxy)-6-methoxy-4-[7-[(1-methyl-5-oxo-pyrrolidin-3-yl)methoxy]imidazo[1,2-a]pyridin-3-yl]benzamide, 4-[7-(2-acetamidoethoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[(1-methylpyrrolidin-2-yl)methoxy]imidazo[1,2-a]pyridin-3-yl]benzamide, N-cyclopropyl-2-(difluoromethoxy)-6-methoxy-4-[7-(1-methylazetidin-3-yl)oxyimidazo[1,2-a]pyridin-3-yl]benzamide, N-cyclopropyl-2-(difluoromethoxy)-4-[7-(2-hydroxyethoxy)imidazo[1,2-a]pyridin-3-yl]-6-methoxy-benzamide, 4-[7-(2-cyanoethoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(oxazol-2-ylmethoxy)imidazo[1,2-a]pyridin-3-yl]benzamide, N-cyclopropyl-2-(difluoromethoxy)-6-methoxy-4-[7-(oxazol-5-ylmethoxy)imidazo[1,2-a]pyridin-3-yl]benzamide, 4-[7-(2-cyano-2-methyl-propoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(oxetan-2-ylmethoxy)imidazo[1,2-a]pyridin-3-yl]benzamide, N-cyclopropyl-2-(difluoromethoxy)-4-[7-(2-fluoroethoxy)imidazo[1,2-a]pyridin-3-yl]-6-methoxy-benzamide, N-cyclopropyl-2-(difluoromethoxy)-4-[7-[2-(ethylamino)ethoxy]imidazo[1,2-a]pyridin-3-yl]-6-methoxy-benzamide, N-cyclopropyl-2-(difluoromethoxy)-6-methoxy-4-[7-[2-(2-methoxyethoxy)ethoxy]imidazo[1,2-a]pyridin-3-yl]benzamide, 8-methoxy-6-[7-[(1-methylazetidin-3-yl)methoxy]imidazo[1,2-a]pyridin-3-yl]-2-(2,2,2-trifluoroethyl)-3,4-dihydroisoquinolin-1-one, 8-methoxy-6-[7-[2-(1-piperidyl)ethoxy]imidazo[1,2-a]pyridin-3-yl]-2-(2,2,2-trifluoroethyl)-3,4-dihydroisoquinolin-1-one, 6-[7-[2-(1,1-dioxo-1,4-thiazinan-4-yl)ethoxy]imidazo[1,2-a]pyridin-3-yl]-8-methoxy-2-(2,2,2-trifluoroethyl)-3,4-dihydroisoquinolin-1-one, N-cyclopropyl-4-[7-[(2,2-difluorocyclopropyl)methoxy]imidazo[1,2-a]pyridin-3-yl]-2-(difluoromethoxy)-6-methoxy-benzamide, N-cyclopropyl-2-(difluoromethoxy)-6-methoxy-4-[7-(3-pyridylmethoxy)imidazo[1,2-a]pyridin-3-yl]benzamide, N-cyclopropyl-2-(difluoromethoxy)-6-methoxy-4-[7-[(2-methylpyrazol-3-yl)methoxy]imidazo[1,2-a]pyridin-3-yl]benzamide, N-cyclopropyl-2-(difluoromethoxy)-6-methoxy-4-[7-(2,2,2-trifluoro-1-methyl-ethoxy)imidazo[1,2-a]pyridin-3-yl]benzamide, N-cyclopropyl-2-(difluoromethoxy)-6-methoxy-4-[7-(thiazol-4-ylmethoxy)imidazo[1,2-a]pyridin-3-yl]benzamide, N-cyclopropyl-2-(difluoromethoxy)-6-methoxy-4-[7-(thiazol-2-ylmethoxy)imidazo[1,2-a]pyridin-3-yl]benzamide, N-cyclopropyl-2-(difluoromethoxy)-6-methoxy-4-[7-(tetrahydropyran-2-ylmethoxy)imidazo[1,2-a]pyridin-3-yl]benzamide, N-cyclopropyl-2-(difluoromethoxy)-6-methoxy-4-[7-(tetrahydropyran-4-ylmethoxy)imidazo[1,2-a]pyridin-3-yl]benzamide, N-cyclopropyl-2-(difluoromethoxy)-4-[7-[[(2R)-1,4-dioxan-2-yl]methoxy]imidazo[1,2-a]pyridin-3-yl]-6-methoxy-benzamide, N-cyclopropyl-4-[7-[2-(dimethylamino)ethoxy]imidazo[1,2-a]pyridin-3-yl]-2-fluoro-6-methoxy-benzamide, N-cyclopropyl-4-[7-[(3,3-difluorocyclobutyl)methoxy]imidazo[1,2-a]pyridin-3-yl]-2-(difluoromethoxy)-6-methoxy-benzamide, 6-[7-[2-(dimethylamino)ethoxy]imidazo[1,2-a]pyridin-3-yl]-2-ethyl-8-methoxy-3,4-dihydroisoquinolin-1-one, 2-(2,2-difluoroethyl)-6-[7-[2-(dimethylamino)ethoxy]imidazo[1,2-a]pyridin-3-yl]-8-methoxy-3,4-dihydroisoquinolin-1-one, 8-methoxy-6-[7-(3-morpholinopropoxy)imidazo[1,2-a]pyridin-3-yl]-2-(2,2,2-trifluoroethyl)-3,4-dihydroisoquinolin-1-one, N-cyclopropyl-4-[7-[2-(dimethylamino)ethoxy]imidazo[1,2-a]pyridin-3-yl]-2-(2-ethoxyethoxy)-6-methoxy-benzamide, methyl 1-[[3-[4-(cyclopropylcarbamoyl)-3-(difluoromethoxy)-5-methoxy-phenyl]imidazo[1,2-a]pyridin-7-yl]oxymethyl]cyclopropanecarboxylate, N-cyclopropyl-2-(difluoromethoxy)-6-methoxy-4-(7-norbornan-2-yloxyimidazo[1,2-a]pyridin-3-yl)benzamide, N-cyclopropyl-2-(difluoromethoxy)-6-methoxy-4-[7-(tetrahydropyran-3-ylmethoxy)imidazo[1,2-a]pyridin-3-yl]benzamide, N-cyclopropyl-2-(difluoromethoxy)-6-methoxy-4-[7-(oxazol-4-ylmethoxy)imidazo[1,2-a]pyridin-3-yl]benzamide, 4-[7-(cyclopentylmethoxy)imidazo[1,2-a]pyridin-3-yl]-N-cyclopropyl-2-(difluoromethoxy)-6-methoxy-benzamide, N-cyclopropyl-4-[7-(3,3-difluorocyclopentoxy)imidazo[1,2-a]pyridin-3-yl]-2-(difluoromethoxy)-6-methoxy-benzamide, N-cyclopropyl-2-(difluoromethoxy)-6-methoxy-4-[7-[2-(2-oxopyrrolidin-1-yl)ethoxy]imidazo[1,2-a]pyridin-3-yl]benzamide, N-cyclopropyl-2-(difluoromethoxy)-6-methoxy-4-[7-(2-tetrahydropyran-4-ylethoxy)imidazo[1,2-a]pyridin-3-yl]benzamide, N-cyclopropyl-2-(difluoromethoxy)-4-[7-[2-[2-(dimethylamino)ethoxy]ethoxy]imidazo[1,2-a]pyridin-3-yl]-6-methoxy-benzamide, N-cyclopropyl-2-(difluoromethoxy)-4-[7-(2,2-dimethylpropoxy)imidazo[1,2-a]pyridin-3-yl]-6-methoxy-benzamide, 2-[6-[7-[2-(dimethylamino)ethoxy]imidazo[1,2-a]pyridin-3-yl]-8-methoxy-1-oxo-3,4-dihydroisoquinolin-2-yl]acetonitrile, 4-(7-benzyloxyimidazo[1,2-a]pyridin-3-yl)-N-cyclopropyl-2-(difluoromethoxy)-6-methoxy-benzamide,
4-[7-(cyclohexylmethoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(2-methoxyethoxy)imidazo[1,2-a]pyridin-3-yl]benzamide,
4-[7-(cyclobutylmethoxy)imidazo[1,2-a]pyridin-3-yl]-N-cyclopropyl-2-(difluoromethoxy)-6-methoxy-benzamide,
N-cyclopropyl-2-(difluoromethoxy)-4-[7-(2-ethoxyethoxy)imidazo[1,2-a]pyridin-3-yl]-6-methoxy-benzamide,
N-cyclopropyl-2-(difluoromethoxy)-4-[7-[2-(2-hydroxyethoxy)ethoxy]imidazo[1,2-a]pyridin-3-yl]-6-methoxy-benzamide,
N-cyclopropyl-2-(difluoromethoxy)-4-[7-(3-hydroxy-2,2-dimethyl-propoxy)imidazo[1,2-a]pyridin-3-yl]-6-methoxy-benzamide,
N-cyclopropyl-4-[7-[(3,3-difluorocyclopentyl)methoxy]imidazo[1,2-a]pyridin-3-yl]-2-(difluoromethoxy)-6-methoxy-benzamide,
N-cyclopropyl-4-[7-[2-(3,3-difluorocyclobutyl)ethoxy]imidazo[1,2-a]pyridin-3-yl]-2-(difluoromethoxy)-6-methoxy-benzamide,
N-cyclopropyl-4-[7-(4,4-difluorocyclohexoxy)imidazo[1,2-a]pyridin-3-yl]-2-(difluoromethoxy)-6-methoxy-benzamide,
N-cyclopropyl-2-(difluoromethoxy)-4-[7-[2-(diisopropylamino)ethoxy]imidazo[1,2-a]pyridin-3-yl]-6-methoxy-benzamide,
N-cyclopropyl-2-(difluoromethoxy)-6-methoxy-4-[7-[[(2S)-1-methylpyrrolidin-2-yl]methoxy]imidazo[1,2-a]pyridin-3-yl]benzamide,
N-cyclopropyl-4-[7-[[(2R)-1-(2,2-difluoroethyl)pyrrolidin-2-yl]methoxy]imidazo[1,2-a]pyridin-3-yl]-2-(difluoromethoxy)-6-methoxy-benzamide,
N-cyclopropyl-2-(difluoromethoxy)-6-methoxy-4-[7-[[(2R)-1-methylpyrrolidin-2-yl]methoxy]imidazo[1,2-a]pyridin-3-yl]benzamide,
N-cyclopropyl-2-(difluoromethoxy)-6-methoxy-4-[7-[(4-methylmorpholin-2-yl)methoxy]imidazo[1,2-a]pyridin-3-yl]benzamide,
N-cyclopropyl-2-(difluoromethoxy)-4-[7-[(1-ethyl-2-piperidyl)methoxy]imidazo[1,2-a]pyridin-3-yl]-6-methoxy-benzamide,
8-methoxy-6-[7-[(2-methylpyrazol-3-yl)methoxy]imidazo[1,2-a]pyridin-3-yl]-2-(2,2,2-trifluoroethyl)-3,4-dihydroisoquinolin-1-one,
8-methoxy-6-[7-[(3-methylimidazol-4-yl)methoxy]imidazo[1,2-a]pyridin-3-yl]-2-(2,2,2-trifluoroethyl)-3,4-dihydroisoquinolin-1-one,
6-[7-[[(2R)-1,4-dioxan-2-yl]methoxy]imidazo[1,2-a]pyridin-3-yl]-8-methoxy-2-(2,2,2-trifluoroethyl)-3,4-dihydroisoquinolin-1-one,
tert-butyl 2-[[3-[4-(cyclopropylcarbamoyl)-3-(difluoromethoxy)-5-methoxy-phenyl]imidazo[1,2-a]pyridin-7-yl]oxymethyl]azetidine-1-carboxylate,
8-methoxy-6-[7-(2-morpholinoethoxy)imidazo[1,2-a]pyridin-3-yl]-2-(2,2,2-trifluoroethyl)-3,4-dihydroisoquinolin-1-one,
N-cyclopropyl-2-(difluoromethoxy)-6-methoxy-4-[7-[(3-methyloxetan-3-yl)methoxy]imidazo[1,2-a]pyridin-3-yl]benzamide,
N-cyclopropyl-4-[7-(2,2-difluoroethoxy)imidazo[1,2-a]pyridin-3-yl]-2-(difluoromethoxy)-6-methoxy-benzamide,
N-cyclopropyl-2-(difluoromethoxy)-6-methoxy-4-[7-(2,2,2-trifluoroethoxy)imidazo[1,2-a]pyridin-3-yl]benzamide,
N-cyclopropyl-2-(difluoromethoxy)-6-methoxy-4-[7-(tetrahydrofuran-3-ylmethoxy)imidazo[1,2-a]pyridin-3-yl]benzamide,
N-cyclopropyl-2-(difluoromethoxy)-6-methoxy-4-[7-(tetrahydrofuran-2-ylmethoxy)imidazo[1,2-a]pyridin-3-yl]benzamide,
N-cyclopropyl-2-(difluoromethoxy)-6-methoxy-4-[7-(pyrimidin-2-ylmethoxy)imidazo[1,2-a]pyridin-3-yl]benzamide,
N-cyclopropyl-2-(difluoromethoxy)-6-methoxy-4-[7-(thiazol-5-ylmethoxy)imidazo[1,2-a]pyridin-3-yl]benzamide,
N-cyclopropyl-4-[7-(cyclopropylmethoxy)imidazo[1,2-a]pyridin-3-yl]-2-(difluoromethoxy)-6-methoxy-benzamide,
N-cyclopropyl-2-(difluoromethoxy)-6-methoxy-4-[7-[(1-methylcyclopropyl)methoxy]imidazo[1,2-a]pyridin-3-yl]benzamide,
N-cyclopropyl-2-(difluoromethoxy)-4-[7-(1,4-dioxan-2-ylmethoxy)imidazo[1,2-a]pyridin-3-yl]-6-methoxy-benzamide,
N-cyclopropyl-2-(difluoromethoxy)-6-methoxy-4-[7-[(5-oxopyrrolidin-2-yl)methoxy]imidazo[1,2-a]pyridin-3-yl]benzamide,
N-cyclopropyl-2-(difluoromethoxy)-4-[7-[2-(dimethylamino)-2-oxo-ethoxy]imidazo[1,2-a]pyridin-3-yl]-6-methoxy-benzamide,
N-cyclopropyl-2-(difluoromethoxy)-6-methoxy-4-[7-[(1-methylimidazol-4-yl)methoxy]imidazo[1,2-a]pyridin-3-yl]benzamide,
N-cyclopropyl-2-(difluoromethoxy)-6-methoxy-4-[7-[(5-oxopyrrolidin-3-yl)methoxy]imidazo[1,2-a]pyridin-3-yl]benzamide,
N-cyclopropyl-2-(difluoromethoxy)-6-methoxy-4-[7-(4-pyridylmethoxy)imidazo[1,2-a]pyridin-3-yl]benzamide,
4-[7-(2-amino-2-methyl-propoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(2-pyridylmethoxy)imidazo[1,2-a]pyridin-3-yl]benzamide,
N-cyclopropyl-2-(difluoromethoxy)-4-[7-[2-(dimethylamino)-2-methyl-propoxy]imidazo[1,2-a]pyridin-3-yl]-6-methoxy-benzamide,
N-cyclopropyl-4-[7-[2-(diethylamino)ethoxy]imidazo[1,2-a]pyridin-3-yl]-2-(difluoromethoxy)-6-methoxy-benzamide,
4-[7-[(3-aminocyclobutyl)methoxy]imidazo[1,2-a]pyridin-3-yl]-N-cyclopropyl-2-(difluoromethoxy)-6-methoxy-benzamide,
4-[7-(azetidin-2-ylmethoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-[(1-methylimidazol-2-yl)methoxy]imidazo[1,2-a]pyridin-3-yl]benzamide,
N-cyclopropyl-2-(difluoromethoxy)-6-methoxy-4-[7-[[(2R)-1-methyl-2-piperidyl]methoxy]imidazo[1,2-a]pyridin-3-yl]benzamide,
4-[7-[2-(azetidin-1-yl)ethoxy]imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(morpholin-3-ylmethoxy)imidazo[1,2-a]pyridin-3-yl]benzamide,
N-cyclopropyl-2-(difluoromethoxy)-4-[7-[2-(2-hydroxyethylamino)ethoxy]imidazo[1,2-a]pyridin-3-yl]-6-methoxy-benzamide, 4-[7-(3-aminopropoxy)imidazo[1,2-a]pyridin-3-yl]-N-cyclopropyl-2-(difluoromethoxy)-6-methoxy-benzamide,
4-[7-[[1-(aminomethyl)cyclobutyl]methoxy]imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-[2-(methylamino)ethoxy]imidazo[1,2-a]pyridin-3-yl]benzamide,
4-[7-(2-aminoethoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(2-piperidylmethoxy)imidazo[1,2-a]pyridin-3-yl]benzamide,
N-cyclopropyl-2-(difluoromethoxy)-4-[7-[[(2S)-1,4-dioxan-2-yl]methoxy]imidazo[1,2-a]pyridin-3-yl]-6-methoxy-benzamide,
4-[7-(2-amino-3-methyl-butoxy)imidazo[1,2-a]pyridin-3-yl]-N-cyclopropyl-2-(difluoromethoxy)-6-methoxy-benzamide,
8-methoxy-6-[7-[2-(1-methylpyrrolidin-2-yl)ethoxy]imidazo[1,2-a]pyridin-3-yl]-2-(2,2,2-trifluoroethyl)-3,4-dihydroisoquinolin-1-one,
8-methoxy-6-[7-(2-pyrrolidin-1-ylethoxy)imidazo[1,2-a]pyridin-3-yl]-2-(2,2,2-trifluoroethyl)-3,4-dihydroisoquinolin-1-one,
8-methoxy-6-[7-[[(2R)-1-methylpyrrolidin-2-yl]methoxy]imidazo[1,2-a]pyridin-3-yl]-2-(2,2,2-trifluoroethyl)-3,4-dihydroisoquinolin-1-one,
8-methoxy-6-[7-(oxetan-2-ylmethoxy)imidazo[1,2-a]pyridin-3-yl]-2-(2,2,2-trifluoroethyl)-3,4-dihydroisoquinolin-1-one,
8-methoxy-6-[7-(oxazol-5-ylmethoxy)imidazo[1,2-a]pyridin-3-yl]-2-(2,2,2-trifluoroethyl)-3,4-dihydroisoquinolin-1-one,
8-methoxy-6-[7-[(4-methylmorpholin-2-yl)methoxy]imidazo[1,2-a]pyridin-3-yl]-2-(2,2,2-trifluoroethyl)-3,4-dihydroisoquinolin-1-one,
6-[7-[2-(diethylamino)ethoxy]imidazo[1,2-a]pyridin-3-yl]-8-methoxy-2-(2,2,2-trifluoroethyl)-3,4-dihydroisoquinolin-1-one,
N-cyclopropyl-2-(difluoromethoxy)-6-methoxy-4-[7-[(1-methylsulfonyl-2-piperidyl)methoxy]imidazo[1,2-a]pyridin-3-yl]benzamide,
methyl 2-[[3-[4-(cyclopropylcarbamoyl)-3-(difluoromethoxy)-5-methoxy-phenyl]imidazo[1,2-a]pyridin-7-yl]oxymethyl]piperidine-1-carboxylate,
4-[7-(2-aminobutoxy)imidazo[1,2-a]pyridin-3-yl]-N-cyclopropyl-2-(difluoromethoxy)-6-methoxy-benzamide,
4-[7-[(2S)-2-amino-4-methyl-pentoxy]imidazo[1,2-a]pyridin-3-yl]-N-cyclopropyl-2-(difluoromethoxy)-6-methoxy-benzamide,
4-[7-[(2S)-2-amino-2-cyclohexyl-ethoxy]imidazo[1,2-a]pyridin-3-yl]-N-cyclopropyl-2-(difluoromethoxy)-6-methoxy-benzamide,
4-[7-(2-amino-2-tetrahydrofuran-3-yl-ethoxy)imidazo[1,2-a]pyridin-3-yl]-N-cyclopropyl-2-(difluoromethoxy)-6-methoxy-benzamide,
4-[7-(2-amino-2-tetrahydropyran-4-yl-ethoxy)imidazo[1,2-a]pyridin-3-yl]-N-cyclopropyl-2-(difluoromethoxy)-6-methoxy-benzamide,
4-[7-(2-amino-2-tetrahydrofuran-2-yl-ethoxy)imidazo[1,2-a]pyridin-3-yl]-N-cyclopropyl-2-(difluoromethoxy)-6-methoxy-benzamide,
4-[7-(2-amino-2-cyclopropyl-ethoxy)imidazo[1,2-a]pyridin-3-yl]-N-cyclopropyl-2-(difluoromethoxy)-6-methoxy-benzamide,
4-[7-(2-aminopropoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-[[(2S)-1-methyl-2-piperidyl]methoxy]imidazo[1,2-a]pyridin-3-yl]benzamide,
6-[7-[2-(dimethylamino)ethoxy]imidazo[1,2-a]pyridin-3-yl]-8-ethoxy-2-(2,2,2-trifluoroethyl)-3,4-dihydroisoquinolin-1-one,
4-[7-[(1-acetyl-2-piperidyl)methoxy]imidazo[1,2-a]pyridin-3-yl]-N-cyclopropyl-2-(difluoromethoxy)-6-methoxy-benzamide,
N-cyclopropyl-2-(difluoromethoxy)-4-[7-[(1-formyl-3-piperidyl)methoxy]imidazo[1,2-a]pyridin-3-yl]-6-methoxy-benzamide,
N-cyclopropyl-2-(difluoromethoxy)-6-methoxy-4-[7-(3-piperidylmethoxy)imidazo[1,2-a]pyridin-3-yl]benzamide,
N-cyclopropyl-2-(difluoromethoxy)-6-methoxy-4-[7-[(1-methylpyrrolidin-3-yl)methoxy]imidazo[1,2-a]pyridin-3-yl]benzamide,
N-cyclopropyl-2-(difluoromethoxy)-6-methoxy-4-[7-(2-pyridyloxy)imidazo[1,2-a]pyridin-3-yl]benzamide,
N-cyclopropyl-2-(difluoromethoxy)-4-[7-[2-(dimethylamino)ethoxy]imidazo[1,2-a]pyridin-3-yl]-6-fluoro-benzamide,
N-cyclopropyl-2-(difluoromethoxy)-4-[7-[2-(dimethylamino)ethoxy]imidazo[1,2-a]pyridin-3-yl]-6-(methylamino)benzamide,
N-cyclopropyl-2-(difluoromethoxy)-4-[7-[(1-isopropyl-2-piperidyl)methoxy]imidazo[1,2-a]pyridin-3-yl]-6-methoxy-benzamide,
N-cyclopropyl-4-[7-[[1-(2,2-difluoroethyl)-2-piperidyl]methoxy]imidazo[1,2-a]pyridin-3-yl]-2-(difluoromethoxy)-6-methoxy-benzamide,
2-(2,2-difluoroethyl)-8-(difluoromethoxy)-6-[7-[2-(dimethylamino)ethoxy]imidazo[1,2-a]pyridin-3-yl]-3,4-dihydroisoquinolin-1-one,
4-[7-(cyclobutoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(oxetan-3-yloxy)imidazo[1,2-a]pyridin-3-yl]benzamide,
N-cyclopropyl-2-(difluoromethoxy)-6-methoxy-4-[7-[2-methyl-2-(methylamino)propoxy]imidazo[1,2-a]pyridin-3-yl]benzamide,
N-cyclopropyl-2-(difluoromethoxy)-6-methoxy-4-[7-(pyrrolidin-2-ylmethoxy)imidazo[1,2-a]pyridin-3-yl]benzamide,
2-(difluoromethoxy)-4-[7-[2-(dimethylamino)ethoxy]imidazo[1,2-a]pyridin-3-yl]-6-fluoro-N-(2,2,2-trifluoroethyl)benzamide,
N-cyclopropyl-2,6-bis(difluoromethoxy)-4-[7-[2-(dimethylamino)ethoxy]imidazo[1,2-a]pyridin-3-yl]benzamide,
N-cyclopropyl-2-(difluoromethoxy)-6-methoxy-4-(7-phenoxyimidazo[1,2-a]pyridin-3-yl)benzamide,
N-cyclopropyl-2-(difluoromethoxy)-6-methoxy-4-[7-[2-[2-(methoxymethyl)morpholin-4-yl]ethoxy]imidazo[1,2-a]pyridin-3-yl]benzamide,
4-(7-benzyloxyimidazo[1,2-c]pyrimidin-3-yl)-N-cyclopropyl-2-(difluoromethoxy)-6-methoxy-benzamide,
N-cyclopropyl-2-(difluoromethoxy)-4-[7-[2-[(3S)-3-fluoropyrrolidin-1-yl]ethoxy]imidazo[1,2-a]pyridin-3-yl]-6-methoxy-benzamide,
N-cyclopropyl-2-(difluoromethoxy)-6-methoxy-4-[7-[3-(methylamino)cyclobutoxy]imidazo[1,2-a]pyridin-3-yl]benzamide,
N-cyclopropyl-2-(difluoromethoxy)-6-methoxy-4-[7-(2-oxaspiro[3.3]heptan-6-yloxy)imidazo[1,2-a]pyridin-3-yl]benzamide, N-cyclopropyl-2-(difluoromethoxy)-6-methoxy-4-(7-tetrahydrofuran-3-yloxyimidazo[1,2-a]pyridin-3-yl)benzamide, 4-[7-(3-cyanocyclobutoxy)imidazo[1,2-a]pyridin-3-yl]-N-cyclopropyl-2-(difluoromethoxy)-6-methoxy-benzamide, 2-(difluoromethoxy)-4-[7-[2-(dimethylamino)ethoxy]imidazo[1,2-a]pyridin-3-yl]-6-(methylamino)-N-(2,2,2-trifluoroethyl)benzamide, 2-(difluoromethoxy)-4-[7-[2-(dimethylamino)ethoxy]imidazo[1,2-a]pyridin-3-yl]-6-methoxy-N-(2,2,2-trifluoroethyl)benzamide, 6-[7-[2-(dimethylamino)ethoxy]imidazo[1,2-a]pyridin-3-yl]-8-(methylamino)-2-(2,2,2-trifluoroethyl)-3,4-dihydroisoquinolin-1-one, N-cyclopropyl-2-(difluoromethoxy)-6-methoxy-4-[7-[(2-methylpyrrolidin-2-yl)methoxy]imidazo[1,2-a]pyridin-3-yl]benzamide, 4-[7-[(1-aminocyclohexyl)methoxy]imidazo[1,2-a]pyridin-3-yl]-N-cyclopropyl-2-(difluoromethoxy)-6-methoxy-benzamide, 4-[7-[(3-aminooxetan-3-yl)methoxy]imidazo[1,2-a]pyridin-3-yl]-N-cyclopropyl-2-(difluoromethoxy)-6-methoxy-benzamide, 4-[7-[(1-aminocyclopropyl)methoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[(2-methyl-2-piperidyl)methoxy]imidazo[1,2-a]pyridin-3-yl]benzamide, N-cyclopropyl-2-(difluoromethoxy)-4-[7-[(1-ethylimidazol-2-yl)methoxy]imidazo[1,2-a]pyridin-3-yl]-6-methoxy-benzamide, 4-[7-[(1-aminocyclobutyl)methoxy]imidazo[1,2-a]pyridin-3-yl]-N-cyclopropyl-2-(difluoromethoxy)-6-methoxy-benzamide, N-cyclopropyl-2-(difluoromethoxy)-4-[7-[(1-isopropylimidazol-2-yl)methoxy]imidazo[1,2-a]pyridin-3-yl]-6-methoxy-benzamide, 4-[7-[(3-aminotetrahydrofuran-3-yl)methoxy]imidazo[1,2-a]pyridin-3-yl]-N-cyclopropyl-2-(difluoromethoxy)-6-methoxy-benzamide, N-cyclopropyl-2-(difluoromethoxy)-4-[7-[2-(2,6-dimethylmorpholin-4-yl)ethoxy]imidazo[1,2-a]pyridin-3-yl]-6-methoxy-benzamide, 4-[7-[2-(3-cyanomorpholin-4-yl)ethoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[2-[2-(trifluoromethyl)morpholin-4-yl]ethoxy]imidazo[1,2-a]pyridin-3-yl]benzamide, N-cyclopropyl-2-(difluoromethoxy)-4-[7-[2-(3,3-difluoropyrrolidin-1-yl)ethoxy]imidazo[1,2-a]pyridin-3-yl]-6-methoxy-benzamide, N-cyclopropyl-2-(difluoromethoxy)-4-[7-[2-(4,4-difluoro-1-piperidyl)ethoxy]imidazo[1,2-a]pyridin-3-yl]-6-methoxy-benzamide, N-cyclopropyl-2-(difluoromethoxy)-6-methoxy-4-[7-[[1-(2,2,2-trifluoroethyl)-2-piperidyl]methoxy]imidazo[1,2-a]pyridin-3-yl]benzamide, N-cyclopropyl-2-(difluoromethoxy)-6-methoxy-4-[7-[2-[methyl(2-pyridyl)amino]ethoxy]imidazo[1,2-a]pyridin-3-yl]benzamide, N-cyclopropyl-2-(difluoromethoxy)-6-methoxy-4-[7-[2-(N-methylanilino)ethoxy]imidazo[1,2-a]pyridin-3-yl]benzamide, 8-methoxy-6-[7-[2-(methylamino)ethoxy]imidazo[1,2-a]pyridin-3-yl]-2-(2,2,2-trifluoroethyl)-3,4-dihydroisoquinolin-1-one, N-cyclopropyl-4-[7-[2-(3,3-difluoroazetidin-1-yl)ethoxy]imidazo[1,2-a]pyridin-3-yl]-2-(difluoromethoxy)-6-methoxy-benzamide, tert-butyl 3-[[3-[4-(cyclopropylcarbamoyl)-3-(difluoromethoxy)-5-methoxy-phenyl]imidazo[1,2-a]pyridin-7-yl]oxymethyl]-3-fluoro-azetidine-1-carboxylate, tert-butyl 3-[[3-[4-(cyclopropylcarbamoyl)-3-(difluoromethoxy)-5-methoxy-phenyl]imidazo[1,2-a]pyridin-7-yl]oxymethyl]-3-methyl-azetidine-1-carboxylate, N-cyclopropyl-2-(difluoromethoxy)-4-[7-[[(2S)-4,4-difluoro-1-methyl-pyrrolidin-2-yl]methoxy]imidazo[1,2-a]pyridin-3-yl]-6-methoxy-benzamide, 8-methoxy-6-[7-[[(2R)-4-methylmorpholin-2-yl]methoxy]imidazo[1,2-a]pyridin-3-yl]-2-(2,2,2-trifluoroethyl)-3,4-dihydroisoquinolin-1-one, 8-methoxy-6-[7-[[(2S)-4-methylmorpholin-2-yl]methoxy]imidazo[1,2-a]pyridin-3-yl]-2-(2,2,2-trifluoroethyl)-3,4-dihydroisoquinolin-1-one, N-cyclopropyl-2-(difluoromethoxy)-4-[7-[2-(3,3-dimethylmorpholin-4-yl)ethoxy]imidazo[1,2-a]pyridin-3-yl]-6-methoxy-benzamide, N-cyclopropyl-2-(difluoromethoxy)-6-methoxy-4-[7-[2-(3-oxa-8-azabicyclo[3.2.1]octan-8-yl)ethoxy]imidazo[1,2-a]pyridin-3-yl]benzamide, N-cyclopropyl-2-(difluoromethoxy)-4-[7-[2-(2,2-dimethylmorpholin-4-yl)ethoxy]imidazo[1,2-a]pyridin-3-yl]-6-methoxy-benzamide, N-cyclopropyl-2-(difluoromethoxy)-6-methoxy-4-[7-[2-(8-oxa-3-azabicyclo[3.2.1]octan-3-yl)ethoxy]imidazo[1,2-a]pyridin-3-yl]benzamide, N-cyclopropyl-4-[7-[2-(2-cyclopropylmorpholin-4-yl)ethoxy]imidazo[1,2-a]pyridin-3-yl]-2-(difluoromethoxy)-6-methoxy-benzamide, 2-cyclopropyl-8-methoxy-6-[7-(2-morpholinoethoxy)imidazo[1,2-a]pyridin-3-yl]-3,4-dihydroisoquinolin-1-one, N-cyclopropyl-2-(difluoromethoxy)-4-[7-[(2,5-dimethylpyrazol-3-yl)methoxy]imidazo[1,2-a]pyridin-3-yl]-6-methoxy-benzamide, N-cyclopropyl-2-(difluoromethoxy)-6-methoxy-4-[7-[(1-methylpyrazol-4-yl)methoxy]imidazo[1,2-a]pyridin-3-yl]benzamide, N-cyclopropyl-2-(difluoromethoxy)-6-methoxy-4-[7-[(1-methylpyrazol-3-yl)methoxy]imidazo[1,2-a]pyridin-3-yl]benzamide, N-cyclopropyl-2-(difluoromethoxy)-6-methoxy-4-[7-[(4-methylmorpholin-3-yl)methoxy]imidazo[1,2-a]pyridin-3-yl]benzamide, N-cyclopropyl-2-(difluoromethoxy)-4-[7-[2-(dimethylamino)propoxy]imidazo[1,2-a]pyridin-3-yl]-6-methoxy-benzamide, N-cyclopropyl-2-(difluoromethoxy)-4-[7-[2-(dimethylamino)butoxy]imidazo[1,2-a]pyridin-3-yl]-6-methoxy-benzamide, N-cyclopropyl-2-(difluoromethoxy)-6-methoxy-4-[7-[2-(1-methylpyrazol-4-yl)ethoxy]imidazo[1,2-a]pyridin-3-yl]benzamide, N-cyclopropyl-4-[7-[(5-cyclopropyl-1,3,4-oxadiazol-2-yl)methoxy]imidazo[1,2-a]pyridin-3-yl]-2-(difluoromethoxy)-6-methoxy-benzamide, N-cyclopropyl-2-(difluoromethoxy)-6-methoxy-4-[7-[2-[(1S,4S)-2-oxa-5-azabicyclo[2.2.1]heptan-5-yl]ethoxy]imidazo[1,2-a]pyridin-3-yl]benzamide, N-cyclopropyl-2-(difluoromethoxy)-4-[7-[(3-fluoroazetidin-3-yl)methoxy]imidazo[1,2-a]pyridin-3-yl]-6-methoxy-benzamide, N-cyclopropyl-2-(difluoromethoxy)-6-methoxy-4-[7-[(3-methylazetidin-3-yl)methoxy]imidazo[1,2-a]pyridin-3-yl]benzamide, N-cyclopropyl-2-(difluoromethoxy)-4-[7-(2-hydroxy-1,1-dimethyl-ethoxy)imidazo[1,2-a]pyridin-3-yl]-6-methoxy-benzamide, 8-methoxy-6-[7-(2-morpholinoethoxy)imidazo[1,2-a]pyridin-3-yl]-2H-isoquinolin-1-one, N-cyclopropyl-2-(difluoromethoxy)-4-[7-[2-(3,3-difluoro-1-piperidyl)ethoxy]imidazo[1,2-a]pyridin-3-yl]-6-methoxy-benzamide, N-cyclopropyl-2-(difluoromethoxy)-4-[7-[2-(3-fluoro-1-piperidyl)ethoxy]imidazo[1,2-a]pyridin-3-yl]-6-methoxy-benzamide, 4-[7-[2-(2-cyanomorpholin-4-yl)ethoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[2-(2-methylmorpholin-4-yl)ethoxy]imidazo[1,2-a]pyridin-3-yl]benzamide, 4-[7-[2-[cyanomethyl(methyl)amino]ethoxy]imidazo[1,2-a]pyridin-3-yl]-N-cyclopropyl-2-(difluoromethoxy)-6-methoxy-benzamide, 4-[7-[2-(3-cyano-1-piperidyl)ethoxy]imidazo[1,2-a]pyridin-3-yl]-N-cyclopropyl-2-(difluoromethoxy)-6-methoxy-benzamide, 8-methoxy-6-[7-(2-morpholinoethoxy)imidazo[1,2-a]pyridin-3-yl]-3,4-dihydro-2H-isoquinolin-1-one, 2-(2,2-difluoroethyl)-8-methoxy-6-[7-(2-morpholinoethoxy)imidazo[1,2-a]pyridin-3-yl]-3,4-dihydroisoquinolin-1-one, 2-(2,2-difluoroethyl)-6-[7-[[(2R)-1,4-dioxan-2-yl]methoxy]imidazo[1,2-a]pyridin-3-yl]-8-methoxy-3,4-dihydroisoquinolin-1-one, N-cyclopropyl-2-(difluoromethoxy)-4-[7-[(1,3-dimethylazetidin-3-yl)methoxy]imidazo[1,2-a]pyridin-3-yl]-6-methoxy-benzamide, 8-methoxy-6-[7-(2-morpholinoethoxy)imidazo[1,2-a]pyridin-3-yl]-2-(2,2,2-trifluoroethyl)isoquinolin-1-one, N-cyclopropyl-2-methoxy-6-methyl-4-[7-(2-morpholinoethoxy)imidazo[1,2-a]pyridin-3-yl]benzamide, N-cyclopropyl-2-(difluoromethoxy)-6-methoxy-4-[7-[2-[methyl(4-pyridyl)amino]ethoxy]imidazo[1,2-a]pyridin-3-yl]benzamide, 2-cyclopropyl-8-(difluoromethoxy)-6-[7-(2-morpholinoethoxy)imidazo[1,2-a]pyridin-3-yl]-3,4-dihydroisoquinolin-1-one, 6-[7-[[(2S)-1,4-dioxan-2-yl]methoxy]imidazo[1,2-a]pyridin-3-yl]-8-methoxy-2-(2,2,2-trifluoroethyl)-3,4-dihydroisoquinolin-1-one, N-cyclopropyl-2-(difluoromethoxy)-6-methoxy-4-[7-(pyridazin-3-ylmethoxy)imidazo[1,2-a]pyridin-3-yl]benzamide, N-cyclopropyl-2-(difluoromethoxy)-6-methoxy-4-[7-[(4-methyl-1,2,4-triazol-3-yl)methoxy]imidazo[1,2-a]pyridin-3-yl]benzamide, N-cyclopropyl-2-(difluoromethoxy)-6-methoxy-4-[7-[(3-methyl-2-oxo-oxazolidin-5-yl)methoxy]imidazo[1,2-a]pyridin-3-yl]benzamide, N-cyclopropyl-2-(difluoromethoxy)-6-methoxy-4-[7-[(3-methyl-1,2,4-oxadiazol-5-yl)methoxy]imidazo[1,2-a]pyridin-3-yl]benzamide, 2-(difluoromethoxy)-6-methoxy-4-[7-(2-morpholinoethoxy)imidazo[1,2-a]pyridin-3-yl]-N-(2,2,2-trifluoroethyl)benzamide, N-cyclopropyl-2-(difluoromethoxy)-6-methoxy-4-[7-[(5-methyl-1,2,4-oxadiazol-3-yl)methoxy]imidazo[1,2-a]pyridin-3-yl]benzamide, N-cyclopropyl-2-(difluoromethoxy)-6-methoxy-4-[7-[2-(3-methylmorpholin-4-yl)ethoxy]imidazo[1,2-a]pyridin-3-yl]benzamide, N-cyclopropyl-2-(difluoromethoxy)-6-methoxy-4-[7-[2-[(3S)-3-methylmorpholin-4-yl]ethoxy]imidazo[1,2-a]pyridin-3-yl]benzamide, N-cyclopropyl-2-(difluoromethoxy)-6-methoxy-4-[7-[2-[(3R)-3-methylmorpholin-4-yl]ethoxy]imidazo[1,2-a]pyridin-3-yl]benzamide, N-cyclopropyl-4-[7-[2-[cyclopropyl(2,2-difluoroethyl)amino]ethoxy]imidazo[1,2-a]pyridin-3-yl]-2-(difluoromethoxy)-6-methoxy-benzamide, N-cyclopropyl-4-[7-[2-[2,2-difluoroethyl(methyl)amino]ethoxy]imidazo[1,2-a]pyridin-3-yl]-2-(difluoromethoxy)-6-methoxy-benzamide, N-cyclopropyl-4-[7-[2-[2,2-difluoroethyl(2-methoxyethyl)amino]ethoxy]imidazo[1,2-a]pyridin-3-yl]-2-(difluoromethoxy)-6-methoxy-benzamide, N-cyclopropyl-2-(difluoromethoxy)-6-methoxy-4-[7-[2-[methyl(pyrimidin-2-yl)amino]ethoxy]imidazo[1,2-a]pyridin-3-yl]benzamide, N-cyclopropyl-2-(difluoromethoxy)-6-methoxy-4-[7-[2-[methyl(pyrimidin-4-yl)amino]ethoxy]imidazo[1,2-a]pyridin-3-yl]benzamide, N-cyclopropyl-2-(difluoromethoxy)-6-methoxy-4-[7-[2-[methyl(pyridazin-4-yl)amino]ethoxy]imidazo[1,2-a]pyridin-3-yl]benzamide, N-cyclopropyl-2-(difluoromethoxy)-6-methyl-4-[7-(2-morpholinoethoxy)imidazo[1,2-a]pyridin-3-yl]benzamide, 6-[7-[[(2R)-1,4-dioxan-2-yl]methoxy]imidazo[1,2-a]pyridin-3-yl]-8-methoxy-3,4-dihydro-2H-isoquinolin-1-one, 2-(difluoromethoxy)-6-methyl-4-[7-(2-morpholinoethoxy)imidazo[1,2-a]pyridin-3-yl]-N-(2,2,2-trifluoroethyl)benzamide, 6-[7-[2-(3,3-difluoroazetidin-1-yl)ethoxy]imidazo[1,2-a]pyridin-3-yl]-8-methoxy-2-(2,2,2-trifluoroethyl)-3,4-dihydroisoquinolin-1-one, 8-methoxy-6-[7-[2-[(1S,4S)-2-oxa-5-azabicyclo[2.2.1]heptan-5-yl]ethoxy]imidazo[1,2-a]pyridin-3-yl]-2-(2,2,2-trifluoroethyl)-3,4-dihydroisoquinolin-1-one, 8-methoxy-6-[7-[2-(3-oxa-8-azabicyclo[3.2.1]octan-8-yl)ethoxy]imidazo[1,2-a]pyridin-3-yl]-2-(2,2,2-trifluoroethyl)-3,4-dihydroisoquinolin-1-one, 2-(2,2-difluoroethyl)-8-(difluoromethoxy)-6-[7-(2-morpholinoethoxy)imidazo[1,2-a]pyridin-3-yl]-3,4-dihydroisoquinolin-1-one, tert-butyl 3-fluoro-3-[[3-[8-methoxy-1-oxo-2-(2,2,2-trifluoroethyl)-3,4-dihydroisoquinolin-6-yl]imidazo[1,2-a]pyridin-7-yl]oxymethyl]azetidine-1-carboxylate, tert-butyl 3-[[3-[8-methoxy-1-oxo-2-(2,2,2-trifluoroethyl)-3,4-dihydroisoquinolin-6-yl]imidazo[1,2-a]pyridin-7-yl]oxymethyl]-3-methyl-azetidine-1-carboxylate, 6-[7-[(3-fluoroazetidin-3-yl)methoxy]imidazo[1,2-a]pyridin-3-yl]-8-methoxy-2-(2,2,2-trifluoroethyl)-3,4-dihydroisoquinolin-1-one, 8-methoxy-6-[7-[(3-methylazetidin-3-yl)methoxy]imidazo[1,2-a]pyridin-3-yl]-2-(2,2,2-trifluoroethyl)-3,4-dihydroisoquinolin-1-one, 6-[7-[(3-fluoro-1-methyl-azetidin-3-yl)methoxy]imidazo[1,2-a]pyridin-3-yl]-8-methoxy-2-(2,2,2-trifluoroethyl)-3,4-dihydroisoquinolin-1-one, 6-[7-[(1,3-dimethylazetidin-3-yl)methoxy]imidazo[1,2-a]pyridin-3-yl]-8-methoxy-2-(2,2,2-trifluoroethyl)-3,4-dihydroisoquinolin-1-one, N-cyclopropyl-3-methoxy-5-[7-(2-morpholinoethoxy)imidazo[1,2-a]pyridin-3-yl]pyridine-2-carboxamide, 4-[7-(1-cyanocyclopentoxy)imidazo[1,2-a]pyridin-3-yl]-N-cyclopropyl-2-(difluoromethoxy)-6-methoxy-benzamide, 8-methoxy-6-(7-methoxyimidazo[1,2-a]pyridin-3-yl)-2-(2,2,2-trifluoroethyl)-3,4-dihydroisoquinolin-1-one, 8-methoxy-6-[7-[2-[(3S)-3-methylmorpholin-4-yl]ethoxy]imidazo[1,2-a]pyridin-3-yl]-2-(2,2,2-trifluoroethyl)-3,4-dihydroisoquinolin-1-one, 6-[7-(2-hydroxyethoxy)imidazo[1,2-a]pyridin-3-yl]-8-methoxy-2-(2,2,2-trifluoroethyl)-3,4-dihydroisoquinolin-1-one, 8-methoxy-6-[7-[2-[(3R)-3-methylmorpholin-4-yl]ethoxy]imidazo[1,2-a]pyridin-3-yl]-2-(2,2,2-trifluoroethyl)-3,4-dihydroisoquinolin-1-one, N-cyclopropyl-2-(difluoromethoxy)-6-methoxy-4-[7-(2-methoxy-1,1-dimethyl-ethoxy)imidazo[1,2-a]pyridin-3-yl]benzamide, 3-methoxy-5-[7-(2-morpholinoethoxy)imidazo[1,2-a]pyridin-3-yl]-N-(2,2,2-trifluoroethyl)pyridine-2-carboxamide, 3-methoxy-5-[7-[(2-methylpyrazol-3-yl)methoxy]imidazo[1,2-a]pyridin-3-yl]-N-(2,2,2-trifluoroethyl)pyridine-2-carboxamide, 4-[7-(1-cyano-1-methyl-ethoxy)imidazo[1,2-a]pyridin-3-yl]-N-cyclopropyl-2-(difluoromethoxy)-6-methoxy-benzamide, 6-(7-ethoxyimidazo[1,2-a]pyridin-3-yl)-8-methoxy-2-(2,2,2-trifluoroethyl)-3,4-dihydroisoquinolin-1-one, 5-[7-[[(2R)-1,4-dioxan-2-yl]methoxy]imidazo[1,2-a]pyridin-3-yl]-3-methoxy-N-(2,2,2-trifluoroethyl)pyridine-2-carboxamide, 3-[7-(2-morpholinoethoxy)imidazo[1,2-a]pyridin-3-yl]-6-(2,2,2-trifluoroethyl)-5H-pyrrolo[3,4-b]pyridin-7-one, N-cyclopropyl-3-(difluoromethoxy)-5-[7-(2-morpholinoethoxy)imidazo[1,2-a]pyridin-3-yl]pyridine-2-carboxamide, ethyl 2-[3-[4-(cyclopropylcarbamoyl)-3-(difluoromethoxy)-5-methoxy-phenyl]imidazo[1,2-a]pyridin-7-yl]oxyacetate, 4-[7-[[1-(cyanomethyl)-2-piperidyl]methoxy]imidazo[1,2-a]pyridin-3-yl]-N-cyclopropyl-2-(difluoromethoxy)-6-methoxy-benzamide, 4-[7-[[(1R,5S)-8-azabicyclo[3.2.1]octan-3-yl]oxy]imidazo[1,2-a]pyridin-3-yl]-N-cyclopropyl-2-(difluoromethoxy)-6-methoxy-benzamide, 4-[7-[[(1S,5R)-8-(2-cyanoethyl)-8-azabicyclo[3.2.1]octan-3-yl]oxy]imidazo[1,2-a]pyridin-3-yl]-N-cyclopropyl-2-(difluoromethoxy)-6-methoxy-benzamide, ethyl 2-[(1R,5S)-3-[3-[4-(cyclopropylcarbamoyl)-3-(difluoromethoxy)-5-methoxy-phenyl]imidazo[1,2-a]pyridin-7-yl]oxy-8-azabicyclo[3.2.1]octan-8-yl]acetate, N-cyclopropyl-2-(difluoromethoxy)-6-methoxy-4-[7-[3-(2-oxa-6-azaspiro[3.3]heptan-6-yl)propoxy]imidazo[1,2-a]pyridin-3-yl]benzamide, 4-[7-[3-(azetidin-1-yl)propoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(3-pyrrolidin-1-ylpropoxy)imidazo[1,2-a]pyridin-3-yl]benzamide, N-cyclopropyl-2-(difluoromethoxy)-4-[7-[2-(4-isopropylpiperazin-1-yl)ethoxy]imidazo[1,2-a]pyridin-3-yl]-6-methoxy-benzamide, N-cyclopropyl-2-(difluoromethoxy)-4-[7-[3-(4-hydroxy-1-piperidyl)propoxy]imidazo[1,2-a]pyridin-3-yl]-6-methoxy-benzamide, N-cyclopropyl-2-(difluoromethoxy)-6-methoxy-4-[7-(3-piperazin-1-ylpropoxy)imidazo[1,2-a]pyridin-3-yl]benzamide, N-cyclopropyl-2-(difluoromethoxy)-4-[7-[3-(4-isopropylpiperazin-1-yl)propoxy]imidazo[1,2-a]pyridin-3-yl]-6-methoxy-benzamide, N-cyclopropyl-2-(difluoromethoxy)-4-[7-[(1-isopropyl-3-piperidyl)methoxy]imidazo[1,2-a]pyridin-3-yl]-6-methoxy-benzamide, N-cyclopropyl-2-(difluoromethoxy)-6-methoxy-4-[7-[3-(8-oxa-5-azaspiro[3.5]nonan-5-yl)propoxy]imidazo[1,2-a]pyridin-3-yl]benzamide, 3-[3-[4-(cyclopropylcarbamoyl)-3-(difluoromethoxy)-5-methoxy-phenyl]imidazo[1,2-a]pyridin-7-yl]oxypropyl acetate, N-cyclopropyl-2-(difluoromethoxy)-4-[7-[(4-isopropylmorpholin-3-yl)methoxy]imidazo[1,2-a]pyridin-3-yl]-6-methoxy-benzamide, N-cyclopropyl-2-(difluoromethoxy)-6-methoxy-4-[7-[3-(2-oxa-5-azabicyclo[2.2.1]heptan-5-yl)propoxy]imidazo[1,2-a]pyridin-3-yl]benzamide, N-cyclopropyl-2-(difluoromethoxy)-6-methoxy-4-[7-[3-(2-oxa-7-azaspiro[3.4]octan-7-yl)propoxy]imidazo[1,2-a]pyridin-3-yl]benzamide, N-cyclopropyl-2-(difluoromethoxy)-4-[7-[3-(3-hydroxyazetidin-1-yl)propoxy]imidazo[1,2-a]pyridin-3-yl]-6-methoxy-benzamide, N-cyclopropyl-2-(difluoromethoxy)-4-[7-[(1-isopropylpyrrolidin-3-yl)methoxy]imidazo[1,2-a]pyridin-3-yl]-6-methoxy-benzamide, N-cyclopropyl-2-(difluoromethoxy)-6-methoxy-4-[7-[[1-(oxetan-3-yl)pyrrolidin-3-yl]methoxy]imidazo[1,2-a]pyridin-3-yl]benzamide, N-cyclopropyl-2-(difluoromethoxy)-6-methoxy-4-[7-[[1-(oxetan-3-yl)pyrrolidin-2-yl]methoxy]imidazo[1,2-a]pyridin-3-yl]benzamide, N-cyclopropyl-2-(difluoromethoxy)-4-[7-[3-(2,6-dimethyl-1-piperidyl)propoxy]imidazo[1,2-a]pyridin-3-yl]-6-methoxy-benzamide, N-cyclopropyl-2-(difluoromethoxy)-6-methoxy-4-[7-[3-(8-oxa-3-azabicyclo[3.2.1]octan-3-yl)propoxy]imidazo[1,2-a]pyridin-3-yl]benzamide, N-cyclopropyl-2-(difluoromethoxy)-6-methoxy-4-[7-[3-(3-oxa-8-azabicyclo[3.2.1]octan-8-yl)propoxy]imidazo[1,2-a]pyridin-3-yl]benzamide, 4-[7-[3-(2-azaspiro[3.3]heptan-2-yl)propoxy]imidazo[1,2-a]pyridin-3-yl]-N-cyclopropyl-2-(difluoromethoxy)-6-methoxy-benzamide, N-cyclopropyl-2-(difluoromethoxy)-4-[7-[2-(2,6-dimethyl-1-piperidyl)ethoxy]imidazo[1,2-a]pyridin-3-yl]-6-methoxy-benzamide, N-cyclopropyl-2-(difluoromethoxy)-4-[7-[(1-isopropylpyrrolidin-2-yl)methoxy]imidazo[1,2-a]pyridin-3-yl]-6-methoxy-benzamide, N-cyclopropyl-2-(difluoromethoxy)-4-[7-[3-(2,8-dioxa-5-azaspiro[3.5]nonan-5-yl)propoxy]imidazo[1,2-a]pyridin-3-yl]-6-methoxy-benzamide, N-cyclopropyl-2-(difluoromethoxy)-4-[7-[3-(6-hydroxy-2-azaspiro[3.3]heptan-2-yl)propoxy]imidazo[1,2-a]pyridin-3-yl]-6-methoxy-benzamide, N-cyclopropyl-2-(difluoromethoxy)-4-[7-[2-[2-(4-isopropylpiperazin-1-yl)ethoxy]ethoxy]imidazo[1,2-a]pyridin-3-yl]-6-methoxy-benzamide, N-cyclopropyl-2-(difluoromethoxy)-6-methoxy-4-[7-[2-[1-(oxetan-3-yl)pyrrolidin-2-yl]ethoxy]imidazo[1,2-a]pyridin-3-yl]benzamide,
N-cyclopropyl-2-(difluoromethoxy)-6-methoxy-4-[7-[3-(6-oxa-1-azaspiro[3.3]heptan-1-yl)propoxy]imidazo[1,2-a]pyridin-3-yl]benzamide,
N-cyclopropyl-2-(difluoromethoxy)-4-[7-[2-(1-isopropylpyrrolidin-2-yl)ethoxy]imidazo[1,2-a]pyridin-3-yl]-6-methoxy-benzamide,
4-[7-[3-(1-azaspiro[3.3]heptan-1-yl)propoxy]imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-[3-(2-oxa-8-azaspiro[3.5]nonan-8-yl)propoxy]imidazo[1,2-a]pyridin-3-yl]benzamide,
N-cyclopropyl-2-(difluoromethoxy)-4-[7-[3-(7,8-dihydro-5H-pyrido[4,3-d]pyrimidin-6-yl)propoxy]imidazo[1,2-a]pyridin-3-yl]-6-methoxy-benzamide,
N-cyclopropyl-2-(difluoromethoxy)-6-methoxy-4-[7-[2-[2-(1-piperidyl)ethoxy]ethoxy]imidazo[1,2-a]pyridin-3-yl]benzamide,
N-cyclopropyl-2-(difluoromethoxy)-6-methoxy-4-[7-[2-(2-morpholinoethoxy)ethoxy]imidazo[1,2-a]pyridin-3-yl]benzamide,
N-cyclopropyl-4-[7-[2-[2-(diethylamino)ethoxy]ethoxy]imidazo[1,2-a]pyridin-3-yl]-2-(difluoromethoxy)-6-methoxy-benzamide,
N-cyclopropyl-2-(difluoromethoxy)-4-[7-[2-[4-(2-hydroxyethyl)piperazin-1-yl]ethoxy]imidazo[1,2-a]pyridin-3-yl]-6-methoxy-benzamide,
N-cyclopropyl-2-(difluoromethoxy)-6-methoxy-4-[7-[3-(1-methyl-6,7-dihydro-4H-imidazo[4,5-c]pyridin-5-yl)propoxy]imidazo[1,2-a]pyridin-3-yl]benzamide,
N-cyclopropyl-2-(difluoromethoxy)-4-[7-[3-(3,4-dihydro-1H-pyrrolo[1,2-a]pyrazin-2-yl)propoxy]imidazo[1,2-a]pyridin-3-yl]-6-methoxy-benzamide,
N-cyclopropyl-2-(difluoromethoxy)-4-[7-[3-(7,8-dihydro-5H-1,6-naphthyridin-6-yl)propoxy]imidazo[1,2-a]pyridin-3-yl]-6-methoxy-benzamide,
N-cyclopropyl-2-(difluoromethoxy)-4-[7-[3-(6,8-dihydro-5H-imidazo[1,2-a]pyrazin-7-yl)propoxy]imidazo[1,2-a]pyridin-3-yl]-6-methoxy-benzamide,
N-cyclopropyl-2-(difluoromethoxy)-4-[7-[3-(6,8-dihydro-5H-[1,2,4]triazolo[1,5-a]pyrazin-7-yl)propoxy]imidazo[1,2-a]pyridin-3-yl]-6-methoxy-benzamide,
N-cyclopropyl-2-(difluoromethoxy)-6-methoxy-4-[7-[[(3S)-pyrrolidin-3-yl]methoxy]imidazo[1,2-a]pyridin-3-yl]benzamide,
N-cyclopropyl-2-(difluoromethoxy)-6-methoxy-4-[7-[[(3S)-3-piperidyl]methoxy]imidazo[1,2-a]pyridin-3-yl]benzamide,
N-cyclopropyl-2-(difluoromethoxy)-4-[7-[[(3S)-1-isopropylpyrrolidin-3-yl]methoxy]imidazo[1,2-a]pyridin-3-yl]-6-methoxy-benzamide,
N-cyclopropyl-2-(difluoromethoxy)-6-methoxy-4-[7-[[(3S)-1-(oxetan-3-yl)pyrrolidin-3-yl]methoxy]imidazo[1,2-a]pyridin-3-yl]benzamide,
N-cyclopropyl-2-(difluoromethoxy)-6-methoxy-4-[7-[[(3S)-1-(oxetan-3-yl)-3-piperidyl]methoxy]imidazo[1,2-a]pyridin-3-yl]benzamide,
N-cyclopropyl-2-(difluoromethoxy)-4-[7-[3-(3-hydroxypyrrolidin-1-yl)propoxy]imidazo[1,2-a]pyridin-3-yl]-6-methoxy-benzamide,
N-cyclopropyl-2-(difluoromethoxy)-6-methoxy-4-[7-[3-(2-methyl-6,7-dihydro-4H-thiazolo[5,4-c]pyridin-5-yl)propoxy]imidazo[1,2-a]pyridin-3-yl]benzamide,
N-cyclopropyl-2-(difluoromethoxy)-4-[7-[2-hydroxy-3-(1-piperidyl)propoxy]imidazo[1,2-a]pyridin-3-yl]-6-methoxy-benzamide,
4-[7-[[1-(cyanomethyl)azetidin-3-yl]methoxy]imidazo[1,2-a]pyridin-3-yl]-N-cyclopropyl-2-(difluoromethoxy)-6-methoxy-benzamide,
4-[7-[[1-(2-cyanoethyl)azetidin-3-yl]methoxy]imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-[3-(2-oxo-1-oxa-3,8-diazaspiro[4.5]decan-8-yl)propoxy]imidazo[1,2-a]pyridin-3-yl]benzamide,
N-cyclopropyl-2-(difluoromethoxy)-6-methoxy-4-[7-[3-(3-methyl-2-oxo-1-oxa-3,8-diazaspiro[4.5]decan-8-yl)propoxy]imidazo[1,2-a]pyridin-3-yl]benzamide,
N-cyclopropyl-2-(difluoromethoxy)-6-methoxy-4-[7-[3-[4-[methyl(methylsulfonyl)amino]-1-piperidyl]propoxy]imidazo[1,2-a]pyridin-3-yl]benzamide,
N-cyclopropyl-2-(difluoromethoxy)-4-[7-[3-(1-imino-1-oxo-1,4-thiazinan-4-yl)propoxy]imidazo[1,2-a]pyridin-3-yl]-6-methoxy-benzamide,
N-cyclopropyl-2-(difluoromethoxy)-4-[7-[3-(3-hydroxy-1-piperidyl)propoxy]imidazo[1,2-a]pyridin-3-yl]-6-methoxy-benzamide,
N-cyclopropyl-2-(difluoromethoxy)-4-[7-[[(3S)-1-isopropyl-3-piperidyl]methoxy]imidazo[1,2-a]pyridin-3-yl]-6-methoxy-benzamide,
N-cyclopropyl-2-(difluoromethoxy)-4-[7-(2-hydroxy-3-morpholino-propoxy)imidazo[1,2-a]pyridin-3-yl]-6-methoxy-benzamide,
N-cyclopropyl-2-(difluoromethoxy)-4-[7-[3-(1,1-dioxo-1,4-thiazinan-4-yl)propoxy]imidazo[1,2-a]pyridin-3-yl]-6-methoxy-benzamide,
N-cyclopropyl-2-(difluoromethoxy)-4-[7-[3-(1,1-dioxo-1Â>>ˆ{6}-thia-6-azaspiro[3.3]heptan-6-yl)propoxy]imidazo[1,2-a]pyridin-3-yl]-6-methoxy-benzamide,
3-[3-[4-(cyclopropylcarbamoyl)-3-(difluoromethoxy)-5-methoxy-phenyl]imidazo[1,2-a]pyridin-7-yl]oxypropyl methanesulfonate,
N-cyclopropyl-2-(difluoromethoxy)-6-methoxy-4-[7-[[(3R)-pyrrolidin-3-yl]methoxy]imidazo[1,2-a]pyridin-3-yl]benzamide,
N-cyclopropyl-2-(difluoromethoxy)-6-methoxy-4-[7-[[(3R)-3-piperidyl]methoxy]imidazo[1,2-a]pyridin-3-yl]benzamide,
N-cyclopropyl-2-(difluoromethoxy)-6-methoxy-4-[7-[[(3R)-1-(oxetan-3-yl)pyrrolidin-3-yl]methoxy]imidazo[1,2-a]pyridin-3-yl]benzamide,
N-cyclopropyl-2-(difluoromethoxy)-4-[7-[[(3R)-1-isopropylpyrrolidin-3-yl]methoxy]imidazo[1,2-a]pyridin-3-yl]-6-methoxy-benzamide,
N-cyclopropyl-2-(difluoromethoxy)-4-[7-[[(3R)-1-isopropyl-3-piperidyl]methoxy]imidazo[1,2-a]pyridin-3-yl]-6-methoxy-benzamide,
N-cyclopropyl-2-(difluoromethoxy)-6-methoxy-4-[7-[[(3R)-1-(oxetan-3-yl)-3-piperidyl]methoxy]imidazo[1,2-a]pyridin-3-yl]benzamide,
N-cyclopropyl-2-(difluoromethoxy)-4-[7-[[(3S)-1-(2-hydroxyethyl)-3-piperidyl]methoxy]imidazo[1,2-a]pyridin-3-yl]-6-methoxy-benzamide,
N-cyclopropyl-2-(difluoromethoxy)-4-[7-[[(3S)-1-(2-hydroxyethyl)pyrrolidin-3-yl]methoxy]imidazo[1,2-a]pyridin-3-yl]-6-methoxy-benzamide,
N-cyclopropyl-2-(difluoromethoxy)-4-[7-[[1-(2-hydroxy-2-methyl-propyl)azetidin-3-yl]methoxy]imidazo[1,2-a]pyridin-3-yl]-6-methoxy-benzamide, N-cyclopropyl-2-(difluoromethoxy)-4-[7-[[1-(2-hydroxy-ethyl)azetidin-3-yl]methoxy]imidazo[1,2-a]pyridin-3-yl]-6-methoxy-benzamide, N-cyclopropyl-4-[7-[3-(4,4-difluoro-3-hydroxy-1-piperidyl)propoxy]imidazo[1,2-a]pyridin-3-yl]-2-(difluoromethoxy)-6-methoxy-benzamide, N-cyclopropyl-4-[7-[3-(3,3-difluoro-4-hydroxy-pyrrolidin-1-yl)propoxy]imidazo[1,2-a]pyridin-3-yl]-2-(difluoromethoxy)-6-methoxy-benzamide, 4-[7-[3-(3-cyano-1-piperidyl)propoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[3-(4-methylsulfonyl-1-piperidyl)propoxy]imidazo[1,2-a]pyridin-3-yl]benzamide, N-cyclopropyl-2-(difluoromethoxy)-4-[7-[3-[3-hydroxy-3-(trifluoromethyl)azetidin-1-yl]propoxy]imidazo[1,2-a]pyridin-3-yl]-6-methoxy-benzamide, N-cyclopropyl-2-(difluoromethoxy)-4-[7-[[(3R)-1-(2-hydroxyethyl)pyrrolidin-3-yl]methoxy]imidazo[1,2-a]pyridin-3-yl]-6-methoxy-benzamide, 4-[7-[[(3S)-1-(2-cyanoethyl)pyrrolidin-3-yl]methoxy]imidazo[1,2-a]pyridin-3-yl]-N-cyclopropyl-2-(difluoromethoxy)-6-methoxy-benzamide, 4-[7-[[(3S)-1-(2-cyanoethyl)-3-piperidyl]methoxy]imidazo[1,2-a]pyridin-3-yl]-N-cyclopropyl-2-(difluoromethoxy)-6-methoxy-benzamide, N-cyclopropyl-2-(difluoromethoxy)-4-[7-[3-[(2R,6S)-2,6-dimethyl-1-piperidyl]propoxy]imidazo[1,2-a]pyridin-3-yl]-6-methoxy-benzamide, 2-(difluoromethoxy)-N-[(1S,2R)-2-hydroxycyclobutyl]-6-methoxy-4-[7-[3-(1-piperidyl)propoxy]imidazo[1,2-a]pyridin-3-yl]benzamide, 2-(difluoromethoxy)-N-[(1R,2S)-2-hydroxycyclobutyl]-6-methoxy-4-[7-[3-(1-piperidyl)propoxy]imidazo[1,2-a]pyridin-3-yl]benzamide,

[2-(difluoromethoxy)-6-methoxy-4-[7-[3-(1-piperidyl)propoxy]imidazo[1,2-a]pyridin-3-yl]phenyl]-[3-hydroxy-3-(trifluoromethyl)azetidin-1-yl]methanone, 2-[1-[2-(difluoromethoxy)-6-methoxy-4-[7-[3-(1-piperidyl)propoxy]imidazo[1,2-a]pyridin-3-yl]benzoyl]-3-hydroxy-azetidin-3-yl]acetonitrile, N-(cyanomethyl)-2-(difluoromethoxy)-6-methoxy-4-[7-[3-(1-piperidyl)propoxy]imidazo[1,2-a]pyridin-3-yl]benzamide, 1-[2-(difluoromethoxy)-6-methoxy-4-[7-[3-(1-piperidyl)propoxy]imidazo[1,2-a]pyridin-3-yl]benzoyl]azetidine-3-carbonitrile,

[2-(difluoromethoxy)-6-methoxy-4-[7-[3-(1-piperidyl)propoxy]imidazo[1,2-a]pyridin-3-yl]phenyl]-[3-(difluoromethyl)-3-hydroxy-azetidin-1-yl]methanone, 2-(difluoromethoxy)-N-[(1R,2R)-2-hydroxycyclobutyl]-6-methoxy-4-[7-[3-(1-piperidyl)propoxy]imidazo[1,2-a]pyridin-3-yl]benzamide, 2-(difluoromethoxy)-N-[(1S,2S)-2-hydroxycyclobutyl]-6-methoxy-4-[7-[3-(1-piperidyl)propoxy]imidazo[1,2-a]pyridin-3-yl]benzamide, N-cyclopropyl-2-(difluoromethoxy)-4-[7-[3-[4-fluoro-4-(hydroxymethyl)-1-piperidyl]propoxy]imidazo[1,2-a]pyridin-3-yl]-6-methoxy-benzamide, 1-[3-[3-[4-(cyclopropylcarbamoyl)-3-(difluoromethoxy)-5-methoxy-phenyl]imidazo[1,2-a]pyridin-7-yl]oxypropyl]-4-fluoro-piperidine-4-carboxamide, N-cyclopropyl-2-(difluoromethoxy)-4-[7-[3-(3-hydroxy-3-methyl-azetidin-1-yl)propoxy]imidazo[1,2-a]pyridin-3-yl]-6-methoxy-benzamide, ethyl 1-[3-[3-[4-(cyclopropylcarbamoyl)-3-(difluoromethoxy)-5-methoxy-phenyl]imidazo[1,2-a]pyridin-7-yl]oxypropyl]-4-fluoro-piperidine-4-carboxylate, 4-[7-(3-amino-2,2-difluoro-propoxy)imidazo[1,2-a]pyridin-3-yl]-N-cyclopropyl-2-(difluoromethoxy)-6-methoxy-benzamide, methyl N-[3-[3-[4-(cyclopropylcarbamoyl)-3-(difluoromethoxy)-5-methoxy-phenyl]imidazo[1,2-a]pyridin-7-yl]oxy-2,2-difluoro-propyl]carbamate, 1-[3-[3-[4-(cyclopropylcarbamoyl)-3-(difluoromethoxy)-5-methoxy-phenyl]imidazo[1,2-a]pyridin-7-yl]oxypropyl]-4-fluoro-piperidine-4-carboxylic acid, N-cyclopropyl-2-(difluoromethoxy)-6-methoxy-4-[7-[2-(2-pyridylamino)ethoxy]imidazo[1,2-a]pyridin-3-yl]benzamide, N-cyclopropyl-2-(difluoromethoxy)-6-methoxy-4-[7-[2-(pyrimidin-2-ylamino)ethoxy]imidazo[1,2-a]pyridin-3-yl]benzamide, N-cyclopropyl-2-(difluoromethoxy)-6-methoxy-4-[7-[2-(pyrimidin-4-ylamino)ethoxy]imidazo[1,2-a]pyridin-3-yl]benzamide, N-cyclopropyl-2-(difluoromethoxy)-4-[7-[[(3R)-1-(2-hydroxyethyl)-3-piperidyl]methoxy]imidazo[1,2-a]pyridin-3-yl]-6-methoxy-benzamide, N-cyclopropyl-4-[7-[2-[(2,2-difluoroacetyl)amino]ethoxy]imidazo[1,2-a]pyridin-3-yl]-2-(difluoromethoxy)-6-methoxy-benzamide, N-cyclopropyl-2-(difluoromethoxy)-4-[7-[(3-hydroxy-1-isopropyl-pyrrolidin-3-yl)methoxy]imidazo[1,2-a]pyridin-3-yl]-6-methoxy-benzamide, N-cyclopropyl-2-(difluoromethoxy)-4-[7-[[(3R,4S)-4-hydroxy-3-piperidyl]methoxy]imidazo[1,2-a]pyridin-3-yl]-6-methoxy-benzamide, N-cyclopropyl-2-(difluoromethoxy)-4-[7-[[(3S,4R)-4-hydroxy-3-piperidyl]methoxy]imidazo[1,2-a]pyridin-3-yl]-6-methoxy-benzamide, N-cyclopropyl-2-(difluoromethoxy)-4-[7-[3-(1,1-dioxo-1,4-thiazinan-4-yl)-2-hydroxy-propoxy]imidazo[1,2-a]pyridin-3-yl]-6-methoxy-benzamide, N-cyclopropyl-2-(difluoromethoxy)-4-[7-[2-hydroxy-3-[3-hydroxy-3-(trifluoromethyl)azetidin-1-yl]propoxy]imidazo[1,2-a]pyridin-3-yl]-6-methoxy-benzamide, N-cyclopropyl-2-(difluoromethoxy)-4-[7-[2-hydroxy-3-[(3R)-3-hydroxypyrrolidin-1-yl]propoxy]imidazo[1,2-a]pyridin-3-yl]-6-methoxy-benzamide, ethyl 1-[3-[3-[4-(cyclopropylcarbamoyl)-3-(difluoromethoxy)-5-methoxy-phenyl]imidazo[1,2-a]pyridin-7-yl]oxypropyl]piperidine-4-carboxylate, ethyl 1-[3-[3-[4-(cyclopropylcarbamoyl)-3-(difluoromethoxy)-5-methoxy-phenyl]imidazo[1,2-a]pyridin-7-yl]oxypropyl]-4-phenyl-piperidine-4-carboxylate, N-cyclopropyl-2-(difluoromethoxy)-4-[7-[2-hydroxy-3-(4-hydroxy-1-piperidyl)propoxy]imidazo[1,2-a]pyridin-3-yl]-6-methoxy-benzamide, ethyl 1-[3-[3-[4-(cyclopropylcarbamoyl)-3-(difluoromethoxy)-5-methoxy-phenyl]imidazo[1,2-a]pyridin-7-yl]oxypropyl]-4-methyl-piperidine-4-carboxylate, ethyl 1-[3-[3-[4-(cyclopropylcarbamoyl)-3-(difluoromethoxy)-5-methoxy-phenyl]imidazo[1,2-a]pyridin-7-yl]oxypropyl]-4-hydroxy-piperidine-4-carboxylate, ethyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]-4-methyl-piperidine-4-carboxylate, ethyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]-4-hydroxy-piperidine-4-carboxylate,
ethyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]-4-fluoro-piperidine-4-carboxylate,
ethyl 1-[3-[3-[4-(cyclopropylcarbamoyl)-3-(difluoromethoxy)-5-methoxy-phenyl]imidazo[1,2-a]pyridin-7-yl]oxypropyl]-3-methyl-azetidine-3-carboxylate,
methyl (2S)-4-[3-[3-[4-(cyclopropylcarbamoyl)-3-(difluoromethoxy)-5-methoxy-phenyl]imidazo[1,2-a]pyridin-7-yl]oxy-2-hydroxy-propyl]morpholine-2-carboxylate,
methyl (2S)-4-[2-[3-[4-(cyclopropylcarbamoyl)-3-(difluoromethoxy)-5-methoxy-phenyl]imidazo[1,2-a]pyridin-7-yl]oxyethyl]morpholine-2-carboxylate,
ethyl 1-[2-[3-[4-(cyclopropylcarbamoyl)-3-(difluoromethoxy)-5-methoxy-phenyl]imidazo[1,2-a]pyridin-7-yl]oxyethyl]-4-fluoro-piperidine-4-carboxylate,
tert-butyl 1-[3-[3-[4-(cyclopropylcarbamoyl)-3-(difluoromethoxy)-5-methoxy-phenyl]imidazo[1,2-a]pyridin-7-yl]oxypropyl]azetidine-3-carboxylate,
ethyl 1-[2-[3-[4-(cyclopropylcarbamoyl)-3-(difluoromethoxy)-5-methoxy-phenyl]imidazo[1,2-a]pyridin-7-yl]oxyethyl]piperidine-3-carboxylate,
methyl 1-[2-[3-[4-(cyclopropylcarbamoyl)-3-(difluoromethoxy)-5-methoxy-phenyl]imidazo[1,2-a]pyridin-7-yl]oxyethyl]azetidine-3-carboxylate,
tert-butyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]azetidine-3-carboxylate,
ethyl 1-[3-[3-[4-(cyclopropylcarbamoyl)-3-(difluoromethoxy)-5-methoxy-phenyl]imidazo[1,2-a]pyridin-7-yl]oxypropyl]piperidine-3-carboxylate,
2-[3-[4-(cyclopropylcarbamoyl)-3-(difluoromethoxy)-5-methoxy-phenyl]imidazo[1,2-a]pyridin-7-yl]oxyacetic acid, and
ethyl 2-[2-[[3-[4-(cyclopropylcarbamoyl)-3-(difluoromethoxy)-5-methoxy-phenyl]imidazo[1,2-a]pyridin-7-yl]oxymethyl]-1-piperidyl]acetate.

In one embodiment, the compound of the invention is according to Formula I, wherein the compound is selected from:
N-cyclopropyl-2-(difluoromethoxy)-6-methoxy-4-(7-tetrahydropyran-4-yloxyimidazo[1,2-a]pyridin-3-yl)benzamide,
N-cyclopropyl-2-(difluoromethoxy)-6-methoxy-4-[7-[(1-methyl-3-piperidyl)oxy]imidazo[1,2-a]pyridin-3-yl]benzamide,
N-cyclopropyl-2-(difluoromethoxy)-6-methoxy-4-[7-(2-methoxy-2-methyl-propoxy)imidazo[1,2-a]pyridin-3-yl]benzamide,
2,6-dimethoxy-4-(7-tetrahydropyran-4-yloxyimidazo[1,2-a]pyridin-3-yl)-N-(2,2,2-trifluoroethyl)benzamide,
2,6-dimethoxy-4-[7-[(1-methyl-3-piperidyl)oxy]imidazo[1,2-a]pyridin-3-yl]-N-(2,2,2-trifluoroethyl)benzamide,
N-cyclopropyl-2-(difluoromethoxy)-4-[7-[2-(dimethylamino)ethoxy]imidazo[1,2-a]pyridin-3-yl]-6-methoxy-benzamide,
N-cyclopropyl-2-(difluoromethoxy)-6-methoxy-4-[7-[(1-methyl-4-piperidyl)oxy]imidazo[1,2-a]pyridin-3-yl]benzamide,
N-cyclopropyl-2-(difluoromethoxy)-6-methoxy-4-[7-(2-morpholinoethoxy)imidazo[1,2-a]pyridin-3-yl]benzamide,
N-cyclopropyl-2-(difluoromethoxy)-6-methoxy-4-[7-[2-(4-methylpiperazin-1-yl)ethoxy]imidazo[1,2-a]pyridin-3-yl]benzamide,
N-cyclopropyl-2-(difluoromethoxy)-6-methoxy-4-[7-[2-(1-piperidyl)ethoxy]imidazo[1,2-a]pyridin-3-yl]benzamide,
N-cyclopropyl-2-(difluoromethoxy)-6-methoxy-4-[7-(2-methyl-2-morpholino-propoxy)imidazo[1,2-a]pyridin-3-yl]benzamide,
N-cyclopropyl-2-(difluoromethoxy)-6-methoxy-4-[7-(1-methyl-2-morpholino-ethoxy)imidazo[1,2-a]pyridin-3-yl]benzamide,
N-cyclopropyl-2-(difluoromethoxy)-4-[7-[3-(dimethylamino)propoxy]imidazo[1,2-a]pyridin-3-yl]-6-methoxy-benzamide,
N-cyclopropyl-2-(difluoromethoxy)-6-methoxy-4-[7-[(1-methylazetidin-3-yl)methoxy]imidazo[1,2-a]pyridin-3-yl]benzamide,
N-cyclopropyl-2-(difluoromethoxy)-6-methoxy-4-[7-(1-methylpyrrolidin-3-yl)oxyimidazo[1,2-a]pyridin-3-yl]benzamide,
N-cyclopropyl-2-(difluoromethoxy)-6-methoxy-4-[7-[3-(1-piperidyl)propoxy]imidazo[1,2-a]pyridin-3-yl]benzamide,
N-cyclopropyl-2-(difluoromethoxy)-6-methoxy-4-[7-[2-(1-methylpyrrolidin-2-yl)ethoxy]imidazo[1,2-a]pyridin-3-yl]benzamide,
6-[7-[2-(dimethylamino)ethoxy]imidazo[1,2-a]pyridin-3-yl]-8-methoxy-2-(2,2,2-trifluoroethyl)-3,4-dihydroisoquinolin-1-one,
N-cyclopropyl-2-(difluoromethoxy)-6-methoxy-4-[7-[(3-methylimidazol-4-yl)methoxy]imidazo[1,2-a]pyridin-3-yl]benzamide,
N-cyclopropyl-2-(difluoromethoxy)-6-methoxy-4-[7-(2-pyrrolidin-1-ylethoxy)imidazo[1,2-a]pyridin-3-yl]benzamide,
N-cyclopropyl-2-(difluoromethoxy)-6-methoxy-4-[7-(3-morpholinopropoxy)imidazo[1,2-a]pyridin-3-yl]benzamide,
N-cyclopropyl-2-(difluoromethoxy)-4-[7-[2-(1,1-dioxo-1,4-thiazinan-4-yl)ethoxy]imidazo[1,2-a]pyridin-3-yl]-6-methoxy-benzamide,
N-cyclopropyl-2-(difluoromethoxy)-6-methoxy-4-[7-[(1-methyl-2-piperidyl)methoxy]imidazo[1,2-a]pyridin-3-yl]benzamide,
N-cyclopropyl-2-(difluoromethoxy)-6-methoxy-4-[7-[2-(1-methyl-2-piperidyl)ethoxy]imidazo[1,2-a]pyridin-3-yl]benzamide,
N-cyclopropyl-2-(difluoromethoxy)-6-methoxy-4-[7-[(1-methyl-4-piperidyl)methoxy]imidazo[1,2-a]pyridin-3-yl]benzamide,
N-cyclopropyl-2-(difluoromethoxy)-6-methoxy-4-[7-[(1-methyl-5-oxo-pyrrolidin-3-yl)methoxy]imidazo[1,2-a]pyridin-3-yl]benzamide,
4-[7-(2-acetamidoethoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-[(1-methylpyrrolidin-2-yl)methoxy]imidazo[1,2-a]pyridin-3-yl]benzamide,
N-cyclopropyl-2-(difluoromethoxy)-6-methoxy-4-[7-(1-methylazetidin-3-yl)oxyimidazo[1,2-a]pyridin-3-yl]benzamide,
N-cyclopropyl-2-(difluoromethoxy)-4-[7-(2-hydroxyethoxy)imidazo[1,2-a]pyridin-3-yl]-6-methoxy-benzamide,
4-[7-(2-cyanoethoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(oxazol-2-ylmethoxy)imidazo[1,2-a]pyridin-3-yl]benzamide,
N-cyclopropyl-2-(difluoromethoxy)-6-methoxy-4-[7-(oxazol-5-ylmethoxy)imidazo[1,2-a]pyridin-3-yl]benzamide,
4-[7-(2-cyano-2-methyl-propoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(oxetan-2-ylmethoxy)imidazo[1,2-a]pyridin-3-yl]benzamide,
N-cyclopropyl-2-(difluoromethoxy)-4-[7-(2-fluoroethoxy)imidazo[1,2-a]pyridin-3-yl]-6-methoxy-benzamide,
N-cyclopropyl-2-(difluoromethoxy)-4-[7-[2-(ethylamino)ethoxy]imidazo[1,2-a]pyridin-3-yl]-6-methoxy-benzamide,
N-cyclopropyl-2-(difluoromethoxy)-6-methoxy-4-[7-[2-(2-methoxyethoxy)ethoxy]imidazo[1,2-a]pyridin-3-yl]benzamide,
8-methoxy-6-[7-[(1-methylazetidin-3-yl)methoxy]imidazo[1,2-a]pyridin-3-yl]-2-(2,2,2-trifluoroethyl)-3,4-dihydroisoquinolin-1-one,
8-methoxy-6-[7-[2-(1-piperidyl)ethoxy]imidazo[1,2-a]pyridin-3-yl]-2-(2,2,2-trifluoroethyl)-3,4-dihydroisoquinolin-1-one,
6-[7-[2-(1,1-dioxo-1,4-thiazinan-4-yl)ethoxy]imidazo[1,2-a]pyridin-3-yl]-8-methoxy-2-(2,2,2-trifluoroethyl)-3,4-dihydroisoquinolin-1-one,
N-cyclopropyl-4-[7-[(2,2-difluorocyclopropyl)methoxy]imidazo[1,2-a]pyridin-3-yl]-2-(difluoromethoxy)-6-methoxy-benzamide,
N-cyclopropyl-2-(difluoromethoxy)-6-methoxy-4-[7-(3-pyridylmethoxy)imidazo[1,2-a]pyridin-3-yl]benzamide,
N-cyclopropyl-2-(difluoromethoxy)-6-methoxy-4-[7-[(2-methylpyrazol-3-yl)methoxy]imidazo[1,2-a]pyridin-3-yl]benzamide,
N-cyclopropyl-2-(difluoromethoxy)-6-methoxy-4-[7-(2,2,2-trifluoro-1-methyl-ethoxy)imidazo[1,2-a]pyridin-3-yl]benzamide,
N-cyclopropyl-2-(difluoromethoxy)-6-methoxy-4-[7-(thiazol-4-ylmethoxy)imidazo[1,2-a]pyridin-3-yl]benzamide,
N-cyclopropyl-2-(difluoromethoxy)-6-methoxy-4-[7-(thiazol-2-ylmethoxy)imidazo[1,2-a]pyridin-3-yl]benzamide,
N-cyclopropyl-2-(difluoromethoxy)-6-methoxy-4-[7-(tetrahydropyran-2-ylmethoxy)imidazo[1,2-a]pyridin-3-yl]benzamide,
N-cyclopropyl-2-(difluoromethoxy)-6-methoxy-4-[7-(tetrahydropyran-4-ylmethoxy)imidazo[1,2-a]pyridin-3-yl]benzamide,
N-cyclopropyl-2-(difluoromethoxy)-4-[7-[[(2R)-1,4-dioxan-2-yl]methoxy]imidazo[1,2-a]pyridin-3-yl]-6-methoxy-benzamide,
N-cyclopropyl-4-[7-[2-(dimethylamino)ethoxy]imidazo[1,2-a]pyridin-3-yl]-2-fluoro-6-methoxy-benzamide,
N-cyclopropyl-4-[7-[(3,3-difluorocyclobutyl)methoxy]imidazo[1,2-a]pyridin-3-yl]-2-(difluoromethoxy)-6-methoxy-benzamide,
6-[7-[2-(dimethylamino)ethoxy]imidazo[1,2-a]pyridin-3-yl]-2-ethyl-8-methoxy-3,4-dihydroisoquinolin-1-one,
2-(2,2-difluoroethyl)-6-[7-[2-(dimethylamino)ethoxy]imidazo[1,2-a]pyridin-3-yl]-8-methoxy-3,4-dihydroisoquinolin-1-one,
8-methoxy-6-[7-(3-morpholinopropoxy)imidazo[1,2-a]pyridin-3-yl]-2-(2,2,2-trifluoroethyl)-3,4-dihydroisoquinolin-1-one,
N-cyclopropyl-4-[7-[2-(dimethylamino)ethoxy]imidazo[1,2-a]pyridin-3-yl]-2-(2-ethoxyethoxy)-6-methoxy-benzamide,
methyl 1-[[3-[4-(cyclopropylcarbamoyl)-3-(difluoromethoxy)-5-methoxy-phenyl]imidazo[1,2-a]pyridin-7-yl]oxymethyl]cyclopropanecarboxylate,
N-cyclopropyl-2-(difluoromethoxy)-6-methoxy-4-(7-norbornan-2-yloxyimidazo[1,2-a]pyridin-3-yl)benzamide,
N-cyclopropyl-2-(difluoromethoxy)-6-methoxy-4-[7-(tetrahydropyran-3-ylmethoxy)imidazo[1,2-a]pyridin-3-yl]benzamide,
N-cyclopropyl-2-(difluoromethoxy)-6-methoxy-4-[7-(oxazol-4-ylmethoxy)imidazo[1,2-a]pyridin-3-yl]benzamide,
4-[7-(cyclopentylmethoxy)imidazo[1,2-a]pyridin-3-yl]-N-cyclopropyl-2-(difluoromethoxy)-6-methoxy-benzamide,
N-cyclopropyl-4-[7-(3,3-difluorocyclopentoxy)imidazo[1,2-a]pyridin-3-yl]-2-(difluoromethoxy)-6-methoxy-benzamide,
N-cyclopropyl-2-(difluoromethoxy)-6-methoxy-4-[7-[2-(2-oxopyrrolidin-1-yl)ethoxy]imidazo[1,2-a]pyridin-3-yl]benzamide,
N-cyclopropyl-2-(difluoromethoxy)-6-methoxy-4-[7-(2-tetrahydropyran-4-ylethoxy)imidazo[1,2-a]pyridin-3-yl]benzamide,
N-cyclopropyl-2-(difluoromethoxy)-4-[7-[2-[2-(dimethylamino)ethoxy]ethoxy]imidazo[1,2-a]pyridin-3-yl]-6-methoxy-benzamide,
N-cyclopropyl-2-(difluoromethoxy)-4-[7-(2,2-dimethylpropoxy)imidazo[1,2-a]pyridin-3-yl]-6-methoxy-benzamide,
2-[6-[7-[2-(dimethylamino)ethoxy]imidazo[1,2-a]pyridin-3-yl]-8-methoxy-1-oxo-3,4-dihydroisoquinolin-2-yl]acetonitrile,
4-(7-benzyloxyimidazo[1,2-a]pyridin-3-yl)-N-cyclopropyl-2-(difluoromethoxy)-6-methoxy-benzamide,
4-[7-(cyclohexylmethoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(2-methoxyethoxy)imidazo[1,2-a]pyridin-3-yl]benzamide,
4-[7-(cyclobutylmethoxy)imidazo[1,2-a]pyridin-3-yl]-N-cyclopropyl-2-(difluoromethoxy)-6-methoxy-benzamide,
N-cyclopropyl-2-(difluoromethoxy)-4-[7-(2-ethoxyethoxy)imidazo[1,2-a]pyridin-3-yl]-6-methoxy-benzamide,
N-cyclopropyl-2-(difluoromethoxy)-4-[7-[2-(2-hydroxyethoxy)ethoxy]imidazo[1,2-a]pyridin-3-yl]-6-methoxy-benzamide,
N-cyclopropyl-2-(difluoromethoxy)-4-[7-(3-hydroxy-2,2-dimethyl-propoxy)imidazo[1,2-a]pyridin-3-yl]-6-methoxy-benzamide,
N-cyclopropyl-4-[7-[(3,3-difluorocyclopentyl)methoxy]imidazo[1,2-a]pyridin-3-yl]-2-(difluoromethoxy)-6-methoxy-benzamide,
N-cyclopropyl-4-[7-[2-(3,3-difluorocyclobutyl)ethoxy]imidazo[1,2-a]pyridin-3-yl]-2-(difluoromethoxy)-6-methoxy-benzamide,
N-cyclopropyl-4-[7-(4,4-difluorocyclohexoxy)imidazo[1,2-a]pyridin-3-yl]-2-(difluoromethoxy)-6-methoxy-benzamide,
N-cyclopropyl-2-(difluoromethoxy)-4-[7-[2-(diisopropylamino)ethoxy]imidazo[1,2-a]pyridin-3-yl]-6-methoxy-benzamide,
N-cyclopropyl-2-(difluoromethoxy)-6-methoxy-4-[7-[[(2S)-1-methylpyrrolidin-2-yl]methoxy]imidazo[1,2-a]pyridin-3-yl]benzamide,
N-cyclopropyl-4-[7-[[(2R)-1-(2,2-difluoroethyl)pyrrolidin-2-yl]methoxy]imidazo[1,2-a]pyridin-3-yl]-2-(difluoromethoxy)-6-methoxy-benzamide, N-cyclopropyl-2-(difluoromethoxy)-6-methoxy-4-[7-[[(2R)-1-methylpyrrolidin-2-yl]methoxy]imidazo[1,2-a]pyridin-3-yl]benzamide, N-cyclopropyl-2-(difluoromethoxy)-6-methoxy-4-[7-[(4-methylmorpholin-2-yl)methoxy]imidazo[1,2-a]pyridin-3-yl]benzamide, N-cyclopropyl-2-(difluoromethoxy)-4-[7-[(1-ethyl-2-piperidyl)methoxy]imidazo[1,2-a]pyridin-3-yl]-6-methoxy-benzamide, 8-methoxy-6-[7-[(2-methylpyrazol-3-yl)methoxy]imidazo[1,2-a]pyridin-3-yl]-2-(2,2,2-trifluoroethyl)-3,4-dihydroisoquinolin-1-one, 8-methoxy-6-[7-[(3-methylimidazol-4-yl)methoxy]imidazo[1,2-a]pyridin-3-yl]-2-(2,2,2-trifluoroethyl)-3,4-dihydroisoquinolin-1-one, 6-[7-[[(2R)-1,4-dioxan-2-yl]methoxy]imidazo[1,2-a]pyridin-3-yl]-8-methoxy-2-(2,2,2-trifluoroethyl)-3,4-dihydroisoquinolin-1-one, tert-butyl 2-[[3-[4-(cyclopropylcarbamoyl)-3-(difluoromethoxy)-5-methoxy-phenyl]imidazo[1,2-a]pyridin-7-yl]oxymethyl]azetidine-1-carboxylate, 8-methoxy-6-[7-(2-morpholinoethoxy)imidazo[1,2-a]pyridin-3-yl]-2-(2,2,2-trifluoroethyl)-3,4-dihydroisoquinolin-1-one, N-cyclopropyl-2-(difluoromethoxy)-6-methoxy-4-[7-[(3-methyloxetan-3-yl)methoxy]imidazo[1,2-a]pyridin-3-yl]benzamide, N-cyclopropyl-4-[7-(2,2-difluoroethoxy)imidazo[1,2-a]pyridin-3-yl]-2-(difluoromethoxy)-6-methoxy-benzamide, N-cyclopropyl-2-(difluoromethoxy)-6-methoxy-4-[7-(2,2,2-trifluoroethoxy)imidazo[1,2-a]pyridin-3-yl]benzamide, N-cyclopropyl-2-(difluoromethoxy)-6-methoxy-4-[7-(tetrahydrofuran-3-ylmethoxy)imidazo[1,2-a]pyridin-3-yl]benzamide, N-cyclopropyl-2-(difluoromethoxy)-6-methoxy-4-[7-(tetrahydrofuran-2-ylmethoxy)imidazo[1,2-a]pyridin-3-yl]benzamide, N-cyclopropyl-2-(difluoromethoxy)-6-methoxy-4-[7-(pyrimidin-2-ylmethoxy)imidazo[1,2-a]pyridin-3-yl]benzamide, N-cyclopropyl-2-(difluoromethoxy)-6-methoxy-4-[7-(thiazol-5-ylmethoxy)imidazo[1,2-a]pyridin-3-yl]benzamide, N-cyclopropyl-4-[7-(cyclopropylmethoxy)imidazo[1,2-a]pyridin-3-yl]-2-(difluoromethoxy)-6-methoxy-benzamide, N-cyclopropyl-2-(difluoromethoxy)-6-methoxy-4-[7-[(1-methylcyclopropyl)methoxy]imidazo[1,2-a]pyridin-3-yl]benzamide, N-cyclopropyl-2-(difluoromethoxy)-4-[7-(1,4-dioxan-2-ylmethoxy)imidazo[1,2-a]pyridin-3-yl]-6-methoxy-benzamide, N-cyclopropyl-2-(difluoromethoxy)-6-methoxy-4-[7-[(5-oxopyrrolidin-2-yl)methoxy]imidazo[1,2-a]pyridin-3-yl]benzamide, N-cyclopropyl-2-(difluoromethoxy)-4-[7-[2-(dimethylamino)-2-oxo-ethoxy]imidazo[1,2-a]pyridin-3-yl]-6-methoxy-benzamide, N-cyclopropyl-2-(difluoromethoxy)-6-methoxy-4-[7-[(1-methylimidazol-4-yl)methoxy]imidazo[1,2-a]pyridin-3-yl]benzamide, N-cyclopropyl-2-(difluoromethoxy)-6-methoxy-4-[7-[(5-oxopyrrolidin-3-yl)methoxy]imidazo[1,2-a]pyridin-3-yl]benzamide, N-cyclopropyl-2-(difluoromethoxy)-6-methoxy-4-[7-(4-pyridylmethoxy)imidazo[1,2-a]pyridin-3-yl]benzamide, 4-[7-(2-amino-2-methyl-propoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(2-pyridylmethoxy)imidazo[1,2-a]pyridin-3-yl]benzamide, N-cyclopropyl-2-(difluoromethoxy)-4-[7-[2-(dimethylamino)-2-methyl-propoxy]imidazo[1,2-a]pyridin-3-yl]-6-methoxy-benzamide, N-cyclopropyl-4-[7-[2-(diethylamino)ethoxy]imidazo[1,2-a]pyridin-3-yl]-2-(difluoromethoxy)-6-methoxy-benzamide, 4-[7-[(3-aminocyclobutyl)methoxy]imidazo[1,2-a]pyridin-3-yl]-N-cyclopropyl-2-(difluoromethoxy)-6-methoxy-benzamide, 4-[7-(azetidin-2-ylmethoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[(1-methylimidazol-2-yl)methoxy]imidazo[1,2-a]pyridin-3-yl]benzamide, N-cyclopropyl-2-(difluoromethoxy)-6-methoxy-4-[7-[[(2R)-1-methyl-2-piperidyl]methoxy]imidazo[1,2-a]pyridin-3-yl]benzamide, 4-[7-[2-(azetidin-1-yl)ethoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(morpholin-3-ylmethoxy)imidazo[1,2-a]pyridin-3-yl]benzamide, N-cyclopropyl-2-(difluoromethoxy)-4-[7-[2-(2-hydroxyethylamino)ethoxy]imidazo[1,2-a]pyridin-3-yl]-6-methoxy-benzamide, 4-[7-(3-aminopropoxy)imidazo[1,2-a]pyridin-3-yl]-N-cyclopropyl-2-(difluoromethoxy)-6-methoxy-benzamide, 4-[7-[[1-(aminomethyl)cyclobutyl]methoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[2-(methylamino)ethoxy]imidazo[1,2-a]pyridin-3-yl]benzamide, 4-[7-(2-aminoethoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(2-piperidylmethoxy)imidazo[1,2-a]pyridin-3-yl]benzamide, N-cyclopropyl-2-(difluoromethoxy)-4-[7-[[(2S)-1,4-dioxan-2-yl]methoxy]imidazo[1,2-a]pyridin-3-yl]-6-methoxy-benzamide, 4-[7-(2-amino-3-methyl-butoxy)imidazo[1,2-a]pyridin-3-yl]-N-cyclopropyl-2-(difluoromethoxy)-6-methoxy-benzamide, 8-methoxy-6-[7-[2-(1-methylpyrrolidin-2-yl)ethoxy]imidazo[1,2-a]pyridin-3-yl]-2-(2,2,2-trifluoroethyl)-3,4-dihydroisoquinolin-1-one, 8-methoxy-6-[7-(2-pyrrolidin-1-ylethoxy)imidazo[1,2-a]pyridin-3-yl]-2-(2,2,2-trifluoroethyl)-3,4-dihydroisoquinolin-1-one, 8-methoxy-6-[7-[[(2R)-1-methylpyrrolidin-2-yl]methoxy]imidazo[1,2-a]pyridin-3-yl]-2-(2,2,2-trifluoroethyl)-3,4-dihydroisoquinolin-1-one, 8-methoxy-6-[7-(oxetan-2-ylmethoxy)imidazo[1,2-a]pyridin-3-yl]-2-(2,2,2-trifluoroethyl)-3,4-dihydroisoquinolin-1-one, 8-methoxy-6-[7-(oxazol-5-ylmethoxy)imidazo[1,2-a]pyridin-3-yl]-2-(2,2,2-trifluoroethyl)-3,4-dihydroisoquinolin-1-one, 8-methoxy-6-[7-[(4-methylmorpholin-2-yl)methoxy]imidazo[1,2-a]pyridin-3-yl]-2-(2,2,2-trifluoroethyl)-3,4-dihydroisoquinolin-1-one, 6-[7-[2-(diethylamino)ethoxy]imidazo[1,2-a]pyridin-3-yl]-8-methoxy-2-(2,2,2-trifluoroethyl)-3,4-dihydroisoquinolin-1-one, N-cyclopropyl-2-(difluoromethoxy)-6-methoxy-4-[7-[(1-methylsulfonyl-2-piperidyl)methoxy]imidazo[1,2-a]pyridin-3-yl]benzamide, methyl 2-[[3-[4-(cyclopropylcarbamoyl)-3-(difluoromethoxy)-5-methoxy-phenyl]imidazo[1,2-a]pyridin-7-yl]oxymethyl]piperidine-1-carboxylate, 4-[7-(2-aminobutoxy)imidazo[1,2-a]pyridin-3-yl]-N-cyclopropyl-2-(difluoromethoxy)-6-methoxy-benzamide, 4-[7-[(2S)-2-amino-4-methyl-pentoxy]imidazo[1,2-a]pyridin-3-yl]-N-cyclopropyl-2-(difluoromethoxy)-6-methoxy-benzamide, 4-[7-[(2S)-2-amino-2-cyclohexyl-ethoxy]imidazo[1,2-a]pyridin-3-yl]-N-cyclopropyl-2-(difluoromethoxy)-6-methoxy-benzamide, 4-[7-(2-amino-2-tetrahydrofuran-3-yl-ethoxy)imidazo[1,2-a]pyridin-3-yl]-N-cyclopropyl-2-(difluoromethoxy)-6-methoxy-benzamide, 4-[7-(2-amino-2-tetrahydropyran-4-yl-ethoxy)imidazo[1,2-a]pyridin-3-yl]-N-cyclopropyl-2-(difluoromethoxy)-6-methoxy-benzamide, 4-[7-(2-amino-2-tetrahydrofuran-2-yl-ethoxy)imidazo[1,2-a]pyridin-3-yl]-N-cyclopropyl-2-(difluoromethoxy)-6-methoxy-benzamide, 4-[7-(2-amino-2-cyclopropyl-ethoxy)imidazo[1,2-a]pyridin-3-yl]-N-cyclopropyl-2-(difluoromethoxy)-6-methoxy-benzamide, 4-[7-(2-aminopropoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[[(2S)-1-methyl-2-piperidyl]methoxy]imidazo[1,2-a]pyridin-3-yl]benzamide, 6-[7-[2-(dimethylamino)ethoxy]imidazo[1,2-a]pyridin-3-yl]-8-ethoxy-2-(2,2,2-trifluoroethyl)-3,4-dihydroisoquinolin-1-one, 4-[7-[(1-acetyl-2-piperidyl)methoxy]imidazo[1,2-a]pyridin-3-yl]-N-cyclopropyl-2-(difluoromethoxy)-6-methoxy-benzamide, N-cyclopropyl-2-(difluoromethoxy)-4-[7-[(1-formyl-3-piperidyl)methoxy]imidazo[1,2-a]pyridin-3-yl]-6-methoxy-benzamide, N-cyclopropyl-2-(difluoromethoxy)-6-methoxy-4-[7-(3-piperidylmethoxy)imidazo[1,2-a]pyridin-3-yl]benzamide, N-cyclopropyl-2-(difluoromethoxy)-6-methoxy-4-[7-[(1-methylpyrrolidin-3-yl)methoxy]imidazo[1,2-a]pyridin-3-yl]benzamide, N-cyclopropyl-2-(difluoromethoxy)-6-methoxy-4-[7-(2-pyridyloxy)imidazo[1,2-a]pyridin-3-yl]benzamide, N-cyclopropyl-2-(difluoromethoxy)-4-[7-[2-(dimethylamino)ethoxy]imidazo[1,2-a]pyridin-3-yl]-6-fluoro-benzamide, N-cyclopropyl-2-(difluoromethoxy)-4-[7-[2-(dimethylamino)ethoxy]imidazo[1,2-a]pyridin-3-yl]-6-(methylamino)benzamide, N-cyclopropyl-2-(difluoromethoxy)-4-[7-[(1-isopropyl-2-piperidyl)methoxy]imidazo[1,2-a]pyridin-3-yl]-6-methoxy-benzamide, N-cyclopropyl-4-[7-[[1-(2,2-difluoroethyl)-2-piperidyl]methoxy]imidazo[1,2-a]pyridin-3-yl]-2-(difluoromethoxy)-6-methoxy-benzamide, 2-(2,2-difluoroethyl)-8-(difluoromethoxy)-6-[7-[2-(dimethylamino)ethoxy]imidazo[1,2-a]pyridin-3-yl]-3,4-dihydroisoquinolin-1-one, 4-[7-(cyclobutoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(oxetan-3-yloxy)imidazo[1,2-a]pyridin-3-yl]benzamide, N-cyclopropyl-2-(difluoromethoxy)-6-methoxy-4-[7-[2-methyl-2-(methylamino)propoxy]imidazo[1,2-a]pyridin-3-yl]benzamide, N-cyclopropyl-2-(difluoromethoxy)-6-methoxy-4-[7-(pyrrolidin-2-ylmethoxy)imidazo[1,2-a]pyridin-3-yl]benzamide, 2-(difluoromethoxy)-4-[7-[2-(dimethylamino)ethoxy]imidazo[1,2-a]pyridin-3-yl]-6-fluoro-N-(2,2,2-trifluoroethyl)benzamide, N-cyclopropyl-2,6-bis(difluoromethoxy)-4-[7-[2-(dimethylamino)ethoxy]imidazo[1,2-a]pyridin-3-yl]benzamide, N-cyclopropyl-2-(difluoromethoxy)-6-methoxy-4-(7-phenoxyimidazo[1,2-a]pyridin-3-yl)benzamide, N-cyclopropyl-2-(difluoromethoxy)-6-methoxy-4-[7-[2-[2-(methoxymethyl)morpholin-4-yl]ethoxy]imidazo[1,2-a]pyridin-3-yl]benzamide, 4-(7-benzyloxyimidazo[1,2-c]pyrimidin-3-yl)-N-cyclopropyl-2-(difluoromethoxy)-6-methoxy-benzamide, N-cyclopropyl-2-(difluoromethoxy)-4-[7-[2-[(3S)-3-fluoropyrrolidin-1-yl]ethoxy]imidazo[1,2-a]pyridin-3-yl]-6-methoxy-benzamide, N-cyclopropyl-2-(difluoromethoxy)-6-methoxy-4-[7-[3-(methylamino)cyclobutoxy]imidazo[1,2-a]pyridin-3-yl]benzamide, N-cyclopropyl-2-(difluoromethoxy)-6-methoxy-4-[7-(2-oxaspiro[3.3]heptan-6-yloxy)imidazo[1,2-a]pyridin-3-yl]benzamide, N-cyclopropyl-2-(difluoromethoxy)-6-methoxy-4-(7-tetrahydrofuran-3-yloxyimidazo[1,2-a]pyridin-3-yl)benzamide, 4-[7-(3-cyanocyclobutoxy)imidazo[1,2-a]pyridin-3-yl]-N-cyclopropyl-2-(difluoromethoxy)-6-methoxy-benzamide, 2-(difluoromethoxy)-4-[7-[2-(dimethylamino)ethoxy]imidazo[1,2-a]pyridin-3-yl]-6-(methylamino)-N-(2,2,2-trifluoroethyl)benzamide, 2-(difluoromethoxy)-4-[7-[2-(dimethylamino)ethoxy]imidazo[1,2-a]pyridin-3-yl]-6-methoxy-N-(2,2,2-trifluoroethyl)benzamide, 6-[7-[2-(dimethylamino)ethoxy]imidazo[1,2-a]pyridin-3-yl]-8-(methylamino)-2-(2,2,2-trifluoroethyl)-3,4-dihydroisoquinolin-1-one, N-cyclopropyl-2-(difluoromethoxy)-6-methoxy-4-[7-[(2-methylpyrrolidin-2-yl)methoxy]imidazo[1,2-a]pyridin-3-yl]benzamide, 4-[7-[(1-aminocyclohexyl)methoxy]imidazo[1,2-a]pyridin-3-yl]-N-cyclopropyl-2-(difluoromethoxy)-6-methoxy-benzamide, 4-[7-[(3-aminooxetan-3-yl)methoxy]imidazo[1,2-a]pyridin-3-yl]-N-cyclopropyl-2-(difluoromethoxy)-6-methoxy-benzamide, 4-[7-[(1-aminocyclopropyl)methoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[(2-methyl-2-piperidyl)methoxy]imidazo[1,2-a]pyridin-3-yl]benzamide, N-cyclopropyl-2-(difluoromethoxy)-4-[7-[(1-ethylimidazol-2-yl)methoxy]imidazo[1,2-a]pyridin-3-yl]-6-methoxy-benzamide, 4-[7-[(1-aminocyclobutyl)methoxy]imidazo[1,2-a]pyridin-3-yl]-N-cyclopropyl-2-(difluoromethoxy)-6-methoxy-benzamide, N-cyclopropyl-2-(difluoromethoxy)-4-[7-[(1-isopropylimidazol-2-yl)methoxy]imidazo[1,2-a]pyridin-3-yl]-6-methoxy-benzamide, 4-[7-[(3-aminotetrahydrofuran-3-yl)methoxy]imidazo[1,2-a]pyridin-3-yl]-N-cyclopropyl-2-(difluoromethoxy)-6-methoxy-benzamide, N-cyclopropyl-2-(difluoromethoxy)-4-[7-[2-(2,6-dimethyl-morpholin-4-yl)ethoxy]imidazo[1,2-a]pyridin-3-yl]-6-methoxy-benzamide, 4-[7-[2-(3-cyanomorpholin-4-yl)ethoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[2-[2-(trifluoromethyl)morpholin-4-yl]ethoxy]imidazo[1,2-a]pyridin-3-yl]benzamide, N-cyclopropyl-2-(difluoromethoxy)-4-[7-[2-(3,3-difluoropyrrolidin-1-yl)ethoxy]imidazo[1,2-a]pyridin-3-yl]-6-methoxy-benzamide, N-cyclopropyl-2-(difluoromethoxy)-4-[7-[2-(4,4-difluoro-1-piperidyl)ethoxy]imidazo[1,2-a]pyridin-3-yl]-6-methoxy-benzamide, N-cyclopropyl-2-(difluoromethoxy)-6-methoxy-4-[7-[[1-(2,2,2-trifluoroethyl)-2-piperidyl]methoxy]imidazo[1,2-a]pyridin-3-yl]benzamide, N-cyclopropyl-2-(difluoromethoxy)-6-methoxy-4-[7-[2-[methyl(2-pyridyl)amino]ethoxy]imidazo[1,2-a]pyridin-3-yl]benzamide, N-cyclopropyl-2-(difluoromethoxy)-6-methoxy-4-[7-[2-(N-methylanilino)ethoxy]imidazo[1,2-a]pyridin-3-yl]benzamide, 8-methoxy-6-[7-[2-(methylamino)ethoxy]imidazo[1,2-a]pyridin-3-yl]-2-(2,2,2-trifluoroethyl)-3,4-dihydroisoquinolin-1-one, N-cyclopropyl-4-[7-[2-(3,3-difluoroazetidin-1-yl)ethoxy]imidazo[1,2-a]pyridin-3-yl]-2-(difluoromethoxy)-6-methoxy-benzamide, tert-butyl 3-[[3-[4-(cyclopropylcarbamoyl)-3-(difluoromethoxy)-5-methoxy-phenyl]imidazo[1,2-a]pyridin-7-yl]oxymethyl]-3-fluoro-azetidine-1-carboxylate, tert-butyl 3-[[3-[4-(cyclopropylcarbamoyl)-3-(difluoromethoxy)-5-methoxy-phenyl]imidazo[1,2-a]pyridin-7-yl]oxymethyl]-3-methyl-azetidine-1-carboxylate, N-cyclopropyl-2-(difluoromethoxy)-4-[7-[[(2S)-4,4-difluoro-1-methyl-pyrrolidin-2-yl]methoxy]imidazo[1,2-a]pyridin-3-yl]-6-methoxy-benzamide, 8-methoxy-6-[7-[[(2R)-4-methylmorpholin-2-yl]methoxy]imidazo[1,2-a]pyridin-3-yl]-2-(2,2,2-trifluoroethyl)-3,4-dihydroisoquinolin-1-one, 8-methoxy-6-[7-[[(2S)-4-methylmorpholin-2-yl]methoxy]imidazo[1,2-a]pyridin-3-yl]-2-(2,2,2-trifluoroethyl)-3,4-dihydroisoquinolin-1-one, N-cyclopropyl-2-(difluoromethoxy)-4-[7-[2-(3,3-dimethyl-morpholin-4-yl)ethoxy]imidazo[1,2-a]pyridin-3-yl]-6-methoxy-benzamide, N-cyclopropyl-2-(difluoromethoxy)-6-methoxy-4-[7-[2-(3-oxa-8-azabicyclo[3.2.1]octan-8-yl)ethoxy]imidazo[1,2-a]pyridin-3-yl]benzamide, N-cyclopropyl-2-(difluoromethoxy)-4-[7-[2-(2,2-dimethyl-morpholin-4-yl)ethoxy]imidazo[1,2-a]pyridin-3-yl]-6-methoxy-benzamide, N-cyclopropyl-2-(difluoromethoxy)-6-methoxy-4-[7-[2-(8-oxa-3-azabicyclo[3.2.1]octan-3-yl)ethoxy]imidazo[1,2-a]pyridin-3-yl]benzamide, N-cyclopropyl-4-[7-[2-(2-cyclopropylmorpholin-4-yl)ethoxy]imidazo[1,2-a]pyridin-3-yl]-2-(difluoromethoxy)-6-methoxy-benzamide, 2-cyclopropyl-8-methoxy-6-[7-(2-morpholinoethoxy)imidazo[1,2-a]pyridin-3-yl]-3,4-dihydroisoquinolin-1-one, N-cyclopropyl-2-(difluoromethoxy)-4-[7-[(2,5-dimethylpyrazol-3-yl)methoxy]imidazo[1,2-a]pyridin-3-yl]-6-methoxy-benzamide, N-cyclopropyl-2-(difluoromethoxy)-6-methoxy-4-[7-[(1-methylpyrazol-4-yl)methoxy]imidazo[1,2-a]pyridin-3-yl]benzamide, N-cyclopropyl-2-(difluoromethoxy)-6-methoxy-4-[7-[(1-methylpyrazol-3-yl)methoxy]imidazo[1,2-a]pyridin-3-yl]benzamide, N-cyclopropyl-2-(difluoromethoxy)-6-methoxy-4-[7-[(4-methylmorpholin-3-yl)methoxy]imidazo[1,2-a]pyridin-3-yl]benzamide, N-cyclopropyl-2-(difluoromethoxy)-4-[7-[2-(dimethylamino)propoxy]imidazo[1,2-a]pyridin-3-yl]-6-methoxy-benzamide, N-cyclopropyl-2-(difluoromethoxy)-4-[7-[2-(dimethylamino)butoxy]imidazo[1,2-a]pyridin-3-yl]-6-methoxy-benzamide, N-cyclopropyl-2-(difluoromethoxy)-6-methoxy-4-[7-[2-(1-methylpyrazol-4-yl)ethoxy]imidazo[1,2-a]pyridin-3-yl]benzamide, N-cyclopropyl-4-[7-[(5-cyclopropyl-1,3,4-oxadiazol-2-yl)methoxy]imidazo[1,2-a]pyridin-3-yl]-2-(difluoromethoxy)-6-methoxy-benzamide, N-cyclopropyl-2-(difluoromethoxy)-6-methoxy-4-[7-[2-[(1S,4S)-2-oxa-5-azabicyclo[2.2.1]heptan-5-yl]ethoxy]imidazo[1,2-a]pyridin-3-yl]benzamide, N-cyclopropyl-2-(difluoromethoxy)-4-[7-[(3-fluoroazetidin-3-yl)methoxy]imidazo[1,2-a]pyridin-3-yl]-6-methoxy-benzamide, N-cyclopropyl-2-(difluoromethoxy)-6-methoxy-4-[7-[(3-methylazetidin-3-yl)methoxy]imidazo[1,2-a]pyridin-3-yl]benzamide, N-cyclopropyl-2-(difluoromethoxy)-4-[7-(2-hydroxy-1,1-dimethyl-ethoxy)imidazo[1,2-a]pyridin-3-yl]-6-methoxy-benzamide, 8-methoxy-6-[7-(2-morpholinoethoxy)imidazo[1,2-a]pyridin-3-yl]-2H-isoquinolin-1-one, N-cyclopropyl-2-(difluoromethoxy)-4-[7-[2-(3,3-difluoro-1-piperidyl)ethoxy]imidazo[1,2-a]pyridin-3-yl]-6-methoxy-benzamide, N-cyclopropyl-2-(difluoromethoxy)-4-[7-[2-(3-fluoro-1-piperidyl)ethoxy]imidazo[1,2-a]pyridin-3-yl]-6-methoxy-benzamide, 4-[7-[2-(2-cyanomorpholin-4-yl)ethoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[2-(2-methylmorpholin-4-yl)ethoxy]imidazo[1,2-a]pyridin-3-yl]benzamide, 4-[7-[2-[cyanomethyl(methyl)amino]ethoxy]imidazo[1,2-a]pyridin-3-yl]-N-cyclopropyl-2-(difluoromethoxy)-6-methoxy-benzamide, 4-[7-[2-(3-cyano-1-piperidyl)ethoxy]imidazo[1,2-a]pyridin-3-yl]-N-cyclopropyl-2-(difluoromethoxy)-6-methoxy-benzamide, 8-methoxy-6-[7-(2-morpholinoethoxy)imidazo[1,2-a]pyridin-3-yl]-3,4-dihydro-2H-isoquinolin-1-one, 2-(2,2-difluoroethyl)-8-methoxy-6-[7-(2-morpholinoethoxy)imidazo[1,2-a]pyridin-3-yl]-3,4-dihydroisoquinolin-1-one, 2-(2,2-difluoroethyl)-6-[7-[[(2R)-1,4-dioxan-2-yl]methoxy]imidazo[1,2-a]pyridin-3-yl]-8-methoxy-3,4-dihydroisoquinolin-1-one, N-cyclopropyl-2-(difluoromethoxy)-4-[7-[(1,3-dimethylazetidin-3-yl)methoxy]imidazo[1,2-a]pyridin-3-yl]-6-methoxy-benzamide, 8-methoxy-6-[7-(2-morpholinoethoxy)imidazo[1,2-a]pyridin-3-yl]-2-(2,2,2-trifluoroethyl)isoquinolin-1-one, N-cyclopropyl-2-methoxy-6-methyl-4-[7-(2-morpholinoethoxy)imidazo[1,2-a]pyridin-3-yl]benzamide, N-cyclopropyl-2-(difluoromethoxy)-6-methoxy-4-[7-[2-[methyl(4-pyridyl)amino]ethoxy]imidazo[1,2-a]pyridin-3-yl]benzamide, 2-cyclopropyl-8-(difluoromethoxy)-6-[7-(2-morpholinoethoxy)imidazo[1,2-a]pyridin-3-yl]-3,4-dihydroisoquinolin-1-one, 6-[7-[[(2S)-1,4-dioxan-2-yl]methoxy]imidazo[1,2-a]pyridin-3-yl]-8-methoxy-2-(2,2,2-trifluoroethyl)-3,4-dihydroisoquinolin-1-one, N-cyclopropyl-2-(difluoromethoxy)-6-methoxy-4-[7-(pyridazin-3-ylmethoxy)imidazo[1,2-a]pyridin-3-yl]benzamide, N-cyclopropyl-2-(difluoromethoxy)-6-methoxy-4-[7-[(4-methyl-1,2,4-triazol-3-yl)methoxy]imidazo[1,2-a]pyridin-3-yl]benzamide, N-cyclopropyl-2-(difluoromethoxy)-6-methoxy-4-[7-[(3-methyl-2-oxo-oxazolidin-5-yl)methoxy]imidazo[1,2-a]pyridin-3-yl]benzamide, N-cyclopropyl-2-(difluoromethoxy)-6-methoxy-4-[7-[(3-methyl-1,2,4-oxadiazol-5-yl)methoxy]imidazo[1,2-a]pyridin-3-yl]benzamide, 2-(difluoromethoxy)-6-methoxy-4-[7-(2-morpholinoethoxy)imidazo[1,2-a]pyridin-3-yl]-N-(2,2,2-trifluoroethyl)benzamide, N-cyclopropyl-2-(difluoromethoxy)-6-methoxy-4-[7-[(5-methyl-1,2,4-oxadiazol-3-yl)methoxy]imidazo[1,2-a]pyridin-3-yl]benzamide, N-cyclopropyl-2-(difluoromethoxy)-6-methoxy-4-[7-[2-(3-methylmorpholin-4-yl)ethoxy]imidazo[1,2-a]pyridin-3-yl]benzamide, N-cyclopropyl-2-(difluoromethoxy)-6-methoxy-4-[7-[2-[(3S)-3-methylmorpholin-4-yl]ethoxy]imidazo[1,2-a]pyridin-3-yl]benzamide, N-cyclopropyl-2-(difluoromethoxy)-6-methoxy-4-[7-[2-[(3R)-3-methylmorpholin-4-yl]ethoxy]imidazo[1,2-a]pyridin-3-yl]benzamide, N-cyclopropyl-4-[7-[2-[cyclopropyl(2,2-difluoroethyl)amino]ethoxy]imidazo[1,2-a]pyridin-3-yl]-2-(difluoromethoxy)-6-methoxy-benzamide, N-cyclopropyl-4-[7-[2-[2,2-difluoroethyl(methyl)amino]ethoxy]imidazo[1,2-a]pyridin-3-yl]-2-(difluoromethoxy)-6-methoxy-benzamide, N-cyclopropyl-4-[7-[2-[2,2-difluoroethyl(2-methoxyethyl)amino]ethoxy]imidazo[1,2-a]pyridin-3-yl]-2-(difluoromethoxy)-6-methoxy-benzamide, N-cyclopropyl-2-(difluoromethoxy)-6-methoxy-4-[7-[2-[methyl(pyrimidin-2-yl)amino]ethoxy]imidazo[1,2-a]pyridin-3-yl]benzamide, N-cyclopropyl-2-(difluoromethoxy)-6-methoxy-4-[7-[2-[methyl(pyrimidin-4-yl)amino]ethoxy]imidazo[1,2-a]pyridin-3-yl]benzamide, N-cyclopropyl-2-(difluoromethoxy)-6-methoxy-4-[7-[2-[methyl(pyridazin-4-yl)amino]ethoxy]imidazo[1,2-a]pyridin-3-yl]benzamide, N-cyclopropyl-2-(difluoromethoxy)-6-methyl-4-[7-(2-morpholinoethoxy)imidazo[1,2-a]pyridin-3-yl]benzamide, 6-[7-[[(2R)-1,4-dioxan-2-yl]methoxy]imidazo[1,2-a]pyridin-3-yl]-8-methoxy-3,4-dihydro-2H-isoquinolin-1-one, 2-(difluoromethoxy)-6-methyl-4-[7-(2-morpholinoethoxy)imidazo[1,2-a]pyridin-3-yl]-N-(2,2,2-trifluoroethyl)benzamide, 6-[7-[2-(3,3-difluoroazetidin-1-yl)ethoxy]imidazo[1,2-a]pyridin-3-yl]-8-methoxy-2-(2,2,2-trifluoroethyl)-3,4-dihydroisoquinolin-1-one, 8-methoxy-6-[7-[2-[(1S,4S)-2-oxa-5-azabicyclo[2.2.1]heptan-5-yl]ethoxy]imidazo[1,2-a]pyridin-3-yl]-2-(2,2,2-trifluoroethyl)-3,4-dihydroisoquinolin-1-one, 8-methoxy-6-[7-[2-(3-oxa-8-azabicyclo[3.2.1]octan-8-yl)ethoxy]imidazo[1,2-a]pyridin-3-yl]-2-(2,2,2-trifluoroethyl)-3,4-dihydroisoquinolin-1-one, 2-(2,2-difluoroethyl)-8-(difluoromethoxy)-6-[7-(2-morpholinoethoxy)imidazo[1,2-a]pyridin-3-yl]-3,4-dihydroisoquinolin-1-one, tert-butyl 3-fluoro-3-[[3-[8-methoxy-1-oxo-2-(2,2,2-trifluoroethyl)-3,4-dihydroisoquinolin-6-yl]imidazo[1,2-a]pyridin-7-yl]oxymethyl]azetidine-1-carboxylate, tert-butyl 3-[[3-[8-methoxy-1-oxo-2-(2,2,2-trifluoroethyl)-3,4-dihydroisoquinolin-6-yl]imidazo[1,2-a]pyridin-7-yl]oxymethyl]-3-methyl-azetidine-1-carboxylate, 6-[7-[(3-fluoroazetidin-3-yl)methoxy]imidazo[1,2-a]pyridin-3-yl]-8-methoxy-2-(2,2,2-trifluoroethyl)-3,4-dihydroisoquinolin-1-one, 8-methoxy-6-[7-[(3-methylazetidin-3-yl)methoxy]imidazo[1,2-a]pyridin-3-yl]-2-(2,2,2-trifluoroethyl)-3,4-dihydroisoquinolin-1-one, 6-[7-[(3-fluoro-1-methyl-azetidin-3-yl)methoxy]imidazo[1,2-a]pyridin-3-yl]-8-methoxy-2-(2,2,2-trifluoroethyl)-3,4-dihydroisoquinolin-1-one, 6-[7-[(1,3-dimethylazetidin-3-yl)methoxy]imidazo[1,2-a]pyridin-3-yl]-8-methoxy-2-(2,2,2-trifluoroethyl)-3,4-dihydroisoquinolin-1-one, N-cyclopropyl-3-methoxy-5-[7-(2-morpholinoethoxy)imidazo[1,2-a]pyridin-3-yl]pyridine-2-carboxamide, 4-[7-(1-cyanocyclopentoxy)imidazo[1,2-a]pyridin-3-yl]-N-cyclopropyl-2-(difluoromethoxy)-6-methoxy-benzamide, 8-methoxy-6-(7-methoxyimidazo[1,2-a]pyridin-3-yl)-2-(2,2,2-trifluoroethyl)-3,4-dihydroisoquinolin-1-one, 8-methoxy-6-[7-[2-[(3S)-3-methylmorpholin-4-yl]ethoxy]imidazo[1,2-a]pyridin-3-yl]-2-(2,2,2-trifluoroethyl)-3,4-dihydroisoquinolin-1-one, 6-[7-(2-hydroxyethoxy)imidazo[1,2-a]pyridin-3-yl]-8-methoxy-2-(2,2,2-trifluoroethyl)-3,4-dihydroisoquinolin-1-one, 8-methoxy-6-[7-[2-[(3R)-3-methylmorpholin-4-yl]ethoxy]imidazo[1,2-a]pyridin-3-yl]-2-(2,2,2-trifluoroethyl)-3,4-dihydroisoquinolin-1-one, N-cyclopropyl-2-(difluoromethoxy)-6-methoxy-4-[7-(2-methoxy-1,1-dimethyl-ethoxy)imidazo[1,2-a]pyridin-3-yl]benzamide, 3-methoxy-5-[7-(2-morpholinoethoxy)imidazo[1,2-a]pyridin-3-yl]-N-(2,2,2-trifluoroethyl)pyridine-2-carboxamide, 3-methoxy-5-[7-[(2-methylpyrazol-3-yl)methoxy]imidazo[1,2-a]pyridin-3-yl]-N-(2,2,2-trifluoroethyl)pyridine-2-carboxamide, 4-[7-(1-cyano-1-methyl-ethoxy)imidazo[1,2-a]pyridin-3-yl]-N-cyclopropyl-2-(difluoromethoxy)-6-methoxy-benzamide, 6-(7-ethoxyimidazo[1,2-a]pyridin-3-yl)-8-methoxy-2-(2,2,2-trifluoroethyl)-3,4-dihydroisoquinolin-1-one, 5-[7-[[(2R)-1,4-dioxan-2-yl]methoxy]imidazo[1,2-a]pyridin-3-yl]-3-methoxy-N-(2,2,2-trifluoroethyl)pyridine-2-carboxamide, 3-[7-(2-morpholinoethoxy)imidazo[1,2-a]pyridin-3-yl]-6-(2,2,2-trifluoroethyl)-5H-pyrrolo[3,4-b]pyridin-7-one, and N-cyclopropyl-3-(difluoromethoxy)-5-[7-(2-morpholino-ethoxy)imidazo[1,2-a]pyridin-3-yl]pyridine-2-carboxamide.

In one embodiment, the compound of the invention according to Formula I is selected from
N-cyclopropyl-2-(difluoromethoxy)-4-[7-(2,2-dimethoxyethoxy)imidazo[1,2-a]pyridin-3-yl]-6-methoxy-benzamide,
6-[7-(2,2-dimethoxyethoxy)imidazo[1,2-a]pyridin-3-yl]-8-methoxy-2-(2,2,2-trifluoroethyl)-3,4-dihydroisoquinolin-1-one
ethyl 2-[3-[4-(cyclopropylcarbamoyl)-3-(difluoromethoxy)-5-methoxy-phenyl]imidazo[1,2-a]pyridin-7-yl]oxy-2-methyl-propanoate,
4-[7-(azetidin-3-ylmethoxy)imidazo[1,2-a]pyridin-3-yl]-N-cyclopropyl-2-(difluoromethoxy)-6-methoxy-benzamide,
2-[3-[4-(cyclopropylcarbamoyl)-3-(difluoromethoxy)-5-methoxy-phenyl]imidazo[1,2-a]pyridin-7-yl]oxyethyl methanesulfonate,
N-cyclopropyl-2-(difluoromethoxy)-6-methoxy-4-[7-(pyrrolidin-3-ylmethoxy)imidazo[1,2-a]pyridin-3-yl]benzamide, and
N-cyclopropyl-2-(difluoromethoxy)-6-methoxy-4-[7-(2-pyrrolidin-2-ylethoxy)imidazo[1,2-a]pyridin-3-yl]benzamide In one embodiment, the compound of the invention is according to Formula I, wherein the compound is 8-methoxy-6-[7-(2-morpholinoethoxy)imidazo[1,2-a]pyridin-3-yl]-2-(2,2,2-trifluoroethyl)-3,4-dihydroisoquinolin-1-one.

In one embodiment, the compound of the invention is according to Formula I, wherein the compound is not 8-methoxy-6-[7-(2-morpholinoethoxy)imidazo[1,2-a]pyridin-3-yl]-2-(2,2,2-trifluoroethyl)-3,4-dihydroisoquinolin-1-one.

In one embodiment, the compound of the invention is according to Formula I, wherein the compound is 6-[7-[[(2R)-1,4-dioxan-2-yl]methoxy]imidazo[1,2-a]pyridin-3-yl]-8-methoxy-2-(2,2,2-trifluoroethyl)-3,4-dihydroisoquinolin-1-one.

In one embodiment, the compound of the invention is according to Formula I, wherein the compound is not 6-[7-[[(2R)-1,4-dioxan-2-yl]methoxy]imidazo[1,2-a]pyridin-3-yl]-8-methoxy-2-(2,2,2-trifluoroethyl)-3,4-dihydroisoquinolin-1-one.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgaard 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Particularly useful are the C1 to C8 alkyl, C2-C8 alkenyl, aryl, C7-C12 substituted aryl, and $C_7$-$C_{12}$ arylalkyl esters of the compounds of the invention.

Clauses

1. A compound according to Formula I.

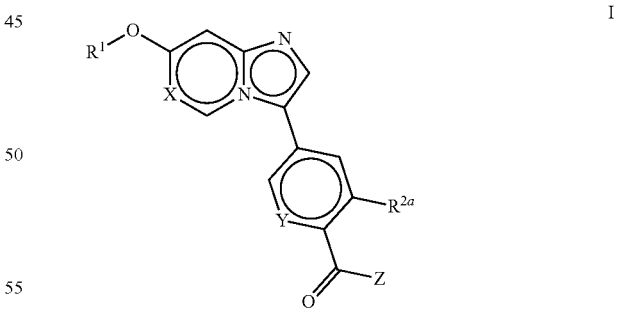

I wherein,
X is N or CH;
Y is N or $CR^{2b}$;
Z is
—$NHR^{3a}$,
N-linked 4-7 membered heterocycloalkyl further comprising zero, one, or two additional heteroatoms independently selected from N, O, and S, optionally substituted with one or more independently selected $R^{15}$ groups, or —NR³ᵇ—, wherein the N atom and R²ᵃ together with the atoms onto which they are attached form a fused 5-6 membered heterocycloalkenyl comprising one or two double bonds;

$R^1$ is
  $C_{1-8}$ alkyl optionally substituted with one or more independently selected $R^4$ groups,
  phenyl,
  $C_{3-8}$ monocyclic or bridged polycyclic cycloalkyl optionally substituted with one or more independently selected $R^5$ groups,
  4-8 membered monocyclic, spirocyclic, or bridged polycyclic heterocycloalkyl comprising one, two, or three heteroatoms independently selected from N, O, and S, which heterocycloalkyl is optionally substituted with one or more independently selected $C_{1-4}$ alkyl optionally substituted with one or more independently selected —CN or —C(=O)—$C_{1-4}$ alkoxy, or
  5-6 membered monocyclic heteroaryl comprising one, two, or three heteroatoms independently selected from N, O, and S;

$R^{2a}$ and $R^{2b}$ are independently selected from
  halo,
  $C_{1-4}$ alkyl,
  $C_{1-4}$ alkoxy optionally substituted with one or more independently selected halo or $C_{1-4}$ alkoxy, and
  —NR⁶ᵃR⁶ᵇ;

$R^{3a}$ is
  $C_{1-6}$ alkyl optionally substituted with one or more independently selected halo or —CN, or
  $C_{3-7}$ cycloalkyl optionally substituted with one or more independently selected halo or —OH;

$R^{3b}$ is selected from H, $C_{3-7}$ cycloalkyl and $C_{1-6}$ alkyl optionally substituted with one or more independently selected halo or —CN;

each $R^4$ is independently selected from
  halo,
  —OH,
  —CN,
  phenyl,
  —C(=O)OH,
  —O—C(=O)—$C_{1-4}$ alkyl,
  —O—S(=O)₂—$C_{1-4}$ alkyl,
  $C_{1-4}$ alkoxy optionally substituted with one or more independently selected
    —OH,
    $C_{1-4}$ alkoxy,
    4-8 membered monocyclic heterocycloalkyl comprising one, two, or three heteroatoms independently selected from N, O, and S, which heterocycloalkyl is optionally substituted with one or more independently selected $C_{1-4}$ alkyl, or
    —NR⁷ᵃR⁷ᵇ, wherein each $R^{7a}$ and $R^{7b}$ is independently selected from H and $C_{1-4}$ alkyl,
  $C_{3-7}$ cycloalkyl optionally substituted with one or more independently selected halo, —C(=O)—$C_{1-4}$ alkoxy, —NR⁸ᵃR⁸ᵇ, or $C_{1-4}$ alkyl optionally substituted with one or more independently selected —NR⁹ᵃR⁹ᵇ,
  5-6 membered monocyclic heterocycloalkyl comprising one or two N atoms fused to a 5-6 membered monocyclic heteroaryl comprising one, two, or three heteroatoms independently selected from N, O, and S, which heteroaryl is optionally substituted with one or more independently selected $C_{1-4}$ alkyl,
  5-6 membered monocyclic heteroaryl comprising one, two, or three heteroatoms independently selected from N, O, and S, which heteroaryl is optionally substituted with one or more independently selected $C_{1-4}$ alkyl or $C_{3-7}$ cycloalkyl,
  4-11 membered monocyclic, spirocyclic, or bridged polycyclic heterocycloalkyl comprising one, two, or three heteroatoms independently selected from N, O, and S, which heterocycloalkyl is optionally substituted with one or more independently selected $R^{10}$,
    —NR¹¹ᵃR¹¹ᵇ,
    —C(=O)—$C_{1-4}$ alkoxy, and
    —C(=O)—NR¹²ᵃR¹²ᵇ;

each R is selected from
  halo,
  —CN, and
  —NR¹³ᵃR¹³ᵇ;

each $R^{6a}$ and $R^{6b}$ is independently selected from H and $C_{1-4}$ alkyl;

each $R^{10}$ is selected from
  —OH,
  phenyl,
  =NH,
  halo,
  oxo,
  —CN,
  —C(=O)H,
  —C(=O)NH₂,
  —C(=O)OH,
  —NR¹⁴ᵃR¹⁴ᵇ,
  $C_{1-4}$ alkyl optionally substituted with one or more independently selected halo, —CN, —OH, —C(=O)—$C_{1-4}$ alkoxy, or $C_{1-4}$ alkoxy,
  $C_{3-7}$ cycloalkyl,
  4-6 membered monocyclic heterocycloalkyl comprising one, two, or three heteroatoms independently selected from N, O, and S,
  —C(=O)—$C_{1-4}$ alkyl,
  —S(=O)₂—$C_{1-4}$ alkyl, and
  —C(=O)—$C_{1-6}$ alkoxy;

each $R^{11a}$, $R^{11b}$ is independently selected from
  H,
  phenyl,
  $C_{1-4}$ alkyl optionally substituted with one or more independently selected halo, —OH, —CN, or $C_{1-4}$ alkoxy,
  $C_{3-7}$ cycloalkyl,
  —C(=O)—$C_{1-4}$ alkoxy,
  —C(=O)—$C_{1-4}$ alkyl optionally substituted with one or more independently selected halo, and
  5-6 membered monocyclic heteroaryl comprising one, two, or three heteroatoms independently selected from N, O, and S;

each $R^{8a}$, $R^{8b}$, $R^{9a}$, $R^{9b}$, $R^{12a}$, $R^{12b}$ $R^{13a}$, and $R^{13b}$ is independently selected from H and $C_{1-4}$ alkyl;

each $R^{14a}$ and $R^{14b}$ is independently selected from H, $C_{1-4}$ alkyl, and —S(=O)₂—$C_{1-4}$ alkyl; and each $R^{15}$ is independently selected from —OH, —CN, and $C_{1-4}$ alkyl optionally substituted with one or more independently selected halo or —CN;

or a pharmaceutically acceptable salt, solvate, or salt of the solvate thereof.

2. A compound or pharmaceutically acceptable salt thereof, according to clause 1, wherein z is
— $NHR^{3a}$, or
— $NR^{3b}$—, wherein the N atom and $R^{2a}$ together with the atoms onto which they are attached form a fused 5-6 membered heterocycloalkenyl comprising one or two double bonds;

$R^1$ is
$C_{1-8}$ alkyl optionally substituted with one or more independently selected $R^4$ groups,
phenyl,
$C_{3-8}$ monocyclic or bridged polycyclic cycloalkyl optionally substituted with one or more independently selected $R^5$ groups,
4-8 membered monocyclic or spirocyclic heterocycloalkyl comprising one, two, or three heteroatoms independently selected from N, O, and S, which heterocycloalkyl is optionally substituted with one or more independently selected $C_{1-4}$ alkyl, or
5-6 membered monocyclic heteroaryl comprising one, two, or three heteroatoms independently selected from N, O, and S;

$R^{3a}$ is
$C_{1-6}$ alkyl optionally substituted with one or more independently selected halo or —CN, or
$C_{3-7}$ cycloalkyl;

each $R^4$ is independently selected from:
halo,
—OH,
—CN,
phenyl,
$C_{1-4}$ alkoxy optionally substituted with one or more independently selected —OH, $C_{1-4}$ alkoxy, or —$NR^{7a}R^{7b}$, wherein each $R^{7a}$ and $R^{7b}$ is independently selected from H and $C_{1-4}$ alkyl,
$C_{3-7}$ cycloalkyl optionally substituted with one or more independently selected halo, —C(=O)—$C_{1-4}$ alkoxy, —$NR^{8a}R^{8b}$, or $C_{1-4}$ alkyl optionally substituted with one or more independently selected —$NR^{9a}R^{9b}$,
5-6 membered monocyclic heteroaryl comprising one, two, or three heteroatoms independently selected from N, O, and S, which heteroaryl is optionally substituted with one or more independently selected $C_{1-4}$ alkyl or $C_{3-7}$ cycloalkyl,
4-8 membered monocyclic or bridged polycyclic heterocycloalkyl comprising one, two, or three heteroatoms independently selected from N, O, and S, which heterocycloalkyl is optionally substituted with one or more independently selected $R^{10}$,
—$NR^{11a}R^{11b}$, and
—C(=O)—$NR^{12a}R^{12b}$;

each $R^{10}$ is selected from
halo,
oxo,
—CN,
—C(=O)H,
—$NR^{14a}R^{14b}$,
$C_{1-4}$ alkyl optionally substituted with one or more independently selected halo or $C_{1-4}$ alkoxy,
$C_{3-7}$ cycloalkyl,
—C(=O)—$C_{1-4}$ alkyl,
—S(=O)$_2$—$C_{1-4}$ alkyl, and
—C(=O)—$C_{1-6}$ alkoxy;

each $R^{11a}$, $R^{11b}$ is independently selected from
H,
phenyl,
$C_{1-4}$ alkyl optionally substituted with one or more independently selected halo, —OH, —CN, or $C_{1-4}$ alkoxy,
$C_{3-7}$ cycloalkyl,
—C(=O)—$C_{1-4}$ alkyl, and
5-6 membered monocyclic heteroaryl comprising one, two, or three heteroatoms independently selected from N, O, and S; and each $R^{14a}$, and $R^{14b}$ is independently selected from H and $C_{1-4}$ alkyl.

3. A compound or pharmaceutically acceptable salt thereof, according to clause 1 or 2, wherein X is N.

4. A compound or pharmaceutically acceptable salt thereof, according to clause 1 or 2, wherein X is CH.

5. A compound or pharmaceutically acceptable salt thereof, according to any one of clauses 1-4, wherein $R^{2a}$ is F, Cl, or Br.

6. A compound or pharmaceutically acceptable salt thereof, according to any one of clauses 1-4, wherein $R^{2a}$ is F.

7. A compound or pharmaceutically acceptable salt thereof, according to any one of clauses 1-4, wherein $R^{2a}$ is —$CH_3$, —$CH_2CH_3$, or —$CH(CH_3)_2$.

8. A compound or pharmaceutically acceptable salt thereof, according to any one of clauses 1-4, wherein $R^{2a}$ is —$CH_3$.

9. A compound or pharmaceutically acceptable salt thereof, according to any one of clauses 1-4, wherein $R^{2a}$ is —O—$CH_3$, —O—$CH_2CH_3$, or —O—CH($CH_3$)$_2$.

10. A compound or pharmaceutically acceptable salt thereof, according to any one of clauses 1-4, wherein $R^{2a}$ is —O—$CH_3$.

11. A compound or pharmaceutically acceptable salt thereof, according to any one of clauses 1-4, wherein $R^{2a}$ is —O—$CH_3$, —O—$CH_2CH_3$, or —O—CH($CH_3$)$_2$, each of which is substituted with one or more independently selected halo or $C_{1-4}$ alkoxy.

12. A compound or pharmaceutically acceptable salt thereof, according to any one of clauses 1-4, wherein $R^{2a}$ is —O—$CH_2CH_3$, substituted with one, two, or three independently selected halo or $C_{1-4}$ alkoxy.

13. A compound or pharmaceutically acceptable salt thereof, according to any one of clauses 1-4, wherein $R^{2a}$ is —O—$CH_2CH_2$—O—$CH_2CH_3$.

14. A compound or pharmaceutically acceptable salt thereof, according to any one of clauses 1-4, wherein $R^{2a}$ is —O—$CH_3$, substituted with one, two, or three independently selected halo.

15. A compound or pharmaceutically acceptable salt thereof, according to any one of clauses 1-4, wherein $R^{2a}$ is —O—$CHF_2$.

16. A compound or pharmaceutically acceptable salt thereof, according to any one of clauses 1-4, wherein $R^{2a}$ is —$NR^{6a}R^{6b}$, and $R^{6a}$ and $R^{6b}$ are independently selected from H and $C_{1-4}$ alkyl.

17. A compound or pharmaceutically acceptable salt thereof, according to any one of clauses 1-4, wherein $R^{2a}$ is —$NR^{6a}R^{6b}$, and one of $R^{6a}$ and $R^{6b}$ is H, and the other is —$CH_3$, —$CH_2CH_3$, or —$CH(CH_3)_2$.

18. A compound or pharmaceutically acceptable salt thereof, according to any one of clauses 1-4, wherein $R^{2a}$ is —NH—$CH_3$.

19. A compound or pharmaceutically acceptable salt thereof, according to any one of clauses 1-18, wherein Z is —$NR^{3b}$—, wherein the N atom and $R^{2a}$ together with the atoms onto which they are attached form a fused 5-6 membered heterocycloalkenyl comprising one or two double bonds.

20. A compound or pharmaceutically acceptable salt thereof, according to any one of clauses 1-18, wherein Z is —NR$^{3b}$—, wherein the N atom and R$^{2a}$ together with the atoms onto which they are attached form a fused 3-pyrroline, 1,2-dihydropyridine, or 1,2,3,6-tetrahydropyridine.

21. A compound or pharmaceutically acceptable salt thereof, according to any one of clauses 1-18, wherein Z is —NR$^{3b}$—, wherein the N atom and R$^{2a}$ together with the atoms onto which they are attached form a fused 1,2,3,6-tetrahydropyridine.

22. A compound or pharmaceutically acceptable salt thereof, according to clause 1, wherein the compound is according to any one of Formulae IIa-IIc:

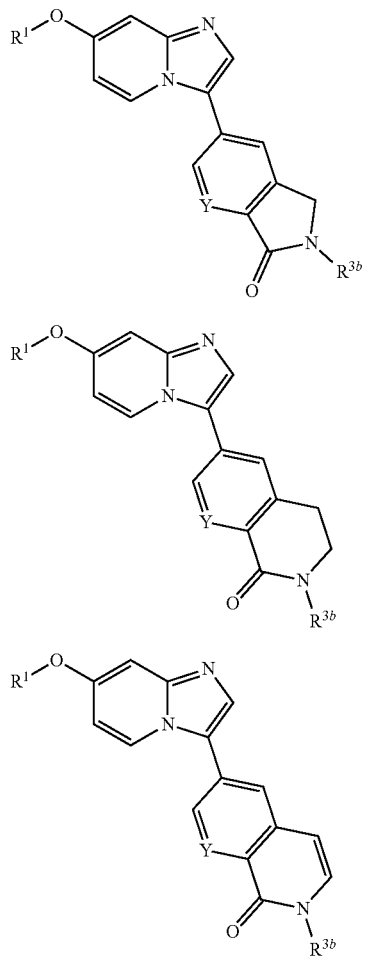

23. A compound or pharmaceutically acceptable salt thereof, according to any one of clauses 1-22, wherein R$^{3b}$ is H.

24. A compound or pharmaceutically acceptable salt thereof, according to any one of clauses 1-22, wherein R$^{3b}$ is C$_{3-7}$ cycloalkyl.

25. A compound or pharmaceutically acceptable salt thereof, according to any one of clauses 1-22, wherein R$^{3b}$ is cyclopropyl, cyclobutyl, or cyclopentyl.

26. A compound or pharmaceutically acceptable salt thereof, according to any one of clauses 1-22, wherein R$^{3b}$ is cyclopropyl.

27. A compound or pharmaceutically acceptable salt thereof, according to any one of clauses 1-22, wherein R$^{3b}$ is C$_{1-6}$ alkyl.

28. A compound or pharmaceutically acceptable salt thereof, according to any one of clauses 1-22, wherein R$^{3b}$ is —CH$_3$, —CH$_2$CH$_3$, —CH$_2$CH$_2$CH$_3$, —CH(CH$_3$)$_2$, or —C(CH$_3$)$_3$.

29. A compound or pharmaceutically acceptable salt thereof, according to any one of clauses 1-22, wherein R$^{3b}$ is —CH$_2$CH$_3$.

30. A compound or pharmaceutically acceptable salt thereof, according to any one of clauses 1-22, wherein R$^{3b}$ is C$_{1-6}$ alkyl substituted with one or more independently selected halo or —CN.

31. A compound or pharmaceutically acceptable salt thereof, according to any one of clauses 1-22, wherein R$^{3b}$ is —CH$_3$, —CH$_2$CH$_3$, —CH$_2$CH$_2$CH$_3$, —CH(CH$_3$)$_2$, or —C(CH$_3$)$_3$, each of which is substituted with one, two, or three independently selected halo or —CN.

32. A compound or pharmaceutically acceptable salt thereof, according to any one of clauses 1-22, wherein R$^{3b}$ is —CH$_2$·CN.

33. A compound or pharmaceutically acceptable salt thereof, according to any one of clauses 1-22, wherein R$^{3b}$ is —CH$_2$CH$_3$ substituted with one, two, or three F.

34. A compound or pharmaceutically acceptable salt thereof, according to any one of clauses 1-22, wherein R$^{3b}$ is —CH$_2$CF$_3$.

35. A compound or pharmaceutically acceptable salt thereof, according to any one of clauses 1-18, wherein Z is N-linked 4-7 membered heterocycloalkyl further comprising zero, one, or two additional heteroatoms independently selected from N, O, and S.

36. A compound or pharmaceutically acceptable salt thereof, according to any one of clauses 1-18, wherein Z is azetidinyl, pyrrolidinyl, piperidinyl, morpholinyl, thiomorpholinyl, or piperazinyl.

37. A compound or pharmaceutically acceptable salt thereof, according to any one of clauses 1-18, wherein Z is N-linked 4-7 membered heterocycloalkyl further comprising zero, one, or two additional heteroatoms independently selected from N, O, and S, substituted with one or more independently selected R$^{15}$ groups.

38. A compound or pharmaceutically acceptable salt thereof, according to any one of clauses 1-18, wherein Z is azetidinyl, pyrrolidinyl, piperidinyl, morpholinyl, thiomorpholinyl, or piperazinyl, each of which is substituted with one or more independently selected R$^{15}$ groups.

39. A compound or pharmaceutically acceptable salt thereof, according to any one of clauses 1-18, wherein Z is azetidinyl substituted with one or more independently selected R$^{15}$ groups.

40. A compound or pharmaceutically acceptable salt thereof, according to any one of clauses 37-39, wherein R$^{15}$ is —OH, —CN, —CH$_3$, —CH$_2$CH$_3$, or —CH(CH$_3$)$_2$.

41. A compound or pharmaceutically acceptable salt thereof, according to any one of clauses 37-39, wherein R$^{15}$ is —CH$_3$, —CH$_2$CH$_3$, or —CH(CH$_3$)$_2$, each of which is substituted with one or more independently selected halo or —CN.

42. A compound or pharmaceutically acceptable salt thereof, according to any one of clauses 37-39, wherein $R^{15}$ is —$CH_3$, —$CH_2CH_3$, or —$CH(CH_3)_2$, each of which is substituted with one or more independently selected F, Cl, Br, or —CN.

43. A compound or pharmaceutically acceptable salt thereof, according to any one of clauses 37-39, wherein $R^{15}$ is —$CH_3$ substituted with one or more, two, or three independently selected F, Cl, Br, or —CN.

44. A compound or pharmaceutically acceptable salt thereof, according to any one of clauses 1-18, wherein Z is —$NHR^{3a}$, and $R^{3a}$ is $C_{1-6}$ alkyl.

45. A compound or pharmaceutically acceptable salt thereof, according to any one of clauses 1-18, wherein Z is —$NHR^{3a}$, and $R^{3a}$ is —$CH_3$, —$CH_2CH_3$, —$CH_2CH_2CH_3$, —$CH(CH_3)_2$, or —$C(CH_3)_3$.

46. A compound or pharmaceutically acceptable salt thereof, according to any one of clauses 1-18, wherein Z is —$NHR^{3a}$, and $R^{3a}$ is —$CH_2CH_3$.

47. A compound or pharmaceutically acceptable salt thereof, according to any one of clauses 1-18, wherein Z is —$NHR^{3a}$, and $R^{3a}$ is $C_{1-6}$ alkyl substituted with one or more independently selected halo or —CN.

48. A compound or pharmaceutically acceptable salt thereof, according to any one of clauses 1-18, wherein Z is —$NHR^{3a}$, and $R^{3a}$ is —$CH_3$, —$CH_2CH_3$, —$CH_2CH_2CH_3$, —$CH(CH_3)_2$, or —$C(CH_3)_3$, each of which is substituted with one, two, or three independently selected halo or —CN.

49. A compound or pharmaceutically acceptable salt thereof, according to any one of clauses 1-18, wherein Z is —$NHR^{3a}$, and $R^{3a}$ is —$CH_2$—CN.

50. A compound or pharmaceutically acceptable salt thereof, according to any one of clauses 1-18, wherein Z is —$NHR^{3a}$, and $R^{3a}$ is —$CH_2CH_3$ substituted with one, two, or three F.

51. A compound or pharmaceutically acceptable salt thereof, according to any one of clauses 1-18, wherein Z is —$NHR^{3a}$, and $R^{3a}$ is —$CH_2CF_3$.

52. A compound or pharmaceutically acceptable salt thereof, according to any one of clauses 1-18, wherein Z is —$NHR^{3a}$, and $R^{3a}$ is $C_{3-7}$ cycloalkyl.

53. A compound or pharmaceutically acceptable salt thereof, according to any one of clauses 1-18, wherein Z is —$NHR^{3a}$, and $R^{3a}$ is cyclopropyl, cyclobutyl, or cyclopentyl.

54. A compound or pharmaceutically acceptable salt thereof, according to any one of clauses 1-18, wherein Z is —$NHR^{3a}$, and $R^{3a}$ is cyclopropyl.

55. A compound or pharmaceutically acceptable salt thereof, according to any one of clauses 1-54, wherein Y is N.

56. A compound or pharmaceutically acceptable salt thereof, according to any one of clauses 1-54, wherein Y is $CR^{2b}$ and $R^{2b}$ is halo.

57. A compound or pharmaceutically acceptable salt thereof, according to any one of clauses 1-54, wherein Y is $CR^{2b}$ and $R^{2b}$ is F.

58. A compound or pharmaceutically acceptable salt thereof, according to any one of clauses 1-54, wherein Y is $CR^{2b}$ and $R^{2b}$ is $C_{1-4}$ alkyl.

59. A compound or pharmaceutically acceptable salt thereof, according to any one of clauses 1-54, wherein Y is $CR^{2b}$ and $R^{2b}$ is —$CH_3$, —$CH_2CH_3$, or —$CH(CH_3)_2$.

60. A compound or pharmaceutically acceptable salt thereof, according to any one of clauses 1-54, wherein Y is $CR^{2b}$ and $R^{2b}$ is —$CH_3$.

61. A compound or pharmaceutically acceptable salt thereof, according to any one of clauses 1-54, wherein Y is $CR^{2b}$ and $R^{2b}$ is $C_{1-4}$ alkoxy.

62. A compound or pharmaceutically acceptable salt thereof, according to any one of clauses 1-54, wherein Y is $CR^{2b}$ and $R^{2b}$ is —O—$CH_3$, —O—$CH_2CH_3$, or —O—$CH(CH_3)_2$.

63. A compound or pharmaceutically acceptable salt thereof, according to any one of clauses 1-54, wherein Y is $CR^{2b}$ and $R^{2b}$ is —O—$CH_3$ or —O—$CH_2CH_3$.

64. A compound or pharmaceutically acceptable salt thereof, according to any one of clauses 1-54, wherein Y is $CR^{2b}$ and $R^{2b}$ is —O—$CH_3$.

65. A compound or pharmaceutically acceptable salt thereof, according to any one of clauses 1-54, wherein Y is $CR^{2b}$ and $R^{2b}$ is $C_{1-4}$ alkoxy substituted with one or more independently selected halo or $C_{1-4}$ alkoxy.

66. A compound or pharmaceutically acceptable salt thereof, according to any one of clauses 1-54, wherein Y is $CR^{2b}$ and $R^{2b}$ is —O—$CH_3$, —O—$CH_2CH_3$, or —O—$CH(CH_3)_2$, each of which is substituted with one, two, or three independently selected halo or $C_{1-4}$ alkoxy.

67. A compound or pharmaceutically acceptable salt thereof, according to any one of clauses 1-54, wherein Y is $CR^{2b}$ and $R^{2b}$ is —O—$CHF_2$ or —O—$CH_2CH_2$—O—$CH_2CH_3$.

68. A compound or pharmaceutically acceptable salt thereof, according to any one of clauses 1-54, wherein Y is $CR^{2b}$ and $R^{2b}$ is —O—$CHF_2$.

69. A compound or pharmaceutically acceptable salt thereof, according to any one of clauses 1-54, wherein Y is $CR^{2b}$, $R^{2b}$ is —$NR^{6a}R^{6b}$, and $R^{6a}$ and $R^{6b}$ are both H.

70. A compound or pharmaceutically acceptable salt thereof, according to any one of clauses 1-54, wherein Y is $CR^{2b}$, $R^{2b}$ is —$NR^{6a}R^{6b}$, and one of $R^{6a}$ and $R^{6b}$ is H, and the other is —$CH_3$, —$CH_2CH_3$, or —$CH(CH_3)_2$.

71. A compound or pharmaceutically acceptable salt thereof, according to any one of clauses 1-54, wherein Y is $CR^{2b}$ and $R^{2b}$ is —NH—$CH_3$.

72. A compound or pharmaceutically acceptable salt thereof, according to clause 1, wherein the compound is according to any one of Formulae IIIa-IIIc:

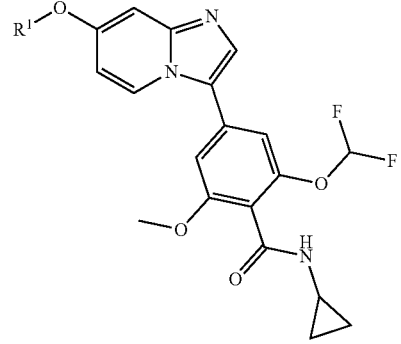

IIIa

73. A compound or pharmaceutically acceptable salt thereof, according to any one of clauses 1-72, wherein $R^1$ is $C_{1-8}$ alkyl.

74. A compound or pharmaceutically acceptable salt thereof, according to any one of clauses 1-72, wherein $R^1$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —CH$_2$CH$_2$CH(CH$_3$)$_2$, —CH$_2$C(CH$_3$)$_3$, or —CH$_2$CH$_2$CH$_2$CH(CH$_3$)$_2$.

75. A compound or pharmaceutically acceptable salt thereof, according to any one of clauses 1-72, wherein $R^1$ is —CH$_3$, —CH$_2$CH$_3$, or —CH$_2$C(CH$_3$)$_3$.

76. A compound or pharmaceutically acceptable salt thereof, according to any one of clauses 1-72, wherein $R^1$ is $C_{1-8}$ alkyl substituted with one or more independently selected $R^4$ groups 77. A compound or pharmaceutically acceptable salt thereof, according to any one of clauses 1-72, wherein $R^1$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —CH$_2$CH$_2$CH(CH$_3$)$_2$, —CH$_2$C(CH$_3$)$_3$, or —CH$_2$CH$_2$CH$_2$CH(CH$_3$)$_2$, each of which is substituted with one, two, or three independently selected $R^4$ groups.

78. A compound or pharmaceutically acceptable salt thereof, according to any one of clauses 1-72, wherein $R^1$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —CH$_2$CH$_2$CH(CH$_3$)$_2$, —CH$_2$C(CH$_3$)$_3$, or —CH$_2$CH$_2$CH$_2$CH(CH$_3$)$_2$, each of which is substituted with one $R^4$ group.

79. A compound or pharmaceutically acceptable salt thereof, according to any one of clauses 1-72, wherein $R^1$ is phenyl.

80. A compound or pharmaceutically acceptable salt thereof, according to any one of clauses 1-72, wherein $R^1$ is $C_{3-8}$ monocyclic or bridged polycyclic cycloalkyl.

81. A compound or pharmaceutically acceptable salt thereof, according to any one of clauses 1-72, wherein $R^1$ is cyclopropyl, cyclobutyl, cyclopentyl, cyclohexyl, bicyclo[2.1.1]hexanyl, bicyclo[2.2.1]heptanyl, or bicyclo[2.2.2]octanyl.

82. A compound or pharmaceutically acceptable salt thereof, according to any one of clauses 1-72, wherein $R^1$ is cyclobutyl, cyclopentyl, cyclohexyl, or bicyclo[2.2.1]heptanyl.

83. A compound or pharmaceutically acceptable salt thereof, according to any one of clauses 1-72, wherein $R^1$ is $C_{3-8}$ monocyclic or bridged polycyclic cycloalkyl substituted with one or more independently selected $R^{15}$ groups.

84. A compound or pharmaceutically acceptable salt thereof, according to any one of clauses 1-72, wherein $R^1$ is cyclopropyl, cyclobutyl, cyclopentyl, cyclohexyl, bicyclo[2.1.1]hexanyl, bicyclo[2.2.1]heptanyl, or bicyclo[2.2.2]octanyl, each of which is substituted with one, two, or three independently selected $R^5$ groups.

85. A compound or pharmaceutically acceptable salt thereof, according to any one of clauses 1-72, wherein $R^1$ is cyclobutyl, cyclopentyl, or cyclohexyl, each of which is substituted with one R group.

86. A compound or pharmaceutically acceptable salt thereof, according to any one of clauses 1-72, wherein $R^1$ is 4-8 membered monocyclic, spirocyclic, or bridged polycyclic heterocycloalkyl comprising one, two, or three heteroatoms independently selected from N, O, and S.

87. A compound or pharmaceutically acceptable salt thereof, according to any one of clauses 1-72, wherein $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, 6-thiaspiro[3.4]octanyl, 7-azabicyclo[2.2.1]heptanyl, 2-azabicyclo[2.2.1]heptanyl, 7-oxabicyclo[2.2.1]heptanyl, 2-oxabicyclo[2.2.1]heptanyl, 7-thiabicyclo[2.2.1]heptanyl, 2-thiabicyclo[2.2.1]heptanyl, quinuclidinyl, 1,4-diazabicyclo[2.2.2]octanyl, 2-azabicyclo[2.2.2]octanyl, 2-oxabicyclo[2.2.2]octanyl, 2-thiabicyclo[2.2.2]octanyl, 8-azabicyclo[3.2.1]octanyl, 3,8-diazabicyclo[3.2.1]octanyl, 3-oxa-8-azabicyclo[3.2.1]octanyl, 3-thia-8-azabicyclo[3.2.1]octanyl, 8-oxabicyclo[3.2.1]octanyl, or 8-thiabicyclo[3.2.1]octanyl.

88. A compound or pharmaceutically acceptable salt thereof, according to any one of clauses 1-72, wherein $R^1$ is oxetanyl, tetrahydrofuranyl, tetrahydropyranyl, 2-oxaspiro[3.3]heptanyl, or 8-azabicyclo[3.2.1]octanyl.

89. A compound or pharmaceutically acceptable salt thereof, according to any one of clauses 1-72, wherein $R^1$ is 4-8 membered monocyclic or spirocyclic heterocycloalkyl comprising one, two, or three heteroatoms independently selected from N, O, and S.

90. A compound or pharmaceutically acceptable salt thereof, according to any one of clauses 1-72, wherein $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, or 6-thiaspiro[3.4]octanyl.

91. A compound or pharmaceutically acceptable salt thereof, according to any one of clauses 1-72, wherein $R^1$ is oxetanyl, tetrahydrofuranyl, tetrahydropyranyl, or 2-oxaspiro[3.3]heptanyl.

92. A compound or pharmaceutically acceptable salt thereof, according to any one of clauses 1-72, wherein $R^1$ is 4-8 membered monocyclic, spirocyclic, or bridged polycyclic heterocycloalkyl comprising one, two, or three heteroatoms independently selected from N, O, and S, which heterocycloalkyl is substituted with one or more independently selected $C_{1-4}$ alkyl optionally substituted with one or more independently selected —CN or —C(=O)—$C_{1-4}$ alkoxy.

93. A compound or pharmaceutically acceptable salt thereof, according to any one of clauses 1-72, wherein $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, 6-thiaspiro[3.4]octanyl, 7-azabicyclo[2.2.1]heptanyl, 2-azabicyclo[2.2.1]heptanyl, 7-oxabicyclo[2.2.1]heptanyl, 2-oxabicyclo[2.2.1]heptanyl, 7-thiabicyclo[2.2.1]heptanyl, 2-thiabicyclo[2.2.1]heptanyl, quinuclidinyl, 1,4-diazabicyclo[2.2.2]octanyl, 2-azabicyclo[2.2.2]octanyl, 2-oxabicyclo[2.2.2]octanyl, 2-thiabicyclo[2.2.2]octanyl, 8-azabicyclo[3.2.1]octanyl, 3,8-diazabicyclo[3.2.1]octanyl, 3-oxa-8-azabicyclo[3.2.1]octanyl, 3-thia-8-azabicyclo[3.2.1]octanyl, 8-oxabicyclo[3.2.1]octanyl, or 8-thiabicyclo[3.2.1]octanyl, each of which is substituted with one, two, or three independently selected $C_{1-4}$ alkyl optionally substituted with one or more independently selected —CN or —C(=O)—$C_{1-4}$ alkoxy.

94. A compound or pharmaceutically acceptable salt thereof, according to any one of clauses 1-72, wherein $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, 6-thiaspiro[3.4]octanyl, 7-azabicyclo[2.2.1]heptanyl, 2-azabicyclo[2.2.1]heptanyl, 7-oxabicyclo[2.2.1]heptanyl, 2-oxabicyclo[2.2.1]heptanyl, 7-thiabicyclo[2.2.1]heptanyl, 2-thiabicyclo[2.2.1]heptanyl, quinuclidinyl, 1,4-diazabicyclo[2.2.2]octanyl, 2-azabicyclo[2.2.2]octanyl, 2-oxabicyclo[2.2.2]octanyl, 2-thiabicyclo[2.2.2]octanyl, 8-azabicyclo[3.2.1]octanyl, 3,8-diazabicyclo[3.2.1]octanyl, 3-oxa-8-azabicyclo[3.2.1]octanyl, 3-thia-8-azabicyclo[3.2.1]octanyl, 8-oxabicyclo[3.2.1]octanyl, or 8-thiabicyclo[3.2.1]octanyl, each of which is substituted with one, two, or three independently selected —$CH_3$, —$CH_2CH_3$, or —$CH(CH_3)_2$, each of which is optionally substituted with one, two, or three independently selected —CN, —C(=O)—O—$CH_3$, —C(=O)—O—$CH_2CH_3$, or —C(=O)—O—$CH(CH_3)_2$.

95. A compound or pharmaceutically acceptable salt thereof, according to any one of clauses 1-72, wherein $R^1$ is azetidinyl, pyrrolidinyl, piperidinyl, or 8-azabicyclo[3.2.1]octanyl, each of which is substituted with one —$CH_3$, —$CH_2$—$CH_2$—CN, or —$CH_2$—C(=O)—O—$CH_2CH_3$.

96. A compound or pharmaceutically acceptable salt thereof, according to any one of clauses 1-72, wherein $R^1$ is 4-8 membered monocyclic or spirocyclic heterocycloalkyl comprising one, two, or three heteroatoms independently selected from N, O, and S, which heterocycloalkyl is substituted with one or more independently selected $C_{1-4}$ alkyl.

97. A compound or pharmaceutically acceptable salt thereof, according to any one of clauses 1-72, wherein $R^1$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, 1-oxaspiro[3.3]heptanyl, 2-oxaspiro[3.3]heptanyl, 1-azaspiro[3.3]heptanyl, 2-azaspiro[3.3]heptanyl, 1-thiaspiro[3.3]heptanyl, 2-thiaspiro[3.3]heptanyl, 1-oxaspiro[3.4]octanyl, 2-oxaspiro[3.4]octanyl, 5-oxaspiro[3.4]octanyl, 6-oxaspiro[3.4]octanyl, 1-azaspiro[3.4]octanyl, 2-azaspiro[3.4]octanyl, 5-azaspiro[3.4]octanyl, 6-azaspiro[3.4]octanyl, 1-thiaspiro[3.4]octanyl, 2-thiaspiro[3.4]octanyl, 5-thiaspiro[3.4]octanyl, or 6-thiaspiro[3.4]octanyl, each of which is substituted with one, two, or three independently selected —$CH_3$, —$CH_2CH_3$, or —$CH(CH_3)_2$.

98. A compound or pharmaceutically acceptable salt thereof, according to any one of clauses 1-72, wherein $R^1$ is azetidinyl, pyrrolidinyl, or piperidinyl, each of which is substituted with one, two, or three independently selected —$CH_3$, —$CH_2CH_3$, or —$CH(CH_3)_2$.

99. A compound or pharmaceutically acceptable salt thereof, according to any one of clauses 1-72, wherein $R^1$ is azetidinyl, pyrrolidinyl, or piperidinyl, each of which is substituted with one —$CH_3$.

100. A compound or pharmaceutically acceptable salt thereof, according to any one of clauses 1-72, wherein $R^1$ is 5-6 membered monocyclic heteroaryl comprising one, two, or three heteroatoms independently selected from N, O, and S.

101. A compound or pharmaceutically acceptable salt thereof, according to any one of clauses 1-72, wherein $R^1$ is pyridinyl, pyrazinyl, pyridazinyl, or pyrimidinyl.

102. A compound or pharmaceutically acceptable salt thereof, according to any one of clauses 1-72, wherein $R^1$ is pyridinyl.

103. A compound or pharmaceutically acceptable salt thereof, according to any one of clauses 1-72 and 83-85, wherein $R^5$ is halo or —CN.
104. A compound or pharmaceutically acceptable salt thereof, according to any one of clauses 1-72 and 83-85, wherein $R^5$ is F, Cl, Br, or —CN.
105. A compound or pharmaceutically acceptable salt thereof, according to any one of clauses 1-72 and 83-85, wherein $R^5$ is F or —CN.
106. A compound or pharmaceutically acceptable salt thereof, according to any one of clauses 1-72 and 83-85, wherein $R^5$ is —$NR^{13a}R^{13b}$, and $R^{13a}$ and $R^{13b}$ are both H.
107. A compound or pharmaceutically acceptable salt thereof, according to any one of clauses 1-72 and 83-85, wherein $R^5$ is —$NR^{13a}R^{13b}$, and $R^{13a}$ and $R^{13b}$ are both $C_{1-4}$ alkyl.
108. A compound or pharmaceutically acceptable salt thereof, according to any one of clauses 1-72 and 83-85, wherein $R^5$ is —$NR^{13a}R^{13b}$, one of $R^{13a}$ and $R^{13b}$ is H, and the other is $C_{1-4}$ alkyl.
109. A compound or pharmaceutically acceptable salt thereof, according to any one of clauses 1-72 and 83-85, wherein $R^5$ is —NH—$CH_3$.
110. A compound or pharmaceutically acceptable salt thereof, according to clause 1, wherein the compound is according to any one of Formulae IVa-IVf.

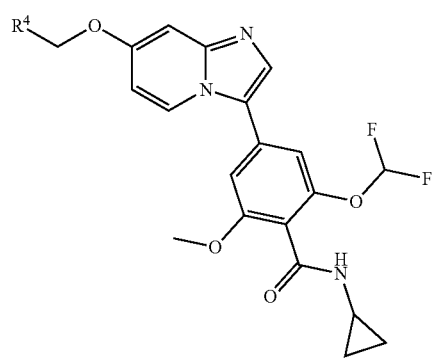

IVa

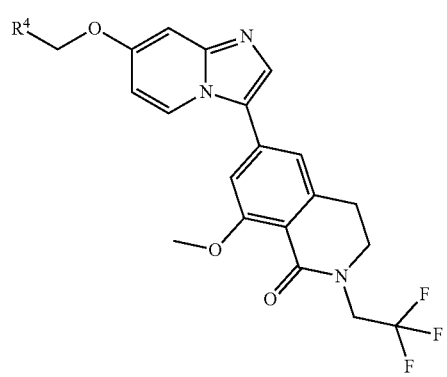

IVb

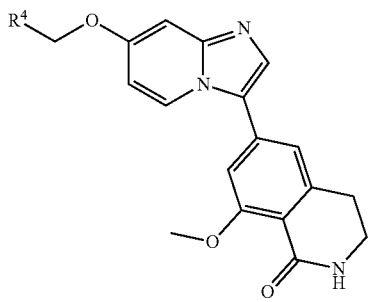

IVc

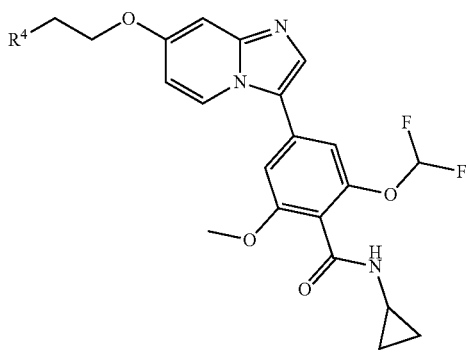

IVd

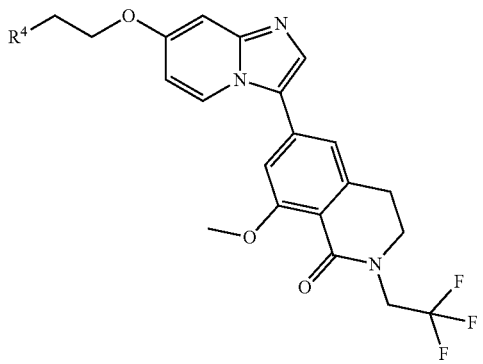

IVe

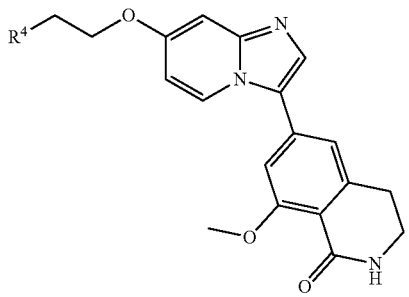

IVf

111. A compound or pharmaceutically acceptable salt thereof, according to any one of clauses 1-72, 76-78, and 110, wherein $R^4$ is halo, —OH, —CN, phenyl, or —C(=O)OH.
112. A compound or pharmaceutically acceptable salt thereof, according to any one of clauses 1-72, 76-78, and 110, wherein $R^4$ is F, —OH, —CN, phenyl, or —C(=O)OH.
113. A compound or pharmaceutically acceptable salt thereof, according to any one of clauses 1-72, 76-78, and 110, wherein $R^4$ is halo, —OH, —CN, or phenyl.

114. A compound or pharmaceutically acceptable salt thereof, according to any one of clauses 1-72, 76-78, and 110, wherein $R^4$ is F, Cl, Br, —OH, —CN, or phenyl.

115. A compound or pharmaceutically acceptable salt thereof, according to any one of clauses 1-72, 76-78, and 110, wherein $R^4$ is F, —OH, —CN, or phenyl.

116. A compound or pharmaceutically acceptable salt thereof, according to any one of clauses 1-72, 76-78, and 110, wherein $R^4$ is —O—C(=O)—$CH_3$, —O—C(=O)—$CH_2CH_3$, or —O—C(=O)—CH($CH_3$)$_2$.

117. A compound or pharmaceutically acceptable salt thereof, according to any one of clauses 1-72, 76-78, and 110, wherein $R^4$ is —O—C(=O)—$CH_3$.

118. A compound or pharmaceutically acceptable salt thereof, according to any one of clauses 1-72, 76-78, and 110, wherein $R^4$ is —O—S(=O)$_2$—$CH_3$, —O—S(=O)$_2$—$CH_2CH_3$, or —O—S(=O)$_2$—CH($CH_3$)$_2$.

119. A compound or pharmaceutically acceptable salt thereof, according to any one of clauses 1-72, 76-78, and 110, wherein $R^4$ is —O—S(=O)$_2$—$CH_3$.

120. A compound or pharmaceutically acceptable salt thereof, according to any one of clauses 1-72, 76-78, and 110, wherein $R^4$ is $C_{1-4}$ alkoxy.

121. A compound or pharmaceutically acceptable salt thereof, according to any one of clauses 1-72, 76-78, and 110, wherein $R^4$ is —O—$CH_3$, —O—$CH_2CH_3$, or —O—CH($CH_3$)$_2$.

122. A compound or pharmaceutically acceptable salt thereof, according to any one of clauses 1-72, 76-78, and 110, wherein $R^4$ is —O—$CH_3$ or —O—$CH_2CH_3$.

123. A compound or pharmaceutically acceptable salt thereof, according to any one of clauses 1-72, 76-78, and 110, wherein $R^4$ is $C_{1-4}$ alkoxy substituted with one or more independently selected 4-8 membered monocyclic heterocycloalkyl comprising one, two, or three heteroatoms independently selected from N, O, and S, which heterocycloalkyl is optionally substituted with one or more independently selected $C_{1-4}$ alkyl.

124. A compound or pharmaceutically acceptable salt thereof, according to any one of clauses 1-72, 76-78, and 110, wherein $R^4$ is —O—$CH_3$, —O—$CH_2CH_3$, or —O—CH($CH_3$)$_2$, each of which is substituted with one or more independently selected 4-8 membered monocyclic heterocycloalkyl comprising one, two, or three heteroatoms independently selected from N, O, and S, which heterocycloalkyl is optionally substituted with one or more independently selected $C_{1-4}$ alkyl.

125. A compound or pharmaceutically acceptable salt thereof, according to any one of clauses 1-72, 76-78, and 110, wherein $R^4$ is $C_{1-4}$ alkoxy substituted with one or more independently selected azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, or piperazinyl, each of which is optionally substituted with one, two, or three —$CH_3$, —$CH_2CH_3$, or —CH($CH_3$)$_2$.

126. A compound or pharmaceutically acceptable salt thereof, according to any one of clauses 1-72, 76-78, and 110, wherein $R^4$ is —O—$CH_3$, —O—$CH_2CH_3$, or —O—CH($CH_3$)$_2$, each of which is substituted with one or more independently selected azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, or piperazinyl, each of which is optionally substituted with one, two, or three —$CH_3$, —$CH_2CH_3$, or —CH($CH_3$)$_2$.

127. A compound or pharmaceutically acceptable salt thereof, according to any one of clauses 1-72, 76-78, and 110, wherein $R^4$ is —O—$CH_2CH_3$ substituted with one piperidinyl, morpholinyl, or piperazinyl, each of which is optionally substituted with one —CH($CH_3$)$_2$.

128. A compound or pharmaceutically acceptable salt thereof, according to any one of clauses 1-72, 76-78, and 110, wherein $R^4$ is $C_{1-4}$ alkoxy substituted with one or more independently selected —OH, $C_{1-4}$ alkoxy, or —$NR^{7a}R^{7b}$.

129. A compound or pharmaceutically acceptable salt thereof, according to any one of clauses 1-72, 76-78, and 110, wherein $R^4$ is —O—$CH_3$, —O—$CH_2CH_3$, or —O—CH($CH_3$)$_2$, each of which is substituted with one, two or three independently selected —OH, $C_{1-4}$ alkoxy, or —$NR^{7a}R^{7b}$.

130. A compound or pharmaceutically acceptable salt thereof, according to any one of clauses 1-72, 76-78, and 110, wherein $R^4$ is —O—$CH_3$, —O—$CH_2CH_3$, or —O—CH($CH_3$)$_2$, each of which is substituted with one, two, or three independently selected —OH, —O—$CH_3$, —O—$CH_2CH_3$, —O—CH($CH_3$)$_2$, —$NH_2$, —NH—$CH_3$, —NH—$CH_2CH_3$, —NH—CH($CH_3$)$_2$, —N($CH_3$)$_2$, —N($CH_3$)—$CH_2CH_3$, —N($CH_3$)—CH($CH_3$)$_2$, —N($CH_2CH_3$)$_2$, —N($CH_2CH_3$)—CH($CH_3$)$_2$, or —N(CH($CH_3$)$_2$)$_2$.

131. A compound or pharmaceutically acceptable salt thereof, according to any one of clauses 1-72, 76-78, and 110, wherein $R^4$ is —O—$CH_3$, —O—$CH_2CH_3$, or —O—CH($CH_3$)$_2$, each of which is substituted with one —OH, —O—$CH_3$, or —N($CH_3$)$_2$.

132. A compound or pharmaceutically acceptable salt thereof, according to any one of clauses 1-72, 76-78, and 110, wherein $R^4$ is —O—$CH_2CH_3$ substituted with one —OH, —O—$CH_3$, or —N($CH_3$)$_2$.

133. A compound or pharmaceutically acceptable salt thereof, according to any one of clauses 1-72, 76-78, and 110, wherein $R^4$ is $C_{3-7}$ cycloalkyl.

134. A compound or pharmaceutically acceptable salt thereof, according to any one of clauses 1-72, 76-78, and 110, wherein $R^4$ is cyclopropyl, cyclobutyl, cyclopentyl, or cyclohexyl.

135. A compound or pharmaceutically acceptable salt thereof, according to any one of clauses 1-72, 76-78, and 110, wherein $R^4$ is $C_{3-7}$ cycloalkyl substituted with one or more independently selected halo, —C(=O)—$C_{1-4}$ alkoxy, —$NR^{8a}R^{8b}$, or $C_{1-4}$ alkyl optionally substituted with one or more independently selected —$NR^{9a}R^{9b}$.

136. A compound or pharmaceutically acceptable salt thereof, according to any one of clauses 1-72, 76-78, and 110, wherein $R^4$ is cyclopropyl, cyclobutyl, cyclopentyl, or cyclohexyl, each of which is substituted with one, two, or three independently selected halo, —C(=O)—$C_{1-4}$ alkoxy, —$NR^{8a}R^{8b}$, or $C_{1-4}$ alkyl optionally substituted with one or more independently selected —$NR^{9a}R^{9b}$.

137. A compound or pharmaceutically acceptable salt thereof, according to any one of clauses 1-72, 76-78, and 110, wherein $R^4$ is cyclopropyl, cyclobutyl, cyclopentyl, or cyclohexyl, each of which is substituted with one, two, or three independently selected F, Cl, Br, —C(=O)—O—$CH_3$, —C(=O)—O—$CH_2CH_3$, —C(=O)—O—CH($CH_3$)$_2$, —$NR^{8a}R^{8b}$, —$CH_3$ optionally substituted with one —NR$^{9a}$R$^{9b}$, —CH$_2$CH$_3$ optionally substituted with one —NR$^{9a}$R$^{9b}$, or —CH(CH$_3$)$_2$ optionally substituted with one —NR$^{9a}$R$^{9b}$.

138. A compound or pharmaceutically acceptable salt thereof, according to any one of clauses 1-72, 76-78, and 110, wherein R$^4$ is cyclopropyl, cyclobutyl, cyclopentyl, or cyclohexyl, each of which is substituted with one, two, or three independently selected F, —C(=O)—O—CH$_3$, —NR$^{8a}$R$^{8b}$, —CH$_3$, or —CH$_2$—NR$^{9a}$R$^{9b}$.

139. A compound or pharmaceutically acceptable salt thereof, according to any one of clauses 1-72, 76-78, and 110, wherein R$^4$ is cyclopropyl, cyclobutyl, cyclopentyl, or cyclohexyl, each of which is substituted with one —C(=O)—O—CH$_3$, —NR$^{8a}$R$^{8b}$, —CH$_3$, or —CH$_2$—NR$^{9a}$R$^{9b}$.

140. A compound or pharmaceutically acceptable salt thereof, according to any one of clauses 1-72, 76-78, 110 and 135-139, wherein R$^{8a}$ and R$^{8b}$ are both H.

141. A compound or pharmaceutically acceptable salt thereof, according to any one of clauses 1-72, 76-78, 110 and 135-139, wherein one of R$^{8a}$ and R$^{8b}$ is H, and the other is C$_{1-4}$ alkyl.

142. A compound or pharmaceutically acceptable salt thereof, according to any one of clauses 1-72, 76-78, 110 and 135-139, wherein one of R$^{8a}$ and R$^{8b}$ is H, and the other is —CH$_3$, —CH$_2$CH$_3$, or —CH(CH$_3$)$_2$.

143. A compound or pharmaceutically acceptable salt thereof, according to any one of clauses 1-72, 76-78, 110 and 135-139, wherein R$^{8a}$ and R$^{8b}$ are both C$_{1-4}$ alkyl.

144. A compound or pharmaceutically acceptable salt thereof, according to any one of clauses 1-72, 76-78, 110 and 135-139, wherein R$^{8a}$ and R$^{8b}$ are independently —CH$_3$, —CH$_2$CH$_3$, or —CH(CH$_3$)$_2$.

145. A compound or pharmaceutically acceptable salt thereof, according to any one of clauses 1-72, 76-78, 110 and 135-139, wherein R$^{9a}$ and R$^{9b}$ are both H.

146. A compound or pharmaceutically acceptable salt thereof, according to any one of clauses 1-72, 76-78, 110 and 135-139, wherein one of R$^{9a}$ and R$^{9b}$ is H, and the other is C$_{1-4}$ alkyl.

147. A compound or pharmaceutically acceptable salt thereof, according to any one of clauses 1-72, 76-78, 110 and 135-139, wherein one of R$^{9a}$ and R$^{9b}$ is H, and the other is —CH$_3$, —CH$_2$CH$_3$, or —CH(CH$_3$)$_2$.

148. A compound or pharmaceutically acceptable salt thereof, according to any one of clauses 1-72, 76-78, 110 and 135-139, wherein R$^{9a}$ and R$^{9b}$ are both C$_{1-4}$ alkyl.

149. A compound or pharmaceutically acceptable salt thereof, according to any one of clauses 1-72, 76-78, 110 and 135-139, wherein R$^{9a}$ and R$^{9b}$ are independently —CH$_3$, —CH$_2$CH$_3$, or —CH(CH$_3$)$_2$.

150. A compound or pharmaceutically acceptable salt thereof, according to any one of clauses 1-72, 76-78, and 110, wherein R$^4$ is cyclopropyl, cyclobutyl, cyclopentyl, or cyclohexyl, each of which is substituted with one, two or three F.

151. A compound or pharmaceutically acceptable salt thereof, according to any one of clauses 1-72, 76-78, and 110, wherein R$^4$ is 5-6 membered monocyclic heterocycloalkyl comprising one or two N atoms fused to a 5-6 membered monocyclic heteroaryl comprising one, two, or three heteroatoms independently selected from N, O, and S.

152. A compound or pharmaceutically acceptable salt thereof, according to any one of clauses 1-72, 76-78, and 110, wherein R$^4$ is pyrrolidinyl, piperidinyl, or piperazinyl, each of which is fused to a 5-6 membered monocyclic heteroaryl comprising one, two, or three heteroatoms independently selected from N, O, and S.

153. A compound or pharmaceutically acceptable salt thereof, according to any one of clauses 1-72, 76-78, and 110, wherein R$^4$ is 5-6 membered monocyclic heterocycloalkyl comprising one or two N atoms fused to a pyrrole, furane, thiophene, imidazole, furazane, oxazole, oxadiazole, isoxazole, thiazole, isothiazole, pyrazole, triazole, pyridine, pyrazine, pyridazine, or pyrimidine.

154. A compound or pharmaceutically acceptable salt thereof, according to any one of clauses 1-72, 76-78, and 110, wherein R$^4$ is 1H,2H,3H,4H-pyrrolo[1,2-a]pyrazinyl, 5H,6H,7H,8H-imidazo[1,2-a]pyrazinyl, 5H,6H,7H,8H-[1,2,4]triazolo[1,5-a]pyrazinyl, 5,6,7,8-tetrahydro-1,6-naphthyridinyl, or 5H,6H,7H,8H-pyrido[4,3-d]pyrimidinyl.

155. A compound or pharmaceutically acceptable salt thereof, according to any one of clauses 1-72, 76-78, and 110, wherein R$^4$ is 5-6 membered monocyclic heterocycloalkyl comprising one or two N atoms fused to a 5-6 membered monocyclic heteroaryl comprising one, two, or three heteroatoms independently selected from N, O, and S, which heteroaryl is substituted with one or more independently selected C$_{1-4}$ alkyl.

156. A compound or pharmaceutically acceptable salt thereof, according to any one of clauses 1-72, 76-78, and 110, wherein R$^4$ is 5-6 membered monocyclic heterocycloalkyl comprising one or two N atoms fused to a pyrrole, furane, thiophene, imidazole, furazane, oxazole, oxadiazole, isoxazole, thiazole, isothiazole, pyrazole, triazole, pyridine, pyrazine, pyridazine, or pyrimidine, each of which is substituted with one, two, or three independently selected —CH$_3$, —CH$_2$CH$_3$, or —CH(CH$_3$)$_2$.

157. A compound or pharmaceutically acceptable salt thereof, according to any one of clauses 1-72, 76-78, and 110, wherein R$^4$ is piperidinyl fused to an imidazole substituted with one —CH$_3$.

158. A compound or pharmaceutically acceptable salt thereof, according to any one of clauses 1-72, 76-78, and 110, wherein R$^4$ is 5-6 membered monocyclic heteroaryl comprising one, two, or three heteroatoms independently selected from N, O, and S.

159. A compound or pharmaceutically acceptable salt thereof, according to any one of clauses 1-72, 76-78, and 110, wherein R$^4$ is pyrrolyl, imidazolyl, pyrazolyl, triazolyl, oxazolyl, thiazolyl, isoxazolyl, isothiazolyl, oxadiazolyl, thiadiazolyl, pyridinyl, pyridazinyl, pyrimidinyl, or pyrazinyl.

160. A compound or pharmaceutically acceptable salt thereof, according to any one of clauses 1-72, 76-78, and 110, wherein R$^4$ is thiazolyl, oxazolyl, pyridinyl, pyridazinyl, or pyrimidinyl.

161. A compound or pharmaceutically acceptable salt thereof, according to any one of clauses 1-72, 76-78, and 110, wherein R$^4$ is 5-6 membered monocyclic heteroaryl comprising one, two, or three heteroatoms independently selected from N, O, and S, which heteroaryl is substituted with one or more independently selected C$_{1-4}$ alkyl or C$_{3-7}$ cycloalkyl.

162. A compound or pharmaceutically acceptable salt thereof, according to any one of clauses 1-72, 76-78, and 110, wherein $R^4$ is 5-6 membered monocyclic heteroaryl comprising one, two, or three heteroatoms independently selected from N, O, and S, which heteroaryl is substituted with one, two, or three independently selected $C_{1-4}$ alkyl or $C_{3-7}$ cycloalkyl.

163. A compound or pharmaceutically acceptable salt thereof, according to any one of clauses 1-72, 76-78, and 110, wherein $R^4$ is pyrrolyl, imidazolyl, pyrazolyl, triazolyl, oxazolyl, thiazolyl, isoxazolyl, isothiazolyl, oxadiazolyl, thiadiazolyl, pyridinyl, pyridazinyl, pyrimidinyl, or pyrazinyl, each of which is substituted with one, two, or three independently selected $C_{1-4}$ alkyl or $C_{3-7}$ cycloalkyl.

164. A compound or pharmaceutically acceptable salt thereof, according to any one of clauses 1-72, 76-78, and 110, wherein $R^4$ is imidazolyl, pyrazolyl, triazolyl, thiazolyl, or oxadiazolyl, each of which is substituted with one or two independently selected —$CH_3$, —$CH_2CH_3$, —$CH(CH_3)_2$, or cyclopropyl.

165. A compound or pharmaceutically acceptable salt thereof, according to any one of clauses 1-72, 76-78, and 110, wherein $R^4$ is 4-11 membered monocyclic, spirocyclic, or bridged polycyclic heterocycloalkyl comprising one, two, or three heteroatoms independently selected from N, O, and S.

166. A compound or pharmaceutically acceptable salt thereof, according to any one of clauses 1-72, 76-78, and 110, wherein $R^4$ is azetidinyl, oxetanyl, pyrrolidinyl, tetrahydrofuranyl, piperidinyl, tetrahydropyranyl, morpholinyl, dioxanyl, 1-azaspiro[3.3]heptanyl, 2-azaspiro[3.3]heptanyl, 2-oxa-6-azaspiro[3.3]heptanyl, 6-oxa-1-azaspiro[3.3]heptanyl, 2-oxa-6-azaspiro[3.4]octanyl, 2,8-dioxa-5-azaspiro[3.5]nonanyl, 2-oxa-6-azaspiro[3.5]nonanyl, 8-oxa-5-azaspiro[3.5]nonanyl, 2-oxa-5-azabicyclo[2.2.1]heptanyl, 3-oxa-8-azabicyclo[3.2.1]octanyl, or 8-oxa-3-azabicyclo[3.2.1]octanyl.

167. A compound or pharmaceutically acceptable salt thereof, according to any one of clauses 1-72, 76-78, and 110, wherein $R^4$ is 4-8 membered monocyclic or bridged polycyclic heterocycloalkyl comprising one, two, or three heteroatoms independently selected from N, O, and S.

168. A compound or pharmaceutically acceptable salt thereof, according to any one of clauses 1-72, 76-78, and 110, wherein $R^4$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, oxazolidinyl, thiazolidinyl, morpholinyl, thiomorpholinyl, dioxanyl, piperazinyl, 2-oxabicyclo[2.1.1]hexanyl, 5-oxabicyclo[2.1.1]hexanyl, 2-azabicyclo[2.1.1]hexanyl, 5-azabicyclo[2.1.1]hexanyl, 2-thiabicyclo[2.1.1]hexanyl, 5-thiabicyclo[2.1.1]hexanyl, 2-oxabicyclo[2.2.1]heptanyl, 7-oxabicyclo[2.2.1]heptanyl, 2-oxabicyclo[3.1.1]heptanyl, 3-oxabicyclo[3.1.1]heptanyl, 6-oxabicyclo[3.1.1]heptanyl, 2-azabicyclo[2.2.1]heptanyl, 7-azabicyclo[2.2.1]heptanyl, 2-azabicyclo[3.1.1]heptanyl, 3-azabicyclo[3.1.1]heptanyl, 6-azabicyclo[3.1.1]heptanyl, 2-thiabicyclo[2.2.1]heptanyl, 7-thiabicyclo[2.2.1]heptanyl, 2-thiabicyclo[3.1.1]heptanyl, 3-thiabicyclo[3.1.1]heptanyl, 6-thiabicyclo[3.1.1]heptanyl, 2-oxabicyclo[3.2.1]octanyl, 3-oxabicyclo[3.2.1]octanyl, 6-oxabicyclo[3.2.1]octanyl, 8-oxabicyclo[3.2.1]octanyl, 2-azabicyclo[3.2.1]octanyl, 3-azabicyclo[3.2.1]octanyl, 6-azabicyclo[3.2.1]octanyl, 8-azabicyclo[3.2.1]octanyl, 2-thiabicyclo[3.2.1]octanyl, 3-thiabicyclo[3.2.1]octanyl, 6-thiabicyclo[3.2.1]octanyl, 8-thiabicyclo[3.2.1]octanyl, 2-oxa-5-azabicyclo[2.2.1]heptanyl, 3-oxa-6-azabicyclo[3.1.1]heptanyl, 6-oxa-3-azabicyclo[3.1.1]heptanyl, 2-oxa-6-azabicyclo[3.2.1]octanyl, 3-oxa-6-azabicyclo[3.2.1]octanyl, 3-oxa-8-azabicyclo[3.2.1]octanyl, 8-oxa-2-azabicyclo[3.2.1]octanyl, 8-oxa-3-azabicyclo[3.2.1]octanyl, 8-oxa-6-azabicyclo[3.2.1]octanyl, 2-thia-5-azabicyclo[2.2.1]heptanyl, 3-thia-6-azabicyclo[3.1.1]heptanyl, 6-thia-3-azabicyclo[3.1.1]heptanyl, 2-thia-6-azabicyclo[3.2.1]octanyl, 3-thia-6-azabicyclo[3.2.1]octanyl, 3-thia-8-azabicyclo[3.2.1]octanyl, 8-thia-2-azabicyclo[3.2.1]octanyl, 8-thia-3-azabicyclo[3.2.1]octanyl, or 8-thia-6-azabicyclo[3.2.1]octanyl.

169. A compound or pharmaceutically acceptable salt thereof, according to any one of clauses 1-72, 76-78, and 110, wherein $R^4$ is azetidinyl, oxetanyl, pyrrolidinyl, tetrahydrofuranyl, piperidinyl, tetrahydropyranyl, morpholinyl, dioxanyl, 2-oxa-5-azabicyclo[2.2.1]heptanyl, 3-oxa-8-azabicyclo[3.2.1]octanyl, 8-oxa-3-azabicyclo[3.2.1]octanyl.

170. A compound or pharmaceutically acceptable salt thereof, according to any one of clauses 1-72, 76-78, and 110, wherein $R^4$ is 4-11 membered monocyclic, spirocyclic, or bridged polycyclic heterocycloalkyl comprising one, two, or three heteroatoms independently selected from N, O, and S, which heterocycloalkyl is substituted with one, two, or three independently independently selected $R^{10}$.

171. A compound or pharmaceutically acceptable salt thereof, according to any one of clauses 1-72, 76-78, and 110, wherein $R^4$ is azetidinyl, oxetanyl, pyrrolidinyl, tetrahydrofuranyl, piperidinyl, oxazolidinyl, morpholinyl, thiomorpholinyl, piperazinyl, 1-thia-6-azaspiro[3.3]heptanyl, 2-azaspiro[3.3]heptanyl, or 1-oxa-3,8-diazaspiro[4.5]decanyl, each of which is substituted with one or more independently selected $R^{10}$.

172. A compound or pharmaceutically acceptable salt thereof, according to any one of clauses 1-72, 76-78, and 110, wherein $R^4$ is azetidinyl, oxetanyl, pyrrolidinyl, tetrahydrofuranyl, piperidinyl, oxazolidinyl, morpholinyl, thiomorpholinyl, piperazinyl, 1-thia-6-azaspiro[3.3]heptanyl, 2-azaspiro[3.3]heptanyl, or 1-oxa-3,8-diazaspiro[4.5]decanyl, each of which is substituted with one, two, or three independently selected $R^{10}$.

173. A compound or pharmaceutically acceptable salt thereof, according to any one of clauses 1-72, 76-78, and 110, wherein $R^4$ is 4-8 membered monocyclic or bridged polycyclic heterocycloalkyl comprising one, two, or three heteroatoms independently selected from N, O, and S, which heterocycloalkyl is substituted with one or more independently selected $R^{10}$.

174. A compound or pharmaceutically acceptable salt thereof, according to any one of clauses 1-72, 76-78, and 110, wherein $R^4$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, oxazolidinyl, thiazolidinyl, morpholinyl, thiomorpholinyl, dioxanyl, piperazinyl, 2-oxabicyclo[2.1.1]hexanyl, 5-oxabicyclo[2.1.1]hexanyl, 2-azabicyclo[2.1.1]hexanyl, 5-azabicyclo[2.1.1]hexanyl, 2-thiabicyclo[2.1.1]hexanyl, 5-thiabicyclo[2.1.1]hexanyl, 2-oxabicyclo[2.2.1]heptanyl, 7-oxabicyclo[2.2.1]heptanyl, 2-oxabicyclo[3.1.1]heptanyl, 3-oxabicyclo[3.1.1]heptanyl, 6-oxabicyclo[3.1.1]heptanyl, 2-azabicyclo[2.2.1]heptanyl, 7-azabicyclo[2.2.1]heptanyl, 2-azabicyclo

[3.1.1]heptanyl, 3-azabicyclo[3.1.1]heptanyl, 6-azabicyclo[3.1.1]heptanyl, 2-thiabicyclo[2.2.1]heptanyl, 7-thiabicyclo[2.2.1]heptanyl, 2-thiabicyclo[3.1.1]heptanyl, 3-thiabicyclo[3.1.1]heptanyl, 6-thiabicyclo[3.1.1]heptanyl, 2-oxabicyclo[3.2.1]octanyl, 3-oxabicyclo[3.2.1]octanyl, 6-oxabicyclo[3.2.1]octanyl, 8-oxabicyclo[3.2.1]octanyl, 2-azabicyclo[3.2.1]octanyl, 3-azabicyclo[3.2.1]octanyl, 6-azabicyclo[3.2.1]octanyl, 8-azabicyclo[3.2.1]octanyl, 2-thiabicyclo[3.2.1]octanyl, 3-thiabicyclo[3.2.1]octanyl, 6-thiabicyclo[3.2.1]octanyl, 8-thiabicyclo[3.2.1]octanyl, 2-oxa-5-azabicyclo[2.2.1]heptanyl, 3-oxa-6-azabicyclo[3.1.1]heptanyl, 6-oxa-3-azabicyclo[3.1.1]heptanyl, 2-oxa-6-azabicyclo[3.2.1]octanyl, 3-oxa-6-azabicyclo[3.2.1]octanyl, 3-oxa-8-azabicyclo[3.2.1]octanyl, 8-oxa-2-azabicyclo[3.2.1]octanyl, 8-oxa-3-azabicyclo[3.2.1]octanyl, 8-oxa-6-azabicyclo[3.2.1]octanyl, 2-thia-5-azabicyclo[2.2.1]heptanyl, 3-thia-6-azabicyclo[3.1.1]heptanyl, 6-thia-3-azabicyclo[3.1.1]heptanyl, 2-thia-6-azabicyclo[3.2.1]octanyl, 3-thia-6-azabicyclo[3.2.1]octanyl, 3-thia-8-azabicyclo[3.2.1]octanyl, 8-thia-2-azabicyclo[3.2.1]octanyl, 8-thia-3-azabicyclo[3.2.1]octanyl, or 8-thia-6-azabicyclo[3.2.1]octanyl, each of which is substituted with one, two, or three independently selected $R^{10}$.

175. A compound or pharmaceutically acceptable salt thereof, according to any one of clauses 1-72, 76-78, and 110, wherein $R^4$ is azetidinyl, oxetanyl, pyrrolidinyl, tetrahydrofuranyl, piperidinyl, oxazolidinyl, morpholinyl, thiomorpholinyl, piperazinyl, each of which is substituted with one, two, or three independently selected $R^{10}$.

176. A compound or pharmaceutically acceptable salt thereof, according to any one of clauses 1-72, 76-78, and 110, and 170-175, wherein $R^{10}$ is —OH, phenyl, =NH, halo, oxo, —CN, —C(=O)H, —C(=O)NH$_2$, —C(=O)OH, —NR$^{14a}$R$^{14b}$, $C_{1-4}$ alkyl optionally substituted with one or more independently selected halo, —CN, —OH, —C(=O)—$C_{1-4}$ alkoxy, or $C_{1-4}$ alkoxy, $C_{3-7}$ cycloalkyl, 4-6 membered monocyclic heterocycloalkyl comprising one, two, or three heteroatoms independently selected from N, O, and S, —C(=O)—$C_{1-4}$ alkyl, —S(=O)$_2$—$C_{1-4}$ alkyl, or —C(=O)—$C_{1-6}$ alkoxy.

177. A compound or pharmaceutically acceptable salt thereof, according to any one of clauses 1-72, 76-78, and 110, and 170-175, wherein $R^{10}$ is —OH, phenyl, =NH, F, Cl, Br, oxo, —CN, —C(=O)H, —C(=O)NH$_2$, —C(=O)OH, —NR$^{14a}$R$^{14b}$, —CH$_3$, —CH$_2$CH$_3$, —CH(CH$_3$)$_2$, —CHF$_2$, —CF$_3$, —CH$_2$—CHF$_2$, —CH$_2$—CF$_3$, —CH$_2$—CN, —CH$_2$—CH$_2$—CN, —CH(CH$_3$)—CN, —C(CH$_3$)$_2$—CN, —CH(CH$_3$)—CH$_2$—CN, —CH$_2$—C(CH$_3$)$_2$—CN, —CH$_2$—OH, —CH$_2$—CH$_2$—OH, —CH(CH$_3$)—OH, —C(CH$_3$)$_2$—OH, —CH(CH$_3$)—CH$_2$—OH, —CH$_2$—C(CH$_3$)$_2$—OH, —CH$_2$—C(=O)—O—CH$_3$, —CH$_2$—C(=O)—O—CH$_2$—CH$_3$, —CH$_2$—CH$_2$—C(=O)—O—CH$_3$, —CH$_2$—CH$_2$—C(=O)—O—CH$_2$—CH$_3$, —CH(CH$_3$)—C(=O)—O—CH$_3$, —CH(CH$_3$)—C(=O)—O—CH$_2$—CH$_3$, —C(CH$_3$)$_2$—C(=O)—O—CH$_3$, —C(CH$_3$)$_2$—C(=O)—O—CH$_2$—CH$_3$, —CH(CH$_3$)—CH$_2$—C(=O)—O—CH$_3$, —CH(CH$_3$)—CH$_2$—C(=O)—O—CH$_2$—CH$_3$, —CH$_2$—CH(CH$_3$)—C(=O)—O—CH$_3$, —CH$_2$—CH(CH$_3$)—C(=O)—O—CH$_2$—CH$_3$, —CH$_2$—C(CH$_3$)$_2$—C(=O)—O—CH$_3$, —CH$_2$—C(CH$_3$)$_2$—C(=O)—O—CH$_2$—CH$_3$, —CH$_2$—O—CH$_3$, —CH$_2$CH$_2$—O—CH$_3$, cyclopropyl, cyclobutyl, cyclopentyl, cyclohexyl, azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, piperazinyl, —C(=O)—CH$_3$, —C(=O)—CH$_2$CH$_3$, —C(=O)—CH(CH$_3$)$_2$, —S(=O)$_2$—CH$_3$, —S(=O)$_2$—CH$_2$CH$_3$, —S(=O)$_2$—CH(CH$_3$)$_2$, —C(=O)—O—CH$_3$, —C(=O)—O—CH$_2$CH$_3$, —C(=O)—O—CH(CH$_3$)$_2$, or —C(=O)—O—C(CH$_3$)$_3$.

178. A compound or pharmaceutically acceptable salt thereof, according to any one of clauses 1-72, 76-78, and 110, and 170-175, wherein $R^{10}$ is —OH, phenyl, =NH, F, oxo, —CN, —C(=O)H, —NR$^{14a}$R$^{14b}$, —CH$_3$, —CH$_2$CH$_3$, —CH(CH$_3$)$_2$, —CF$_3$, —CH$_2$—CHF$_2$, —CH$_2$—CF$_3$, —CH$_2$—CN, —CH$_2$—CH$_2$—CN, —CH$_2$—OH, —CH$_2$—CH$_2$—OH, —CH$_2$—C(CH$_3$)$_2$—OH, —CH$_2$—C(=O)—O—CH$_2$—CH$_3$, —CH$_2$—O—CH$_3$, cyclopropyl, oxetanyl, —C(=O)—CH$_3$, —S(=O)$_2$—CH$_3$, —C(=O)—O—CH$_3$, —C(=O)—O—CH$_2$CH$_3$, or —C(=O)—O—C(CH$_3$)$_3$.

179. A compound or pharmaceutically acceptable salt thereof, according to any one of clauses 1-72, 76-78, and 110, and 170-175, wherein $R^{10}$ is halo, oxo, —CN, —C(=O)H, —NR$^{14a}$R$^{14b}$, $C_{1-4}$ alkyl optionally substituted with one or more independently selected halo or $C_{1-4}$ alkoxy, $C_{3-7}$ cycloalkyl, —C(=O)—$C_{1-4}$ alkyl, —S(=O)$_2$—$C_{1-4}$ alkyl, or —C(=O)—$C_{1-6}$ alkoxy.

180. A compound or pharmaceutically acceptable salt thereof, according to any one of clauses 1-72, 76-78, and 110, and 170-175, wherein $R^{10}$ is F, Cl, Br, oxo, —CN, —C(=O)H, —NR$^{14a}$R$^{14b}$, —CH$_3$, —CH$_2$CH$_3$, —CH(CH$_3$)$_2$, —CHF$_2$, —CF$_3$, —CH$_2$—CHF$_2$, —CH$_2$—CF$_3$, —CH$_2$—O—CH$_3$, —CH$_2$CH$_2$—O—CH$_3$, cyclopropyl, cyclobutyl, cyclopentyl, cyclohexyl, —C(=O)—CH$_3$, —C(=O)—CH$_2$CH$_3$, —C(=O)—CH(CH$_3$)$_2$, —S(=O)$_2$—CH$_3$, —S(=O)$_2$—CH$_2$CH$_3$, —S(=O)$_2$—CH(CH$_3$)$_2$, —C(=O)—O—CH$_3$, —C(=O)—O—CH$_2$CH$_3$, —C(=O)—O—CH(CH$_3$)$_2$, or —C(=O)—O—C(CH$_3$)$_3$.

181. A compound or pharmaceutically acceptable salt thereof, according to any one of clauses 1-72, 76-78, and 110, and 170-175, wherein $R^{10}$ is F, oxo, —CN, —C(=O)H, —NR$^{14a}$R$^{14b}$, —CH$_3$, —CH$_2$CH$_3$, —CH(CH$_3$)$_2$, —CF$_3$, —CH$_2$—CHF$_2$, —CH$_2$—CF$_3$, —CH$_2$—O—CH$_3$, cyclopropyl, —C(=O)—CH$_3$, —S(=O)$_2$—CH$_3$, —C(=O)—O—CH$_3$, or —C(=O)—O—C(CH$_3$)$_3$.

182. A compound or pharmaceutically acceptable salt thereof, according to any one of clauses 1-72, 76-78, and 110, and 170-175, wherein $R^{10}$ is —NR$^{14a}$R$^{14b}$, and $R^{14a}$ and $R^{14b}$ are both H.

183. A compound or pharmaceutically acceptable salt thereof, according to any one of clauses 1-72, 76-78, and 110, and 170-175, wherein $R^{10}$ is —NR$^{14a}$R$^{14b}$, and one of $R^{14a}$ and $R^{14b}$ is H, and the other is $C_{1-4}$ alkyl or —S(=O)$_2$—$C_{1-4}$ alkyl.

184. A compound or pharmaceutically acceptable salt thereof, according to any one of clauses 1-72, 76-78, and 110, and 170-175, wherein $R^{10}$ is —NR$^{14a}$R$^{14b}$, and one of $R^{14a}$ and $R^{14b}$ is H, and the other is —CH$_3$, —CH$_2$CH$_3$, —CH(CH$_3$)$_2$, or —S(=O)$_2$—CH$_3$.

185. A compound or pharmaceutically acceptable salt thereof, according to any one of clauses 1-72, 76-78, and 110, and 170-175, wherein $R^{10}$ is —NR$^{14a}$R$^{14b}$, and $R^{14a}$ and $R^{14b}$ are independently —$CH_3$, —$CH_2CH_3$, —$CH(CH_3)_2$, or —$S(=O)_2$—$CH_3$.

186. A compound or pharmaceutically acceptable salt thereof, according to any one of clauses 1-72, 76-78, and 110, and 170-175, wherein $R^{14a}$ and $R^{14b}$ are both H.

187. A compound or pharmaceutically acceptable salt thereof, according to any one of clauses 1-72, 76-78, and 110, and 170-175, wherein one of $R^{14a}$ and $R^{14b}$ is H, and the other is $C_{1-4}$ alkyl.

188. A compound or pharmaceutically acceptable salt thereof, according to any one of clauses 1-72, 76-78, and 110, and 170-175, wherein one of $R^{14a}$ and $R^{14b}$ is H, and the other is —$CH_3$, —$CH_2CH_3$, or —$CH(CH_3)_2$.

189. A compound or pharmaceutically acceptable salt thereof, according to any one of clauses 1-72, 76-78, and 110, and 170-175, wherein $R^{14a}$ and $R^{14b}$ are both $C_{1-4}$ alkyl.

190. A compound or pharmaceutically acceptable salt thereof, according to any one of clauses 1-72, 76-78, and 110, and 170-175, wherein $R^{14a}$ and $R^{14b}$ are independently —$CH_3$, —$CH_2CH_3$, or —$CH(CH_3)_2$.

191. A compound or pharmaceutically acceptable salt thereof, according to any one of clauses 1-72, 76-78, and 110, wherein $R^4$ is —$NR^{11a}R^{11b}$.

192. A compound or pharmaceutically acceptable salt thereof, according to any one of clauses 1-72, 76-78, 110 and 191, wherein $R^{11a}$ is H.

193. A compound or pharmaceutically acceptable salt thereof, according to any one of clauses 1-72, 76-78, 110 and 191, wherein $R^{11a}$ is $C_{1-4}$ alkyl optionally substituted with one or more independently selected halo, —OH, —CN, or $C_{1-4}$ alkoxy.

194. A compound or pharmaceutically acceptable salt thereof, according to any one of clauses 1-72, 76-78, 110 and 191, wherein $R^{11a}$ is —$CH_3$, —$CH_2CH_3$, —$CH(CH_3)_2$, or —$CH_2CHF_2$.

195. A compound or pharmaceutically acceptable salt thereof, according to any one of clauses 1-72, 76-78, 110 and 191, wherein $R^{11a}$ is —$CH_3$.

196. A compound or pharmaceutically acceptable salt thereof, according to any one of clauses 1-72, 76-78, 110 and 191-195, wherein $R^{11b}$ is H or phenyl.

197. A compound or pharmaceutically acceptable salt thereof, according to any one of clauses 1-72, 76-78, 110 and 191, wherein $R^4$ is —$NH_2$.

198. A compound or pharmaceutically acceptable salt thereof, according to any one of clauses 1-72, 76-78, 110 and 191-195, wherein $R^{11b}$ is $C_{1-4}$ alkyl.

199. A compound or pharmaceutically acceptable salt thereof, according to any one of clauses 1-72, 76-78, 110 and 191-195, wherein $R^{11b}$ is —$CH_3$, —$CH_2CH_3$, or —$CH(CH_3)_2$.

200. A compound or pharmaceutically acceptable salt thereof, according to any one of clauses 1-72, 76-78, and 110 191, wherein $R^4$ is —NH—$CH_3$, —$N(CH_3)_2$, —NH—$CH_2CH_3$, —$N(CH_2CH_3)_2$, —$N(CH(CH_3)_2)_2$, or —$N(CH_3)$—$CH_2CHF_2$.

201. A compound or pharmaceutically acceptable salt thereof, according to any one of clauses 1-72, 76-78, 110 and 191, and 144-148, wherein $R^{11b}$ is $C_{1-4}$ alkyl substituted with one or more independently selected halo, —OH, —CN, or $C_{1-4}$ alkoxy.

202. A compound or pharmaceutically acceptable salt thereof, according to any one of clauses 1-72, 76-78, 110 and 191, wherein $R^{11b}$ is —$CH_3$, —$CH_2CH_3$, or —$CH(CH_3)_2$, each of which is substituted with one or more independently selected halo, —OH, —CN, or $C_{1-4}$ alkoxy.

203. A compound or pharmaceutically acceptable salt thereof, according to any one of clauses 1-72, 76-78, 110 and 191, wherein $R^{11b}$ is —$CH_3$, or —$CH_2CH_3$, each of which is substituted with one F, —OH, —CN, or —O—$CH_3$.

204. A compound or pharmaceutically acceptable salt thereof, according to any one of clauses 1-72, 76-78, 110 and 191-195, wherein $R^{11b}$ is —$CH_2$—CN, —$CH_2CH_2$—OH, or —$CH_2CH_2$—O—$CH_3$.

205. A compound or pharmaceutically acceptable salt thereof, according to any one of clauses 1-72, 76-78, 110 and 191-195, wherein $R^{11b}$ is $C_{3-7}$ cycloalkyl.

206. A compound or pharmaceutically acceptable salt thereof, according to any one of clauses 1-72, 76-78, 110 and 191-195, wherein $R^{11b}$ is cyclopropyl, cyclobutyl, cyclopentyl, or cyclohexyl.

207. A compound or pharmaceutically acceptable salt thereof, according to any one of clauses 1-72, 76-78, 110 and 191-195, wherein $R^{11b}$ is cyclopropyl.

208. A compound or pharmaceutically acceptable salt thereof, according to any one of clauses 1-72, 76-78, 110 and 191-195, wherein $R^{11b}$ is —C(=O)—$C_{1-4}$ alkoxy.

209. A compound or pharmaceutically acceptable salt thereof, according to any one of clauses 1-72, 76-78, 110 and 191-195, wherein $R^{11b}$ is —C(=O)—O—$CH_3$, —C(=O)—O—$CH_2CH_3$, or —C(=O)—O—$CH(CH_3)_2$.

210. A compound or pharmaceutically acceptable salt thereof, according to any one of clauses 1-72, 76-78, 110 and 191-195, wherein $R^{11b}$ is —C(=O)—O—$CH_3$.

211. A compound or pharmaceutically acceptable salt thereof, according to any one of clauses 1-72, 76-78, 110 and 191-195, wherein $R^{11b}$ is —C(=O)—$C_{1-4}$ alkyl.

212. A compound or pharmaceutically acceptable salt thereof, according to any one of clauses 1-62, 66-68, 93, and 144-148, wherein $R^{11b}$ is —C(=O)—$CH_3$, —C(=O)—$CH_2CH_3$, or —C(=O)—$CH(CH_3)_2$.

213. A compound or pharmaceutically acceptable salt thereof, according to any one of clauses 1-72, 76-78, 110 and 191-195, wherein $R^{11b}$ is —C(=O)—$CH_3$.

214. A compound or pharmaceutically acceptable salt thereof, according to any one of clauses 1-72, 76-78, 110 and 191-195, wherein $R^{11b}$ is —C(=O)—$C_{1-4}$ alkyl substituted with one or more independently selected halo.

215. A compound or pharmaceutically acceptable salt thereof, according to any one of clauses 1-72, 76-78, 110 and 191-195, wherein $R^{11b}$ is —C(=O)—$CHF_2$ 216. A compound or pharmaceutically acceptable salt thereof, according to any one of clauses 1-72, 76-78, 110 and 191-195, wherein $R^{11b}$ is 5-6 membered monocyclic heteroaryl comprising one, two, or three heteroatoms independently selected from N, O, and S.

217. A compound or pharmaceutically acceptable salt thereof, according to any one of clauses 1-72, 76-78, 110 and 191-195, wherein $R^{11b}$ is pyrrolyl, furanyl, thiophenyl, pyrazolyl, isoxazolyl, isothiazolyl, imidazolyl, oxazolyl, thiazolyl, triazolyl, furazanyl, thiadiazolyl, oxadiazolyl, tetrazolyl, oxatriazolyl, thiatriazolyl, pyridinyl, pyrazinyl, pyridazinyl, or pyrimidinyl.

218. A compound or pharmaceutically acceptable salt thereof, according to any one of clauses 1-72, 76-78, 110 and 191-195, wherein $R^{11b}$ is pyridinyl, pyridazinyl, or pyrimidinyl.

219. A compound or pharmaceutically acceptable salt thereof, according to any one of clauses 1-72, 76-78, and 110, wherein $R^4$ is —C(=O)—O—CH$_3$, —C(=O)—O—CH$_2$CH$_3$, or —C(=O)—O—CH(CH$_3$)$_2$.

220. A compound or pharmaceutically acceptable salt thereof, according to any one of clauses 1-72, 76-78, and 110, wherein $R^4$ is —C(=O)—NR$^{12a}$R$^{12b}$.

221. A compound or pharmaceutically acceptable salt thereof, according to any one of clauses 1-72, 76-78, 110 and 220, wherein $R^{12a}$ and $R^{12b}$ are both H.

222. A compound or pharmaceutically acceptable salt thereof, according to any one of clauses 1-72, 76-78, 110 and 220, wherein one of $R^{12a}$ and $R^{12b}$ is H, and the other is $C_{1-4}$ alkyl.

223. A compound or pharmaceutically acceptable salt thereof, according to any one of clauses 1-72, 76-78, 110 and 220, wherein one of $R^{12a}$ and $R^{12b}$ is H, and the other is —CH$_3$, —CH$_2$CH$_3$, or —CH(CH$_3$)$_2$.

224. A compound or pharmaceutically acceptable salt thereof, according to any one of clauses 1-72, 76-78, 110 and 220, wherein $R^{12a}$ and $R^{12b}$ are both $C_{1-4}$ alkyl.

225. A compound or pharmaceutically acceptable salt thereof, according to any one of clauses 1-72, 76-78, 110 and 220, wherein each $R^{12a}$ and $R^{12b}$ is independently —CH$_3$, —CH$_2$CH$_3$, or —CH(CH$_3$)$_2$.

226. A compound or pharmaceutically acceptable salt thereof, according to any one of clauses 1-72, 76-78, 110 and 220, wherein $R^{12a}$ and $R^{12b}$ are —CH$_3$.

227. A compound or pharmaceutically acceptable salt thereof, according to clause 1, wherein the compound is selected from Table III.

228. A pharmaceutical composition comprising a pharmaceutically acceptable carrier and a pharmaceutically effective amount of a compound or pharmaceutically acceptable salt thereof according to any one of clauses 1-227.

229. A pharmaceutical composition according to clause 228 comprising a further therapeutic agent.

230. A compound or pharmaceutically acceptable salt thereof, according to any one of clauses 1-227, or a pharmaceutical composition according to clause 228 or 229 for use in medicine.

231. A compound or pharmaceutically acceptable salt thereof, according to any one of clauses 1-227, or a pharmaceutical composition according to clause 228 or 229 for use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of TNFα, interferons, IL-6, IL-12 and/or IL-23, respiratory diseases, endocrine and/or metabolic diseases, cardiovascular diseases, dermatological diseases, and/or abnormal angiogenesis associated diseases.

232. A compound or pharmaceutically acceptable salt thereof, according to any one of clauses 1-227, or a pharmaceutical composition according to clause 228 or 229, wherein said compound or pharmaceutical composition is administered in combination with a further therapeutic agent.

233. The pharmaceutical composition according to clause 229, or the use according to clause 232, wherein the further therapeutic agent is an agent for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration or stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, EastoPennsylvaniaPa, which is incorporated herein by reference.

A compound of the invention can also be administered in sustained release forms or from sustained release drug delivery systems. A description of representative sustained release materials can be found in Remington's Pharmaceutical Sciences. (Remington 1985)

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine.

In one embodiment, the present invention provides compounds of the invention or pharmaceutical compositions comprising a compound of the invention, for use in the prophylaxis and/or treatment of inflammatory diseases. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In another embodiment, the present invention provides the use of compounds of the invention or pharmaceutical compositions comprising a compound of the invention in the manufacture of a medicament for the prophylaxis and/or treatment of inflammatory diseases. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In additional method of treatment aspects, this invention provides methods of prophylaxis and/or treatment of a mammal afflicted with inflammatory diseases, which methods comprise the administration of an effective amount of a compound of the invention or one or more of the pharmaceutical compositions herein described for the treatment or prophylaxis of said condition. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In one embodiment, the present invention provides pharmaceutical compositions comprising a compound of the invention, and another therapeutic agent. In a particular embodiment, the other therapeutic agent is a inflammatory diseases treatment agent. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In one embodiment, the present invention provides compounds of the invention or pharmaceutical compositions comprising a compound of the invention, for use in the prophylaxis and/or treatment of autoinflammatory diseases. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In another embodiment, the present invention provides the use of compounds of the invention or pharmaceutical compositions comprising a compound of the invention in the manufacture of a medicament for the prophylaxis and/or treatment of autoinflammatory diseases. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In additional method of treatment aspects, this invention provides methods of prophylaxis and/or treatment of a mammal afflicted with autoinflammatory diseases, which methods comprise the administration of an effective amount of a compound of the invention or one or more of the pharmaceutical compositions herein described for the treatment or prophylaxis of said condition. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In one embodiment, the present invention provides pharmaceutical compositions comprising a compound of the invention, and another therapeutic agent. In a particular embodiment, the other therapeutic agent is a autoinflammatory diseases treatment agent. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In one embodiment, the present invention provides compounds of the invention or pharmaceutical compositions comprising a compound of the invention, for use in the prophylaxis and/or treatment of autoimmune diseases. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosus, type I diabetes mellitus and inflammatory bowel disease.

In another embodiment, the present invention provides the use of compounds of the invention or pharmaceutical compositions comprising a compound of the invention in the manufacture of a medicament for the prophylaxis and/or treatment of autoimmune diseases. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosus, type I diabetes mellitus and inflammatory bowel disease.

In additional method of treatment aspects, this invention provides methods of prophylaxis and/or treatment of a mammal afflicted with autoimmune diseases, which methods comprise the administration of an effective amount of a compound of the invention or one or more of the pharmaceutical compositions herein described for the treatment or prophylaxis of said condition. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosus, type I diabetes mellitus and inflammatory bowel disease.

In one embodiment, the present invention provides pharmaceutical compositions comprising a compound of the invention, and another therapeutic agent. In a particular embodiment, the other therapeutic agent is an autoimmune diseases treatment agent. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosis, type I diabetes mellitus and inflammatory bowel disease.

In one embodiment, the present invention provides compounds of the invention or pharmaceutical compositions comprising a compound of the invention, for use in the prophylaxis and/or treatment of proliferative diseases. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In another embodiment, the present invention provides the use of compounds of the invention or pharmaceutical compositions comprising a compound of the invention in the manufacture of a medicament for the prophylaxis and/or treatment of proliferative diseases. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In additional method of treatment aspects, this invention provides methods of prophylaxis and/or treatment of a mammal afflicted with proliferative diseases, which methods comprise the administration of an effective amount of a compound of the invention or one or more of the pharmaceutical compositions herein described for the treatment or prophylaxis of said condition. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In one embodiment, the present invention provides pharmaceutical compositions comprising a compound of the invention, and another therapeutic agent. In a particular embodiment, the other therapeutic agent is a proliferative diseases treatment agent. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In one embodiment, the present invention provides compounds of the invention or pharmaceutical compositions comprising a compound of the invention, for use in the prophylaxis and/or treatment of fibrotic diseases. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In another embodiment, the present invention provides the use of compounds of the invention or pharmaceutical compositions comprising a compound of the invention in the manufacture of a medicament for the prophylaxis and/or treatment of fibrotic diseases. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In additional method of treatment aspects, this invention provides methods of prophylaxis and/or treatment of a mammal afflicted with fibrotic diseases, which methods comprise the administration of an effective amount of a compound of the invention or one or more of the pharmaceutical compositions herein described for the treatment or prophylaxis of said condition. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In one embodiment, the present invention provides pharmaceutical compositions comprising a compound of the invention, and another therapeutic agent. In a particular embodiment, the other therapeutic agent is a fibrotic diseases treatment agent. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In one embodiment, the present invention provides compounds of the invention or pharmaceutical compositions comprising a compound of the invention, for use in the prophylaxis and/or treatment of transplantation rejection. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to agraft-versus-host disease.

In another embodiment, the present invention provides the use of compounds of the invention or pharmaceutical compositions comprising a compound of the invention in the manufacture of a medicament for the prophylaxis and/or treatment of transplantation rejection. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to agraft-versus-host disease.

In additional method of treatment aspects, this invention provides methods of prophylaxis and/or treatment of a mammal afflicted with transplantation rejection, which methods comprise the administration of an effective amount of a compound of the invention or one or more of the pharmaceutical compositions herein described for the treatment or prophylaxis of said condition. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to agraft-versus-host disease.

In one embodiment, the present invention provides pharmaceutical compositions comprising a compound of the invention, and another therapeutic agent. In a particular embodiment, the other therapeutic agent is a transplantation rejection treatment agent. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to agraft-versus-host disease.

In one embodiment, the present invention provides compounds of the invention or pharmaceutical compositions comprising a compound of the invention, for use in the prophylaxis and/or treatment of diseases involving impairment of cartilage turnover. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In another embodiment, the present invention provides the use of compounds of the invention or pharmaceutical compositions comprising a compound of the invention in the manufacture of a medicament for the prophylaxis and/or treatment of diseases involving impairment of cartilage turnover. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In additional method of treatment aspects, this invention provides methods of prophylaxis and/or treatment of a mammal afflicted with diseases involving impairment of cartilage turnover, which methods comprise the administration of an effective amount of a compound of the invention or one or more of the pharmaceutical compositions herein described for the treatment or prophylaxis of said condition. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In one embodiment, the present invention provides pharmaceutical compositions comprising a compound of the invention, and another therapeutic agent. In a particular embodiment, the other therapeutic agent is a diseases involving impairment of cartilage turnover treatment agent. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In one embodiment, the present invention provides compounds of the invention or pharmaceutical compositions comprising a compound of the invention, for use in the prophylaxis and/or treatment of congenital cartilage malformation. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In another embodiment, the present invention provides the use of compounds of the invention or pharmaceutical compositions comprising a compound of the invention in the manufacture of a medicament for the prophylaxis and/or treatment of congenital cartilage malformation. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In additional method of treatment aspects, this invention provides methods of prophylaxis and/or treatment of a mammal afflicted with congenital cartilage malformation, which methods comprise the administration of an effective amount of a compound of the invention or one or more of the pharmaceutical compositions herein described for the treatment or prophylaxis of said condition. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In one embodiment, the present invention provides pharmaceutical compositions comprising a compound of the invention, and another therapeutic agent. In a particular embodiment, the other therapeutic agent is a congenital cartilage malformation treatment agent. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In one embodiment, the present invention provides compounds of the invention or pharmaceutical compositions comprising a compound of the invention, for use in the prophylaxis and/or treatment of diseases involving impairment of bone turnover. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In another embodiment, the present invention provides the use of compounds of the invention or pharmaceutical compositions comprising a compound of the invention in the manufacture of a medicament for the prophylaxis and/or treatment of diseases involving impairment of bone turnover. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In additional method of treatment aspects, this invention provides methods of prophylaxis and/or treatment of a mammal afflicted with diseases involving impairment of bone turnover, which methods comprise the administration of an effective amount of a compound of the invention or one or more of the pharmaceutical compositions herein described for the treatment or prophylaxis of said condition. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In one embodiment, the present invention provides pharmaceutical compositions comprising a compound of the invention, and another therapeutic agent. In a particular embodiment, the other therapeutic agent is a diseases involving impairment of bone turnover treatment agent. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In one embodiment, the present invention provides compounds of the invention or pharmaceutical compositions comprising a compound of the invention, for use in the prophylaxis and/or treatment of diseases associated with hypersecretion of IL-6. In particular, the term diseases associated with hypersecretion of IL-6 refers to Castleman's disease, multiple myeloma, psoriasis, Kaposi's sarcoma and/or mesangial proliferative glomerulonephritis.

In another embodiment, the present invention provides the use of compounds of the invention or pharmaceutical compositions comprising a compound of the invention in the manufacture of a medicament for the prophylaxis and/or treatment of diseases associated with hypersecretion of IL-6. In particular, the term diseases associated with hypersecretion of IL-6 refers to Castleman's disease, multiple myeloma, psoriasis, Kaposi's sarcoma and/or mesangial proliferative glomerulonephritis.

In additional method of treatment aspects, this invention provides methods of prophylaxis and/or treatment of a mammal afflicted with diseases associated with hypersecretion of IL-6, which methods comprise the administration of an effective amount of a compound of the invention or one or more of the pharmaceutical compositions herein described for the treatment or prophylaxis of said condition. In particular, the term diseases associated with hypersecretion of IL-6 refers to Castleman's disease, multiple myeloma, psoriasis, Kaposi's sarcoma and/or mesangial proliferative glomerulonephritis.

In one embodiment, the present invention provides pharmaceutical compositions comprising a compound of the invention, and another therapeutic agent. In a particular embodiment, the other therapeutic agent is a diseases associated with hypersecretion of IL-6 treatment agent. In particular, the term diseases associated with hypersecretion of IL-6 refers to Castleman's disease, multiple myeloma, psoriasis, Kaposi's sarcoma and/or mesangial proliferative glomerulonephritis.

In one embodiment, the present invention provides compounds of the invention or pharmaceutical compositions comprising a compound of the invention, for use in the prophylaxis and/or treatment of diseases associated with hypersecretion of TNFα, interferons, IL-12 and/or IL-23. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In another embodiment, the present invention provides the use of compounds of the invention or pharmaceutical compositions comprising a compound of the invention in the manufacture of a medicament for the prophylaxis and/or treatment of diseases associated with hypersecretion of TNFα, interferons, IL-12 and/or IL-23. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In additional method of treatment aspects, this invention provides methods of prophylaxis and/or treatment of a mammal afflicted with diseases associated with hypersecretion of TNFα, interferons, IL-12 and/or IL-23, which methods comprise the administration of an effective amount of a compound of the invention or one or more of the pharmaceutical compositions herein described for the treatment or prophylaxis of said condition. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In one embodiment, the present invention provides pharmaceutical compositions comprising a compound of the invention, and another therapeutic agent. In a particular embodiment, the other therapeutic agent is a diseases associated with hypersecretion of TNFα, interferons, IL-12 and/or IL-23 treatment agent. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In one embodiment, the present invention provides compounds of the invention or pharmaceutical compositions comprising a compound of the invention, for use in the prophylaxis and/or treatment of respiratory diseases. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In another embodiment, the present invention provides the use of compounds of the invention or pharmaceutical compositions comprising a compound of the invention in the manufacture of a medicament for the prophylaxis and/or treatment of respiratory diseases. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In additional method of treatment aspects, this invention provides methods of prophylaxis and/or treatment of a mammal afflicted with respiratory diseases, which methods comprise the administration of an effective amount of a compound of the invention or one or more of the pharmaceutical compositions herein described for the treatment or prophylaxis of said condition. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In one embodiment, the present invention provides pharmaceutical compositions comprising a compound of the invention, and another therapeutic agent. In a particular embodiment, the other therapeutic agent is a respiratory diseases treatment agent. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In one embodiment, the present invention provides compounds of the invention or pharmaceutical compositions comprising a compound of the invention, for use in the prophylaxis and/or treatment of endocrine and/or metabolic diseases. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or type II diabetes.

In another embodiment, the present invention provides the use of compounds of the invention or pharmaceutical compositions comprising a compound of the invention in the manufacture of a medicament for the prophylaxis and/or treatment of endocrine and/or metabolic diseases. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or type II diabetes.

In additional method of treatment aspects, this invention provides methods of prophylaxis and/or treatment of a mammal afflicted with endocrine and/or metabolic diseases, which methods comprise the administration of an effective amount of a compound of the invention or one or more of the pharmaceutical compositions herein described for the treatment or prophylaxis of said condition. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or type II diabetes.

In one embodiment, the present invention provides pharmaceutical compositions comprising a compound of the invention, and another therapeutic agent. In a particular embodiment, the other therapeutic agent is a endocrine and/or metabolic diseases treatment agent. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or type II diabetes.

In one embodiment, the present invention provides compounds of the invention or pharmaceutical compositions comprising a compound of the invention, for use in the prophylaxis and/or treatment of cardiovascular diseases. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; vasoconstriction (including that associated with migraines); vascular abnormality, inflammation, or insufficiency limited to a single organ or tissue. More particularly, the term refers to atherosclerosis.

In another embodiment, the present invention provides the use of compounds of the invention or pharmaceutical compositions comprising a compound of the invention in the manufacture of a medicament for the prophylaxis and/or treatment of cardiovascular diseases. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; vasoconstriction (including that associated with migraines); vascular abnormality, inflammation, or insufficiency limited to a single organ or tissue. More particularly, the term refers to atherosclerosis.

In additional method of treatment aspects, this invention provides methods of prophylaxis and/or treatment of a mammal afflicted with cardiovascular diseases, which methods comprise the administration of an effective amount of a compound of the invention or one or more of the pharmaceutical compositions herein described for the treatment or prophylaxis of said condition. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; vasoconstriction (including that associated with migraines); vascular abnormality, inflammation, or insufficiency limited to a single organ or tissue. More particularly, the term refers to atherosclerosis.

In one embodiment, the present invention provides pharmaceutical compositions comprising a compound of the invention, and another therapeutic agent. In a particular embodiment, the other therapeutic agent is a cardiovascular diseases treatment agent. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; vasoconstriction (including that associated with migraines); vascular abnormality, inflammation, or insufficiency limited to a single organ or tissue. More particularly, the term refers to atherosclerosis.

In one embodiment, the present invention provides compounds of the invention or pharmaceutical compositions comprising a compound of the invention, for use in the prophylaxis and/or treatment of dermatological diseases. In particular, the term dermatological diseases refers to atopic dermatitis, bullous disorders, collagenoses, psoriasis, psoriatic lesions, dermatitis, contact dermatitis, eczema, vitiligo, pruritus, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, or urticaria.

In another embodiment, the present invention provides the use of compounds of the invention or pharmaceutical compositions comprising a compound of the invention in the manufacture of a medicament for the prophylaxis and/or treatment of dermatological diseases. In particular, the term dermatological diseases refers to atopic dermatitis, bullous disorders, collagenoses, psoriasis, psoriatic lesions, dermatitis, contact dermatitis, eczema, vitiligo, pruritus, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, or urticaria.

In additional method of treatment aspects, this invention provides methods of prophylaxis and/or treatment of a mammal afflicted with dermatological diseases, which methods comprise the administration of an effective amount of a compound of the invention or one or more of the pharmaceutical compositions herein described for the treatment or prophylaxis of said condition. In particular, the term dermatological diseases refers to atopic dermatitis, bullous disorders, collagenoses, psoriasis, psoriatic lesions, dermatitis, contact dermatitis, eczema, vitiligo, pruritus, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, or urticaria.

In one embodiment, the present invention provides pharmaceutical compositions comprising a compound of the invention, and another therapeutic agent. In a particular embodiment, the other therapeutic agent is a dermatological diseases treatment agent. In particular, the term dermatological diseases refers to atopic dermatitis, bullous disorders, collagenoses, psoriasis, psoriatic lesions, dermatitis, contact dermatitis, eczema, vitiligo, pruritus, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, or urticaria.

In one embodiment, the present invention provides compounds of the invention or pharmaceutical compositions comprising a compound of the invention, for use in the prophylaxis and/or treatment of abnormal angiogenesis associated diseases. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

In another embodiment, the present invention provides the use of compounds of the invention or pharmaceutical compositions comprising a compound of the invention in the manufacture of a medicament for the prophylaxis and/or treatment of abnormal angiogenesis associated diseases. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

In additional method of treatment aspects, this invention provides methods of prophylaxis and/or treatment of a mammal afflicted with abnormal angiogenesis associated diseases, which methods comprise the administration of an effective amount of a compound of the invention or one or more of the pharmaceutical compositions herein described for the treatment or prophylaxis of said condition. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

In one embodiment, the present invention provides pharmaceutical compositions comprising a compound of the invention, and another therapeutic agent. In a particular embodiment, the other therapeutic agent is a abnormal angiogenesis associated diseases treatment agent. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 10 to about 500 mg and especially about 30 to about 250 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a compound of the invention is co-administered with another therapeutic agent for the treatment and/or prophylaxis of proliferative disorders, particular agents include but are not limited to: methotrexate, leucovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin®), capecitabine, raloxifene hydrochloride, EGFR inhibitors (e.g. Iressa®, Tarceva®, Erbitux®), VEGF inhibitors (e.g. Avastin®), proteasome inhibitors (e.g. Velcade®), Glivec® and hsp90 inhibitors (e.g. 17-AAG). Additionally, the compound of the invention according to Formula I may be administered in combination with other therapies including, but not limited to, radiotherapy or surgery. In a specific embodiment the proliferative disorder is selected from cancer, myeloproliferative disease or leukemia.

In one embodiment, a compound of the invention is co-administered with another therapeutic agent for the treatment and/or prophylaxis of autoimmune diseases, particular agents include but are not limited to: glucocorticoids, cytostatic agents (e.g. purine analogs), alkylating agents, (e.g nitrogen mustards (cyclophosphamide), nitrosoureas, platinum compound of the inventions, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab, etanercept, or adalimumab), mycophenolate, fingolimod and myriocin.

In one embodiment, a compound of the invention is co-administered with another therapeutic agent for the treatment and/or prophylaxis of transplant rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), antibodies (e.g. monoclonal anti-IL-2Ra receptor antibodies, basiliximab, daclizumab), polyclonal anti-T-cell antibodies (e.g. anti-thymocyte globulin (ATG), anti-lymphocyte globulin (ALG)).

In one embodiment, a compound of the invention is co-administered with another therapeutic agent for the treatment and/or prophylaxis of asthma and/or rhinitis and/or COPD, particular agents include but are not limited to: beta2-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled), long-acting β2-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. cetirizine, cinnarizine, fexofenadine) and vasoconstrictors (e.g. oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol orterbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, a compound of the invention is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a compound of the invention is co-administered with another therapeutic agent for the treatment and/or prophylaxis of SLE, particular agents include but are not limited to: human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort®), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive®, Enbrel®, Humira®, Remicade®, Raptiva® and ustekinumab (an IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

In one embodiment, a compound of the invention is co-administered with another therapeutic agent for the treatment and/or prophylaxis of allergic reaction, particular agents include but are not limited to: antihistamines (e.g. cetirizine, diphenhydramine, fexofenadine, levocetirizine), glucocorticoids (e.g. prednisone, betamethasone, beclomethasone, dexamethasone), epinephrine, theophylline or anti-leukotrienes (e.g. montelukast or zafirlukast), anti-cholinergics and decongestants.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

The compound of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Wuts & Greene 2006).

The following methods are presented with details as to the preparation of a compound of the invention as defined hereinabove and the comparative examples. A compound of the invention may be prepared from known or commercially available starting materials and reagents by one skilled in the art of organic synthesis.

All reagents are of commercial grade and are used as received without further purification, unless otherwise stated. Commercially available anhydrous solvents are used for reactions conducted under inert atmosphere. Reagent grade solvents are used in all other cases, unless otherwise specified. Column chromatography is performed on silica gel 60 (35-70 μm) or with Biotage® SNAP KP—NH, Biotage® SNAP Ultra, or Interchim® PuriFlash® Si HC flash chromatography cartridges. Thin layer chromatography is carried out using pre-coated silica gel F-254 plates (thickness 0.25 mm). Biotage® ISOLUTE® phase separators (e.g., Cat #120-1907-E) are used for aqueous phase separation. $^1$H NMR spectra are recorded on a Bruker DPX 400 NMR spectrometer (400 MHz) or a Bruker Avance 300 NMR spectrometer (300 MHz). Chemical shifts (δ) for $^1$H NMR spectra are reported in parts per million (ppm) relative to tetramethylsilane (δ 0.00) or the appropriate residual solvent peak, i.e. CHCl$_3$ (δ 7.27), as internal reference. Multiplicities are given as singlet (s), doublet (d), triplet (t), quartet (q), quintet (quin), multiplet (in) and broad (br). Electrospray MS spectra are obtained on a Waters Acquity H-Class UPLC system coupled to a UV PDA detector and to a Waters SQD or SQD2 mass spectrometer. Columns used: Waters Acquity UPLC BEH C18 1.7 μm, 2.1 mm ID×30/50 mm L; Waters Acquity UPLC CSH C18 1.7 μm, 2.1 mm ID×50/100 mm L; Waters Acquity UPLC CSH PhenylHexyl 1.7 μm, 2.1 mm ID×100 mm L; Waters Acquity UPLC HSS PFP 1.8 μm, 2.1 mm ID×100 mm L. The methods are using ACN/H$_2$O or MeOH/water gradients with either 0.1% formic acid in both mobile phases, 0.05% NH$_3$ in both mobile phases, or 10 mM NH$_4$HCO$_3$ in H$_2$O (adjusted to pH 10 with ammonia). Preparative HPLC is performed on a Waters AutoPurification system with UV and MS detection using Waters XBRIDGE BEH C18 OBD 30 mm ID×100/150 mm L columns and ACN/H$_2$O gradients with either 0.1% formic acid in both mobile phases, 0.1% diethylamine in both mobile phases, 0.1% formic acid in $H_2O$, or 10 mM $NH_4HCO_3$ in $H_2O$ (adjusted to pH 10 with ammonia). Microwave heating is performed with a Biotage® Initiator.

TABLE I

List of abbreviations used in the experimental section:

| | |
|---|---|
| ACN | acetonitrile |
| AcOH | acetic acid |
| ANOVA | analysis of variance |
| aq. | aqueous |
| ATP | adenosine 5'-triphosphate |
| BBBPY | 4,4'-di-tert-butyl-2,2'-dipyridyl |
| b.i.d. | bis in die (twice a day) |
| Boc | tert-butyloxy-carbonyl |
| $B_2pin_2$ | 4,4,5,5-tetramethyl-2-(4,4,5,5-tetramethyl-1,3,2-dioxaborolan-2-yl)-1,3,2-dioxaborolane |
| BrettPhos | 2-(Dicyclohexylphosphino)3,6-dimethoxy-2',4',6'-triisopropyl-1,1'-biphenyl |
| br s | broad singlet |
| calcd | calculated |
| d | doublet |
| DCM | dichloromethane |
| dd | doublet of doublets |
| DIPEA | N,N-diisopropylethylamine |
| DMAC | dimethylacetamide |
| DMF | N,N-dimethylformamide |
| DMSO | Dimethylsulfoxide |
| DPPF | 1,1'-bis(diphenylphosphino)ferrocene |
| $Et_3N$ | triethylamine |
| $Et_2O$ | diethyl ether |
| EtOAc | ethyl acetate |
| EtOH | ethanol |
| eq. | equivalent |
| h | hour |
| HATU | 1-[bis(dimethylamino)methylene]-1H-1,2,3-triazolo[4,5-b]pyridinium 3-oxid hexafluorophosphate |
| HPLC | high-performance liquid chromatography |
| i.n. | intranasal |
| i.p. | intraperitoneal |
| i-PrOH | isopropanol |
| $[Ir(OMe)(COD)]_2$ | (1,5-cyclooctadiene)(methoxy)iridium(I) dimer |
| i.v. | intravenous |
| KOAc | potassium acetate |
| LCMS | liquid chromatography-mass spectrometry |
| LiHMDS | lithium hexamethyldisilazane |
| m | multiplet |
| MeOH | methanol |
| MeONa | sodium methoxide |
| mg | milligram |
| min | minute |
| mL | milliliter |
| mmol | millimole |
| MS | mass spectrometry |
| MTBE | methyl tert-butyl ether |
| MW | molecular weight |
| MW (calc) | molecular weight calculated |
| MW (obs) | molecular weight observed |
| NA | not available |
| NMP | N-methyl-2-pyrrolidone |
| obsd | observed |
| $Pd(dppf)Cl_2$•DCM | 1,1'-bis(diphenylphosphino)ferrocene]dichloropalladium(II), complex with dichloromethane |
| $Pd(PPh_3)_4$ | tetrakis(triphenylphosphine)palladium(0) |
| p.o. | per os |
| ppm | part-per-million |
| q | quadruplet |
| q.d. | quaque die (once a day) |
| RT | room temperature |
| s | singlet |

TABLE I-continued

List of abbreviations used in the experimental section:

| | |
|---|---|
| sat. | saturated |
| sc | subcutaneous |
| SEM | standard error of the mean |
| SM | starting material |
| t | triplet |
| td | triplet of doublets |
| TFA | trifluoroacetic acid |
| THF | tetrahydrofuran |
| tt | triplet of triplets |

SYNTHETIC PREPARATION OF THE COMPOUNDS OF THE INVENTION

Example 1. General Synthetic Methods

1.1. Synthetic Methods Overview

General method A: $S_NAr$ of an alcohol on a 7-fluoroimidazo[1,2-a]pyridine derivative General method B: C—H activation on position 3 of an imidazopyridine General method C: Suzuki coupling of a boronic ester with 7-fluoro-3-iodo-imidazo[1,2-a]pyridine General method D: Fluorine displacement with an alkoxide on a trisubstituted benzamide General method E: Lactam alkylation with LiHMDS General method F: Demethylation of an aromatic methoxy substituent with $BCl_3$ or $BBr_3$ General method G: Difluoromethylation of a phenol intermediate General method H: Amine alkylation General method I: Aldehyde deprotection and reductive amination with or without $Et_3N$ General method J: Methylation of an azetidine derivative by reductive amination General method J1: Akylation of amines by reductive amination General method K: Boc cleavage using TFA General method K1: Boc cleavage using HCl General method L: Michael addition General method M: Mesylate displacement General method N: Peptidic coupling General method O: Epoxide aminolysis General method P: Silyl deprotection General method Q: Synthesis of 3,4-dihydro-1(2H)-isoquinolinones by Rh-catalyzed C—H activation

1.2. General Methods 1.2.1. Method A: $S_NAr$ of an Alcohol on a 7-fluoroimidazo[1,2-a]pyridine derivative

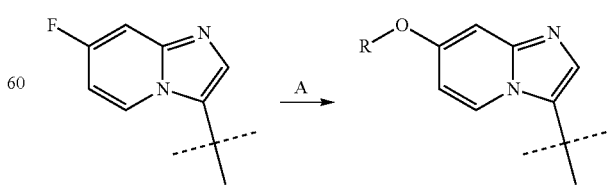

To a solution of alcohol (2 to 10 eq.) in DMF at 5° C. or RT is added NaH (60% dispersion in mineral oil, 2 to 10 eq.)

and the mixture is stirred for 5 to 20 min. Then the 7-fluoroimidazo[1,2-a]pyridine derivative (1 eq.) is added at the same temperature and the reaction mixture is stirred at RT to 80° C. for 1 h to 5 days. More alcohol (0 to 81 eq.) and NaH (60% dispersion in mineral oil, 0 to 18 eq.) are added portionwise during the reaction time. The reaction mixture is then directly submitted to preparative HPLC or work-up: the reaction mixture is concentrated to dryness and submitted to purification.

- Alternative work-up 1: the reaction mixture is concentrated to dryness, the residue is taken up in EtOAc and filtered. Then, the filtrate is concentrated.
- Alternative work-up 2: the reaction mixture is concentrated, the residue is taken up in EtOAc and 2N aq. NaOH. The aqueous phase is extracted with EtOAc and the combined organic layers are concentrated.
- Alternative work-up 3: the reaction mixture is quenched with a sat. aq. NaHCO$_3$ solution and extracted with EtOAc. The combined organic layers are directly evaporated or are dried on a desiccant, filtered and evaporated, or are washed with brine, passed through a phase separator, and concentrated.
- Alternative work-up 4: the reaction mixture is quenched with 2N aq. NaOH and extracted with EtOAc. The combined organic layers are dried on Na$_2$SO$_4$, filtered and evaporated
- Alternative work-up 5: the reaction mixture is diluted with DCM and water. The aqueous phase is extracted with DCM and the combined organic layers are concentrated, or are dried over Na$_2$SO$_4$, filtered and concentrated.

The obtained residues are purified by chromatography on silica gel or by preparative HPLC or by a combination of both purification methods to afford the expected compound.

Illustrative Synthesis of Int 31

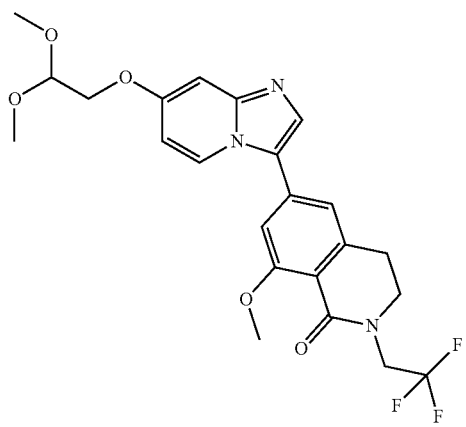 [SMILES: COc1cc(-c2cnc3cc(OCC(OC)OC)ccn23)cc2c1C(=O)N(CC(F)(F)F)CC2]

To a solution of 2,2-dimethoxyethanol (CAS #30934-97-5; 385 µL, 1.27 mmol) in dry DMF (8 mL) is added NaH (60% dispersion in mineral oil, 152 mg, 3.81 mmol) and the mixture is stirred at RT for 10 min. Int 2 (500 mg, 1.27 mmol) is added and the reaction mixture is stirred at RT for 1 h. The reaction mixture is hydrolyzed with a 2N aq. NaOH solution and the aqueous layer is extracted with EtOAc. The combined organic layers are dried over Na$_2$SO$_4$, filtered and concentrated. The crude is purified by chromatography on silica gel (eluting with 10 to 100% EtOAc in DCM, then with 2 to 4% MeOH in DCM) to afford the expected compound Int 31.

Illustrative Synthesis of Cpd 18

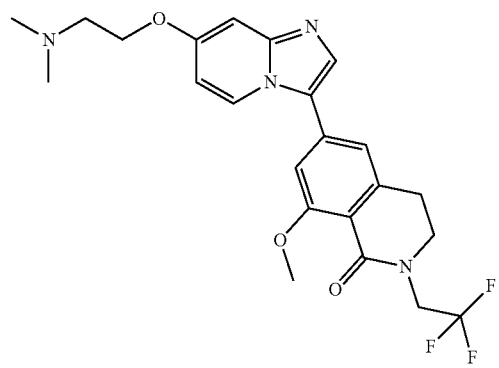 [SMILES: COc1cc(-c2cnc3cc(OCCN(C)C)ccn23)cc2c1C(=O)N(CC(F)(F)F)CC2]

To a solution of 2-(dimethylamino)ethanol (CAS #108-01-0; 512 mg, 5.08 mmol) in dry DMF (6.8 mL) is added NaH (60% dispersion in mineral oil, 122 mg, 5.08 mmol) and the mixture is stirred at RT for 5 min. Int 2 (200 mg, 0.51 mmol) is added and the reaction mixture is stirred at RT overnight. The reaction mixture is quenched with a sat. aq. NaHCO$_3$ solution and extracted with EtOAc. The combined organic layers are washed with brine, passed through a phase separator, and concentrated. The crude material is purified by chromatography on silica gel (eluting with 0 to 10% MeOH in DCM) to afford the expected compound Cpd 18.

Illustrative Synthesis of Cpd 71

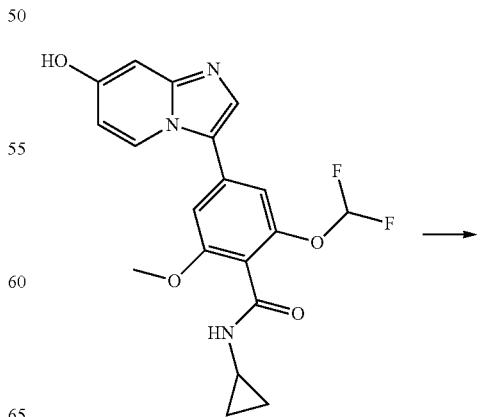

131

-continued

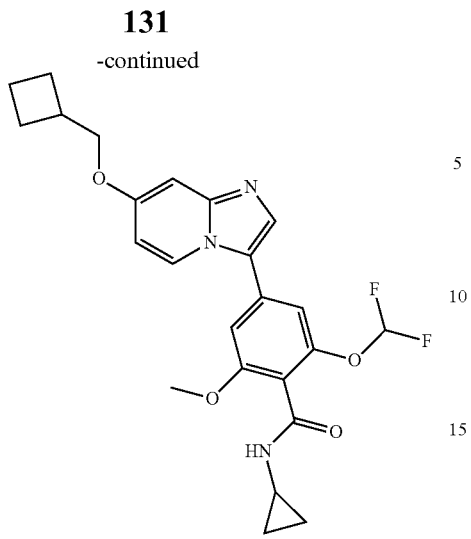

To a solution of cyclobutylmethanol (CAS #4415-82-1; 29 µL, 0.31 mmol, 4 eq.) in dry DMF (1 mL) at 5° C. is added NaH (60% dispersion in mineral oil, 12 mg, 0.31 mmol, 4 eq.) and the mixture is stirred at 5° C. for 10 min. Int 1 (30 mg, 0.08 mmol, 1 eq.) is added and the reaction mixture is stirred at 45° C. for 2 h. The reaction mixture is cooled to RT and diluted with DCM and water. The aqueous phase is extracted with DCM and the combined organic layers are concentrated. The residue is purified by chromatography on silica gel (eluting with 0 to 3% MeOH in DCM) to afford the expected product Cpd 71.

1.2.2. Method B: C—H Activation on Position 3 of an Imidazopyridine

The imidazopyridine derivative (1 eq.), the bromo derivative (0.7 to 1.5 eq.) and KOAc (2 to 3 eq.) are suspended in dry DMAC, the mixture is degassed with $N_2$ before Pd(dppf)Cl$_2$·DCM adduct (CAS #95464-05-4, 0.03 to 0.1 eq.) is added, or all the reagents are suspended in dry and degassed DMAC, or all the reagents are suspended in dry DMAC. The mixture is stirred at 105-120° C. for 1 h to 20 h. The reaction medium is concentrated, or is diluted or not with EtOAc, filtered over Celite® and the filtrate concentrated in vacuo. The crude residue is purified by flash chromatography on silica gel or preparative HPLC to afford the expected product.

Illustrative Synthesis of Int 2

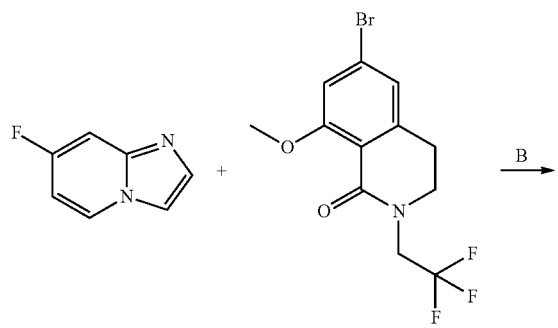

132

-continued

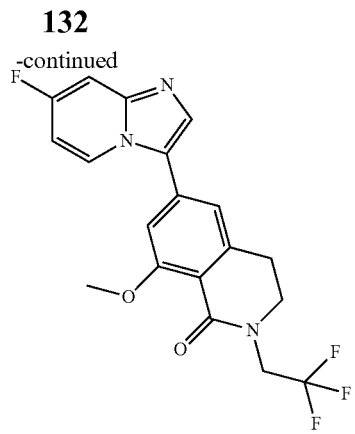

To a solution of Int 39 (1.40 g, 4.14 mmol) in dry and degassed DMAC (17 mL) are added 7-fluoroimidazo[1,2-a]pyridine (CAS #1260903-17-0; 620 mg, 4.55 mmol), KOAc (1.0 g, 10.35 mmol) and Pd(dppf)Cl$_2$·DCM (CAS #95464-05-4; 237 mg, 0.29 mmol), and the mixture is stirred at 120° C. for 3 h. The solvent is concentrated in vacuo and the crude material is purified by flash chromatography on Biotage® SNAP KP—NH cartridge (eluting with a gradient of 0 to 100% EtOAc in DCM) to afford the expected compound.

1.2.3. Method C: Suzuki Coupling of a Boronic Ester with 7-fluoro-3-iodo-imidazo[1,2-a]pyridine

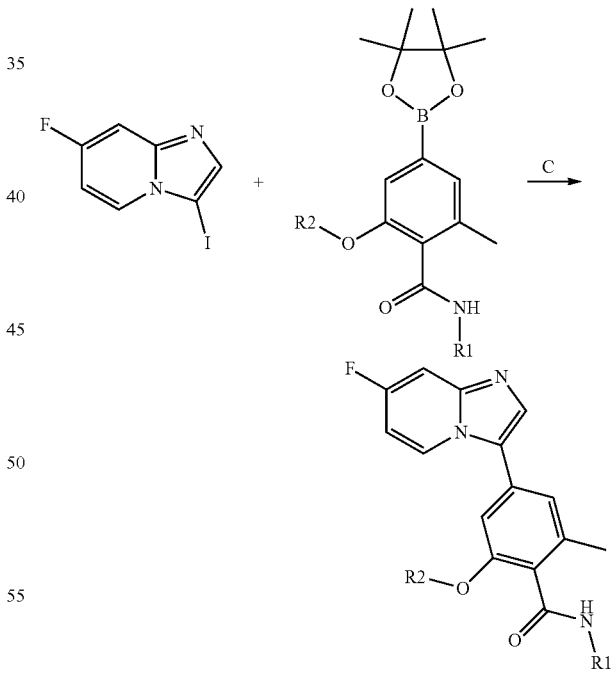

To a solution of 7-fluoro-3-iodo-imidazo[1,2-a]pyridine (CAS #2089326-83-8, 1 eq.) in a degassed mixture of dioxane and water (4/1) are added pinacolboronate ester (1.2 eq.), Cs$_2$CO$_3$ (2 eq.) and Pd(dppf)Cl$_2$·DCM (0.1 eq.) and the reaction mixture is stirred at 90° C. for 1 h to 2 h. The reaction medium is cooled to RT and concentrated. The residue is taken up in a sat. aq. NaHCO$_3$ solution and extracted with EtOAc. The combined organic layers are either dried over MgSO₄ and filtered, or passed through a phase separator. The filtrate is concentrated and the residue is purified by flash chromatography on silica gel to afford the expected product.

Illustrative Synthesis of Int 29

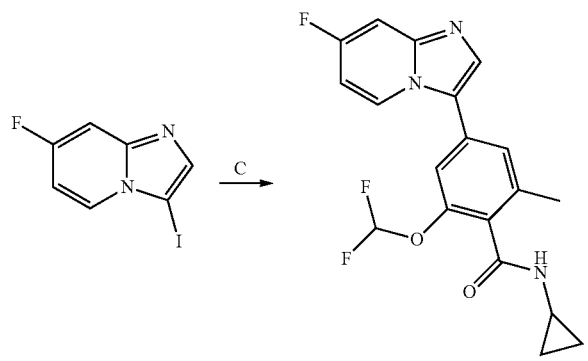

To a solution of 7-fluoro-3-iodo-imidazo[1,2-a]pyridine (CAS #2089326-83-8; 264 mg, 1.01 mmol, 1 eq.) in a degassed mixture of dioxane/water (14.2 mL/3.5 mL) are added Int 54 (444 mg, 1.21 mmol, 1.2 eq.), $Cs_2CO_3$ (657 mg, 2.02 mmol, 2 eq.) and Pd(dppf)$Cl_2$·DCM (82 mg, 0.10 mmol, 0.1 eq.) and the reaction mixture is stirred at 90° C. for 1.5 h. The reaction mixture is cooled to RT, concentrated in vacuo and the crude material is hydrolyzed with a sat. aq. $NaHCO_3$ solution. The aqueous layer is extracted with EtOAc. The combined organic layers are passed through a phase separator and concentrated under reduced pressure. The residue is purified by chromatography on silica gel (eluting with 0 to 80% EtOAc in DCM) to afford Int 29.

1.2.4. Method D: Fluorine Displacement with an Alkoxide on a Trisubstituted Benzamide

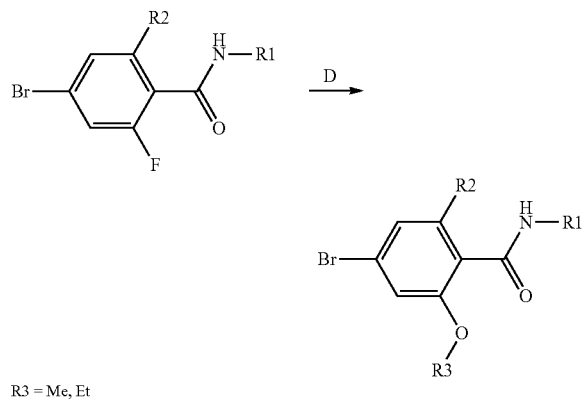

R3 = Me, Et

To a solution of fluoro derivative (1 eq.) in THF or DMF is added dropwise MeONa (25% in MeOH, 1.2 eq.) or EtONa (25% in EtOH, 1.2 eq.) and the suspension is stirred for 1.5 h to 20 h. More alkoxide solution (0 to 4.8 eq.) can be added to push the conversion further. The reaction is quenched with a sat. aq. NH₄Cl solution and the organic solvent is evaporated in vacuo. If a precipitate forms in the aqueous phase, it is filtered, washed with water and dried to afford the expected product. If no precipitation occurs, the aqueous phase is extracted with DCM, the organic layer is dried over MgSO₄, filtered and concentrated to give the expected compound.

Illustrative Synthesis of Int 40

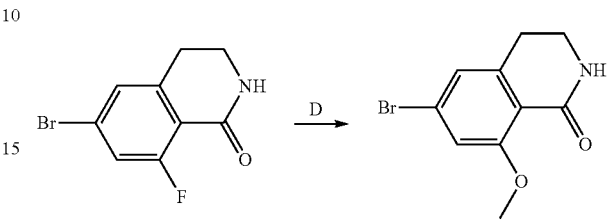

To a stirred solution of 6-bromo-8-fluoro-3,4-dihydro-2H-isoquinolin-1-one (CAS #1242157-15-8; 3 g, 12.29 mmol, 1 eq.) in THF (30 mL) is added dropwise a solution of MeONa 25 w % in MeOH (3.35 mL, 14.75 mmol, 1.2 eq.). The reaction mixture is stirred at RT for 2 h, quenched with a sat. aq. NH₄Cl solution and THF is evaporated. The solid obtained in the remaining aq. phase is filtered to afford the desired compound Int 40.

1.25. Method E: Lactam Alkylation with LiHMDS

To a solution of the lactam derivative (1 eq.) in THF at 0° C. is added dropwise LiHMDS (1M in THF, 1 to 1.5 eq.) and the mixture is stirred at 0° C. for 20 to 45 min. The appropriate triflate reagent (1 to 1.5 eq.) is then added and the reaction mixture is allowed to heat up to RT for 20 h. Additional LiHMDS and triflate reagent are added until the conversion does not increase anymore. The reaction is then quenched with water or sat. aq. NH₄Cl solution, THF is concentrated and the aqueous phase is extracted with EtOAc. The combined organic phases are dried over a desiccant and filtered, or are passed through a phase separator. The filtrate is concentrated and the residue is purified by flash chromatography on silica gel to afford the expected intermediate.

Illustrative Synthesis of Int 39

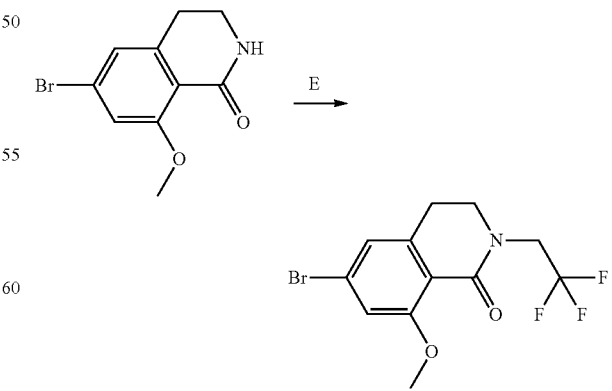

To a stirred solution of Int 40 (10 g, 39.1 mmol, 1 eq.) in THF (240 mL) at 0° C. is added dropwise a solution of LiHMDS (1 N in THF, 59 mL, 58.6 mmol, 1.5 eq.). The resulting mixture is stirred for 45 min at 0° C. and 2,2,2-trifluoroethyl trifluoromethanesulfonate (CAS #6226-25-1; 8.44 mL, 58.6 mmol, 1.5 eq.) is added dropwise at 0° C. The reaction mixture is warmed slowly to RT and stirred at RT for 22 h. The reaction mixture is quenched with water and brine. THF is evaporated and the aqueous layer is extracted with EtOAc. The combined organic layers are dried over anhydrous $Na_2SO_4$, filtered and concentrated in vacuo. The residue is purified by flash chromatography on silica gel (eluting with DCM/MeOH 100/0 to 99/1) to afford Int 39.

1.2.6. Method F: Demethylation of an Aromatic Methoxy Substituent with $BCl_3$ or $BBr_3$

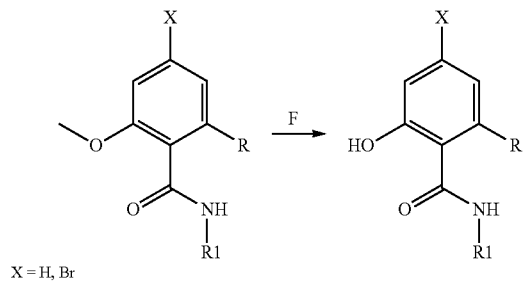

X = H, Br

To a solution of methoxy derivative (1 eq.) in DCM at 0° C. is added dropwise $BCl_3$ (1M in DCM, 2.2 eq.) or $BBr_3$ (1M in DCM, 2.2 eq.) and the mixture is stirred at 0° C. for 45 min to 3 h. The reaction medium is poured in a 0.1N aq. HCl/ice/DCM mixture and the aqueous layer is extracted with DCM and a few drops of MeOH. The organic phase is dried on a desiccant and filtered, or is passed through a phase separator. The filtrate is then concentrated and the residue is either used as such or is purified by flash chromatography on silica gel to afford the expected intermediate.

Illustrative Synthesis of Int 56

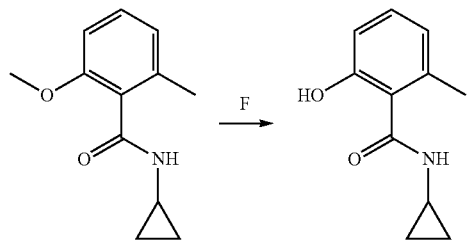

To a solution of Int 53 (400 mg, 1.95 mmol) in DCM (26.7 mL) at 0° C. is added dropwise 1M $BCl_3$ in DCM (4.3 mL, 4.29 mmol), and the reaction mixture is stirred at 0° C. for 3 h. The reaction is poured in a 0.1N aq. HCl/ice/DCM mixture. The aqueous layer is extracted with DCM with several drops of MeOH. The organic layer is passed through a phase separator and the filtrate is concentrated. The crude material is purified by chromatography on silica gel (eluting with a gradient of 0 to 5% MeOH in DCM, then with a gradient of 0 to 40% EtOAc in heptane) to afford Int 56.

1.2.7. Method G: Difluoromethylation of a Phenol Intermediate

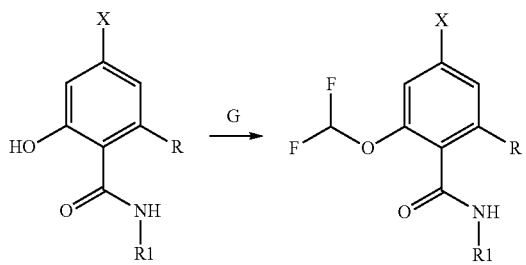

To a solution of phenol intermediate (1 eq.) in ACN at 0° C. is added a cold solution of KOH (10 eq.) in water (water/ACN 1/1 final concentration). Diethyl (bromodifluoromethyl)phosphonate (CAS #65094-22-6; 1.4 eq.) is added dropwise while keeping the temperature below 20° C. The reaction is worked-up at the end of the addition or is stirred for 30 min at 0° C. Water is added and the aqueous layer is extracted with EtOAc. The combined organic layers are either dried over $MgSO_4$ and filtered, or are passed through a phase separator. The filtrate is concentrated to dryness and the residue is used as such or is purified by flash chromatography on silica gel to afford the expected product.

Illustrative Synthesis of Int 15

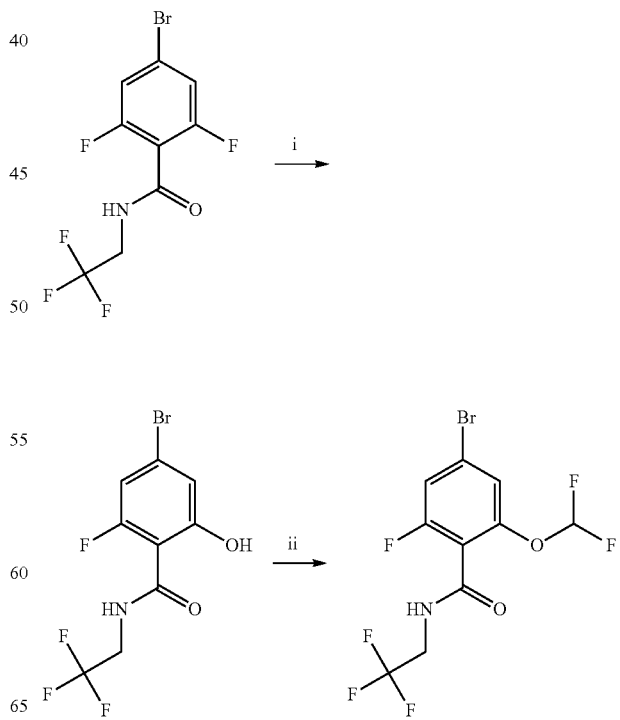

Step i. 4-bromo-2-fluoro-6-hydroxy-N-(2,2,2-trifluoroethyl)benzamide

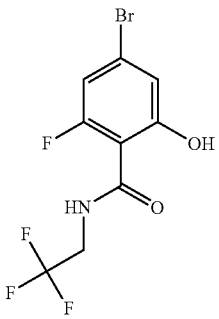 [SMILES: O=C(NCC(F)(F)F)c1c(O)cc(Br)cc1F]

To a solution of Int 44 (300 mg, 0.94 mmol, 1.0 eq.) in DMSO (459 µL) is added a 4M aq. NaOH solution (521 µL, 2.36 mmol, 2.5 eq.). The mixture is stirred at 90° C. for 20 h. The reaction medium is cooled to RT and HCl 2M is added to reach pH 3. Precipitation occurs and the suspension is stirred for 5 min. Then the precipitate is filtered, washed with water and dried under reduced pressure. The solid is purified by flash chromatography on silica gel (eluting with a gradient 0 to 10% EtOAc in heptane) to afford the expected product.

LCMS: MW (calcd): 316.1; m/z MW (obsd): 314.0/316.1 (M−H)

Step ii: Int 15

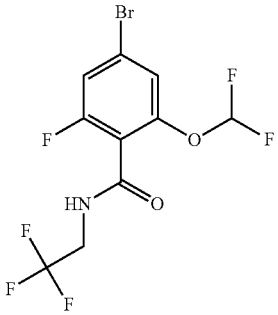 [SMILES: O=C(NCC(F)(F)F)c1c(F)cc(Br)cc1OC(F)F]

To a solution of 4-bromo-2-fluoro-6-hydroxy-N-(2,2,2-trifluoroethyl)benzamide (150 mg, 0.47 mmol, 1 eq.) in ACN (750 µL) at 0° C. is added a cold solution of KOH (266 mg, 4.75 mmol, 10 eq.) in water (750 µL). Diethyl (bromodifluoromethyl)phosphonate (CAS #65094-22-6; 118 µL, 0.66 mmol, 1.4 eq.) is added dropwise while keeping the temperature below 20° C. At the end of the addition the reaction medium is warmed up to RT and diluted with water. The aqueous layer is extracted with EtOAc. The combined organic layers are washed with brine, dried over MgSO₄, filtered and concentrated. The crude residue is purified by flash chromatography on silica gel (eluting with a gradient of EtOAc 0 to 20% in heptane) to give Int 15.

1.2.8. Method H: Amine Alkylation

To a solution of the amine (1 eq.) in dry ACN are added bromoethanol (CAS #540-51-2, 1.1 eq.) and K₂CO₃ (1.5 eq.) and the mixture is stirred for 20 h to 4 days at RT. The reaction mixture is diluted with water, pH is adjusted to 7 and the mixture is extracted with DCM. Organic layers are combined, dried over Na₂SO₄ and concentrated. The crude material is purified by flash chromatography on silica gel to afford the expected product.

Illustrative Synthesis of Int 63

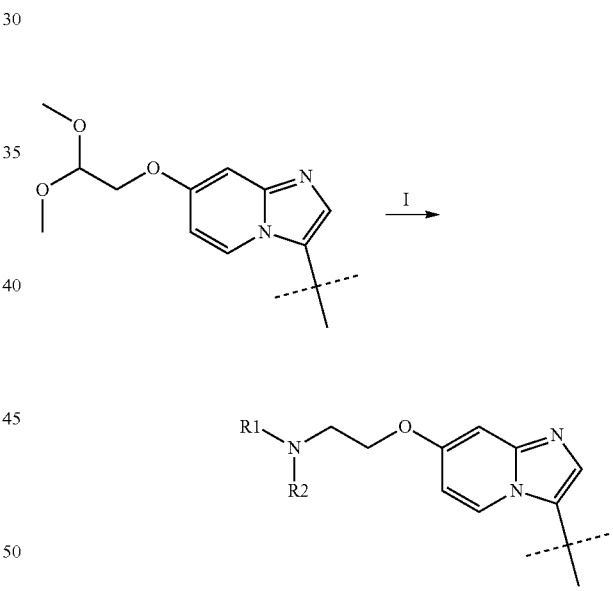

(3S)-3-fluoropyrrolidine hydrochloride (CAS #136725-53-6; 100 mg, 0.80 mmol), 2-bromoethanol (CAS #540-51-2; 62.1 µL, 0.88 mmol) and K₂CO₃ (660.7 mg, 4.78 mmol) are placed in dry ACN (1 mL) and the reaction mixture is stirred at RT overnight. The reaction medium is diluted with water, pH is adjusted to 7 and the mixture is extracted with DCM. The organic layers are combined, dried over Na₂SO₄ and concentrated. The crude material is purified by flash chromatography on silica gel (eluting with a gradient of 0 to 7% MeOH in DCM) to afford Int 63.

1.2.9. Method I: Aldehyde Deprotection and Reductive Amination with or without Et₃N A solution of the protected aldehyde (1 eq.) in a DCM/TFA 1/1 mixture is stirred at RT for 4 to 5 h before being concentrated. The residue is taken up in toluene and the solvent is evaporated to dryness. The crude residue is then dissolved in DCM and the amine (1.5 eq.) and NaBH(OAc)₃ (CAS #56553-60-7; 1.5 eq.) are added. Et₃N (1.5 eq.) can optionally be added to the mixture. The reaction mixture is then stirred at RT for 2 h to 20 h. The reaction medium is either concentrated or quenched with aq. NaOH (1N or 2N aq. solution), extracted with DCM and passed through a phase separator. The crude residue is purified by flash chromatography on silica gel or by preparative HPLC to afford the expected compound.

Illustrative Synthesis of Cpd 177 (without Et₃N)

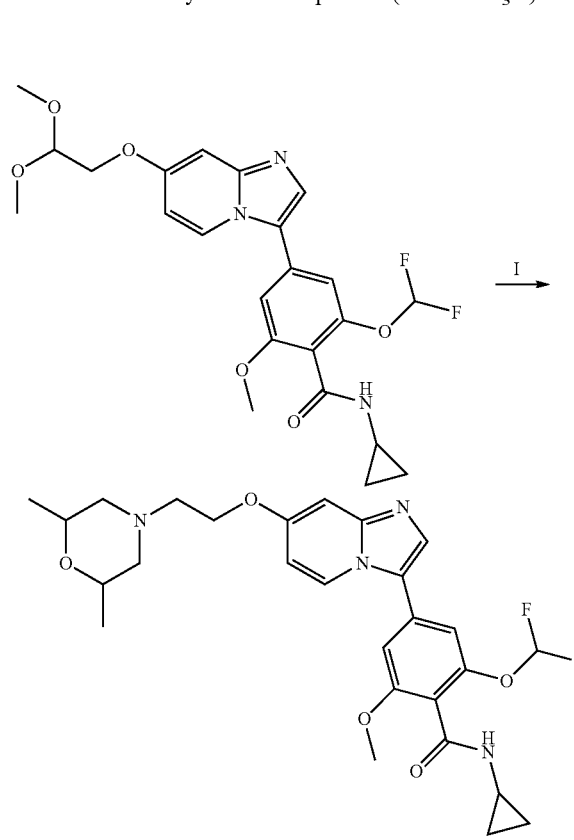

A solution of Int 18 (200 mg, 0.42 mmol) in DCM (3 mL) and TFA (3 mL) is stirred at RT for 5 h before being concentrated. The residue is taken up in toluene and the solvent is evaporated to dryness. Part of the crude residue (50 mg, 0.15 mmol, 1 eq.) is then dissolved in DCM (2 mL) and 2,6-dimethylmorpholine (CAS #141-91-3; 19 mg, 0.16 mmol, 1.5 eq.) and NaBH(OAc)₃ (34 mg, 0.16 mmol, 1.5 eq.) are added. The mixture is stirred at RT overnight and then hydrolyzed with 1N aq. NaOH. The aqueous phase is extracted with DCM and passed through a phase separator. The filtrate is concentrated and the crude residue is purified by preparative HPLC to afford Cpd 177.

Illustrative Synthesis of Cpd 244 (with Et₃N)

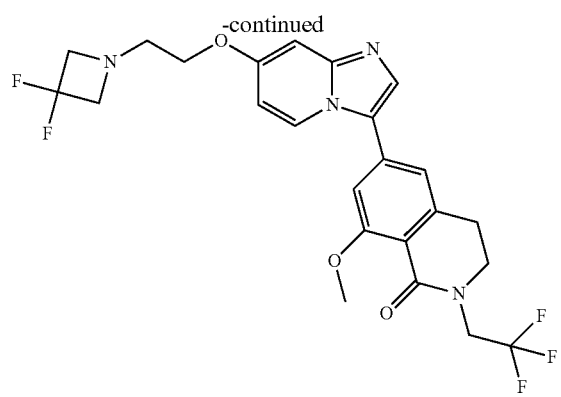

To a solution of Int 31 (150 mg, 0.31 mmol) in dry DCM (2 mL) is added TFA (2 mL) and the reaction mixture is stirred at RT for 5 h before being concentrated. The residue is taken up in toluene and the solvent is evaporated to dryness. To a solution of the latter intermediate (50 mg, 0.10 mmol) in dry DCM (2 mL) are added 3,3-difluoroazetidine hydrochloride (CAS #288315-03-7; 13.5 mg, 0.16 mmol), Et₃N (22 µL, 0.16 mmol) and NaBH(OAc)₃ (34 mg, 0.16 mmol) and the reaction mixture is stirred at RT overnight. The solvent is removed under reduced pressure and the crude material is purified by preparative HPLC to afford Cpd 244.

Illustrative Synthesis of Cpd 257 and Cpd 258 (with Et₃N)

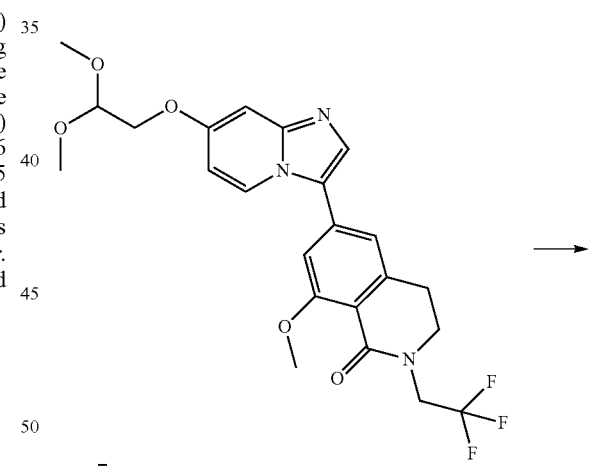

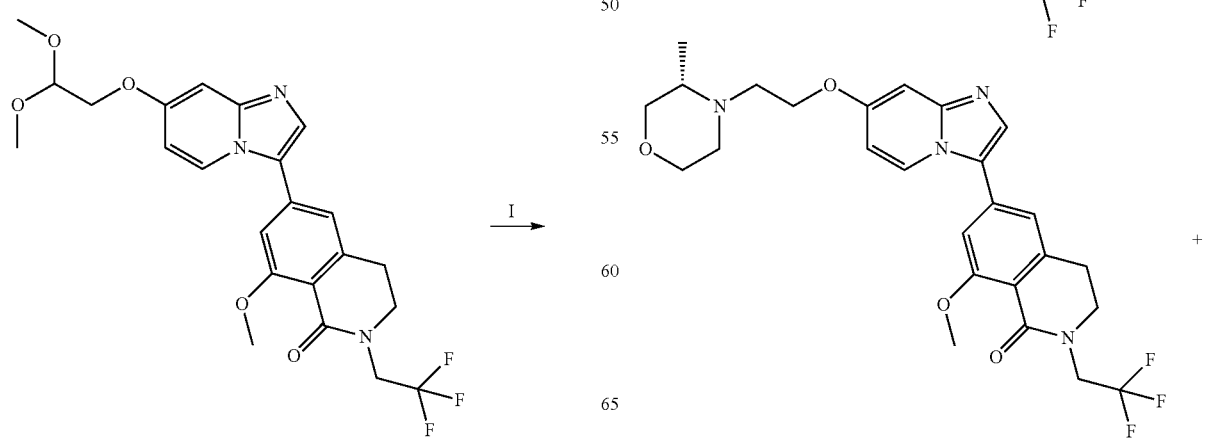

-continued

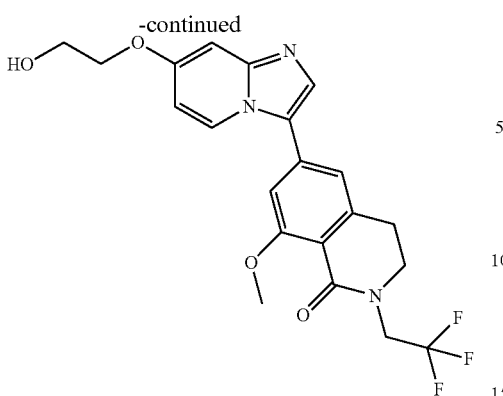

To a solution of Int 31 (150 mg, 0.31 mmol) in dry DCM (2 mL) is added TFA (2 mL) and the reaction mixture is stirred at RT for 5 h before being concentrated. The residue is taken up in toluene and the solvent is evaporated to dryness. To a solution of the latter intermediate (75 mg, 0.16 mmol, 1 eq.) in dry DCM (3 mL) are added (3S)-3-methylmorpholine hydrochloride (CAS #1022094-03-6; 24 mg, 0.23 mmol), Et$_3$N (33 µL, 0.23 mmol, 1.5 eq.) and NaBH(OAc)$_3$ (49 mg, 0.23 mmol, 1.5 eq.). The reaction mixture is stirred at RT overnight and then hydrolysed with 1N aq. NaOH. The aqueous phase is extracted with DCM and passed through a phase separator. The filtrate is concentrated and the crude residue is purified by flash chromatography on a Biotage® SNAP KP—NH cartridge (eluting with a gradient of AcOEt 0 to 100% in heptane then a gradient of MeOH 0 to 4% in DCM) to afford the expected compound Cpd 257, and Cpd 258 as a by-product of the reaction.

1.2.10. Method J: Methylation of an Azetidine Derivative by Reductive Amination

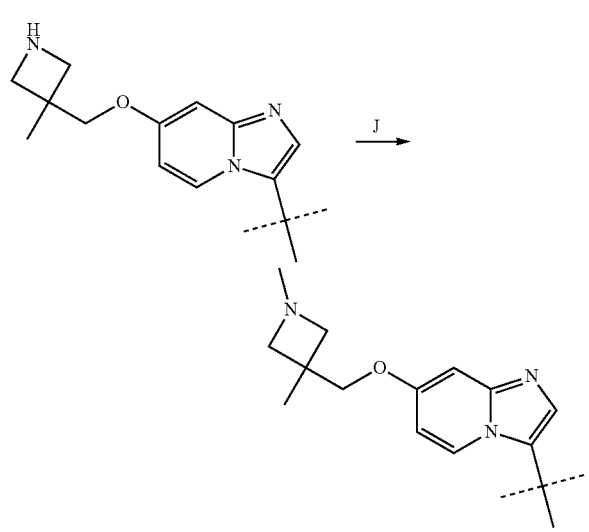

To a solution of the azetidine derivative (1 eq.) in DCM are added formaldehyde (37% in water, 5.5 eq.) and NaBH(OAc)$_3$ (CAS #56553-60-7; 1.4 eq.). Et$_3$N (1.4 eq.) can also be added. The mixture is stirred at RT for 20 h and the solvents are concentrated to dryness. The residue is purified by preparative HPLC to afford the expected product.

Illustrative Synthesis of Cpd 253

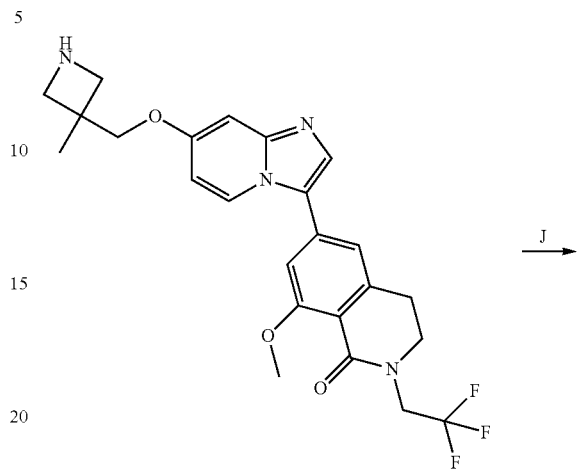

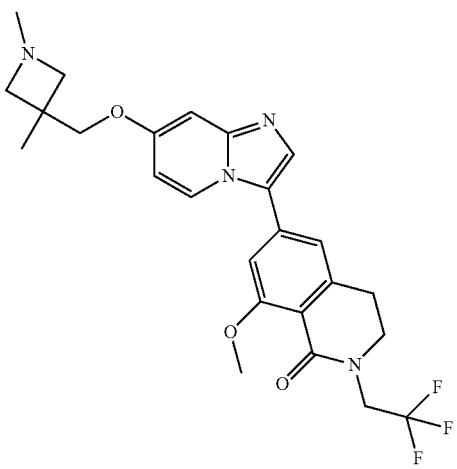

To a solution of Cpd 251 (33 mg, 0.7 mmol, 1 eq.) in DCM (1.5 mL) are added formaldehyde (37% in water, 27 µL, 5.5 eq.) and NaBH(OAc)$_3$ (22 mg, 0.10 mmol, 1.4 eq.) and Et$_3$N (15 µL, 0.10 mmol, 1.4 eq.). The mixture is stirred at RT for 20 h and the solvents are concentrated to dryness. The residue is purified by preparative HPLC to afford Cpd 253.

1.2.11. Method J1: Alkylation of Amines by Reductive Amination

To a solution of amine derivative (1 eq.) in THF or acetone are added 2 drops of AcOH. The reaction mixture is cooled in an ice bath and NaBH(OAc)$_3$ (CAS #56553-60-7; 2 to 5 eq.) followed by the addition of a ketone derivative (2 to 10 eq.). The reaction mixture is allowed to warm to RT and stirred for 2 to 72 h. The reaction mixture is diluted with water and extracted with DCM. The organic layers are combined, dried over Na$_2$SO$_4$, filtered and evaporated under reduced pressure. The crude residue is purified by flash chromatography on silica gel.

Illustrative Synthesis of Cpd 287

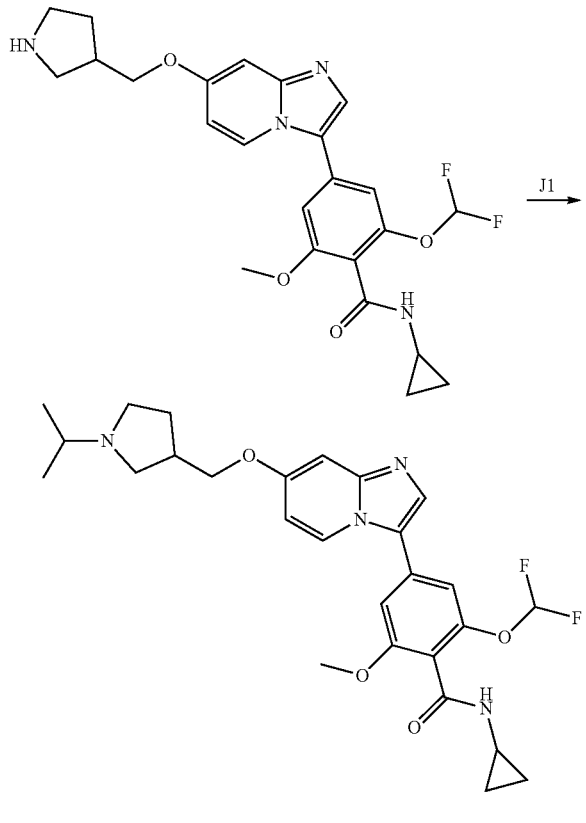

Int 99 (100 mg, 0.21 mmol, 1 eq.) is dissolved in dry acetone (2 mL), two drops of AcOH are added. The reaction mixture is cooled in an ice bath and NaBH(OAc)₃ (89.7 mg, 0.42 mmol, 2 eq.) is added. The reaction mixture is allowed to warm to RT and stirred for 2 hours. The reaction mixture is diluted with water and extracted with DCM. The organic layers are combined, dried over Na₂SO₄, filtered and evaporated under reduced pressure. The crude residue is purified by flash chromatography on silica gel (eluting with 0 to 30% MeOH in DCM) to afford Cpd 287.

Illustrative Synthesis of Cpd 288

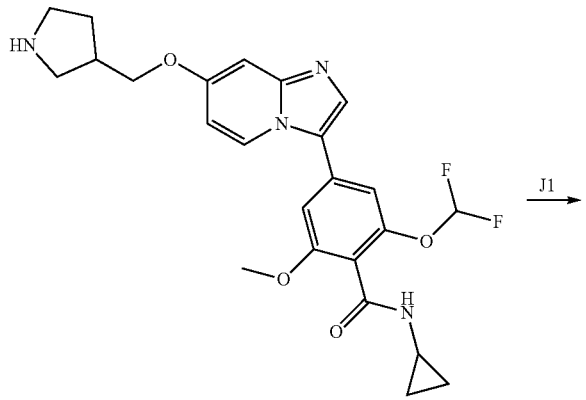

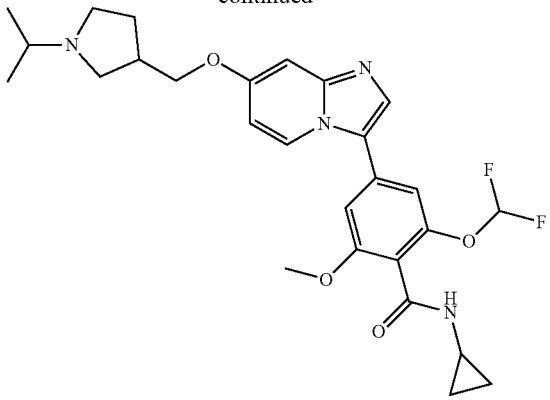

Int 99 (82 mg, 0.17 mmol, 1 eq.) is dissolved in dry THF (2 mL), two drops of AcOH are added. The reaction mixture is cooled in an ice bath and oxetan-3-one (CAS #6704-31-0; 125 mg, 1.7 mmol, 10 eq.) and NaBH(OAc)₃ (73.6 mg, 0.34 mmol, 2 eq.) are added. The reaction mixture is allowed to warm to RT and stirred for 2 hours. The reaction mixture is diluted with water and extracted with DCM. The organic layers are combined, dried over Na₂SO₄, filtered and evaporated under reduced pressure. The crude residue is purified by flash chromatography on silica gel (eluting with 0 to 10% MeOH in DCM) to afford Cpd 288.

1.2.12. Method K: Boc Cleavage Using TFA

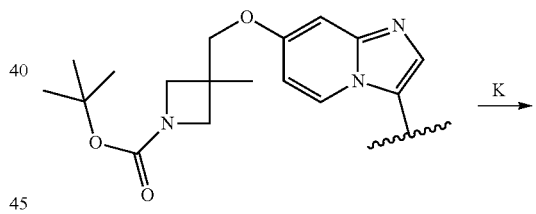

To the Boc-protected amine (1 eq.) in DCM is added TFA (DCM/TFA 1/1), the mixture is stirred at RT for 1.5 h to 2 h and the solvents are evaporated in vacuo. The residue is either directly purified by preparative HPLC to give the targeted compound, or taken up in water and 1N aq. NaOH and extracted with an EtOAc/i-PrOH mixture. The obtained organic phases are combined, dried over Na₂SO₄, filtered and concentrated to dryness. The residue is then purified by preparative HPLC to afford the expected product.

Illustrative Synthesis of Cpd 251

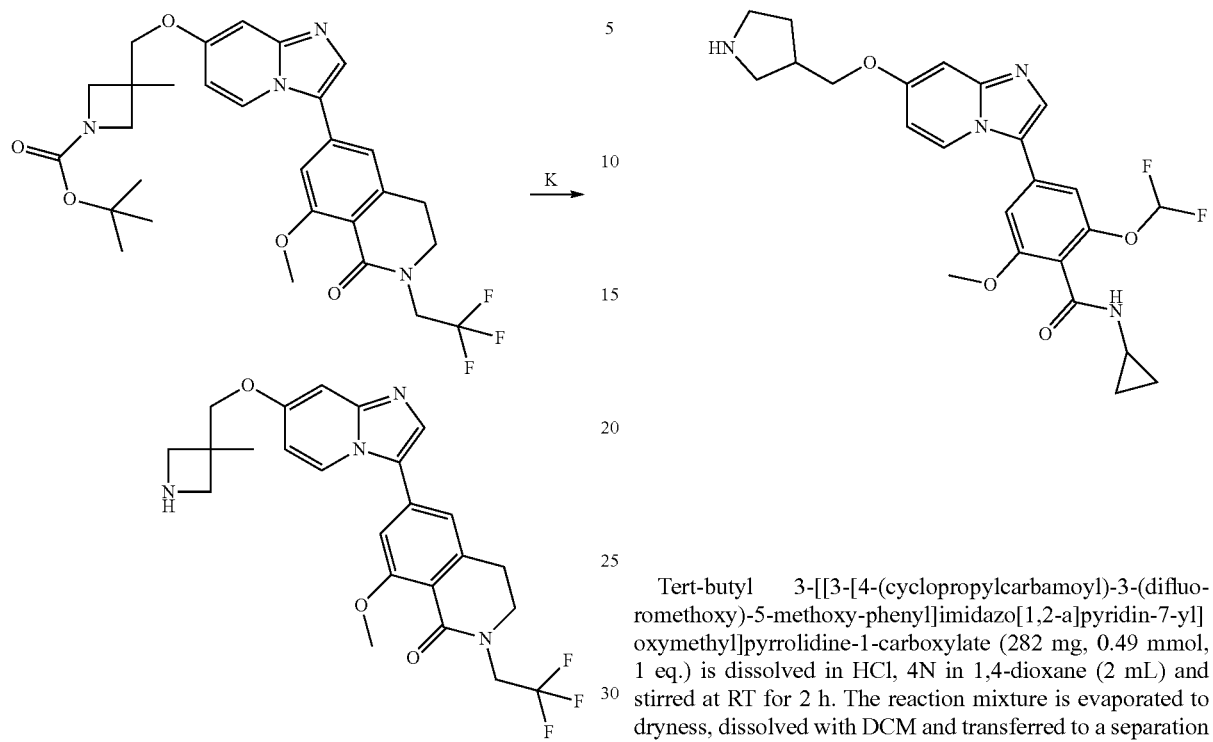

To a solution of Cpd 249 (80 mg, 0.14 mmol, 1 eq.) in DCM (1 mL) is added TFA (1 mL) and the mixture is stirred at RT for 2 h. The solvents are evaporated in vacuo and the residue is purified by preparative HPLC to afford the expected compound.

1.2.13. Method K1: Boc Cleavage Using HC

To the Boc-protected amine (1 eq.) is added HCl, 4N in 1,4-dioxane. The mixture is stirred at RT for 2 h. The solvents are evaporated in vacuo to afford the expected product as hydrochloride salt, or an alternative work up is carried out: the residue is dissolved in DCM then, water and a NaHCO$_3$ sat. aq. solution are added. The mixture is extracted with DCM. The organic layers are combined, dried over Na$_2$SO$_4$, filtered and evaporated in vacuo to afford the expected product as a free base.

Illustrative Synthesis of Int 99

Tert-butyl 3-[[3-[4-(cyclopropylcarbamoyl)-3-(difluoromethoxy)-5-methoxy-phenyl]imidazo[1,2-a]pyridin-7-yl]oxymethyl]pyrrolidine-1-carboxylate (282 mg, 0.49 mmol, 1 eq.) is dissolved in HCl, 4N in 1,4-dioxane (2 mL) and stirred at RT for 2 h. The reaction mixture is evaporated to dryness, dissolved with DCM and transferred to a separation funnel. Water and a sat. aq. NaHCO$_3$ solution are added and extracted with DCM. The organic layers are combined, dried over Na$_2$SO$_4$, filtered and evaporated under reduced pressure to afford Int 99.

Illustrative Synthesis of Cpd 270

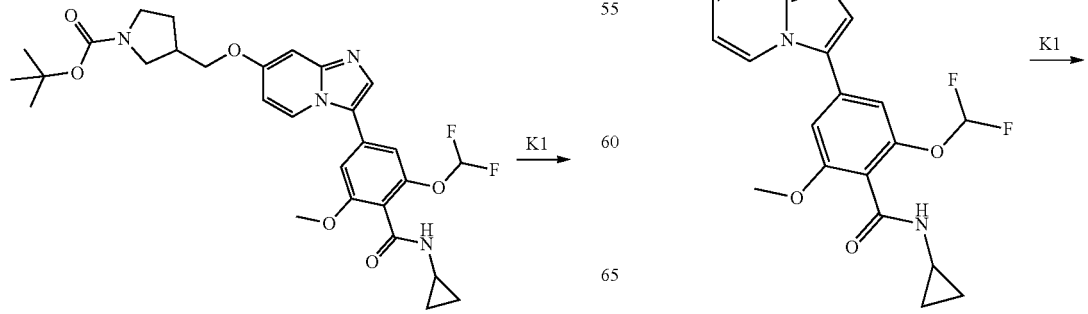

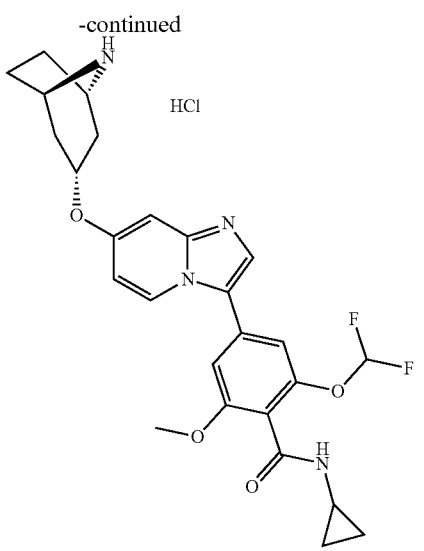

HCl, 4N in 1,4-dioxane (1.84 mL) is added to tert-butyl (1R,5S)-3-[3-[4-(cyclopropylcarbamoyl)-3-(difluoromethoxy)-5-methoxy-phenyl]imidazo[1,2-a]pyridin-7-yl]oxy-8-azabicyclo[3.2.1]octane-8-carboxylate. The reaction mixture is stirred at RT. After 2 h, the reaction mixture is evaporated under reduced pressure to afford Cpd 270.

Illustrative Synthesis of Cpd 314

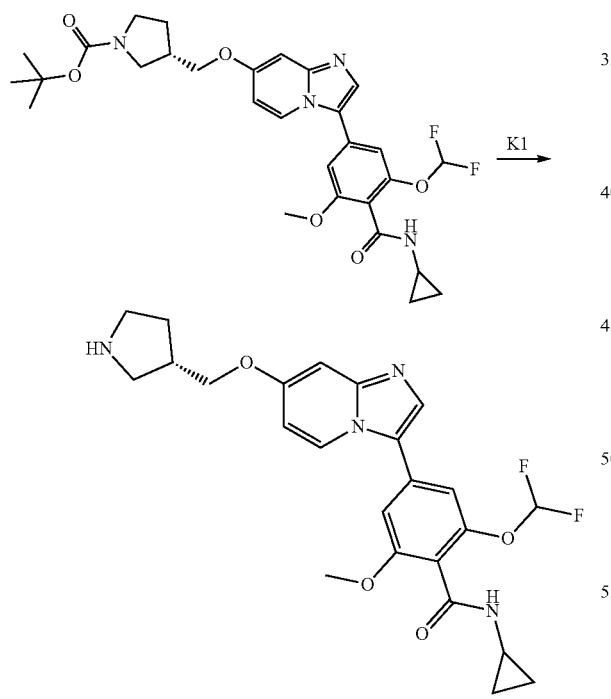

Tert-butyl (3S)-3-[[3-[4-(cyclopropylcarbamoyl)-3-(difluoromethoxy)-5-methoxy-phenyl]imidazo[1,2-a]pyridin-7-yl]oxymethyl]pyrrolidine-1-carboxylate (446 mg, 0.78 mmol, 1 eq.) is dissolved in HCl, 4N in 1,4-dioxane (3 mL) and stirred at RT for 2 h. The reaction mixture is evaporated to dryness, dissolved with DCM and transferred to a separation funnel. Water and a sat. NaHCO₃ aq. solution are added and extracted with DCM. The organic layers are combined, dried over Na₂SO₄, filtered and evaporated under reduced pressure to afford Cpd 314.

1.2.14. Method L: Michael Addition

To a mixture of amine derivative (free base or hydrochloride salt, 1 eq.) and acrylonitrile derivative (14.7 to 20 eq.) is added DIPEA (2 to 4.8 eq.). The mixture is stirred at RT from 2 to 18 h. The reaction medium is diluted with water and extracted with DCM. The combined organic layers are dried over Na₂SO₄, filtered and concentrated. The crude product is purified by flash chromatography on silica gel.

Illustrative Synthesis of Cpd 271

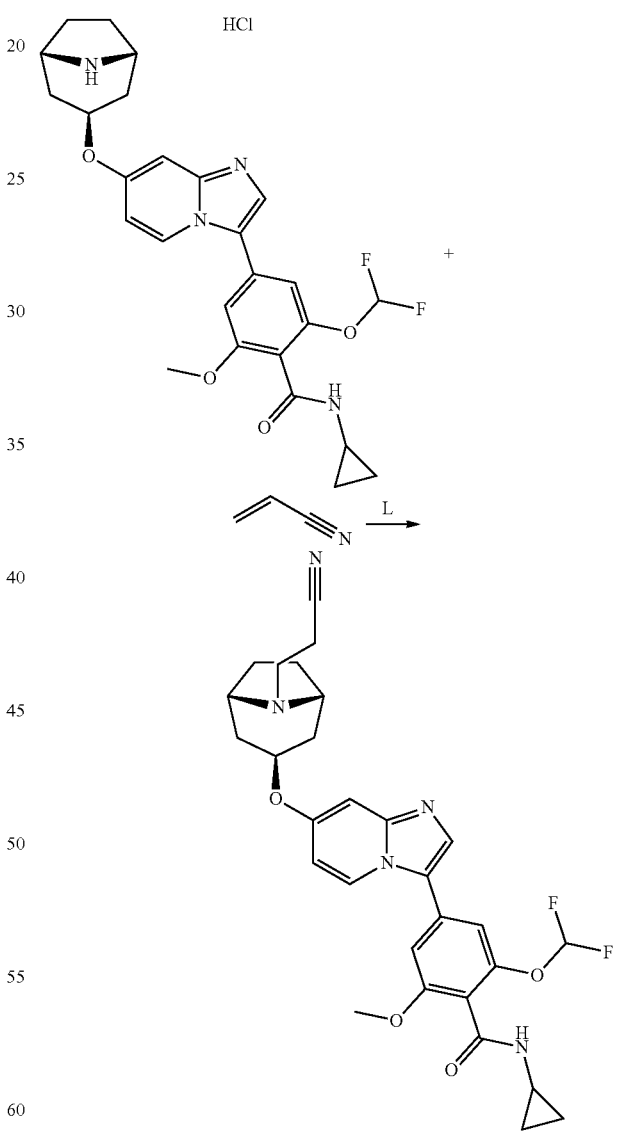

To a mixture of Cpd 270 (40 mg, 0.075 mmol, 1 eq.) and acrylonitrile (CAS #107-13-1; 0.980 mL, 1.5 mmol, 20 eq.) is added DIPEA (0.064 mL, 0.36 mmol, 4.8 eq.). The mixture is stirred at RT for 18 h. The reaction mixture is then diluted with water and extracted with DCM. The combined organic layers are dried over Na$_2$SO$_4$, filtered, and concentrated. The crude product is purified by flash chromatography on silica gel (eluting with 0 to 10% MeOH in DCM) to afford the expected product Cpd 271.

1.2.15 Method M: Mesylate Displacement

A suspension of mesylate derivative (1 eq.), amine derivative (1.2 to 2.0 eq.), potassium iodide (1.1 to 1.3 eq.), and NaHCO$_3$ (2.2 to 3.2 eq.) are stirred in DMF at 85° C. for 2 to 5 h. The mixture is cooled to RT, diluted with EtOAc and washed with a sat. NaHCO$_3$ aq. solution. The organic layers are dried over Na$_2$SO$_4$, filtered and concentrated to dryness. Purification by flash chromatography on silica gel or preparative HPLC affords the expected product.

Illustrative Synthesis of Cpd 363

Illustrative Synthesis of Cpd 324

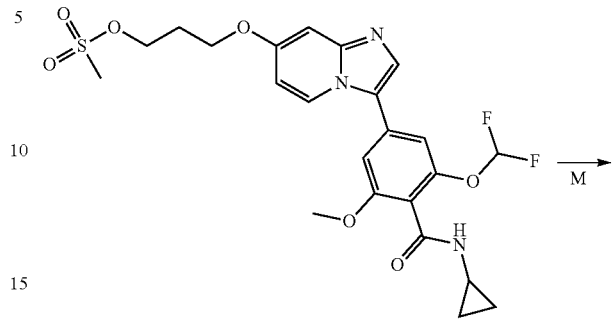

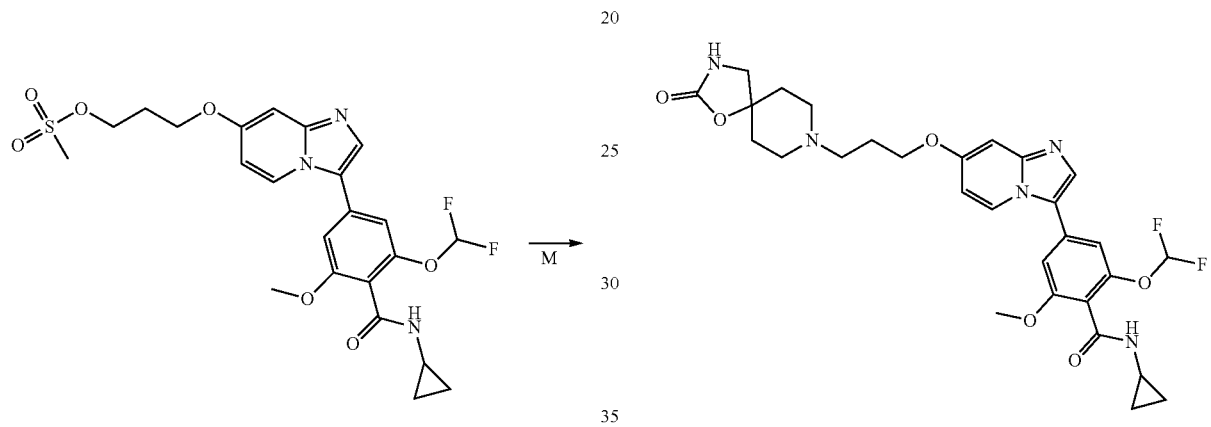

A suspension of Cpd 333 (45.0 mg, 0.0848 mmol, 1 eq.), 1-oxa-3,8-diazaspiro[4.5]decan-2-one hydrochloride (CAS #5052-96-0; 27.8 mg, 0.144 mmol), NaHCO$_3$ (22.8 mg, 0.271 mmol, 3.2 eq.), and potassium iodide (17.1 mg, 0.102 mmol, 1.2 eq.) in dry DMF (1 mL) is stirred at 85° C. for 5 h. The reaction mixture is cooled to RT and diluted with 1 mL of DMF and filtered. The filtrate is evaporated and the crude product is purified by flash chromatography on silica gel (eluting with a gradient DCM/(DCM/MeOH/NH$_3$ in water 90/9.5/0.5) 100/0 to 25/75). The residue obtained after evaporation is dissolved in 1 mL of DCM and concentrated to afford Cpd 324.

Illustrative Synthesis of Cpd 331

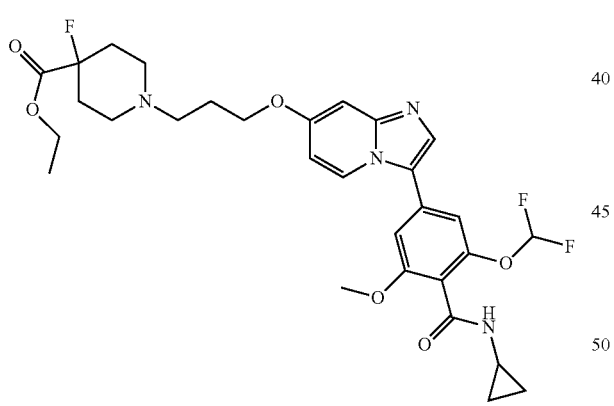

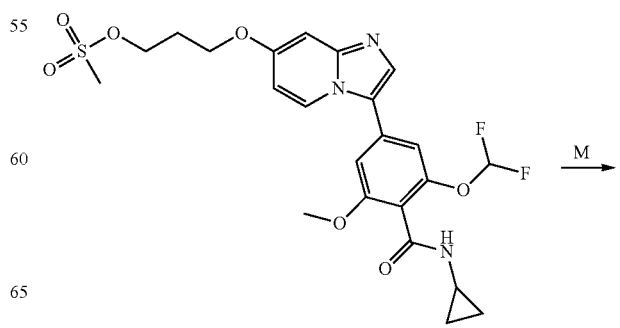

A suspension of Cpd 333 (50 mg, 0.093 mmol, 1 eq.), ethyl 4-fluoropiperidin-1-ium-4-carboxylate chloride (CAS #845909-49-1; 23.7 mg, 0.112 mmol, 1.2 eq.), potassium iodide (20.3 mg, 0.121 mmol, 1.3 eq.) and NaHCO$_3$ (23.5 mg, 0.280 mmol, 3 eq.) in dry DMF (0.7 mL) is stirred at 85° C. for 2 h. The mixture is cooled to RT, diluted with EtOAc (20 mL) and washed with a sat. NaHCO$_3$ aq. solution. The organic layer is dried over Na$_2$SO$_4$, filtered and concentrated to dryness. The resulting crude product is purified by flash chromatography on silica gel (eluting with 0 to 7% MeOH in DCM) to afford Cpd 363.

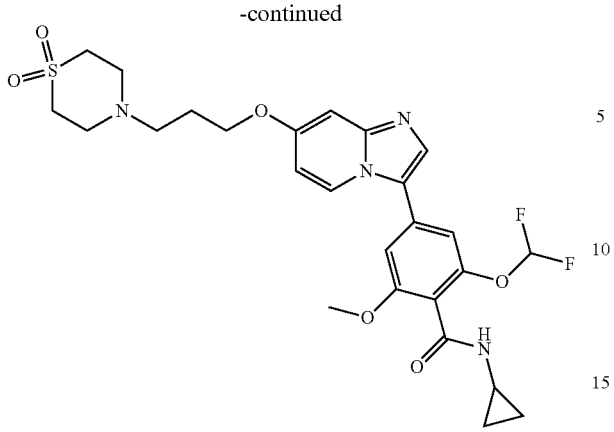

To a solution of Cpd 333 (121 mg, 0.226 mmol, 1 eq.) in dry DMF (2 mL) are added thiomorpholine 1,1-dioxide (CAS #39093-93-1; 35.8 mg, 0.259 mmol, 1.5 eq.), potassium iodide (45.4 mg, 0.271 mmol, 1.2 eq.) and NaHCO₃ (56.9 mg, 0.677 mmol, 3 eq.). The reaction mixture is stirred at 85° C. for 2 h, then cooled to RT, diluted with EtOAc (15 mL) and washed with water. The organic layer is dried over Na₂SO₄ and filtered. The filtrate is evaporated and the crude product is purified by flash chromatography on silica gel (eluting with 1-8% MeOH in DCM) to afford Cpd 331.

Illustrative Synthesis of Cpd 286

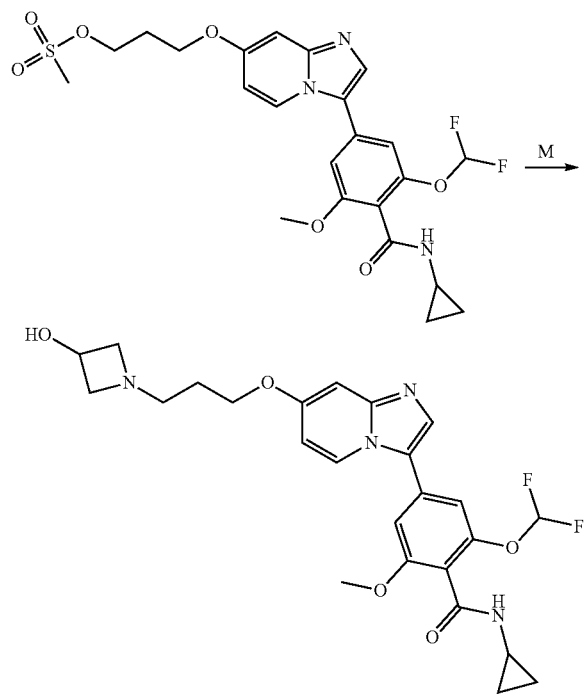

A suspension of Cpd 333 (100 mg, 0.186 mmol, 1 eq.), azetidin-3-ol (CAS #45347-82-8; 28.7 mg, 0.373 mmol), potassium iodide (34.4 mg, 0.205 mmol, 1.1 eq.) and NaHCO₃ (34.5 mg, 0.410 mmol, 2.2 eq.) is stirred in dry DMF (1 mL) at 85° C. for 2 h. The reaction mixture is diluted with 1 mL of DMF and is filtered. Solvent from the filtrate is evaporated and the resulting crude is purified by preparative HPLC to give Cpd 286.

1.2.16. Method N: Peptidic Coupling

To a solution of acid derivative (1 eq.) in dry DMSO is added HATU (2 eq.) and DIPEA (3 to 6 eq.). The mixture is stirred at RT for 5 min and then the amine derivative (2.0 eq.) is added. The mixture is stirred at RT for 2-18 h and then purified by preparative HPLC to afford the expected product.

Illustrative Synthesis of Cpd 357

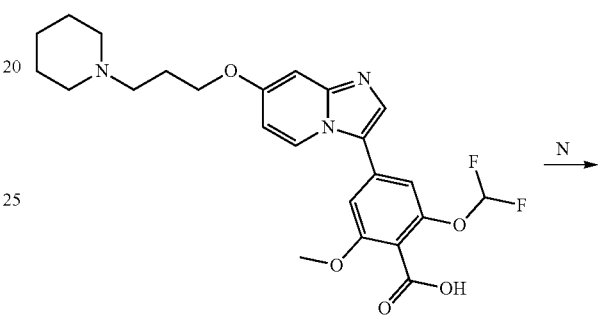

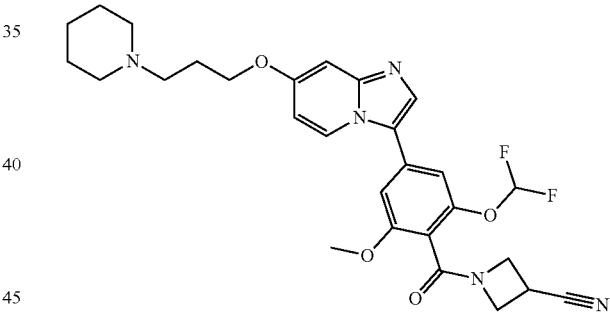

To a solution of Int 94 (43 mg, 0.090 mmol, 1 eq.) in dry DMSO (0.5 mL) is added HATU (41 mg, 0.179 mmol, 2 eq.) and DIPEA (47 µL, 0.269 mmol, 3 eq.). The mixture is stirred at RT for 5 min and then 3-cyanoazetidine hydrochloride (CAS #345954-83-8; 21 mg, 0.178 mmol, 2.0 eq.) is added. The mixture is stirred at RT for 2 h and then purified by preparative HPLC to afford Cpd 357.

1.2.17. Method O: Epoxide Aminolysis

The epoxide derivative is dissolved in DMSO, then water or ACN is added followed by the amine derivative (1.2 to 5.eq.) and optionally, Et₃N (5 eq.) when the amine derivative is a salt. The reaction mixture is stirred at RT for 18 to 72 h and then diluted with EtOAc. Water and a sat. NaHCO₃ aq. solution are added and extracted with DCM. Purification by flash chromatography on silica gel affords the expected product.

153
Illustrative Synthesis of Cpd 330

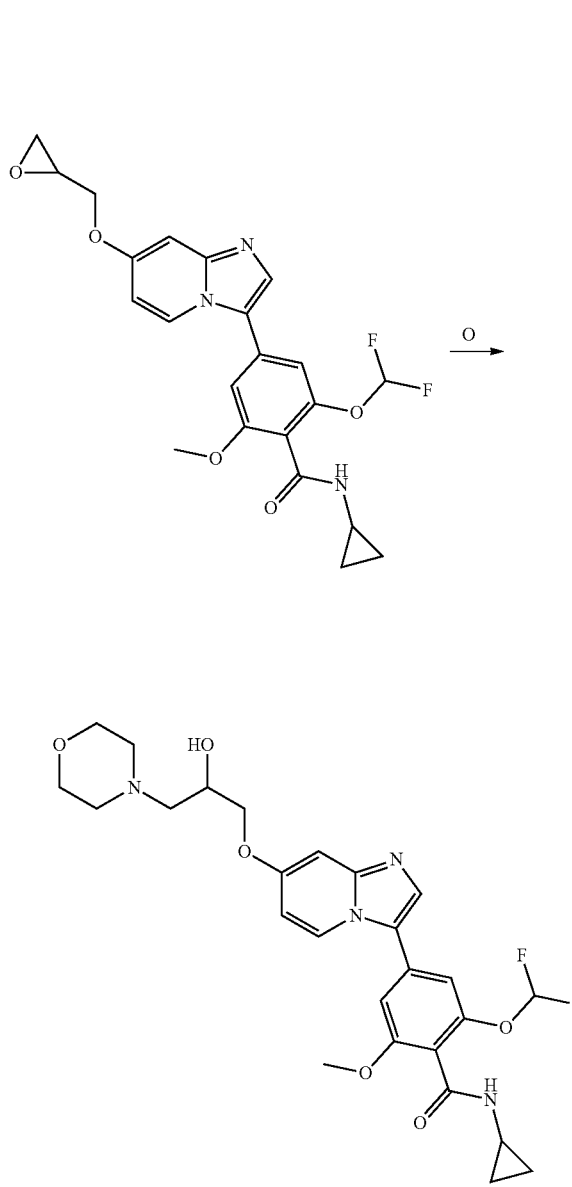

Int 92 (250 mg, 0.561 mmol, 1 eq.) is dissolved in DMSO (10 mL) and water (10 mL) is added followed by morpholine (CAS #110-91-8; 242 µL, 2.81 mmol, 5 eq.). The reaction mixture is stirred at RT overnight. The reaction mixture is diluted with EtOAc and transferred to a separation funnel. Water and a sat. NaHCO₃ aq. solution are added and extracted with EtOAc. The organic layers are combined, dried over Na₂SO₄, filtered, and evaporated under reduced pressure. The crude product is purified by flash chromatography on silica gel (eluting with a gradient DCM/(DCM/MeOH/NH₃ in water 90/9.5/0.5) 100/0 to 20/80) to afford Cpd 330.

154
Illustrative Synthesis of Cpd 321

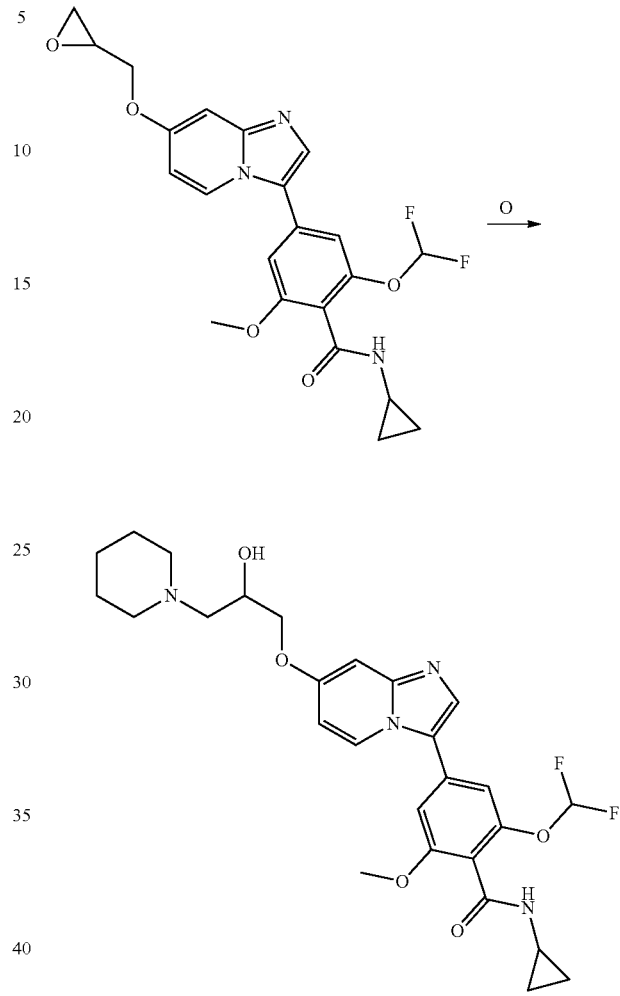

Int 92 (25 mg, 0.056 mmol, 1 eq.) is dissolved in DMSO (0.5 mL) and water (1 mL) is added followed by piperidine (CAS #110-89-4; 6.65 µL, 0.067 mmol, 1.2 eq.). The reaction mixture is stirred at RT for 48 h. Another portion of piperidine (6.65 µL, 0.067 mmol, 1.2 eq.) is added. The reaction mixture is stirred at RT for 48 h. Another portion of piperidine (6.65 µL, 0.067 mmol, 1.2 eq.) is added. The reaction mixture is stirred at RT for 18 h, diluted with DCM and transferred to a separation funnel. Water and a sat. NaHCO₃ aq. solution are added and extracted with DCM. The organic layers are combined, dried over Na₂SO₄, filtered, and evaporated under reduced pressure. The crude product is purified by flash chromatography on silica gel (eluting with a gradient DCM/(DCM/MeOH/NH₃ in water 90/9.5/0.5) 0 to 80%) to afford Cpd 321.

1.2.18. Method P: Silyl Deprotection

The silyl ether derivative (1 eq.) is dissolved in ACN and water is added followed by 3 drops of concentrated HCl. The reaction mixture is stirred at RT. After 30 min, the reaction mixture is evaporated to dryness. Purification by preparative HPLC affords the expected product.

Illustrative Synthesis of Cpd 340

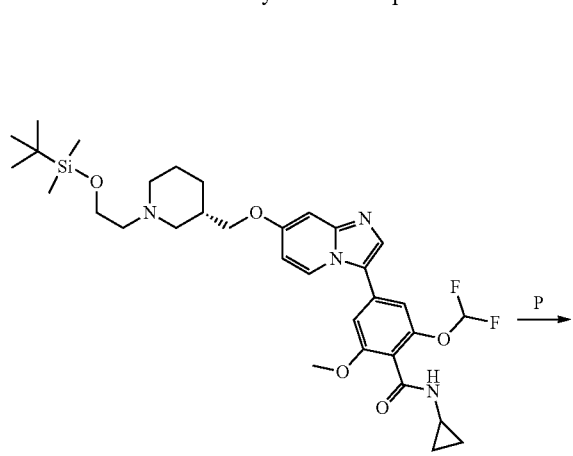

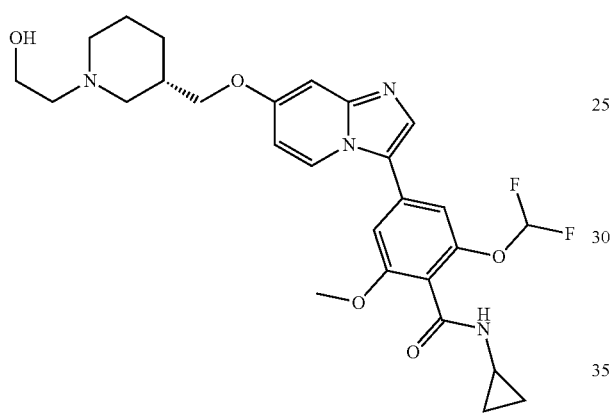

4-[7-[[(3S)-1-[2-[tert-butyl(dimethyl)silyl]oxyethyl]-3-piperidyl]methoxy]imidazo[1,2-a]pyridin-3-yl]-N-cyclopropyl-2-(difluoromethoxy)-6-methoxy-benzamide (66 mg, 0.1 mmol, 1 eq.) is dissolved in ACN (2 mL) and water (100 µL) is added followed by 3 drops of concentrated HCl. The reaction mixture is stirred at RT. After 30 min, the reaction mixture is evaporated to dryness, dissolved in DMSO (1 mL) and purified by preparative HPLC to afford Cpd 340.

Illustrative Synthesis of Cpd 370

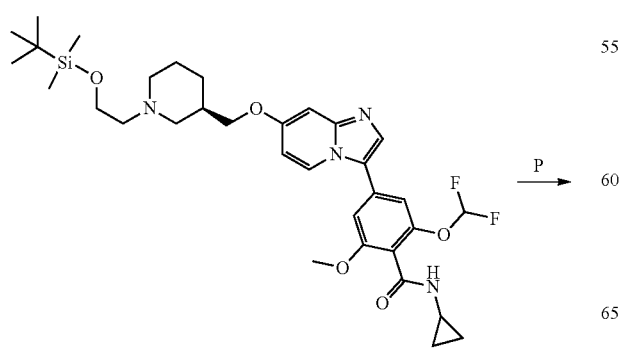

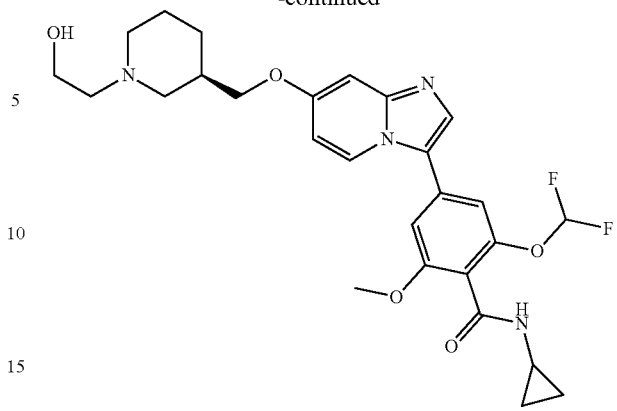

4-[7-[[(3R)-1-[2-[tert-butyl(dimethyl)silyl]oxyethyl]-3-piperidyl]methoxy]imidazo[1,2-a]pyridin-3-yl]-N-cyclopropyl-2-(difluoromethoxy)-6-methoxy-benzamide (63 mg, 0.1 mmol, 1 eq.) is dissolved in ACN (2 mL) and water (100 µL) is added followed by 3 drops of concentrated HCl. The reaction mixture is stirred at RT. After 30 min, the reaction mixture is evaporated to dryness, dissolved in DMF (1 mL) and purified by preparative HPLC to afford Cpd 370.

1.2.19. Method Q: Synthesis of 3,4-dihydro-1(2H)-isoquinolinones by Rh-Catalyzed C—H Activation

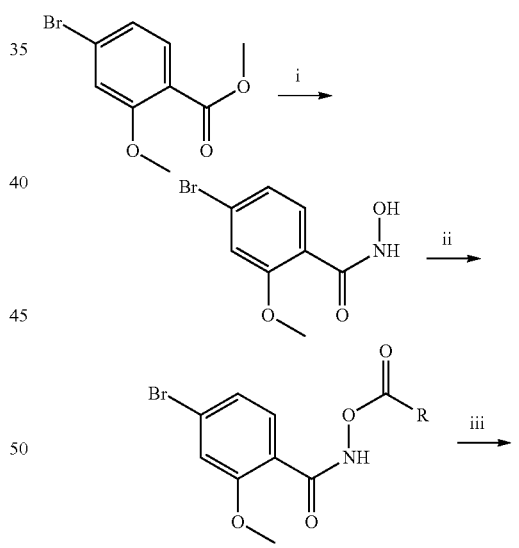

1.2.19.1. Step i: 4-bromo-2-methoxy-benzenecarbohydroxamic

A suspension of methyl 4-bromo-2-methoxybenzoate (CAS #139102-34-4; 1 eq.) and hydroxylamine (50 wt % in water; 10 eq.) is heated at 60 to 63° C. for 5 h to 17 h. The reaction mixture is then cooled down to RT. The suspension is filtered and the solid rinsed with water to afford 4-bromo-2-methoxy-benzenecarbohydroxamic.

1.2.19.2. Step ii: Acyl Hydroxamates

To a solution of 4-bromo-2-methoxy-benzenecarbohydroxamic (1.0 eq.) in THF or MTBE is added triethylamine (1.05 to 1.1 eq.). The reaction mixture is cooled down to 10° C. and acid chloride (e.g., acetyl chloride, 2,2-dimethylpropanoyl chloride, or benzoyl chloride; 1.0 to 1.1 eq.) is added dropwise. The reaction mixture is stirred for 1 to 3 h at 20° C. The reaction mixture is diluted with EtOAc or MTBE. The organic layer is washed with water, brine, dried over $Na_2SO_4$ and evaporated to afford the desired product. Alternatively, a solvent exchange with heptane is performed instead of the aqueous washing, the solvents are partially evaporated and the desired product precipitates and is filtered out.

1.2.19.3. Step iii: Int 40

In a pressure reactor is added the acyl hydroxamate (1.0 eq.), $K_2CO_3$ (0.3 eq.), pivalic acid (1 eq.), pentamethylcyclopentadienylrhodium(III) chloride dimer (CAS #12354-85-7; 2.5 mol %) in i-PrOH. The resulting mixture is put under vacuum for 10 seconds. Ethylene gas is charged under 3 to 4 bars and the reaction mixture is stirred vigorously at 20° C. for 12 to 24 h. The crude residue is purified by flash chromatography on silica gel or by reslurry (water/heptane) to afford Int 40.

Illustrative Synthesis of Int 40 via
[(4-bromo-2-methoxy-benzoyl)amino]
2,2-dimethylpropanoate

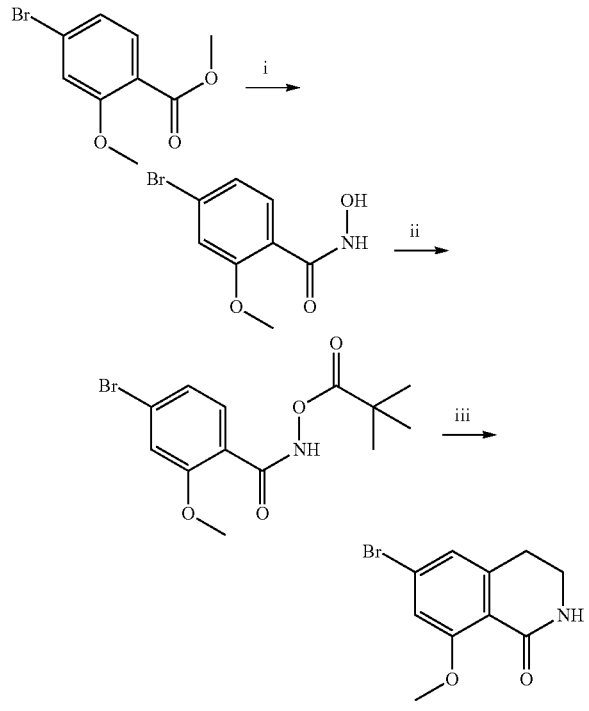

Step i: 4-bromo-N-hydroxy-2-methoxybenzamide

A suspension of methyl 4-bromo-2-methoxybenzoate (CAS #139102-34-4; 4.328 mol, 1 eq.) in hydroxylamine (50 wt % in water, 2859 mL, 10 eq.) is heated at 60 to 63° C. for 14 h. The reaction mixture is cooled down to RT and the suspension is filtered. The solid is washed with water (10 L) and dried at 50° C. in a vacuum oven to afford 4-bromo-N-hydroxy-2-methoxybenzamide.

LCMS: MW (calcd): 246.1; m/z MW (obsd): 246.0/248.0 (M+H)

Step ii:
4-bromo-2-methoxy-N-(pivaloyloxy)benzamide

In a single jacketed process reactor charged with methyl tertbutyl ether (10.3 L) is added 4-bromo-N-hydroxy-2-methoxybenzamide (1030 g, 4.186 mol, 1.0 eq.) and $Et_3N$ (613 mL, 4.40 mol, 1.05 eq.). The resulting suspension is cooled at 10° C. and 2,2-dimethylpropanoyl chloride (521 mL, 4.23 mol, 1.01 eq.) is added dropwise such as to maintain the reaction temperature below 20° C. The reaction mixture is stirred at 20° C. for 1 h. The reaction mixture is extracted with water (2×3 L). The combined aqueous layers are extracted with MTBE (1 L). All MTBE layers are combined and heptane (4 L) is added. The organic phase is concentrated until all MTBE is removed at which point a suspension is obtained. The solid is filtered and dried to afford 4-bromo-2-methoxy-N-(pivaloyloxy)benzamide.

LCMS: MW (calcd): 330.2; m/z MW (obsd): 330.0/332.0 (M+H)

Step iii: Int 40

In a 2 L pressure vessel is added 4-bromo-2-methoxy-N-(pivaloyloxy)benzamide (200 g, 0.606 mol, 1.0 eq.), $K_2CO_3$ (25.1 g, 0.182 mol, 0.3 eq.), pivalic acid (62 g, 0.606 mol, 1 eq.), pentamethylcyclopentadienylrhodium(III) chloride dimer (CAS #12354-85-7; 9.4 g, 15.14 mmol, 2.5 mol %) in i-PrOH (1 L). The resulting mixture is put under vacuum for 10 seconds. Ethylene gas is added under 3 to 4 bars and the reaction mixture is stirred vigorously at 20° C. for 17 h. Two identical reactions are combined for the work-up. The combined reaction mixtures are concentrated, heptane (700 mL) and water (700 mL) are added and the resulting mixture is stirred at 20° C. for 1 h. The precipitate is filtered out and washed with heptane (500 mL) to afford Int 40.

LCMS: MW (calcd): 256.1; m/z MW (obsd): 256.1/258.0 (M+H)

Illustrative Synthesis of Cpd 370

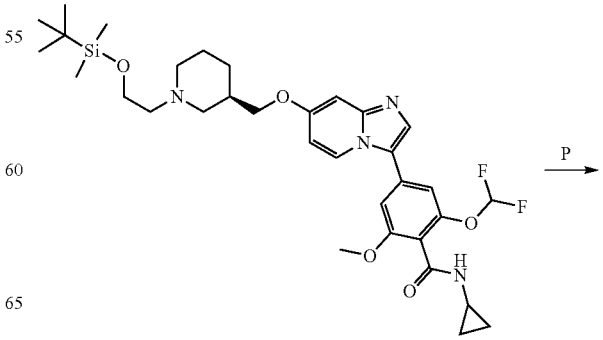

-continued

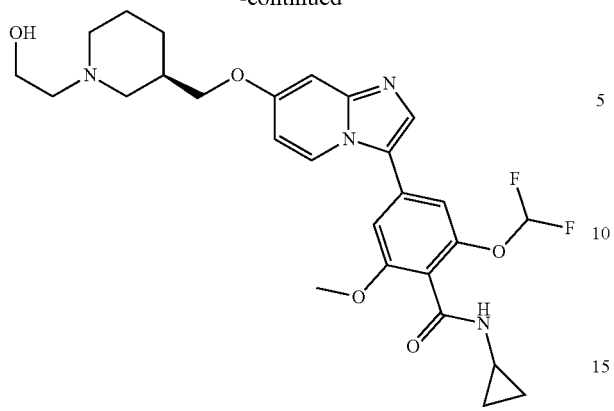

4-[7-[[(3R)-1-[2-[tert-butyl(dimethyl)silyl]oxyethyl]-3-piperidyl]methoxy]imidazo[1,2-a]pyridin-3-yl]-N-cyclopropyl-2-(difluoromethoxy)-6-methoxy-benzamide (63 mg, 0.1 mmol, 1 eq.) is dissolved in ACN (2 mL) and water (100 μL) is added followed by 3 drops of concentrated HCl. The reaction mixture is stirred at RT. After 30 min, the reaction mixture is evaporated to dryness, dissolved in DMF (1 mL) and purified by preparative HPLC to afford Cpd 370.

Example 2. Preparation of the Compounds of the Invention 2.1. Int 1

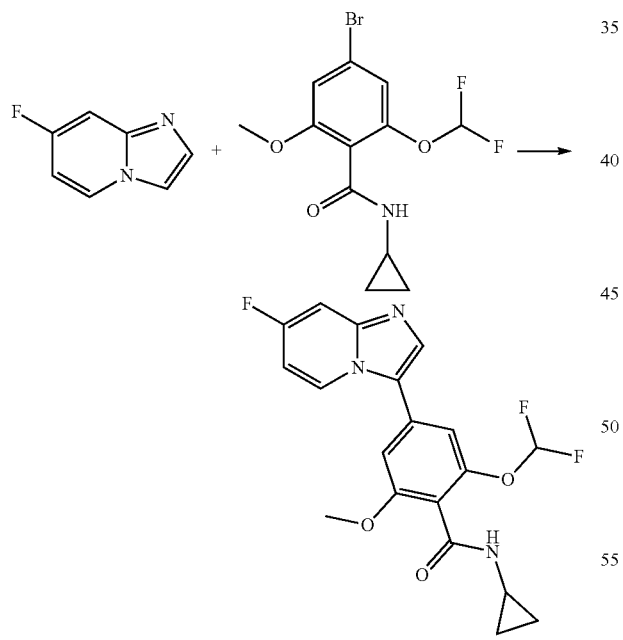

A solution of 7-fluoroimidazo[1,2-a]pyridine (CAS #1260903-17-0; 2 g, 14.7 mmol) in dry DMAC (40 mL) is degassed with $N_2$ and then Int 11 (6 g, 17.6 mmol), KOAc (4.3 g, 44.1 mmol) and Pd(dppf)Cl$_2$·DCM (CAS #95464-05-4; 600 mg, 0.73 mmol) are added. The mixture is degassed with $N_2$ for 10 min and is then stirred at 110° C. for 4 h. The reaction medium is filtered and the filtrate is concentrated. The crude material is purified by flash chromatography on silica gel (eluting with a gradient of 0 to 2% MeOH in EtOAc) to give a solid that is triturated in EtOH to afford Int 1.

2.2. Int 3

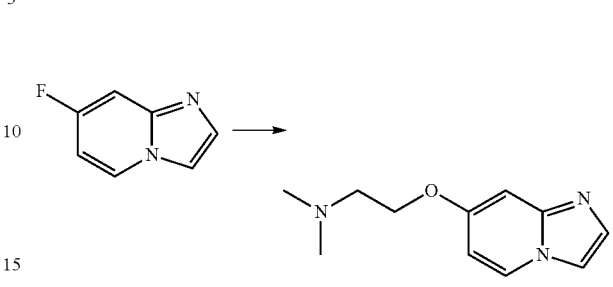

To a solution of 2-(dimethylamino)ethanol (CAS #108-01-0; 890 μL, 8.81 mmol) in dry DMF (8 mL) is added NaH (60% dispersion in mineral oil, 352 mg, 8.81 mmol) and the mixture is stirred at RT for 10 min. 7-Fluoroimidazo[1,2-a]pyridine (CAS #1260903-17-0; 200 mg, 1.47 mmol) is added and the reaction mixture is stirred at RT for 4.5 h. The reaction medium is quenched with a mixture of water and sat. aq. NaHCO$_3$ solution and diluted with EtOAc. Phases are separated and the aqueous layer is extracted with EtOAc. The combined organic layers are washed with brine, dried over Na$_2$SO$_4$, filtered and concentrated. The crude material is triturated in DCM, filtered, rinsed with pentane and the filtrate is concentrated to afford Int 3.

2.3. Int 4

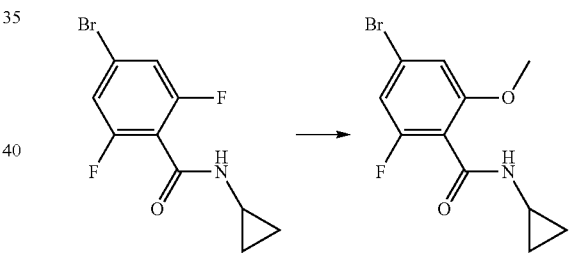

A mixture of Int 88 (1 g, 3.62 mmol, 1 eq.) and sodium methoxide (0.23 g, 4.35 mmol, 1.2 eq.) in DMSO (5 mL) is heated at 60° C. for 24 h. The reaction mixture is cooled down to room temperature and poured into water (50 mL). The solid formed is filtered, washed with water, and dried to give Int 4.

2.4. Int 5

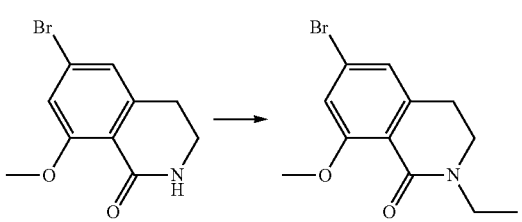 [SMILES: COc1cc(Br)cc2c1C(=O)NCC2 ; CCN1CCc2cc(Br)cc(OC)c2C1=O]

To a solution of Int 40 (300 mg, 1.17 mmol) in dry THF (6 mL) is added NaH (60% dispersion in mineral oil, 52 mg, 1.29 mmol) and the mixture is stirred at RT for 45 min. Iodoethane (104 µL, 1.29 mmol) is added and the reaction mixture is stirred at RT for 2 h. NaH (60% dispersion in mineral oil, 25 mg, 0.62 mmol) is added and the mixture is stirred at RT for 20 min. Iodoethane (104 µL, 1.29 mmol) is added and the reaction mixture is stirred at RT overnight. The reaction is quenched with water, the THF is concentrated and the suspension is extracted with EtOAc. The combined organic phases are passed through a phase separator and the filtrate is concentrated. The crude material is purified by chromatography on silica gel (eluting with a gradient of 0 to 80% EtOAc in heptane) to afford Int 5.

2.5. Int 8

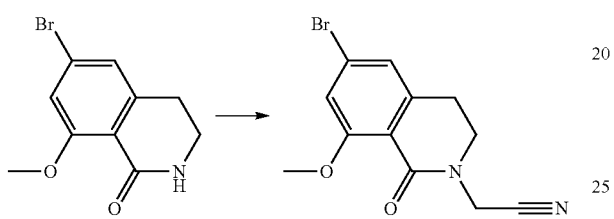

To a solution of Int 40 (300 mg, 1.17 mmol) in dry THF (6 mL) is added NaH (60% dispersion in mineral oil, 70 mg, 1.76 mmol) and the mixture is stirred at RT for 45 min. 2-bromoacetonitrile (CAS #590-17-0; 123 µL, 1.76 mmol) is added and the reaction mixture is stirred at RT for 2 h. The reaction is quenched with a sat. aq. $NH_4Cl$ solution and water. THF is removed in vacuo and the suspension is extracted with EtOAc. The organic phase is passed through a phase separator and the filtrate is concentrated. The crude material is purified by chromatography on silica gel (eluting with a gradient of 0 to 3% MeOH in DCM) to afford Int 8.

2.6. Int 10

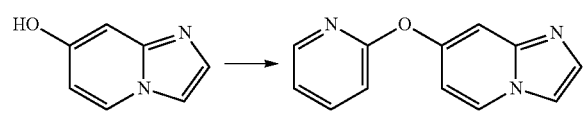 [SMILES: Oc1ccn2ccnc2c1 ; c1ccc(Oc2ccn3ccnc3c2)nc1]

To a solution of imidazo[1,2-a]pyridin-7-ol (CAS #896139-85-8; 100 mg, 0.745 mmol) in dry NMP (3 mL) are added 2-fluoropyridine (CAS #372-48-5; 218 mg, 2.24 mmol) and $K_2CO_3$ (309 mg, 2.24 mmol) and the mixture is degassed with $N_2$ for 5 min. Then the vial is sealed and heated at 160° C. for 2 h under microwave irradiation. The reaction medium is quenched with a mixture of water and sat. aq. $NaHCO_3$ solution and extracted with EtOAc. The organic layers are combined, dried over $MgSO_4$, filtered and concentrated. The crude is purified by chromatography on silica gel (eluting with a gradient of 1 to 3% MeOH in DCM) to give Int 10.

2.7. Int 11

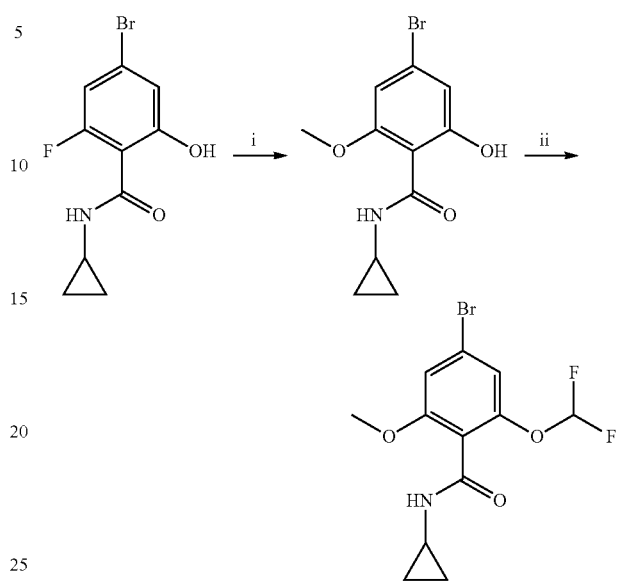

2.7.1. Step i: 4-bromo-N-cyclopropyl-2-hydroxy-6-methoxy-benzamide

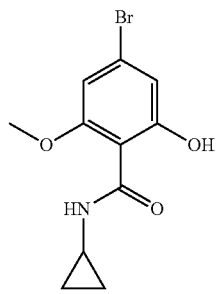 [SMILES: COc1cc(Br)cc(O)c1C(=O)NC1CC1]

In a 15 L single jacketed process reactor, NaOMe (717 g, 13.27 mol, 3.5 eq.) is added over 20 min to a solution of Int 42 (1040 g, 3.79 mol, 1 eq.) in DMSO (5 V, 5200 mL) under N2 atmosphere. The reaction mixture is heated to 100° C. (jacket temperature from 20° C. to 100° C. over 30 min) and stirred at 250 rpm overnight.

The reaction mixture is cooled to 20° C. (jacket temperature; ramp from 100° C. to 10° C. in 45 min) and HCl 2 N (5.3 L, 10.6 mol, 0.8 eq./NaOMe) is added in 2 h while maintaining internal temperature below 30° C. The suspension is cooled to 20° C., stirred for 15 min and filtered. The cake is washed with water (2*2 L, 2*2 V). The solid is dried in a vacuum oven at 50° C.

In the 15 L reactor, the crude solid (1040 g) is dissolved in acetone (3 L, 3 V). The solution is cooled at 15° C. (jacket temperature from 20° C. to 10° C. in 20 min) and water (3 L, 3 V) is progressively added over 30 min. Crystallization starts after adding 800 mL of water. At the end of the addition, the suspension is cooled down to 15° C. and stirred for 15 min. The suspension is filtered and the cake is washed with water (2*3 L, 2*3 V). The solid is dried in a vacuum oven at 50° C. to afford 4-bromo-N-cyclopropyl-2-hydroxy-6-methoxy-benzamide.

LCMS: MW (calcd): 286.1; m/z MW (obsd): 286.3-288.2 (M+H)

2.7.2. Step ii: Int 11

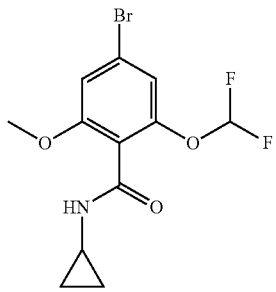 [SMILES: COc1cc(Br)cc(OC(F)F)c1C(=O)NC1CC1]

In a 15 L single jacketed process reactor, potassium hydroxide (10 eq., 243 g) is added to a solution of 4-bromo-N-cyclopropyl-2-hydroxy-6-methoxy-benzamide (1 eq., 124 g) in ACN/water (ACN/H$_2$O 1/1, 10 V, 1240 mL). The reaction mixture is cooled to 5° C. (jacket temperature from 20° C. to 0° C. in 40 min). Diethyl (bromodifluoromethyl) phosphonate (CAS #65094-22-6; 2 eq., 154 mL) is added neat over 1 h into the solution at 5° C. (jacket temperature set at 0° C.), while keeping the reaction temperature below 18° C. At the end of the addition, the reaction mixture is warmed up to 20° C. and stirred at 20° C. for 30 min.

The aqueous phase is extracted three times with EtOAc (3*650 mL, 3*5 V). The organic phases are combined and washed once with NaCl 20% (5 V, 650 mL) and concentrated.

The crude is re-slurried in MTBE (3 V/theoretical mass, 400 mL) for 30 min at 20° C. The suspension is filtered and the solid is washed with MTBE (140 mL). The solid is dried to afford Int 11.

LCMS: MW (calcd): 275.3; m/z MW (obsd): 276.3 (M+H)

2.8. Int 13

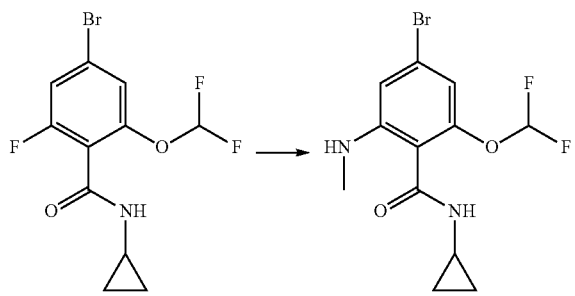 [SMILES: O=C(NC1CC1)c1c(F)cc(Br)cc1OC(F)F ; CNc1cc(Br)cc(OC(F)F)c1C(=O)NC1CC1]

In a flask equipped with a reflux condenser methylamine hydrochloride (CAS #593-51-1; 63 mg, 0.93 mmol) and DIPEA (CAS #7087-68-5; 322 µL, 1.85 mmol) are added to a solution of Int 12 (100 mg, 0.31 mmol) in dry DMAC (1.5 mL). The reaction mixture is stirred at 80° C. for 1 h and then at 100° C. for 2 days. Methylamine hydrochloride (63 mg, 0.93 mmol) and DIPEA (322 µL, 1.85 mmol) are added and the reaction mixture is stirred at 100° C. for 2 h. The reaction mixture is transferred in a vial that is sealed and heated at 100° C. overnight. The reaction is quenched with water, a precipitate appeared and the suspension is stirred for 10 min before being filtered. The solid is rinsed with water to afford Int 13.

2.9. Int 14

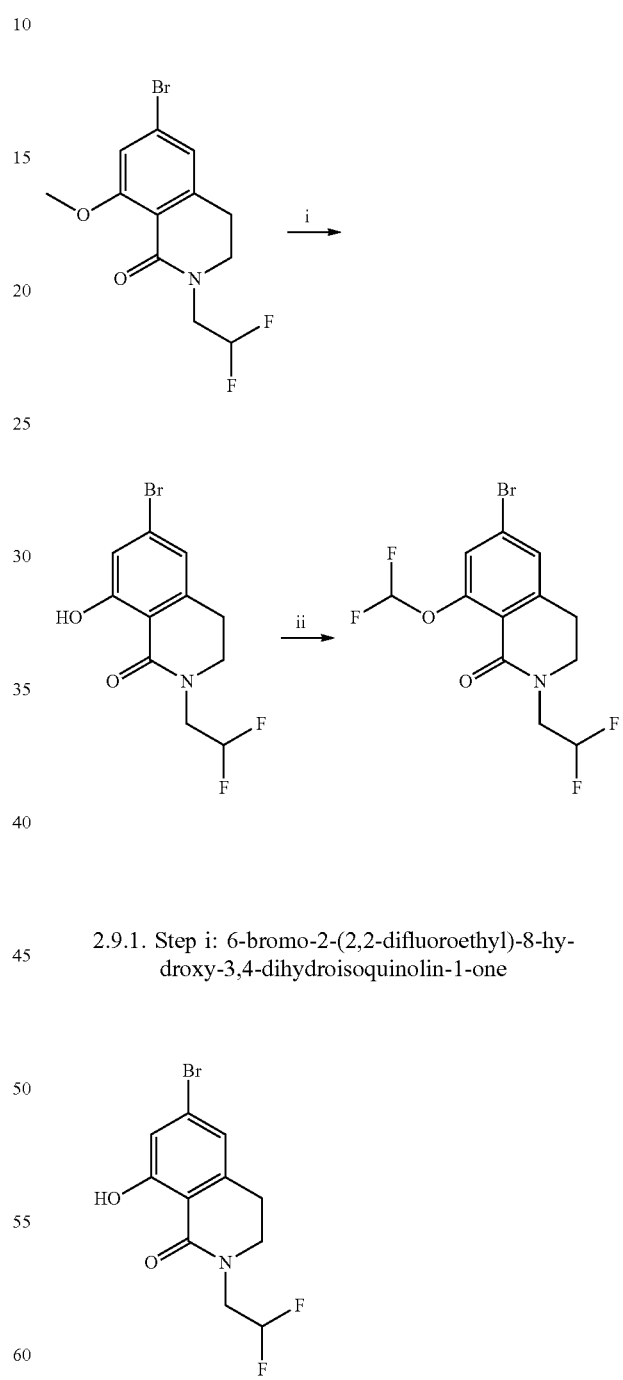

2.9.1. Step i: 6-bromo-2-(2,2-difluoroethyl)-8-hydroxy-3,4-dihydroisoquinolin-1-one 6-Bromo-2-(2,2-difluoroethyl)-8-hydroxy-3,4-dihydroisoquinolin-1-one is prepared from Int 6 according to general method F using BBr$_3$.

LCMS: MW (calcd): 306.1; m/z MW (obsd): 305.9 (M−H)

2.9.2. Step ii: Int 14

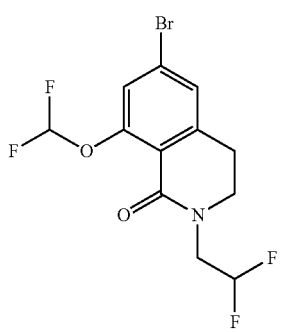 [SMILES: O=C1c2c(cc(Br)cc2OC(F)F)CCN1CC(F)F]

To a solution of 6-bromo-2-(2,2-difluoroethyl)-8-hydroxy-3,4-dihydroisoquinolin-1-one (529 mg, 1.73 mmol, 1 eq.) in dry ACN (5 mL) at 0° C. are added a cold solution of KOH (971 mg, 17.3 mmol, 10 eq.) in water (2.65 mL) and diethyl (bromodifluoromethyl)phosphonate (CAS #65094-22-6; 430 µL, 2.42 mmol, 1.4 eq.) dropwise. The mixture is stirred for 5 min at 0° C., EtOAc is added and the phases are separated. The aqueous layer is extracted again with EtOAc and the combined organic phases are washed with brine before being evaporated to dryness. The residue is purified by flash chromatography on silica gel to afford Int 14.

2.10. Int 16

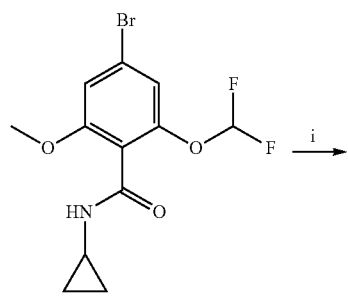

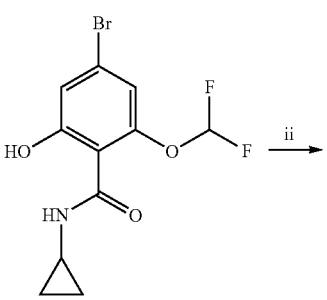

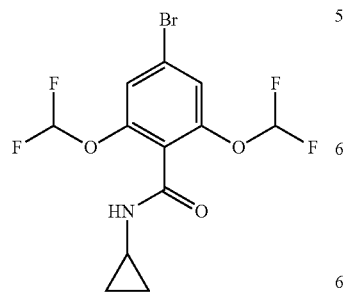

2.10.1. Step i: 4-bromo-N-cyclopropyl-2-(difluoromethoxy)-6-hydroxy-benzamide

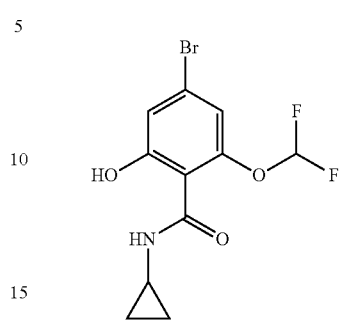

4-bromo-N-cyclopropyl-2-(difluoromethoxy)-6-hydroxy-benzamide is prepared from Int 11 according to general method F using $BCl_3$.

LCMS: MW (calcd): 322.1; m/z MW (obsd): 322.1/324.1 (M+H)

2.10.2. Step ii: Int 16

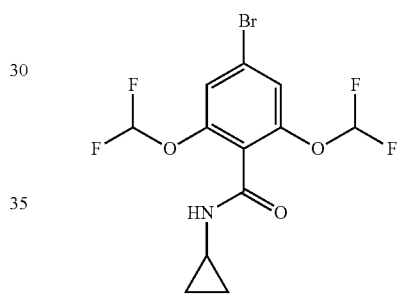

Int 16 is prepared from 4-bromo-N-cyclopropyl-2-(difluoromethoxy)-6-hydroxy-benzamide according to general method G.

2.11. Int 17

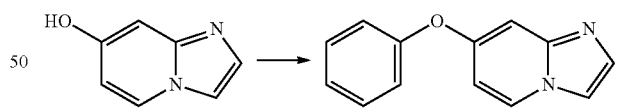

To a solution of imidazo[1,2-a]pyridin-7-ol (CAS #896139-85-8; 128 mg, 0.955 mmol) in dry NMP (2 mL) is added $Cs_2CO_3$ (311 mg, 0.955 mmol). The reaction mixture is degassed with $N_2$ for 5 min and stirred at RT for 45 min. Copper(I) chloride (CAS #7758-89-6; 10 mg, 0.10 mmol) and bromobenzene (CAS #108-86-1; 100 mg, 0.64 mmol) are added and the mixture is stirred at 160° C. for 3 h under microwave irradiation. Copper (I) chloride (10 mg, 0.10 mmol) is added and the reaction mixture is heated at 160° C. for 1 h under microwave irradiation. Imidazo[1,2-a]pyridin-7-ol (86 mg, 0.64 mmol) is added and the reaction mixture is heated at 160° C. for 1 h under microwave irradiation. The reaction medium is quenched with a water and sat. aq. $NaHCO_3$ solution mixture and extracted with EtOAc. The organic layers are combined, dried over Na₂SO₄, filtered and concentrated. Traces of NMP are removed under nitrogen flush to afford Int 17 that is used as such.

2.12. Int 19

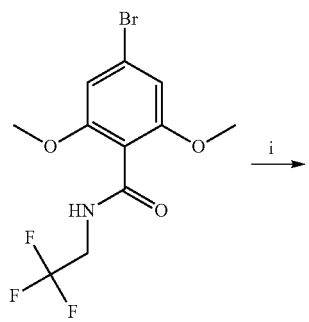

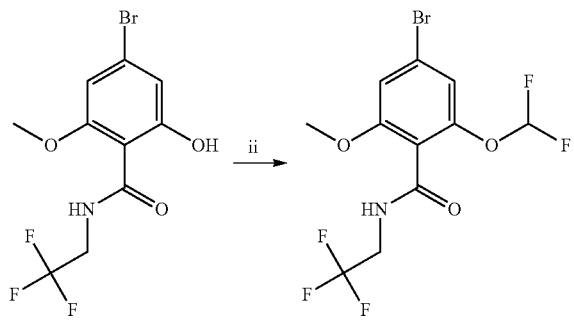

2.12.1. Step i: 4-bromo-2-hydroxy-6-methoxy-N-(2,2,2-trifluoroethyl)benzamide

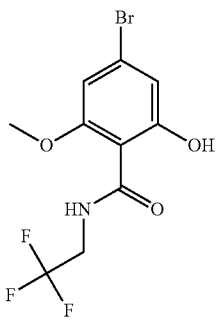 [SMILES: COc1cc(Br)cc(O)c1C(=O)NCC(F)(F)F]

4-bromo-2-hydroxy-6-methoxy-N-(2,2,2-trifluoroethyl)benzamide is prepared from Int 47 according to general method F using BCl₃.

LCMS: MW (calcd): 328.1; m/z MW (obsd): 328.1/330.1 (M+H)

2.12.2 Step ii: Int 19

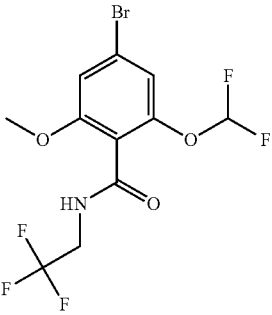 [SMILES: COc1cc(Br)cc(OC(F)F)c1C(=O)NCC(F)(F)F]

Int 19 is prepared from 4-bromo-2-hydroxy-6-methoxy-N-(2,2,2-trifluoroethyl)benzamide according to general method G.

2.13. Int 20

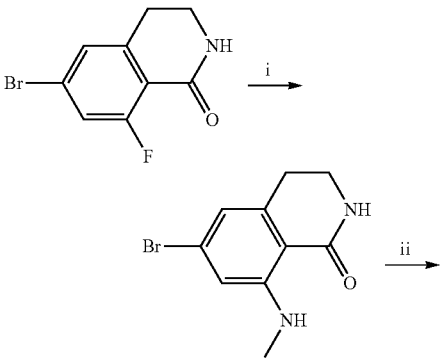

2.13.1. Step i: 6-bromo-8-(methylamino)-3,4-dihydro-2H-isoquinolin-1-one

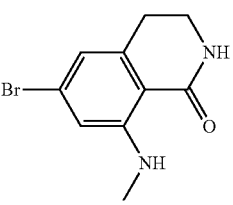

To a solution of 6-bromo-8-fluoro-3,4-dihydro-2H-isoquinolin-1-one (CAS #1242157-15-8; 200 mg, 0.82 mmol) in DMAC (4.0 mL) are added methylamine hydrochloride (CAS #593-51-1; 166 mg, 2.46 mmol) and DIPEA (856 μL, 4.92 mmol). The vial is sealed and the mixture is stirred at 100° C. for 2 days. The reaction medium is quenched with water and precipitation occurred. The mixture is stirred for 10 min and then filtered. The solid is rinsed with water and is dried under reduced pressure overnight to afford the expected 6-bromo-8-(methylamino)-3,4-dihydro-2H-isoquinolin-1-one.

LCMS: MW (calcd): 255.1; m/z MW (obsd): 255.1/257.1 (M+H)

2.13.2. Step ii: Int 20

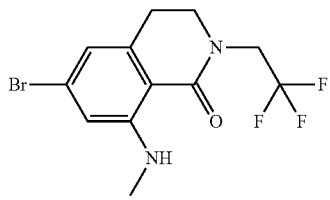 [SMILES: CNc1cc(Br)cc2c1C(=O)N(CC(F)(F)F)CC2]

Int 20 is prepared from 6-bromo-8-(methylamino)-3,4-dihydro-2H-isoquinolin-1-one following general method E with 2,2,2-trifluoroethyl trifluoromethanesulfonate.

2.14. Int 25

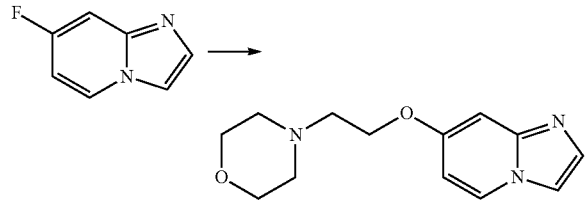

To a solution of 2-morpholinoethanol (CAS #622-40-2; 1.6 mL, 13.2 mmol, 6 eq.) in DMF (22 mL) is added NaH (60% dispersion in mineral oil, 13.2 mmol, 6 eq.) portionwise. After stirring for 30 min at RT, 7-fluoroimidazo[1,2-a]pyridine (CAS #1260903-17-0, 2.2 mmol, 1.0 eq.) is added and the mixture is stirred at RT for 20 h. The reaction medium is quenched with a sat. aq. NaHCO₃ solution, diluted with EtOAc and stirred at RT for 15 min. The solid is filtered and the filtrate is concentrated under reduced pressure. To the obtained residue is added pentane that is then removed with a Pasteur pipette. This operation is done 3 times. The remaining crude material is purified by flash chromatography on Biotage® SNAP KP—NH cartridge (eluting with a gradient MeOH 0 to 10% in DCM) to afford Int 25.

2.15. Int 26

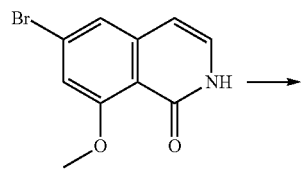

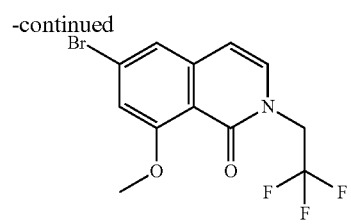

To a solution of Int 51 (100 m g, 0.39 mmol, 1 eq.) in DMF (0.2 mL) are added 1,1,1-trifluoro-2-iodo-ethane (CAS #353-83-3; 58 µL, 0.59 mmol, 1.5 eq.) and Cs₂CO₃ (192 mg, 0.59 mmol, 1.5 eq.) and the mixture is stirred at 50° C. for 20 h. Then 1,1,1-trifluoro-2-iodo-ethane (19 µL, 0.0.20 mmol, 0.5 eq.) is added and the reaction is stirred for another 2 h at 50° C. The reaction mixture is then diluted with EtOAc and washed with water and brine. The organic phase is dried over MgSO₄, filtered and concentrated to dryness. The crude residue is purified twice by flash chromatography on silica gel (eluting 0 to 5% methanol in DCM, then 0 to 40% EtOAc in heptane) to afford Int 26.

2.16. Int 28

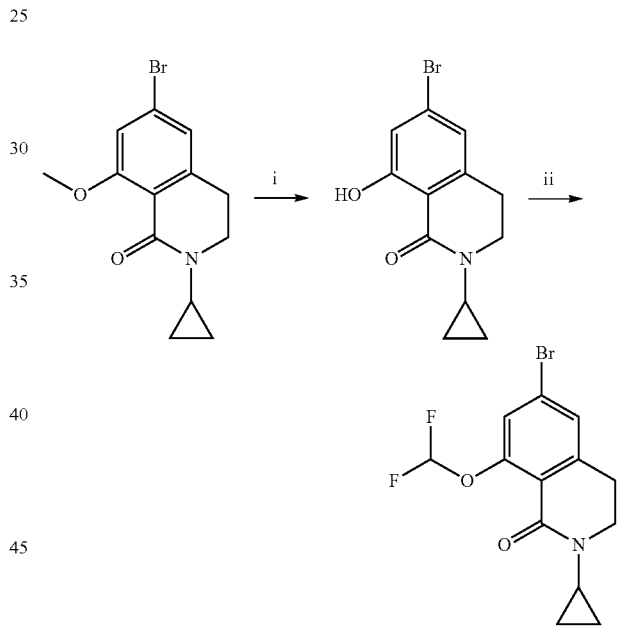

2.16.1. Step i: 6-bromo-2-cyclopropyl-8-hydroxy-3,4-dihydroisoquinolin-1-one

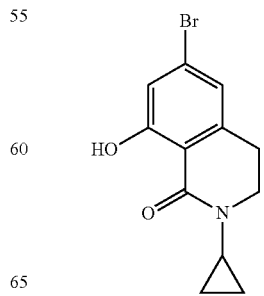

6-Bromo-2-cyclopropyl-8-hydroxy-3,4-dihydroisoquinolin-1-one is prepared from Int 49 following the general method F using BBr₃.

2.16.2. Step ii: Int 28

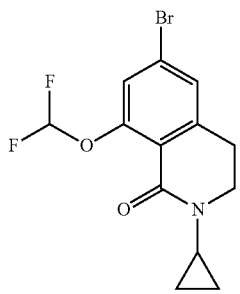 [SMILES: O=C1c2c(cc(Br)cc2OC(F)F)CCN1C1CC1]

To a solution of 6-bromo-2-cyclopropyl-8-hydroxy-3,4-dihydroisoquinolin-1-one (99 mg, 0.35 mmol, 1 eq.) in dry ACN (5 mL) at 0° C. are added a cold solution of KOH (197 mg, 3.5 mmol, 10 eq.) in water (5 mL) and then diethyl (bromodifluoromethyl)phosphonate (CAS #65094-22-6; 131 mg, 0.79 mmol, 1.4 eq.) portionwise. The mixture allowed to warm up slowly to RT and stirred at RT for 20 h. The reaction mixture is diluted with water and extracted with DCM. The organic layer is dried over Na₂SO₄, filtered and concentrated in vacuo. The residue is purified by flash chromatography on silica gel to afford Int 28.

2.17. Int 33

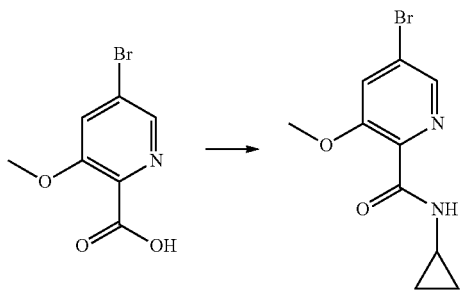

To a solution of 5-bromo-3-methoxy-pyridine-2-carboxylic acid (CAS #1142191-66-9, 60 mg, 0.26 mmol, 1.0 eq.) in anhydrous DMF (1 mL) are added DIPEA (68 μL, 0.39 mmol, 1.5 eq.) and HATU (108 mg, 0.28 mmol, 1.1 eq.). The reaction medium is stirred at RT for 1 h and cyclopropylamine (CAS #765-30-0, 22 μL, 0.31 mmol, 1.2 eq.) is added. The reaction medium is stirred at RT for 20 h before being concentrated. The residue is diluted with DCM, washed with a 1N aq. solution of NaOH and passed through a phase separator. The filtrate is concentrated and the crude is purified by flash chromatography on silica gel (eluting with heptane/EtOAc 8/2 to 1/9) to afford Int 33.

2.18. Int 34

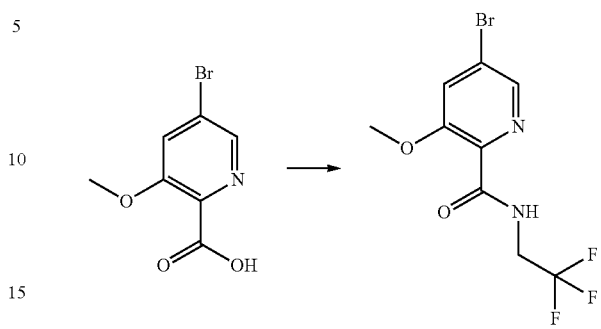

To a solution of 5-bromo-3-methoxy-pyridine-2-carboxylic acid (CAS #1142191-66-9, 500 mg, 2.15 mmol, 1.0 eq.) in anhydrous DMF (8.3 mL) are added DIPEA (563 μL, 3.23 mmol, 1.5 eq.) and HATU (901 mg, 2.37 mmol, 1.1 eq.). The mixture is stirred at RT for 30 min and 2,2,2-trifluoroethanamine hydrochloride (CAS #373-88-6, 350 mg, 2.59 mmol, 1.2 eq.) is added. The reaction mixture is stirred at RT for 20 h and is then evaporated to dryness. The residue is diluted with DCM and a precipitate forms. The solid is filtered, the filtrate is concentrated and the residue is purified by flash chromatography on silica gel (eluting with heptane/EtOAc 10/0 to 1/1) to afford Int 34.

2.19. Int 36

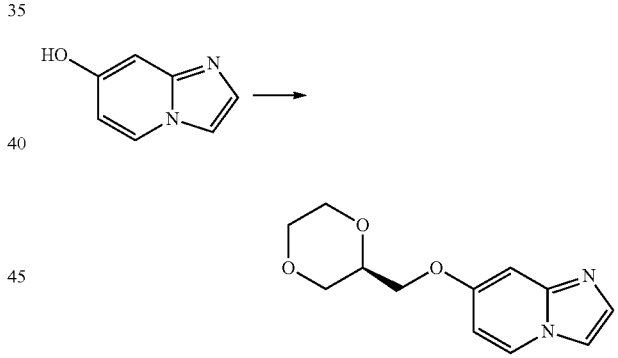

To a solution of [(2S)-1,4-dioxan-2-yl]methanol (CAS #406913-93-7; 635 mg, 5.38 mmol) in dry DMF (13.4 mL) is added NaH (60% dispersion in mineral oil, 215 mg, 5.38 mmol) and the mixture is stirred at RT for 10 min. 7-Fluoroimidazo[1,2-a]pyridine (CAS #1260903-17-0; 183 mg, 1.34 mmol) is added and the reaction mixture is stirred at RT overnight. A mixture of [(2S)-1,4-dioxan-2-yl]methanol (159 mg, 1.34 mmol) and NaH (60% dispersion in mineral oil, 54 mg, 1.34 mmol) in dry DMF (1 mL) is added and the reaction mixture is stirred at RT for 3 h. The reaction medium is quenched with a mixture of water and sat. aq. NaHCO₃ solution and diluted with EtOAc. The phases are separated and the aqueous layer is extracted with EtOAc. The combined organic layers are washed with brine, dried over Na₂SO₄, filtered and concentrated. The crude material is purified by chromatography on silica gel (eluting with a gradient of 0 to 10% MeOH in DCM) to afford Int 36.

2.20. Int 38

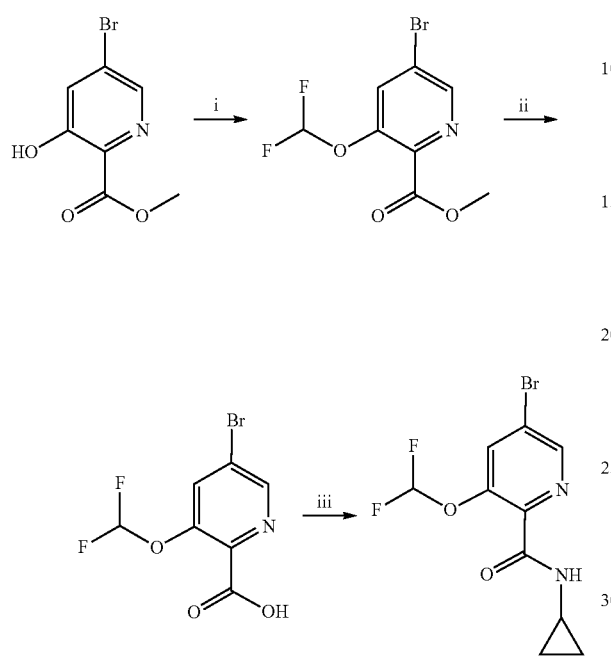

2.20.1. Step i: methyl 5-bromo-3-(difluoromethoxy)pyridine-2-carboxylate

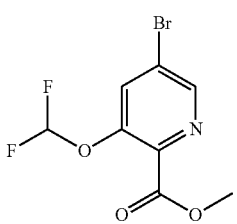

Methyl 5-bromo-3-hydroxy-pyridine-2-carboxylate (CAS #1242320-57-5; 50 mg, 0.215 mmol), sodium chlorodifluoroacetate (CAS #1895-39-2; 35 mg, 0.26 mmol) and $K_2CO_3$ (60 mg, 0.63 mmol) are mixed in ACN (1.5 mL) and the reaction mixture is stirred at reflux for 2 h. The reaction medium is quenched with a sat. aq. $NaHCO_3$ solution and ice. The mixture is extracted with DCM and then EtOAc. The combined organic layers are dried over $Na_2SO_4$, filtered and concentrated. The crude material is purified by chromatography on silica gel (eluting with EtOAc in heptane) to afford the desired methyl 5-bromo-3-(difluoromethoxy)pyridine-2-carboxylate.

LCMS: MW (calcd): 282.0; m/z MW (obsd): 282.0/284.0 (M+H)

2.20.2. Step ii: 5-bromo-3-(difluoromethoxy)pyridine-2-carboxylic acid

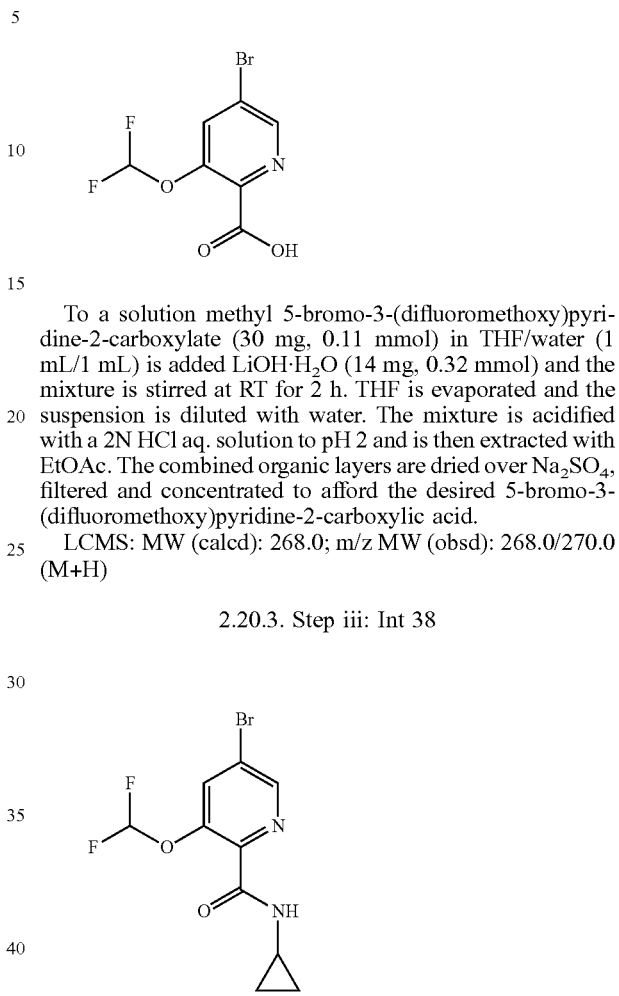

To a solution methyl 5-bromo-3-(difluoromethoxy)pyridine-2-carboxylate (30 mg, 0.11 mmol) in THF/water (1 mL/1 mL) is added LiOH·$H_2O$ (14 mg, 0.32 mmol) and the mixture is stirred at RT for 2 h. THF is evaporated and the suspension is diluted with water. The mixture is acidified with a 2N HCl aq. solution to pH 2 and is then extracted with EtOAc. The combined organic layers are dried over $Na_2SO_4$, filtered and concentrated to afford the desired 5-bromo-3-(difluoromethoxy)pyridine-2-carboxylic acid.

LCMS: MW (calcd): 268.0; m/z MW (obsd): 268.0/270.0 (M+H)

2.20.3. Step iii: Int 38

To a solution of 5-bromo-3-(difluoromethoxy)pyridine-2-carboxylic acid (24 mg, 0.09 mmol) in DMF (0.5 mL) are added HATU (38 mg, 0.10 mmol, 1.1 eq.) and DIPEA (22 µL, 0.13 mmol, 1.5 eq.) and the mixture is stirred at RT for 15 min. Then, cyclopropylamine (CAS #765-30-0; 6 mg, 0.11 mmol, 1.2 eq.) is added and the mixture is stirred for 17 h at RT. The reaction is hydrolysed with a sat. aq. $NaHCO_3$ solution and extracted with EtOAc. The combined organic layers are dried over $Na_2SO_4$, filtered and concentrated. The residue is purified by flash chromatography on silica gel (eluting with heptane/EtOAc 9/1 to 7/3) to give Int 38.

2.21. Int 39 (Alternative Synthesis)

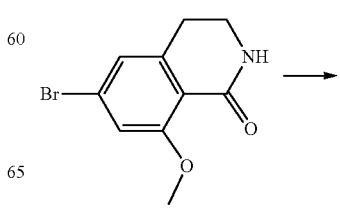

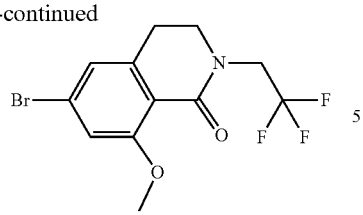

Under stirring, a solution of Int 40 (600 g, 2.34 mol, 1.0 eq.) in THF (2.4 L) is cooled down to 15° C. LiHMDS (1.3M in THF, 2001 mL, 2.60 mol, 1.11 eq.) is added dropwise in 1 h such as to maintain the reaction temperature below 25° C. The reaction mixture is stirred at 20° C. for 2 h, then 2,2,2-trifluoroethyl trifluoromethanesulfonate (CAS #6226-25-1; 429 mL, 2.98 mol, 1.27 eq.) is added dropwise in 10 min, maintaining the reaction temperature below 30° C. The reaction mixture is heated at 65-70° C. for 2 h. The reaction mixture is cooled down to 10° C. and additional LiHMDS (1.0M in THF, 200 mL, 0.200 mol, 0.085 eq.) is added dropwise in 15 min. The reaction mixture is stirred at 20° C. for 30 min. Then 2,2,2-trifluoroethyl trifluoromethanesulfonate (CAS #6226-25-1; 30 mL, 0.208 mmol, 0.09 eq.) is added in one portion and the reaction mixture is heated from 20° C. to 65° C. in 1 h. The reaction mixture is then cooled down to 10° C. and a 1N HCl aq. solution is added dropwise until pH 1 is reached (~4 L). The suspension is stirred for 1 h at 20° C. and THF is completely evaporated under reduced pressure. The resulting suspension is filtered and the solid is washed twice with water (1.8 L). The solid is suspended in MTBE (2 L) and stirred at RT for 1 h. The suspension is filtered and the solid is washed with heptane (2 L) and dried to afford Int 39.

2.22. Int 42

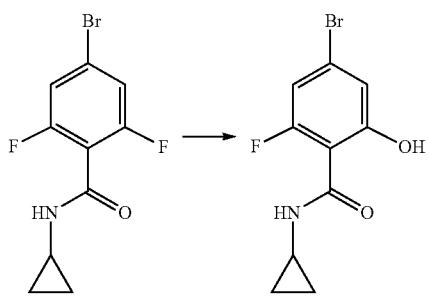 [SMILES: O=C(NC1CC1)c1c(F)cc(Br)cc1F ; O=C(NC1CC1)c1c(O)cc(Br)cc1F]

In a 15 L jacketed reactor, 4N aq. NaOH (2155 mL, 8.62 mol, 2.5 eq.) is added in one portion to a solution of Int 88 (952 g, 3.45 mol, 1 eq.) in DMSO (2 V, 1.9 L). The suspension is heated to 90° C. (jacket temperature from 50° C. to 90° C. over 20 min then hold at 90° C. for 2 h).

The reaction mixture is then cooled to 25° C. (jacket temperature from 90° C. to 5° C. over 45 min) and HCl 2 N (2.7 L, 5.4 mol, 0.63 eq./NaOH) is added until pH 3 is reached. The temperature is kept below 30° C. during the addition of HCl (addition over 20 min and jacket temperature set at 5° C.). The suspension is stirred at 200 rpm for 2 h while the temperature decreases to 20° C. (jacket temperature set at 5° C.). The suspension is then filtered. The wet cake is washed with water (twice with 2 L, 2*2 V) and the solid is dried on a fritted funnel overnight.

The solid is dried in a vacuum oven at 50° C. for 3 days to afford Int 42.

2.23. Int 44

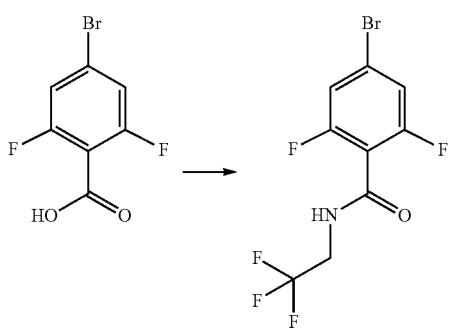 [SMILES: O=C(O)c1c(F)cc(Br)cc1F ; O=C(NCC(F)(F)F)c1c(F)cc(Br)cc1F]

4-bromo-2,6-difluorobenzoic acid (90.5 g, 381.86 mmol, 1.0 eq.) is added to SOCl$_2$ (181 mL, 2 volumes, 6.5 eq.). The reaction mixture is stirred at reflux. After 6 h of reflux, the heating is stopped and the reaction mixture is cooled down to RT and then concentrated in vacuo. The residue is diluted with toluene (181 mL, 2 volumes) and concentrated to eliminate residual thionyl chloride.

The liquid residue is diluted with DCM (453 mL, 5 volumes). Trifluoro ethylamine hydrochloride (54.34 g, 400.95 mmol, 1.05 eq.) is added to the reaction mixture under N$_2$ atmosphere and the latter is cooled to 5° C. Et$_3$N (117.09 mL, 840.08 mmol, 2.2 eq.) is then added dropwise keeping the temperature of the reaction mixture under 27° C. The reaction mixture is then stirred under N$_2$ at RT for 14 h. The suspension is diluted with DCM (1000 mL, 10 volumes). The organic phase is washed with water (500 mL, 5 volumes) and sat. NaHCO$_3$ (500 mL, 5 volumes). The organic phase is dried on Na$_2$SO$_4$ (100 g), filtered, concentrated and triturated with heptane (500 mL, 6 volumes). The suspension is filtered and washed with heptane (500 mL, 6 volumes) and the solid is dried under reduced pressure to give Int 44.

2.24. Int 47

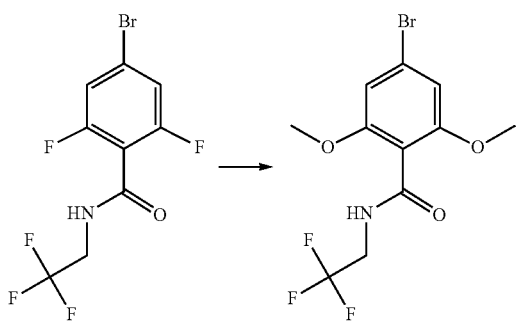

To a solution of Int 44 (110.20 g, 346.50 mmol, 1.0 eq.) in NMP (551 mL, 5 volumes) under N$_2$ is added sodium methoxide (56.15 g, 1.04 mol., 3 eq.). The reaction mixture is heated to 90° C. After 1.5 h at 90° C., the reaction mixture is cooled to RT and water (1100 mL, 10 volumes) is added and precipitation occurs. The suspension is filtered and the cake is washed with water (3*1100 mL). The solid is dried at 55° C. under vacuum (3 days) to afford the expected Int 47.

2.25. Int 49

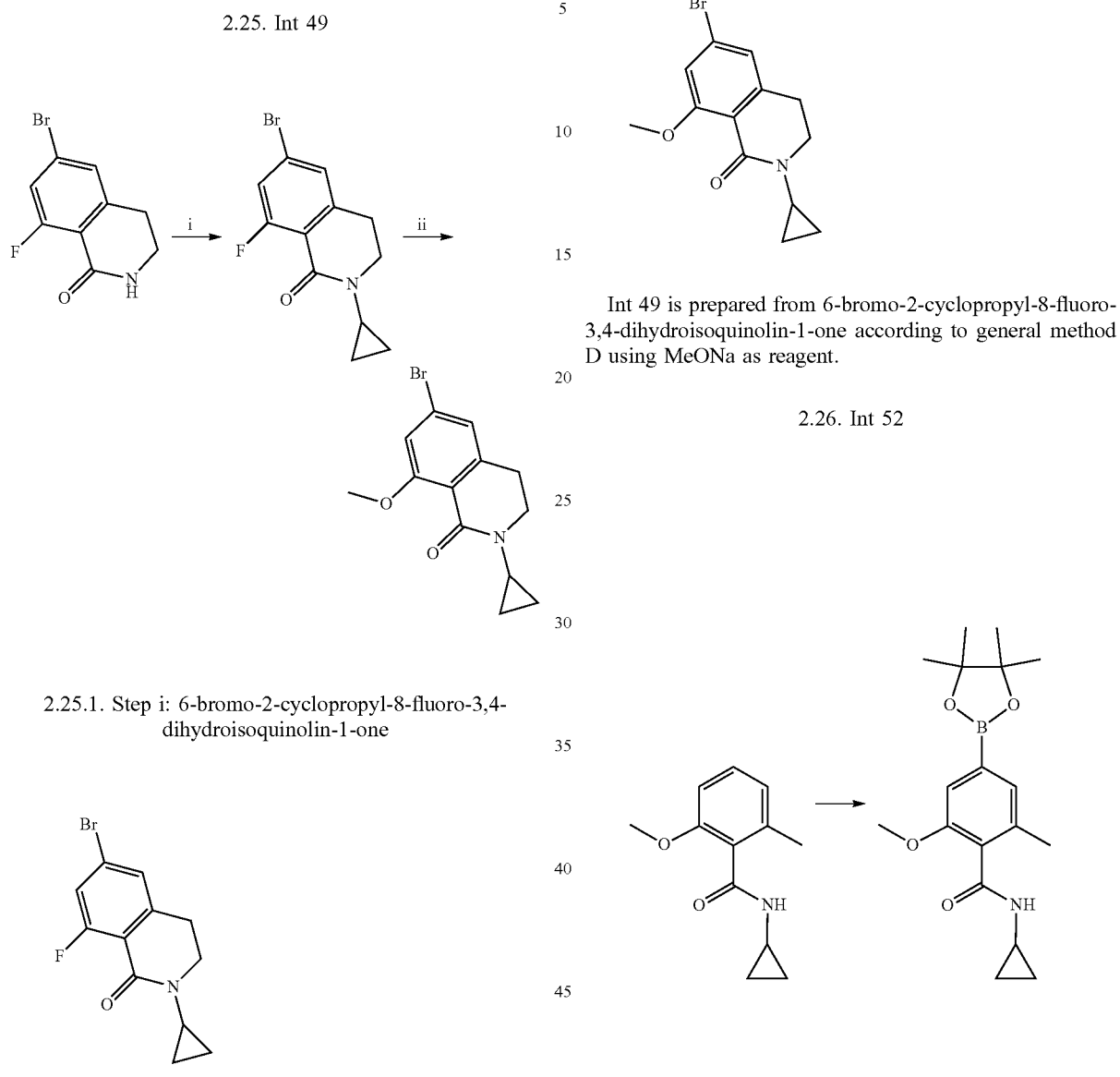

2.25.1. Step i: 6-bromo-2-cyclopropyl-8-fluoro-3,4-dihydroisoquinolin-1-one To a solution of 6-bromo-8-fluoro-3,4-dihydro-2H-isoquinolin-1-one (CAS #1242157-15-8; 500 mg, 2.05 mmol) in dry THF (20.5 mL) are added Et$_3$N (1.4 mL, 10.2 mmol), pyridine (1.3 mL, 16.4 mmol), Cu(OAc)$_2$ (818 mg, 4.10 mmol) and cyclopropylboronic acid (CAS #411235-57-9; 528 mg, 6.15 mmol). The reaction mixture is stirred at 70° C. overnight. Cyclopropylboronic acid (176 mg, 2.05 mmol) is added and the reaction mixture is stirred at 70° C. for 2 h. The reaction medium is quenched with a sat. aq. NaHCO$_3$ solution and extracted with EtOAc. The combined organic layers are dried over MgSO$_4$, filtered and concentrated. The crude material is purified by chromatography on silica gel (eluting with a gradient of 0 to 60% EtOAc in heptane) twice to afford the expected 6-bromo-2-cyclopropyl-8-fluoro-3,4-dihydroisoquinolin-1-one.

LCMS: MW (calcd): 284.1; m/z MW (obsd): 284.2/286.2 (M+H)

2.252. Step ii: Int 49

Int 49 is prepared from 6-bromo-2-cyclopropyl-8-fluoro-3,4-dihydroisoquinolin-1-one according to general method D using MeONa as reagent.

2.26. Int 52

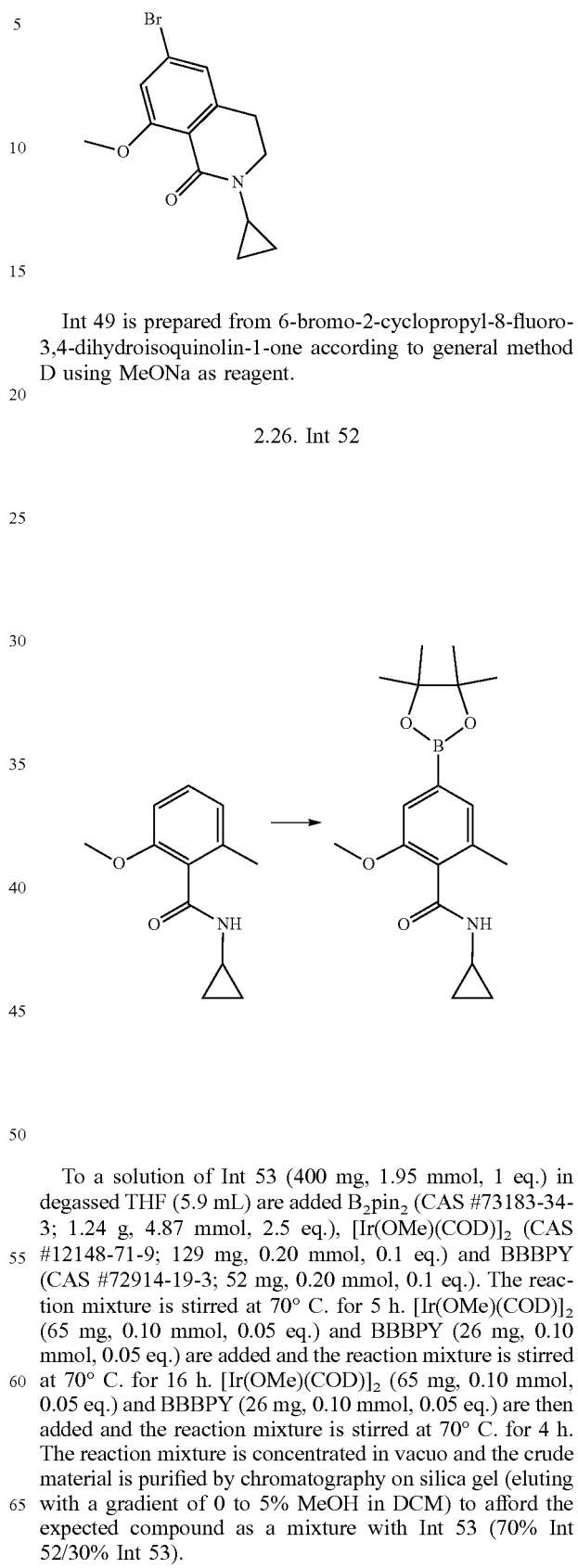

To a solution of Int 53 (400 mg, 1.95 mmol, 1 eq.) in degassed THF (5.9 mL) are added B$_2$pin$_2$ (CAS #73183-34-3; 1.24 g, 4.87 mmol, 2.5 eq.), [Ir(OMe)(COD)]$_2$ (CAS #12148-71-9; 129 mg, 0.20 mmol, 0.1 eq.) and BBBPY (CAS #72914-19-3; 52 mg, 0.20 mmol, 0.1 eq.). The reaction mixture is stirred at 70° C. for 5 h. [Ir(OMe)(COD)]$_2$ (65 mg, 0.10 mmol, 0.05 eq.) and BBBPY (26 mg, 0.10 mmol, 0.05 eq.) are added and the reaction mixture is stirred at 70° C. for 16 h. [Ir(OMe)(COD)]$_2$ (65 mg, 0.10 mmol, 0.05 eq.) and BBBPY (26 mg, 0.10 mmol, 0.05 eq.) are then added and the reaction mixture is stirred at 70° C. for 4 h. The reaction mixture is concentrated in vacuo and the crude material is purified by chromatography on silica gel (eluting with a gradient of 0 to 5% MeOH in DCM) to afford the expected compound as a mixture with Int 53 (70% Int 52/30% Int 53).

2.27. Int 53

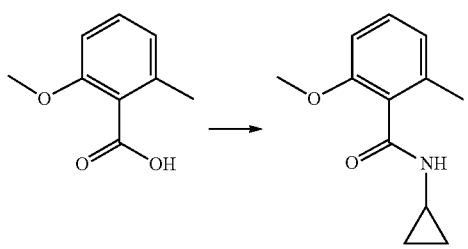

To a solution of 2-methoxy-6-methyl-benzoic acid (CAS #6161-65-5; 1.0 g, 6.02 mmol) and HATU (CAS #148893-10-1; 2.5 g, 6.62 mmol) in dry DMF (37.6 mL) is added DIPEA (CAS #7087-68-5; 3.2 mL, 12.04 mmol) and the mixture is stirred at RT for 10 min. Cyclopropanamine (CAS #765-30-0; 503 µL, 7.22 mmol) is added and the reaction mixture is stirred at RT for 4 h. The reaction mixture is concentrated to dryness and the crude material is purified by flash chromatography on Biotage© SNAP KP—NH cartridge (eluting with a gradient of 0 to 10% MeOH in DCM) to afford Int 53.

2.28. Int 54

2.28.1. Step i: N-cyclopropyl-2-(difluoromethoxy)-6-methyl-benzamide

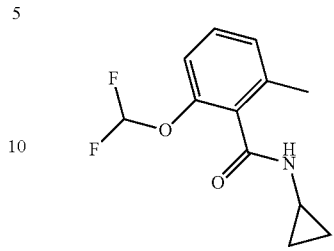

Int 56 (284 mg, 1.49 mmol) is suspended in a mixture of ACN (1.4 mL)/H₂O (1.4 mL). Potassium hydroxyde (833 mg, 14.85 mmol) is added portionwise at 0° C. Then diethyl (bromodifluoromethyl)phosphonate (CAS #65094-22-6; 528 µL, 2.97 mmol) is added dropwise while keeping the temperature below 20° C. The reaction mixture is stirred at 0° C. for 30 min and then it is allowed to warm up to RT. The aqueous layer is extracted with EtOAc. The combined organic layers are washed with brine, dried over MgSO₄, filtered and concentrated to afford the desired compound N-cyclopropyl-2-(difluoromethoxy)-6-methyl-benzamide that is used as such.

LCMS: MW (calcd): 241.2; m/z MW (obsd): 242.3 (M+H)

2.28.2. Step ii: Int 54

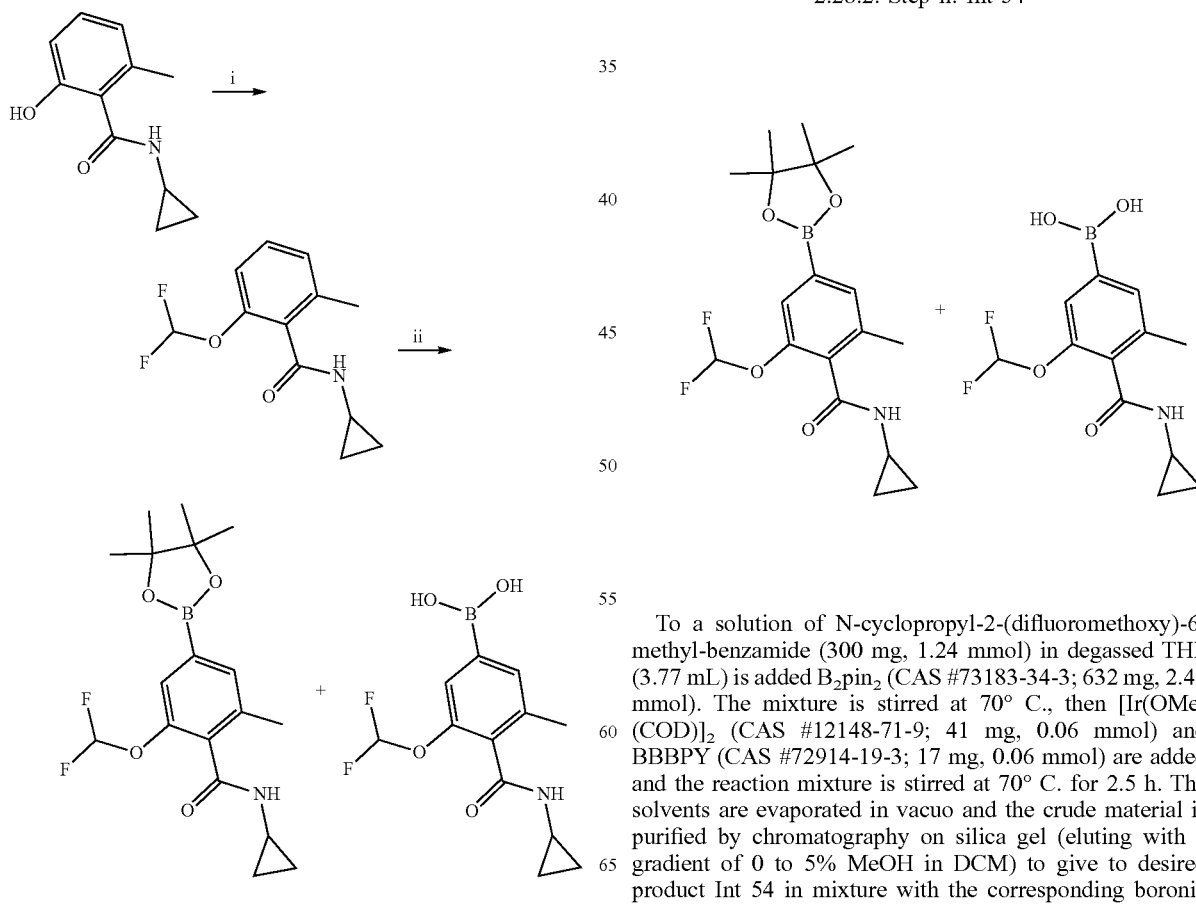

To a solution of N-cyclopropyl-2-(difluoromethoxy)-6-methyl-benzamide (300 mg, 1.24 mmol) in degassed THF (3.77 mL) is added B₂pin₂ (CAS #73183-34-3; 632 mg, 2.49 mmol). The mixture is stirred at 70° C., then [Ir(OMe)(COD)]₂ (CAS #12148-71-9; 41 mg, 0.06 mmol) and BBBPY (CAS #72914-19-3; 17 mg, 0.06 mmol) are added and the reaction mixture is stirred at 70° C. for 2.5 h. The solvents are evaporated in vacuo and the crude material is purified by chromatography on silica gel (eluting with a gradient of 0 to 5% MeOH in DCM) to give to desired product Int 54 in mixture with the corresponding boronic acid.

2.29. Int 57

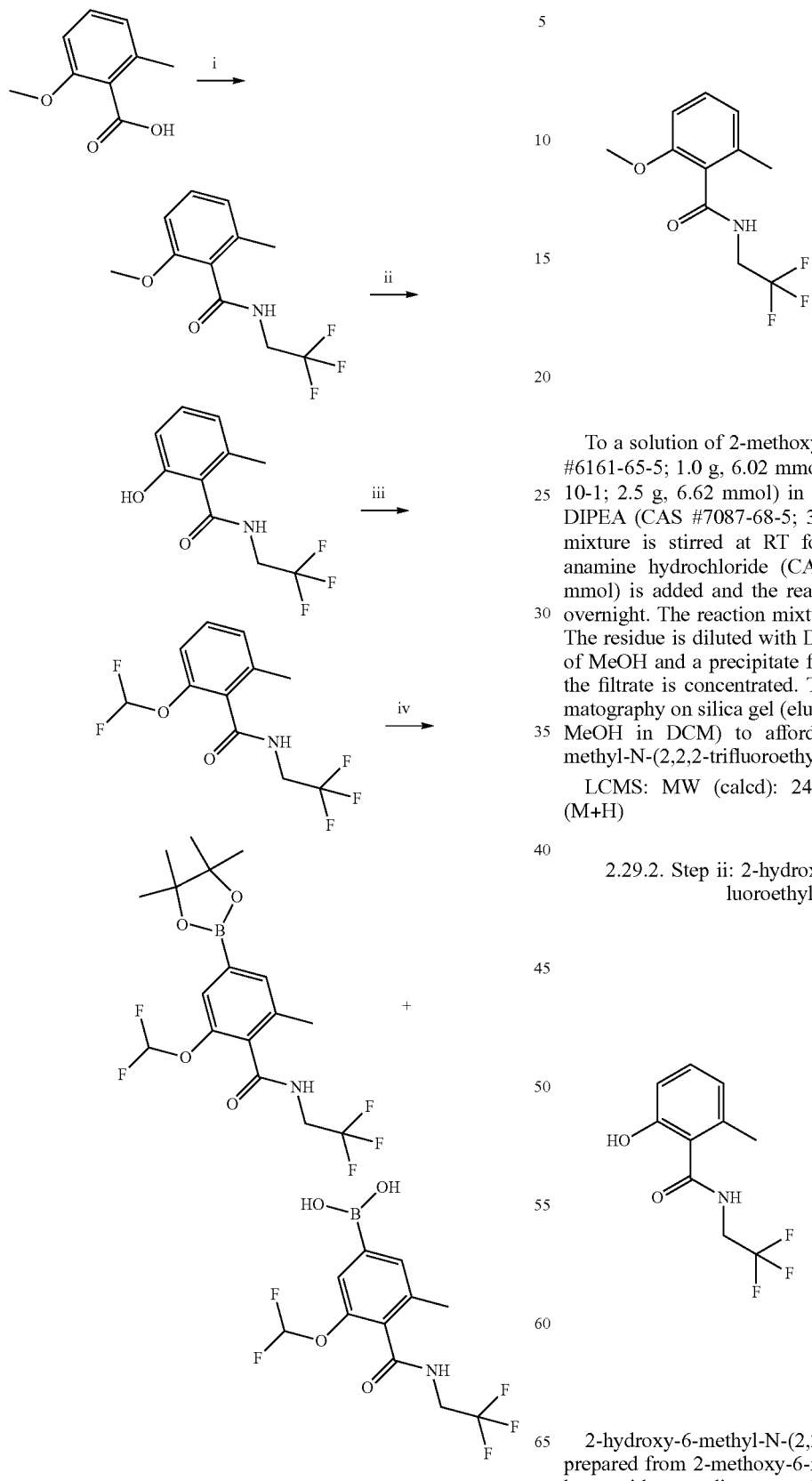

2.29.1. Step i: 2-methoxy-6-methyl-N-(2,2,2-trifluoroethyl)benzamide

To a solution of 2-methoxy-6-methyl-benzoic acid (CAS #6161-65-5; 1.0 g, 6.02 mmol) and HATU (CAS #148893-10-1; 2.5 g, 6.62 mmol) in dry DMF (37.6 mL) is added DIPEA (CAS #7087-68-5; 3.2 mL, 12.04 mmol) and the mixture is stirred at RT for 10 min. 2,2,2-trifluoroethanamine hydrochloride (CAS #373-88-6; 979 mg, 7.22 mmol) is added and the reaction mixture is stirred at RT overnight. The reaction mixture is concentrated to dryness. The residue is diluted with DCM/EtOAc and several drops of MeOH and a precipitate forms. The solid is filtered and the filtrate is concentrated. The crude is purified by chromatography on silica gel (eluting with a gradient of 0 to 5% MeOH in DCM) to afford the expected 2-methoxy-6-methyl-N-(2,2,2-trifluoroethyl)benzamide.

LCMS: MW (calcd): 247.2; m/z MW (obsd): 248.2 (M+H)

2.29.2. Step ii: 2-hydroxy-6-methyl-N-(2,2,2-trifluoroethyl)benzamide 2-hydroxy-6-methyl-N-(2,2,2-trifluoroethyl)benzamide is prepared from 2-methoxy-6-methyl-N-(2,2,2-trifluoroethyl)benzamide according general method G using BCl$_3$.

2.29.3. Step iii: 2-(difluoromethoxy)-6-methyl-N-(2,2,2-trifluoroethyl)benzamide

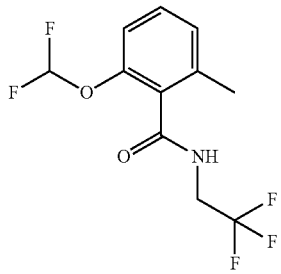 [SMILES: Cc1cccc(OC(F)F)c1C(=O)NCC(F)(F)F]

2-hydroxy-6-methyl-N-(2,2,2-trifluoroethyl)benzamide (490 mg, 2.10 mmol) is suspended in a ACN (2.5 mL)/H₂O (2.5 mL) mixture. KOH (1.18 g, 21.01 mmol) is added portionwise at 0° C. Then diethyl (bromodifluoromethyl)phosphonate (CAS #65094-22-6; 747 μL, 4.20 mmol) is added dropwise keeping the temperature below 20° C. The reaction mixture is stirred at 0° C. for 30 min before being warmed up to RT. The aqueous layer is extracted with EtOAc. The combined organic layers are washed with brine, passed through a phase separator and concentrated. The crude material is purified by chromatography on silica gel (eluting with a gradient of 0 to 20% EtOAc in heptane) to afford the desired 2-(difluoromethoxy)-6-methyl-N-(2,2,2-trifluoroethyl)benzamide.

LCMS: MW (calcd): 283.2; m/z MW (obsd): 284.2 (M+H)

2.29.4. Step iv: Int 57

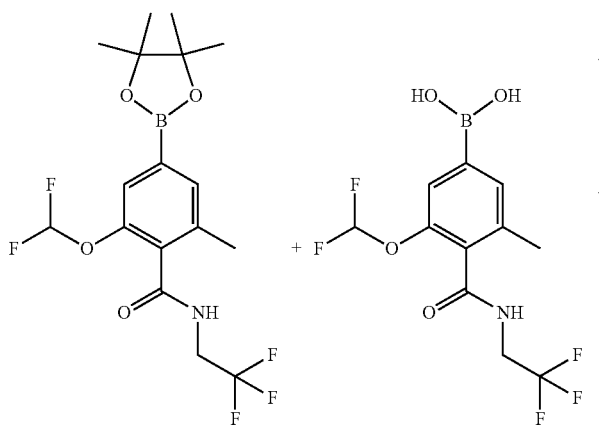

To a solution of 2-(difluoromethoxy)-6-methyl-N-(2,2,2-trifluoroethyl)benzamide (314 mg, 1.11 mmol) in degassed THF (3.4 mL) is added B₂pin₂ (CAS #73183-34-3; 563 mg, 2.22 mmol). The mixture is stirred at 70° C., then [Ir(OMe)(COD)]₂ (CAS #12148-71-9; 37 mg, 0.055 mmol) and BBBPY (CAS #72914-19-3; 15 mg, 0.055 mmol) are added and the reaction mixture is stirred at 70° C. for 2.5 h. [Ir(OMe)(COD)]₂ (37 mg, 0.055 mmol) and BBBPY (15 mg, 0.055 mmol) are added and the reaction mixture is stirred at 70° C. for 1.5 h more. The reaction mixture is concentrated and the crude material is purified by chromatography on silica gel (eluting with a gradient of 0 to 3% MeOH in DCM) to afford the desired product as a mixture with the 2-(difluoromethoxy)-6-methyl-N-(2,2,2-trifluoroethyl)benzamide starting material.

2.30. Int 65

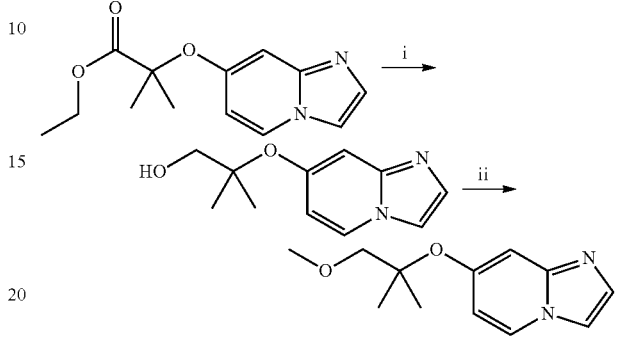

2.30.1. Step i: 2-imidazo[1,2-a]pyridin-7-yloxy-2-methyl-propan-1-ol

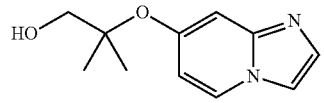

To a solution of Int 67 (65 mg, 0.26 mmol) in dry THF (2 mL) at 0° C. is added dropwise LiAlH₄ (1M in THF, 1.04 mL, 1.05 mmol). At the end of the addition the mixture is allowed to slowly warm up to RT for 1 h. The reaction mixture is concentrated and the crude material is purified by chromatography on silica gel (eluting with a gradient of 0 to 15% MeOH in EtOAc) to afford the expected 2-imidazo[1,2-a]pyridin-7-yloxy-2-methyl-propan-1-ol.

LCMS: MW (calcd): 206.2; m/z MW (obsd): 207.1 (M+H)

2.30.2. Step ii: Int 65

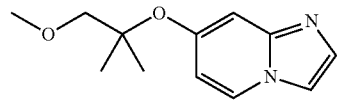 [SMILES: COCC(C)(C)Oc1ccn2ccnc2c1]

To a solution of 2-imidazo[1,2-a]pyridin-7-yloxy-2-methyl-propan-1-ol (34 mg, 0.16 mmol) in dry THF (2 mL) at 0° C. is added NaH (60% in mineral oil, 7 mg, 0.16 mmol) and the mixture is stirred at 0° C. for 10 min. Iodomethane (CAS #74-88-4; 10 μL, 0.16 mmol) is added at 0° C. and the mixture is stirred at RT for 20 h. The reaction medium is diluted with water and extracted with EtOAc. The combined organic layers are dried over Na₂SO₄, filtered and concentrated. The crude material is purified by chromatography on silica gel (eluting with a gradient of 0 to 15% MeOH in EtOAc) to afford Int 65.

2.31. Int 67

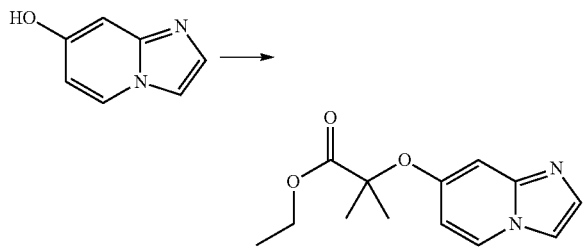

To a solution of imidazo[1,2-a]pyridin-7-ol (CAS #896139-85-8; 100 mg, 0.745 mmol) in dry DMF (4 mL) are added ethyl 2-bromo-2-methyl-propanoate (CAS #600-00-0; 444 µL, 2.98 mmol) and $K_2CO_3$ (412 mg, 2.98 mmol). The mixture is stirred at 60° C. for 6 h. The reaction medium is diluted with water and extracted with DCM. Organic layers are combined, dried over $Na_2SO_4$, filtered and concentrated. The crude material is purified by chromatography on silica gel (eluting with a gradient of 0 to 10% MeOH in DCM) to afford Int 67.

2.32. Int 68

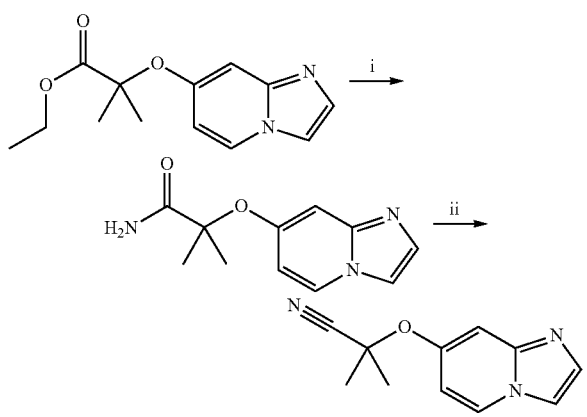

2.32.1. Step i: 2-imidazo[1,2-a]pyridin-7-yloxy-2-methyl-propanamide

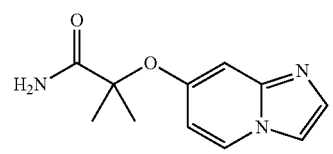 [SMILES: CC(C)(Oc1ccn2ccnc2c1)C(N)=O]

To ammonia 25% in water (3 mL) at 0° C. is added Int 67 (146 mg, 1.49 mmol), and the reaction mixture is warmed up to RT and stirred overnight. The reaction medium is diluted with water and extracted with EtOAc. The combined organic layers are dried over $Na_2SO_4$, filtered and concentrated to afford the desired 2-imidazo[1,2-a]pyridin-7-yloxy-2-methyl-propanamide.

LCMS: MW (calcd): 219.2; m/z MW (obsd): 220.1 (M+H)

2.32.2. Step ii: Int 68

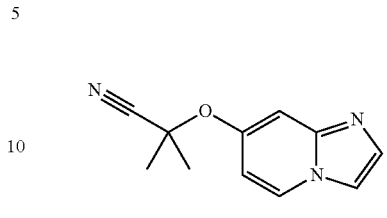

To 2-imidazo[1,2-a]pyridin-7-yloxy-2-methyl-propanamide (92 mg, 0.42 mmol) is added diethyl chlorophosphate (CAS #814-49-3; 72 mg, 0.42 mmol) and the reaction mixture is heated at 120° C. for 10 min. The reaction medium is diluted with water and extracted with EtOAc. The combined organic layers are dried over $Na_2SO_4$, filtered and concentrated. The crude material is purified by chromatography on silica gel (eluting with a gradient of 0 to 10% MeOH in DCM) to afford Int 68.

2.33. Int 71

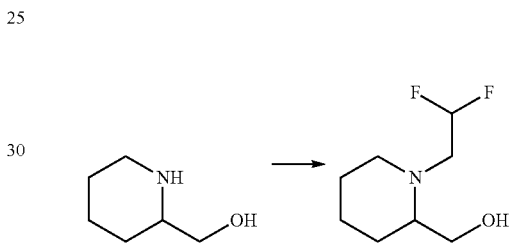

To a solution of 2-piperidylmethanol (CAS #3433-37-2; 200 mg, 1.74 mmol) and acetone (CAS #67-64-1; 1.05 mL, 34.73 mmol) in dry DCM (4 mL) is added $NaBH(OAc)_3$ (CAS #56553-60-7; 552 mg, 2.60 mmol) and the reaction mixture is stirred at RT for 2 days. The reaction medium is diluted with DCM and a 10% NaOH aq. solution. The mixture is stirred at RT for 2 h. The phases are separated and the aqueous layer is extracted with DCM. The combined organic layers are washed with brine, dried over $Na_2SO_4$, filtered and concentrated to approximately 0.5 mL. Cyclohexane is added and a solid precipitates. The solid is filtered and the filtrate is concentrated to afford Int 71.

2.34. Int 72

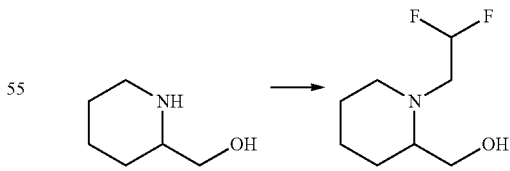

To a solution of 2-piperidylmethanol (CAS #3433-37-2; 200 mg, 1.74 mmol) in dry THF (6 mL) at 0° C. is added $Cs_2CO_3$ (848 mg, 2.60 mmol) and the mixture is stirred at 0° C. for 20 min. 2,2-difluoroethyl trifluoromethanesulfonate (CAS #74427-22-8; 346 µL, 2.60 mmol) is added and the reaction mixture is stirred at RT for 2 h. The reaction medium is concentrated to dryness and the residue is diluted with DCM and water. The phases are separated and the aqueous layer is extracted with DCM. Organic layers are combined, dried over Na₂SO₄, filtered and concentrated. The crude material is purified by chromatography on silica gel (eluting with a gradient of 0 to 2% MeOH in DCM) to afford Int 72.

2.35. Int 73

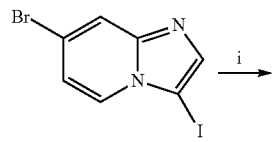

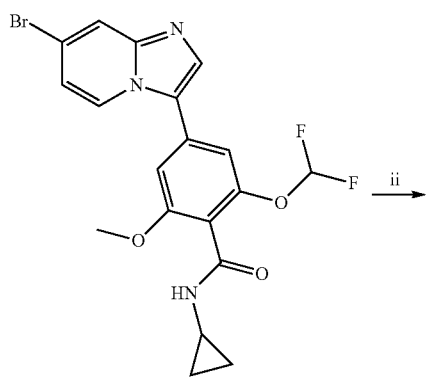

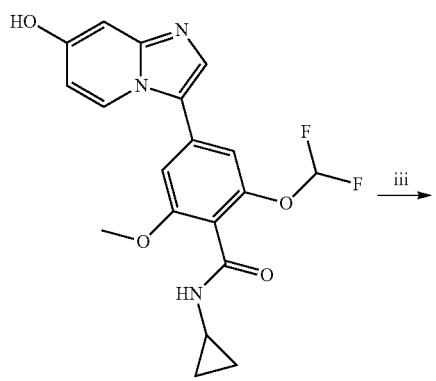

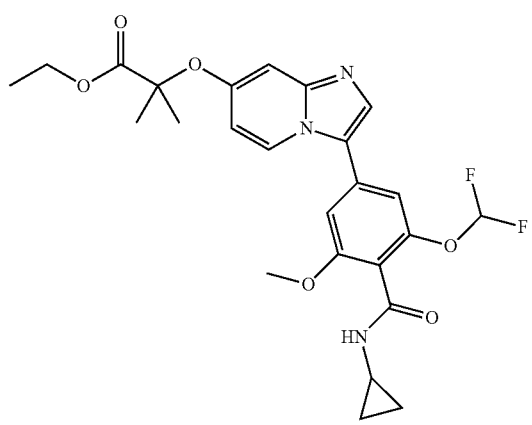

2.351. Step i: 4-(7-bromoimidazo[1,2-a]pyridin-3-yl)-N-cyclopropyl-2-(difluoromethoxy)-6-methoxy-benzamide A flask is charged with 7-bromo-3-iodo-imidazo[1,2-a]pyridine (CAS #1246184-55-3, 2 g, 6.19 mmol, 1 eq.), Int 89 (2.37 g, 6.19 mmol, 1 eq.), Cs₂CO₃ (4.04 g, 12.39 mmol, 2 eq.) and degassed with N₂ dioxane/water solvent mixture: 4/1 (70 mL). Pd(PPh₃)₄ (537 mg, 0.46 mmol, 0.075 eq.) is added and the system is purged with N₂ then the mixture is stirred to 90° C. for 20 h. Dioxane is evaporated, water is added and the mixture is extracted with EtOAc. The combined organic layers are washed with water and brine, dried over anhydrous MgSO₄, filtered and concentrated in vacuo until about 100 mL of EtOAc is left. The precipitating solid is filtered, rinsed with EtOAc then Et₂O to afford the expected bromo derivative.

LCMS: MW (calcd): 452.2; m/z MW (obsd): 452.1-454.1 (M+H)

2.352. Step ii: N-cyclopropyl-2-(difluoromethoxy)-4-(7-hydroxyimidazo[1,2-a]pyridin-3-yl)-6-methoxy-benzamide

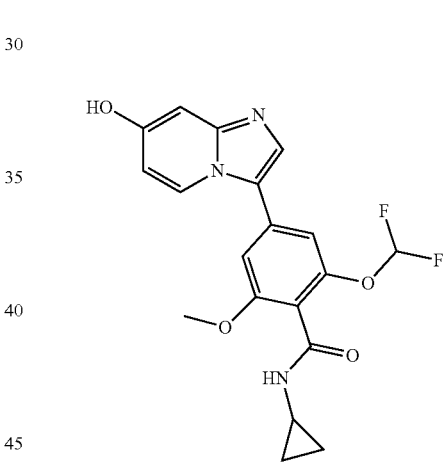

A solution of 4-(7-bromoimidazo[1,2-a]pyridin-3-yl)-N-cyclopropyl-2-(difluoromethoxy)-6-methoxy-benzamide (1.0 g, 2.21 mmol) and KOH (620 mg, 11.06 mmol) in a mixture of dioxane and water (10 mL/1.6 mL) is degassed with Ar for 10 min. tBuBrettPhos Pd G3 (CAS #1536473-72-9; 38 mg, 0.044 mmol) is added and the reaction medium is degassed with N₂ for 5 min. The reaction mixture is stirred at 50° C. overnight. The reaction medium is concentrated, the residue is taken up in water and the pH adjusted to 6. The aqueous phase is extracted with a i-PrOH/DCM mixture. Organic layers are combined, dried over Na₂SO₄, filtered and concentrated. The crude material is purified by chromatography on silica gel (eluting with a gradient of 0 to 4% MeOH in DCM) to afford the desired product.

LCMS: MW (calcd): 389.4; m/z MW (obsd): 390.7 (M+H)

2.35.3. Step iii: Int 73

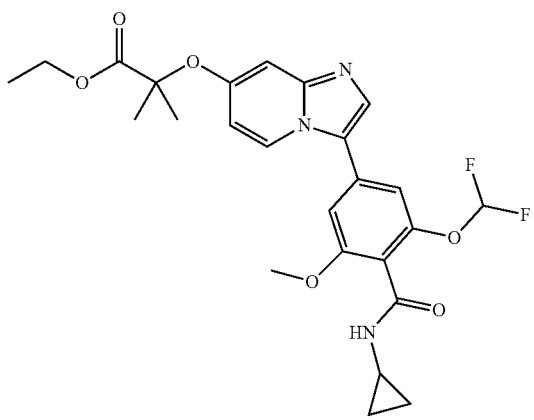 [SMILES: CCOC(=O)C(C)(C)Oc1ccn2c(-c3cc(OC)c(C(=O)NC4CC4)c(OC(F)F)c3)cnc2c1]

To a solution of N-cyclopropyl-2-(difluoromethoxy)-4-(7-hydroxyimidazo[1,2-a]pyridin-3-yl)-6-methoxy-benzamide (70 mg, 0.18 mmol) in dry DMF (1.5 mL) are added K₂CO₃ (99 mg, 0.72 mmol) and ethyl 2-bromo-2-methyl-propanoate (CAS #600-00-0; 105 µL, 0.72 mmol) and the mixture is stirred at 60° C. overnight. The reaction medium is concentrated and the residue is diluted with DCM and water. The phases are separated and the aqueous layer is extracted with DCM. The combined organic layers are dried over Na₂SO₄, filtered and concentrated to afford Int 73.

2.36. Int 76

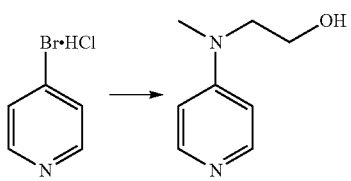

To a solution of 2-(methylamino)ethanol (CAS #109-83-1; 49.4 µL, 0.67 mmol) in dry THF (1 mL) are added 4-bromopyridine hydrochloride (CAS #19524-06-2; 156 mg, 0.80 mmol), RuPhos Pd G3 (CAS #1445085-77-7; 25 mg, 0.03 mmol), RuPhos (CAS #787618-22-8; 19 mg, 0.04 mmol) and t-BuOK (226 mg, 2.35 mmol). The reaction mixture is degassed with N₂ and stirred at 90° C. overnight. The reaction medium is filtered over Celite® and the filtrate is concentrated to afford Int 76 that is used as such.

2.37. Int 77

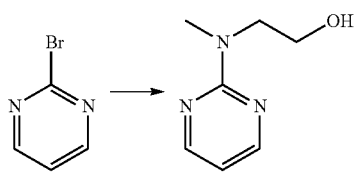

To a solution of 2-bromopyrimidine (CAS #4595-60-2; 211 mg, 1.33 mmol) in dry THF (2 mL) is added 2-(methylamino)ethanol (CAS #109-83-1; 99 µL, 1.33 mmol) and the reaction mixture is stirred at RT for 1 h. The reaction medium is concentrated and the crude material is purified by chromatography on silica gel (eluting with a gradient of 0 to 10% MeOH in DCM) to afford Int 77.

2.38. Int 78

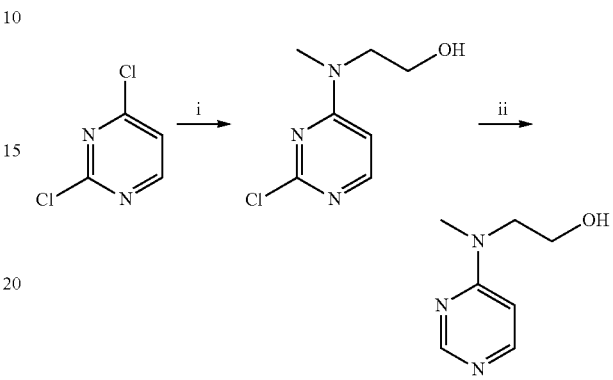

2.38.1. Step i: 2-[(2-chloropyrimidin-4-yl)-methyl-amino]ethanol

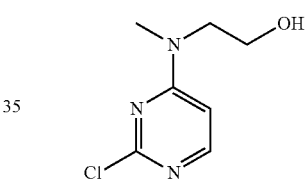

To a solution of 2,4-dichloropyrimidine (CAS #3934-20-1; 992 mg, 6.66 mmol) in dry THF (10 mL) is added 2-(methylamino)ethanol (CAS #109-83-1; 494 µL, 6.66 mmol) and the reaction mixture is stirred at RT for 4.5 h. The reaction medium is concentrated and the residue is taken up in chloroform. The precipitating solid is filtered off and the filtrate is concentrated. The obtained residue is purified by chromatography on silica gel (eluting with a gradient of 0 to 10% MeOH in DCM) to afford the expected compound.

LCMS: MW (calcd): 187.6; m/z MW (obsd): 188.4 (M+H)

2.38.2. Step ii: Int 78

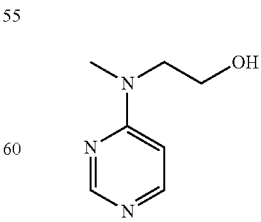

To a solution of 2-[(2-chloropyrimidin-4-yl)-methyl-amino]ethanol (400 mg, 2.13 mmol) in MeOH (5 mL) is added 10% Pd/C (40 mg, 0.23 mmol) and the reaction

2.39. Int 80

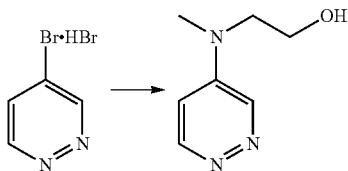

To a solution of 2-(methylamino)ethanol (CAS #109-83-1; 49 µL, 0.67 mmol, 1 eq.) in dry THF (1 mL) are added 4-bromopyridazine hydrobromide (CAS #1220039-64-4; 240 mg, 1.0 mmol, 1.5 eq.), RuPhos Pd G3 (CAS #1445085-77-7; 25 mg, 0.03 mmol, 0.05 eq.), RuPhos (CAS #787618-22-8; 19 mg, 0.04 mmol, 0.06 eq.) and t-BuOK (226 mg, 2.35 mmol, 3.5 eq.). The mixture is degassed with N₂ and stirred at 90° C. for 4 h. It is then cooled down to RT and hydrolysed with brine. The aqueous layer is extracted with EtOAc and the combined organic phases are evaporated in vacuo. The residue is taken up in a MeOH/Et₂O mixture, the obtained precipitate is filtered off and the solid is dried to afford Int 80.

2.40. Int 81

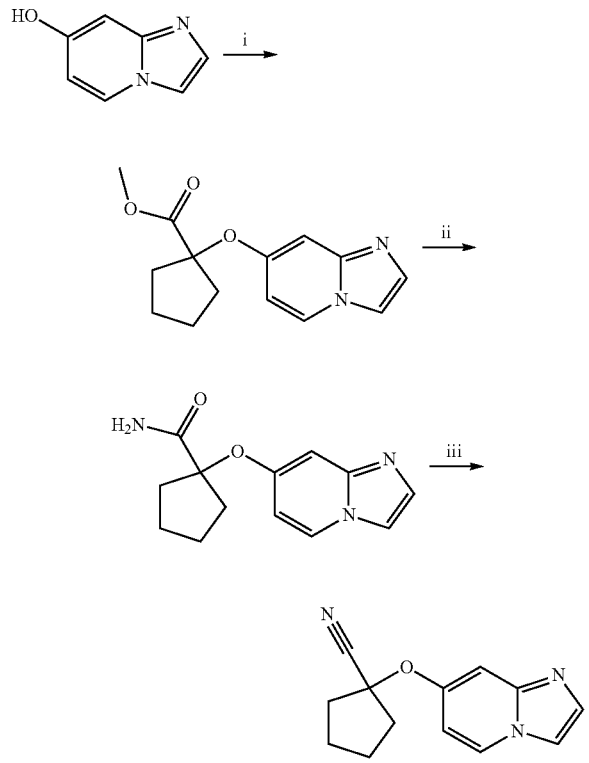

2.40.1. Step i: methyl 1-imidazo[1,2-a]pyridin-7-yloxycyclopentanecarboxylate

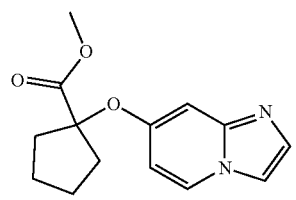 [SMILES: COC(=O)C1(Oc2ccn3ccnc3c2)CCCC1]

To a solution of imidazo[1,2-a]pyridin-7-ol (CAS #896139-85-8; 35 mg, 0.26 mmol) in dry DMF (3 mL) is added NaH (60% in mineral oil, 42 mg, 1.04 mmol) and the mixture is stirred at RT for 10 min. Methyl 1-bromocyclopentane-1-carboxylate (CAS #51572-54-4; 143 µL, 1.04 mmol) is added and the mixture is heated at 50° C. for 20 h. The reaction mixture is concentrated and the residue is diluted with water and DCM. The aqueous phase is extracted with DCM. Organic layers are combined, dried over Na₂SO₄, filtered and concentrated to afford the expected compound.

LCMS: MW (calcd): 260.3; m/z MW (obsd): 261.6 (M+H)

2.40.2. Step ii: 1-imidazo[1,2-a]pyridin-7-yloxycyclopentanecarboxamide

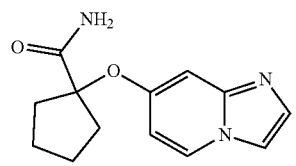 [SMILES: NC(=O)C1(Oc2ccn3ccnc3c2)CCCC1]

To ammonia 25% in water (724 µL, 4.70 mmol) is added methyl 1-imidazo[1,2-a]pyridin-7-yloxycyclopentanecarboxylate (80 mg, 0.307 mmol) and the reaction mixture is stirred at RT for 20 h. Ammonia 25% in water (724 µL, 4.70 mmol) is added and the reaction mixture is stirred at RT overnight. The volatiles are removed in vacuo, the residue is suspended in MeOH and the solvent is removed under reduced pressure to afford the desired product.

2.40.3. Step iii: Int 81

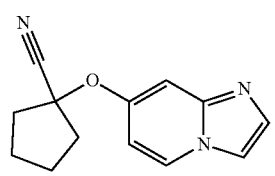 [SMILES: N#CC1(Oc2ccn3ccnc3c2)CCCC1]

To a solution of 1-imidazo[1,2-a]pyridin-7-yloxycyclopentanecarboxamide (67 mg, 0.27 mmol) in dry DMF (1 mL) at 0° C. is added POCl₃ (56 µL, 0.60 mmol) and the mixture is stirred at RT for 1 h. The reaction mixture is poured slowly on iced water (200 mL) and the mixture is neutralized with a 2N aq. NaOH solution to pH 7. The aqueous phase is extracted with EtOAc. The combined organic layers are dried over Na₂SO₄, filtered and concentrated. The crude material is purified by chromatography on silica gel (eluting with a gradient of 0 to 5% MeOH in DCM with 1% ammonia) to afford Int 81.

2.41. Int 84

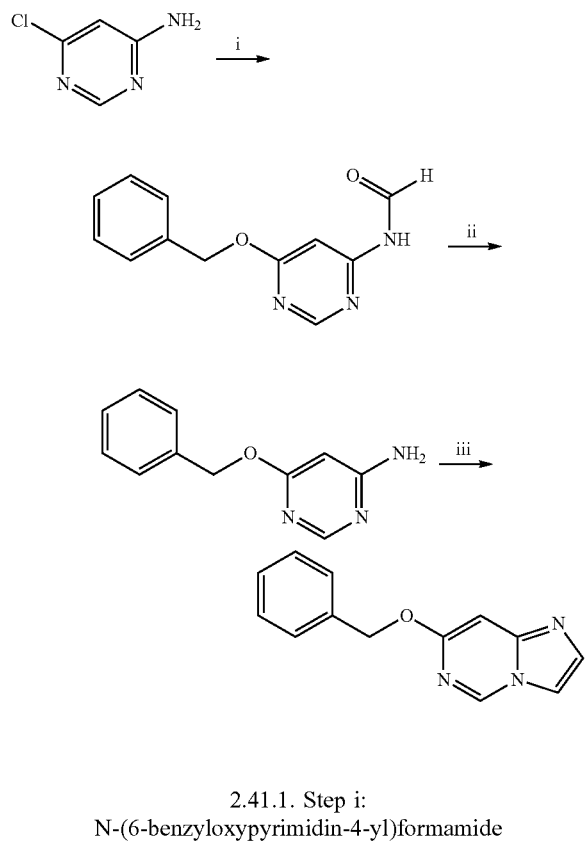

2.41.1. Step i:
N-(6-benzyloxypyrimidin-4-yl)formamide

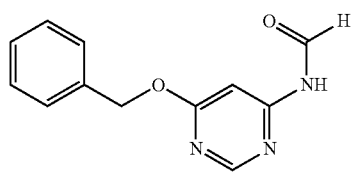 [SMILES: O=CNc1cc(OCc2ccccc2)ncn1]

To a solution of phenylmethanol (CAS #100-51-6; 800 µL, 6.40 mmol) in dry DMF (10 mL) is added NaH (60% dispersion of sodium hydride in mineral oil, 400 mg, 10.0 mmol) and the mixture is stirred at RT for 30 min. 6-chloropyrimidin-4-amine (CAS #5305-59-9; 260 mg, 2.0 mmol) is added and the reaction mixture is stirred at RT overnight. The reaction mixture is concentrated and the residue is taken with DCM and water. The phases are separated. The organic layer is dried over MgSO₄, filtered and concentrated. The crude is triturated in DCM, Et₂O and pentane and then the solid is filtered to afford the expected compound.

LCMS: MW (calcd): 229.3; m/z MW (obsd): 230.2 (M+H)

2.41.2. Step ii: 6-benzyloxypyrimidin-4-amine

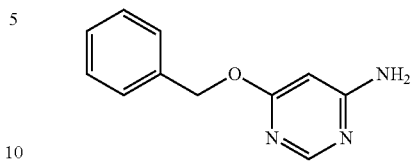

To a solution of N-(6-benzyloxypyrimidin-4-yl)formamide (320 mg, 1.40 mmol) in MeOH (50 mL) is added a 2N aq. NaOH solution (3 mL) and the mixture is stirred at RT for 5 h. The reaction mixture is concentrated and the residue is taken with DCM and water. The phases are separated. The organic layer is dried over MgSO₄, filtered and concentrated to afford the desired compound.

2.41.3. Step iii: Int 84

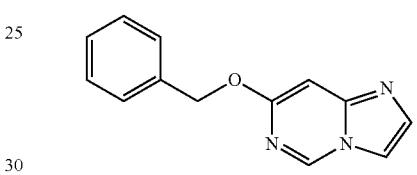

To a solution of 6-benzyloxypyrimidin-4-amine (240 mg, 1.19 mmol) in EtOH (5 mL) are added 2-chloroacetaldehyde (CAS #107-20-0; 320 µL, 5.95 mmol) and NaHCO₃ (450 mg, 5.95 mmol). The reaction mixture is stirred at 110° C. for 5 h. 2-chloroacetaldehyde (43 µL, 0.595 mmol) and NaHCO₃ (50 mg, 0.595 mmol) are added and the reaction mixture is stirred at 110° C. for 20 h. 2-chloroacetaldehyde (86 µL, 1.19 mmol) and NaHCO₃ (100 mg, 1.19 mmol) are added and the mixture is stirred at 110° C. for 6 h. The reaction mixture is concentrated and the residue is taken up in DCM, water and sat. aq. NH₄Cl solution. The phases are separated, then the aqueous layer is basified with a 2N aq. NaOH solution and extracted with a 1/1 mixture of chloroform/i-PrOH. The organic layer is dried over MgSO₄, filtered and concentrated to give Int 84.

2.42. Int 88

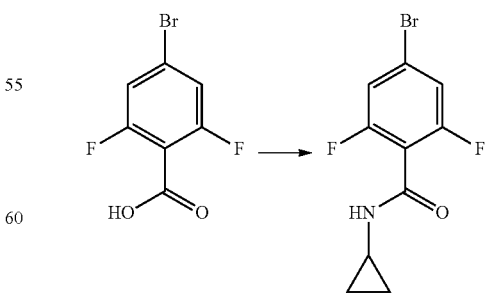

In a 15 L jacketed reactor 4-bromo-2,6-difluorobenzoic acid (CAS #183065-68-1; 900 g, 3.80 mol, 1 eq.) is added to SOCl₂ (5 eq., 1385 mL, 19.07 mol, 5 eq.) in toluene (2 V, 1800 mL) under N₂ flow at 20° C. (jacket temperature). The suspension is then heated to 80° C. for 17 h (jacket temperature set at 80° C.).

The reaction mixture is cooled to 40° C. and concentrated (200 mL of toluene are used to wash the reactor). Toluene (1 V, 900 mL) is added to the residue and the solution is concentrated.

The liquid residue (940 g) is dissolved in DCM (5 V, 4.5 L) under N₂ and placed into the 15 L reactor. The reaction mixture is cooled to 13° C. (jacket temperature: 5° C.) and a mixture of Et₃N (582.22 mL, 4.18 mol, 1.1 eq.) and cyclopropylamine (CAS #765-30-0; 276.21 mL, 3.99 mol, 1.1 eq.) is added over 1.3 h keeping the temperature below 25° C. (jacket temperature set at 5° C. during the addition). The reaction mixture is stirred under N₂ at 20° C. for 14 h.

Water (2.2 V, 2 L) is added to the suspension. The biphasic solution is stirred (200 rpm) for 15 min. The organic phase is then successively washed with NaHCO₃ 5% (1.1 V, 1 L) and 20% NaCl solution (1.1 V, 1 L). The DCM layer is collected and put into a 15 L reactor.

A solvent exchange is performed in the 15 L reactor: to the DCM layer is added 1 L of heptane. The mixture is heated progressively with the jacket temperature set at 65° C. and DCM is removed between 43° C. and 50° C. After removing 2 L of DCM, 1 L of heptane is added. After removing a total of 4 L of solvent, 1 L of heptane is added and the mixture is cooled to 20° C. in 20 min. Finally 1 L of heptane (a total of 4 L of heptane is added) is added and the mixture is stirred at 20° C. for 45 min.

The suspension is filtered and the cake is washed with 1.5 L of heptane.

The solid is dried at 50° C. under vacuum overnight to afford Int 88.

2.43. Int 89

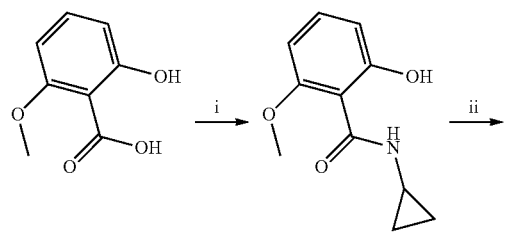

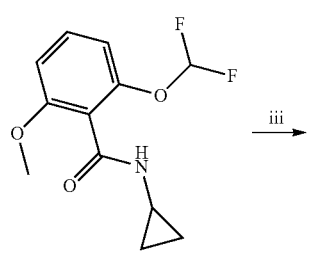

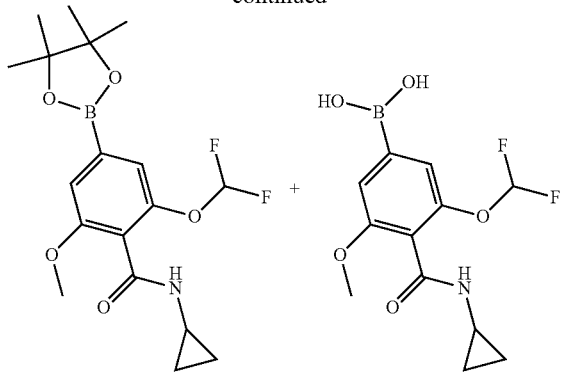

2.43.1. Step i: N-cyclopropyl-2-hydroxy-6-methoxy-benzamide

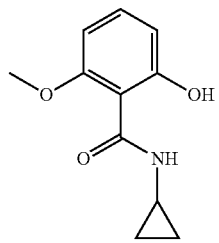

6-methoxysalicyclic acid (CAS #3147-64-6; 10 g, 0.06 mmol, 1 eq.) is dissolved in DMF (50 mL), HATU (33.93 g, 0.09 mmol, 1.5 eq.) is added, followed 15 min later by cyclopropylamine (CAS #765-30-0; 10.18 g, 0.18 mmol, 3 eq.), and DIPEA (34.55 g, 0.26 mmol, 4.5 eq.). The reaction mixture is allowed to stir at RT for 18 h; then 1 eq. of HATU, 2 eq. of cyclopropylamine and 2 eq. of DIPEA are added. The reaction mixture is stirred at RT for 68 h. The reaction mixture is concentrated in vacuo. Purification is performed by flash chromatography on silica gel (eluting with heptane/EtOAc 100/0 to 50/50). The collected fractions are concentrated in vacuo and triturated twice with MeOH/Et₂O. The filtrate is concentrated in vacuo to afford the desired product.

LCMS: MW (calcd): 207.2; m/z MW (obsd): 208.4 (M+H)

2.43.2. Step ii: N-cyclopropyl-2-(difluoromethoxy)-6-methoxy-benzamide

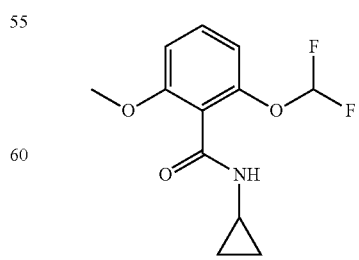

Under an inert atmosphere, N-cyclopropyl-2-hydroxy-6-methoxy-benzamide (2.80 g, 0.013 mmol, 1 eq.) is dissolved in ACN (20 mL) and cooled to −20° C. A solution of KOH (7.57 g, 0.13 mmol, 10 eq.) in water (20 mL) is added and the mixture is stirred for 10 min, then diethyl (bromodifluoromethyl)phosphonate (CAS #65094-22-6; 10.9 g, 0.04 mmol, 3.1 eq.) is added slowly. The reaction mixture is stirred at −20° C. for 30 min then at RT for another 30 min. Water is added and three extractions with EtOAc are performed. The organic layers are dried on Na$_2$SO$_4$, filtered and concentrated in vacuo. Purification by flash chromatography on silica gel (eluting with a gradient heptane/EtOAc 100/0 to 0/100) affords the expected product.

LCMS: MW (calcd): 257.2; m/z MW (obsd): 258.4 (M+H)

2.43.3. Step iii: Int 89: mixture of N-cyclopropyl-2-(difluoromethoxy)-6-methoxy-4-(4,4,5,5-tetramethyl-1,3,2-dioxaborolan-2-yl)benzamide and 4-(cyclopropylcarbamoyl)-3-(difluoromethoxy)-5-methoxyphenylboronic acid

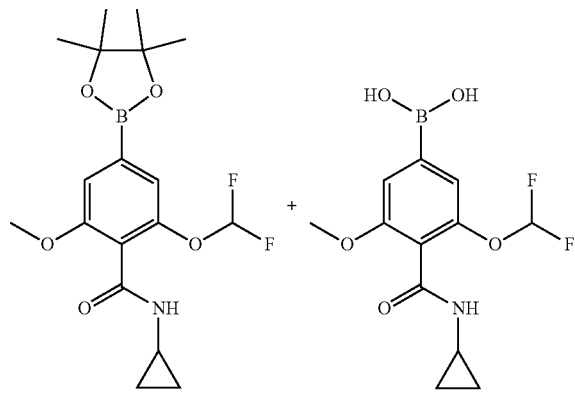

Under an inert atmosphere, N-cyclopropyl-2-(difluoromethoxy)-6-methoxy-benzamide (2.80 g, 10.89 mmol, 1 eq.), B$_2$pin$_2$ (8.30 g, 32.68 mmol, 3 eq.), [Ir(OCH3)(COD)] (360 mg, 0.54 mmol, 0.05 eq.) and BBBPY (120 mg, 0.45 mmol, 0.04 eq.) are dissolved in degassed THF (70 mL). The reaction mixture is stirred at 70° C. under N$_2$ for 3 h then at RT overnight. Purification by flash chromatography on silica gel (eluting with a gradient heptane/EtOAc 100/0 to 30/70) affords the expected product in mixture with the corresponding boronic acid.

2.44. Int 90

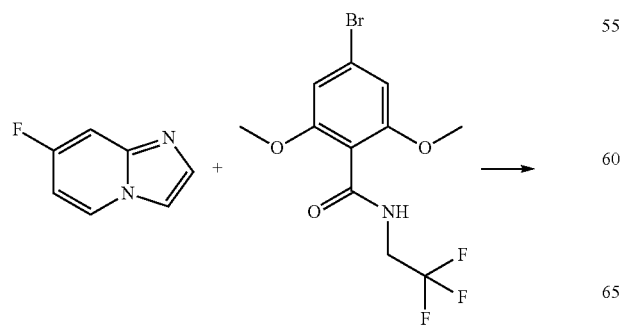

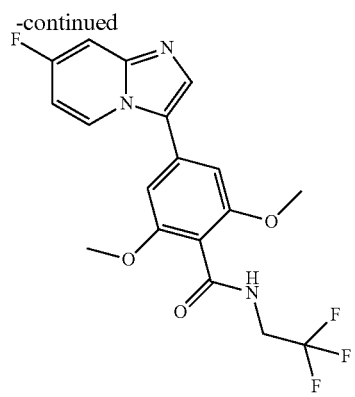

A solution of 7-fluoroimidazo[1,2-a]pyridine (CAS #1260903-17-0; 100 mg, 0.73 mmol, 1 eq.), Int 47 (502 mg, 1.47 mmol, 2 eq.), KOAc (216 mg, 2.20 mmol, 3 eq.) and Pd(dppf)Cl$_2$·DCM (CAS #95464-05-4; 29 mg, 0.04 mmol, 0.05 eq.) in dry DMSO (4 mL) is sparged with N$_2$ and is then stirred at 110° C. for 6 h. The reaction medium is diluted with a sat. aq. NH$_4$Cl solution and the obtained precipitate is filtered. The aqueous phase is then basified with a sat. aq. NaHCO$_3$ solution and extracted with AcOEt. The combined organic layers are dried over Na$_2$SO$_4$, filtered and concentrated. The crude material is purified by flash chromatography on silica gel (eluting with a gradient of 1 to 3% MeOH in DCM) to give the expected product Int 90.

2.45. Int 91

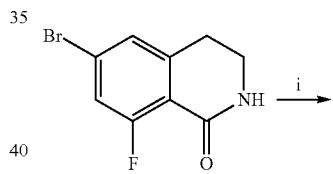

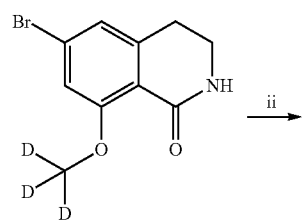

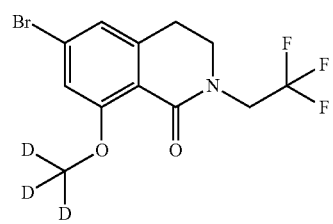

2.45.1. Step i: 6-bromo-8-(trideuteriomethoxy)-3,4-dihydro-2H-isoquinolin-1-one

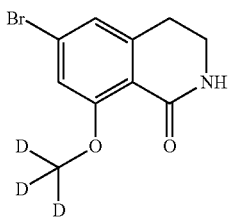

To a stirred solution of CD$_3$OD (CAS #811-98-3; 3.1 mL, 76.2 mmol, 6 eq.) in THF (31 mL) at 0° C. is added portionwise NaH (60% dispersion in mineral oil, 366 mg, 15.24 mmol, 1.2 eq.). The reaction mixture is stirred at 0° C. for 20 min and 6-bromo-8-fluoro-3,4-dihydro-2H-isoquinolin-1-one (CAS #1242157-15-8, 3.1 g, 12.7 mmol, 1 eq.) is added in one portion. The reaction is stirred at RT for 1.5 h and NaH (60% dispersion in mineral oil, 60 mg, 2.5 mmol, 0.2 eq.) is added. The reaction mixture is stirred at RT for 18 h. The reaction mixture is quenched with a sat. NH$_4$Cl solution. THF is evaporated and water (31 mL) is added to the suspension. The suspension is stirred at RT for 1 h and then filtered. The solid is rinsed with water and dried under vacuum to afford the expected product.

2.452. Step ii: Int 91

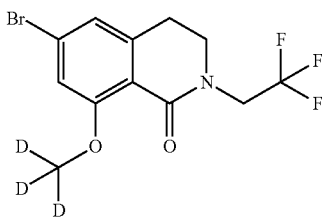 [SMILES: [2H]C([2H])([2H])Oc1cc(Br)cc2c1C(=O)N(CC(F)(F)F)CC2]

To a stirred solution of 6-bromo-8-(trideuteriomethoxy)-3,4-dihydro-2H-isoquinolin-1-one (3.28 g, 12.66 mmol, 1 eq.) in THF (32.8 mL) at 10° C. is added dropwise a solution of LiHMDS (1M in THF, 13.3 mL, 13.3 mmol, 1.05 eq.). The resulting mixture is stirred for 20 min at RT. 2,2,2-trifluoroethyl trifluoromethanesulfonate (CAS #6226-25-1; 2.19 mL, 15.19 mmol, 1.2 eq.) is added dropwise at 15° C. The reaction mixture is heated at 65° C. for 3.5 h. The reaction mixture is cooled down to 15° C. and LiHMDS (1M in THF, 0.53 mL, 0.53 mmol, 0.04 eq.) is added followed 10 min later by 2,2,2-trifluoroethyl trifluoromethanesulfonate (CAS #6226-25-1; 0.087 mL, 0.60 mmol, 0.05 eq.). The reaction mixture is heated at 65° C. for 30 min, then cooled down to 10° C. and an aq. solution of 1N HCl is added until pH 1 is reached. THF is completely evaporated under reduced pressure. The resulting suspension is filtered and the solid is washed twice with water. The solid is suspended in MTBE (10 mL) and stirred at RT for 1 h. The suspension is filtered and the solid is washed with heptane and dried to afford Int 91.

2.46. Int 92

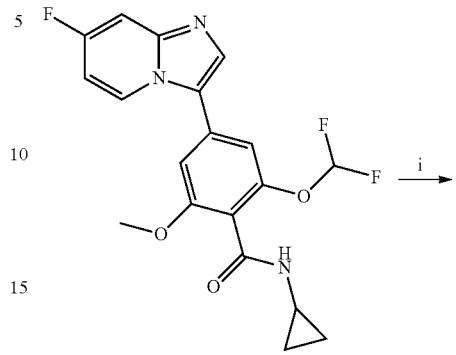

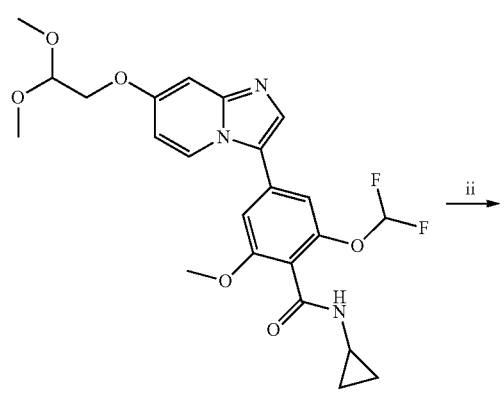

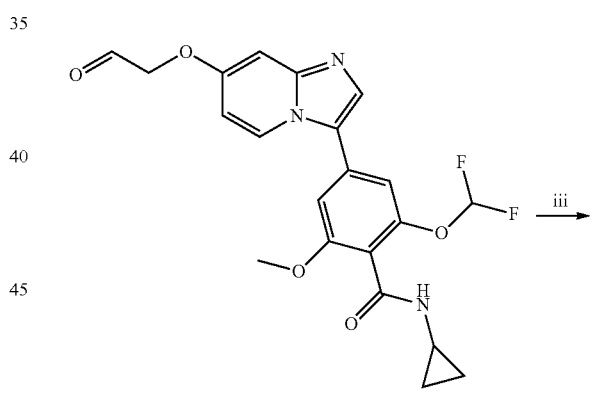

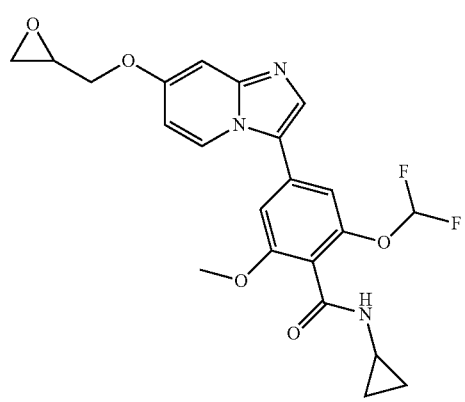

2.46.1. Step i: N-cyclopropyl-2-(difluoromethoxy)-4-[7-(2,2-dimethoxyethoxy)imidazo[1,2-a]pyridin-3-yl]-6-methoxy-benzamide

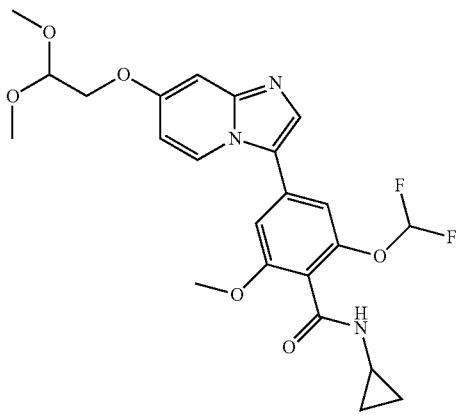 [SMILES: COc1cc(-c2cnc3cc(OCC(OC)OC)ccn23)cc(OC(F)F)c1C(=O)NC1CC1]

2,2-dimethoxyethanol (CAS #30934-97-5; 2.5 g, 0.024 mol, 5 eq.) is added to a suspension of NaH 60% in mineral oil (952 mg, 0.0238 mol, 5 eq.) in anhydrous DMF at 5° C. After 10 min, Int 1 (1.92 g, 4.76 mmol, 1 eq.) is added to the reaction mixture. The reaction mixture is allowed to warm up to RT and stirred overnight. The reaction mixture is diluted with water and extracted with EtOAc. Organic layers are combined, dried over Na$_2$SO$_4$, filtered and evaporated under reduced pressure. The residue is purified by flash chromatography on silica gel (eluting with a gradient of 0 to 6% MeOH in DCM) to afford N-cyclopropyl-2-(difluoromethoxy)-4-[7-(2,2-dimethoxyethoxy)imidazo[1,2-a]pyridin-3-yl]-6-methoxy-benzamide.

2.46.2. Step ii: N-cyclopropyl-2-(difluoromethoxy)-6-methoxy-4-[7-(2-oxoethoxy)imidazo[1,2-a]pyridin-3-yl]benzamide

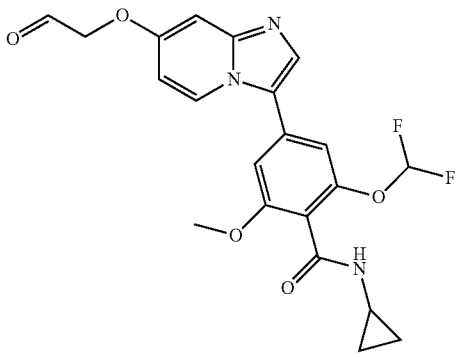 [SMILES: COc1cc(-c2cnc3cc(OCC=O)ccn23)cc(OC(F)F)c1C(=O)NC1CC1]

N-cyclopropyl-2-(difluoromethoxy)-4-[7-(2,2-dimethoxyethoxy)imidazo[1,2-a]pyridin-3-yl]-6-methoxy-benzamide (100 mg, 0.186 mmol, 1 eq.) is dissolved in dry DCM and TFA (2 mL, 0.0269 mmol, 64.3 eq.) is added. The reaction mixture is stirred at RT overnight then evaporated to dryness under reduced pressure. Toluene (2 mL) is added and the reaction mixture is evaporated to dryness to afford N-cyclopropyl-2-(difluoromethoxy)-6-methoxy-4-[7-(2-oxoethoxy)imidazo[1,2-a]pyridin-3-yl]benzamide.

2.46.3. Step iii: Int 92

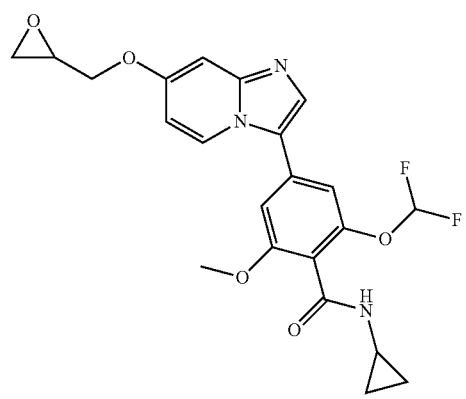 [SMILES: COc1cc(-c2cnc3cc(OCC4CO4)ccn23)cc(OC(F)F)c1C(=O)NC1CC1]

Trimethyl sulfoxonium iodide (CAS #1774-47-6; 81.1 mg, 0.369 mmol, 1 eq.) is dissolved in dry DMSO (2 mL) and NaH 60% in mineral oil (29.5 mg, 7.37 mmol, 2 eq.) is added. The reaction mixture is stirred at RT for 1 h. N-cyclopropyl-2-(difluoromethoxy)-6-methoxy-4-[7-(2-oxoethoxy)imidazo[1,2-a]pyridin-3-yl]benzamide (159 mg, 0.369 mmol, 1 eq.) is then added and the reaction mixture is stirred at RT for 4 h. The reaction mixture is then diluted with water and extracted with DCM. Organic layers are combined, dried over Na$_2$SO$_4$, filtered, and evaporated under reduced pressure. The residue is purified by flash chromatography (eluting with a gradient of 0 to 20% MeOH in DCM) to afford Int 92.

2.47. Int 93

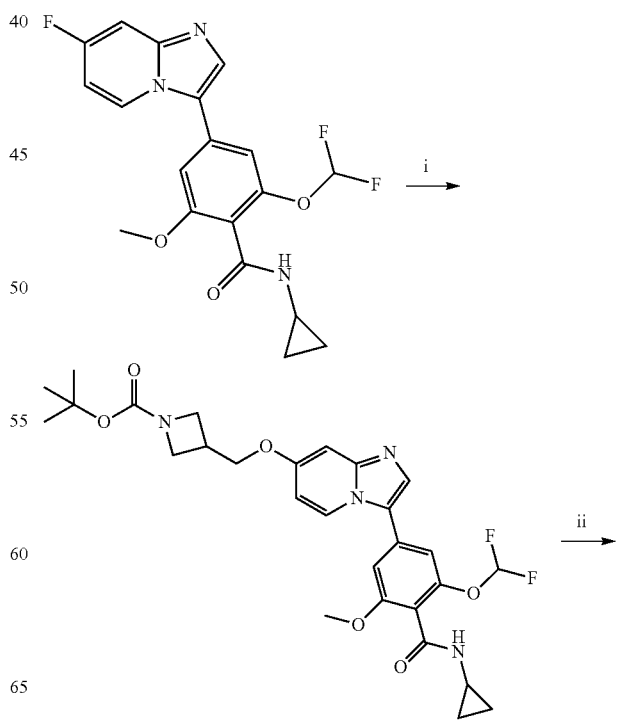

-continued

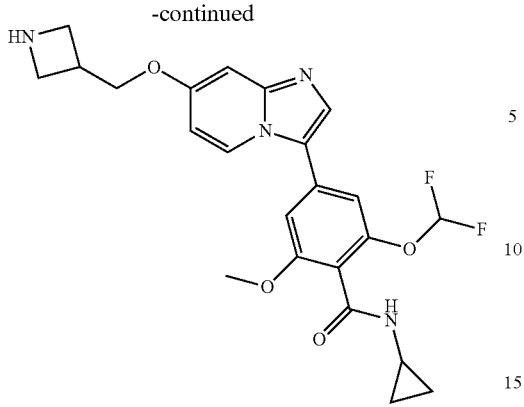

2.47.1. Step i: tert-butyl 3-[[3-[4-(cyclopropylcarbamoyl)-3-(difluoromethoxy)-5-methoxy-phenyl]imidazo[1,2-a]pyridin-7-yl]oxymethyl]azetidine-1-carboxylate NaH (60% in mineral oil; 81.8 mg, 2.04 mmol, 4.0 eq.) is added to a solution of tert-butyl 3-(hydroxymethyl)azetidine-1-carboxylate (CAS #142253-56-3; 402 mg, 2.15 mmol, 4.2 eq.) in anhydrous DMF (5 mL) at 5° C. After 10 min, Int 1 (200 mg, 0.51 mmol, 1.0 eq.) is added to the reaction mixture and the reaction is allowed to stir at RT for 18 h. The reaction is diluted with EtOAc (35 mL), water (5 mL) is added and the mixture is transferred to a separation funnel. The water layer is removed and the organic layer is washed with a sat. aq. sol. of NaHCO₃ (5×20 mL) and dried over Na₂SO₄, filtered and evaporated. The crude product is purified by flash chromatography (eluting with a gradient of 0 to 5% MeOH in DCM) to afford tert-butyl 3-[[3-[4-(cyclopropylcarbamoyl)-3-(difluoromethoxy)-5-methoxy-phenyl]imidazo[1,2-a]pyridin-7-yl]oxymethyl]azetidine-1-carboxylate.

2.47.2. Step ii: Int 93

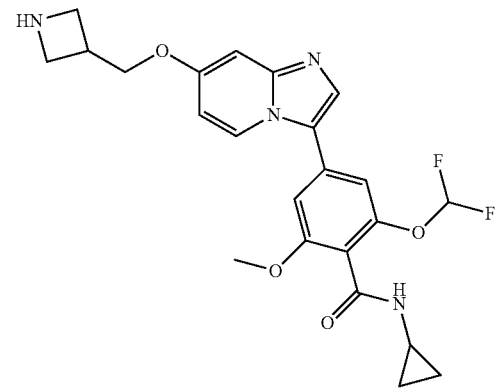 [SMILES: COc1cc(-c2cnc3cc(OCC4CNC4)ccn23)cc(OC(F)F)c1C(=O)NC1CC1]

TFA (572 µL, 7.47 mmol, 15 eq.) is added to a solution of tert-butyl 3-[[3-[4-(cyclopropylcarbamoyl)-3-(difluoromethoxy)-5-methoxy-phenyl]imidazo[1,2-a]pyridin-7-yl]oxymethyl]azetidine-1-carboxylate (278 mg, 0.498 mmol, 1.0 eq.) in anhydrous DCM (4 mL) at RT under stirring. The reaction mixture is stirred 2.5 h at RT and evaporated to dryness. The crude product is dissolved in 1 mL of water and pH is adjusted to 7.5 with a sat. aq. solution of NaHCO₃. The aq. solution is extracted with an i-PrOH/DCM (5×10 mL) mixture. The organic layers are combined, dried over Na₂SO₄ and evaporated to afford Int 93.

2.48. Int 94

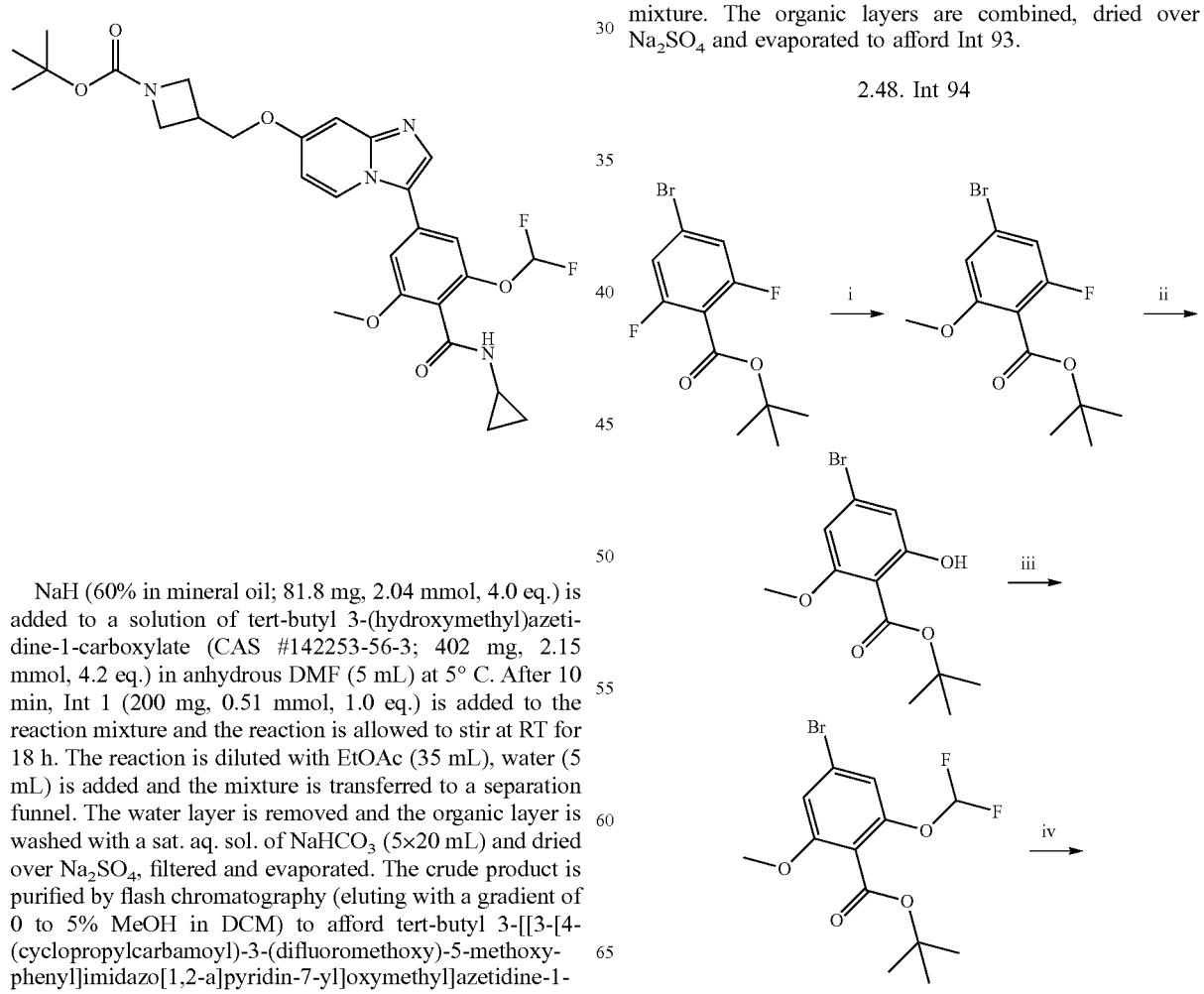

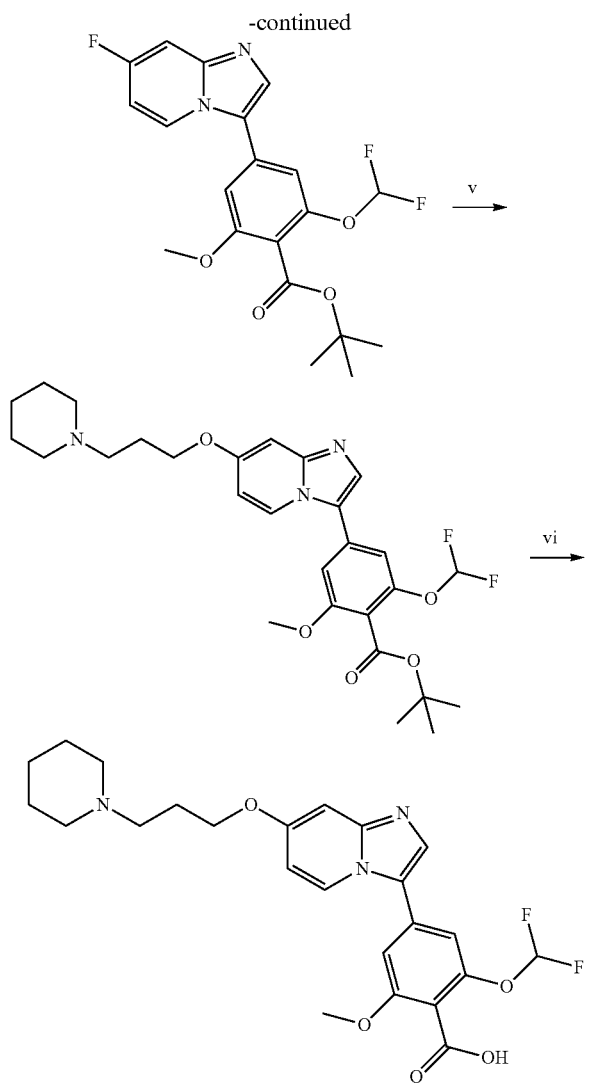

2.48.1. Step i: tert-butyl 4-bromo-2-fluoro-6-methoxy-benzoate

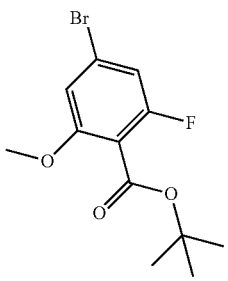 [SMILES: COc1cc(Br)cc(F)c1C(=O)OC(C)(C)C]

To a solution of tert-butyl 4-bromo-2,6-difluoro-benzoate (CAS #955887-09-9; 19 g, 65 mmol, 1.0 eq.) in THF (320 mL) is added sodium methoxide (15 g, 260 mmol, 4.0 eq.). The reaction is stirred at RT overnight. The mixture is quenched with a sat. aq. NH$_4$Cl solution, extracted with EtOAc (3×). The combined organic layers are dried over MgSO$_4$, filtered, and concentrated under reduced pressure to afford tert-butyl 4-bromo-2-fluoro-6-methoxy-benzoate.

LCMS: MW (calcd): 305.1; m/z MW (obsd): 305.3-307.2 (M+H)

2.48.2. Step ii: tert-butyl 4-bromo-2-hydroxy-6-methoxy-benzoate

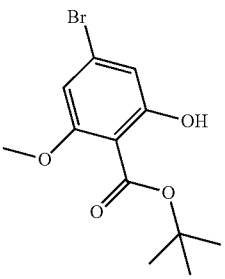 [SMILES: COc1cc(Br)cc(O)c1C(=O)OC(C)(C)C]

Under N$_2$ atmosphere, to a solution of 2-(methylsulfonyl)ethanol (CAS #15205-66-0; 16 g, 120 mmol, 1.5 eq.) in DMF (100 mL) at 0° C. is added NaH (60% dispersion in mineral oil, 9 g, 230 mmol, 2.7 eq.). The reaction mixture is stirred at 0° C. for 10 min and a solution of tert-butyl 4-bromo-2-fluoro-6-methoxy-benzoate (25 g, 82 mmol, 1.0 eq.) in DMF (60 mL) is added. The reaction mixture is stirred to 0° C. and let to warm up to RT overnight. The reaction mixture is quenched by the addition of HCl 2N (170 mL, 4.0 eq.) and extracted with EtOAc (2×). The combined organic layers are washed with water, brine, dried over MgSO$_4$, filtered and concentrated to dryness to afford tert-butyl 4-bromo-2-hydroxy-6-methoxy-benzoate.

LCMS: MW (calcd): 303.1; m/z MW (obsd): 301.1-303.2 (M−H)

2.48.3. Step iii: tert-butyl 4-bromo-2-(difluoromethoxy)-6-methoxy-benzoate

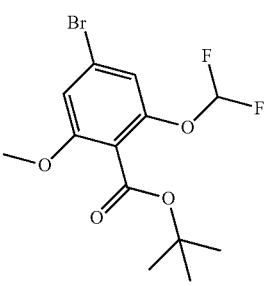 [SMILES: COc1cc(Br)cc(OC(F)F)c1C(=O)OC(C)(C)C]

To a solution of tert-butyl 4-bromo-2-hydroxy-6-methoxy-benzoate (19 g, 53.79 mmol, 0.65 eq.) in ACN (78.3 g, 100 mL, 1910 mmol, 23 eq.) at −35° C. under N$_2$ is added dropwise over 5 min a cold solution of potassium hydroxide (46 g, 820 mmol, 10 eq.) in water (100 mL). The reaction mixture is stirred at −35° C. for 15 min and then diethyl (bromodifluoromethyl)phosphonate (CAS #65094-22-6, 45 g, 30 mL, 160 mmol, 2.0 eq.) is added dropwise keeping the temperature at −35° C. over 5 min. The reaction mixture is allowed to warm to RT over 1.5 h. The reaction mixture is quenched with water. The aqueous layer is extracted with EtOAc (3×). The combined organic layers are washed with brine, dried over MgSO$_4$, filtered and concentrated in vacuo. The crude product is purified by flash chromatography on silica gel (eluting with 0 to 10% EtOAc in heptane) to afford tert-butyl 4-bromo-2-(difluoromethoxy)-6-methoxy-benzoate.

LCMS: MW (calcd): 353.1; m/z MW (obsd): 353.1-355.1 (M+H)

2.48.4. Step iv: tert-butyl 2-(difluoromethoxy)-4-(7-fluoroimidazo[1,2-a]pyridin-3-yl)-6-methoxy-benzoate

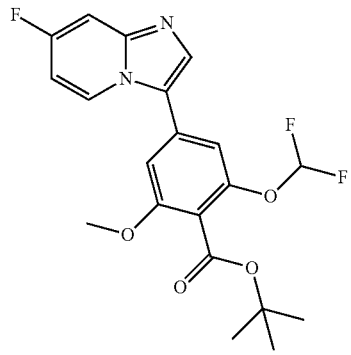 [SMILES: COc1cc(-c2cnc3cc(F)ccn23)cc(OC(F)F)c1C(=O)OC(C)(C)C]

General method B is used to obtain tert-butyl 2-(difluoromethoxy)-4-(7-fluoroimidazo[1,2-a]pyridin-3-yl)-6-methoxy-benzoate starting from 7-fluoro-imidazo[1,2-a]pyridine (CAS #1260903-17-0) and tert-butyl 4-bromo-2-(difluoromethoxy)-6-methoxy-benzoate.

LCMS: MW (calcd): 408.1; m/z MW (obsd): 407.3 (M–H)

2.48.5. Step v: tert-butyl 2-(difluoromethoxy)-6-methoxy-4-[7-[3-(1-piperidyl)propoxy]imidazo[1,2-a]pyridin-3-yl]benzoate

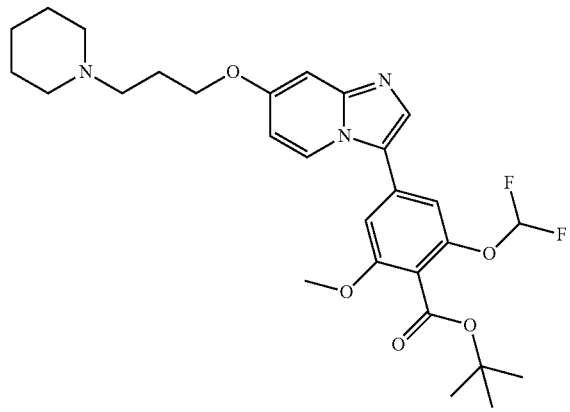 [SMILES: COc1cc(-c2cnc3cc(OCCCN4CCCCC4)ccn23)cc(OC(F)F)c1C(=O)OC(C)(C)C]

To a solution of 1-piperidinepropanol (CAS #104-58-5; 0.440 mL, 2.91 mmol, 2.2 eq.) in dry DMF (4.7 mL) is added portionwise NaH (60% dispersion in mineral oil, 125 mg, 3.12 mmol, 2.4 eq.) at 0° C. The reaction mixture is stirred at 0° C. for 15 min and then tert-butyl 2-(difluoromethoxy)-4-(7-fluoroimidazo[1,2-a]pyridin-3-yl)-6-methoxy-benzoate (540 mg, 1.32 mmol, 1 eq.) is added. The reaction mixture is stirred for 4 h, then quenched with a sat. aq. NaHCO$_3$ solution and extracted with EtOAc. The combined organic layers are dried over MgSO$_4$, filtered and concentrated. The crude product is purified by chromatography on silica gel (eluting with 0 to 5% MeOH in EtOAc) to afford tert-butyl 2-(difluoromethoxy)-6-methoxy-4-[7-[3-(1-piperidyl)propoxy]imidazo[1,2-a]pyridin-3-yl]benzoate.

LCMS: MW (calcd): 531.2; m/z MW (obsd): 532.5 (M+H)

2.48.6. Step vi: Int 94

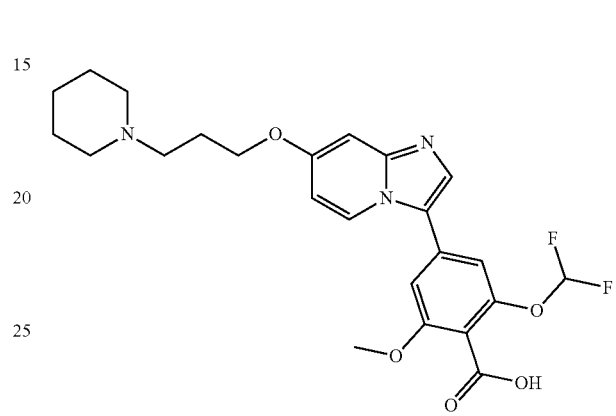

To a solution of tert-butyl 2-(difluoromethoxy)-6-methoxy-4-[7-[3-(1-piperidyl)propoxy]imidazo[1,2-a]pyridin-3-yl]benzoate (332 mg, 0.627 mmol, 1 eq.) in DCM (26 mL) is added TFA (3 mL) and the reaction mixture is stirred at RT for 18 h. Toluene (10 mL) is added and the reaction mixture is concentrated to dryness to afford Int 94.

2.49. Int 95

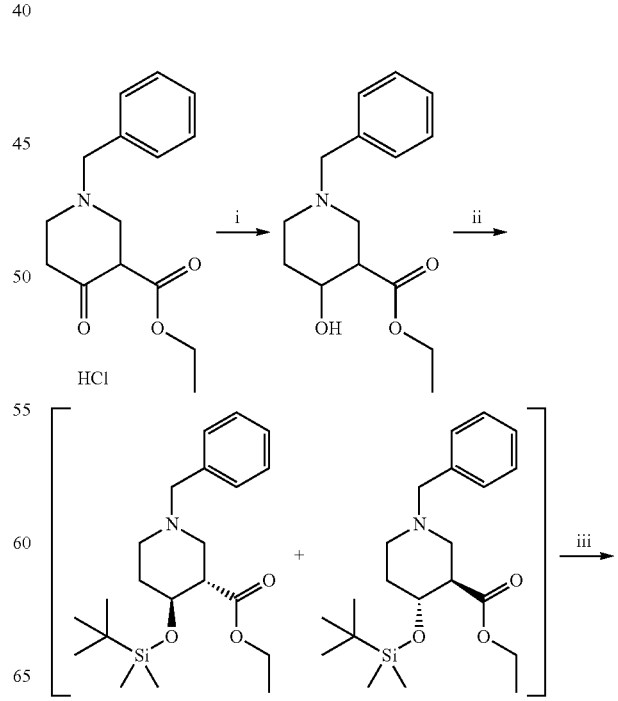

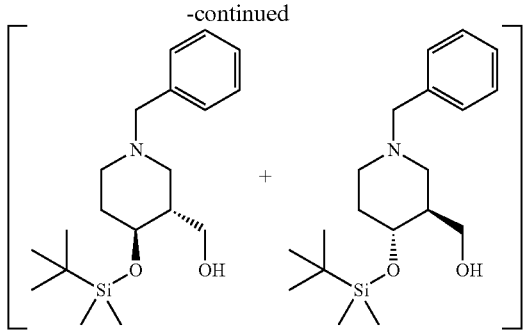

2.49.1. Step i: ethyl
1-benzyl-4-hydroxy-piperidine-3-carboxylate

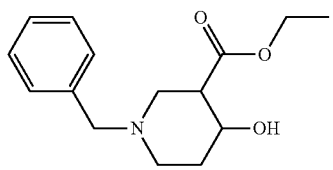 [SMILES: CCOC(=O)C1CN(Cc2ccccc2)CCC1O]

To a solution of ethyl 1-benzyl-4-oxo-3-piperidinecarboxylate hydrochloride (CAS #1454-53-1; 500 mg, 1.646 mmol, 1 eq.) in dry MeOH (10 mL) is added Et₃N (0.241 mL, 1.728 mmol, 1.05 eq.) at 0° C. The reaction mixture is stirred at 0° C. for 10 min and then NaBH₄ (187 mg, 4.937 mmol, 3 eq.) is added portionwise. The reaction mixture is stirred at 0° C. for 2 h and HCl 4M is added to reach pH 3. The solvent is partially removed under vacuum and the residue is neutralized with a sat. aq. NaHCO₃ solution and extracted with DCM. The combined organic layers are dried over Na₂SO₄, filtered and concentrated. The crude product is purified by flash chromatography on silica gel (eluting with 0 to 60% EtOAc in cyclohexane) to afford ethyl 1-benzyl-4-hydroxy-piperidine-3-carboxylate.

LCMS: MW (calcd): 263.2; m/z MW (obsd): 264.2 (M+H)

2.49.2. Step ii: ethyl (3S,4S)-1-benzyl-4-[tert-butyl(dimethyl)silyl]oxy-piperidine-3-carboxylate/ethyl (3R,4R)-1-benzyl-4-[tert-butyl(dimethyl)silyl]oxy-piperidine-3-carboxylate mixture

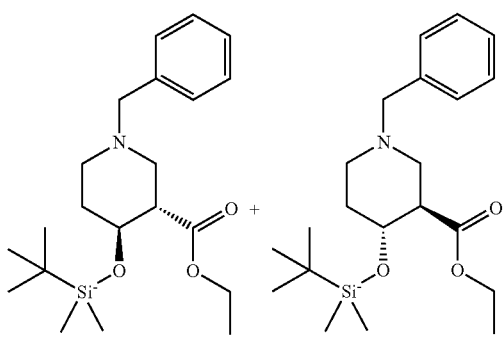

To a suspension of ethyl 1-benzyl-4-hydroxy-piperidine-3-carboxylate (320 mg, 1.191 mmol, 1 eq.) in dry DMF (8 mL) is added imidazole (45 mg, 0.655 mmol, 0.55 eq.) and tert-butyldimethylsilyl chloride (90 mg, 0.595 mmol, 0.5 eq.). The reaction mixture is stirred at RT overnight. Further tert-butyldimethylsilyl chloride (90 mg, 0.595 mmol, 0.5 eq.) is added and the reaction mixture is stirred at RT for 5 h. The reaction mixture is poured into a mixture of ice in water and extracted with DCM. The combined organic layers are dried over Na₂SO₄, filtered and concentrated. The crude product is purified by flash chromatography on silica gel (eluting with 0 to 60% EtOAc in cyclohexane) to afford (3S,4S)-ethyl 1-benzyl-4-hydroxypiperidine-3-carboxylate (racemic mixture) as the first eluting compound and ethyl (3S,4S)-1-benzyl-4-[tert-butyl(dimethyl)silyl]oxy-piperidine-3-carboxylate (racemic mixture) as the second eluting compound.

LCMS: MW (calcd): 377.2; m/z MW (obsd): 378.2 (M+H)

2.49.3. Step iii: Int 95

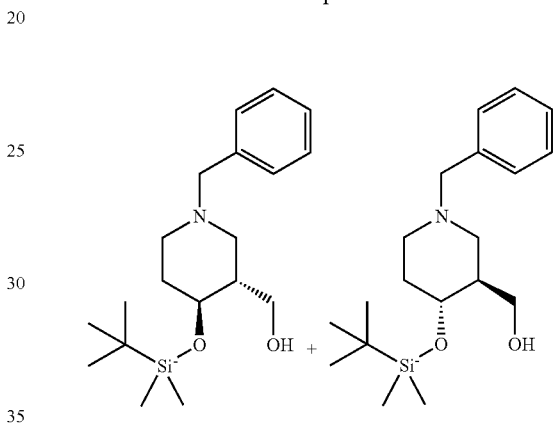

To a suspension of ethyl (3S,4S)-1-benzyl-4-[tert-butyl(dimethyl)silyl]oxy-piperidine-3-carboxylate (124 mg, 0.328 mmol, 1 eq.) in dry THF (10 mL) is added LiBH₄ (14 mg, 0.657 mmol, 2 eq.). The reaction mixture is refluxed for 24 h and then cooled to RT. A sat. aq. NaHSO₄ solution is slowly added and the reaction mixture is extracted with DCM. The combined organic layers are dried over Na₂SO₄, filtered and concentrated. The crude product is purified by flash chromatography on silica gel (eluting with 0 to 30% EtOAc in cyclohexane) to afford Int 95 (racemic mixture).

2.50. Int 96

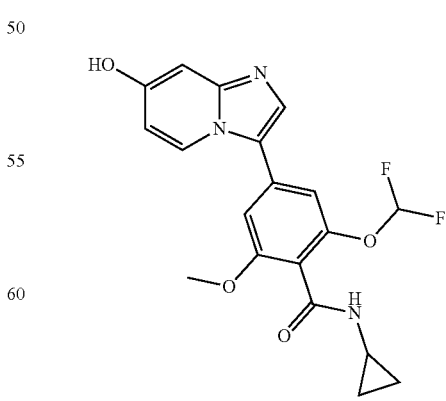

Cpd 68 (1.22 g, 2.45 mmol, 1 eq.) is suspended in water (20 mL) and concentrated HCl (20 mL) is added. The reaction mixture is stirred at 60° C. overnight. The reaction mixture is diluted with water, its pH adjusted to ~9 with 40% NaOH in water, and extracted with EtOAc. The organic layers are combined, dried over Na₂SO₄, filtered and evaporated under reduced pressure. The crude product is purified by flash chromatography on silica gel (eluting with a gradient DCM/(DCM-MeOH—NH₃ in water 80/19/1) 100/0 to 20/80) to afford Int 96.

2.51. Int 97

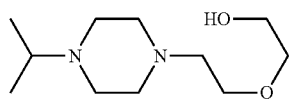

2-Iodopropane (323 µL, 3.31 mmol) is added to a suspension of 2-(2-piperazin-1-ylethoxy)ethanol (CAS #13349-82-1; 550 mg, 3.16 mmol) and K₂CO₃ (567 mg, 4.10 mmol) in ACN (10.0 mL), and the reaction mixture is stirred at RT for 18 h. The reaction mixture is evaporated to dryness, suspended in DCM, and filtered. The DCM solution is evaporated to dryness. The crude product is purified by flash chromatography on silica gel (eluting with 0 to 20% MeOH in DCM) to afford Int 97.

2.52. Int 98

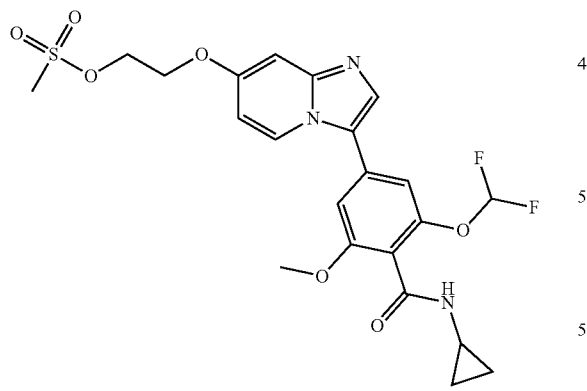

Cpd 30 (873 mg, 1.76 mmol, 1.0 eq.) is dissolved in dry DCM (20 mL) and Et₃N (335 µL, 2.40 mmol, 1.36 eq.) and methanesulfonyl chloride (173 µL, 2.23 mmol, 1.26 eq.) are added. The mixture is left to stir at RT for 2 h. The mixture is diluted with DCM (50 mL) and washed with water (2×20 mL) and brine (2×20 mL). The organic layer is dried over Na₂SO₄, filtered and evaporated to dryness. The resulting crude product is purified by flash chromatography on silica gel (eluting with 0 to 7% MeOH in DCM) to afford Int 98.

2.53. Int 99

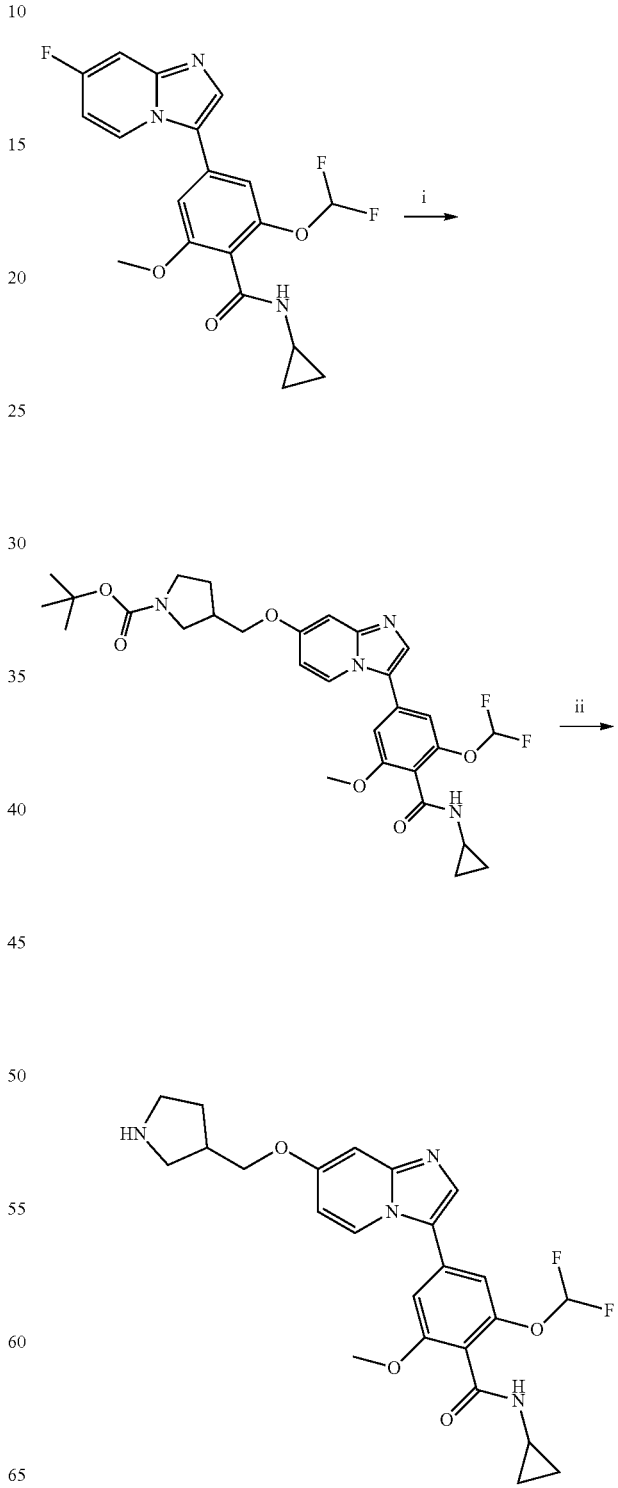

2.53.1. Step i: tert-butyl 3-[[3-[4-(cyclopropylcarbamoyl)-3-(difluoromethoxy)-5-methoxy-phenyl]imidazo[1,2-a]pyridin-7-yl]oxymethyl]pyrrolidine-1-carboxylate

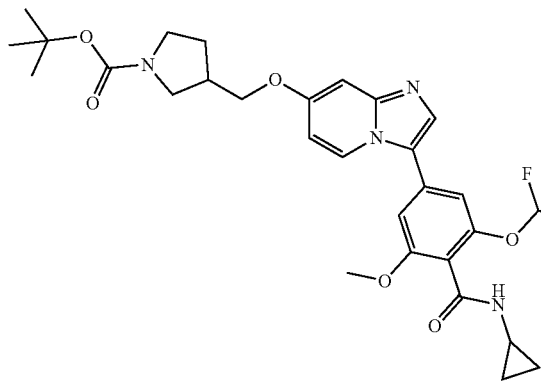

Tert-butyl 3-(hydroxymethyl)pyrrolidine-1-carboxylate (CAS #114214-69-6; 103 mg, 0.5 mmol, 2 eq.) is dissolved in dry DMF, cooled in ice bath and NaH (60% dispersion in mineral oil, 40.9 mg, 1 mmol, 2 eq.) is added portionwise. The reaction mixture is stirred for 10 min and then Int 1 (200 mg, 0.5 mmol, 1 eq.) is added. The reaction mixture is allowed to slowly warm to RT under stirring, and left to stir overnight. Another portion of tert-butyl 3-(hydroxymethyl) pyrrolidine-1-carboxylate (51.5 mg, 0.25 mmol, 1 eq.) and NaH (60% dispersion in mineral oil, 20.4 mg, 0.5 mmol, 1 eq.) are added. The reaction mixture is stirred overnight at RT, then diluted with water and extracted with EtOAc. The organic layers are combined, dried over $Na_2SO_4$, filtered and evaporated under reduced pressure. The crude product is purified by flash chromatography on silica gel (eluting with 0 to 10% MeOH in DCM) to afford tert-butyl 3-[[3-[4-(cyclopropylcarbamoyl)-3-(difluoromethoxy)-5-methoxy-phenyl]imidazo[1,2-a]pyridin-7-yl]oxymethyl]pyrrolidine-1-carboxylate

2.53.2. Step ii: Int 99

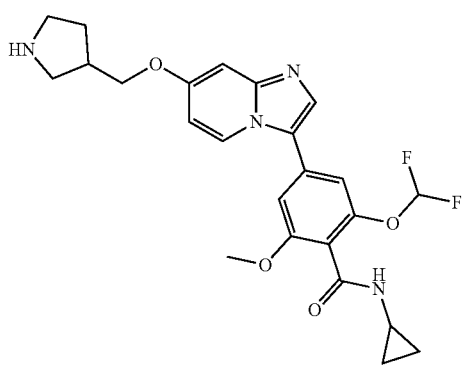 [SMILES: COc1cc(-c2cnc3cc(OCC4CCNC4)ccn23)cc(OC(F)F)c1C(=O)NC1CC1]

Tert-butyl3-[[3-[4-(cyclopropylcarbamoyl)-3-(difluoromethoxy)-5-methoxy-phenyl]imidazo[1,2-a]pyridin-7-yl] oxymethyl]pyrrolidine-1-carboxylate (282 mg, 0.49 mmol, 1 eq.) is dissolved in HCl, 4N in 1,4-dioxane (2 mL) and stirred at RT for 2 h. The reaction mixture is evaporated to dryness, dissolved with DCM and transferred to a separation funnel. Water and a $NaHCO_3$ sat. solution are added and extracted with DCM. The organic layers are combined, dried over $Na_2SO_4$, filtered and evaporated under reduced pressure to afford Int 99.

2.54. Cpd 4

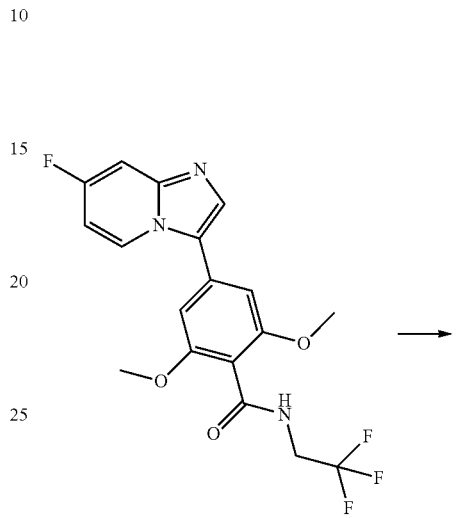

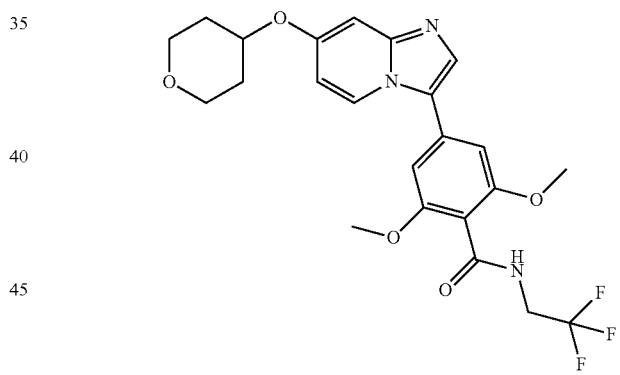

To a solution of tetrahydropyran-4-ol (CAS #2081-44-9; 31 µL, 0.30 mmol, 4 eq.) in DMF (1 mL) at RT is added NaH (60% dispersion in mineral oil, 12 mg, 0.30 mmol, 4 eq.) and the mixture is stirred for 10 min. Then Int 90 (30 mg, 0.08 mmol, 1 eq.) is added and the reaction mixture is stirred at RT for 20 h. Tetrahydropyran-4-ol (31 µL, 0.30 mmol, 4 eq.) and NaH (60% dispersion in mineral oil, 12 mg, 0.30 mmol, 4 eq.) are added and the reaction is stirred at RT for 72 h. The solvent is evaporated to dryness and the residue is taken up in a sat. aq. $NaHCO_3$ solution/DCM mixture that is then passed through a phase separator. The filtrate is concentrated and the residue is purified by flash chromatography on silica gel (eluting with MeOH 0 to 3% in DCM) to afford Cpd 4.

2.55. Cpd 5

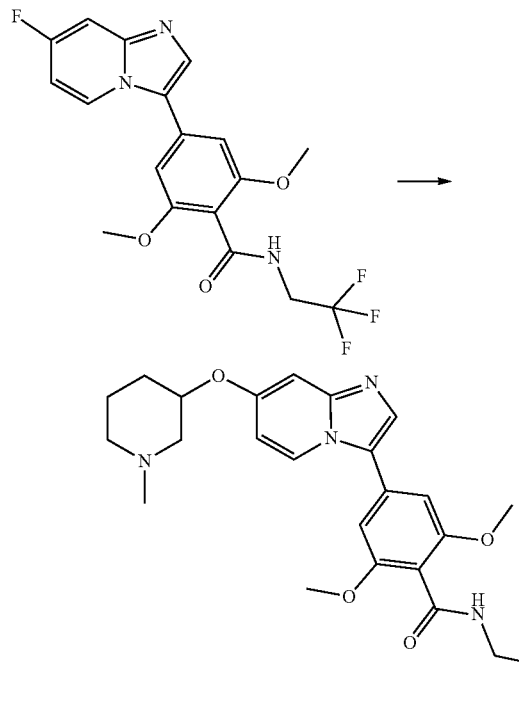

To a solution of 1-methylpiperidin-3-ol (CAS #3554-74-3; 35 µL, 0.30 mmol, 4 eq.) in DMF (1 mL) at RT is added NaH (60% dispersion in mineral oil, 12 m g, 0.30 mmol, 4 eq.) and the mixture is stirred for 10 min. Then Int 90 (30 mg, 0.08 mmol, 1 eq.) is added and the reaction mixture is stirred at RT for 20 h. 1-methylpiperidin-3-ol (35 µL, 0.30 mmol, 4 eq.) and NaH (60% dispersion in mineral oil, 12 mg, 0.30 mmol, 4 eq.) are added and the reaction is stirred at RT for 72 h. The solvent is evaporated to dryness and the residue is taken up in a sat. aq. NaHCO$_3$ solution/DCM mixture that is then passed through a phase separator. The filtrate is concentrated and the residue is purified by flash chromatography on silica gel (eluting with MeOH 0 to 10% in DCM) to afford Cpd 5.

2.56. Cpd 6

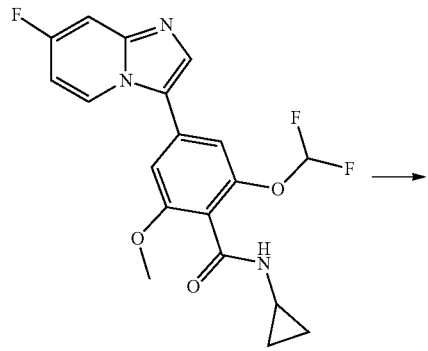

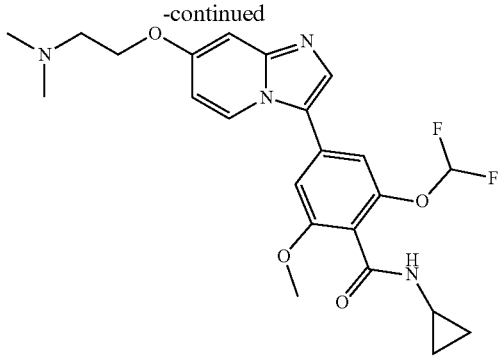

To a solution of 2-(dimethylamino)ethanol (CAS #108-01-0; 27 mg, 0.306 mmol) in dry DMF (1 mL) is added NaH (60% dispersion in mineral oil, 13 mg, 0.306 mmol) and the mixture is stirred at RT for 10 min. Int 1 (30 mg, 0.076 mmol) is added and the reaction mixture is stirred at RT overnight. The solvent is removed under reduced pressure, the residue is taken up in water and DCM. The phases are separated on phase separator and the filtrate is concentrated. The crude material is purified by chromatography on silica gel (eluting with a gradient of 5 to 10% MeOH in DCM) to afford Cpd 6.

2.57. Cpd 13

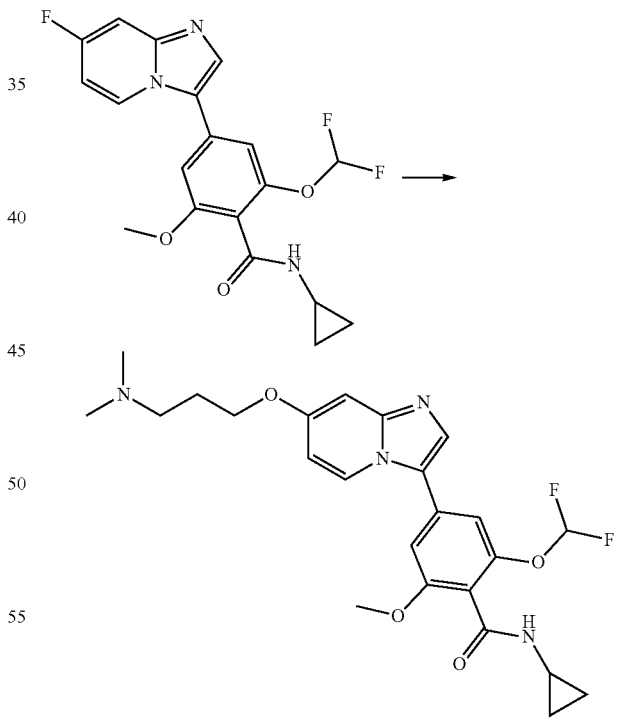

To a solution of 3-(dimethylamino)propan-1-ol (CAS #3179-63-3; 117 µL, 1.0 mmol, 10 eq.) in DMF (1 mL) at RT is added NaH (60% dispersion in mineral oil, 16 mg, 0.41 mmol, 4 eq.) and the mixture is stirred for 10 min. Then Int 1 (40 mg, 0.10 mmol, 1 eq.) is added and the reaction mixture is stirred at RT for 72 h. The reaction mixture is concentrated to dryness and the crude material is purified by flash chromatography on silica gel (eluting with MeOH 0 to 10% in DCM, then DCM/MeOH 90/10 with 1% Et₃N). The obtained residue is then taken up in water and 2N aq. NaOH, extracted with EtOAc and the combined organic layers are dried over Na₂SO₄, filtered and concentrated to afford Cpd 13.

2.58. Cpd 14

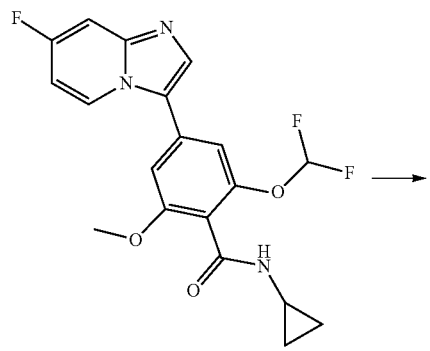

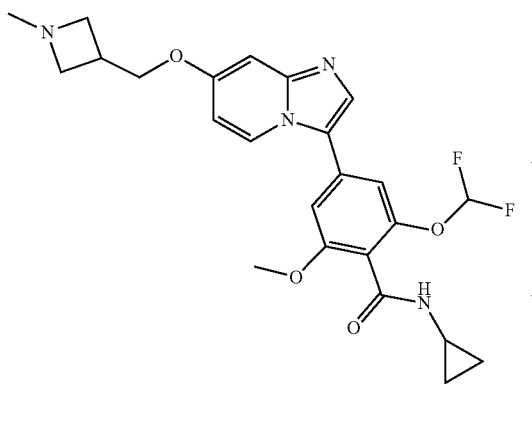

To a solution of (1-methylazetidin-3-yl)methanol (CAS #1499172-23-4; 115 µL, 1.0 mmol, 10 eq.) in DMF (1 mL) at RT is added NaH (60% dispersion in mineral oil, 16 mg, 0.41 mmol, 4 eq.) and the mixture is stirred for 10 min. Then Int 1 (40 mg, 0.10 mmol, 1 eq.) is added and the reaction mixture is stirred at RT for 72 h. The reaction mixture is concentrated to dryness and the crude material is purified by flash chromatography on silica gel (eluting with MeOH 0 to 10% in DCM, then DCM/MeOH 90/10 with 1% Et₃N). The obtained residue is then taken up in water and 2N aq. NaOH, extracted with EtOAc and the combined organic layers are dried over Na₂SO₄, filtered and concentrated to afford Cpd 14.

2.59. Cpd 56

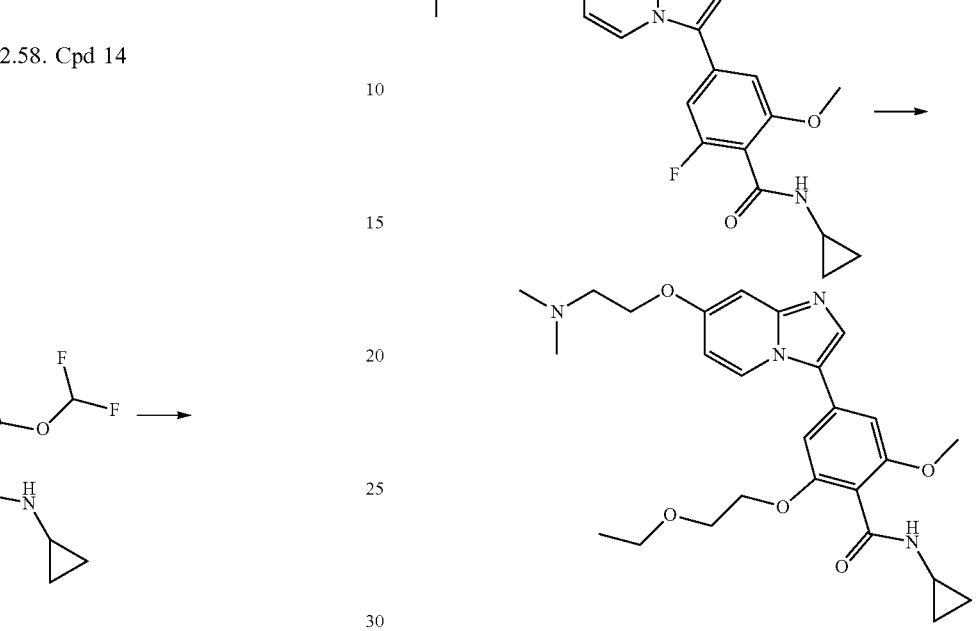

To a solution of Cpd 51 (27 mg, 0.065 mmol, 1 eq.) in 2-ethoxyethanol (0.5 mL) is added tBuOK (22 mg, 0.20 mmol, 3 eq.) and the mixture is stirred at 80° C. for 20 h. The reaction mixture is cooled down to RT, diluted with DCM and quenched with water. The solution is passed through a phase separator and the filtrate is concentrated in vacuo. The residue is purified by chromatography on silica gel (eluting with MeOH 0 to 4% in DCM) to give Cpd 56.

2.60. Cpd 86

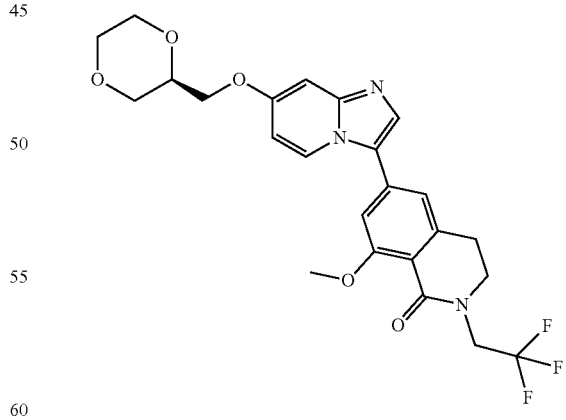

To a solution of [(2S)-1,4-dioxan-2-yl]methanol (CAS #406913-93-7; 6.00 g, 50.84 mmol) in dry DMF (100 mL) at 0° C. is added NaH (60% dispersion in mineral oil, 2.00 g, 50.84 mmol) portionwise and the mixture is stirred at RT for 20 min. The mixture is cooled down to 0° C. and Int 2 (5.00 g, 12.71 mmol) is added in one portion. Dry DMF (100 mL) is added and the reaction mixture is stirred at RT for 3 h. The reaction mixture is quenched with a sat. aq. NaHCO₃ solution and extracted with EtOAc. The aqueous layer is saturated with solid NaCl and extracted with EtOAc. The combined organic layers are washed with brine, dried over Na₂SO₄ and concentrated. The crude residue is purified by chromatography on silica gel (eluting with a gradient of 1 to 10% MeOH in EtOAc). The obtained material is triturated in Et₂O, filtered and dried to afford Cpd 86.

2.61. Cpd 88

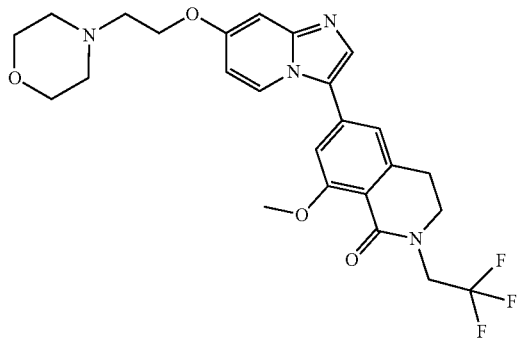 [SMILES: COc1cc(-c2cnc3cc(OCCN4CCOCC4)ccn23)cc2c1C(=O)N(CC(F)(F)F)CC2]

To a solution of 2-morpholinoethanol (CAS #622-40-2; 7.80 mL, 69.55 mmol) in dry DMF (200 mL) at 0° C. is added NaH (60% dispersion in mineral oil, 2.00 g, 50.84 mmol) in one portion and the mixture is stirred at 0° C. for 10 min. At this temperature, Int 2 (5.00 g, 12.71 mmol) is added and the reaction mixture is warmed up to RT and stirred for 3 h. The reaction mixture is cooled down to 0° C. and quenched with a sat. aq. NaHCO₃ solution and water. The mixture is extracted with EtOAc. The combined organic layers are washed with brine, dried over Na₂SO₄, filtered and concentrated. The crude residue is purified by chromatography on silica gel (eluting with a gradient of 0 to 2% MeOH in DCM). The obtained material is dissolved in DCM and washed with a 2N aq. NaOH solution twice. The phases are passed through a phase separator and the filtrate is concentrated. The residue is dissolved in EtOAc (7.5 V) at reflux temperature and the solution is allowed to cool down to RT. The precipitate is filtered, rinsed with cool EtOAc and dried to afford Cpd 88.

To a solution of Cpd 88 (20.6 g, 40.83 mmol) in MeOH (250 mL) is added a 1.25M HCl solution in MeOH (130 mL) and the mixture is stirred at RT for 45 min. The solvent is removed under reduced pressure and the residue is triturated in Et₂O and filtered. The solid is dried under reduced pressure at 40° C. for 2 days to afford the title compound as a dihydrochloride salt.

LCMS: MW (calcd): 504.5 m/z MW (obsd): 505.3 (M+H)

$^1$H NMR (400 MHz, DMSO-d₆) δ 8.87 (d, J=7.6 Hz, 1H), 8.37 (s, 1H), 7.45 (d, J=2.5 Hz, 1H), 7.33 (d, J=1.5 Hz, 1H), 7.27-7.20 (m, 2H), 4.76 (t, J=4.8 Hz, 2H), 4.37 (q, J=9.6 Hz, 2H), 3.95 (t, J=4.8 Hz, 4H), 3.89 (s, 3H), 3.65 (t, J=5.1 Hz, 4H), 3.59-3.41 (m, 2H), 3.25 (s, 2H), 3.01 (t, J=6.1 Hz, 2H).

2.62. Cpd 88 (Alternative Synthesis)

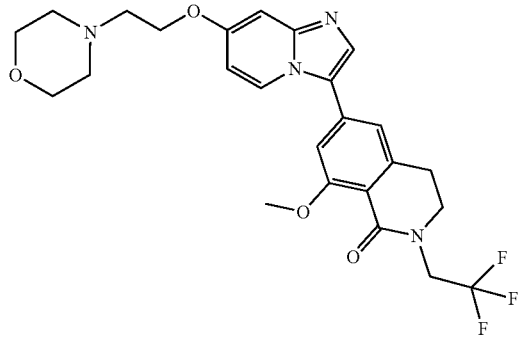 [SMILES: COc1cc(-c2cnc3cc(OCCN4CCOCC4)ccn23)cc2c1C(=O)N(CC(F)(F)F)CC2]

To a solution of Int 39 (597 g, 1.764 mol, 1.13 eq.) in 1,4-dioxane (3 L), under N₂ atmosphere, is added Int 25 as mixture of free base and di-HCl salt (500 g, 1.561 mol, 1 eq.). Under stirring, K₂CO₃ (755 g, 5.463 mol, 3.5 eq.), pivalic acid (CAS #75-98-9, 159 g, 1.561 mol, 1 eq.) and 1,4-dioxane (1 L) are added to the reaction mixture. Pd(dppf)Cl₂·DCM (CAS #95464-05-4; 63.7 g, 0.078 mol, 0.05 eq.) and 1,4-dioxane (1 L) are added. The reaction mixture is heated at 100° C. for 14 h. The reaction mixture is cooled down to 20° C. and filtered through a pad of Dicalite™ topped with a filter paper. The filter cake is rinsed with DCM (2 L). The filtrate is evaporated under reduced pressure and the resulting crude is suspended in a mixture of toluene (1.1 L) and EtOAc (1.1 L). The suspension is heated at reflux for 45 min, cooled down to RT and filtered. The solid is rinsed with EtOAc (1.1 L). The solid is dissolved in DCM (3.3 L) and silica-bound 2,4,6-trimercaptotriazine (SiliaMetS® DMT, SiliCycle Inc. Cat #R79030B; 371 g) is added. The suspension is heated at 35° C. for 1 h, cooled down to 20° C. and filtered on a sintered funnel. The filter cake is rinsed with DCM (1.4 L) and the filtrate is evaporated under reduced pressure. The residue is reslurried in EtOAc (0.8 L) at RT for 2 h. The suspension is filtered and the solid is washed with EtOAc (0.8 L) and dried to afford Cpd 88 as a free base.

To a solution of Cpd 88 (592 g) in EtOH (1.2 L), at 15° C., is slowly added a solution of 4N HCl in 1,4-dioxane (1.2 L). The suspension is stirred at 15° C. for 45 min and warmed to RT. The suspension is filtered, and the solid is washed with acetone (1.5 L), dried at 45° C. in a vacuum oven to afford the title compound as a dihydrochloride salt.

LCMS: MW (calcd): 504.5 m/z MW (obsd): 505.2 (M+H)

2.63. Cpd 101

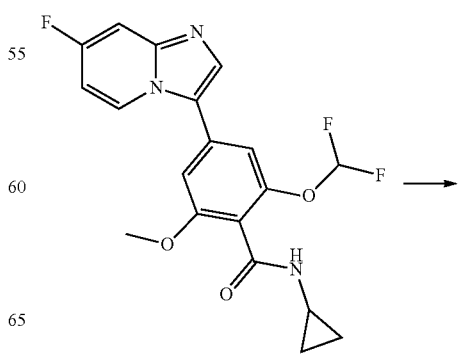

-continued

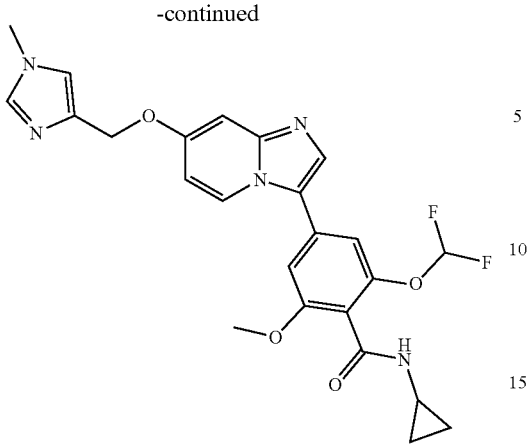

To a solution of (1-methylimidazol-4-yl)methanol (CAS #17289-25-7; 43 mg, 0.38 mmol, 5 eq.) in DMF (1 mL) at RT is added NaH (60% dispersion in mineral oil, 16 mg, 0.38 mmol, 5 eq.) and the mixture is stirred for 10 min. Then Int 1 (30 mg, 0.08 mmol, 1 eq.) is added and the reaction mixture is stirred at RT for 20 h. The reaction mixture is concentrated to dryness and the crude material is purified by flash chromatography on silica gel (eluting with MeOH 0 to 7% in DCM). The obtained residue is then taken up in DCM, the organic phase is washed with a 2N aq. NaOH solution and then passed through a phase separator. The filtrate is concentrated to afford Cpd 101.

2.64. Cpd 109

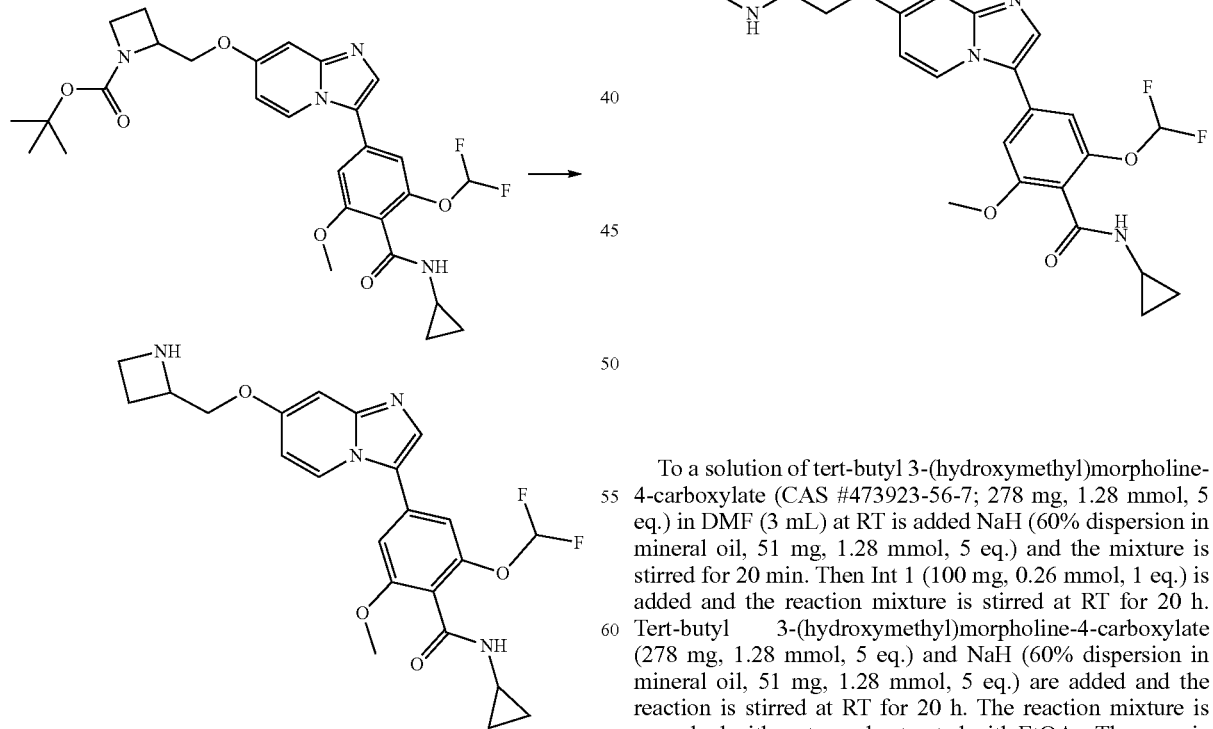

To a solution of Cpd 87 (14 mg, 0.025 mmol, 1 eq.) in DCM (0.2 mL) is added TFA (0.2 mL) and the mixture is stirred at RT for 1 h. The solvents are concentrated. The residue is taken up in water and the aqueous phase is washed with DCM and basified to pH 10 with a 1N NaOH aq. solution. A precipitate forms, the mixture is stirred for 10 min at RT and filtered. The solid is washed twice with water and dried to obtain Cpd 109.

2.65. Cpd 113

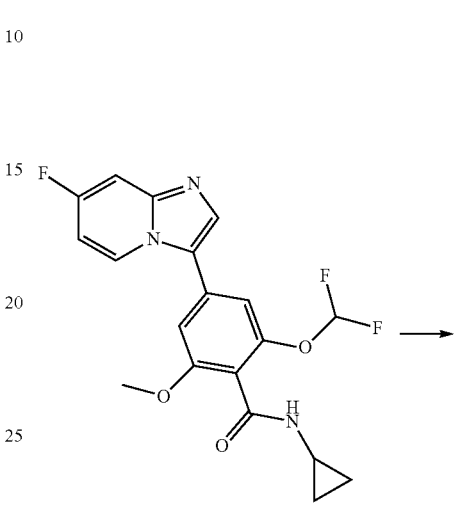

To a solution of tert-butyl 3-(hydroxymethyl)morpholine-4-carboxylate (CAS #473923-56-7; 278 mg, 1.28 mmol, 5 eq.) in DMF (3 mL) at RT is added NaH (60% dispersion in mineral oil, 51 mg, 1.28 mmol, 5 eq.) and the mixture is stirred for 20 min. Then Int 1 (100 mg, 0.26 mmol, 1 eq.) is added and the reaction mixture is stirred at RT for 20 h. Tert-butyl 3-(hydroxymethyl)morpholine-4-carboxylate (278 mg, 1.28 mmol, 5 eq.) and NaH (60% dispersion in mineral oil, 51 mg, 1.28 mmol, 5 eq.) are added and the reaction is stirred at RT for 20 h. The reaction mixture is quenched with water and extracted with EtOAc. The organic phase is washed with brine, dried over MgSO$_4$, filtered and concentrated in vacuo. The residue is purified by preparative HPLC to afford the title compound Cpd 113.

2.66. Cpd 122

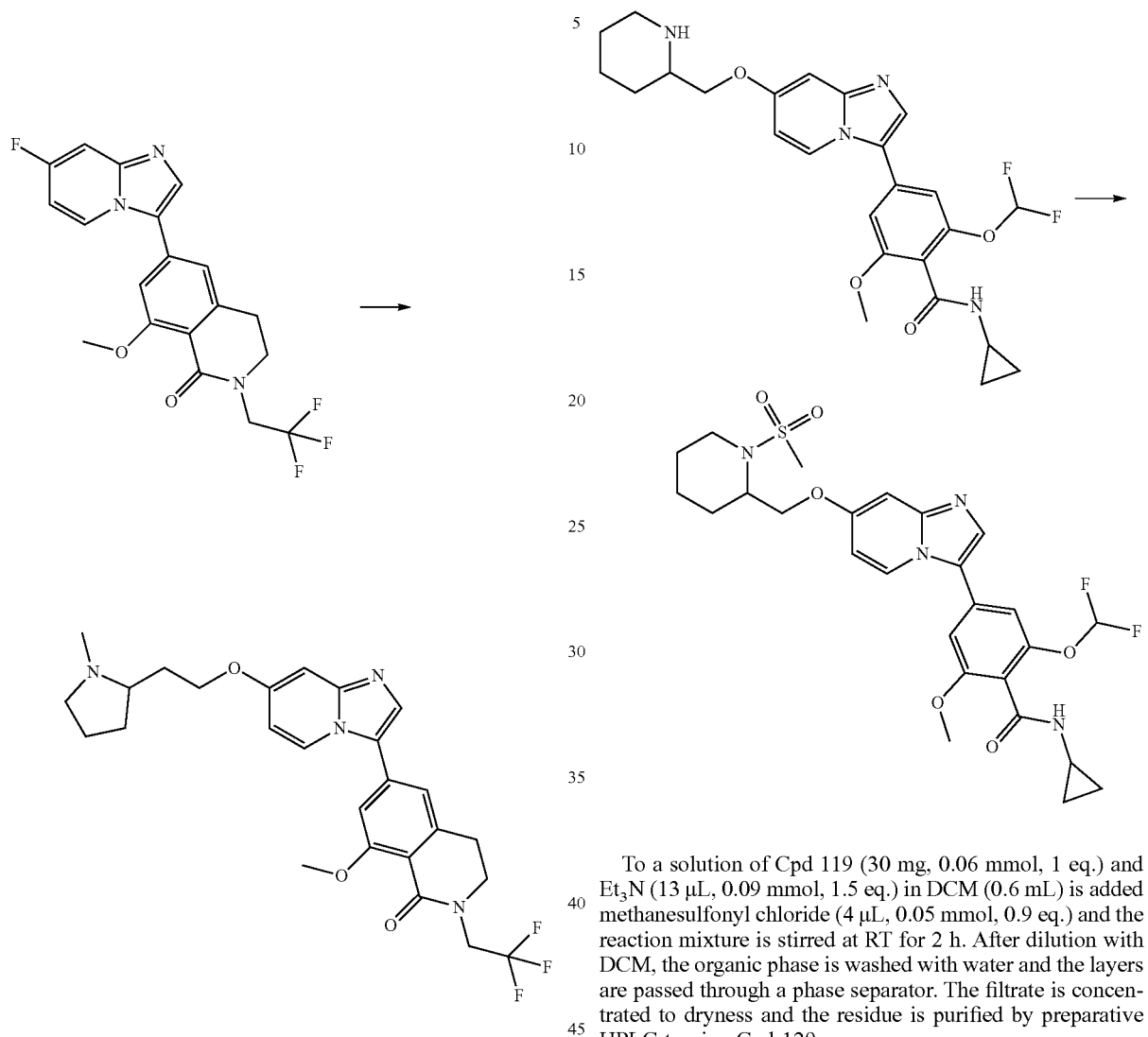

To a solution of 2-(1-methylpyrrolidin-2-yl)ethanol (CAS #67004-64-2; 63 µL, 0.46 mmol, 6 eq.) in DMF (1 mL) at RT is added NaH (60% dispersion in mineral oil, 18 mg, 0.46 mmol, 6 eq.) and the mixture is stirred for 10 min. Then Int 2 (30 mg, 0.08 mmol, 1 eq.) is added and the reaction mixture is stirred at RT for 20 h. 2-(1-methylpyrrolidin-2-yl)ethanol (63 µL, 0.46 mmol, 6 eq.) and NaH (60% dispersion in mineral oil, 18 mg, 0.46 mmol, 6 eq.) are added and the mixture is stirred at RT for 5 h. The reaction medium is concentrated, the residue is taken up in EtOAc and filtered. The filtrate is concentrated and the crude material purified by preparative HPLC. The obtained residue is dissolved in EtOAc, washed with 1N aq. NaOH and the aqueous phase is extracted twice with EtOAc. The combined organic phases are passed through a phase separator and concentrated to afford Cpd 122.

2.67. Cpd 129

To a solution of Cpd 119 (30 mg, 0.06 mmol, 1 eq.) and Et₃N (13 µL, 0.09 mmol, 1.5 eq.) in DCM (0.6 mL) is added methanesulfonyl chloride (4 µL, 0.05 mmol, 0.9 eq.) and the reaction mixture is stirred at RT for 2 h. After dilution with DCM, the organic phase is washed with water and the layers are passed through a phase separator. The filtrate is concentrated to dryness and the residue is purified by preparative HPLC to give Cpd 129.

2.68. Cpd 130

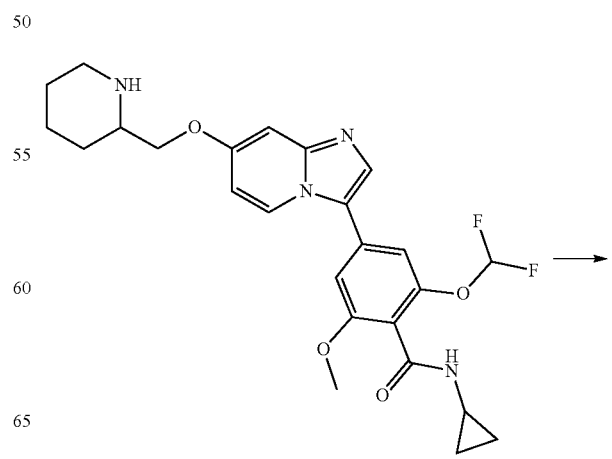

-continued

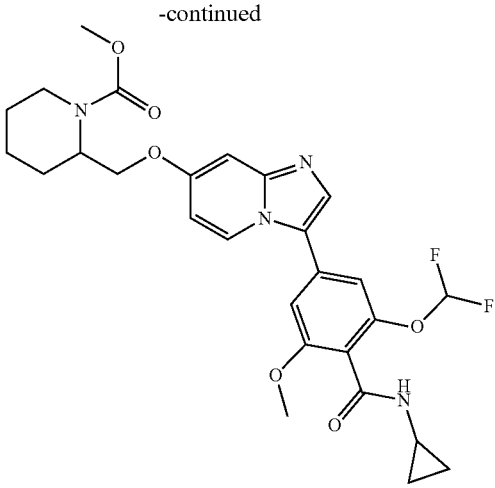

To a solution of Cpd 119 (30 mg, 0.06 mmol, 1 eq.) and Et₃N (13 µL, 0.09 mmol, 1.5 eq.) in DCM (0.6 mL) is added methyl chloroformate (4 µL, 0.05 mmol, 0.9 eq.) and the reaction mixture is stirred at RT for 2 h. After dilution with DCM, the organic phase is washed with water and the layers are passed through a phase separator. The filtrate is concentrated to dryness and the residue is purified by preparative HPLC to give Cpd 130.

2.69. Cpd 141

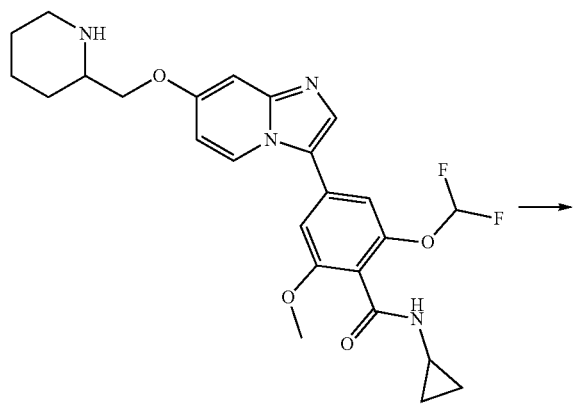

To a solution of Cpd 119 (30 mg, 0.06 mmol, 1 eq.) and Et₃N (13 µL, 0.09 mmol, 1.5 eq.) in DCM (0.6 mL) is added acetyl chloride (4 µL, 0.05 mmol, 0.9 eq.) and the reaction mixture is stirred at RT for 2 h. After dilution with DCM, the organic phase is washed with water and the layers are passed through a phase separator. The filtrate is concentrated to dryness and the residue is purified by preparative HPLC to give Cpd 141.

2.70. Cpd 150

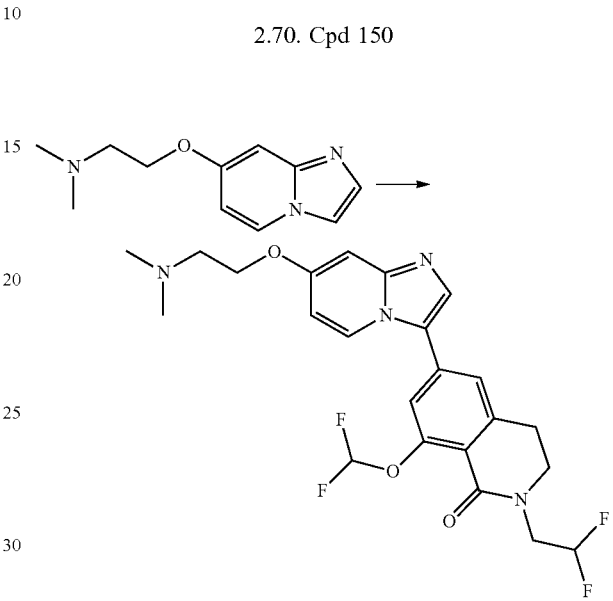

Int 3 (50 mg, 0.24 mmol, 1 eq.), Int 14 (58 mg, 0.16 mmol, 0.7 eq.), KOAc (47 mg, 0.48 mmol, 3 eq.) and Pd(dppf)Cl₂·DCM (CAS #95464-05-4, 7 mg, 0.008 mmol, 0.05 eq.) are suspended in dry and degassed DMAC (1.5 mL). The mixture is stirred at 110° C. for 2.5 h. The reaction medium is diluted with EtOAc, filtered over Celite® and the filtrate concentrated in vacuo. The residue is purified by preparative HPLC to afford on oily solid that is dissolved in minimum DCM. Et₂O is added and the gummy solid obtained is triturated until obtaining a powder. Filtration provides Cpd 150 in the form of a formic acid salt.

2.71. Cpd 153

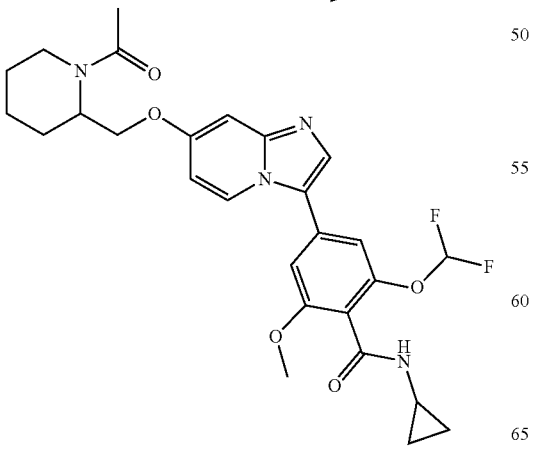

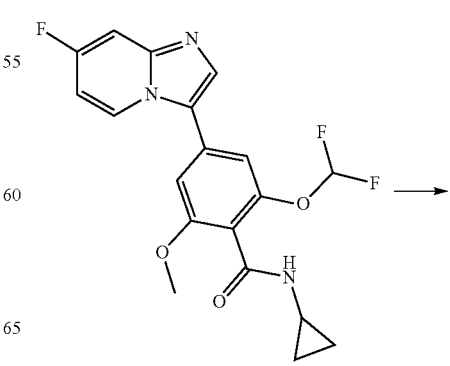

-continued

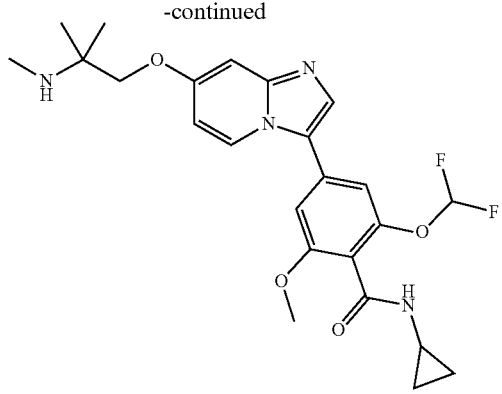

To a solution of 2-methyl-2-(methylamino)propan-1-ol (CAS #27646-80-6; 25 mg, 0.24 mmol) in dry DMF (3 mL) is added NaH (60% dispersion in mineral oil, 9.6 mg, 0.24 mmol) and the mixture is stirred at RT for 10 min. Int 1 (30 mg, 0.08 mmol) is added and the reaction mixture is stirred at 45° C. for 4 h. The reaction medium is diluted in a water/MeOH mixture and purified by preparative HPLC. The obtained product is dissolved in a DCM/water mixture and the aqueous layer is basified to pH 9 with an ammonia solution. The phases are separated and the organic layer is concentrated to afford Cpd 153.

2.72. Cpd 154

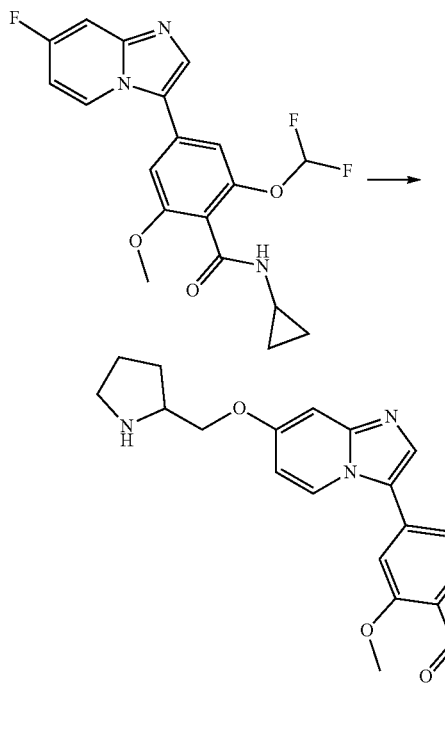

To a solution of pyrrolidin-2-ylmethanol (CAS #498-63-5; 242.8 mg, 2.40 mmol) in dry DMF (3 mL) is added NaH (60% dispersion in mineral oil, 96 mg, 2.40 mmol) and the mixture is stirred at RT for 10 min. Int 1 (300 mg, 0.80 mmol) is added and the reaction mixture is stirred at 45° C.

for 5.5 h. The reaction medium is diluted with DCM and quenched with a sat. aq. NaHCO$_3$ solution. The phases are separated, the organic layer is concentrated and the crude material is purified by chromatography on silica gel (eluting with a gradient of 0 to 1% MeOH in DCM with 0.5% of ammonia). The obtained product is triturated in DCM/i-Pr$_2$O, the solid is filtered and dried to afford Cpd 154.

2.73. Cpd 159

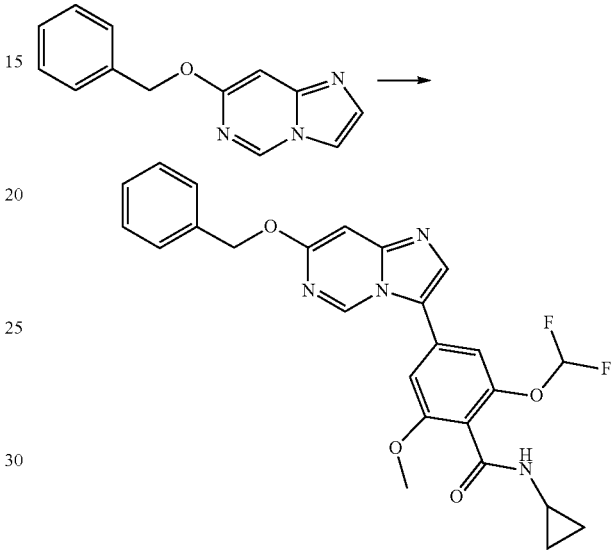

To a solution of Int 84 (65 mg, 0.31 mmol) in dry DMAC (3 mL) are added Int 11 (150 mg, 0.45 mmol), KOAc (150 mg, 1.53 mmol) and Pd(dppf)Cl$_2$ (CAS #72287-26-4; 30 mg, 0.04 mmol). The mixture is stirred at 110° C. for 4 h. The reaction is cooled down to RT, concentrated and the residue is taken up in DCM and water. The phases are separated. The organic layer is dried over MgSO$_4$, filtered and concentrated. The crude material is purified by chromatography on silica gel (eluting with a gradient of 0 to 100% EtOAc in heptane, then with EtOAc/(DCM/MeOH: 95/5): 1/1 and then eluting with EtOAc/(DCM/MeOH: 9/1): 1/1) to afford Cpd 159.

2.74. Cpd 160

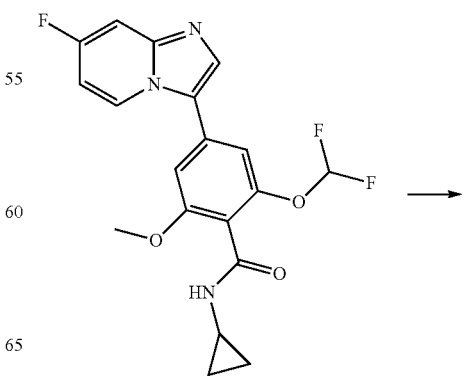

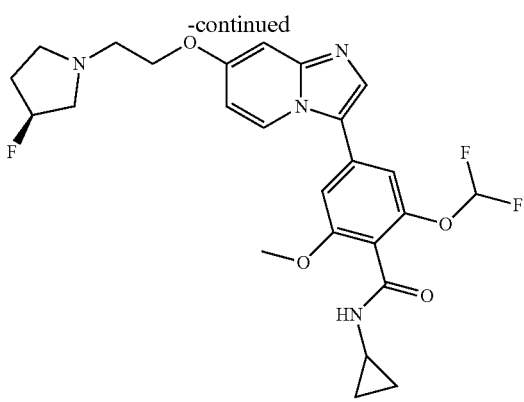

To a suspension of NaH (60% dispersion in mineral oil, 6 mg, 0.15 mmol) in dry DMF (50 μL) at 5° C. is added Int 63 (20 mg, 0.15 mmol) and the mixture is stirred at 5° C. for 10 min. Int 1 (15.0 mg, 0.038 mmol) is added and the reaction mixture is stirred at 45° C. for 2 h. The reaction mixture is diluted with DCM and quenched with water. The phases are separated, the organic layer is concentrated and the crude material is purified by chromatography on silica gel (eluting with a gradient of 0 to 30% MeOH in DCM). The obtained residue is dissolved in DCM and washed with a sat. aq. NaHCO₃ solution and water. The organic layer is dried over Na₂SO₄, filtered and concentrated to afford Cpd 160.

2.75. Cpd 165

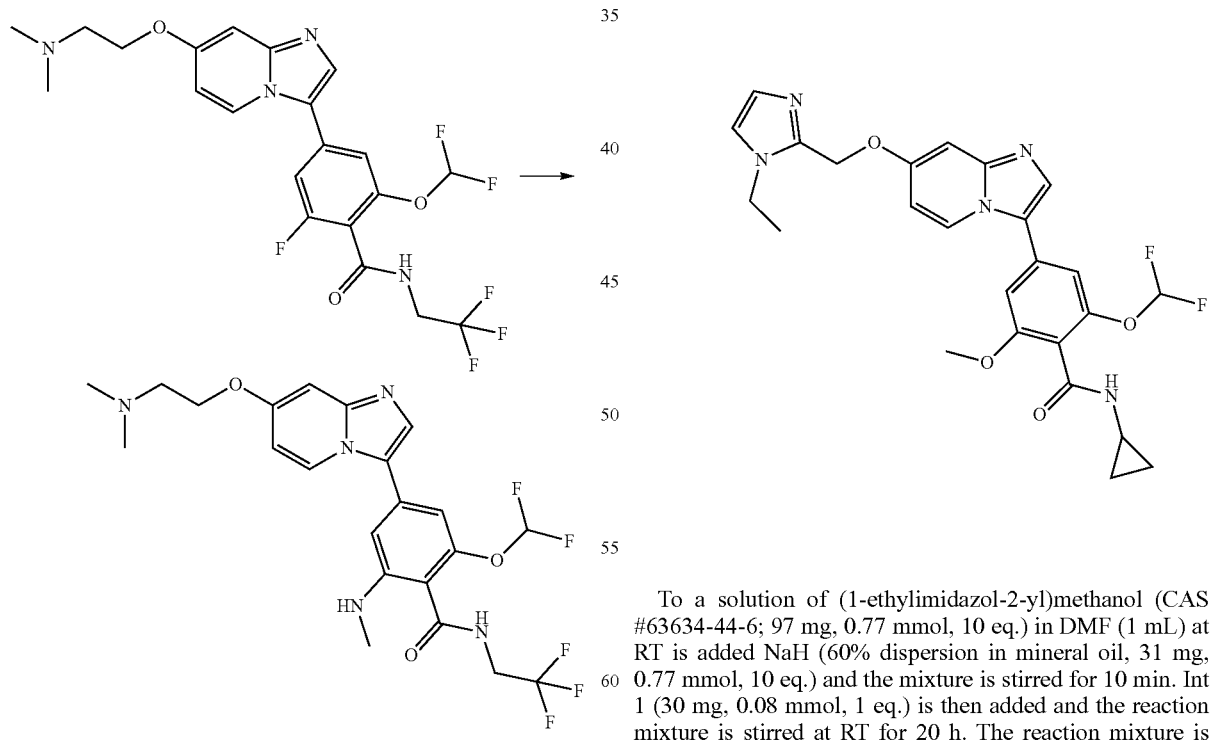

To a solution of Cpd 155 (50 mg, 0.10 mmol) in DMAC (497 μL) are added methylamine hydrochloride (CAS #593-51-1; 21 mg, 0.31 mmol) and DIPEA (107 μL, 0.61 mmol) and the reaction mixture is stirred at 100° C. for 6 h in a sealed vial. Methylamine hydrochloride (21 mg, 0.31 mmol) and DIPEA (107 μL, 0.61 mmol) are added and the reaction mixture heated at 120° C. overnight. Methylamine hydrochloride (21 mg, 0.31 mmol) and DIPEA (107 μL, 0.61 mmol) are added then the reaction mixture is stirred at 120° C. for 2 h and at 100° C. for 2 days. The reaction is quenched with water, the mixture is stirred for 10 min and extracted with DCM. The organic layer is passed through a phase separator and the filtrate is concentrated. The crude material is purified by flash chromatography on a Biotage® SNAP KP—NH cartridge (eluting with a gradient of 0 to 20% MeOH in DCM) to afford Cpd 165.

2.76. Cpd 173

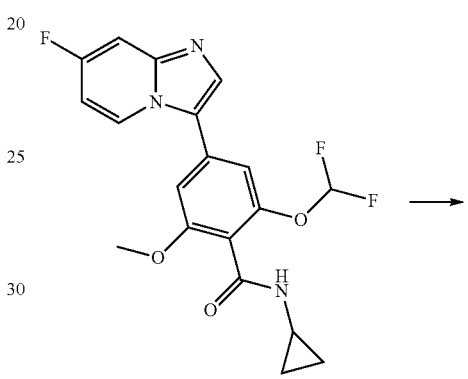

To a solution of (1-ethylimidazol-2-yl)methanol (CAS #63634-44-6; 97 mg, 0.77 mmol, 10 eq.) in DMF (1 mL) at RT is added NaH (60% dispersion in mineral oil, 31 mg, 0.77 mmol, 10 eq.) and the mixture is stirred for 10 min. Int 1 (30 mg, 0.08 mmol, 1 eq.) is then added and the reaction mixture is stirred at RT for 20 h. The reaction mixture is concentrated to dryness and the crude material is taken up in EtOAc and DCM. 2N aq. NaOH is added and the mixture is extracted with EtOAc. The organic phase is dried over Na₂SO₄, filtered and concentrated. The residue is purified by preparative HPLC to give Cpd 173.

2.77. Cpd 181

2.78. Cpd 182

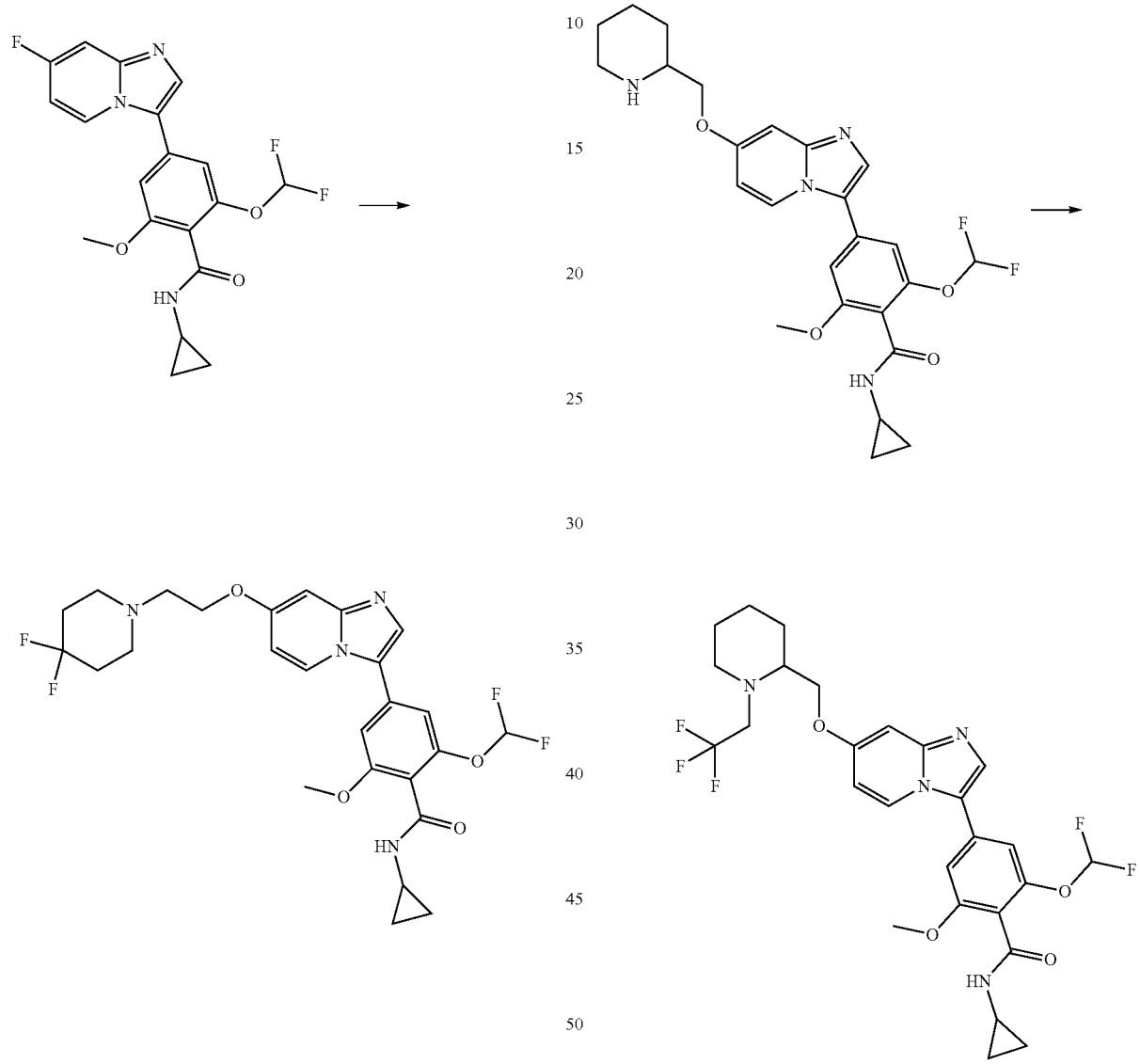

To a suspension of NaH (60% dispersion in mineral oil, 12 m g, 0.31 mmol) in dry DMF (50 µL) at 5° C. is added Int 64 (51 mg, 0.31 mmol) and the mixture is stirred at 5° C. for 10 min. Int 1 (30.0 mg, 0.077 mmol) is added and the reaction mixture is stirred at 45° C. for 4 h. The reaction mixture is diluted with DCM and quenched with water. The phases are separated, the organic layer is concentrated and the crude material is purified by chromatography on silica gel (eluting with a gradient of 0 to 40% MeOH in DCM). The residue is dissolved in DCM and washed with a sat. aq. NaHCO₃ solution, and water. The organic layer is dried over Na₂SO₄, filtered and concentrated to afford Cpd 181.

In an oven-dried flask fitted with a water condenser under Ar Cpd 119 (50 mg, 0.10 mmol) is dissolved in dry THF (3 mL). The reaction medium is heated at 70° C. and phenylsilane (CAS #694-53-1; 25 µL, 0.20 mmol) is added immediately by microsyringe, followed by TFA (14 µL, 0.18 mmol). The reaction mixture is stirred at reflux for 3 h. Phenylsilane (100 µL, 0.80 mmol) and TFA (100 µL) are added and the reaction mixture is heated at reflux overnight. The reaction medium is concentrated and the crude material is purified by preparative HPLC to afford Cpd 182.

2.79. Cpd 183

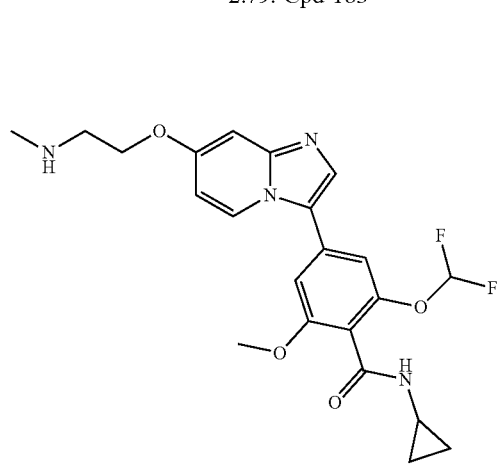

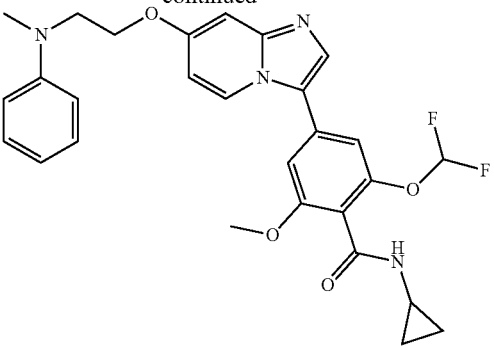

To a solution of Cpd 117 (40 mg, 0.09 mmol) in dry THF (600 µL) are added bromobenzene (CAS #108-86-1; 22 mg, 0.14 mmol), RuPhos Pd G3 (CAS #1445085-77-7; 3.4 mg, 0.004 mmol), RuPhos (CAS #787618-22-8; 2.3 mg, 0.005 mmol) and t-BuOK (31 mg, 0.32 mmol). The reaction mixture is degassed with N₂ and then stirred at 90° C. overnight. The reaction medium is diluted with brine and extracted with DCM. The crude material is purified by preparative HPLC to afford Cpd 184.

2.81. Cpd 187

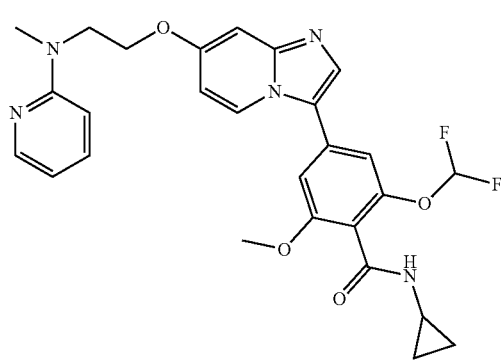

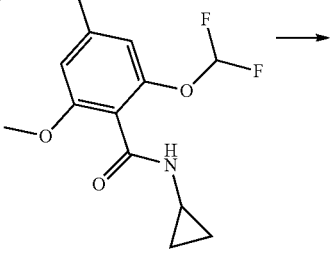

To a solution of Cpd 117 (40 mg, 0.09 mmol) in dry THF (600 µL) are added 2-bromopyridine (CAS #109-04-6; 14 mg, 0.09 mmol), RuPhos Pd G3 (CAS #1445085-77-7; 3 mg, 0.004 mmol), RuPhos (CAS #787618-22-8; 2 mg, 0.005 mmol) and t-BuOK (26 mg, 0.27 mmol). The reaction mixture is degassed with N₂ and then stirred at 90° C. overnight. The reaction medium is diluted with brine and extracted with DCM. The combined organic layers are concentrated to afford Cpd 183.

2.80. Cpd 184

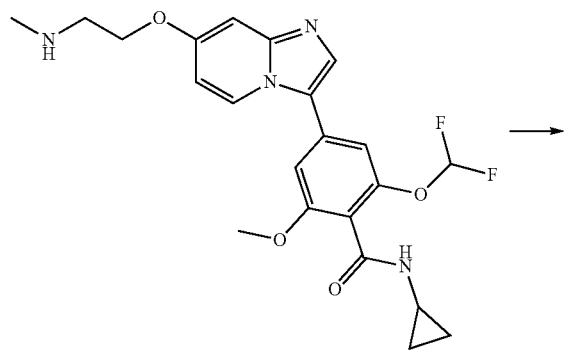

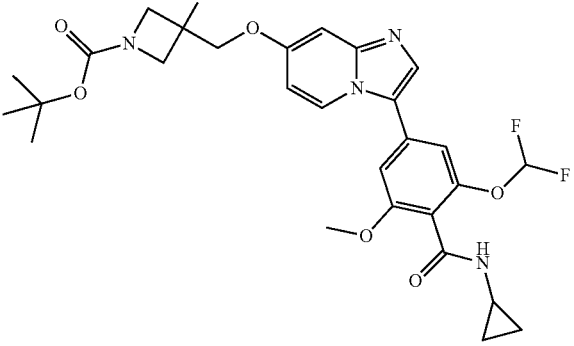

To a solution of tert-butyl 3-fluoro-3-(hydroxymethyl) azetidine-1-carboxylate (CAS #1126650-66-5; 157 mg, 0.77 mmol, 5 eq.) in DMF (1 mL) at RT is added NaH (60% dispersion in mineral oil, 31 mg, 0.77 mmol, 5 eq.) and the mixture is stirred for 10 min. Then Int 1 (60 mg, 0.15 mmol, 1 eq.) is added and the reaction mixture is stirred at RT for 20 h. The reaction is quenched with water and a precipitate forms. The solid is filtered, dried and purified by preparative HPLC to give Cpd 187.

2.82. Cpd 188

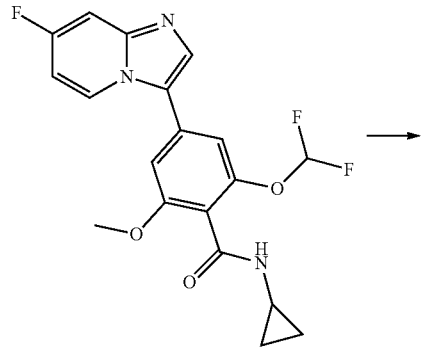

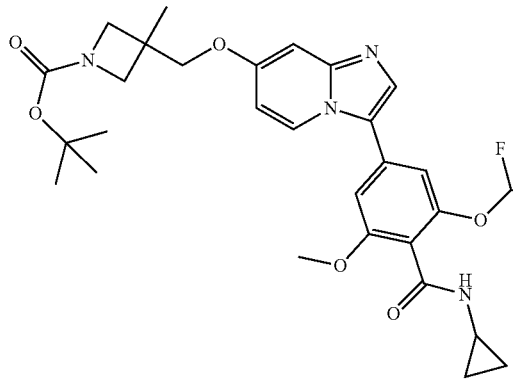

To a solution of tert-butyl tert-butyl 3-(hydroxymethyl)-3-methyl-azetidine-1-carboxylate (CAS #1363382-91-5; 154 mg, 0.77 mmol, 5 eq.) in DMF (1 mL) at RT is added NaH (60% dispersion in mineral oil, 31 mg, 0.77 mmol, 5 eq.) and the mixture is stirred for 10 min. Then Int 1 (60 mg, 0.15 mmol, 1 eq.) is added and the reaction mixture is stirred at RT for 20 h. The reaction is quenched with water and a precipitate forms. The solid is filtered, the filtrate is basified with 2N aq. NaOH and extracted with DCM. The organic phase is dried over $Na_2SO_4$, filtered and concentrated. The residue is purified by flash chromatography on silica gel (eluting with MeOH in DCM, 1 to 2%) to afford Cpd 188.

2.83. Cpd 189

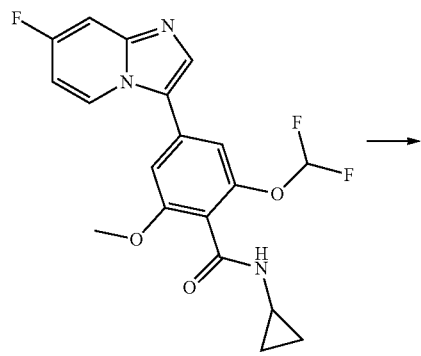

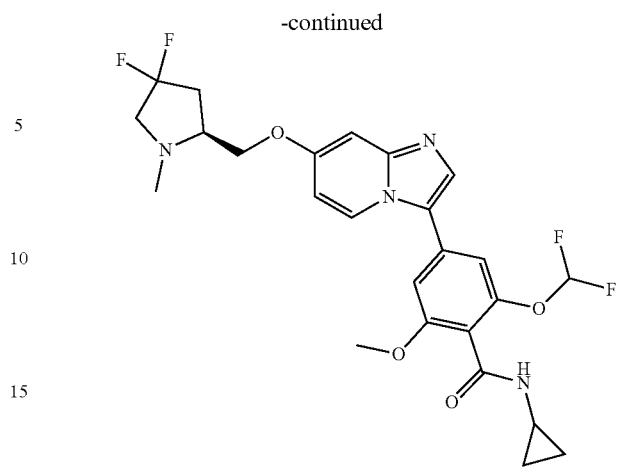

To a solution of [(2S)-4,4-difluoro-1-methyl-pyrrolidin-2-yl]methanol (CAS #1408057-44-2; 115 mg, 0.77 mmol, 10 eq.) in DMF (1 mL) at RT is added NaH (60% dispersion in mineral oil, 31 mg, 0.77 mmol, 10 eq.) and the mixture is stirred for 10 min. Then Int 1 (30 mg, 0.08 mmol, 1 eq.) is added and the reaction mixture is stirred at RT for 20 h. The reaction is quenched with water and 1N aq. NaOH. A precipitate forms and the solid is filtered. The solid is washed with water and pentane and is then purified by flash chromatography on silica gel to give Cpd 189.

2.84. Cpd 197

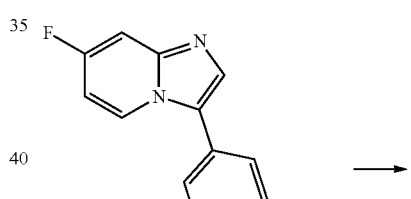

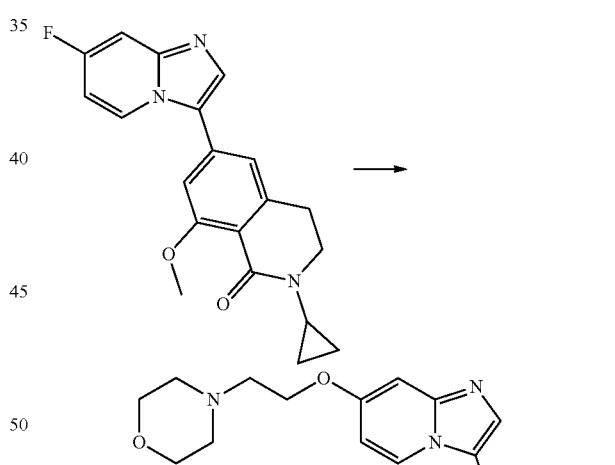

To a solution of 2-morpholinoethanol (CAS #622-40-2; 95 µL, 0.78 mmol) in dry DMF (2.1 mL) is added NaH (60% dispersion in mineral oil, 19 mg, 0.78 mmol) and the mixture is stirred at RT for 5 min. Int 21 (55.0 mg, 0.16 mmol) is added and the reaction mixture is stirred at RT for 3 h.

2-morpholinoethanol (95 µL, 0.78 mmol) and NaH (60% dispersion in mineral oil, 19 mg, 0.78 mmol) are added and the reaction mixture is stirred at RT for 2 h. The reaction mixture is quenched with a sat. aq. NaHCO₃ solution and extracted with EtOAc. The combined organic layers are dried over MgSO₄, filtered and concentrated. The crude material is purified by chromatography on silica gel (eluting with a gradient of 0 to 10% MeOH in DCM). The obtained residue is dissolved in DCM and washed with a 1N aq. NaOH solution. The organic layer is passed through a phase separator and concentrated to afford Cpd 197.

2.85. Cpd 209

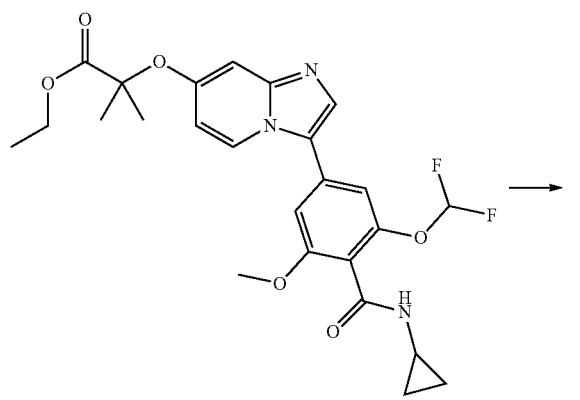

To a solution of Int 73 (70 mg, 0.139 mmol) in dry THF (2 mL) at 0° C. is added dropwise a solution of LiAlH₄ 1M in THF (550 µL, 0.55 mmol) and the reaction mixture is stirred at RT for 1 h. The reaction medium is quenched with a 10% aq. NaOH solution and water, and the resulting mixture is stirred at RT for 20 min. The suspension is filtered through a pad of Celite® and washed with EtOAc. The filtrate is filtered through phase separator and concentrated. The crude material is purified by chromatography on silica gel (eluting with a gradient of 0 to 9% MeOH in DCM with 1.5% ammonia) to afford Cpd 209.

2.86. Cpd 217

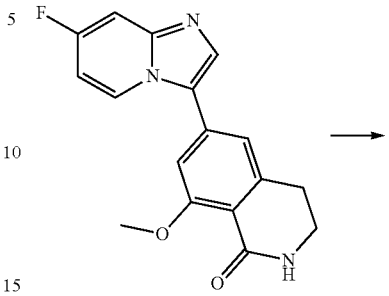

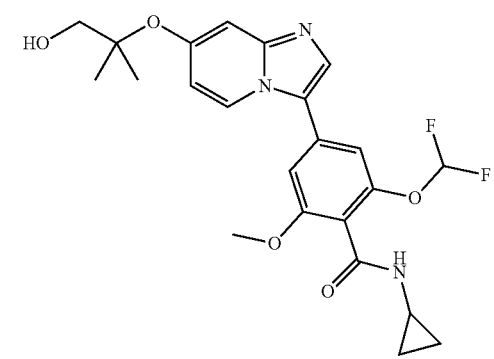

To a solution of 2-morpholinoethanol (195 µM, 1.61 mmol, 10 eq.) in DMF (1.5 mL) at RT is added NaH (60% dispersion in mineral oil, 38 mg, 0.96 mmol, 6 eq.) and the mixture is stirred for 15 min. Then Int 23 (50 mg, 0.16 mmol, 1 eq.) is added and the reaction mixture is stirred at RT for 96 h. The reaction mixture is concentrated, the residue is taken up in EtOAc and DCM and filtered. The filtrate is concentrated and the crude material is purified by flash chromatography on silica gel (eluting with MeOH 0 to 10% in DCM). The obtained residue is taken up with a minimum of EtOAc, Et₂O is added and the mixture sonicated. The obtained precipitate is filtered, dissolved in DCM and washed 3 times with 1N aq. NaOH. The organic layer is passed through a phase separator. The filtrate is evaporated to afford Cpd 217.

2.87. Cpd 221

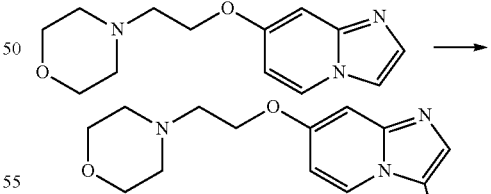

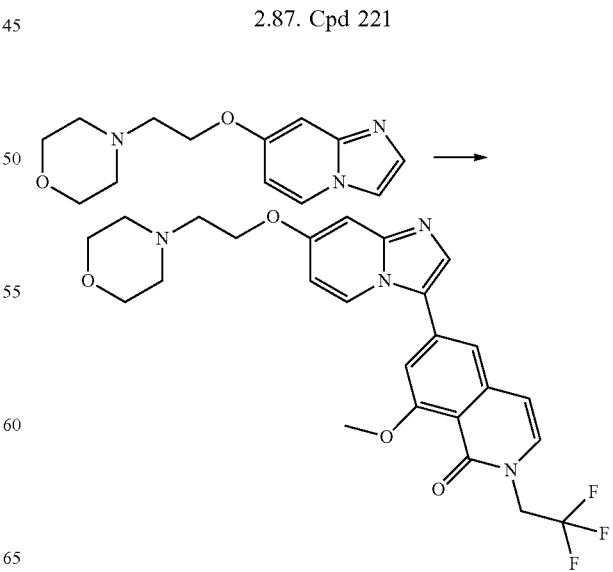

Int 25 (29 mg, 0.12 mmol, 1 eq.), Int 26 (30 mg, 0.09 mmol, 0.77 eq.), KOAc (18 mg, 0.18 mmol, 2 eq.) and Pd(dppf)Cl$_2$·DCM (CAS #95464-05-4, 4 mg, 0.004 mmol, 0.05 eq.) are suspended in dry and degassed DMAC (0.9 mL). The mixture is stirred at 120° C. for 2 h. The reaction medium is concentrated in vacuo. The residue is purified by preparative HPLC to give a solid that is dissolved in EtOAc. The organic phase is washed with a sat. aq. NaHCO$_3$ solution and dried over MgSO$_4$. Filtration and concentration afford Cpd 221.

2.88. Cpd 224

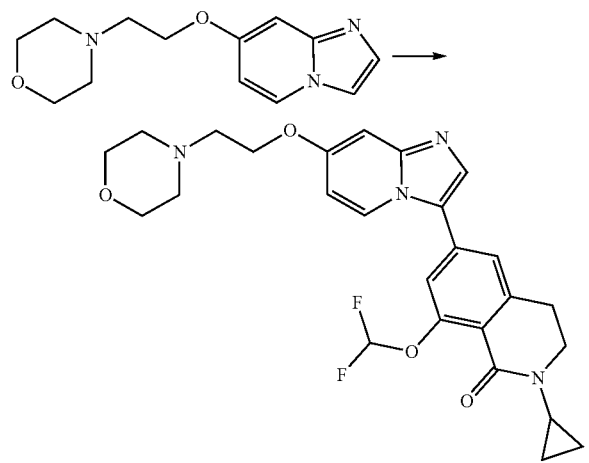

Int 25 (39 mg, 0.16 mmol, 1 eq.), Int 28 (40 mg, 0.12 mmol, 0.77 eq.), KOAc (24 mg, 0.24 mmol, 2 eq.) and Pd(dppf)Cl$_2$·DCM (CAS #95464-05-4, 5 mg, 0.006 mmol, 0.05 eq.) are suspended in dry and degassed DMAC (1.2 mL). The mixture is stirred at 120° C. for 2 h. The reaction medium is concentrated in vacuo. The crude material is purified by flash chromatography on silica gel followed by preparative HPLC. The obtained residue is dissolved in DCM, the organic phase is washed with a sat. aq. NaHCO$_3$ solution and passed through a phase separator. Concentration of the filtrate affords Cpd 224.

2.89. Cpd 247

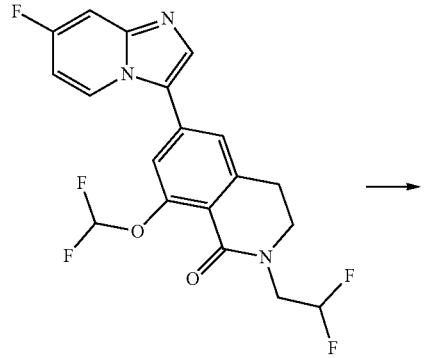

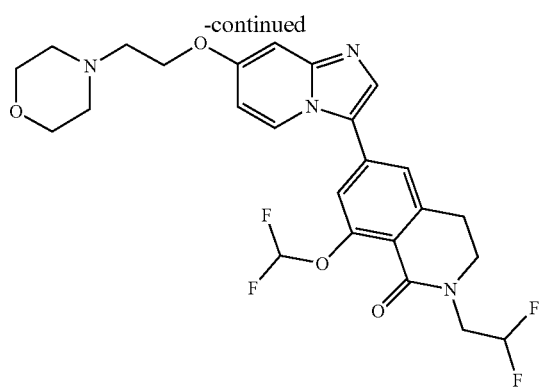

To a solution of 2-morpholinoethanol (CAS #622-40-2; 24 µL, 0.19 mmol) in dry DMF (900 µL) is added NaH (60% dispersion in mineral oil, 8 mg, 0.19 mmol) and the mixture is stirred at RT for 10 min. Int 32 (40 mg, 0.10 mmol) is added and the reaction mixture is stirred at RT for 4 h. A solution of 2-morpholinoethanol (12 µL, 0.10 mmol) and NaH (60% dispersion in mineral oil, 4 mg, 0.10 mmol) in DMF (1 mL) is added and the reaction mixture is stirred at RT overnight. A solution of 2-morpholinoethanol (12 µL, 0.10 mmol) and NaH (60% dispersion in mineral oil, 4 mg, 0.10 mmol) in DMF (1 mL) is added and the reaction mixture is stirred at RT for 1 h. The reaction medium is quenched with a sat. aq. NaHCO$_3$ solution and extracted with EtOAc. The combined organic layers are dried over MgSO$_4$, filtered and concentrated. The crude material is purified by chromatography on silica gel (eluting with a gradient of 0 to 10% MeOH in DCM) and by preparative HPLC to afford Cpd 247.

2.90. Cpd 255

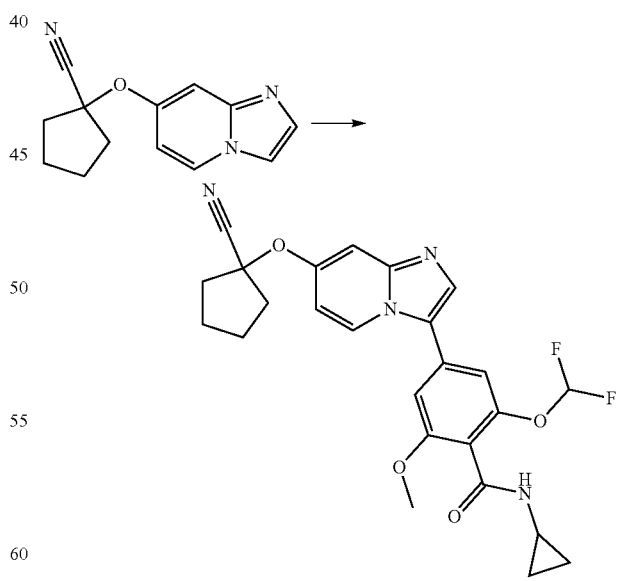

Int 81 (15 mg, 0.07 mmol, 1 eq.), Int 11 (33 mg, 0.10 mmol, 1.5 eq.) and KOAc (19 mg, 0.20 mmol, 3 eq.) are suspended in dry DMAC (1 mL) and the mixture is degassed with N$_2$. Then Pd(dppf)Cl$_2$·DCM (CAS #95464-05-4, 3 mg, 0.003 mmol, 0.05 eq.) is added and the reaction mixture is

2.91. Cpd 256

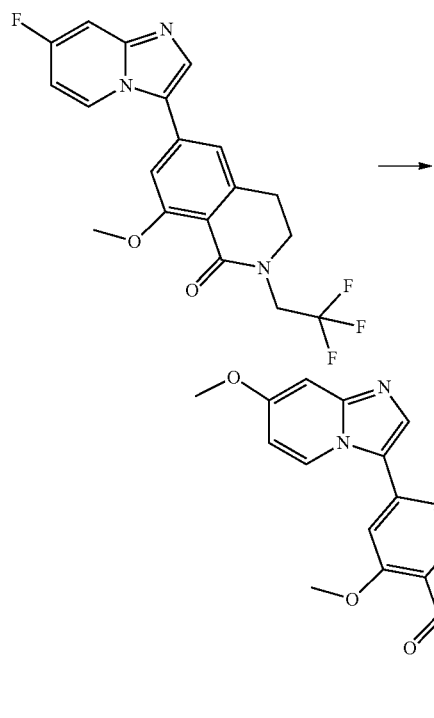

To a solution of 2-morpholinoethanol (6 mL, 49.6 mmol, 5 eq.) in DMF (140 mL) at RT is added NaH (60% dispersion in mineral oil, 1.6 g, 39.7 mmol, 4 eq.) and the mixture is stirred for 10 min. Then the reaction medium is cooled to 0° C. and Int 2 (3.9 g, 9.92 mmol, 1 eq., containing 0.4 mol. eq. % of MeOH) in DMF (20 mL) is added and the mixture is stirred at RT for 2 h. Cpd 256 forms as a by-product of the reaction. The reaction mixture is hydrolyzed by a sat. aq. NaHCO$_3$ solution and water and the aqueous phase is extracted with EtOAc. The combined organic layers are dried over Na$_2$SO$_4$, filtered and concentrated. The obtained residue is dissolved in DCM and washed with 2N aq. NaOH. The combined organic layers are dried over Na$_2$SO$_4$, filtered and concentrated. The crude material is purified by flash chromatography on silica gel (eluting with MeOH 0 to 8% in DCM), the fractions containing Cpd 256 are collected and evaporated. The obtained residue is triturated in Et$_2$O to give Cpd 256.

2.92. Cpd 260

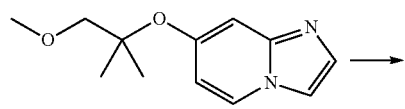

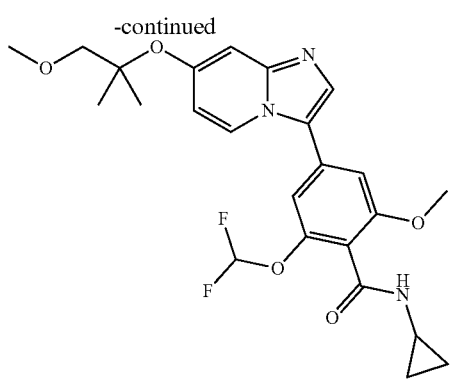

Int 65 (18 mg, 0.08 mmol, 1 eq.), Int 11 (30 mg, 0.09 mmol, 1.1 eq.), KOAc (24 mg, 0.25 mmol, 3 eq.) and Pd(dppf)Cl$_2$·DCM (CAS #95464-05-4, 7 mg, 0.008 mmol, 0.1 eq.) are suspended in dry DMAC (1 mL). The mixture is stirred at 100° C. for 2 h. The reaction medium is diluted with water and extracted with EtOAc. The organic layer is then dried over Na$_2$SO$_4$, filtered and concentrated in vacuo. The crude material is purified by flash chromatography on silica gel to afford Cpd 260.

2.93. Cpd 263

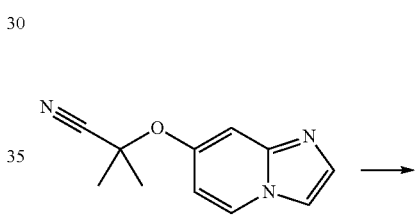

Int 68 (64 mg, 0.32 mmol, 1 eq.), Int 11 (118 mg, 0.35 mmol, 1.1 eq.), KOAc (94 mg, 0.95 mmol, 3 eq.) and Pd(dppf)Cl$_2$·DCM (CAS #95464-05-4, 26 mg, 0.03 mmol, 0.1 eq.) are suspended in dry DMAC (3 mL). The mixture is stirred at 100° C. for 20 h. The reaction medium is diluted with water and extracted with EtOAc. The organic layer is then dried over Na$_2$SO$_4$, filtered and concentrated in vacuo. The crude material is purified by flash chromatography on silica gel to afford Cpd 263.

2.94. Cpd 264

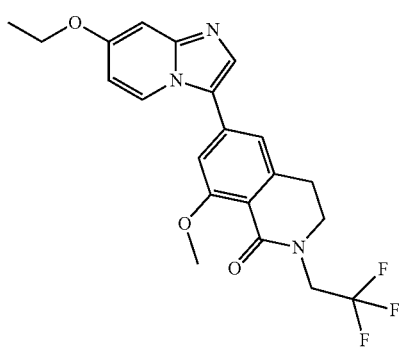 [SMILES: CCOc1ccn2c(-c3cc4c(c(OC)c3)C(=O)N(CC(F)(F)F)CC4)cnc2c1]

To a solution of [(2S)-1,4-dioxan-2-yl]methanol (CAS #406913-93-7; 5.80 g, 49.1 mmol) in dry DMF (100 mL) at 0° C. is added NaH (60% dispersion in mineral oil; 1.96 g, 49.1 mmol) and the mixture is stirred at RT for 20 min. Int 2 (4.83 g, 12.3 mmol) is added, and dry DMF (100 mL) is added. The reaction mixture is stirred at RT for 3 h. The reaction mixture is quenched with a sat. aq. NaHCO$_3$ solution and water under ice cooling. The mixture is extracted with EtOAc. The combined organic layers are washed with brine, dried over MgSO$_4$, filtered and concentrated. The crude is purified by chromatography on silica gel (eluting with a gradient of 0 to 10% MeOH in EtOAc) and the fractions corresponding to 6-(7-ethoxyimidazo[1,2-a]pyridin-3-yl)-8-methoxy-2-(2,2,2-trifluoroethyl)-3,4-dihydroisoquinolin-1-one are concentrated. The obtained residue is purified by preparative HPLC to afford Cpd 264.

2.95. Cpd 266

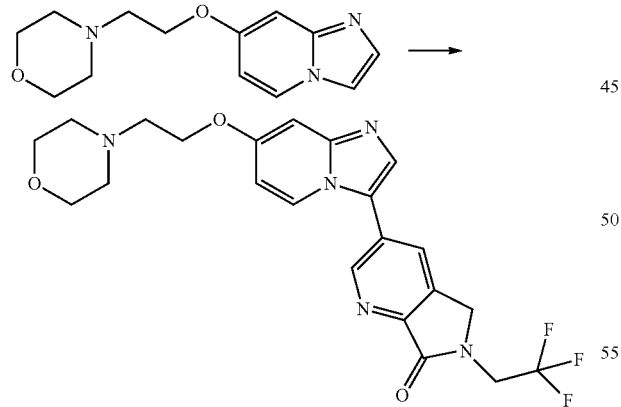

Int 25 (34 mg, 0.14 mmol, 1 eq.), Int 37 (41 mg, 0.14 mmol, 1 eq.), KOAc (27 mg, 0.28 mmol, 2 eq.) and Pd(dppf)Cl$_2$·DCM (CAS #95464-05-4, 11 mg, 0.014 mmol, 0.1 eq.) are suspended in dry and degassed DMAC (1.3 mL). The mixture is stirred at 110° C. for 2 h. The reaction medium is concentrated in vacuo. The crude material is purified by flash chromatography on silica gel. The obtained residue is triturated in MeOH and filtered to afford Cpd 266.

2.96. Cpd 268

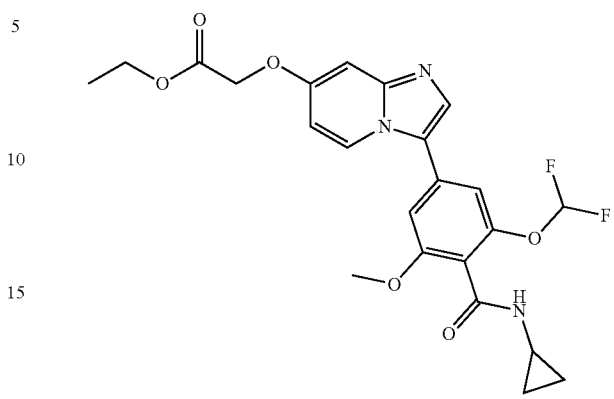

Ethyl 2-iodoacetate (CAS #623-48-3, 15.2 μL, 0.128 mmol, 1.0 eq.) is added to a suspension of Int 96 (50.0 mg, 0.128 mmol, 1 eq.) and Cs$_2$CO$_3$ (50.2 mg, 0.154 mmol, 1.2 eq.) in anhydrous DMF (1.0 mL) and the reaction is stirred at RT. After 1 h, the reaction mixture is diluted with EtOAc (10 mL) and washed with water. The organic layer is dried over Na$_2$SO$_4$, filtered and evaporated to dryness to afford Cpd 268.

2.97. Cpd 270

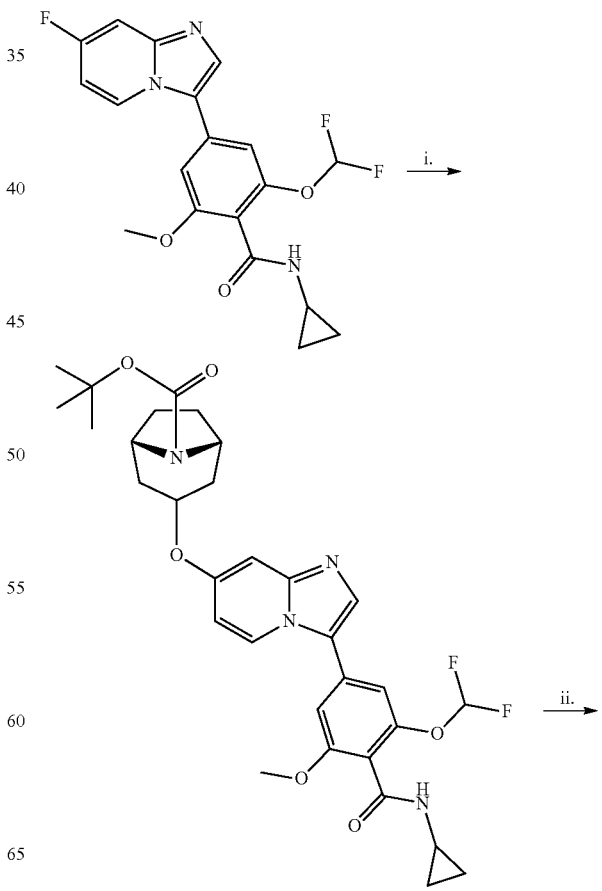

2.97.1. Step i: tert-butyl (1R,5S)-3-[3-[4-(cyclopropylcarbamoyl)-3-(difluoromethoxy)-5-methoxy-phenyl]imidazo[1,2-a]pyridin-7-yl]oxy-8-azabicyclo[3.2.1]octane-8-carboxylate

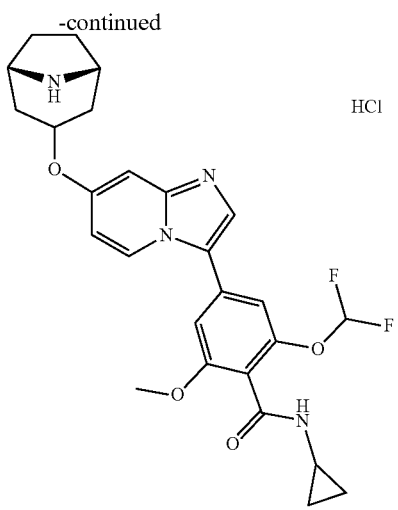

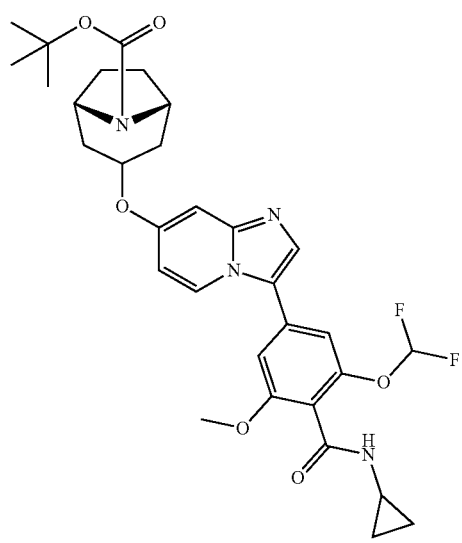 [SMILES: COc1cc(-c2cnc3cc(OC4C[C@H]5CC[C@@H](C4)N5C(=O)OC(C)(C)C)ccn23)cc(OC(F)F)c1C(=O)NC1CC1]

Tert-butyl(1R,5S)-3-hydroxy-8-azabicyclo[3.2.1]octane-8-carboxylate (CAS #478837-18-2; (232 mg, 1 mmol, 4 eq.) is dissolved in dry DMF (2 mL) and NaH (60% dispersion in mineral oil, 40.9 mg, 1 mmol, 4 eq.) is added. The reaction mixture is stirred for 10 min at RT and Int 1 (100 mg, 0.25 mmol, 1.0 eq.) is added. The reaction mixture is stirred at RT overnight. Further NaH (40.9 mg, 1.0 mmol, 4 eq.) and tert-butyl(1R,5S)-3-hydroxy-8-azabicyclo[3.2.1]octane-8-carboxylate (232 mg, 1 mmol, 4 eq.) is added under stirring at RT. The reaction mixture is diluted with water and extracted with DCM. The organic layers are combined, dried over Na₂SO₄, filtered and evaporated under reduced pressure. The crude product is purified by flash chromatography on silica gel (eluting with 0 to 10% MeOH in DCM) to afford tert-butyl (1R,5S)-3-[3-[4-(cyclopropylcarbamoyl)-3-(difluoromethoxy)-5-methoxy-phenyl]imidazo[1,2-a]pyridin-7-yl]oxy-8-azabicyclo[3.2.1]octane-8-carboxylate.

LCMS: MW (calcd): 598.3; m/z MW (obsd): 599.4 (M+H)

2.97.2. Step ii: Cpd 270

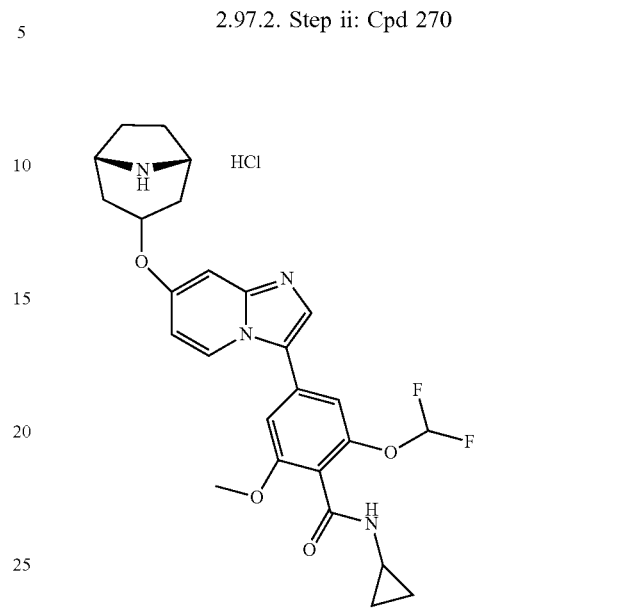

HCl, 4N in 1,4-dioxane (1.84 mL) is added to tert-butyl (1R,5S)-3-[3-[4-(cyclopropylcarbamoyl)-3-(difluoromethoxy)-5-methoxy-phenyl]imidazo[1,2-a]pyridin-7-yl]oxy-8-azabicyclo[3.2.1]octane-8-carboxylate (57 mg, 0.085 mmol, 1.0 eq.). The reaction mixture is stirred at RT for 2 h, then evaporated under reduced pressure to afford Cpd 270 as a hydrochloride salt.

2.98. Cpd 279

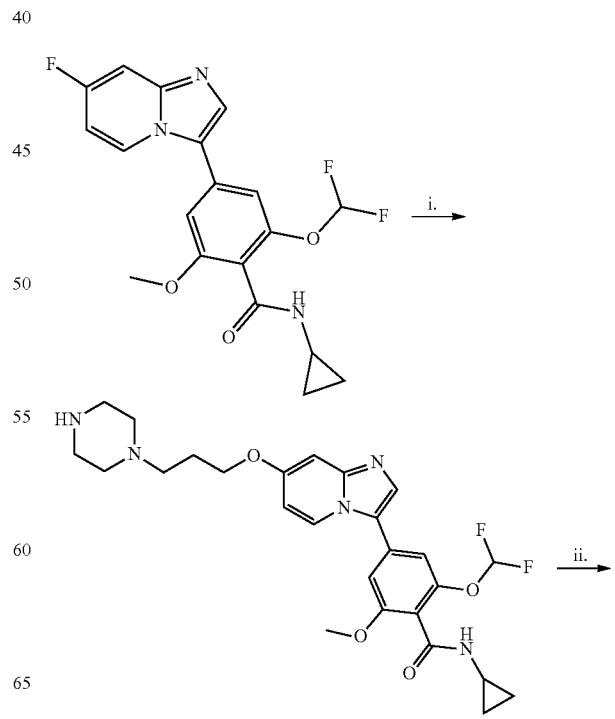

2.98.1. Step i: N-cyclopropyl-2-(difluoromethoxy)-6-methoxy-4-[7-(3-piperazin-1-ylpropoxy)imidazo[1,2-a]pyridin-3-yl]benzamide

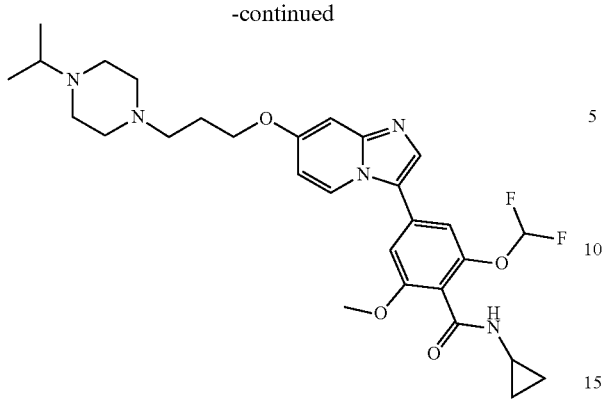

1-Piperazinepropanol (CAS #5317-32-8; 147 mg, 1.02 mmol, 2 eq.) is dissolved in dry DMF (2 mL), cooled in an ice bath and NaH (60% dispersion in mineral oil, 40.9 mg, 1 mmol, 2 eq.) is added portionwise. The reaction mixture is stirred for 10 min and then Int 1 (200 mg, 0.5 mmol, 1 eq.) is added. The reaction mixture is allowed to slowly warm to RT overnight under stirring. Another portion of 1-piperazinepropanol (147 mg, 1 mmol, 2 eq.) and NaH (40.9 mg, 1 mmol, 2 eq.) is added. The reaction mixture is stirred at RT overnight, then diluted with water and extracted with EtOAc. The organic layers are combined, dried over Na$_2$SO$_4$, filtered and evaporated under reduced pressure. The crude product is purified by flash chromatography on silica gel (eluting with 0 to 25% MeOH in DCM) to afford N-cyclopropyl-2-(difluoromethoxy)-6-methoxy-4-[7-(3-piperazin-1-ylpropoxy)imidazo[1,2-a]pyridin-3-yl]benzamide.

LCMS: MW (calcd): 515.2; m/z MW (obsd): 516.1 (M+H)

2.98.2. Step ii: Cpd 279

N-cyclopropyl-2-(difluoromethoxy)-6-methoxy-4-[7-(3-piperazin-1-ylpropoxy)imidazo[1,2-a]pyridin-3-yl]benzamide (100 mg, 0.2 mmol, 1 eq.) is dissolved in dry acetone (2 mL). Two drops of AcOH are added. The reaction mixture is cooled in an ice bath and NaBH(OAc)$_3$ (CAS #56553-60-7; 82.2 mg, 0.4 mmol, 2 eq.) is added. The reaction mixture is allowed to warm to RT for 3 h, and then diluted with water and extracted with DCM. The organic layers are combined, dried over Na$_2$SO$_4$, filtered and evaporated under reduced pressure. The crude product is purified by flash chromatography on silica gel (eluting with 0 to 25% MeOH in DCM) to afford Cpd 279.

2.99. Cpd 282

To a cooled (0° C.) solution of propane-1,3-diol (373 µL, 5.06 mmol, 4.0 eq.) in DMF, dried on 3 Å molecular sieves (2.5 mL) is added NaH (60% dispersion in mineral oil, 96.1 mg, 2.40 mmol, 1.9 eq.). The mixture is warmed-up to RT and is stirred for 30 min. Int 1 (500 mg, 1.26 mmol, 1.0 eq.) is then added in one portion. The mixture is stirred at RT for 16 h, then poured into 50 mL of sat. NaHCO$_3$ aq. solution, and extracted with 3×40 mL of EtAOc. The gathered organic layers are washed with 30 mL of sat. NaHCO$_3$ aq. solution followed by 30 mL of brine, dried over Na$_2$SO$_4$, filtered, and evaporated at 40° C. to dryness. The resulting crude is purified by flash chromatography on silica gel (eluting with 0 to 4% MeOH in DCM) to afford Cpd 282.

2.100. Cpd 287

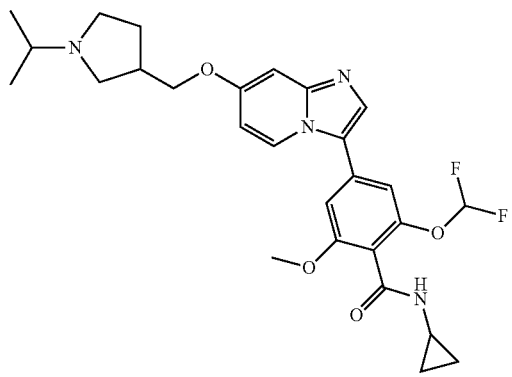 [SMILES: COc1cc(-c2cnc3cc(OCC4CCN(C(C)C)C4)ccn23)cc(OC(F)F)c1C(=O)NC1CC1]

Int 99 (100 mg, 0.21 mmol, 1 eq.) is dissolved in dry acetone (2 mL). Two drops of AcOH are added. The reaction mixture is cooled in an ice bath and NaBH(OAc)$_3$ (CAS #56553-60-7; 89.7 mg, 0.42 mmol, 2 eq.) is added. The reaction mixture is allowed to warm to RT. After 2 h, the reaction is diluted with water and extracted with DCM. The organic layers are combined, dried over Na$_2$SO$_4$, filtered and evaporated under reduced pressure. The crude product is purified by flash chromatography on silica gel (eluting with 0 to 30% MeOH in DCM) to afford Cpd 287.

2.101. Cpd 288

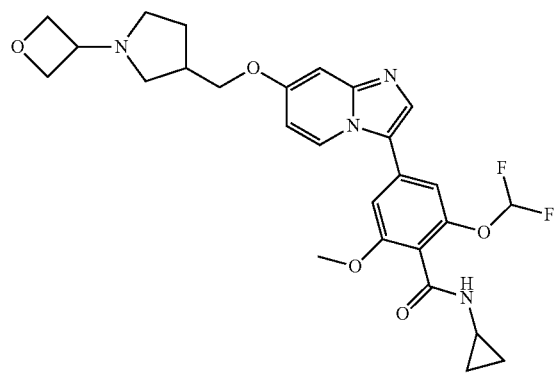 [SMILES: COc1cc(-c2cnc3cc(OCC4CCN(C5COC5)C4)ccn23)cc(OC(F)F)c1C(=O)NC1CC1]

Int 99 (82 mg, 0.17 mmol, 1 eq.) is dissolved in dry THF (2 mL). Two drops of AcOH are added. The reaction mixture is cooled in an ice bath and NaBH(OAc)$_3$ (CAS #56553-60-7; 89.7 mg, 0.42 mmol, 2 eq.) is added. The reaction mixture is allowed to warm to RT. After 2 h, the reaction is diluted with water and extracted with DCM. The organic layers are combined, dried over Na$_2$SO$_4$, filtered and evaporated under reduced pressure. The crude product is purified by flash chromatography on silica gel (eluting with 0 to 30% MeOH in DCM) to afford Cpd 287.

2.102. Cpd 314

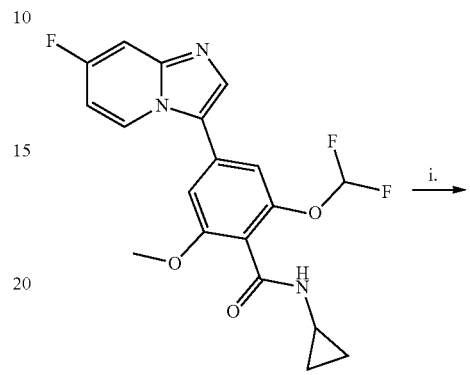

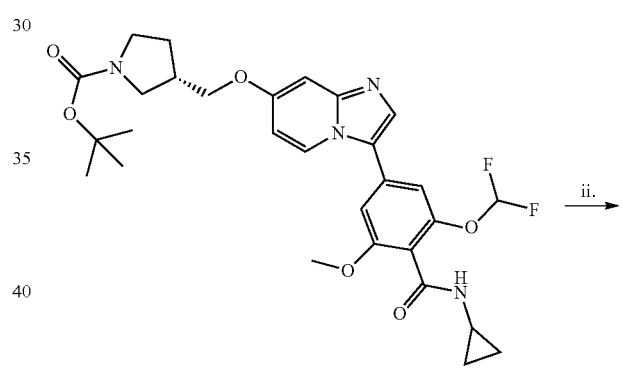

2.102.1. Step i: tert-butyl (3S)-3-[[3-[4-(cyclopropylcarbamoyl)-3-(difluoromethoxy)-5-methoxy-phenyl]imidazo[1,2-a]pyridin-7-yl]oxymethyl]pyrrolidine-1-carboxylate

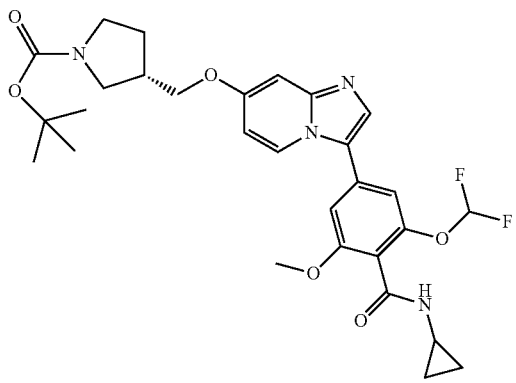 [SMILES: COc1cc(-c2cnc3cc(OC[C@H]4CCN(C(=O)OC(C)(C)C)C4)ccn23)cc(OC(F)F)c1C(=O)NC1CC1]

Tert-butyl (3S)-3-(hydroxymethyl)pyrrolidine-1-carboxylate (CAS #199174-24-8; 360 mg, 1.8 mmol, 2 eq.) is dissolved in dry DMF (3.5 mL), cooled in an ice bath and NaH (60% dispersion in mineral oil, 71.5 mg, 1.8 mmol, 2 eq.) is added portionwise. The reaction mixture is stirred for 10 min and then Int 1 (350 mg, 0.9 mmol, 1 eq.) is added. The reaction mixture is slowly warmed to RT under stirring and left to stir overnight. Another portion of tert-butyl (3S)-3-(hydroxymethyl)pyrrolidine-1-carboxylate (360 mg, 1.8 mmol, 2 eq.) and NaH (71.5 mg, 1.8 mmol, 2 eq.) is added. The reaction mixture is stirred at RT for 2.5 days. Another portion of tert-butyl (3S)-3-(hydroxymethyl)pyrrolidine-1-carboxylate (180 mg, 0.9 mmol, 1 eq.) and NaH (35.7 mg, 0.9 mmol, 1 eq.) is added. The reaction mixture is stirred at RT overnight, then diluted with water and extracted with EtOAc. The organic layers are combined, dried over Na$_2$SO$_4$, filtered and evaporated under reduced pressure. The crude product is purified by flash chromatography on silica gel (eluting with 0 to 6% MeOH in DCM) to afford tert-butyl (3S)-3-[[3-[4-(cyclopropylcarbamoyl)-3-(difluoromethoxy)-5-methoxy-phenyl]imidazo[1,2-a]pyridin-7-yl]oxymethyl]pyrrolidine-1-carboxylate.

LCMS: MW (calcd): 572.2; m/z MW (obsd): 573.1 (M+H)

2.102.2. Step ii: Cpd 314

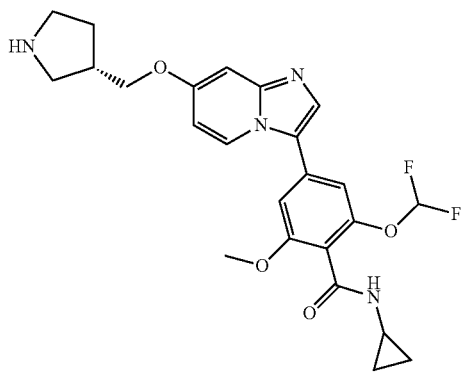 [SMILES: COc1cc(-c2cnc3cc(OC[C@H]4CCNC4)ccn23)cc(OC(F)F)c1C(=O)NC1CC1]

tert-butyl (3S)-3-[[3-[4-(cyclopropylcarbamoyl)-3-(difluoromethoxy)-5-methoxy-phenyl]imidazo[1,2-a]pyridin-7-yl]oxymethyl]pyrrolidine-1-carboxylate (446 mg, 0.78 mmol, 1 eq.) is dissolved in HCl, 4N in 1,4-dioxane (3 mL) and stirred at RT for 2 h. The reaction mixture is evaporated to dryness, dissolved with DCM and transferred to a separation funnel. Water and a sat. NaHCO$_3$ aq. solution are added and extracted with DCM. The organic layers are combined, dried over Na$_2$SO$_4$, filtered and evaporated under reduced pressure to afford Cpd 314.

2.103. Cpd 315

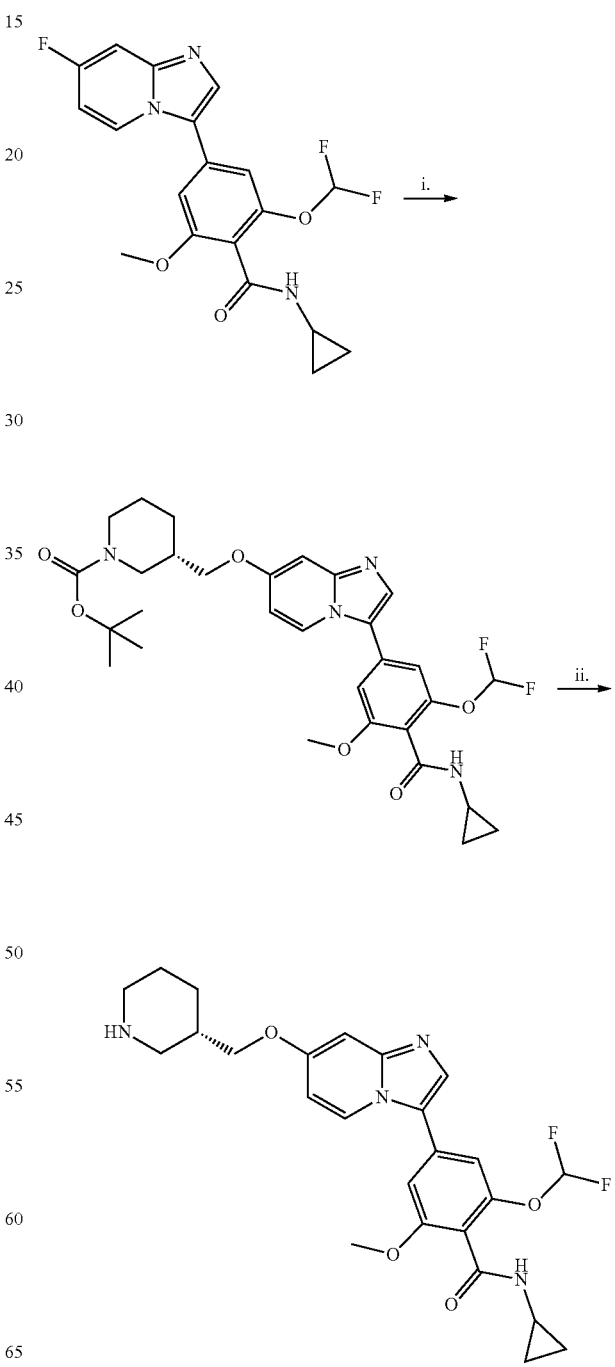

2.103.1. Step i: tert-butyl (3S)-3-[[3-[4-(cyclopropylcarbamoyl)-3-(difluoromethoxy)-5-methoxy-phenyl]imidazo[1,2-a]pyridin-7-yl]oxymethyl]piperidine-1-carboxylate

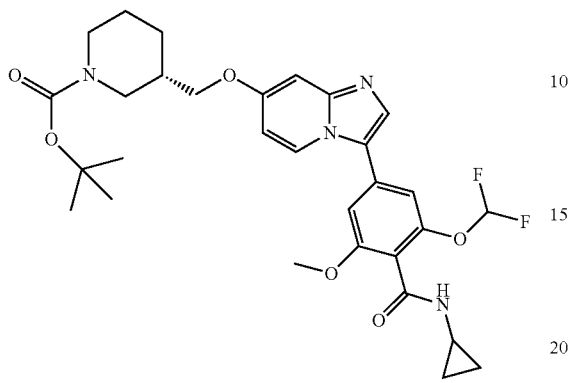

Tert-butyl (3S)-3-(hydroxymethyl)piperidine-1-carboxylate (CAS #140695-84-7; 385 mg, 1.8 mmol, 2 eq.) is dissolved in dry DMF (3.5 mL), cooled in an ice bath and NaH (60% dispersion in mineral oil, 71.5 mg, 1.8 mmol, 2 eq.) is added portionwise. The reaction mixture is stirred for 10 min and then Int 1 (350 mg, 0.9 mmol, 1 eq.) is added. The reaction mixture is slowly warmed to RT under stirring and left to stir overnight. Another portion of Tert-butyl (3S)-3-(hydroxymethyl)piperidine-1-carboxylate (385 mg, 1.8 mmol, 2 eq.) and NaH (71.5 mg, 1.8 mmol, 2 eq.) is added. The reaction mixture is stirred at RT for 2.5 days. Another portion of Tert-butyl (3S)-3-(hydroxymethyl)piperidine-1-carboxylate (192.5 mg, 0.9 mmol, 1 eq.) and NaH (35.7 mg, 0.9 mmol, 1 eq.) is added. The reaction mixture is stirred at RT overnight, then diluted with water and extracted with EtOAc. The organic layers are combined, dried over $Na_2SO_4$, filtered and evaporated under reduced pressure. The crude product is purified by flash chromatography on silica gel (eluting with 0 to 6% MeOH in DCM) to afford tert-butyl (3S)-3-[[3-[4-(cyclopropylcarbamoyl)-3-(difluoromethoxy)-5-methoxy-phenyl]imidazo[1,2-a]pyridin-7-yl]oxymethyl]piperidine-1-carboxylate.

LCMS: MW (calcd): 586.3; m/z MW (obsd): 587.2 (M+H)

2.103.2. Step ii: Cpd 315

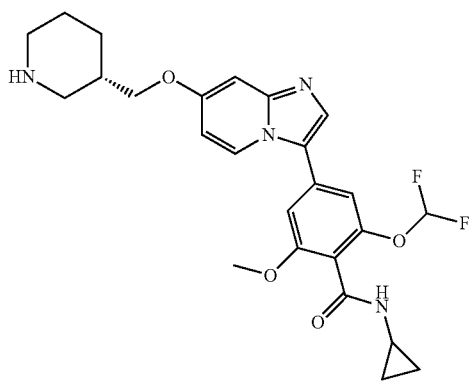 [SMILES: COc1cc(-c2cnc3cc(OC[C@H]4CCCNC4)ccn23)cc(OC(F)F)c1C(=O)NC1CC1]

Tert-butyl (3S)-3-[[3-[4-(cyclopropylcarbamoyl)-3-(difluoromethoxy)-5-methoxy-phenyl]imidazo[1,2-a]pyridin-7-yl]oxymethyl]piperidine-1-carboxylate (522 mg, 0.89 mmol, 1 eq.) is dissolved in HCl, 4N in 1,4-dioxane (3 mL) and stirred at RT for 2 h. The reaction mixture is evaporated to dryness, dissolved with DCM and transferred to a separation funnel. Water and a sat. $NaHCO_3$ aq. solution are added and extracted with DCM. The organic layers are combined, dried over $Na_2SO_4$, filtered and evaporated under reduced pressure to afford Cpd 315.

2.104. Cpd 322

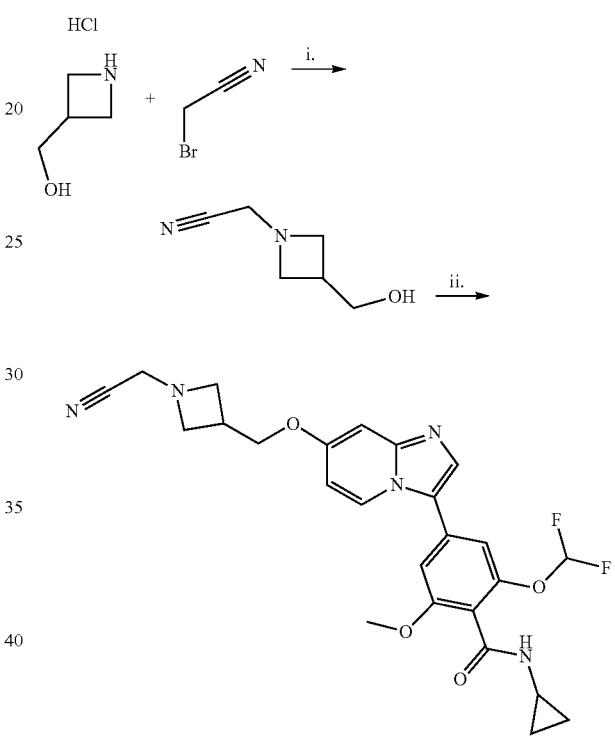

2.104.1. Step i: 2-[3-(hydroxymethyl)azetidin-1-yl]acetonitrile

2-Bromoacetonitrile (CAS #590-17-0, 178 µL, 2.55 mmol, 1.05 eq.) is added to a suspension of azetidin-3-ylmethanol hydrochloride (CAS #928038-44-2, 300 mg, 2.43 mmol, 1 eq.) and $K_2CO_3$ (772 mg, 5.58 mmol, 2.3 eq.) in ACN (10.0 mL). The reaction mixture is stirred at RT overnight, then filtered and evaporated to dryness. The residue is purified by flash chromatography on silica gel (eluting with 0 to 8% MeOH in DCM) to afford 2-[3-(hydroxymethyl)azetidin-1-yl]acetonitrile.

2.104.2. Step ii: Cpd 322

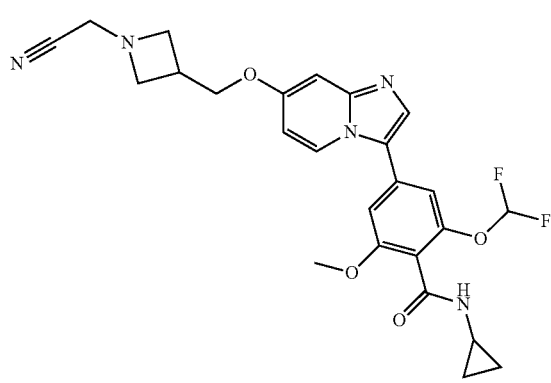 [SMILES: COc1cc(-c2cnc3cc(OCC4CN(CC#N)C4)ccn23)cc(OC(F)F)c1C(=O)NC1CC1]

NaH (60% dispersion in mineral oil, 20.4 mg, 0.511 mmol, 4 eq.) is added to a solution of 2-[3-(hydroxymethyl)azetidin-1-yl]acetonitrile (67.7 mg, 0.537 mmol, 4.2 eq.) in anhydrous DMF (2 mL) at 5° C. over 10 min. Int 1 (50.0 mg, 0.128 mmol, 1 eq.) is added to the reaction mixture and the reaction is stirred at RT overnight. The reaction is diluted with EtOAc (15 mL), then water (1 mL) is added and the layers are separated. The organic layer is washed with a sat. aq. solution of NaHCO$_3$ (3×20 mL), dried over Na$_2$SO$_4$, filtered and evaporated. The crude product is purified by flash chromatography on silica gel (eluting with 0 to 5% MeOH in DCM) to afford Cpd 322.

2.105. Cpd 323

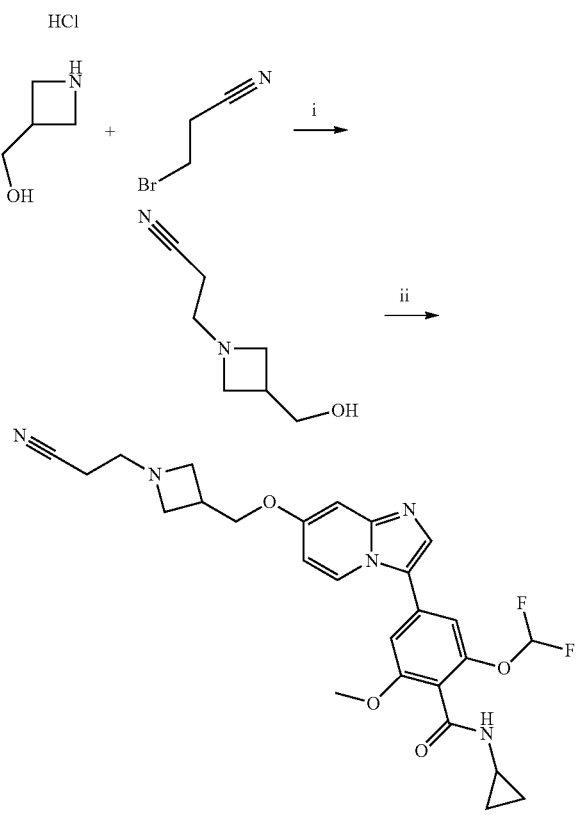

2.105.1. Step i: 3-[3-(hydroxymethyl)azetidin-1-yl]propanenitrile

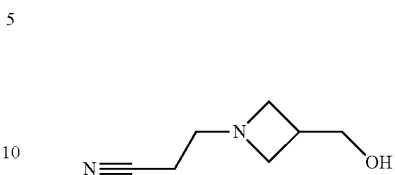

3-Bromopropanenitrile (CAS #19481-82-4, 211 µL, 2.55 mmol, 1.05 eq.) is added to a suspension of azetidin-3-ylmethanol hydrochloride (CAS #928038-44-2, 300 mg, 2.43 mmol, 1 eq.) and K$_2$CO$_3$ (772 mg, 5.58 mmol, 2.3 eq.) in ACN (10.0 mL). The reaction mixture is stirred at RT overnight, then filtered and evaporated to dryness. The residue is purified by flash chromatography on silica gel (eluting with 0 to 8% MeOH in DCM) to afford 3-[3-(hydroxymethyl)azetidin-1-yl]propanenitrile.

2.1052. Step ii: Cpd 322

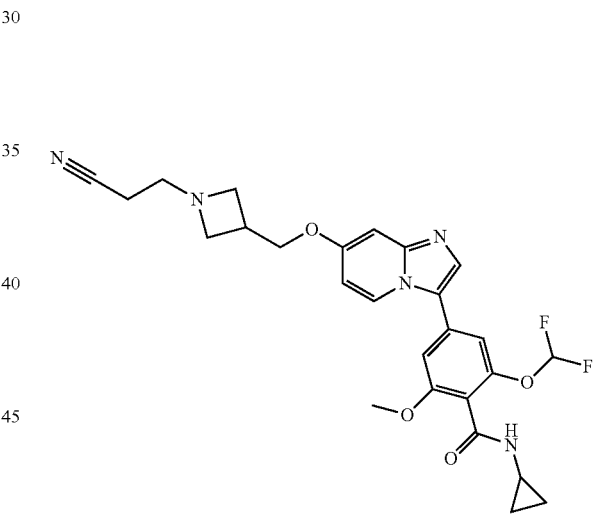

NaH (60% dispersion in mineral oil, 20.4 mg, 0.511 mmol, 4 eq.) is added to a solution of 3-[3-(hydroxymethyl)azetidin-1-yl]propanenitrile (75.2 mg, 0.537 mmol, 4.2 eq.) in anhydrous DMF (1 mL) at 5° C. over 10 min. Int 1 (50.0 mg, 0.128 mmol, 1 eq.) is added to the reaction mixture and the reaction is stirred at RT overnight. The reaction is diluted with EtOAc (15 mL), then water (1 mL) is added and the layers are separated. The organic layer is washed with a sat. aq. solution of NaHCO$_3$ (3×20 mL), dried over Na$_2$SO$_4$, filtered and evaporated. The crude product is purified by flash chromatography on silica gel (eluting with 0 to 5% MeOH in DCM) to afford Cpd 323.

2.106. Cpd 33

2.107. Cpd 334

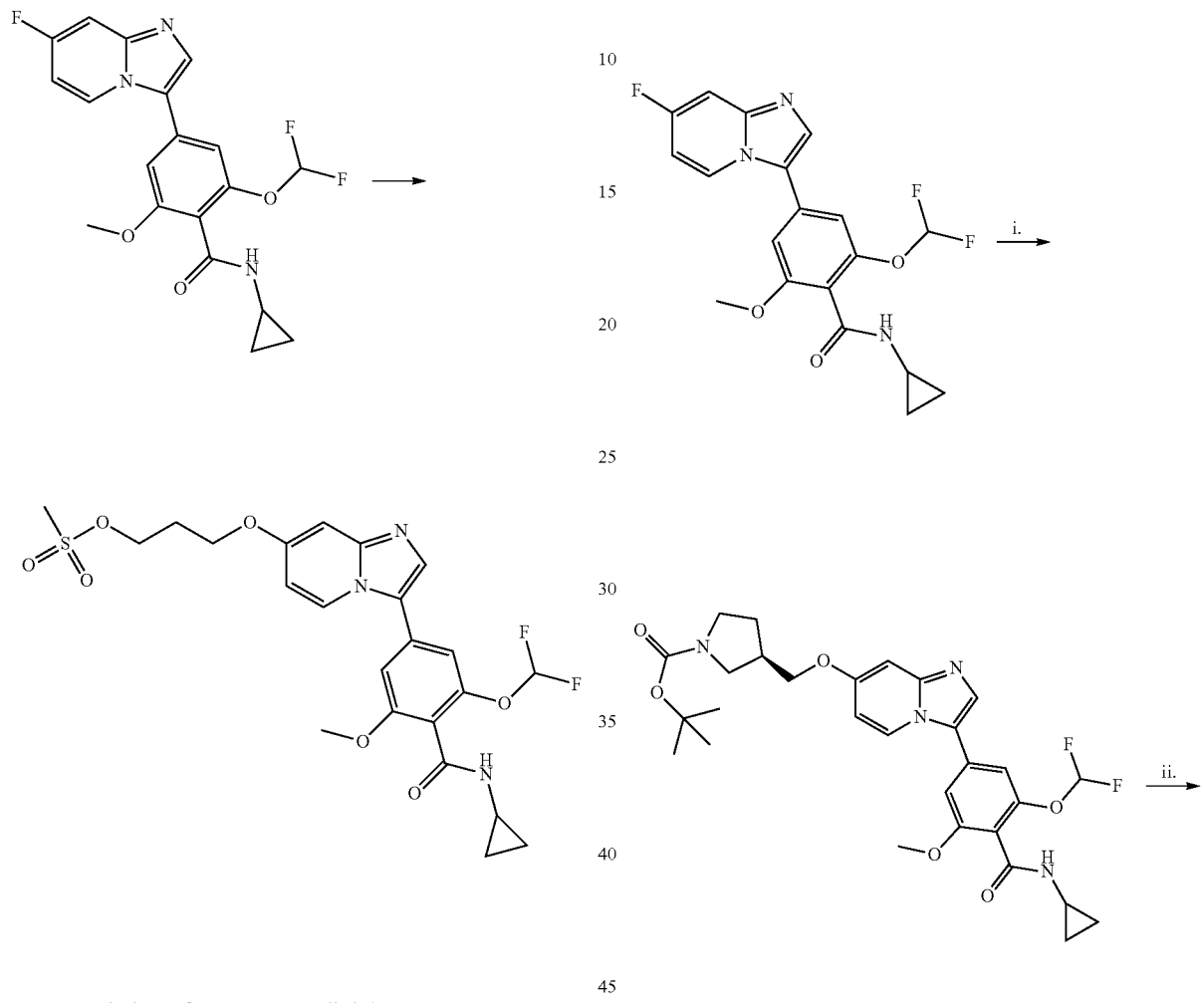

To a solution of propane-1,3-diol (CAS #504-63-2; 1.31 mL, 17.7 mmol, 10 eq.) in dry DMF (3.50 mL) at 0° C. is added NaH (60% dispersion in mineral oil, 156 mg, 3.90 mmol, 2.2 eq.). The reaction mixture is allowed to warm up to RT and stirred for 1 h. Int 1 (700 mg, 1.77 mmol, 1 eq.) is added and the mixture is stirred at RT for 64 h. The reaction mixture is poured into 120 mL of sat. aq. NaHCO₃ solution, and extracted with 2×100 mL of DCM. The gathered organic layers are washed with 100 mL of sat. aq. NaHCO₃ solution, then with 100 mL of brine. The organic phase is dried over Na₂SO₄, filtered and evaporated in vacuo. The residue is suspended in dry DCM (45.0 mL). Et₃N (561 µL, 3.98 mmol, 2.25 eq.) is added followed by methanesulfonyl chloride (CAS #124-63-0; 186 µL, 2.39 mmol, 1.35 eq.). The mixture is stirred at RT for 30 min, and then diluted with 100 mL of DCM, washed with 2×100 mL of sat. aq. NaHCO₃ solution followed by 70 mL of brine. After drying over Na₂SO₄ and filtration, the solvent is evaporated and the resulting crude is purified by flash chromatography (eluting with a gradient of 0 to 2% MeOH in DCM) to afford Cpd 333.

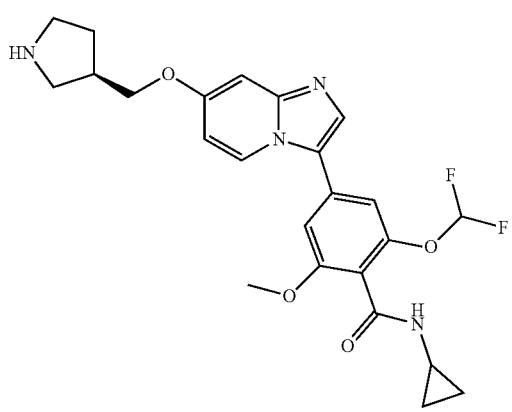

2.107.1. Step i: tert-butyl (3R)-3-[[3-[4-(cyclopropylcarbamoyl)-3-(difluoromethoxy)-5-methoxyphenyl]imidazo[1,2-a]pyridin-7-yl]oxymethyl]pyrrolidine-1-carboxylate

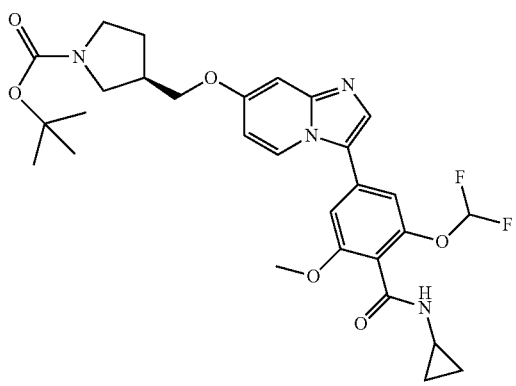 [SMILES: COc1cc(-c2cnc3cc(OC[C@@H]4CCN(C(=O)OC(C)(C)C)C4)ccn23)cc(OC(F)F)c1C(=O)NC1CC1]

Tert-butyl (3R)-3-(hydroxymethyl)pyrrolidine-1-carboxylate (CAS #138108-72-2; 360 mg, 1.8 mmol, 3.6 eq.) is dissolved in dry DMF (2 mL), cooled in an ice bath and NaH (60% dispersion in mineral oil, 40.9 mg, 1.0 mmol, 2 eq.) is added portionwise. The reaction mixture is stirred for 10 min and then Int 1 (200 mg, 0.5 mmol, 1 eq.) is added. The reaction mixture is slowly warmed to RT under stirring and left to stir overnight. Another portion of tert-butyl (3R)-3-(hydroxymethyl)pyrrolidine-1-carboxylate (180 mg, 0.9 mmol, 1.8 eq.) and NaH (20.5 mg, 0.5 mmol, 1 eq.) is added. The reaction mixture is stirred at RT for 2.5 days, then diluted with water and extracted with EtOAc. The organic layers are combined, dried over Na$_2$SO$_4$, filtered and evaporated under reduced pressure. The crude product is purified by flash chromatography on silica gel (eluting with 0 to 6% MeOH in DCM) to afford tert-butyl (3R)-3-[[3-[4-(cyclopropylcarbamoyl)-3-(difluoromethoxy)-5-methoxy-phenyl]imidazo[1,2-a]pyridin-7-yl]oxymethyl]pyrrolidine-1-carboxylate.

LCMS: MW (calcd): 572.2; m/z MW (obsd): 573.1 (M+H)

2.107.2. Step ii: Cpd 334

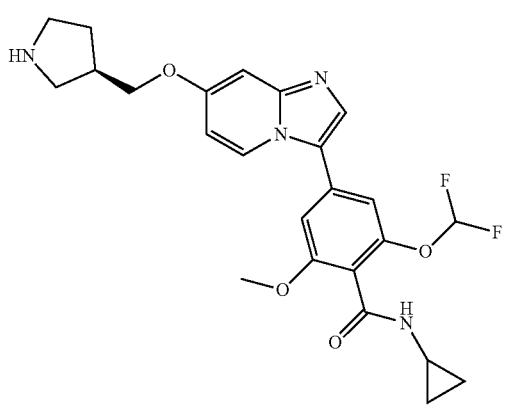 [SMILES: COc1cc(-c2cnc3cc(OC[C@@H]4CCNC4)ccn23)cc(OC(F)F)c1C(=O)NC1CC1]

Tert-butyl (3R)-3-[[3-[4-(cyclopropylcarbamoyl)-3-(difluoromethoxy)-5-methoxy-phenyl]imidazo[1,2-a]pyridin-7-yl]oxymethyl]pyrrolidine-1-carboxylate (271 mg, 0.47 mmol, 1 eq.) is dissolved in HCl, 4N in 1,4-dioxane (2 mL) and stirred at RT for 2 h. The reaction mixture is evaporated to dryness, dissolved with DCM and transferred to a separation funnel. Water and a sat. NaHCO$_3$ aq. solution are added and extracted with DCM. The organic layers are combined, dried over Na$_2$SO$_4$, filtered and evaporated under reduced pressure to afford Cpd 334.

2.108. Cpd 335

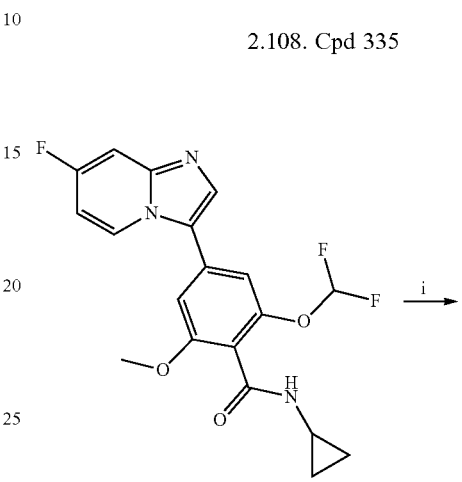

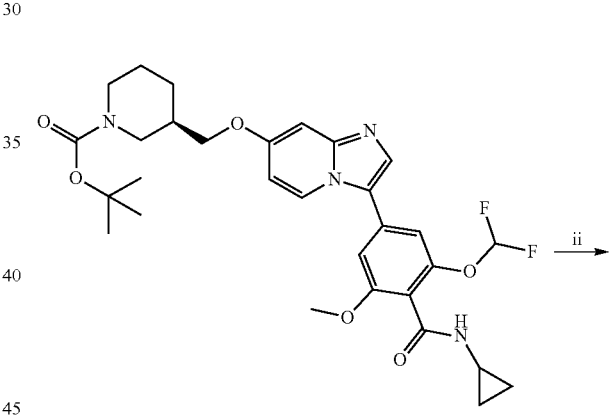

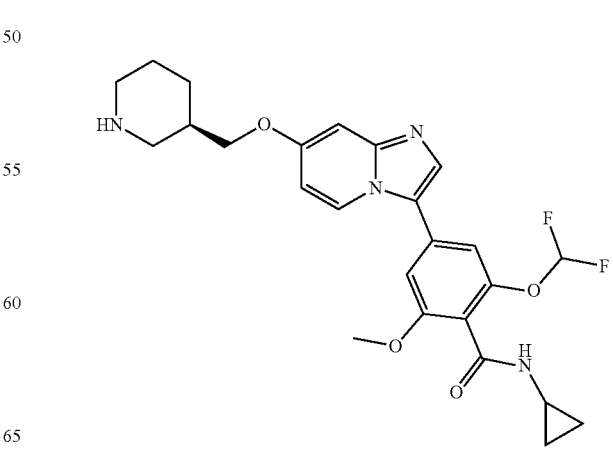

2.108.1. Step i: tert-butyl (3R)-3-[[3-[4-(cyclopropylcarbamoyl)-3-(difluoromethoxy)-5-methoxy-phenyl]imidazo[1,2-a]pyridin-7-yl]oxymethyl]piperidine-1-carboxylate

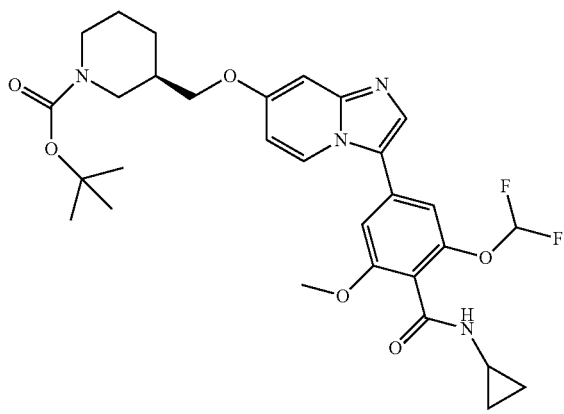 [SMILES: COc1cc(-c2cnc3cc(OC[C@@H]4CCCN(C(=O)OC(C)(C)C)C4)ccn23)cc(OC(F)F)c1C(=O)NC1CC1]

Tert-butyl (3R)-3-(hydroxymethyl)piperidine-1-carboxylate (CAS #140695-85-8, 385 mg, 1.79 mmol, 3.5 eq.) is dissolved in dry DMF (3.5 mL), cooled in an ice bath and NaH (60% dispersion in mineral oil, 40.9 mg, 1.02 mmol, 2 eq.) is added portionwise. The reaction mixture is stirred for 10 min and then Int 1 (200 mg, 0.51 mmol, 1 eq.) is added. The reaction mixture is slowly warmed to RT under stirring and left to stir overnight. Another portion of tert-butyl (3R)-3-(hydroxymethyl)piperidine-1-carboxylate (192.5 mg, 0.89 mmol, 1 eq.) and NaH (20.5 mg, 0.5 mmol, 1 eq.) is added. The reaction mixture is stirred at RT for 2.5 days, then diluted with water and extracted with EtOAc. The organic layers are combined, dried over Na$_2$SO$_4$, filtered and evaporated under reduced pressure. The crude product is purified by flash chromatography on silica gel (eluting with 0 to 8% MeOH in DCM) to afford tert-butyl (3R)-3-[[3-[4-(cyclopropylcarbamoyl)-3-(difluoromethoxy)-5-methoxy-phenyl]imidazo[1,2-a]pyridin-7-yl]oxymethyl]piperidine-1-carboxylate LCMS: MW (calcd): 586.3; m/z MW (obsd): 587.2 (M+H)

2.108.2. Step ii: Cpd 335

Tert-butyl (3R)-3-[[3-[4-(cyclopropylcarbamoyl)-3-(difluoromethoxy)-5-methoxy-phenyl]imidazo[1,2-a]pyridin-7-yl]oxymethyl]piperidine-1-carboxylate (221 mg, 0.37 mmol, 1 eq.) is dissolved in HCl, 4N in 1,4-dioxane (2 mL) and stirred at RT for 2 h. The reaction mixture is evaporated to dryness, dissolved with DCM and transferred to a separation funnel. Water and a sat. NaHCO$_3$ aq. solution are added and extracted with DCM. The organic layers are combined, dried over Na$_2$SO$_4$, filtered and evaporated under reduced pressure to afford Cpd 335.

2.109. Cpd 340

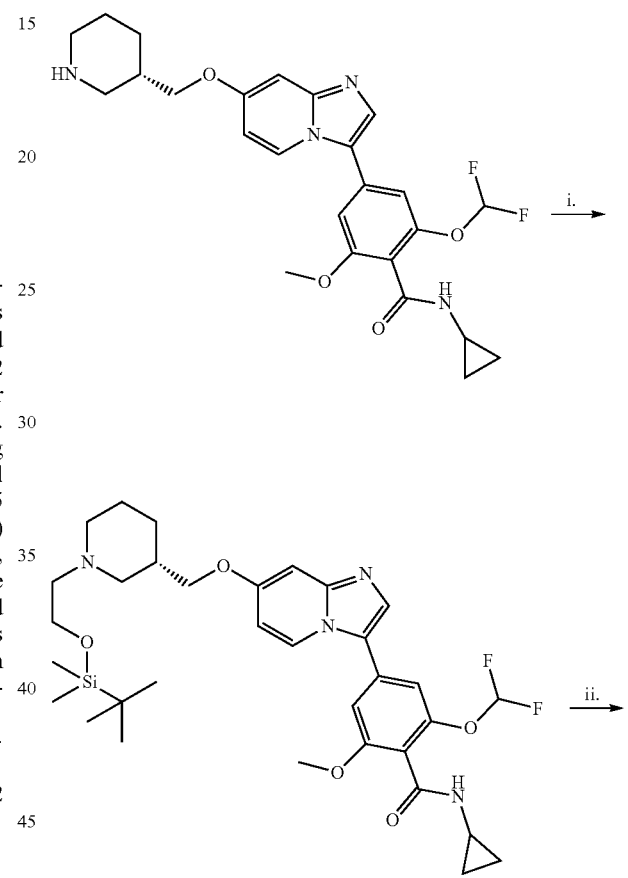

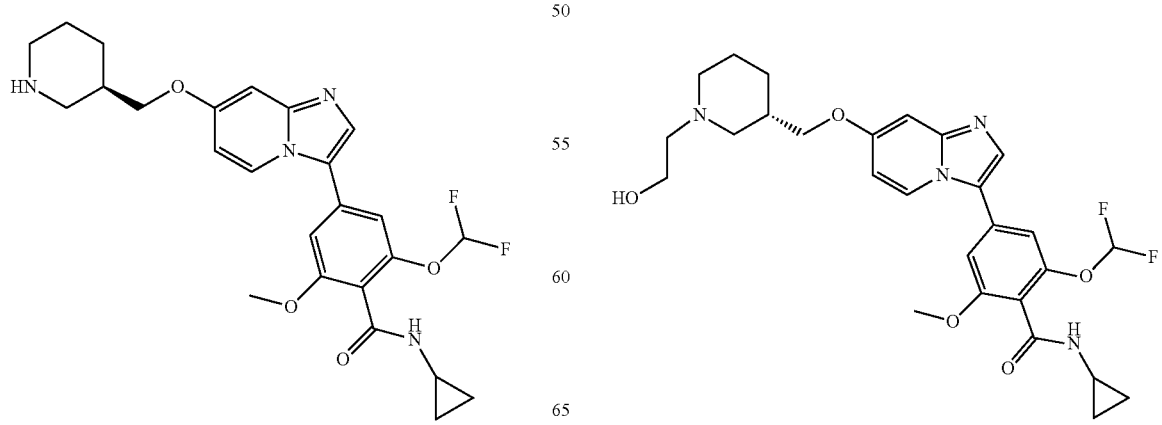

2.109.1. Step i: 4-[7-[[(3S)-1-[2-[tert-butyl(dimethyl)silyl]oxyethyl]-3-piperidyl]methoxy]imidazo[1,2-a]pyridin-3-yl]-N-cyclopropyl-2-(difluoromethoxy)-6-methoxy-benzamide

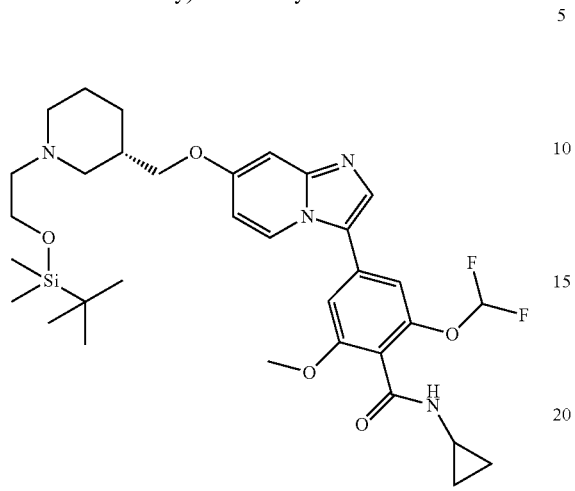

Cpd 315 (50 mg, 0.1 mmol, 1 eq.) is dissolved in dry THF (2 mL). Two drops of AcOH are added. The reaction mixture is cooled in an ice bath and 2-[tert-butyl(dimethyl)silyl]oxyacetaldehyde (CAS #102191-92-4; 39.2 μL, 0.2 mmol, 2 eq.) is added followed by NaBH(OAc)$_3$ (CAS #56553-60-7; 109 mg, 0.5 mmol, 5 eq.). The reaction mixture is allowed to warm to RT for 2 h, then stored at −16° C. for 2.5 days. The reaction mixture is warmed to RT, diluted with water and a sat. NaHCO$_3$ aq. solution, and then extracted with DCM. The organic layers are combined, dried over Na$_2$SO$_4$, filtered and evaporated under reduced pressure to afford 4-[7-[[(3S)-1-[2-[tert-butyl(dimethyl)silyl]oxyethyl]-3-piperidyl]methoxy]imidazo[1,2-a]pyridin-3-yl]-N-cyclopropyl-2-(difluoromethoxy)-6-methoxy-benzamide.

LCMS: MW (calcd): 644.3; m/z MW (obsd): 645.2 (M+H)

2.109.2. Step ii: Cpd 340

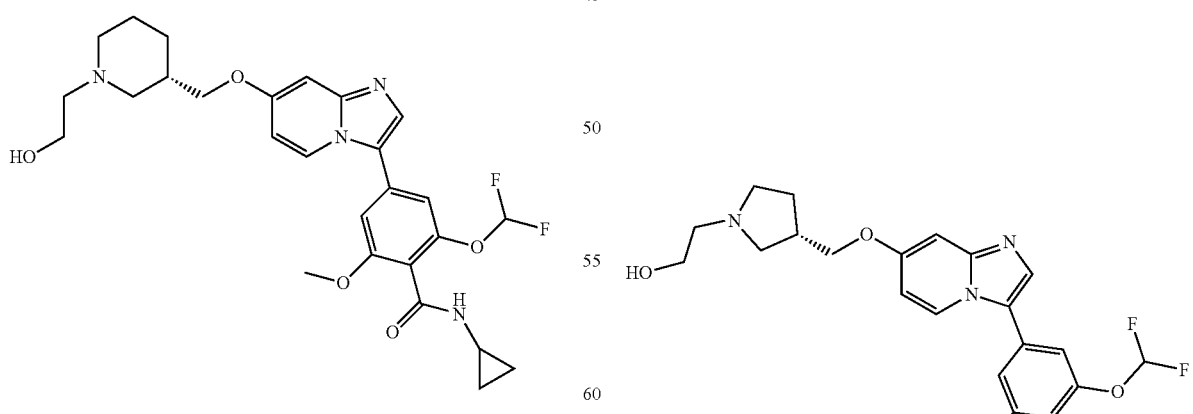

4-[7-[[(3S)-1-[2-[tert-butyl(dimethyl)silyl]oxyethyl]-3-piperidyl]methoxy]imidazo[1,2-a]pyridin-3-yl]-N-cyclopropyl-2-(difluoromethoxy)-6-methoxy-benzamide (66 mg, 0.1 mmol, 1 eq.) is dissolved in ACN (2 mL) and water (100 μL) is added followed by 3 drops of concentrated HCl. The reaction mixture is stirred at RT. After 30 min, the reaction mixture is evaporated to dryness, dissolved in DMSO (1 mL) and purified by preparative HPLC to afford Cpd 340.

2.110. Cpd 341

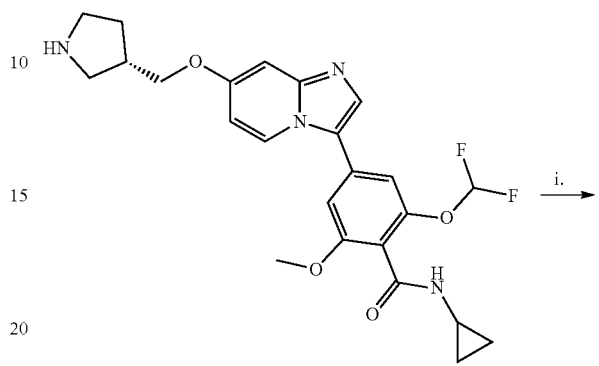

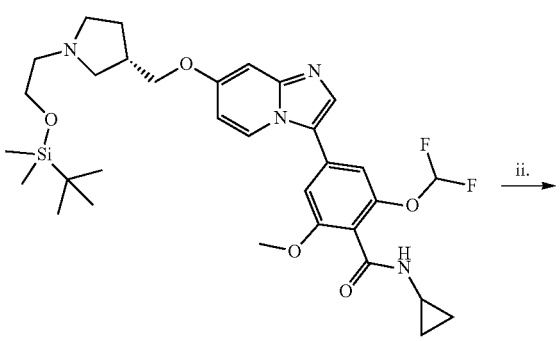

2.110.1. Step i: 4-[7-[[(3S)-1-[2-[tert-butyl(dimethyl)silyl]oxyethyl]pyrrolidin-3-yl]methoxy]imidazo[1,2-a]pyridin-3-yl]-N-cyclopropyl-2-(difluoromethoxy)-6-methoxy-benzamide

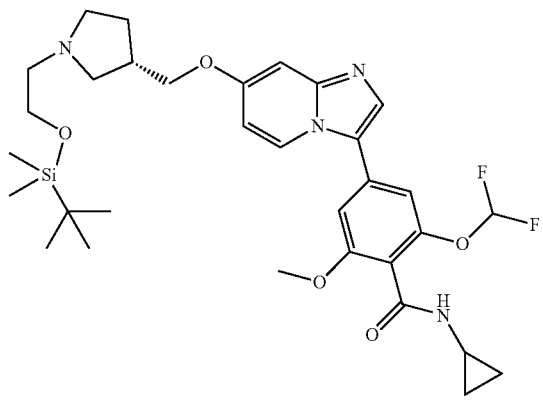 [SMILES: COc1cc(-c2cnc3cc(OC[C@H]4CCN(CCO[Si](C)(C)C(C)(C)C)C4)ccn23)cc(OC(F)F)c1C(=O)NC1CC1]

Cpd 314 (50 mg, 0.1 mmol, 1 eq.) is dissolved in dry THF (2 mL). Two drops of AcOH are added. The reaction mixture is cooled in an ice bath and 2-[tert-butyl(dimethyl)silyl]oxyacetaldehyde (CAS #102191-92-4; 39.3 µL, 0.2 mmol, 2 eq.) is added followed by NaBH(OAc)$_3$ (CAS #56553-60-7; 112 mg, 0.5 mmol, 5 eq.). The reaction mixture is allowed to warm to RT for 2 h, then stored at −16° C. for 2.5 days. The reaction mixture is warmed to RT, diluted with water and a sat. NaHCO$_3$ aq. solution, and then extracted with DCM. The organic layers are combined, dried over Na$_2$SO$_4$, filtered and evaporated under reduced pressure to afford 4-[7-[[(3S)-1-[2-[tert-butyl(dimethyl)silyl]oxyethyl]pyrrolidin-3-yl]methoxy]imidazo[1,2-a]pyridin-3-yl]-N-cyclopropyl-2-(difluoromethoxy)-6-methoxy-benzamide.

LCMS: MW (calcd): 630.3; m/z MW (obsd): 631.2 (M+H)

2.110.2. Step ii: Cpd 341

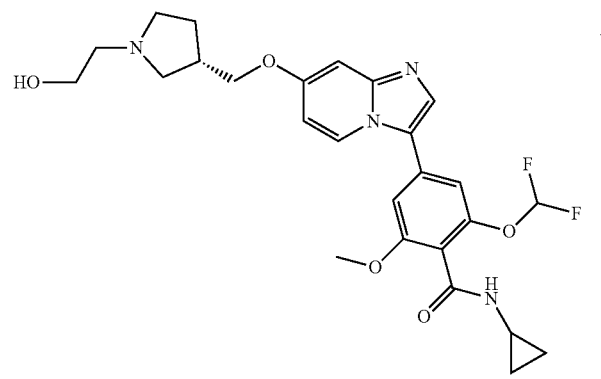

4-[7-[[(3S)-1-[2-[Tert-butyl(dimethyl)silyl]oxyethyl]pyrrolidin-3-yl]methoxy]imidazo[1,2-a]pyridin-3-yl]-N-cyclopropyl-2-(difluoromethoxy)-6-methoxy-benzamide (62 mg, 0.1 mmol, 1 eq.) is dissolved in ACN (2 mL) and water (100 µL) is added followed by 3 drops of concentrated HCl. The reaction mixture is stirred at RT. After 30 min, the reaction mixture is evaporated to dryness, dissolved in DMSO (1 mL) and purified by preparative HPLC to afford Cpd 341.

2.111. Cpd 342

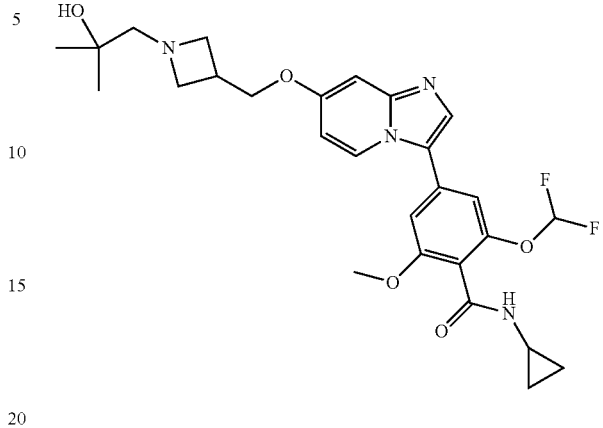

To a suspension of Int 93 (50 mg, 0.109 mmol, 1 eq.) and K$_2$CO$_3$ (15 mg, 0.109 mmol, 1 eq.) in dry ACN (1 mL) is added 1,1-dimethyloxirane (CAS #558-30-5; 16 mg, 0.218 mmol, 2 eq.). The reaction mixture is stirred at RT for 7 days, filtered and concentrated. The obtained residue is purified by preparative HPLC to afford Cpd 342.

2.112. Cpd 343

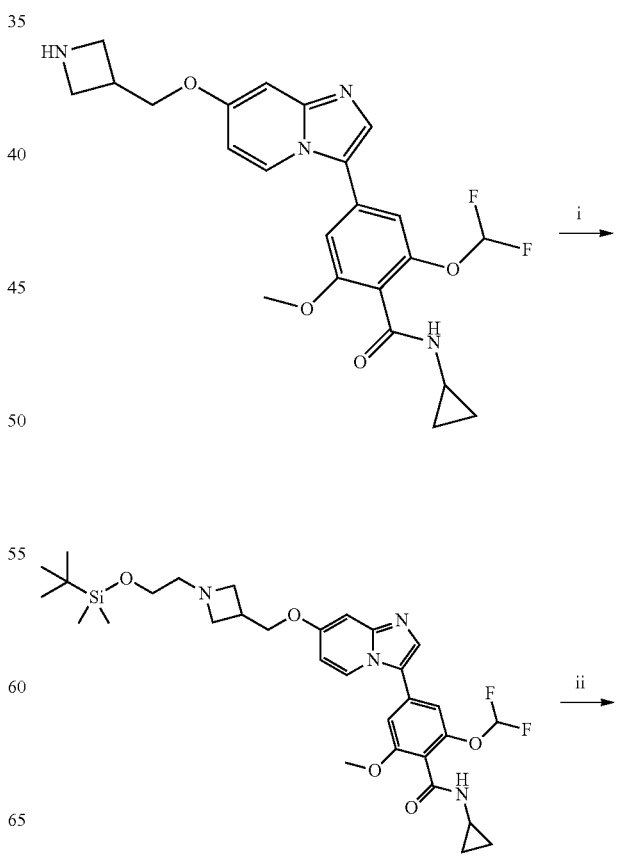

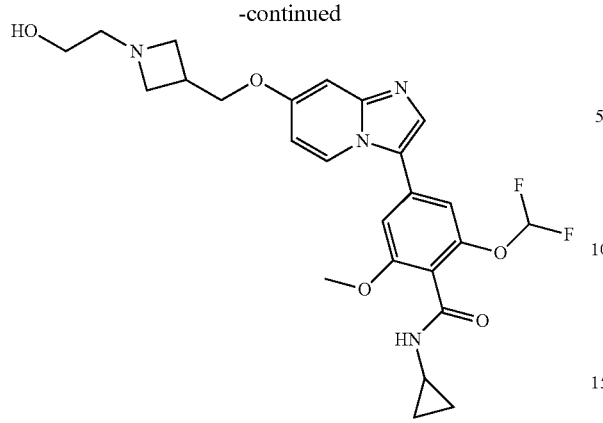

2.112.1. Step i: 4-[7-[[1-[2-[tertbutyl(dimethyl)silyl]oxyethyl]azetidin-3-yl]methoxy]imidazo[1,2-a]pyridine-3-yl]-Ncyclopropyl-2-(difluoromethoxy)-6-methoxy-benzamide To a solution of Int 93 (50 mg, 0.109 mmol, 1 eq.) and (tert-butyldimethylsilyloxy)acetaldehyde (CAS #102191-92-4; 42 µL, 0.218 mmol, 2 eq.) in dry THF (2 mL) are added 2 drops of AcOH. NaBH(OAc)$_3$ (CAS #56553-60-7; 116 mg, 0.545 mmol, 5 eq.) is added at 0° C. and the reaction mixture is slowly warmed to RT and stirred at RT for 24 h. The reaction mixture is diluted with water and extracted with DCM. The combined organic layers are dried over Na$_2$SO$_4$, filtered and concentrated. The crude product is purified by flash chromatography on silica gel (eluting with 0 to 5% MeOH in DCM) to afford the expected compound.

2.112.2. Step ii: Cpd 343

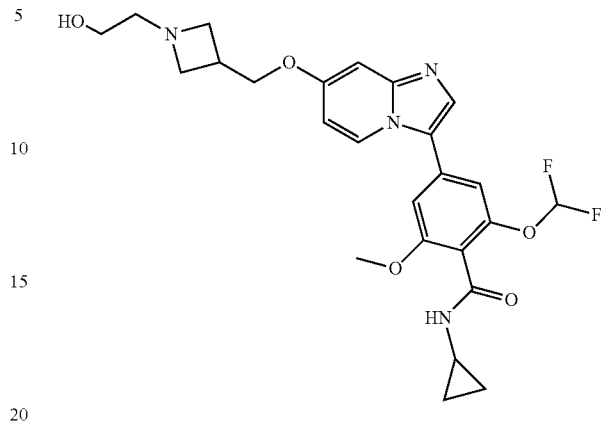

To a solution of 4-[7-[[1-[2-[tertbutyl(dimethyl)silyl]oxyethyl]azetidin-3-yl]methoxy]imidazo[1,2-a]pyridine-3-yl]-Ncyclopropyl-2-(difluoromethoxy)-6-methoxy-benzamide (30 mg, 0.048 mmol, 1 eq.) in ACN (0.5 mL) is added chlorotrimethylsilane (1.2 µL, 0.009 mmol, 2 mol %) and water (0.876 µL, 0.048 mmol, 1 eq.). The reaction mixture is stirred at RT for 24 h. 3 drops of concentrated HCl are added and the reaction mixture is stirred at RT for 2 h. The reaction mixture is concentrated to dryness and the obtained residue is purified by preparative HPLC to afford Cpd 343.

2.113. Cpd 349

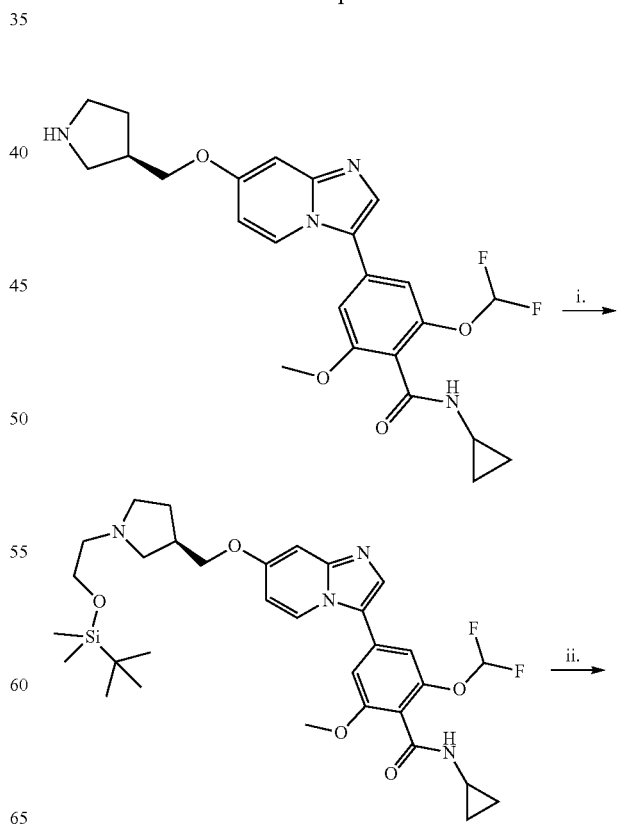

269

-continued

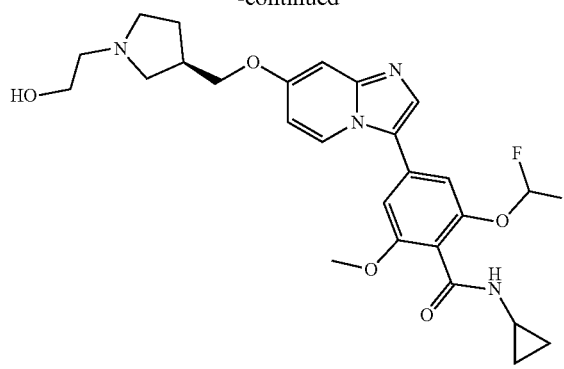

2.113.1. Step i: 4-[7-[[(3R)-1-[2-[tert-butyl(dimethyl)silyl]oxyethyl]pyrrolidin-3-yl]methoxy]imidazo[1,2-a]pyridin-3-yl]-N-cyclopropyl-2-(difluoromethoxy)-6-methoxy-benzamide

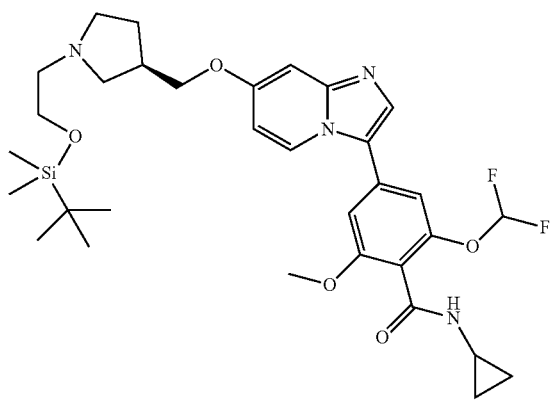 [SMILES: COc1cc(-c2cnc3cc(OC[C@@H]4CCN(CCO[Si](C)(C)C(C)(C)C)C4)ccn23)cc(OC(F)F)c1C(=O)NC1CC1]

Cpd 334 (50 mg, 0.1 mmol, 1 eq.) is dissolved in dry THF (2 mL). Two drops of AcOH are added. The reaction mixture is cooled in an ice bath and 2-[tert-butyl(dimethyl)silyl]oxyacetaldehyde (CAS #102191-92-4; 36 mg, 0.2 mmol, 2 eq.) is added followed by NaBH(OAc)₃ (CAS #56553-60-7; 112 mg, 0.5 mmol, 5 eq.). The reaction mixture is allowed to warm to RT for 2 h, then diluted with water and a sat. NaHCO₃ aq. solution, and then extracted with DCM. The organic layers are combined, dried over Na₂SO₄, filtered and evaporated under reduced pressure to afford 4-[7-[[(3R)-1-[2-[tert-butyl(dimethyl)silyl]oxyethyl]pyrrolidin-3-yl]methoxy]imidazo[1,2-a]pyridin-3-yl]-N-cyclopropyl-2-(difluoromethoxy)-6-methoxy-benzamide.

LCMS: MW (calcd): 630.3; m/z MW (obsd): 631.1 (M+H)

270

2.113.2. Step ii: Cpd 349

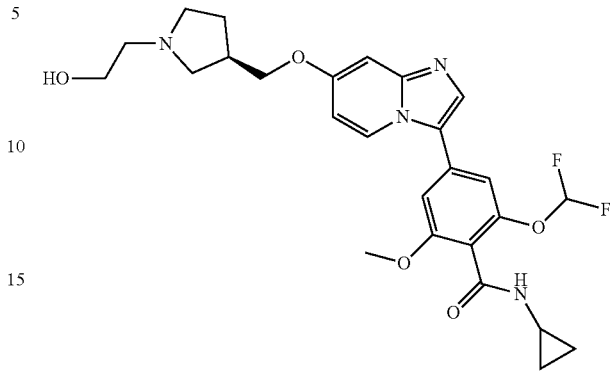

4-[7-[[(3R)-1-[2-[Tert-butyl(dimethyl)silyl]oxyethyl]pyrrolidin-3-yl]methoxy]imidazo[1,2-a]pyridin-3-yl]-N-cyclopropyl-2-(difluoromethoxy)-6-methoxy-benzamide (66 mg, 0.1 mmol, 1 eq.) is dissolved in ACN (2 mL) and water (100 µL) is added followed by 3 drops of concentrated HCl. The reaction mixture is stirred at RT. After 30 min, the reaction mixture is evaporated to dryness, dissolved in DMSO (1 mL) and purified by preparative HPLC to afford Cpd 349.

2.114. Cpd 361

NH₄OH (25% in water; 505 µL, 3.24 mmol) is added to a solution of Cpd 363 (50.0 mg, 0.0810 mmol) in MeOH (1.0 mL) at RT. The reaction is left to stir 3 h, then evaporated to dryness. The crude product is dissolved in 0.7 mL DMSO, filtered and purified by preparative HPLC to afford Cpd 361.

2.115. Cpd 363

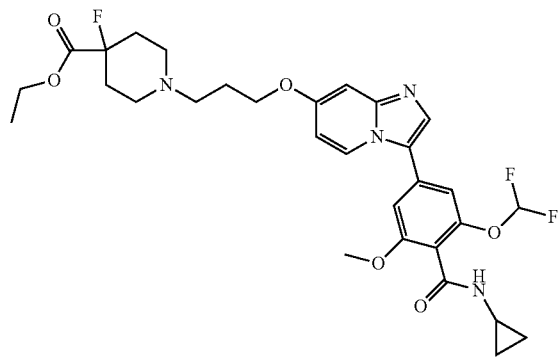 [SMILES: CCOC(=O)C1(F)CCN(CCCOc2ccn3c(-c4cc(OC)c(C(=O)NC5CC5)c(OC(F)F)c4)cnc3c2)CC1]

A suspension of Cpd 333 (50 mg, 0.093 mmol, 1 eq.), ethyl 4-fluoropiperidine-4-carboxylate hydrochloride (CAS #845909-49-1; 23.7 mg, 0.112 mmol, 1.2 eq.), potassium iodide (20.3 mg, 0.121 mmol, 1.3 eq.) and NaHCO$_3$ (23.5 mg, 0.280 mmol, 3 eq.) is stirred in dry DMF (0.7 mL) at 85° C. for 2 h. The mixture is cooled to RT, diluted with EtOAc (20 mL) and washed with a sat. aq. NaHCO$_3$ solution. The organic layer is dried over Na$_2$SO$_4$, filtered and concentrated to dryness to afford Cpd 363.

2.116. Cpd 365

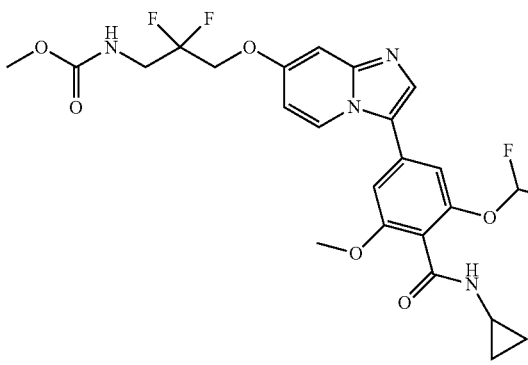

To a solution of Cpd 364 (40 mg, 0.08 mmol, 1 eq.) in dry DCM (2 mL) are added DIPEA (15.6 μL, 0.09 mmol, 1.1 eq.) and methyl chloroformate (6.3 μL, 0.08 mmol, 1 eq.). The reaction mixture is left to stir at RT for 3 h, quenched with 15 mL of sat. NaHCO$_3$ aq. solution, and extracted with 3×15 mL of DCM. The combined organic layers are dried over Na$_2$SO$_4$, filtrated and the solvent is evaporated to dryness to obtain a crude product. A small amount of DCM is added. The solvent is decanted and removed, and the obtained solid is dried to afford Cpd 365.

2.117. Cpd 366

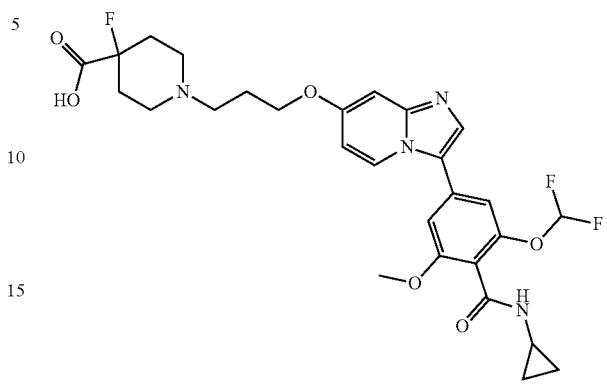

A solution of LiOH (5.19 mg, 0.217 mmol, 3 eq.) in water (1 mL) is added to a solution of Cpd 363 (50.2 mg, 0.072 mmol, 1 eq.) in THF (2 mL) and the reaction is stirred at RT overnight. The mixture is filtered, the filtrate is evaporated and the crude is purified by preparative HPLC to afford Cpd 366.

2.118. Cpd 370

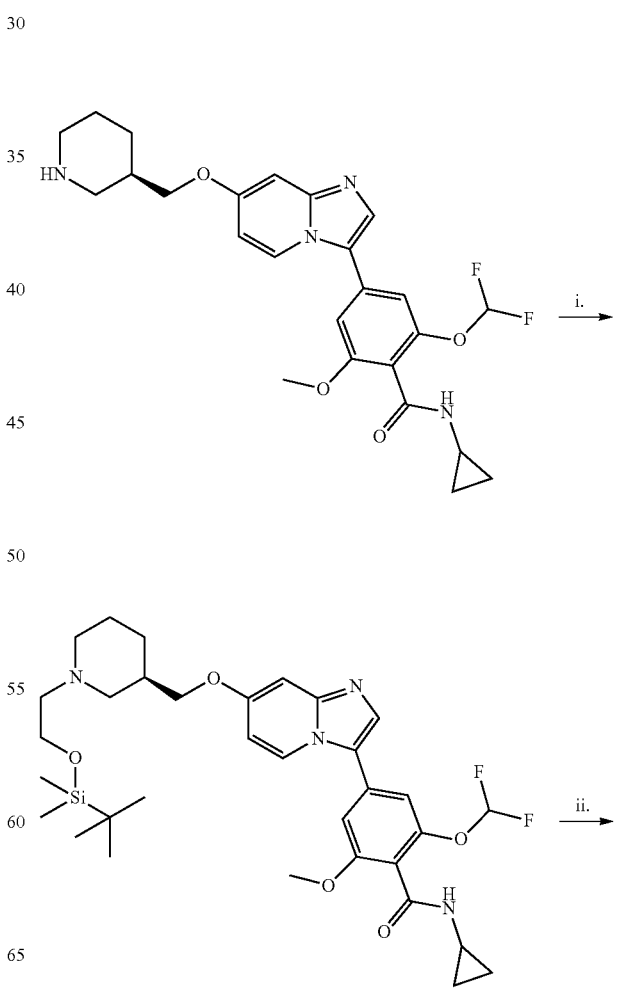

2.118.1. Step i: 4-[7-[[(3R)-1-[2-[tert-butyl(dimethyl)silyl]oxyethyl]-3-piperidyl]methoxy]imidazo[1,2-a]pyridin-3-yl]-N-cyclopropyl-2-(difluoromethoxy)-6-methoxy-benzamide

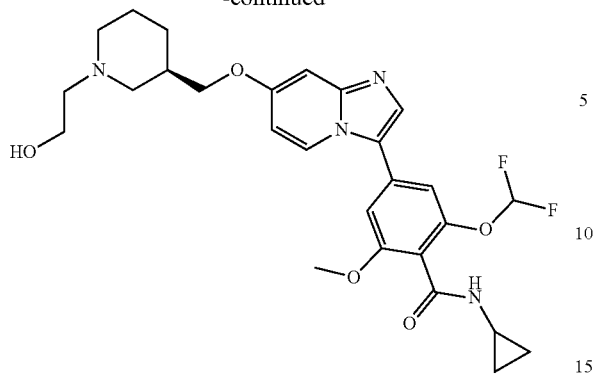

Cpd 335 (50 mg, 0.1 mmol, 1 eq.) is dissolved in dry THF (2 mL). Two drops of AcOH are added. The reaction mixture is cooled in an ice bath and 2-[tert-butyl(dimethyl)silyl]oxyacetaldehyde (CAS #102191-92-4; 39 µL, 0.2 mmol, 2 eq.) is added followed by NaBH(OAc)$_3$ (CAS #56553-60-7; 110 mg, 0.5 mmol, 5 eq.). The reaction mixture is allowed to warm to RT. After 2 h, the reaction mixture is diluted with water and a sat. NaHCO$_3$ aq. solution, and then extracted with DCM. The organic layers are combined, dried over Na$_2$SO$_4$, filtered and evaporated under reduced pressure to afford 4-[7-[[(3R)-1-[2-[tert-butyl(dimethyl)silyl]oxyethyl]-3-piperidyl]methoxy]imidazo[1,2-a]pyridin-3-yl]-N-cyclopropyl-2-(difluoromethoxy)-6-methoxy-benzamide.

LCMS: MW (calcd): 644.3; m/z MW (obsd): 645.0 (M+H)

2.118.2. Step ii: Cpd 370

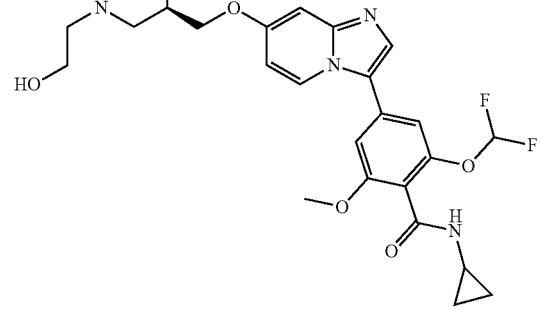

4-[7-[[(3R)-1-[2-[tert-butyl(dimethyl)silyl]oxyethyl]-3-piperidyl]methoxy]imidazo[1,2-a]pyridin-3-yl]-N-cyclopropyl-2-(difluoromethoxy)-6-methoxy-benzamide (63 mg, 0.1 mmol, 1 eq.) is dissolved in ACN (2 mL) and water (100 µL) is added followed by 3 drops of concentrated HCl. The reaction mixture is stirred at RT. After 30 min, the reaction mixture is evaporated to dryness, dissolved in DMF (1 mL) and purified by preparative HPLC to afford Cpd 370.

2.119. Cpd 371

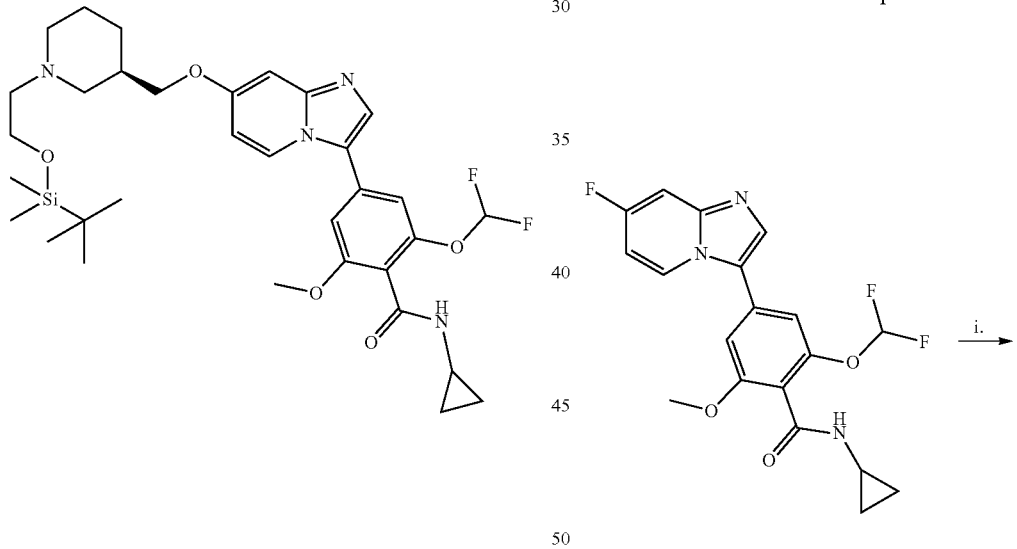

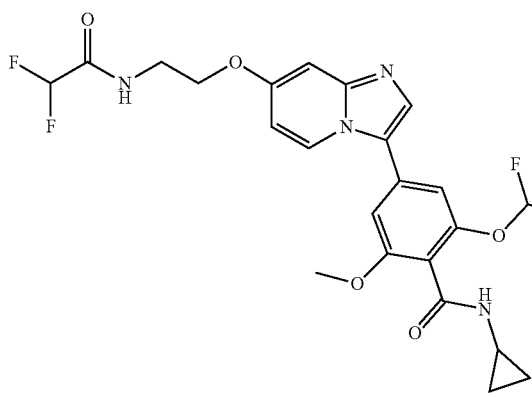

2.119.1. Step i: 4-[7-(2-aminoethoxy)imidazo[1,2-a]pyridin-3-yl]-N-cyclopropyl-2-(difluoromethoxy)-6-methoxybenzamide

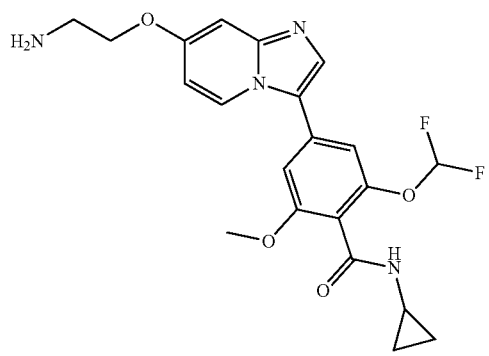

To a solution of 2-aminoethanol (31 µL, 0.511 mmol, 4 eq.) in dry DMF (1 mL) is added NaH (60% dispersion in mineral oil, 21 mg, 0.511 mmol, 4 eq.) at 0° C. and the mixture is stirred at 0° C. for 10 min. Int 1 (50 mg, 0.128 mmol, 1 eq.) is added and the reaction mixture is stirred at RT overnight and then at 40° C. for 48 h. The reaction mixture is quenched with a sat. aq. NaHCO₃ solution and extracted with DCM. The combined organic layers are dried over Na₂SO₄, filtered and concentrated. The crude residue is purified by flash chromatography on silica gel (eluting with 0 to 25% (MeOH+1% NH₃) in DCM) to afford 4-[7-(2-aminoethoxy)imidazo[1,2-a]pyridin-3-yl]-N-cyclopropyl-2-(difluoromethoxy)-6-methoxybenzamide.

LCMS: MW (calcd): 432.2; m/z MW (obsd): 433.0 (M+H)

2.119.2. Step ii: Cpd 371

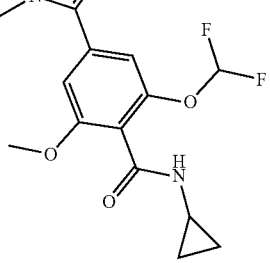

To a solution of difluoroacetic acid (2.9 µL, 0.0462 mmol, 1.1 eq.) in dry DCM (5 mL) is added dry DMF (20 µL) and oxalyl chloride (4.14 µL, 0.0483 mmol, 1.15 eq.). The reaction mixture is stirred at RT for 2 h and concentrated to dryness. The crude residue is dissolved in dry DCM (5 mL) and DIPEA (11 µL, 0.063 mmol, 1.5 eq.) and 4-[7-(2-aminoethoxy)imidazo[1,2-a]pyridin-3-yl]-N-cyclopropyl-2-(difluoromethoxy)-6-methoxybenzamide (18.9 mg, 0.420 mmol, 1 eq.) are added. The reaction mixture is stirred at RT overnight, quenched with a sat. aq. NaHCO₃ solution and extracted with DCM. The combined organic layers are dried over Na₂SO₄, filtered and concentrated. The crude product is purified by flash chromatography on silica gel (eluting with 0 to 25% (MeOH+1% NH₃) in DCM) to afford Cpd 371.

2.120. Cpd 372

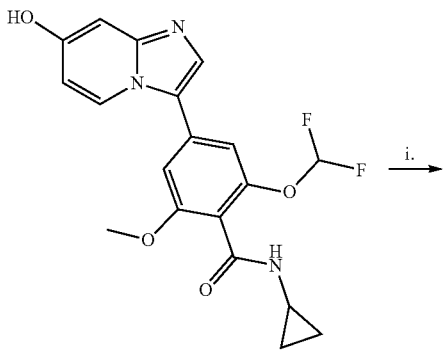

-continued

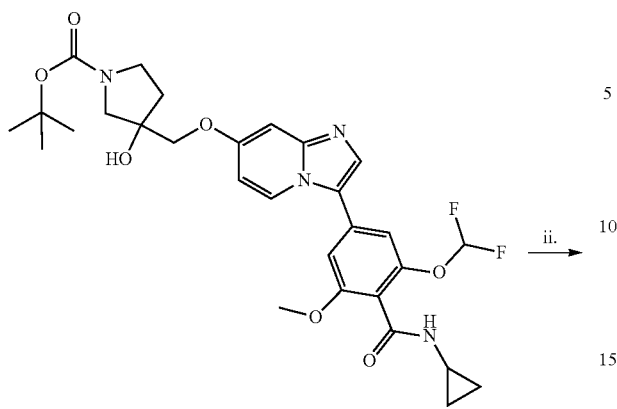

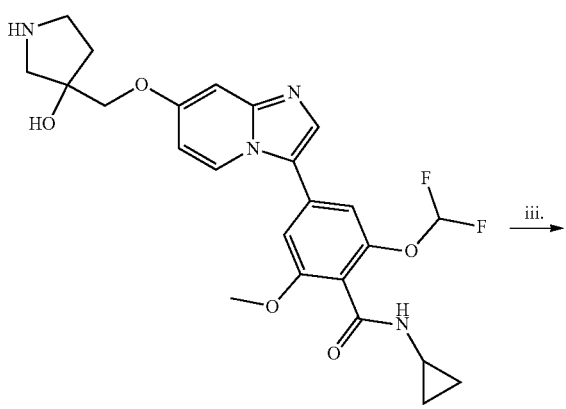

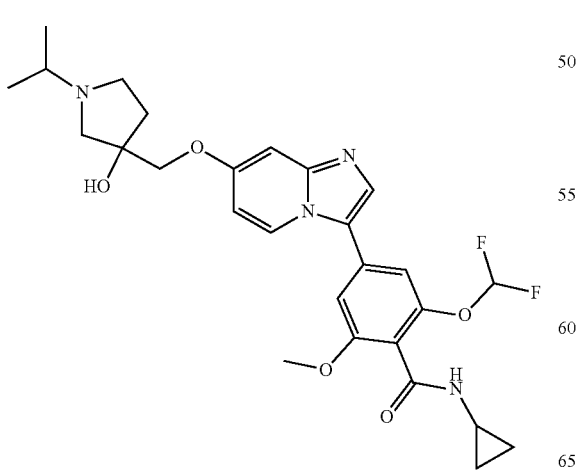

2.120.1. Step i: tert-butyl 3-[[3-[4-(cyclopropylcarbamoyl)-3-(difluoromethoxy)-5-methoxy-phenyl]imidazo[1,2-a]pyridin-7-yl]oxymethyl]-3-hydroxy-pyrrolidine-1-carboxylate

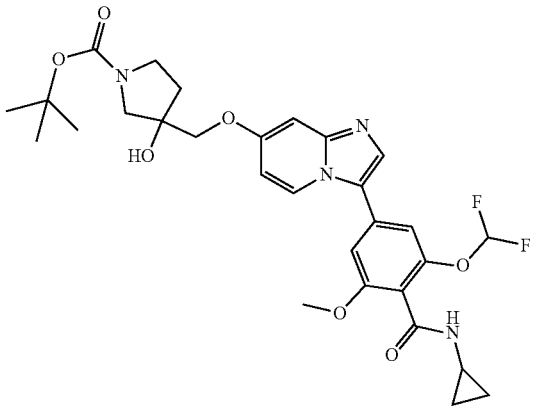

To a solution of Int 96 (24 mg, 0.061 mmol, 1 eq.) in dry DMF (0.6 mL) is added tert-butyl 1-oxa-5-azaspiro[2.4]heptane-5-carboxylate (CAS #301226-25-5; 13 mg, 0.061 mmol, 1 eq.) and $Cs_2CO_3$ (22 mg, 0.067 mmol, 1.1 eq.). The reaction mixture is stirred at 60° C. overnight, diluted with water and extracted with EtOAc. The combined organic layers are dried over $Na_2SO_4$, filtered and concentrated. The crude product is purified by flash chromatography on silica gel (eluting with 0 to 70% (DCM/MeOH/$NH_3$ in water 90/9.5/0.5) in DCM) to afford tert-butyl 3-[[3-[4-(cyclopropylcarbamoyl)-3-(difluoromethoxy)-5-methoxy-henyl]imidazo[1,2-a]pyridin-7-yl]oxymethyl]-3-hydroxy-pyrrolidine-1-carboxylate.

LCMS: MW (calcd): 588.2; m/z MW (obsd): 589.2 (M+H)

2.120.2. Step ii: N-cyclopropyl-2-(difluoromethoxy)-4-[7-[(3-hydroxypyrrolidin-3-yl)methoxy]imidazo[1,2-a]pyridin-3-yl]-6-methoxy-benzamide

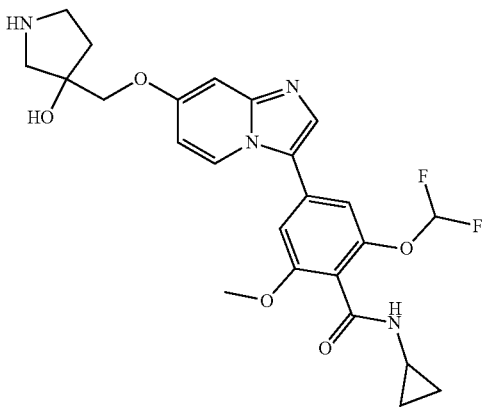

Tert-butyl 3-[[3-[4-(cyclopropylcarbamoyl)-3-(difluoromethoxy)-5-methoxy-henyl]imidazo[1,2-a]pyridin-7-yl]oxymethyl]-3-hydroxy-pyrrolidine-1-carboxylate (32 mg, 0.054 mmol, 1 eq.) is solubilized in HCl, 4N in 1,4-dioxane (1 mL). The reaction mixture is stirred at RT for 2 h, diluted with water, quenched with a sat. aq. NaHCO₃ solution and extracted with DCM. The combined organic layers are dried over Na₂SO₄, filtered and concentrated to dryness to afford N-cyclopropyl-2-(difluoromethoxy)-4-[7-[(3-hydroxypyrrolidin-3-yl)methoxy]imidazo[1,2-a]pyridin-3-yl]-6-methoxy-benzamide.

LCMS: MW (calcd): 488.2; m/z MW (obsd): 489.1 (M+H)

2.120.3. Step iii: Cpd 372

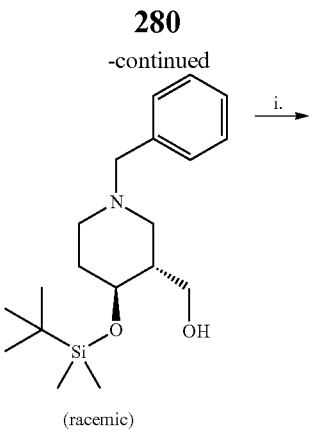
(racemic)

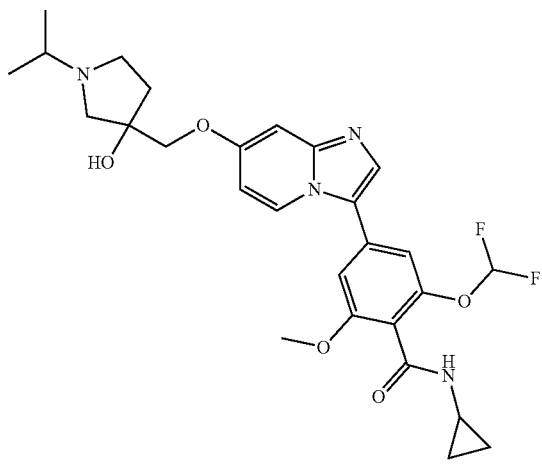 [SMILES: COc1cc(-c2cnc3cc(OCC4(O)CCN(C(C)C)C4)ccn23)cc(OC(F)F)c1C(=O)NC1CC1]

To a solution of N-cyclopropyl-2-(difluoromethoxy)-4-[7-[(3-hydroxypyrrolidin-3-yl)methoxy]imidazo[1,2-a]pyridin-3-yl]-6-methoxy-benzamide (25 mg, 0.045 mmol, 1 eq.) in dry THF (0.9 mL) are added 2 drops of AcOH. The reaction mixture is cooled to 0° C. and acetone (6.6 µL, 0.089 mmol, 2 eq.) and NaBH(OAc)₃ (CAS #56553-60-7; 19 mg, 0.089 mmol, 2 eq.) are added. The mixture is stirred at RT for 2 h, diluted with water, quenched with a sat. aq. NaHCO₃ solution and extracted with DCM. The combined organic layers are dried over Na₂SO₄, filtered and concentrated. The crude is purified by flash chromatography on silica gel (eluting with 0 to 70% (DCM/MeOH/NH₃ in water 80/19/1) in DCM) to afford Cpd 372.

2.121. Cpd 373

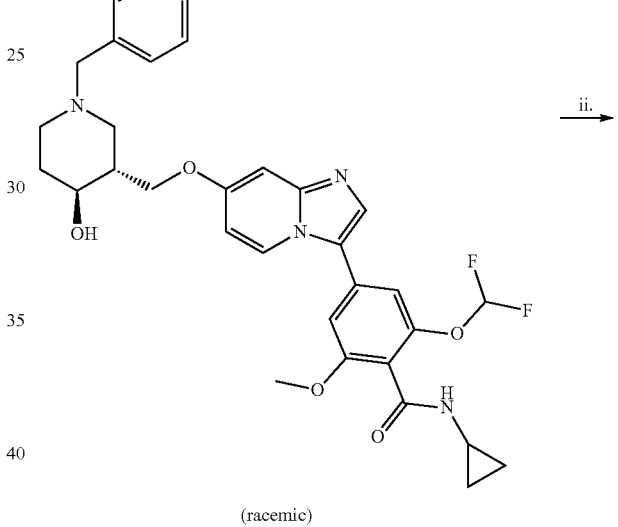
(racemic)

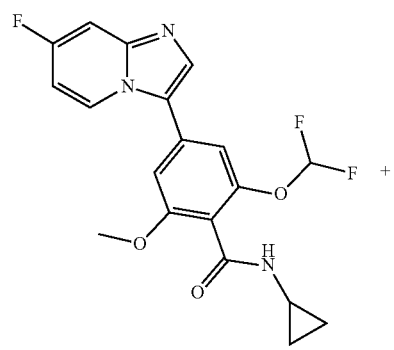 +

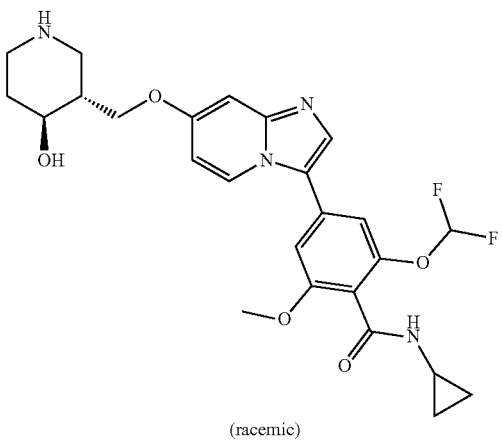
(racemic)

2.121.1. Step i: 4-[7-[[(3R,4S)-1-benzyl-4-hydroxy-3-piperidyl]methoxy]imidazo[1,2-a]pyridin-3-yl]-N-cyclopropyl-2-(difluoromethoxy)-6-methoxy-benzamide/4-[7-[[(3S,4R)-1-benzyl-4-hydroxy-3-piperidyl]methoxy]imidazo[1,2-a]pyridin-3-yl]-N-cyclopropyl-2-(difluoromethoxy)-6-methoxy-benzamide Mixture

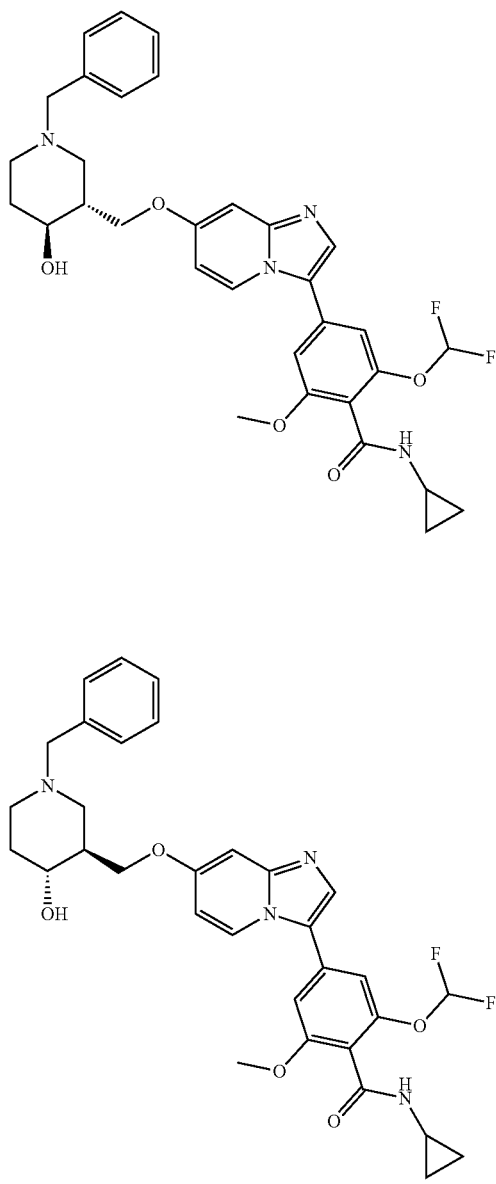

To a solution of Int 95 (33 mg, 0.0754 mmol, 1 eq.) in dry DMF (3 mL) is added NaH (60% dispersion in mineral oil, 6 mg, 0.151 mmol, 2 eq.) at 0° C. and the mixture is stirred for 10 min. Int 1 (30 mg, 0.0754 mmol, 1 eq.) is added and the reaction mixture is stirred at RT for 48 h. NaH (60% dispersion in mineral oil, 6 mg, 0.151 mmol, 2 eq.) is added and the mixture is stirred at RT overnight. The reaction mixture is quenched with a sat. aq. NaHCO$_3$ solution and extracted with DCM. The combined organic layers are dried over Na$_2$SO$_4$, filtered and concentrated. The crude product is purified by flash chromatography on silica gel (eluting with 0 to 25% (MeOH+1% NH$_3$) in DCM) to afford 4-[7-[[(3R,4S)-1-benzyl-4-hydroxy-3-piperidyl]methoxy]imidazo[1,2-a]pyridin-3-yl]-N-cyclopropyl-2-(difluoromethoxy)-6-methoxy-benzamide/4-[7-[[(3S,4R)-1-benzyl-4-hydroxy-3-piperidyl]methoxy]imidazo[1,2-a]pyridin-3-yl]-N-cyclopropyl-2-(difluoromethoxy)-6-methoxy-benzamide racemic mixture.

2.121.2. Step ii: Cpd 0.73

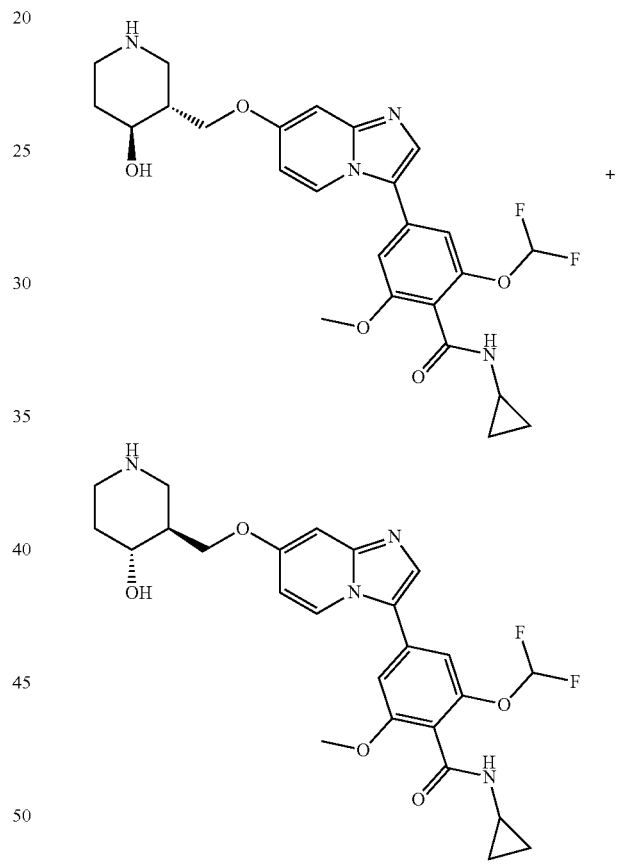

To a solution of 4-[7-[[(3R,4S)-1-benzyl-4-hydroxy-3-piperidyl]methoxy]imidazo[1,2-a]pyridin-3-yl]-N-cyclopropyl-2-(difluoromethoxy)-6-methoxy-benzamide (26 mg, 0.0439 mmol, 1 eq.) in dry isopropanol (2 mL) are added ammonium formate (14 mg, 0.219 mmol, 5 eq.) and 10% Pd/C (14 mg, 0.0133 mmol, 0.3 eq.) under argon atmosphere. The reaction mixture is stirred at 70° C. overnight. Ammonium formate (14 mg, 0.219 mmol, 5 eq.) and 10% Pd/C (14 mg, 0.0133 mmol, 0.3 eq.) are added under argon atmosphere and the reaction mixture is stirred at 70° C. for 7 h. The reaction mixture is filtered over a cotton pad and concentrated to dryness. The crude is purified using a preparative TLC plate (eluting with 10% MeOH+0.5% NH$_3$ in DCM) to afford Cpd 373 (racemic mixture).

2.122. Cpd 396

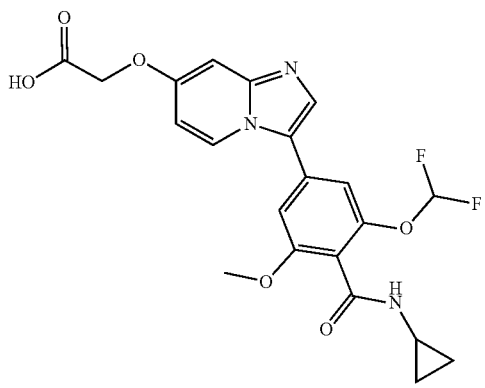

A solution of LiOH (36.3 mg, 1.51 mmol) in water (1.0 mL) is added to a suspension of Cpd 268 (180 mg, 0.379 mmol) in THF (1.0 mL) and the reaction is stirred at RT for 2 h. The reaction mixture is concentrated, diluted with water (4 mL) and the pH is adjusted to 7 with 6N HCl. The obtained precipitate is filtered and dried to obtain Cpd 396.

2.123. Cpd 386 & Cpd 387

Cpd 330 (50 mg) is diluted in MeOH (2 mL) and separated by chiral preparative SFC (Chiralpak IG column, 10 mm ID×250 mm L, 5 μm particle size), eluting with 50% EtOH in liquid $CO_2$ to afford Cpd 386 as the first eluting and Cpd 387 as the second eluting compound.

2.124. Cpd 397

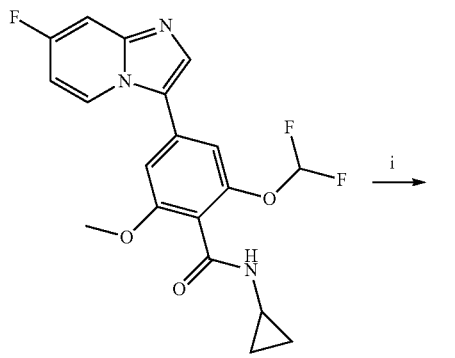

i →

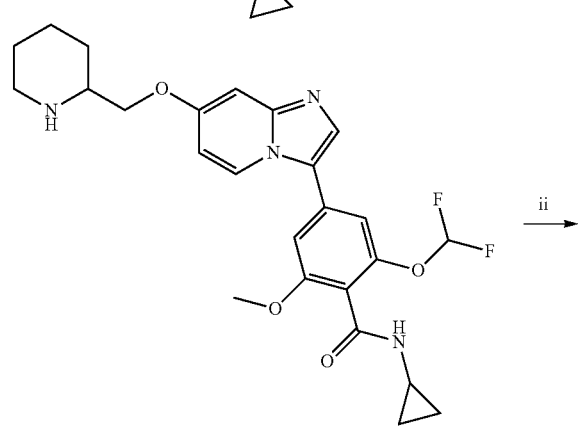

ii →

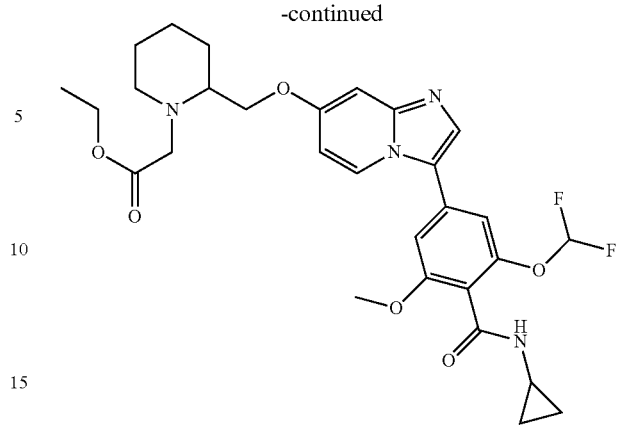

2.124.1. Step i: N-cyclopropyl-2-(difluoromethoxy)-6-methoxy-4-[7-(2-piperidylmethoxy)imidazo[1,2-a]pyridin-3-yl]benzamide

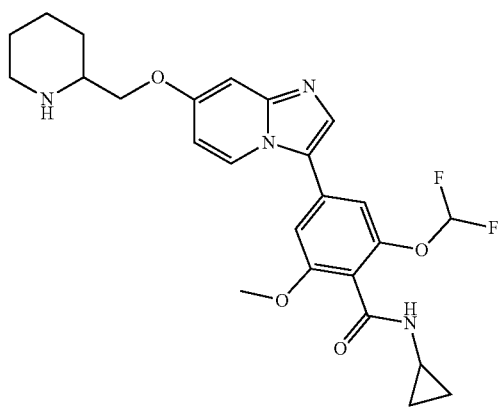

To a solution of 2-piperidinemethanol (CAS #3433-37-2; 177 mg, 1.5 mmol, 2 eq.) in dry DMF (5 mL) is added NaH (60% dispersion in mineral oil, 61 mg, 1.5 mmol, 2 eq.) at 0° C. and the mixture is stirred for 10 min. Int 1 (300 mg, 0.77 mmol, 1 eq.) is added and the reaction mixture is stirred at RT overnight. NaH (60% dispersion in mineral oil, 30 mg, 0.77 mmol, 1 eq.) is added and the reaction mixture is stirred at RT overnight, quenched with water and extracted with EtOAc. The combined organic layers are dried over $Na_2SO_4$, filtered and concentrated. The crude product is purified by flash chromatography on silica gel (eluting with 0 to 15% MeOH in DCM) to afford N-cyclopropyl-2-(difluoromethoxy)-6-methoxy-4-[7-(2-piperidylmethoxy)imidazo[1,2-a]pyridin-3-yl]benzamide.

LCMS: MW (calcd): 486.2; m/z MW (obsd): 487.6 (M+H)

2.124.2. Step ii: Cpd 397

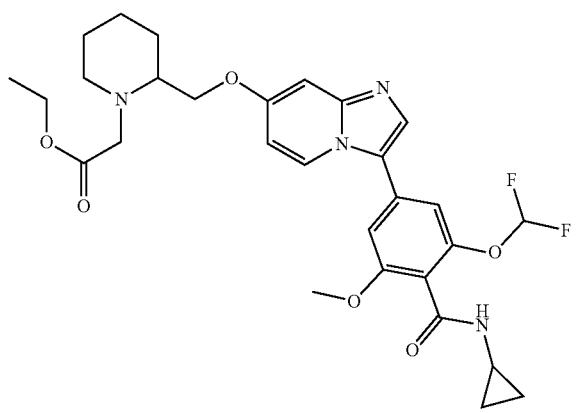

To a solution of N-cyclopropyl-2-(difluoromethoxy)-6-methoxy-4-[7-(2-piperidylmethoxy)imidazo[1,2-a]pyridin-3-yl]benzamide (50 mg, 0.0997 mmol, 1 eq.) and ethyl glyoxylate (CAS #924-44-7; 20 μL, 0.199 mmol, 2 eq.) in dry THF (5 mL) are added 2 drops of AcOH. NaBH(OAc)$_3$ (CAS #56553-60-7; 106 mg, 0.498 mmol, 5 eq.) is added at 0° C. and the reaction mixture is stirred at RT overnight. The reaction mixture is quenched with water and extracted with DCM. The combined organic layers are dried over Na$_2$SO$_4$, filtered and concentrated. The crude product is purified by flash chromatography on silica gel (eluting with 0 to 20% MeOH in DCM) to afford Cpd 397.

2.125. Cpd 398

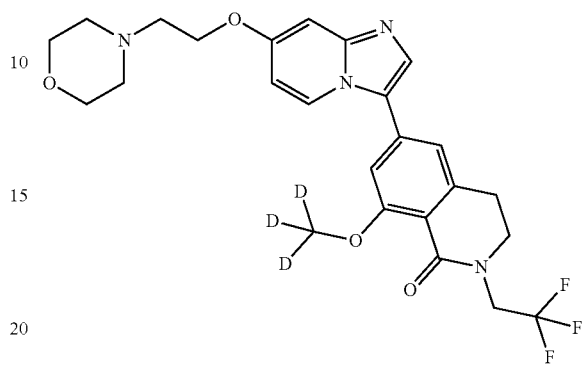

To a solution of Int 91 (3.165 g, 9.28 mmol, 1.13 eq.) in 1,4-dioxane (26 mL), under N$_2$ atmosphere, is added Int 25 di-HCl salt (2.63 g, 8.21 mmol, 1 eq.), K$_2$CO$_3$ (3.972 g, 28.74 mmol, 3.5 eq.) and pivalic acid (CAS #75-98-9; 839 mg, 8.2 mmol, 1 eq.). Pd(dppf)Cl$_2$·DCM (CAS #95464-05-4; 335 mg, 0.41 mmol, 0.05 eq.) is added and the reaction mixture is heated at 100° C. for 8 h. The reaction mixture is cooled down to 20° C. and filtered through a pad of Dicalite™. The filtrate is evaporated under reduced pressure. The resulting crude product is suspended in EtOAc and stirred at RT for 30 min. The solid is filtered and rinsed with heptane. The solid is dissolved in EtOH (9 mL) and a solution of 4N HCl in 1,4-dioxane (9 mL) is added dropwise. The suspension is stirred at RT overnight. The solid is filtered, rinsed with acetone and dried under vacuum to afford the expected product as a di-HCl salt.

TABLE II

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 1 | 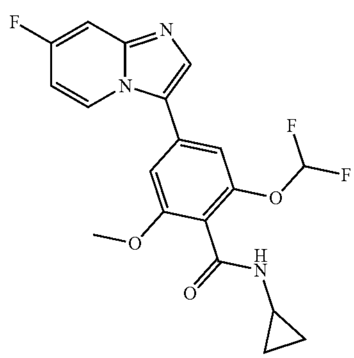 [SMILES: COc1cc(-c2cnc3cc(F)ccn23)cc(OC(F)F)c1C(=O)NC1CC1] | N-cyclopropyl-2-(difluoromethoxy)-4-(7-fluoroimidazo[1,2-a]pyridin-3-yl)-6-methoxy-benzamide | CAS# 1260903-17-0 + Int 11 | Ex. 2.1 | 391.3 | 392.2 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 2 | 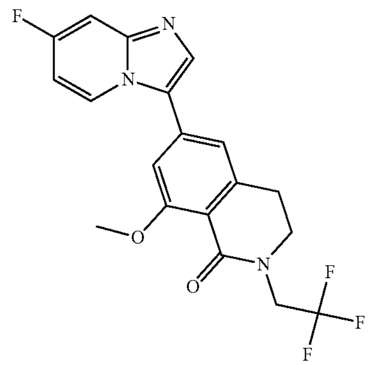 [SMILES: COc1cc(-c2cnc3cc(F)ccn23)cc2c1C(=O)N(CC(F)(F)F)CC2] | 6-(7-fluoroimidazo[1,2-a]pyridin-3-yl)-8-methoxy-2-(2,2,2-trifluoroethyl)-3,4-dihydroisoquinolin-1-one | CAS# 1260903-17-0 + Int 39 | B | 393.3 | 394.3 |
| 3 | 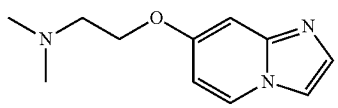 | 2-imidazo[1,2-a]pyridin-7-yloxy-N,N-dimethyl-ethanamine | CAS# 1260903-17-0 + CAS# 108-01-0 | Ex. 2.2 | 205.3 | 206.2 |
| 4 | 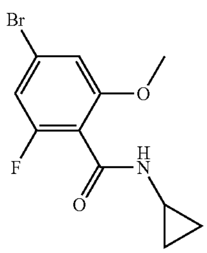 [SMILES: COc1cc(Br)cc(F)c1C(=O)NC1CC1] | 4-bromo-N-cyclopropyl-2-fluoro-6-methoxy-benzamide | Int 88 | Ex. 2.3 | 288.1 | 287.8 + 289.8 |
| 5 | 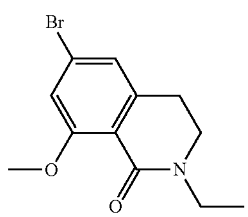 [SMILES: CCN1CCc2cc(Br)cc(OC)c2C1=O] | 6-bromo-2-ethyl-8-methoxy-3,4-dihydroisoquinolin-1-one | Int 40 + CAS# 75-03-6 | Ex. 2.4 | 284.2 | 284.1 + 286.1 |
| 6 | 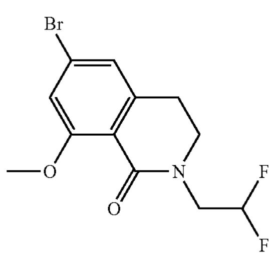 [SMILES: COc1cc(Br)cc2c1C(=O)N(CC(F)F)CC2] | 6-bromo-2-(2,2-difluoroethyl)-8-methoxy-3,4-dihydroisoquinolin-1-one | Int 40 + CAS# 74427-22-8 | E | 320.1 | NA |
| 8 | 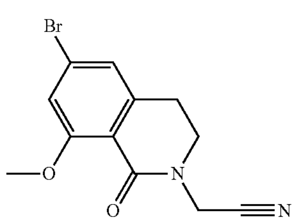 [SMILES: COc1cc(Br)cc2c1C(=O)N(CC#N)CC2] | 2-(6-bromo-8-methoxy-1-oxo-3,4-dihydroisoquinolin-2-yl)acetonitrile | Int 40 + CAS# 590-17-0 | Ex. 2.5 | 295.1 | 295.1 + 297.1 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 9 | 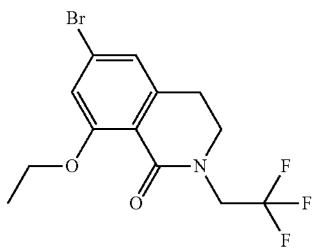 [SMILES: CCOc1cc(Br)cc2c1C(=O)N(CC(F)(F)F)CC2] | 6-bromo-8-ethoxy-2-(2,2,2-trifluoroethyl)-3,4-dihydroisoquinolin-1-one | Int 41 + CAS# 6226-25-1 | E | 352.2 | 352.3 + 354.3 |
| 10 | 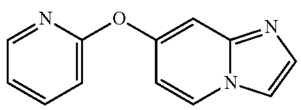 [SMILES: c1ccc(Oc2ccn3ccnc3c2)nc1] | 7-(2-pyridyloxy)imidazo[1,2-a]pyridine | CAS# 896139-85-8 + CAS# 372-48-5 | Ex. 2.6 | 211.2 | 212.2 |
| 11 | 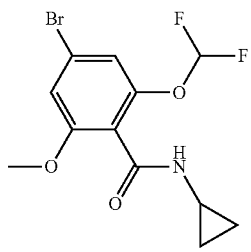 [SMILES: COc1cc(Br)cc(OC(F)F)c1C(=O)NC1CC1] | 4-bromo-N-cyclopropyl-2-(difluoromethoxy)-6-methoxy-benzamide | Int 42 | Ex. 2.7 | 336.1 | 336.3 + 338.3 |
| 12 | 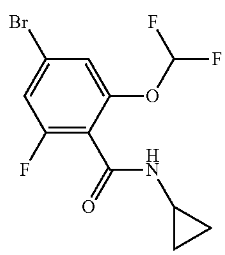 [SMILES: O=C(NC1CC1)c1c(F)cc(Br)cc1OC(F)F] | 4-bromo-N-cyclopropyl-2-(difluoromethoxy)-6-fluoro-benzamide | Int 42 | G | 324.1 | 324.1 + 326.1 |
| 13 | 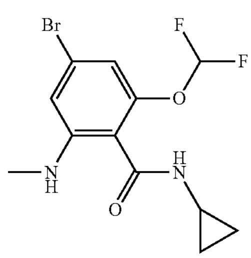 [SMILES: CNc1cc(Br)cc(OC(F)F)c1C(=O)NC1CC1] | 4-bromo-N-cyclopropyl-2-(difluoromethoxy)-6-(methylamino)benzamide | Int 12 + CAS# 593-51-1 | Ex. 2.8 | 335.2 | 335.1 + 337.2 |
| 14 | 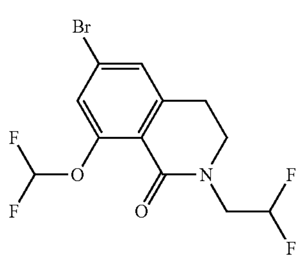 [SMILES: O=C1c2c(cc(Br)cc2OC(F)F)CCN1CC(F)F] | 6-bromo-2-(2,2-difluoroethyl)-8-(difluoromethoxy)-3,4-dihydroisoquinolin-1-one | Int 6 | Ex. 2.9 | 356.1 | 356.6 + 358.3 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 15 | 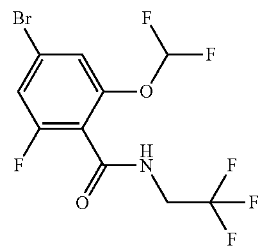 [SMILES: O=C(NCC(F)(F)F)c1c(F)cc(Br)cc1OC(F)F] | 4-bromo-2-(difluoromethoxy)-6-fluoro-N-(2,2,2-trifluoroethyl)benzamide | Int 44 | G | 366.1 | 366.2 + 368.1 |
| 16 | 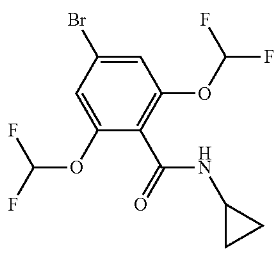 [SMILES: O=C(NC1CC1)c1c(OC(F)F)cc(Br)cc1OC(F)F] | 4-bromo-N-cyclopropyl-2,6-bis(difluoromethoxy)benzamide | Int 11 | Ex. 2.10 | 372.1 | 372.1 + 374.1 |
| 17 | 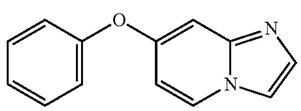 | 7-phenoxyimidazo[1,2-a]pyridine | CAS# 896139-85-8 + CAS# 108-86-1 | Ex. 2.11 | 210.2 | 211.2 |
| 18 | 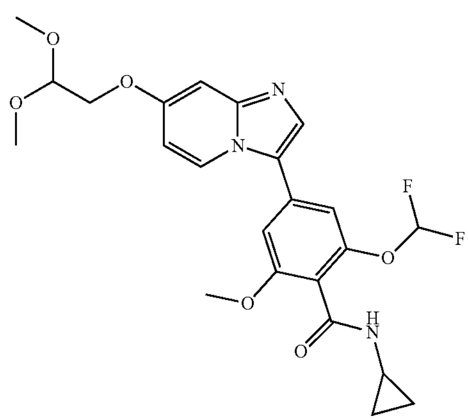 [SMILES: COc1cc(-c2cnc3cc(OCC(OC)OC)ccn23)cc(OC(F)F)c1C(=O)NC1CC1] | N-cyclopropyl-2-(difluoromethoxy)-4-[7-(2,2-dimethoxyethoxy)imidazo[1,2-a]pyridin-3-yl]-6-methoxy-benzamide | Int 1 + CAS# 30934-97-5 | A | 477.5 | 478.4 |
| 19 | 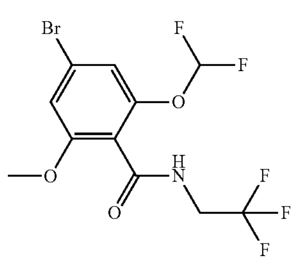 [SMILES: COc1cc(Br)cc(OC(F)F)c1C(=O)NCC(F)(F)F] | 4-bromo-2-(difluoromethoxy)-6-methoxy-N-(2,2,2-trifluoroethyl)benzamide | Int 47 | Ex. 2.12 | 378.1 | 378.1 + 380.1 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 20 | 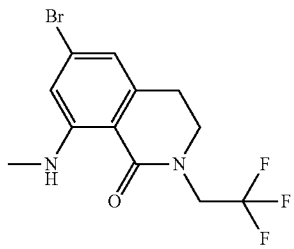 [SMILES: CNc1cc(Br)cc2c1C(=O)N(CC(F)(F)F)CC2] | 6-bromo-8-(methyl amino)-2-(2,2,2-trifluoroethyl)-3,4-dihydroisoquinolin-1-one | CAS# 1242157-15-8 + CAS# 6226-25-1 | Ex. 2.13 | 337.1 | 337.1 + 339.1 |
| 21 | 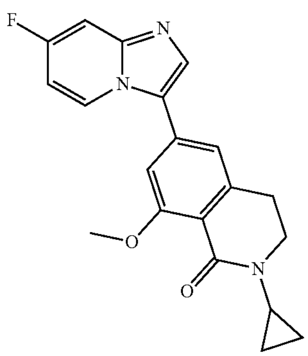 [SMILES: COc1cc(-c2cnc3cc(F)ccn23)cc2c1C(=O)N(C1CC1)CC2] | 2-cyclopropyl-6-(7-fluoroimidazo[1,2-a]pyridin-3-yl)-8-methoxy-3,4-dihydro isoquinolin-1-one | CAS# 1260903-17-0 + Int 49 | B | 351.4 | 352.4 |
| 22 | 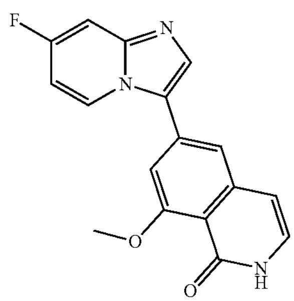 [SMILES: COc1cc(-c2cnc3cc(F)ccn23)cc2cc[nH]c(=O)c12] | 6-(7-fluoroimidazo[1,2-a]pyridin-3-yl)-8-methoxy-2H-isoquinolin-1-one | CAS# 1260903-17-0 + Int 51 | B | 309.3 | 310.4 |
| 23 | 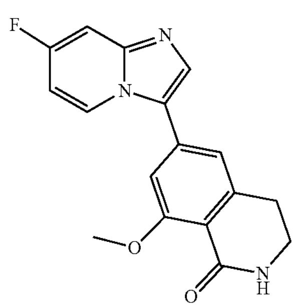 [SMILES: COc1cc(-c2cnc3cc(F)ccn23)cc2c1C(=O)NCC2] | 6-(7-fluoroimidazo[1,2-a]pyridin-3-yl)-8-methoxy-3,4-dihydro-2H-isoquinolin-1-one | CAS# 1260903-17-0 + Int 40 | B | 311.3 | 312.2 |

TABLE II-continued

Intermediates used towards the compounds of the invention.

SM = Starting Material, Mtd = Method, MS Mes'd = Mesured mass, NA = not measured

| Int # | Structure | Name | SM | Mtd | MW | MS Mes'd |
|---|---|---|---|---|---|---|
| 24 | 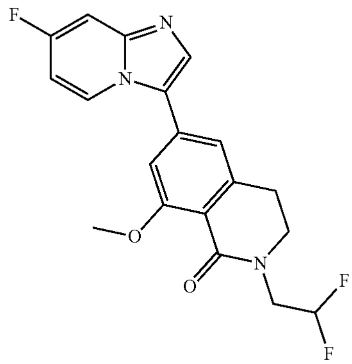 [SMILES: COc1cc(-c2cnc3cc(F)ccn23)cc2c1C(=O)N(CC(F)F)CC2] | 2-(2,2-difluoroethyl)-6-(7-fluoroimidazo[1,2-a]pyridin-3-yl)-8-methoxy-3,4-dihydroisoquinolin-1-one | CAS# 1260903-17-0 + Int 6 | B | 375.3 | 376.2 |
| 25 | 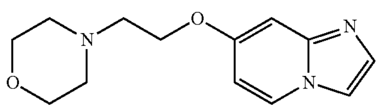 [SMILES: c1cn2ccc(OCCN3CCOCC3)cc2n1] | 4-(2-imidazo[1,2-a]pyridin-7-yloxyethyl)morpholine | CAS# 1260903-17-0 + CAS# 622-40-2 | Ex. 2.14 | 247.3 | 248.2 |
| 26 | 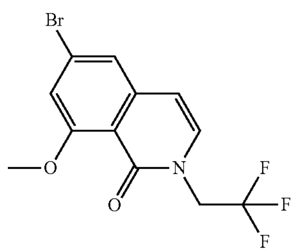 [SMILES: COc1cc(Br)cc2ccn(CC(F)(F)F)c(=O)c12] | 6-bromo-8-methoxy-2-(2,2,2-trifluoroethyl)isoquinolin-1-one | Int 51 + CAS# 6226-25-1 | Ex. 2.15 | 336.1 | 336.2 + 338.3 |
| 27 | 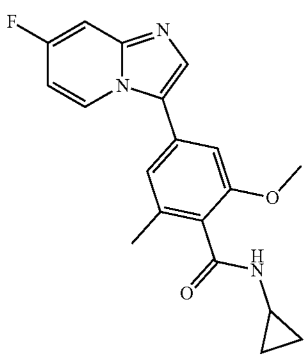 [SMILES: COc1cc(-c2cnc3cc(F)ccn23)cc(C)c1C(=O)NC1CC1] | N-cyclopropyl-4-(7-fluoroimidazo[1,2-a]pyridin-3-yl)-2-methoxy-6-methyl-benzamide | CAS# 2089326-83-8 + Int 52 | C | 339.1 | 340.4 |
| 28 | 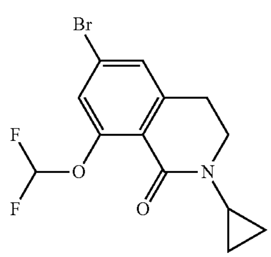 [SMILES: O=C1c2c(cc(Br)cc2OC(F)F)CCN1C1CC1] | 6-bromo-2-cyclopropyl-8-(difluoromethoxy)-3,4-dihydroisoquinolin-1-one | Int 49 | Ex. 2.16 | 332.1 | NA |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 29 | 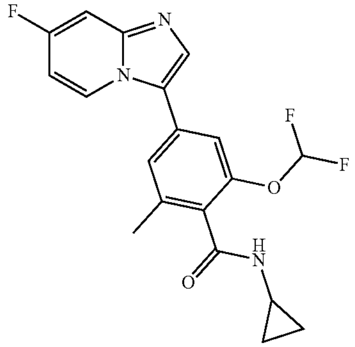 [SMILES: Cc1cc(-c2cnc3cc(F)ccn23)cc(OC(F)F)c1C(=O)NC1CC1] | N-cyclopropyl-2-(difluoromethoxy)-4-(7-fluoroimidazo[1,2-a]pyridin-3-yl)-6-methyl-benzamide | CAS# 2089326-83-8 + Int 54 | C | 375.3 | 376.2 |
| 30 | 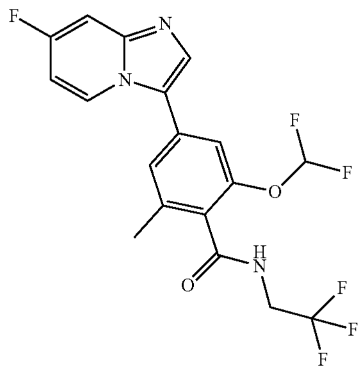 [SMILES: Cc1cc(-c2cnc3cc(F)ccn23)cc(OC(F)F)c1C(=O)NCC(F)(F)F] | 2-(difluoromethoxy)-4-(7-fluoroimidazo[1,2-a]pyridine-3-yl)-6-methyl-N-(2,2,2-trifluoroethyl)benzamide | CAS# 2089326-83-8 + Int 57 | C | 417.3 | 418.2 |
| 31 | 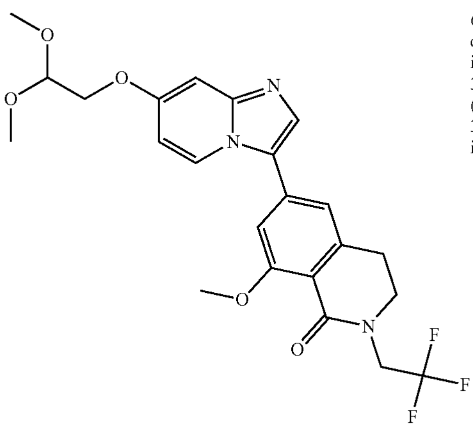 [SMILES: COc1cc(-c2cnc3cc(OCC(OC)OC)ccn23)cc2c1C(=O)N(CC(F)(F)F)CC2] | 6-7-(2,2-dimethoxyethoxy)imidazo[1,2-a]pyridin-3-yl]-8-methoxy-2-(2,2,2-trifluoroethyl)-3,4-dihydro isoquinolin-1-one | Int 2 + CAS# 30934-97-5 | A | 479.5 | 480.3 |
| 32 | 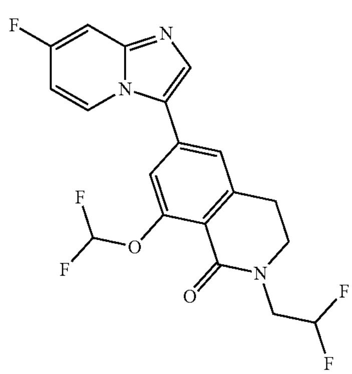 [SMILES: O=C1c2c(cc(-c3cnc4cc(F)ccn34)cc2OC(F)F)CCN1CC(F)F] | 2-(2,2-difluoroethyl)-8-(difluoromethoxy)-6-(7-fluoro imidazo[1,2-a]pyridin-3-yl)-3,4-dihydroisoquinolin-1-one | CAS# 1260903-17-0 + Int 14 | B | 411.3 | 412.5 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 33 | 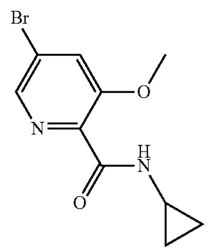 | 5-bromo-N-cyclopropyl-3-methoxy-pyridine-2-carboxamide | CAS# 1142191-66-9 + CAS# 765-30-0 | Ex. 2.17 | 271.1 | 271.2 + 273.2 |
| 34 | 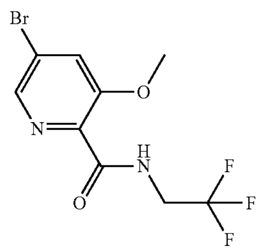 [SMILES: COc1cc(Br)cnc1C(=O)NCC(F)(F)F] | 5-bromo-3-methoxy-N-(2,2,2-trifluoroethyl)pyridine-2-carboxamide | CAS# 1142191-66-9 + CAS# 373-88-6 | Ex. 2.18 | 313.1 | 313.2 + 315.2 |
| 35 | 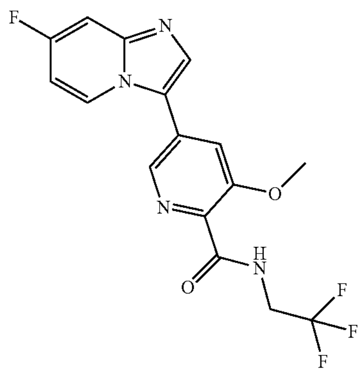 [SMILES: COc1cc(-c2cnc3cc(F)ccn23)cnc1C(=O)NCC(F)(F)F] | 5-(7-fluoroimidazo[1,2-a]pyridin-3-yl)-3-methoxy-N-(2,2,2-trifluoroethyl)pyridine-2-carboxamide | CAS# 1260903-17-0 + Int 34 | B | 368.3 | 369.2 |
| 36 | 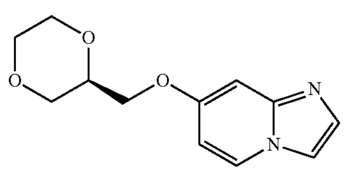 [SMILES: c1cn2ccc(OC[C@H]3COCCO3)cc2n1] | 7-[[(2R)-1,4-dioxan-2-yl]methoxy]imidazo[1,2-a]pyridine | CAS# 1260903-17-0 + CAS# 406913-93-7 | Ex. 2.19 | 234.3 | 235.3 |
| 37 | 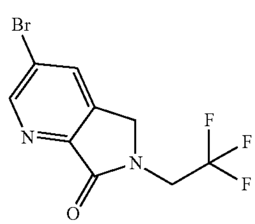 [SMILES: O=C1c2ncc(Br)cc2CN1CC(F)(F)F] | 3-bromo-6-(2,2,2-trifluoroethyl)-5H-pyrrolo[3,4-b]pyridin-7-one | CAS# 1346809-61-7 + CAS# 6226-25-1 | E | 295.1 | 295.1 + 297.1 |
| 38 | 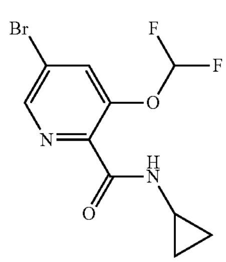 [SMILES: O=C(NC1CC1)c1ncc(Br)cc1OC(F)F] | 5-bromo-N-cyclopropyl-3-(difluoromethoxy)pyridine-2-carboxamide | CAS# 1242320-57-5 | Ex. 2.20 | 307.1 | 307.1 + 309.1 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 39 | 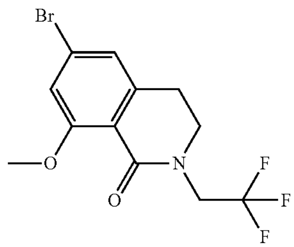 [SMILES: COc1cc(Br)cc2c1C(=O)N(CC(F)(F)F)CC2] | 6-bromo-8-methoxy-2-(2,2,2-trifluoroethyl)-3,4-dihydroisoquinolin-1-one | Int 40 + CAS# 6226-25-1 | E or Ex. 2.21 | 338.1 | 338.1 + 340.1 |
| 40 | 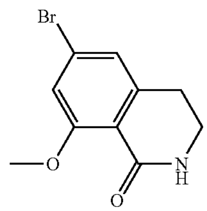 | 6-bromo-8-methoxy-3,4-dihydro-2H-isoquinolin-1-one | CAS# 1242157-15-8 + CAS# 124-41-4 or CAS# 139102-34-4 | D or Q | 256.1 | 256.1 + 258.1 |
| 41 | 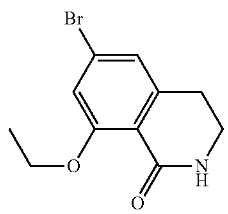 | 6-bromo-8-ethoxy-3,4-dihydro-2H-isoquinolin-1-one | CAS# 1242157-15-8 + CAS# 141-52-6 | D | 270.1 | 270.1 + 272.1 |
| 42 | 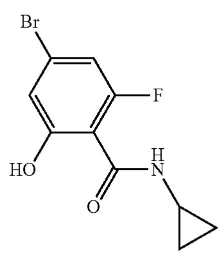 [SMILES: O=C(NC1CC1)c1c(O)cc(Br)cc1F] | 4-bromo-N-cyclopropyl-2-fluoro-6-hydroxy-benzamide | Int 88 | Ex. 2.22 | 274.1 | 273.9 + 275.8 |
| 44 | 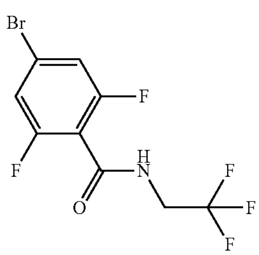 [SMILES: O=C(NCC(F)(F)F)c1c(F)cc(Br)cc1F] | 4-bromo-2,6-difluoro-N-(2,2,2-trifluoroethyl)benzamide | CAS# 183065-68-1 + CAS# 373-88-6 | Ex. 2.23 | 318.0 | 317.8 + 319.8 |
| 47 | 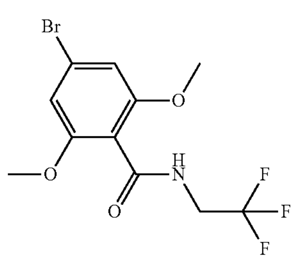 [SMILES: COc1cc(Br)cc(OC)c1C(=O)NCC(F)(F)F] | 4-bromo-2,6-dimethoxy-N-(2,2,2-trifluoroethyl)benzamide | Int 44 | Ex. 2.24 | 342.1 | 343.8 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 49 | 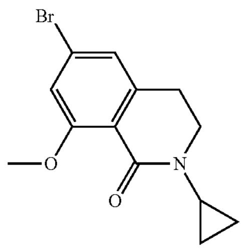 [SMILES: COc1cc(Br)cc2c1C(=O)N(C1CC1)CC2] | 6-bromo-2-cyclo propyl-8-methoxy-3,4-dihydro isoquinolin-1-one | CAS# 1242157-15-8 | Ex. 2.25 | 296.2 | 296.3 + 298.2 |
| 51 | 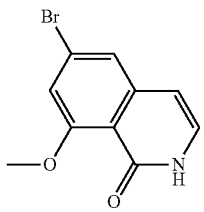 | 6-bromo-8-methoxy-2H-isoquinolin-1-one | CAS# 1803606-88-3 | D | 254.1 | 254.0 + 256.0 |
| 52 | 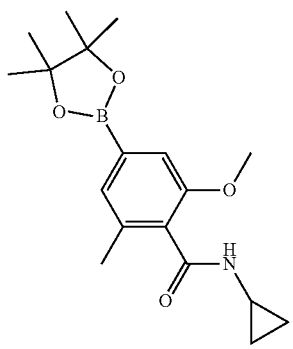 [SMILES: COc1cc(B2OC(C)(C)C(C)(C)O2)cc(C)c1C(=O)NC1CC1] | N-cyclopropyl-2-methoxy-6-methyl-4-(4,4,5,5-tetramethyl-1,3,2-dioxaborolan-2-yl)benzamide | Int 53 + CAS# 73183-34-3 | Ex. 2.26 | 331.2 | 332.4. |
| 53 | 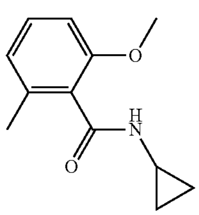 | N-cyclopropyl-2-methoxy-6-methyl-benzamide | CAS# 6161-65-5 + CAS# 765-30-0 | Ex. 2.27 | 205.3 | 206.2. |
| 54 | 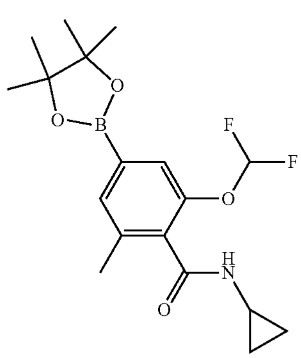 [SMILES: Cc1cc(B2OC(C)(C)C(C)(C)O2)cc(OC(F)F)c1C(=O)NC1CC1] | N-cyclopropyl-2-(difluoromethoxy)-6-methyl-4-(4,4,5,5-tetramethyl-1,3,2-dioxaborolan-2-yl)benzamide/[4-(cyclopropylcarbamoyl)-3-(difluoro methoxy)-5-methyl-phenyl]boronic acid mixture | Int 56 + CAS# 73183-34-3 | Ex. 2.28 | 367.2 + 285.1 | 368.4. + 286.4 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 56 | 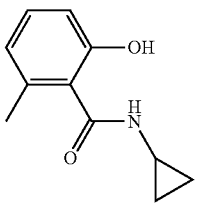 | N-cyclopropyl-2-hydroxy-6-methyl-benzamide | Int 53 + CAS# 10294-34-5 | F | 191.2 | 192.3. |
| 57 | | 2-(difluoromethoxy)-6-methyl-4-(4,4,5,5-tetramethyl-1,3,2-dioxaborolan-2-yl)-N-(2,2,2-trifluoroethyl) benzamide/[3-(difluoromethoxy)-5-methyl-4-(2,2,2-trifluoroethylcarbamoyl) phenyl]boronic acid mixture | CAS# 6161-65-5 | Ex. 2.29 | 409.2 + 327.0 | NA |
| 63 | 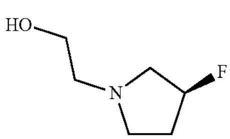 | 2-[(3S)-3-fluoropyrrolidin-1-yl]ethanol | CAS# 136725-53-6 + CAS# 540-51-2 | H | 133.2 | 134.5. |
| 64 | 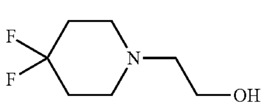 | 2-(4,4-difluoro-1-piperidyl)ethanol | CAS# 21987-29-1 + CAS# 540-51-2 | H | 165.1 | 166.5. |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 65 | 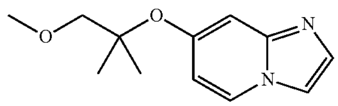 [SMILES: COCC(C)(C)Oc1ccn2ccnc2c1] | 7-(2-methoxy-1,1-dimethyl-ethoxy)imidazo[1,2-a]pyridine | Int 67 | Ex. 2.30 | 220.3 | 221.1. |
| 67 | 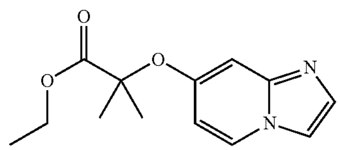 [SMILES: CCOC(=O)C(C)(C)Oc1ccn2ccnc2c1] | ethyl 2-imidazo[1,2-a]pyridin-7-yloxy-2-methyl-propanoate | CAS# 896139-85-8 + CAS# 600-00-0 | Ex. 2.31 | 248.3 | 249.1. |
| 68 | 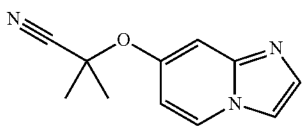 | 2-imidazo[1,2-a]pyridin-7-yloxy-2-methyl-propanenitrile | Int 67 | Ex. 2.32 | 201.2 | 202.1. |
| 71 | 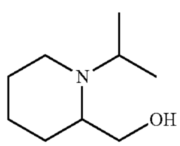 | (1-isopropyl-2-piperidyl)methanol | CAS# 3433-37-2 + CAS# 67-64-1 | Ex. 2.33 | 157.3 | 158.6. |
| 72 | 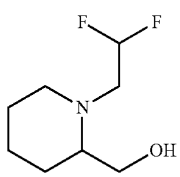 [SMILES: OCC1CCCCN1CC(F)F] | (1-isopropyl-2-piperidyl)methanol | CAS# 3433-37-2 + CAS# 74427-22-8 | Ex. 2.34 | 179.2 | 180.6. |
| 73 | 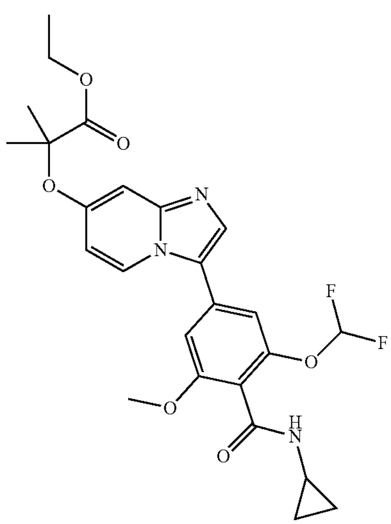 [SMILES: CCOC(=O)C(C)(C)Oc1ccn2c(-c3cc(OC)c(C(=O)NC4CC4)c(OC(F)F)c3)cnc2c1] | ethyl 2-[3-[4-(cyclopropylcarbamoyl)-3-(difluoromethoxy)-5-methoxy-phenyl]imidazo[1,2-a]pyridin-7-yl]oxy-2-methyl-propanoate | Int 89 + CAS# 1246184-55-3 | Ex. 2.35 | 503.5 | 504.7. |
| 76 | 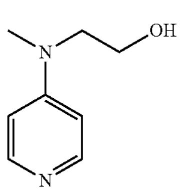 | 2-[methyl(4-pyridyl)amino]ethanol | CAS# 109-83-1 + CAS# 19524-06-2 | Ex. 2.36 | 152.2 | 153.4. |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 77 | 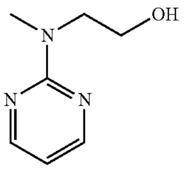 | 2-[methyl(pyrimidin-2-yl)amino]ethanol | CAS# 109-83-1 + CAS# 4595-60-2 | Ex. 2.37 | 153.2 | 154.0. |
| 78 | 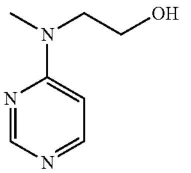 | 2-[methyl(pyrimidin-4-yl)amino]ethanol | CAS# 3934-20-1 + CAS# 109-83-1 | Ex. 2.38 | 153.2 | 154.4. |
| 80 | 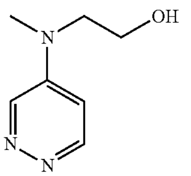 | 2-[methyl(pyridazin-4-yl)amino]ethanol | CAS# 109-83-1 + CAS# 1220039-64-4 | Ex. 2.39 | 153.2 | 154.4. |
| 81 | 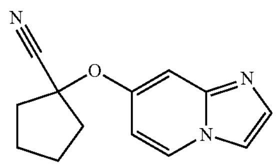 [SMILES: N#CC1(Oc2ccn3ccnc3c2)CCCC1] | 1-imidazo[1,2-a]pyridin-7-yloxycyclopentane-carbonitrile | CAS# 896139-85-8 + CAS# 51572-54-4 | Ex. 2.40 | 227.3 | 228.1. |
| 84 | 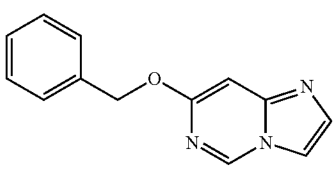 [SMILES: c1ccc(COc2cc3nccn3cn2)cc1] | 7-benzyloxyimidazo[1,2-c]pyrimidine | CAS# 5305-59-9 + CAS# 100-51-6 | Ex. 2.41 | 225.3 | 226.3. |
| 88 | 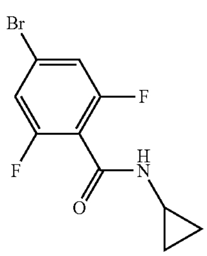 [SMILES: O=C(NC1CC1)c1c(F)cc(Br)cc1F] | 4-bromo-N-cyclopropyl-2,6-difluoro-benzamide | CAS# 183065-68-1 + CAS# 765-30-0 | Ex. 2.42 | 276.1 | 276.2 + 278.2 |
| 89 | 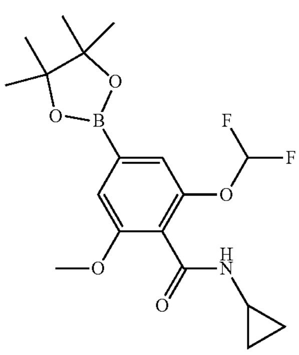 [SMILES: COc1cc(B2OC(C)(C)C(C)(C)O2)cc(OC(F)F)c1C(=O)NC1CC1] | N-cyclopropyl-2-(difluoromethoxy)-6-methoxy-4-(4,4,5,5-tetramethyl-1,3,2-dioxaborolan-2-yl)benzamide/4-(cyclopropylcarbamoyl)-3-(difluoromethoxy)-5-methoxyphenylboronic acid mixture | CAS# 3147-64-6 | Ex. 2.43 | 383.2 + 301.1 | 384.4 + 302.2 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| | (structure) | | | | | |
| 90 | (structure) | 4-(7-fluoroimidazo[1,2-a]pyridin-3-yl)-2,6-dimethoxy-N-(2,2,2-trifluoroethyl)benzamide | CAS# 1260903-17-0 + Int 47 | Ex. 2.44 | 397.3 | 398.6 |
| 91 | (structure) | 6-bromo-8-(trideuteriomethoxy)-2-(2,2,2-trifluoroethyl)-3,4-dihydroisoquinolin-1-one | CAS# 1242157-15-8 + CAS# 811-98-3 + CAS# 6226-25-1 | Ex. 2.45 | 341.1 | 341.0 + 343.0 |
| 92 | (structure) | N-cyclopropyl-2-(difluoromethoxy)-6-methoxy-4-[7-(oxiran-2-ylmethoxy)imidazo[1,2-a]pyridin-3-yl]benzamide | Int 1 | Ex. 2.46 | 445.4 | 446.1 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 93 | 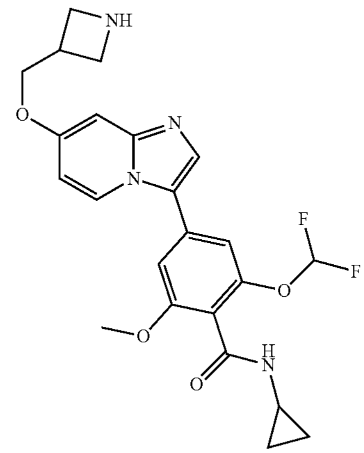 [SMILES: COc1cc(-c2cnc3cc(OCC4CNC4)ccn23)cc(OC(F)F)c1C(=O)NC1CC1] | 4-[7-(azetidin-3-ylmethoxy)imidazo[1,2-a]pyridin-3-yl]-N-cyclopropyl-2-(difluoromethoxy)-6-methoxy-benzamide | Int 1 | Ex. 2.47 | 458.4 | 459.0 |
| 94 | 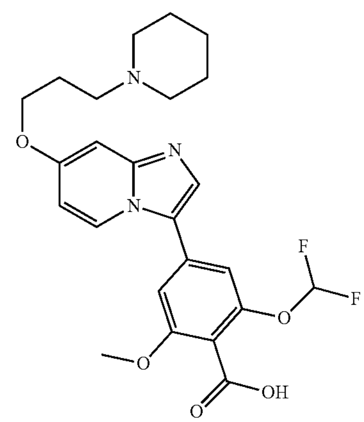 [SMILES: COc1cc(-c2cnc3cc(OCCCN4CCCCC4)ccn23)cc(OC(F)F)c1C(=O)O] | 2-(difluoromethoxy)-6-methoxy-4-[7-[3-(1-piperidyl)propoxy]imidazo[1,2-a]pyridin-3-yl]benzoic acid | Int 1 | Ex. 2.48 | 475.4 | 476.4 |
| 95 | 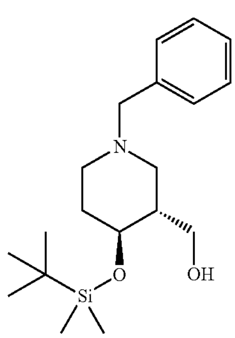 [SMILES: CC(C)(C)[Si](C)(C)O[C@H]1CCN(Cc2ccccc2)C[C@@H]1CO] | [(3R,4S)-1-benzyl-4-[tert-butyl(dimethyl)silyl]oxy-3-piperidyl]methanol/ [(3S,4R)-1-benzyl-4-[tert-butyl(dimethyl)silyl]oxy-3-piperidyl]methanol mixture | CAS# 1454-53-1 | Ex. 2.49 | 335.2 | 336.2 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
|  | [structure: 1-benzyl-piperidine with tert-butyldimethylsilyloxy and hydroxymethyl substituents] |  |  |  |  |  |
| 96 | [structure: N-cyclopropyl-2-(difluoromethoxy)-4-(7-hydroxyimidazo[1,2-a]pyridin-3-yl)-6-methoxy-benzamide] | N-cyclopropyl-2-(difluoromethoxy)-4-(7-hydroxyimidazo[1,2-a]pyridin-3-yl)-6-methoxy-benzamide | Cpd 68 | Ex. 2.50 | 389.3 | 390.1 |
| 97 | [structure: 2-[2-(4-isopropylpiperazin-1-yl)ethoxy]ethanol] | 2-[2-(4-isopropylpiperazin-1-yl)ethoxy]ethanol | CAS# 13349-82-1 + CAS# 75-30-9 | Ex. 2.51 | 216.3 | 217.1 |
| 98 | [structure: 2-[3-[4-(cyclopropylcarbamoyl)-3-(difluoromethoxy)-5-methoxy-phenyl]imidazo[1,2-a]pyridin-7-yl]oxyethyl methanesulfonate] | 2-[3-[4-(cyclopropylcarbamoyl)-3-(difluoromethoxy)-5-methoxy-phenyl]imidazo[1,2-a]pyridin-7-yl]oxyethyl methanesulfonate | Cpd 30 | Ex. 2.52 | 511.5 | 512.0 |

TABLE II-continued

Intermediates used towards the compounds of the invention.
SM = Starting Material, Mtd = Method, MS Mes'd = Mesured mass, NA = not measured

| Int # | Structure | Name | SM | Mtd | MW | MS Mes'd |
|---|---|---|---|---|---|---|
| 99 | 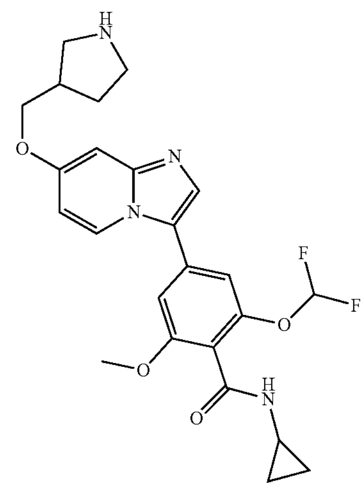 | N-cyclopropyl-2-(difluoromethoxy)-6-methoxy-4-[7-(pyrrolidin-3-ylmethoxy)imidazo[1,2-a]pyridin-3-yl]benzamide | Int 1 + CAS# 114214-69-6 | A + K1 | 472.2 | 473.1 |
| 100 | 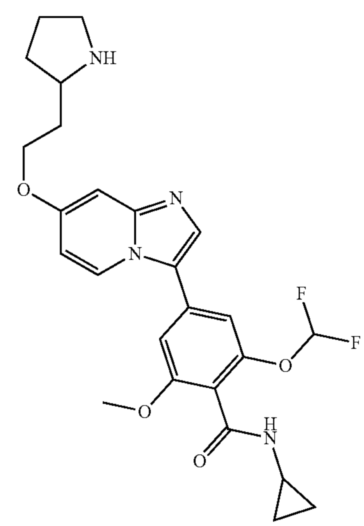 [SMILES: COc1cc(-c2cnc3cc(OCCC4CCCN4)ccn23)cc(OC(F)F)c1C(=O)NC1CC1] | N-cyclopropyl-2-(difluoromethoxy)-6-methoxy-4-[7-(2-pyrrolidin-2-ylethoxy)imidazo[1,2-a]pyridin-3-yl]benzamide | Int 1 + CAS# 19432-88-3 | A | 486.2 | 487.1 |

TABLE III

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 1 | 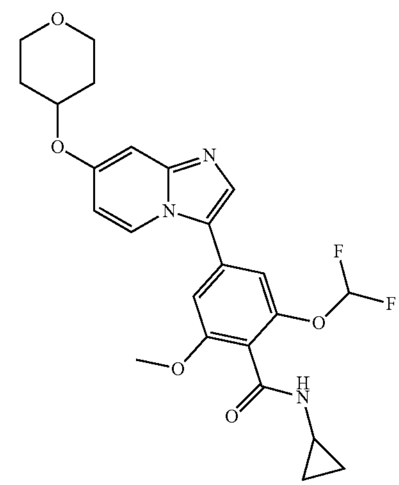 [SMILES: COc1cc(-c2cnc3cc(OC4CCOCC4)ccn23)cc(OC(F)F)c1C(=O)NC1CC1] | N-cyclopropyl-2-(difluoromethoxy)-6-methoxy-4-(7-tetrahydropyran-4-yloxyimidazo[1,2-a]pyridin-3-yl)benzamide | Int 1 + CAS# 2081-44-9 | A | 473.5 | 474.1 |
| 2 | 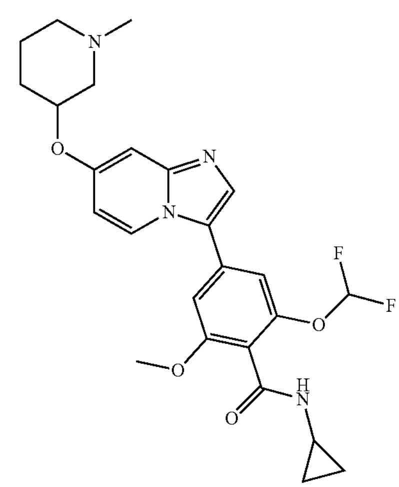 [SMILES: COc1cc(-c2cnc3cc(OC4CCCN(C)C4)ccn23)cc(OC(F)F)c1C(=O)NC1CC1] | N-cyclopropyl-2-(difluoromethoxy)-6-methoxy-4-[7-[(1-methyl-3-piperidyl)oxy]imidazo[1,2-a]pyridin-3-yl]benzamide | Int 1 + CAS# 3554-74-3 | A | 486.5 | 487.4 |
| 3 | 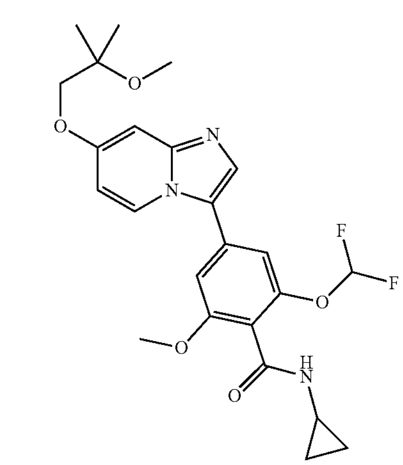 [SMILES: COc1cc(-c2cnc3cc(OCC(C)(C)OC)ccn23)cc(OC(F)F)c1C(=O)NC1CC1] | N-cyclopropyl-2-(difluoromethoxy)-6-methoxy-4-[7-(2-methoxy-2-methyl-propoxy)imidazo[1,2-a]pyridin-3-yl]benzamide | Int 1 + CAS# 22665-67-4 | A | 475.5 | 476.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 4 | 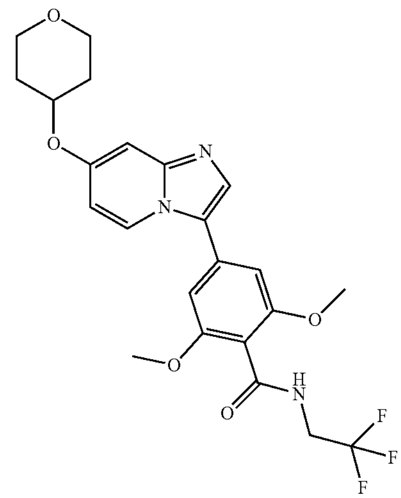 [SMILES: COc1cc(-c2cnc3cc(OC4CCOCC4)ccn23)cc(OC)c1C(=O)NCC(F)(F)F] | 2,6-dimethoxy-4-(7-tetrahydropyran-4-yloxyimidazo[1,2-a]pyridin-3-yl)-N-(2,2,2-trifluoroethyl)benzamide | Int 90 + CAS# 2081-44-9 | Ex. [0461] | 479.4 | 480.3 |
| 5 | 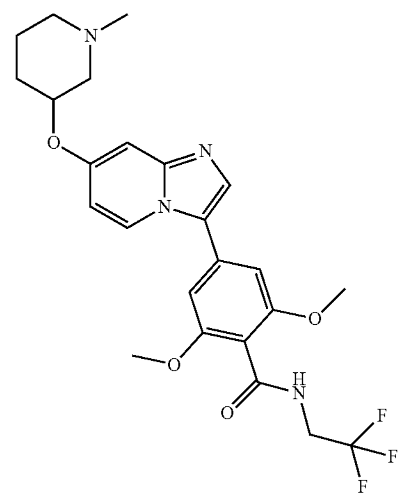 [SMILES: COc1cc(-c2cnc3cc(OC4CCCN(C)C4)ccn23)cc(OC)c1C(=O)NCC(F)(F)F] | 2,6-dimethoxy-4-[7-[(1-methyl-3-piperidyl)oxy]imidazo[1,2-a]pyridin-3-yl]-N-(2,2,2-trifluoroethyl)benzamide | Int 90 + CAS# 3554-74-3 | Ex. 2.55 | 492.5 | 493.3 |
| 6 | 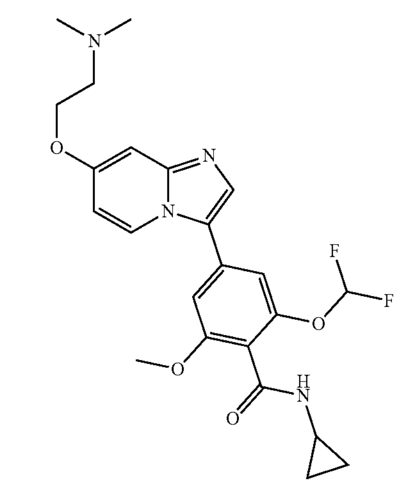 [SMILES: COc1cc(-c2cnc3cc(OCCN(C)C)ccn23)cc(OC(F)F)c1C(=O)NC1CC1] | N-cyclopropyl-2-(difluoromethoxy)-4-[7-[2-(dimethylamino)ethoxy]imidazo[1,2-a]pyridin-3-yl]-6-methoxy-benzamide | Int 1 + CAS# 108-01-0 | Ex. 2.56 | 460.5 | 461.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 7 | 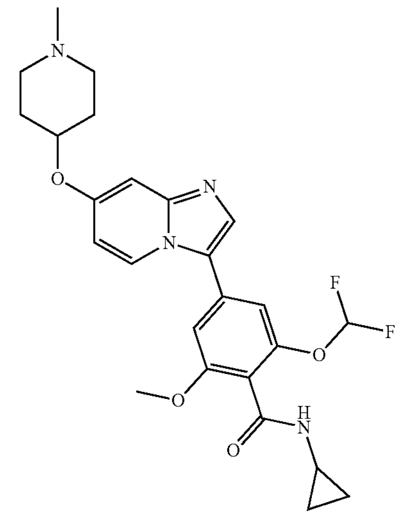 [SMILES: COc1cc(-c2cnc3cc(OC4CCN(C)CC4)ccn23)cc(OC(F)F)c1C(=O)NC1CC1] | N-cyclopropyl-2-(difluoromethoxy)-6-methoxy-4-[7-[(1-methyl-4-piperidyl)oxy]imidazo[1,2-a]pyridin-3-yl]benzamide | Int 1 + CAS# 106-52-5 | A | 486.5 | 487.7 |
| 8 | 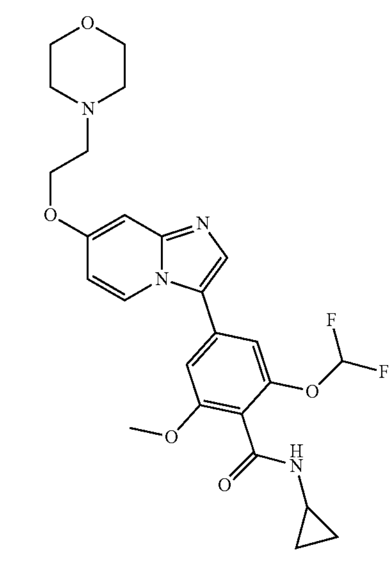 [SMILES: COc1cc(-c2cnc3cc(OCCN4CCOCC4)ccn23)cc(OC(F)F)c1C(=O)NC1CC1] | N-cyclopropyl-2-(difluoromethoxy)-6-methoxy-4-[7-(2-morpholinoethoxy)imidazo[1,2-a]pyridin-3-yl]benzamide | Int 1 + CAS# 622-40-2 | A | 502.5 | 503.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 9 | 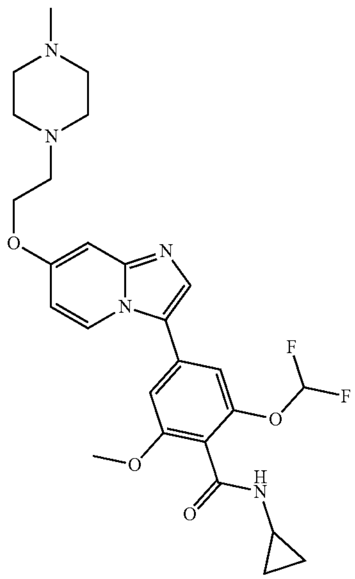 [SMILES: COc1cc(-c2cnc3cc(OCCN4CCN(C)CC4)ccn23)cc(OC(F)F)c1C(=O)NC1CC1] | N-cyclopropyl-2-(difluoromethoxy)-6-methoxy-4-[7-[2-(4-methylpiperazin-1-yl)ethoxy]imidazo[1,2-a]pyridin-3-yl]benzamide | Int 1 + CAS# 5464-12-0 | A | 515.6 | 516.4 |
| 10 | 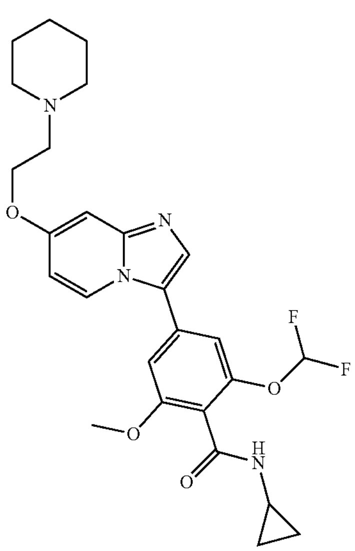 [SMILES: COc1cc(-c2cnc3cc(OCCN4CCCCC4)ccn23)cc(OC(F)F)c1C(=O)NC1CC1] | N-cyclopropyl-2-(difluoromethoxy)-6-methoxy-4-[7-[2-(1-piperidyl)ethoxy]imidazo[1,2-a]pyridin-3-yl]benzamide | Int 1 + CAS# 3040-44-6 | A | 500.5 | 501.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 11 | 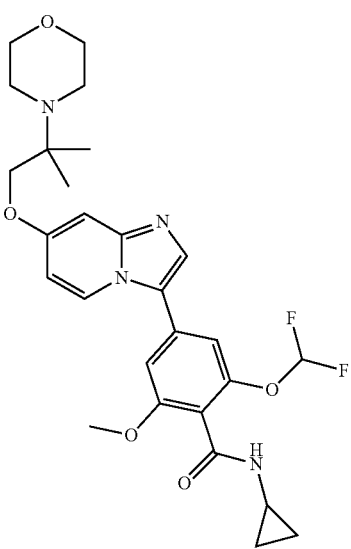 [SMILES: COc1cc(-c2cnc3cc(OCC(C)(C)N4CCOCC4)ccn23)cc(OC(F)F)c1C(=O)NC1CC1] | N-cyclopropyl-2-(difluoromethoxy)-6-methoxy-4-[7-(2-methyl-2-morpholino-propoxy)imidazo[1,2-a]pyridin-3-yl]benzamide | Int 1 + CAS# 858197-58-7 | A | 530.6 | 531.4 |
| 12 | 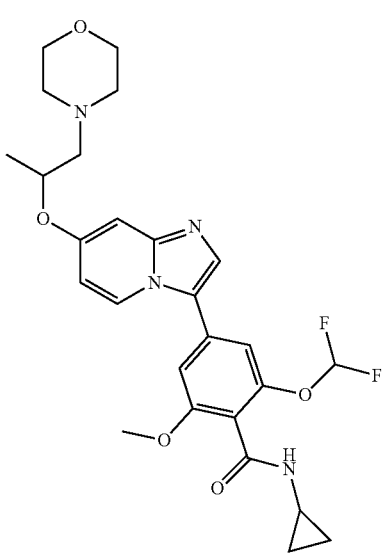 [SMILES: COc1cc(-c2cnc3cc(OC(C)CN4CCOCC4)ccn23)cc(OC(F)F)c1C(=O)NC1CC1] | N-cyclopropyl-2-(difluoromethoxy)-6-methoxy-4-[7-(1-methyl-2-morpholino-ethoxy)imidazo[1,2-a]pyridin-3-yl]benzamide | Int 1 + CAS# 2109-66-2 | A | 516.5 | 517.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 13 | 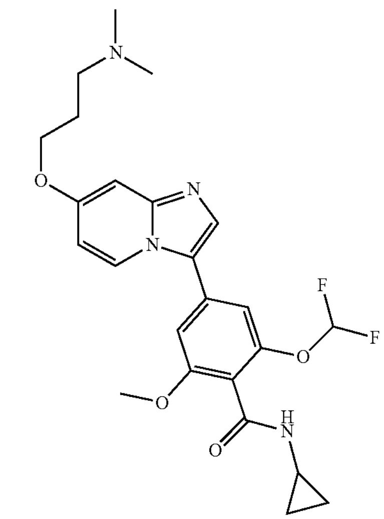 [SMILES: COc1cc(-c2cnc3cc(OCCCN(C)C)ccn23)cc(OC(F)F)c1C(=O)NC1CC1] | N-cyclopropyl-2-(difluoromethoxy)-4-[7-3-(dimethylamino)propoxy]imidazo[1,2-a]pyridin-3-yl]-6-methoxy-benzamide | Int 1 + CAS# 3179-63-3 | Ex. 2.57 | 474.5 | 475.4 |
| 14 | 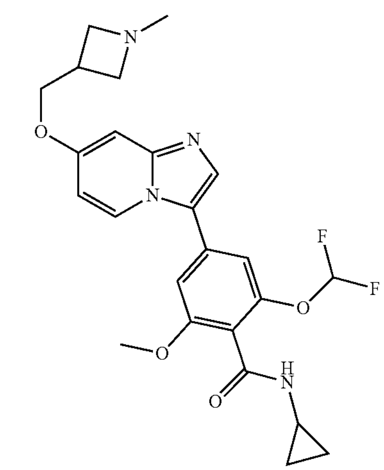 [SMILES: COc1cc(-c2cnc3cc(OCC4CN(C)C4)ccn23)cc(OC(F)F)c1C(=O)NC1CC1] | N-cyclopropyl-2-(difluoromethoxy)-6-methoxy-4-[7-[(1-methylazetidin-3-yl)methoxy]imidazo[1,2-a]pyridin-3-yl]benzamide | Int 1 + CAS# 1499172-23-4 | Ex. 2.58 | 472.5 | 473.3 |
| 15 | 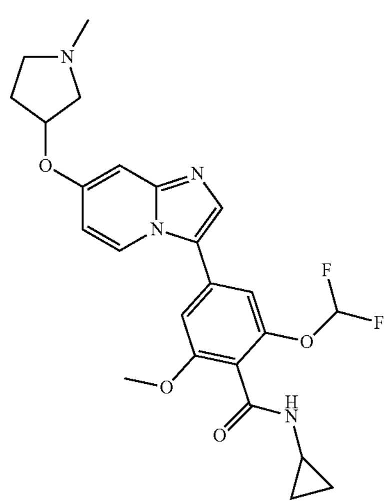 [SMILES: COc1cc(-c2cnc3cc(OC4CCN(C)C4)ccn23)cc(OC(F)F)c1C(=O)NC1CC1] | N-cyclopropyl-2-(difluoromethoxy)-6-methoxy-4-[7-[(1-methylpyrrolidin-3-yl)oxyimidazo[1,2-a]pyridin-3-yl]benzamide | Int 1 + CAS# 13220-33-2 | A | 472.5 | 473.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 16 | 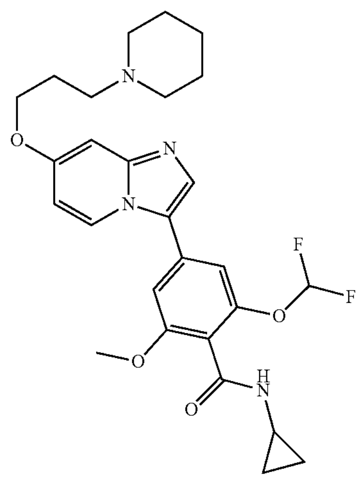 [SMILES: COc1cc(-c2cnc3cc(OCCCN4CCCCC4)ccn23)cc(OC(F)F)c1C(=O)NC1CC1] | N-cyclopropyl-2-(difluoromethoxy)-6-methoxy-4-[7-[3-(1-piperidyl)propoxy]imidazo[1,2-a]pyridin-3-yl]benzamide | Int 1 + CAS# 104-58-5 | A | 514.6 | 515.4 |
| 17 | 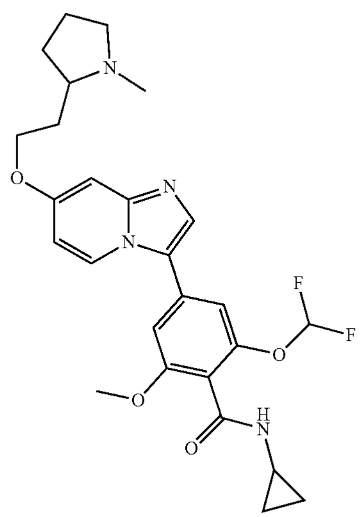 [SMILES: COc1cc(-c2cnc3cc(OCCC4CCCN4C)ccn23)cc(OC(F)F)c1C(=O)NC1CC1] | N-cyclopropyl-2-(difluoromethoxy)-6-methoxy-4-[7-[2-(1-methylpyrrolidin-2-yl)ethoxy]imidazo[1,2-a]pyridin-3-yl]benzamide | Int 1 + CAS# 67004-64-2 | A | 500.5 | 501.4 |
| 18 | 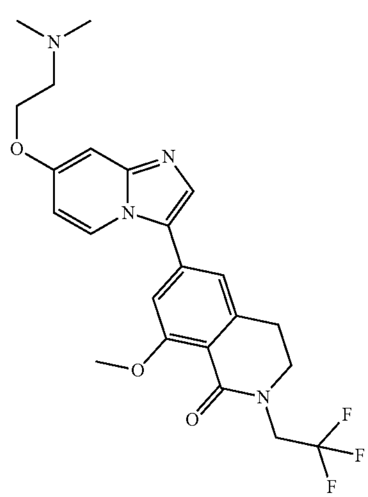 [SMILES: COc1cc(-c2cnc3cc(OCCN(C)C)ccn23)cc2c1C(=O)N(CC(F)(F)F)CC2] | 6-[7-[2-(dimethylamino)ethoxy]imidazo[1,2-a]pyridin-3-yl]-8-methoxy-2-(2,2,2-trifluoroethyl)-3,4-dihydroisoquinolin-1-one | Int 2 + CAS# 108-01-0 | A | 462.5 | 463.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 19 | 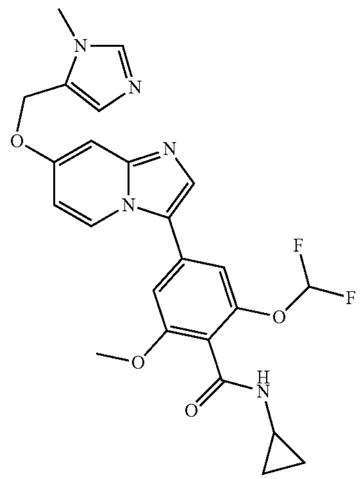 [SMILES: COc1cc(-c2cnc3cc(OCc4cncn4C)ccn23)cc(OC(F)F)c1C(=O)NC1CC1] | N-cyclopropyl-2-(difluoromethoxy)-6-methoxy-4-[7-[(3-methylimidazol-4-yl)methoxy]imidazo[1,2-a]pyridin-3-yl]benzamide | Int 1 + CAS# 38993-84-9 | A | 483.5 | 484.4 |
| 20 | 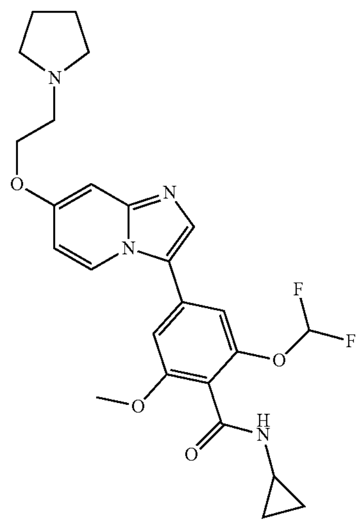 [SMILES: COc1cc(-c2cnc3cc(OCCN4CCCC4)ccn23)cc(OC(F)F)c1C(=O)NC1CC1] | N-cyclopropyl-2-(difluoromethoxy)-6-methoxy-4-[7-(2-pyrrolidin-1-ylethoxy)imidazo[1,2-a]pyridin-3-yl]benzamide | Int 1 + CAS# 2955-88-6 | A | 486.5 | 487.6 |
| 21 | 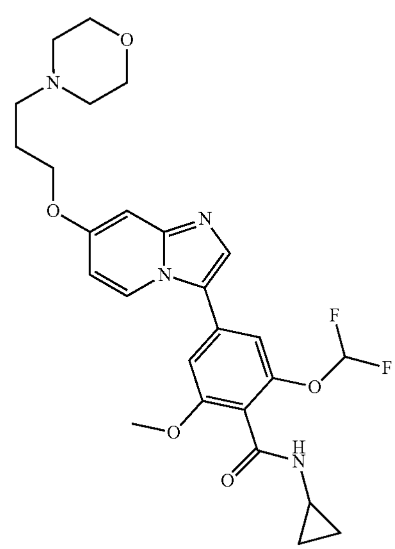 [SMILES: COc1cc(-c2cnc3cc(OCCCN4CCOCC4)ccn23)cc(OC(F)F)c1C(=O)NC1CC1] | N-cyclopropyl-2-(difluoromethoxy)-6-methoxy-4-[7-(3-morpholinopropoxy)imidazo[1,2-a]pyridin-3-yl]benzamide | Int 1 + CAS# 4441-30-9 | A | 516.5 | 517.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 22 | 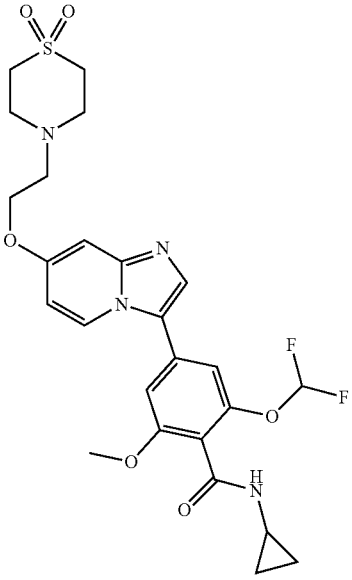 [SMILES: COc1cc(-c2cnc3cc(OCCN4CCS(=O)(=O)CC4)ccn23)cc(OC(F)F)c1C(=O)NC1CC1] | N-cyclopropyl-2-(difluoromethoxy)-4-[7-[2-(1,1-dioxo-1,4-thiazinan-4-yl)ethoxy]imidazo[1,2-a]pyridin-3-yl]-6-methoxy-benzamide | Int 1 + CAS# 26475-62-7 | A | 550.6 | 551.3 |
| 23 | 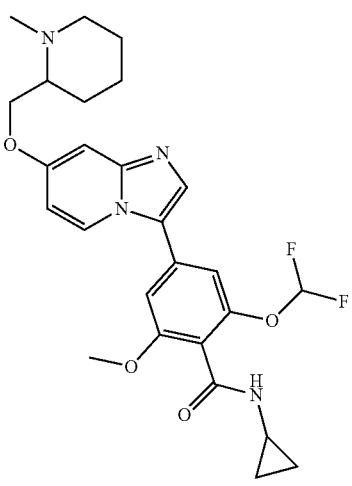 [SMILES: COc1cc(-c2cnc3cc(OCC4CCCCN4C)ccn23)cc(OC(F)F)c1C(=O)NC1CC1] | N-cyclopropyl-2-(difluoromethoxy)-6-methoxy-4-[7-[(1-methyl-2-piperidyl)methoxy]imidazo[1,2-a]pyridin-3-yl]benzamide | Int 1 + CAS# 20845-34-5 | A | 500.5 | 501.9 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 24 | 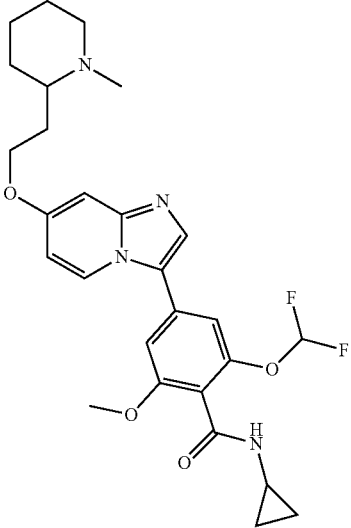 [SMILES: COc1cc(-c2cnc3cc(OCCC4CCCCN4C)ccn23)cc(OC(F)F)c1C(=O)NC1CC1] | N-cyclopropyl-2-(difluoromethoxy)-6-methoxy-4-[7-[2-(1-methyl-2-piperidyl)ethoxy]imidazo[1,2-a]pyridin-3-yl]benzamide | Int 1 + CAS# 533-15-3 | A | 514.6 | 515.6 |
| 25 | 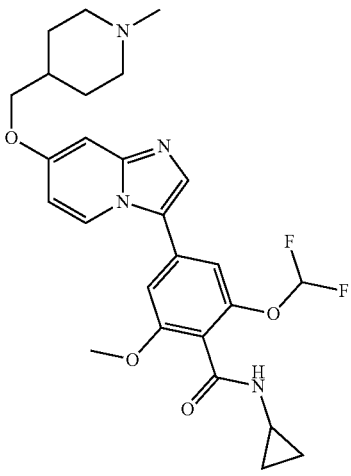 [SMILES: COc1cc(-c2cnc3cc(OCC4CCN(C)CC4)ccn23)cc(OC(F)F)c1C(=O)NC1CC1] | N-cyclopropyl-2-(difluoromethoxy)-6-methoxy-4-[7-[(1-methyl-4-piperidyl)methoxy]imidazo[1,2-a]pyridin-3-yl]benzamide | Int 1 + CAS# 20691-89-8 | A | 500.5 | 501.4 |
| 26 | 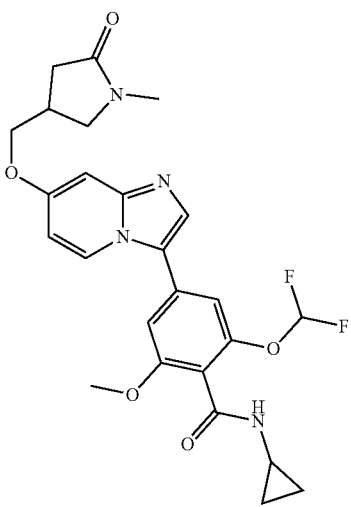 [SMILES: COc1cc(-c2cnc3cc(OCC4CC(=O)N(C)C4)ccn23)cc(OC(F)F)c1C(=O)NC1CC1] | N-cyclopropyl-2-(difluoromethoxy)-6-methoxy-4-[7-[(1-methyl-5-oxo-pyrrolidin-3-yl)methoxy]imidazo[1,2-a]pyridin-3-yl]benzamide | Int 1 + CAS# 59887-20-6 | A | 500.5 | 501.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 27 | 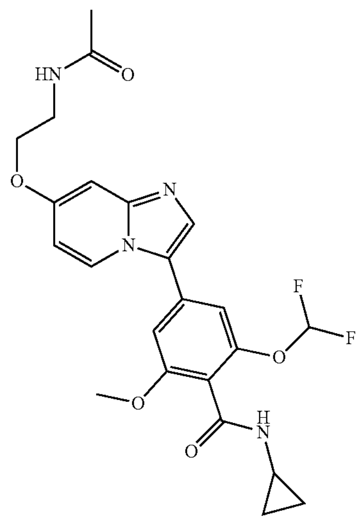 [SMILES: COc1cc(-c2cnc3cc(OCCNC(C)=O)ccn23)cc(OC(F)F)c1C(=O)NC1CC1] | 4-[7-(2-acetamidoethoxy)imidazo[1,2-a]pyridin-3-yl]-N-cyclopropyl-2-(difluoromethoxy)-6-methoxy-benzamide | Int 1 + CAS# 142-26-7 | A | 474.5 | 475.5 |
| 28 | 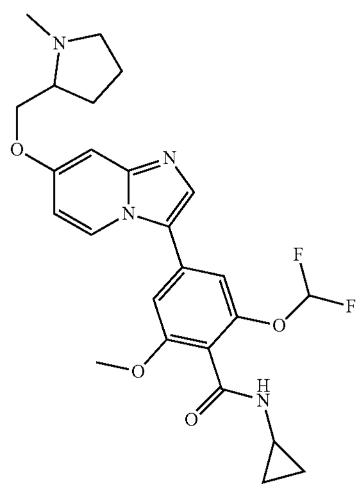 [SMILES: COc1cc(-c2cnc3cc(OCC4CCCN4C)ccn23)cc(OC(F)F)c1C(=O)NC1CC1] | N-cyclopropyl-2-(difluoromethoxy)-6-methoxy-4-[7-[(1-methylpyrrolidin-2-yl)methoxy]imidazo[1,2-a]pyridin-3-yl]benzamide | Int 1 + CAS# 5021-33-0 | A | 486.5 | 487.5 |
| 29 | 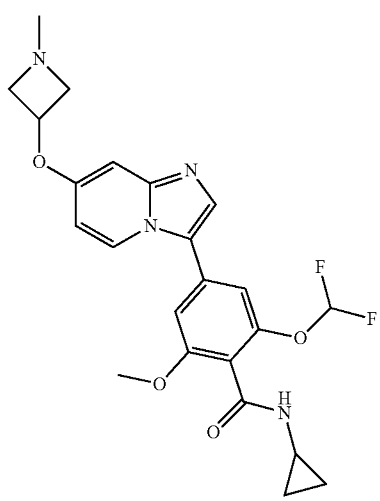 [SMILES: COc1cc(-c2cnc3cc(OC4CN(C)C4)ccn23)cc(OC(F)F)c1C(=O)NC1CC1] | N-cyclopropyl-2-(difluoromethoxy)-6-methoxy-4-[7-(1-methylazetidin-3-yl)oxyimidazo[1,2-a]pyridin-3-yl]benzamide | Int 1 + CAS# 111043-48-2 | A | 458.5 | 459.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 30 | 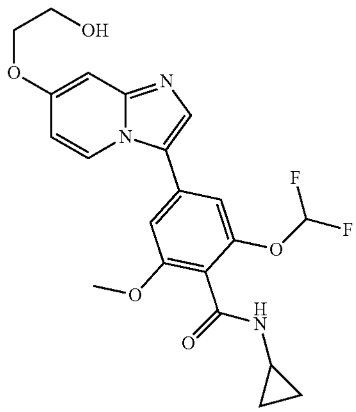 [SMILES: COc1cc(-c2cnc3cc(OCCO)ccn23)cc(OC(F)F)c1C(=O)NC1CC1] | N-cyclopropyl-2-(difluoromethoxy)-4-[7-(2-hydroxyethoxy)imidazo[1,2-a]pyridin-3-yl]-6-methoxy-benzamide | Int 1 + CAS# 107-21-1 | A | 433.4 | 434.5 |
| 31 | 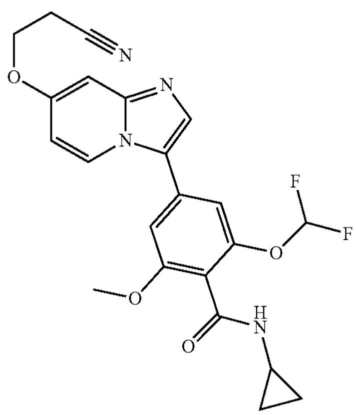 [SMILES: COc1cc(-c2cnc3cc(OCCC#N)ccn23)cc(OC(F)F)c1C(=O)NC1CC1] | 4-[7-(2-cyanoethoxy)imidazo[1,2-a]pyridin-3-yl]-N-cyclopropyl-2-(difluoromethoxy)-6-methoxy-benzamide | Int 1 + CAS# 109-78-4 | A | 442.4 | 443.3 |
| 32 | 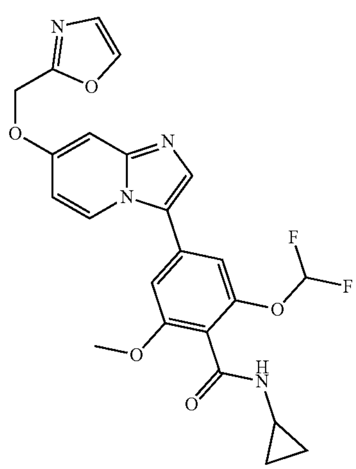 [SMILES: COc1cc(-c2cnc3cc(OCc4ncco4)ccn23)cc(OC(F)F)c1C(=O)NC1CC1] | N-cyclopropyl-2-(difluoromethoxy)-6-methoxy-4-[7-(oxazol-2-ylmethoxy)imidazo[1,2-a]pyridin-3-yl]benzamide | Int 1 + CAS# 130551-92-7 | A | 470.4 | 471.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 33 | 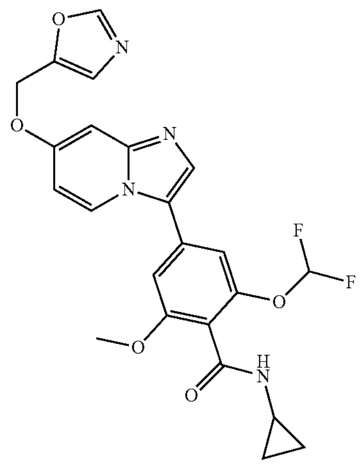 [SMILES: COc1cc(-c2cnc3cc(OCc4cnco4)ccn23)cc(OC(F)F)c1C(=O)NC1CC1] | N-cyclopropyl-2-(difluoromethoxy)-6-methoxy-4-[7-(oxazol-5-ylmethoxy)imidazo[1,2-a]pyridin-3-yl]benzamide | Int 1 + CAS# 127232-41-1 | A | 470.4 | 471.3 |
| 34 | 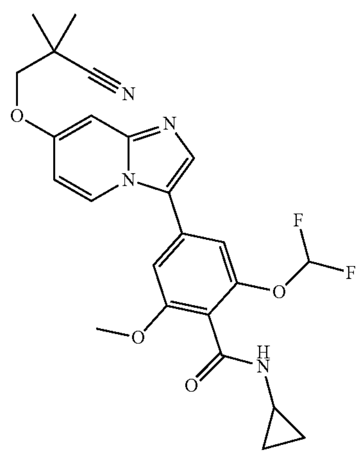 [SMILES: COc1cc(-c2cnc3cc(OCC(C)(C)C#N)ccn23)cc(OC(F)F)c1C(=O)NC1CC1] | 4-[7-(2-cyano-2-methyl-propoxy)imidazo[1,2-a]pyridin-3-yl]-N-cyclopropyl-2-(difluoromethoxy)-6-methoxy-benzamide | Int 1 + CAS# 19295-57-9 | A | 470.5 | 471.3 |
| 35 | 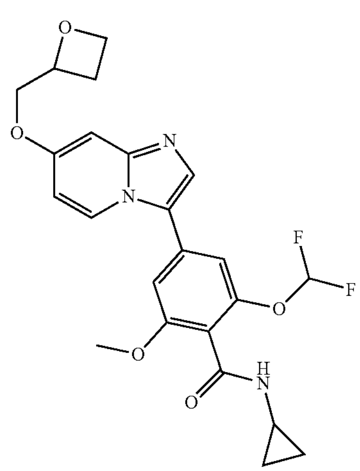 [SMILES: COc1cc(-c2cnc3cc(OCC4CCO4)ccn23)cc(OC(F)F)c1C(=O)NC1CC1] | N-cyclopropyl-2-(difluoromethoxy)-6-methoxy-4-[7-(oxetan-2-ylmethoxy)imidazo[1,2-a]pyridin-3-yl]benzamide | Int 1 + CAS# 61266-70-4 | A | 459.4 | 460.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 36 | 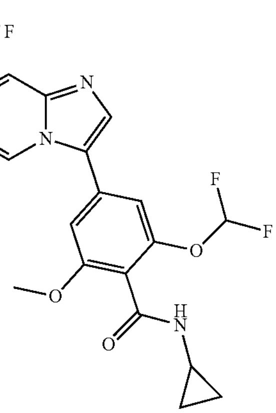 | N-cyclopropyl-2-(difluoromethoxy)-4-[7-(2-fluoroethoxy)imidazo[1,2-a]pyridin-3-yl]-6-methoxy-benzamide | Int 1 + CAS# 371-62-0 | A | 435.4 | 436.5 |
| 37 | 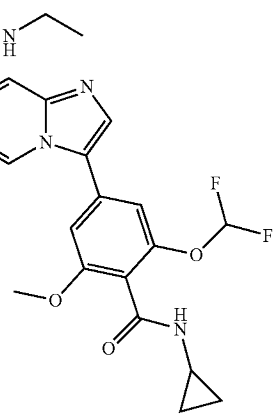 | N-cyclopropyl-2-(difluoromethoxy)-4-[7-[2-(ethylamino)ethoxy]imidazo[1,2-a]pyridin-3-yl]-6-methoxy-benzamide | Int 1 + CAS# 110-73-6 | A | 460.5 | 461.5 |
| 38 | 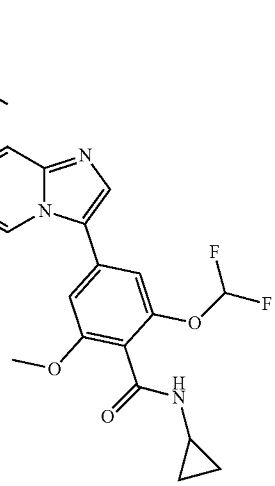 | N-cyclopropyl-2-(difluoromethoxy)-6-methoxy-4-[7-[2-(2-methoxyethoxy)ethoxy]imidazo[1,2-a]pyridin-3-yl]benzamide | Int 1 + CAS# 111-77-3 | A | 491.5 | 492.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 39 | 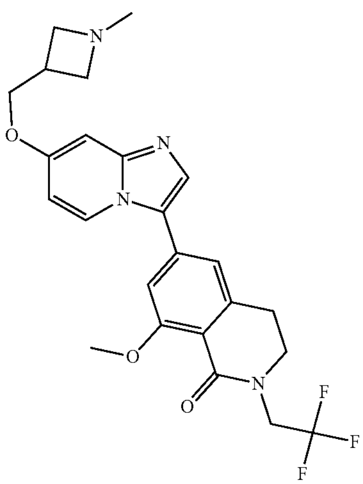 [SMILES: COc1cc(-c2cnc3cc(OCC4CN(C)C4)ccn23)cc2c1C(=O)N(CC(F)(F)F)CC2] | 8-methoxy-6-[7-[(1-methylazetidin-3-yl)methoxy]imidazo[1,2-a]pyridin-3-yl]-2-(2,2,2-trifluoroethyl)-3,4-dihydroisoquinolin-1-one | Int 2 + CAS# 1499172-23-4 | A | 474.5 | 475.4 |
| 40 | 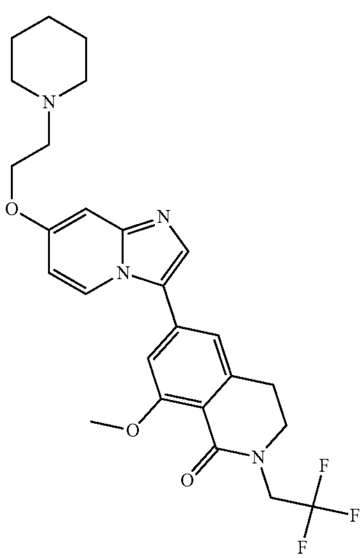 [SMILES: COc1cc(-c2cnc3cc(OCCN4CCCCC4)ccn23)cc2c1C(=O)N(CC(F)(F)F)CC2] | 8-methoxy-6-[7-[2-(1-piperidyl)ethoxy]imidazo[1,2-a]pyridin-3-yl]-2-(2,2,2-trifluoroethyl)-3,4-dihydroisoquinolin-1-one | Int 2 + CAS# 3040-44-6 | A | 502.5 | 503.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 41 | 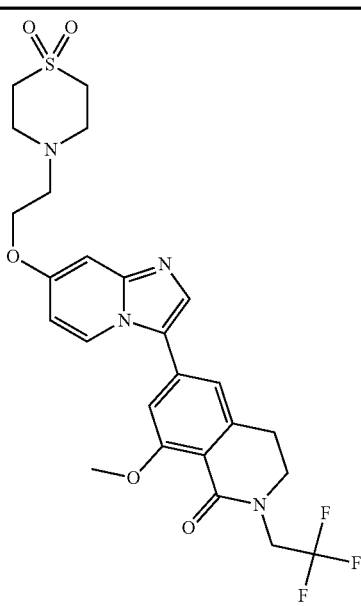 | 6-[7-[2-(1,1-dioxo-1,4-thiazinan-4-yl)ethoxy]imidazo[1,2-a]pyridin-3-yl]-8-methoxy-2-(2,2,2-trifluoroethyl)-3,4-dihydroisoquinolin-1-one | Int 2 + CAS# 26475-62-7 | A | 552.6 | 553.3 |
| 42 | 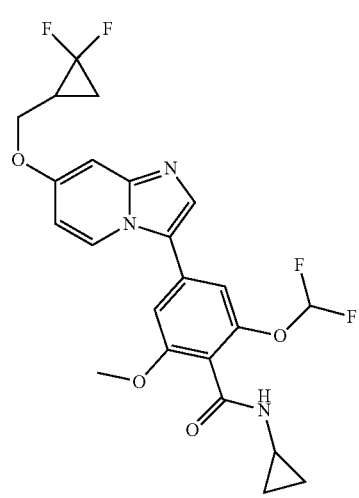 [SMILES: COc1cc(-c2cnc3cc(OCC4CC4(F)F)ccn23)cc(OC(F)F)c1C(=O)NC1CC1] | N-cyclopropyl-4-[7-[(2,2-difluorocyclopropyl)methoxy]imidazo[1,2-a]pyridin-3-yl]-2-(difluoromethoxy)-6-methoxy-benzamide | Int 1 + CAS# 509072-57-5 | A | 479.4 | 480.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 43 | 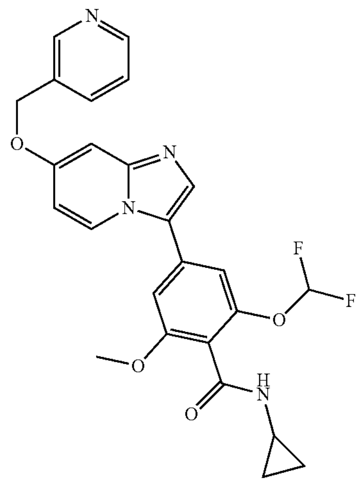 [SMILES: COc1cc(-c2cnc3cc(OCc4cccnc4)ccn23)cc(OC(F)F)c1C(=O)NC1CC1] | N-cyclopropyl-2-(difluoromethoxy)-6-methoxy-4-[7-(3-pyridylmethoxy)imidazo[1,2-a]pyridin-3-yl]benzamide | Int 1 + CAS# 100-55-0 | A | 480.5 | 481.3 |
| 44 | 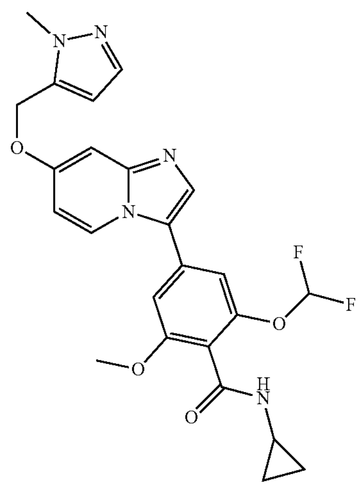 [SMILES: COc1cc(-c2cnc3cc(OCc4ccnn4C)ccn23)cc(OC(F)F)c1C(=O)NC1CC1] | N-cyclopropyl-2-(difluoromethoxy)-6-methoxy-4-[7-[(2-methylpyrazol-3-yl)methoxy]imidazo[1,2-a]pyridin-3-yl]benzamide | Int 1 + CAS# 84547-61-5 | A | 483.5 | 484.6 |
| 45 | 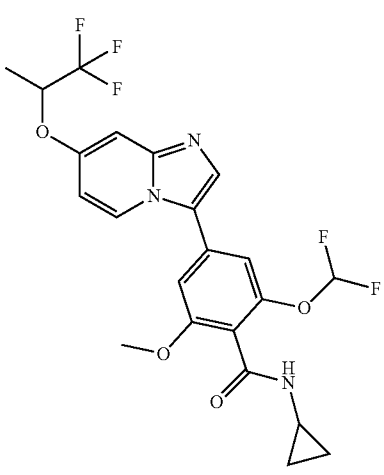 [SMILES: COc1cc(-c2cnc3cc(OC(C)C(F)(F)F)ccn23)cc(OC(F)F)c1C(=O)NC1CC1] | N-cyclopropyl-2-(difluoromethoxy)-6-methoxy-4-[7-(2,2,2-trifluoro-1-methyl-ethoxy)imidazo[1,2-a]pyridin-3-yl]benzamide | Int 1 + CAS# 374-01-6 | A | 485.4 | 486.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|------|-----------|------|-----|-----|-----|---------|
| 46 | 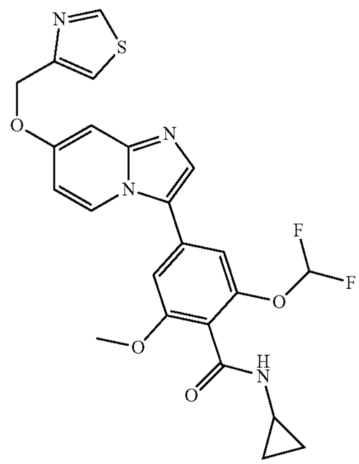 | N-cyclopropyl-2-(difluoromethoxy)-6-methoxy-4-[7-(thiazol-4-ylmethoxy)imidazo[1,2-a]pyridin-3-yl]benzamide | Int 1 + CAS# 7036-04-6 | A | 486.5 | 487.6 |
| 47 | 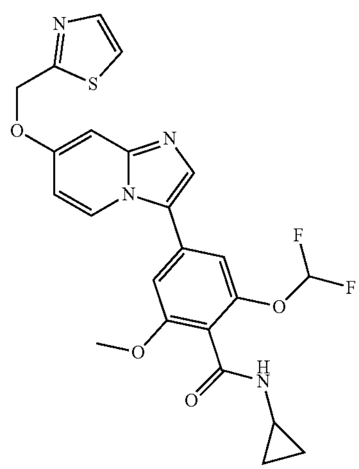 [SMILES: COc1cc(-c2cnc3cc(OCc4nccs4)ccn23)cc(OC(F)F)c1C(=O)NC1CC1] | N-cyclopropyl-2-(difluoromethoxy)-6-methoxy-4-[7-(thiazol-2-ylmethoxy)imidazo[1,2-a]pyridin-3-yl]benzamide | Int 1 + CAS# 14542-12-2 | A | 486.5 | 487.6 |
| 48 | 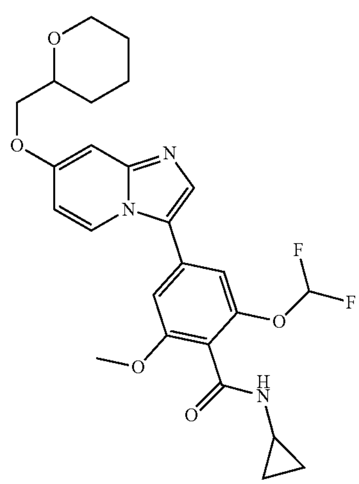 [SMILES: COc1cc(-c2cnc3cc(OCC4CCCCO4)ccn23)cc(OC(F)F)c1C(=O)NC1CC1] | N-cyclopropyl-2-(difluoromethoxy)-6-methoxy-4-[7-(tetrahydropyran-2-ylmethoxy)imidazo[1,2-a]pyridin-3-yl]benzamide | Int 1 + CAS# 100-72-1 | A | 487.5 | 488.7 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 49 | 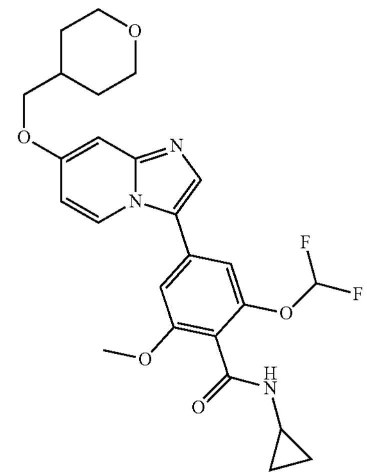 [SMILES: COc1cc(-c2cnc3cc(OCC4CCOCC4)ccn23)cc(OC(F)F)c1C(=O)NC1CC1] | N-cyclopropyl-2-(difluoromethoxy)-6-methoxy-4-[7-(tetrahydropyran-4-ylmethoxy)imidazo[1,2-a]pyridin-3-yl]benzamide | Int 1 + CAS# 14774-37-9 | A | 487.5 | 488.1 |
| 50 | 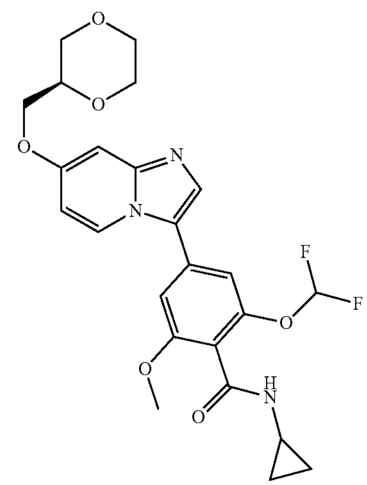 [SMILES: COc1cc(-c2cnc3cc(OC[C@H]4COCCO4)ccn23)cc(OC(F)F)c1C(=O)NC1CC1] | N-cyclopropyl-2-(difluoromethoxy)-4-[7-[[(2R)-1,4-dioxan-2-yl]methoxy]imidazo[1,2-a]pyridin-3-yl]-6-methoxy-benzamide | Int 1 + CAS# 406913-93-7 | A | 489.5 | 490.0 |
| 51 | 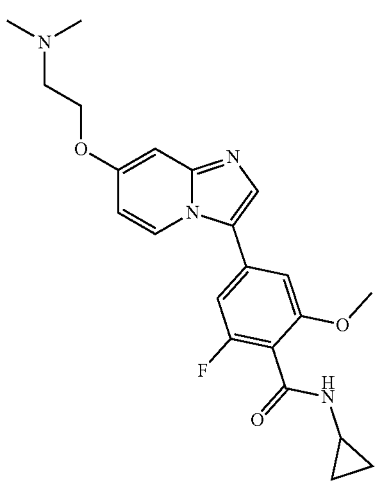 [SMILES: COc1cc(-c2cnc3cc(OCCN(C)C)ccn23)cc(F)c1C(=O)NC1CC1] | N-cyclopropyl-4-[7-[2-(dimethylamino)ethoxy]imidazo[1,2-a]pyridin-3-yl]-2-fluoro-6-methoxy-benzamide | Int 3 + Int 4 | B | 412.5 | 413.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 52 | 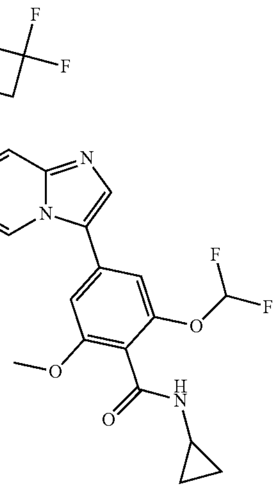 | N-cyclopropyl-4-[7-[(3,3-difluorocyclobutyl)methoxy]imidazo[1,2-a]pyridin-3-yl]-2-(difluoromethoxy)-6-methoxy-benzamide | Int 1 + CAS# 681128-39-2 | A | 493.5 | 494.9 |
| 53 | 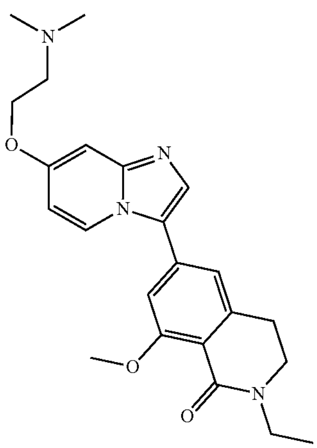 [SMILES: CCN1CCc2cc(-c3cnc4cc(OCCN(C)C)ccn34)cc(OC)c2C1=O] | 6-[7-[2-(dimethylamino)ethoxy]imidazo[1,2-a]pyridin-3-yl]-2-ethyl-8-methoxy-3,4-dihydroisoquinolin-1-one | Int 3 + Int 5 | B | 408.5 | 409.5 |
| 54 | 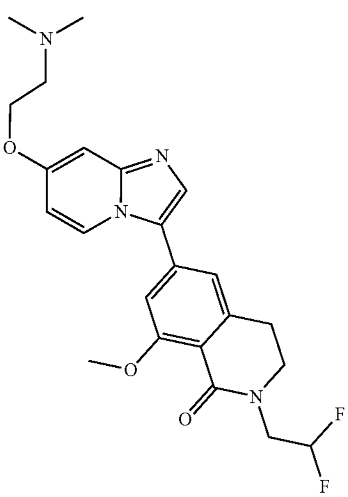 [SMILES: COc1cc(-c2cnc3cc(OCCN(C)C)ccn23)cc2c1C(=O)N(CC(F)F)CC2] | 2-(2,2-difluoroethyl)-6-[7-[2-(dimethylamino)ethoxy]imidazo[1,2-a]pyridin-3-yl]-8-methoxy-3,4-dihydroisoquinolin-1-one | Int 3 + Int 6 | B | 444.5 | 445.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 55 | 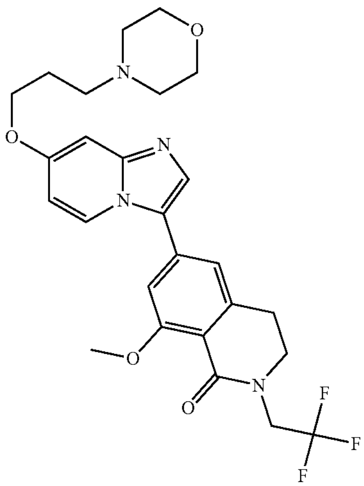 [SMILES: COc1cc(-c2cnc3cc(OCCCN4CCOCC4)ccn23)cc2c1C(=O)N(CC(F)(F)F)CC2] | 8-methoxy-6-[7-(3-morpholinopropoxy) imidazo[1,2-a]pyridin-3-yl]-2-(2,2,2-trifluoro ethyl)-3,4-dihydro isoquinolin-1-one | Int 2 + CAS# 4441-30-9 | A | 518.5 | 519.4 |
| 56 | 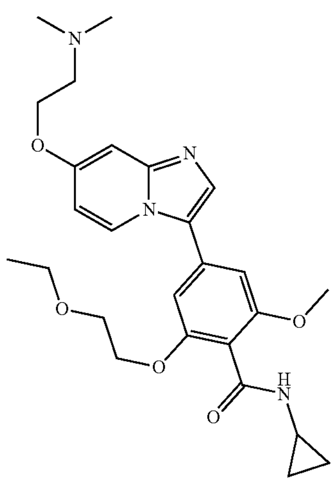 [SMILES: CCOCCOc1cc(-c2cnc3cc(OCCN(C)C)ccn23)cc(OC)c1C(=O)NC1CC1] | N-cyclopropyl-4-[7-[2-(dimethyl amino)ethoxy]imidazo [1,2-a]pyridin-3-yl]-2-(2-ethoxyethoxy)-6-methoxy-benzamide | Cpd 51 | Ex. 2.59 | 482.6 | 483.6 |
| 57 | 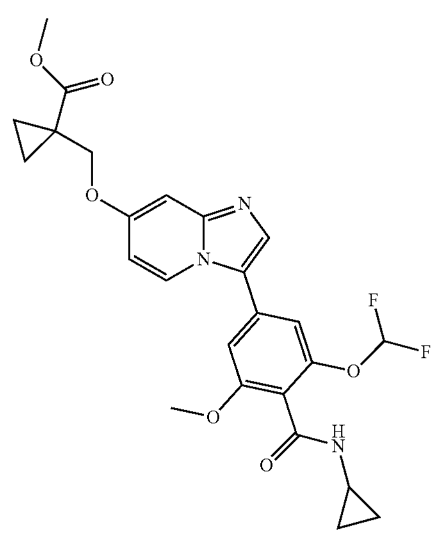 [SMILES: COC(=O)C1(COc2ccn3c(-c4cc(OC)c(C(=O)NC5CC5)c(OC(F)F)c4)cnc3c2)CC1] | methyl 1-[[3-[4-(cyclopropylcarbamoyl)-3-(difluoromethoxy)-5-methoxy-phenyl]imidazo[1,2-a]pyridin-7-yl]oxymethyl] cyclopropanecarboxylate | Int 1 + CAS# 88157-42-0 | A | 501.5 | 502.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 58 | 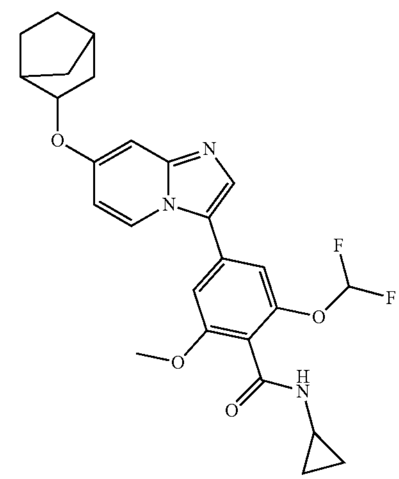 [SMILES: COc1cc(-c2cnc3cc(OC4CC5CCC4C5)ccn23)cc(OC(F)F)c1C(=O)NC1CC1] | N-cyclopropyl-2-(difluoromethoxy)-6-methoxy-4-(7-norbornan-2-yloxy imidazo[1,2-a]pyridin-3-yl)benzamide | Int 1 + CAS# 5240-72-2 | A | 483.5 | 484.5 |
| 59 | 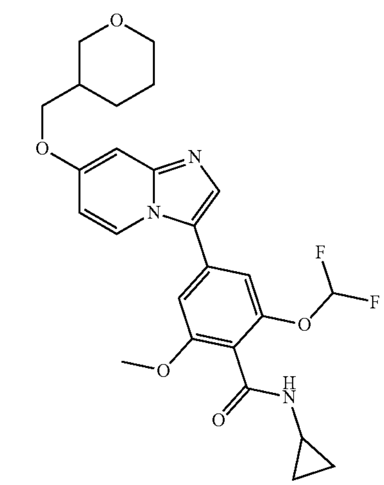 [SMILES: COc1cc(-c2cnc3cc(OCC4CCCOC4)ccn23)cc(OC(F)F)c1C(=O)NC1CC1] | N-cyclopropyl-2-(difluoromethoxy)-6-methoxy-4-[7-(tetrahydropyran-3-ylmethoxy) imidazo[1,2-a]pyridin-3-yl]benzamide | Int 1 + CAS# 14774-36-8 | A | 487.5 | 488.4 |
| 60 | 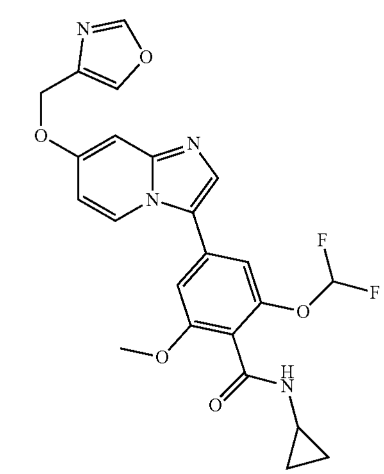 [SMILES: COc1cc(-c2cnc3cc(OCc4cocn4)ccn23)cc(OC(F)F)c1C(=O)NC1CC1] | N-cyclopropyl-2-(difluoromethoxy)-6-methoxy-4-[7-(oxazol-4-ylmethoxy)imidazo[1,2-a]pyridin-3-yl]benzamide | Int 1 + CAS# 155742-48-6 | A | 470.4 | 471.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 61 | 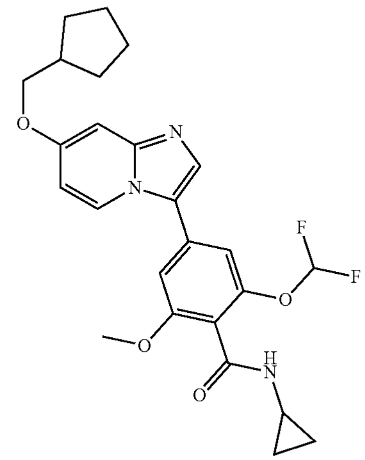 [SMILES: COc1cc(-c2cnc3cc(OCC4CCCC4)ccn23)cc(OC(F)F)c1C(=O)NC1CC1] | 4-[7-(cyclopentyl methoxy)imidazo[1,2-a]pyridin-3-yl]-N-cyclopropyl-2-(difluoromethoxy)-6-methoxy-benzamide | Int 1 + CAS# 3637-61-4 | A | 471.5 | 472.4 |
| 62 | 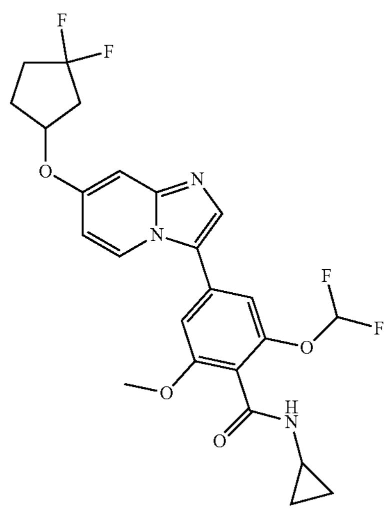 [SMILES: COc1cc(-c2cnc3cc(OC4CCC(F)(F)C4)ccn23)cc(OC(F)F)c1C(=O)NC1CC1] | N-cyclopropyl-4-[7-(3,3-difluorocyclopentoxy)imidazo[1,2-a]pyridin-3-yl]-2-(difluoromethoxy)-6-methoxy-benzamide | Int 1 + CAS# 883731-65-5 | A | 493.5 | 494.4 |
| 63 | 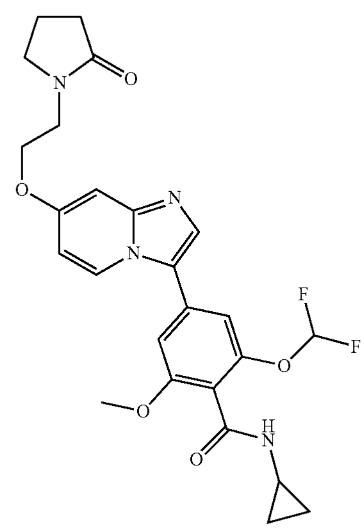 [SMILES: COc1cc(-c2cnc3cc(OCCN4CCCC4=O)ccn23)cc(OC(F)F)c1C(=O)NC1CC1] | N-cyclopropyl-2-(difluoromethoxy)-6-methoxy-4-[7-[2-(2-oxopyrrolidin-1-yl)ethoxy]imidazo[1,2-a]pyridin-3-yl]benzamide | Int 1 + CAS# 3445-11-2 | A | 500.5 | 501.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 64 | 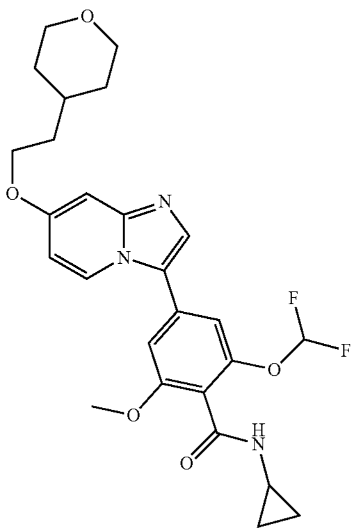 [SMILES: COc1cc(-c2cnc3cc(OCCC4CCOCC4)ccn23)cc(OC(F)F)c1C(=O)NC1CC1] | N-cyclopropyl-2-(difluoromethoxy)-6-methoxy-4-[7-(2-tetrahydropyran-4-ylethoxy)imidazo[1,2-a]pyridin-3-yl]benzamide | Int 1 + CAS# 4677-18-3 | A | 501.5 | 502.6 |
| 65 | 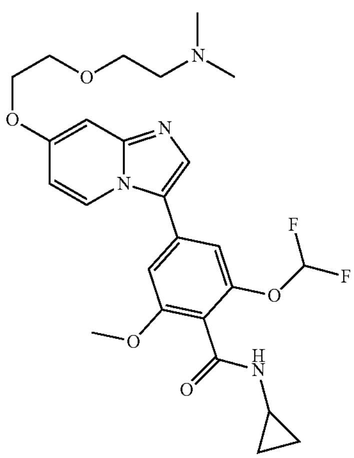 [SMILES: COc1cc(-c2cnc3cc(OCCOCCN(C)C)ccn23)cc(OC(F)F)c1C(=O)NC1CC1] | N-cyclopropyl-2-(difluoromethoxy)-4-[7-[2-[2-(dimethylamino)ethoxy]ethoxy]imidazo[1,2-a]pyridin-3-yl]-6-methoxy-benzamide | Int 1 + CAS# 1704-62-7 | A | 504.5 | 503.8 |
| 66 | 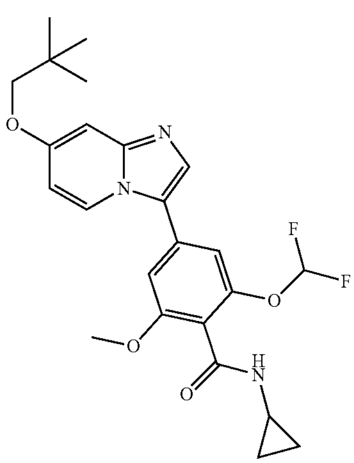 [SMILES: COc1cc(-c2cnc3cc(OCC(C)(C)C)ccn23)cc(OC(F)F)c1C(=O)NC1CC1] | N-cyclopropyl-2-(difluoromethoxy)-4-[7-(2,2-dimethylpropoxy)imidazo[1,2-a]pyridin-3-yl]-6-methoxy-benzamide | Int 1 + CAS# 75-84-3 | A | 459.5 | 460.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 67 | 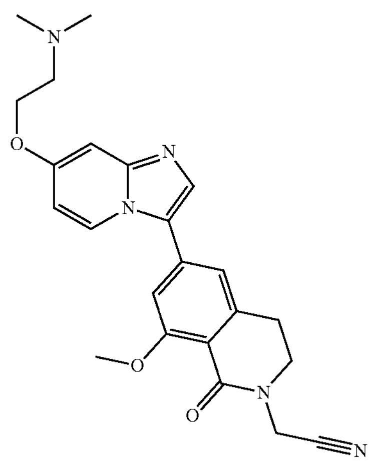 [SMILES: COc1cc(-c2cnc3cc(OCCN(C)C)ccn23)cc2c1C(=O)N(CC#N)CC2] | 2-[6-[7-[2-(dimethylamino)ethoxy]imidazo[1,2-a]pyridin-3-yl]-8-methoxy-1-oxo-3,4-dihydroisoquinolin-2-yl]acetonitrile | Int 3 + Int 8 | B | 419.5 | 420.5 |
| 68 | 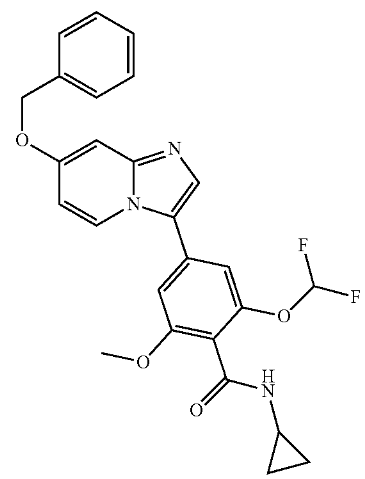 [SMILES: COc1cc(-c2cnc3cc(OCc4ccccc4)ccn23)cc(OC(F)F)c1C(=O)NC1CC1] | 4-(7-benzyloxyimidazo[1,2-a]pyridin-3-yl)-N-cyclopropyl-2-(difluoromethoxy)-6-methoxy-benzamide | Int 1 + CAS# 100-51-6 | A | 479.5 | 480.7 |
| 69 | 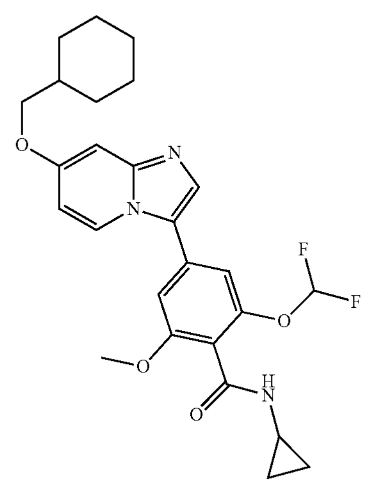 | 4-[7-(cyclohexylmethoxy)imidazo[1,2-a]pyridin-3-yl]-N-cyclopropyl-2-(difluoromethoxy)-6-methoxy-benzamide | Int 1 + CAS# 100-49-2 | A | 485.5 | 486.8 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 70 | 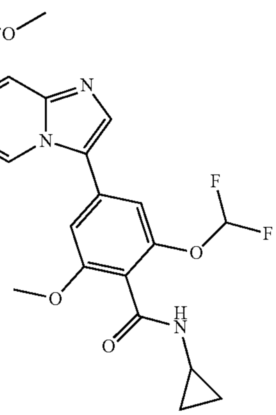 | N-cyclopropyl-2-(difluoromethoxy)-6-methoxy-4-[7-(2-methoxyethoxy)imidazo[1,2-a]pyridin-3-yl]benzamide | Int 1 + CAS# 109-86-4 | A | 447.4 | 448.8 |
| 71 | 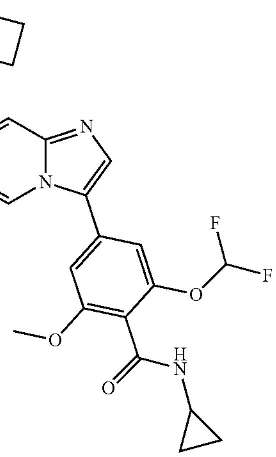 | 4-[7-(cyclobutylmethoxy)imidazo[1,2-a]pyridin-3-yl]-N-cyclopropyl-2-(difluoromethoxy)-6-methoxy-benzamide | Int 1 + CAS# 4415-82-1 | A | 457.5 | 458.8 |
| 72 | 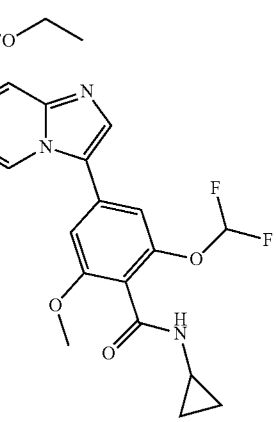 | N-cyclopropyl-2-(difluoromethoxy)-4-[7-(2-ethoxyethoxy)imidazo[1,2-a]pyridin-3-yl]-6-methoxy-benzamide | Int 1 + CAS# 110-80-5 | A | 461.5 | 462.9 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 73 | 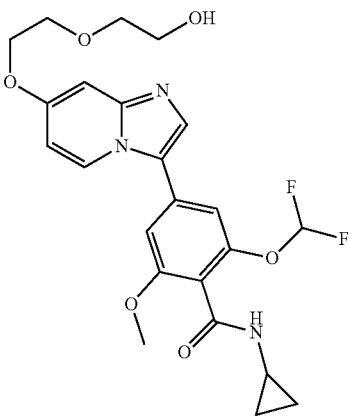 [SMILES: COc1cc(-c2cnc3cc(OCCOCCO)ccn23)cc(OC(F)F)c1C(=O)NC1CC1] | N-cyclopropyl-2-(difluoromethoxy)-4-[7-2-(2-hydroxyethoxy)ethoxy]imidazo[1,2-a]pyridin-3-yl]-6-methoxy-benzamide | Int 1 + CAS# 111-46-6 | A | 477.5 | 478.9 |
| 74 | 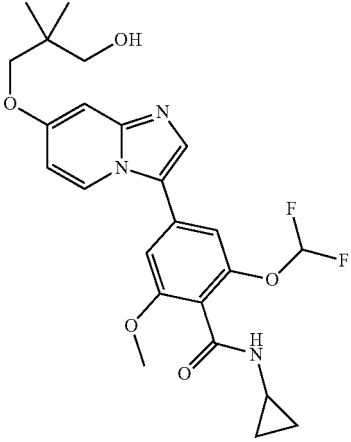 [SMILES: COc1cc(-c2cnc3cc(OCC(C)(C)CO)ccn23)cc(OC(F)F)c1C(=O)NC1CC1] | N-cyclopropyl-2-(difluoromethoxy)-4-[7-(3-hydroxy-2,2-dimethyl-propoxy)imidazo[1,2-a]pyridin-3-yl]-6-methoxy-benzamide | Int 1 + CAS# 126-30-7 | A | 475.5 | 476.9 |
| 75 | 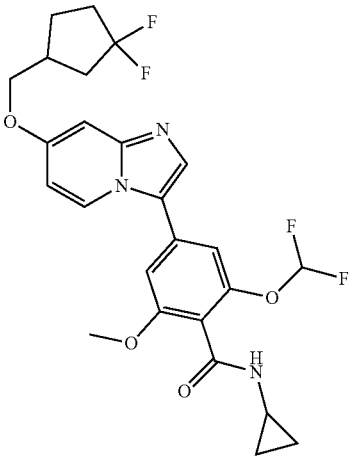 [SMILES: COc1cc(-c2cnc3cc(OCC4CCC(F)(F)C4)ccn23)cc(OC(F)F)c1C(=O)NC1CC1] | N-cyclopropyl-4-[7-[(3,3-difluorocyclopentyl)methoxy]imidazo[1,2-a]pyridin-3-yl]-2-(difluoromethoxy)-6-methoxy-benzamide | Int 1 + CAS# 883731-63-3 | A | 507.5 | 508.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 76 | 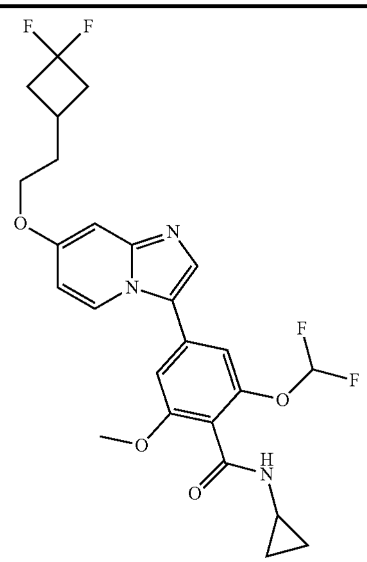 | N-cyclopropyl-4-[7-[2-(3,3-difluorocyclobutyl)ethoxy]imidazo[1,2-a]pyridin-3-yl]-2-(difluoromethoxy)-6-methoxy-benzamide | Int 1 + CAS# 1056467-54-9 | A | 507.5 | 506.5 |
| 77 | 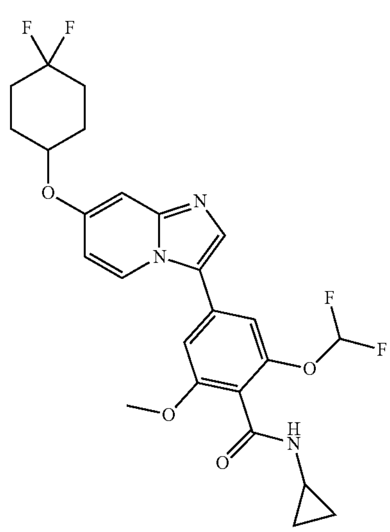 [SMILES: COc1cc(-c2cnc3cc(OC4CCC(F)(F)CC4)ccn23)cc(OC(F)F)c1C(=O)NC1CC1] | N-cyclopropyl-4-[7-(4,4-difluorocyclohexoxy)imidazo[1,2-a]pyridin-3-yl]-2-(difluoromethoxy)-6-methoxy-benzamide | Int 1 + CAS# 22419-35-8 | A | 507.5 | 506.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 78 | 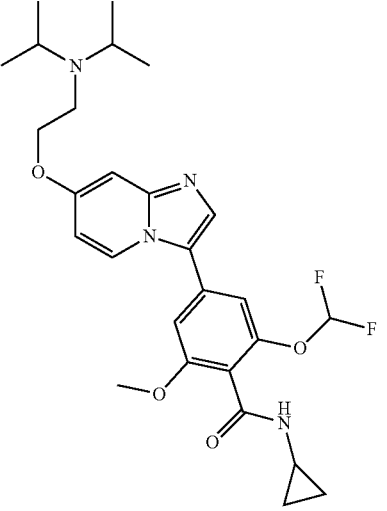 [SMILES: COc1cc(-c2cnc3cc(OCCN(C(C)C)C(C)C)ccn23)cc(OC(F)F)c1C(=O)NC1CC1] | N-cyclopropyl-2-(difluoromethoxy)-4-[7-[2-(diisopropylamino)ethoxy]imidazo[1,2-a]pyridin-3-yl]-6-methoxy-benzamide | Int 1 + CAS# 96-80-0 | A | 516.6 | 517.5 |
| 79 | 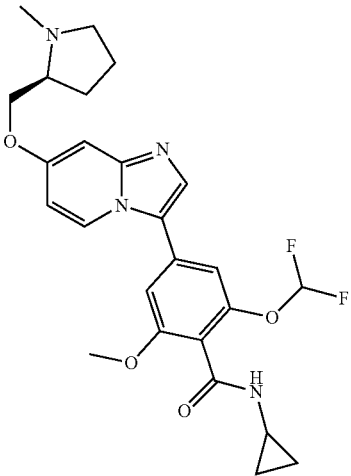 [SMILES: COc1cc(-c2cnc3cc(OC[C@@H]4CCCN4C)ccn23)cc(OC(F)F)c1C(=O)NC1CC1] | N-cyclopropyl-2-(difluoromethoxy)-6-methoxy-4-[7-[[(2S)-1-methylpyrrolidin-2-yl]methoxy]imidazo[1,2-a]pyridin-3-yl]benzamide | Int 1 + CAS# 34381-71-0 | A | 486.5 | 487.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 80 | 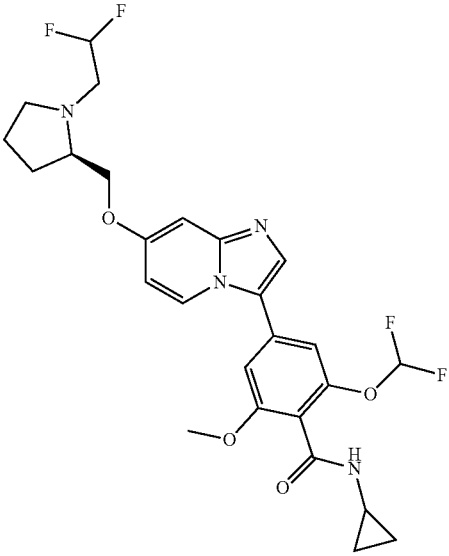 [SMILES: COc1cc(-c2cnc3cc(OC[C@H]4CCCN4CC(F)F)ccn23)cc(OC(F)F)c1C(=O)NC1CC1] | N-cyclopropyl-4-[7-[[(2R)-1-(2,2-difluoroethyl)pyrrolidin-2-yl]methoxy]imidazo[1,2-a]pyridin-3-yl]-2-(difluoromethoxy)-6-methoxy-benzamide | Int 1 + CAS# 1568029-94-6 | A | 536.5 | 537.8 |
| 81 | 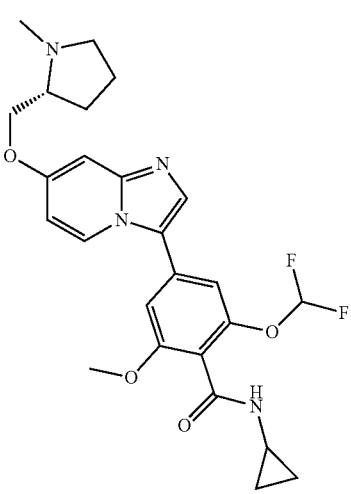 [SMILES: COc1cc(-c2cnc3cc(OC[C@H]4CCCN4C)ccn23)cc(OC(F)F)c1C(=O)NC1CC1] | N-cyclopropyl-2-(difluoromethoxy)-6-methoxy-4-[7-[[(2R)-1-methylpyrrolidin-2-yl]methoxy]imidazo[1,2-a]pyridin-3-yl]benzamide | Int 1 + CAS# 99494-01-6 | A | 486.5 | 487.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 82 | 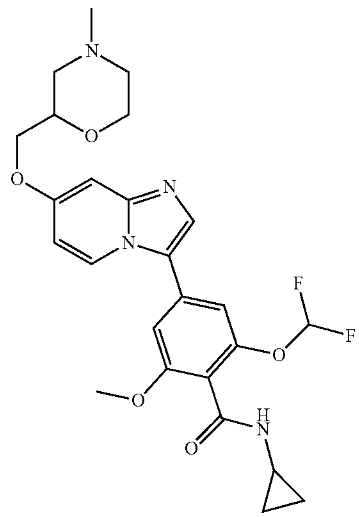 [SMILES: COc1cc(-c2cnc3cc(OCC4CN(C)CCO4)ccn23)cc(OC(F)F)c1C(=O)NC1CC1] | N-cyclopropyl-2-(difluoromethoxy)-6-methoxy-4-[7-[(4-methylmorpholin-2-yl)methoxy]imidazo[1,2-a]pyridin-3-yl]benzamide | Int 1 + CAS# 40987-46-0 | A | 502.5 | 503.4 |
| 83 | 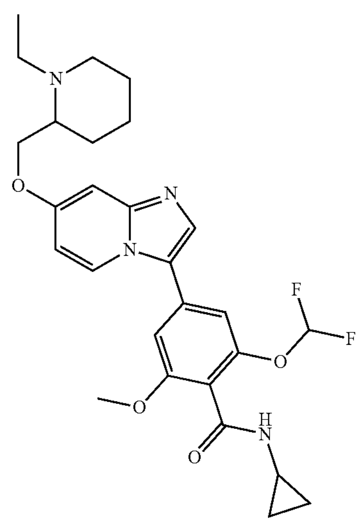 [SMILES: CCN1CCCCC1COc1ccn2c(-c3cc(OC)c(C(=O)NC4CC4)c(OC(F)F)c3)cnc2c1] | N-cyclopropyl-2-(difluoromethoxy)-4-[7-[(1-ethyl-2-piperidyl)methoxy]imidazo[1,2-a]pyridin-3-yl]-6-methoxy-benzamide | Int 1 + CAS# 30727-20-9 | A | 514.6 | 515.4 |
| 84 | 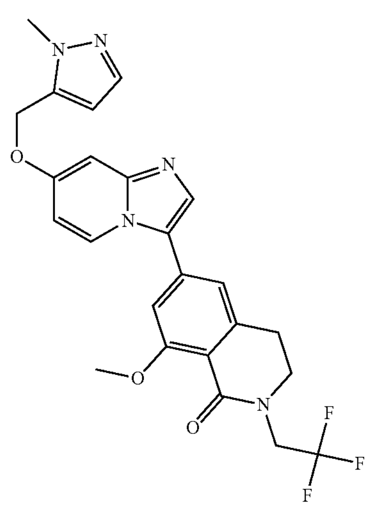 [SMILES: COc1cc(-c2cnc3cc(OCc4ccnn4C)ccn23)cc2c1C(=O)N(CC(F)(F)F)CC2] | 8-methoxy-6-[7-[(2-methylpyrazol-3-yl)methoxy]imidazo[1,2-a]pyridin-3-yl]-2-(2,2,2-trifluoroethyl)-3,4-dihydroisoquinolin-1-one | Int 2 + CAS# 84547-61-5 | A | 485.5 | 486.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 85 | 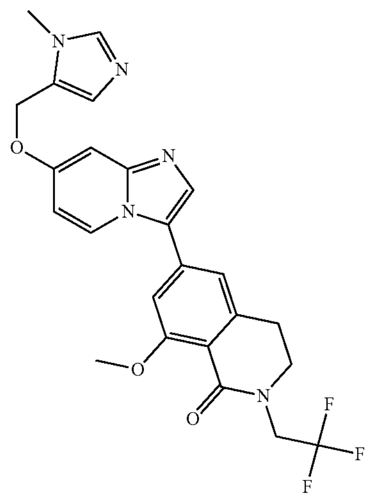 [SMILES: COc1cc(-c2cnc3cc(OCc4cncn4C)ccn23)cc2c1C(=O)N(CC(F)(F)F)CC2] | 8-methoxy-6-[7-[(3-methylimidazol-4-yl)methoxy]imidazo[1,2-a]pyridin-3-yl]-2-(2,2,2-trifluoroethyl)-3,4-dihydroisoquinolin-1-one | Int 2 + CAS# 38993-84-9 | A | 485.5 | 486.5 |
| 86 | 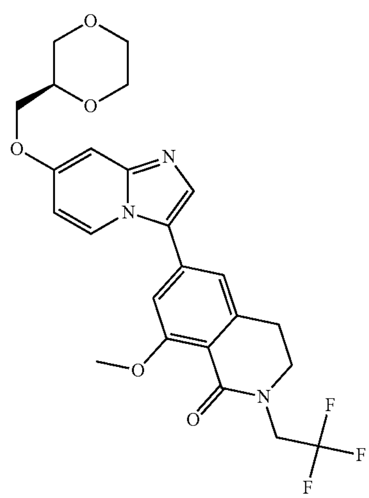 [SMILES: COc1cc(-c2cnc3cc(OC[C@H]4COCCO4)ccn23)cc2c1C(=O)N(CC(F)(F)F)CC2] | 6-[7-[[(2R)-1,4-dioxan-2-yl]methoxy]imidazo[1,2-a]pyridin-3-yl]-8-methoxy-2-(2,2,2-trifluoroethyl)-3,4-dihydroisoquinolin-1-one | Int 2 + CAS# 406913-93-7 | A | 491.5 | 492.6 |
| 87 | 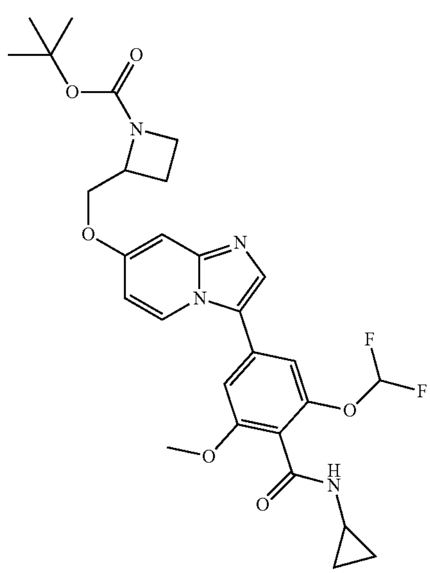 [SMILES: COc1cc(-c2cnc3cc(OCC4CCN4C(=O)OC(C)(C)C)ccn23)cc(OC(F)F)c1C(=O)NC1CC1] | tert-butyl 2-[[3-[4-(cyclopropylcarbamoyl)-3-(difluoromethoxy)-5-methoxy-phenyl]imidazo[1,2-a]pyridin-7-yl]oxymethyl]azetidine-1-carboxylate | Int 1 + CAS# 174346-82-8 | A | 558.6 | 559.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 88 | 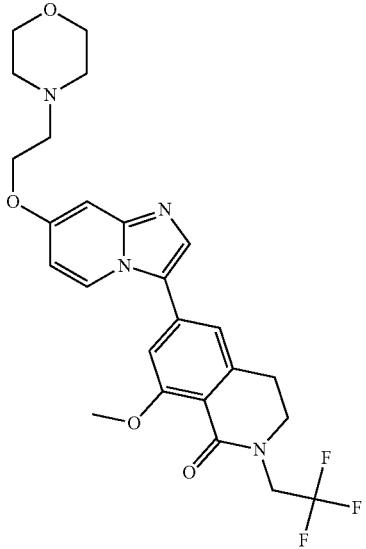 [SMILES: COc1cc(-c2cnc3cc(OCCN4CCOCC4)ccn23)cc2c1C(=O)N(CC(F)(F)F)CC2] | 8-methoxy-6-[7-(2-morpholinoethoxy)imidazo[1,2-a]pyridin-3-yl]-2-(2,2,2-trifluoroethyl)-3,4-dihydroisoquinolin-1-one | Int 2 + CAS# 622-40-2 or Int 25 + Int 39 | A or Ex. 2.62 | 504.5 | 505.3 or 505.2 |
| 89 | 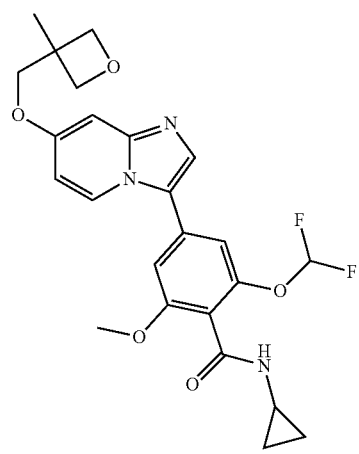 [SMILES: COc1cc(-c2cnc3cc(OCC4(C)COC4)ccn23)cc(OC(F)F)c1C(=O)NC1CC1] | N-cyclopropyl-2-(difluoromethoxy)-6-methoxy-4-[7-[(3-methyloxetan-3-yl)methoxy]imidazo[1,2-a]pyridin-3-yl]benzamide | Int 1 + CAS# 3143-02-0 | A | 473.5 | 474.8 |
| 90 | 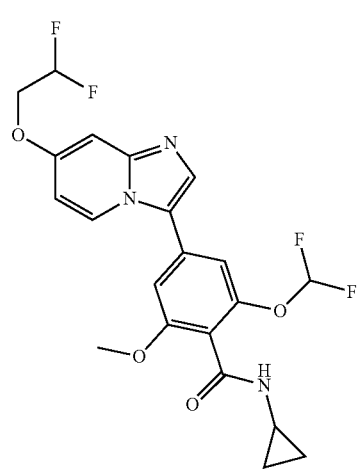 [SMILES: COc1cc(-c2cnc3cc(OCC(F)F)ccn23)cc(OC(F)F)c1C(=O)NC1CC1] | N-cyclopropyl-4-[7-(2,2-difluoroethoxy)imidazo[1,2-a]pyridin-3-yl]-2-(difluoromethoxy)-6-methoxy-benzamide | Int 1 + CAS# 359-13-7 | A | 453.4 | 454.8 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 91 | 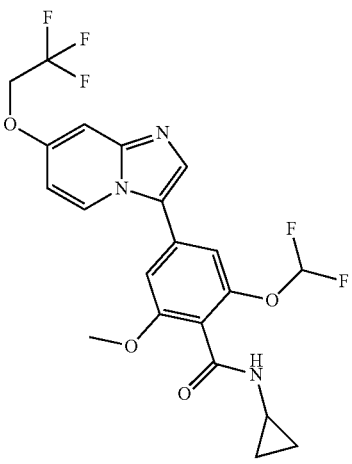 [SMILES: COc1cc(-c2cnc3cc(OCC(F)(F)F)ccn23)cc(OC(F)F)c1C(=O)NC1CC1] | N-cyclopropyl-2-(difluoromethoxy)-6-methoxy-4-[7-(2,2,2-trifluoroethoxy)imidazo[1,2-a]pyridin-3-yl]benzamide | Int 1 + CAS# 75-89-8 | A | 471.4 | 472.8 |
| 92 | 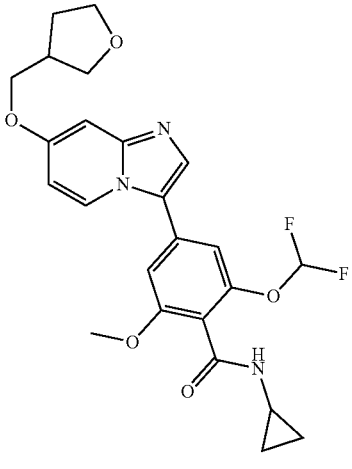 [SMILES: COc1cc(-c2cnc3cc(OCC4CCOC4)ccn23)cc(OC(F)F)c1C(=O)NC1CC1] | N-cyclopropyl-2-(difluoromethoxy)-6-methoxy-4-[7-(tetrahydrofuran-3-ylmethoxy)imidazo[1,2-a]pyridin-3-yl]benzamide | Int 1 + CAS# 15833-61-1 | A | 473.5 | 474.9 |
| 93 | 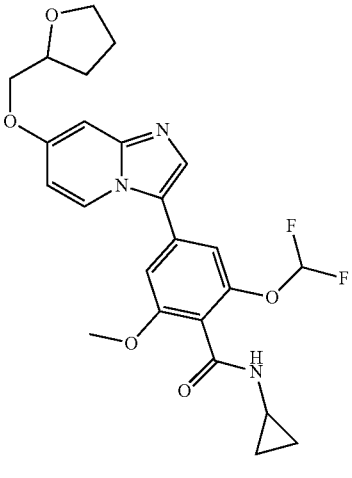 [SMILES: COc1cc(-c2cnc3cc(OCC4CCCO4)ccn23)cc(OC(F)F)c1C(=O)NC1CC1] | N-cyclopropyl-2-(difluoromethoxy)-6-methoxy-4-[7-(tetrahydrofuran-2-ylmethoxy)imidazo[1,2-a]pyridin-3-yl]benzamide | Int 1 + CAS# 97-99-4 | A | 473.5 | 474.9 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 94 | 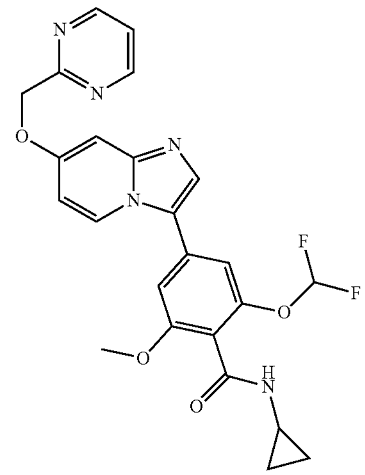 [SMILES: COc1cc(-c2cnc3cc(OCc4ncccn4)ccn23)cc(OC(F)F)c1C(=O)NC1CC1] | N-cyclopropyl-2-(difluoromethoxy)-6-methoxy-4-[7-(pyrimidin-2-ylmethoxy)imidazo[1,2-a]pyridin-3-yl]benzamide | Int 1 + CAS# 42839-09-8 | A | 481.5 | 482.9 |
| 95 | 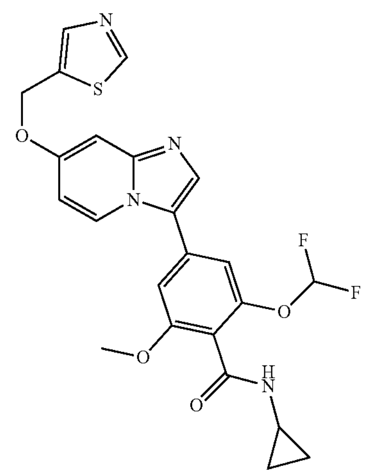 [SMILES: COc1cc(-c2cnc3cc(OCc4cncs4)ccn23)cc(OC(F)F)c1C(=O)NC1CC1] | N-cyclopropyl-2-(difluoromethoxy)-6-methoxy-4-[7-(thiazol-5-ylmethoxy)imidazo[1,2-a]pyridin-3-yl]benzamide | Int 1 + CAS# 38585-74-9 | A | 486.5 | 487.8 |
| 96 | 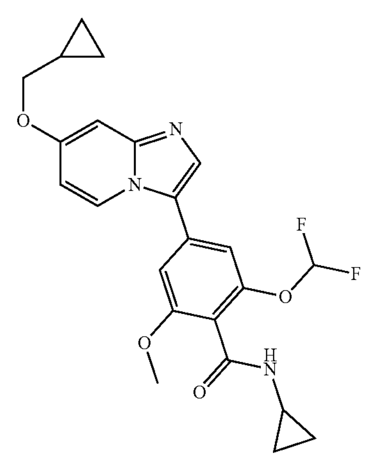 [SMILES: COc1cc(-c2cnc3cc(OCC4CC4)ccn23)cc(OC(F)F)c1C(=O)NC1CC1] | N-cyclopropyl-4-[7-(cyclopropylmethoxy)imidazo[1,2-a]pyridin-3-yl]-2-(difluoromethoxy)-6-methoxy-benzamide | Int 1 + CAS# 2516-33-8 | A | 443.4 | 444.9 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 97 | 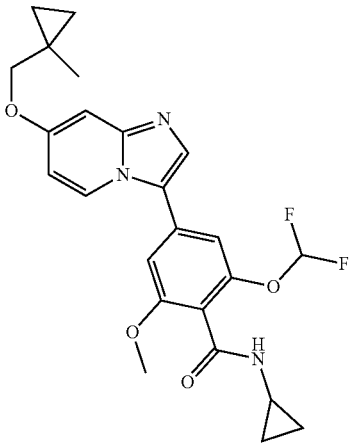 [SMILES: COc1cc(-c2cnc3cc(OCC4(C)CC4)ccn23)cc(OC(F)F)c1C(=O)NC1CC1] | N-cyclopropyl-2-(difluoromethoxy)-6-methoxy-4-[7-[(1-methylcyclopropyl)methoxy]imidazo[1,2-a]pyridin-3-yl]benzamide | Int 1 + CAS# 2746-14-7 | A | 457.5 | 458.2 |
| 98 | 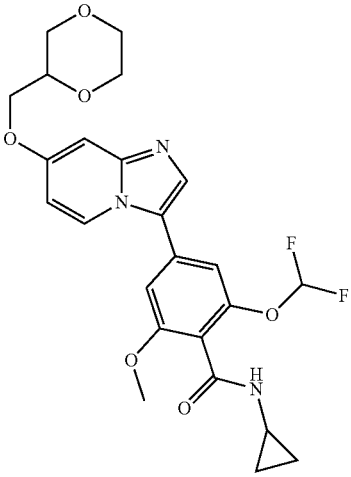 [SMILES: COc1cc(-c2cnc3cc(OCC4COCCO4)ccn23)cc(OC(F)F)c1C(=O)NC1CC1] | N-cyclopropyl-2-(difluoromethoxy)-4-[7-(1,4-dioxan-2-ylmethoxy)imidazo[1,2-a]pyridin-3-yl]-6-methoxy-benzamide | Int 1 + CAS# 29908-11-0 | A | 489.5 | 400.2 |
| 99 | 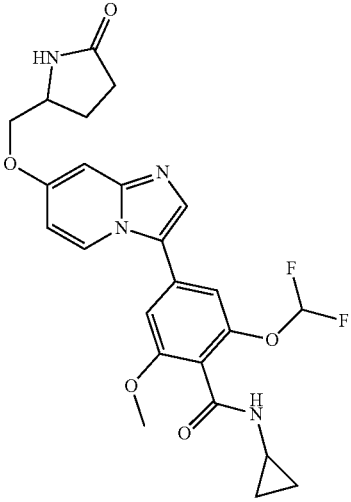 [SMILES: COc1cc(-c2cnc3cc(OCC4CCC(=O)N4)ccn23)cc(OC(F)F)c1C(=O)NC1CC1] | N-cyclopropyl-2-(difluoromethoxy)-6-methoxy-4-[7-[(5-oxopyrrolidin-2-yl)methoxy]imidazo[1,2-a]pyridin-3-yl]benzamide | Int 1 + CAS# 62400-75-3 | A | 486.5 | 487.9 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 100 | 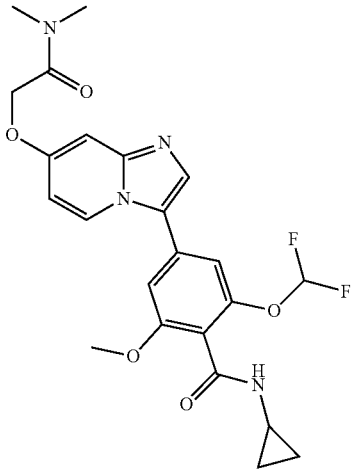 [SMILES: COc1cc(-c2cnc3cc(OCC(=O)N(C)C)ccn23)cc(OC(F)F)c1C(=O)NC1CC1] | N-cyclopropyl-2-(difluoromethoxy)-4-[7-[2-(dimethylamino)-2-oxo-ethoxy]imidazo[1,2-a]pyridin-3-yl]-6-methoxy-benzamide | Int 1 + CAS# 14658-93-6 | A | 474.5 | 475.9 |
| 101 | 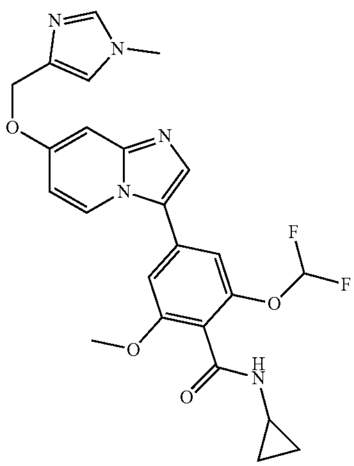 [SMILES: COc1cc(-c2cnc3cc(OCc4cn(C)cn4)ccn23)cc(OC(F)F)c1C(=O)NC1CC1] | N-cyclopropyl-2-(difluoromethoxy)-6-methoxy-4-[7-[(1-methylimidazol-4-yl)methoxy]imidazo[1,2-a]pyridin-3-yl]benzamide | Int 1 + CAS# 17289-25-7 | Ex. 2.62 | 483.5 | 484.3 |
| 102 | 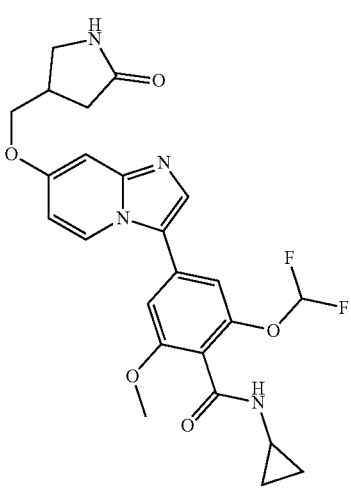 [SMILES: COc1cc(-c2cnc3cc(OCC4CNC(=O)C4)ccn23)cc(OC(F)F)c1C(=O)NC1CC1] | N-cyclopropyl-2-(difluoromethoxy)-6-methoxy-4-[7-[(5-oxopyrrolidin-3-yl)methoxy]imidazo[1,2-a]pyridin-3-yl]benzamide | Int 1 + CAS# 64320-89-4 | A | 486.5 | 487.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 103 | 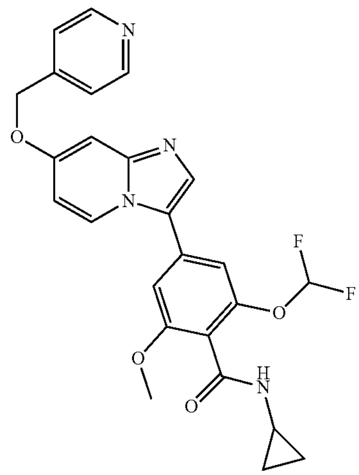 [SMILES: COc1cc(-c2cnc3cc(OCc4ccncc4)ccn23)cc(OC(F)F)c1C(=O)NC1CC1] | N-cyclopropyl-2-(difluoromethoxy)-6-methoxy-4-[7-(4-pyridylmethoxy)imidazo[1,2-a]pyridin-3-yl]benzamide | Int 1 + CAS# 586-95-8 | A | 480.5 | 481.2 |
| 104 | 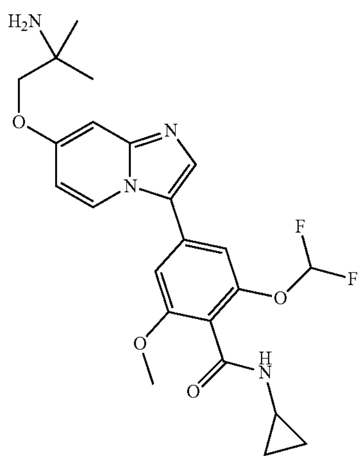 [SMILES: COc1cc(-c2cnc3cc(OCC(C)(C)N)ccn23)cc(OC(F)F)c1C(=O)NC1CC1] | 4-[7-(2-amino-2-methyl-propoxy)imidazo[1,2-a]pyridin-3-yl]-N-cyclopropyl-2-(difluoromethoxy)-6-methoxy-benzamide | Int 1 + CAS# 124-68-5 | A | 460.5 | 461.2 |
| 105 | 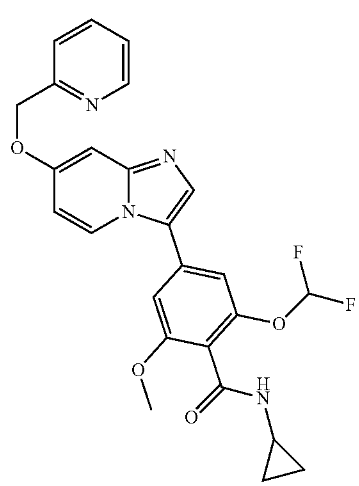 [SMILES: COc1cc(-c2cnc3cc(OCc4ccccn4)ccn23)cc(OC(F)F)c1C(=O)NC1CC1] | N-cyclopropyl-2-(difluoromethoxy)-6-methoxy-4-[7-(2-pyridylmethoxy)imidazo[1,2-a]pyridin-3-yl]benzamide | Int 1 + CAS# 586-98-1 | A | 480.5 | 481.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 106 | 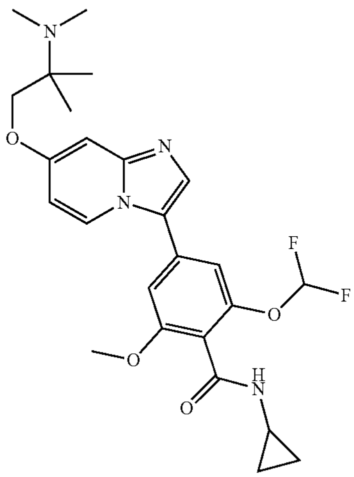 [SMILES: COc1cc(-c2cnc3cc(OCC(C)(C)N(C)C)ccn23)cc(OC(F)F)c1C(=O)NC1CC1] | N-cyclopropyl-2-(difluoromethoxy)-4-[7-[2-(dimethylamino)-2-methyl-propoxy]imidazo[1,2-a]pyridin-3-yl]-6-methoxy-benzamide | Int 1 + CAS# 7005-47-2 | A | 488.5 | 489.3 |
| 107 | 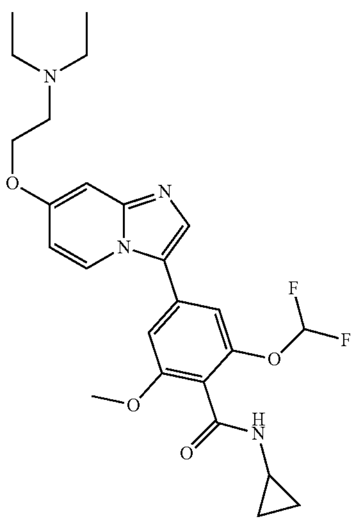 [SMILES: CCN(CC)CCOc1ccn2c(-c3cc(OC)c(C(=O)NC4CC4)c(OC(F)F)c3)cnc2c1] | N-cyclopropyl-4-[7-[2-(diethylamino)ethoxy]imidazo[1,2-a]pyridin-3-yl]-2-(difluoromethoxy)-6-methoxy-benzamide | Int 1 + CAS# 100-37-8 | A | 488.5 | 489.5 |
| 108 | 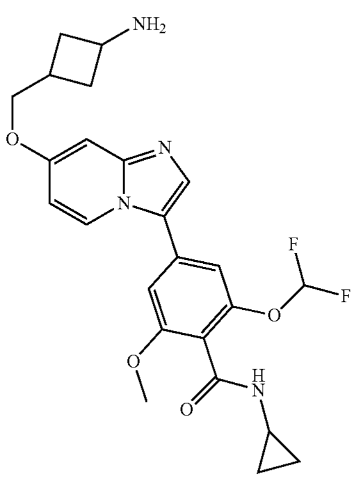 [SMILES: COc1cc(-c2cnc3cc(OCC4CC(N)C4)ccn23)cc(OC(F)F)c1C(=O)NC1CC1] | 4-[7-[(3-aminocyclobutyl)methoxy]imidazo[1,2-a]pyridin-3-yl]-N-cyclopropyl-2-(difluoromethoxy)-6-methoxy-benzamide | Int 1 + CAS# 130369-00-5 | A | 472.5 | 473.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 109 | 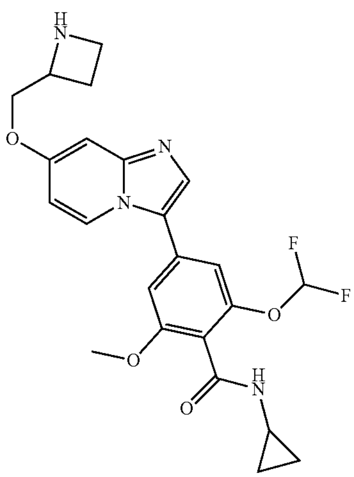 [SMILES: COc1cc(-c2cnc3cc(OCC4CCN4)ccn23)cc(OC(F)F)c1C(=O)NC1CC1] | 4-[7-(azetidin-2-ylmethoxy)imidazo[1,2-a]pyridin-3-yl]-N-cyclopropyl-2-(difluoromethoxy)-6-methoxy-benzamide | Cpd 87 | Ex. 2.64 | 458.5 | 459.4 |
| 110 | 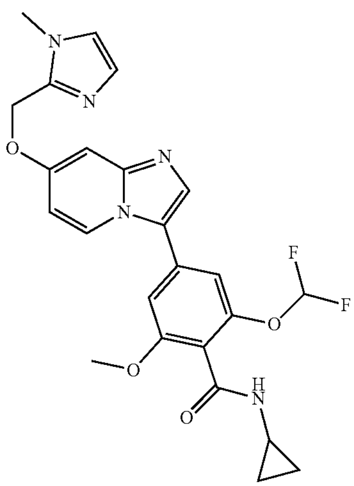 [SMILES: COc1cc(-c2cnc3cc(OCc4nccn4C)ccn23)cc(OC(F)F)c1C(=O)NC1CC1] | N-cyclopropyl-2-(difluoromethoxy)-6-methoxy-4-[7-[(1-methylimidazol-2-yl)methoxy]imidazo[1,2-a]pyridin-3-yl]benzamide | Int 1 + CAS# 17334-08-6 | A | 483.5 | 484.6 |
| 111 | 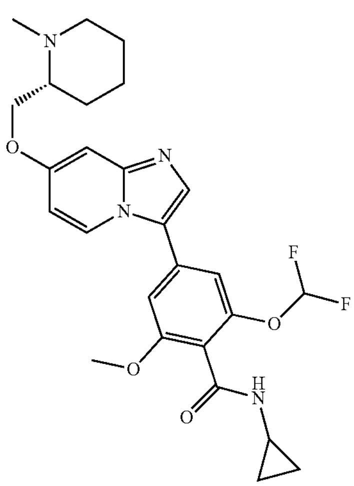 | N-cyclopropyl-2-(difluoromethoxy)-6-methoxy-4-[7-[[(2R)-1-methyl-2-piperidyl]methoxy]imidazo[1,2-a]pyridin-3-yl]benzamide | Int 1 + CAS# 68474-13-5 | A | 500.5 | 501.9 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 112 | 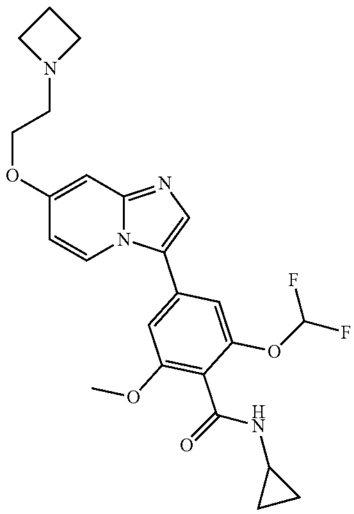 [SMILES: COc1cc(-c2cnc3cc(OCCN4CCC4)ccn23)cc(OC(F)F)c1C(=O)NC1CC1] | 4-[7-[2-(azetidin-1-yl)ethoxy]imidazo[1,2-a]pyridin-3-yl]-N-cyclopropyl-2-(difluoromethoxy)-6-methoxy-benzamide | Int 1 + CAS# 67896-18-8 | A | 472.5 | 473.5 |
| 113 | 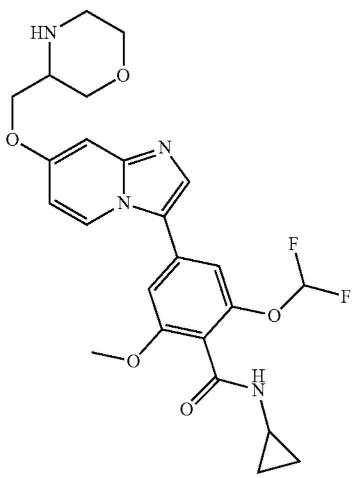 | N-cyclopropyl-2-(difluoromethoxy)-6-methoxy-4-[7-(morpholin-3-ylmethoxy)imidazo[1,2-a]pyridin-3-yl]benzamide | Int 1 + CAS# 473923-56-7 | Ex. 2.65 | 488.5 | 489.5 |
| 114 | 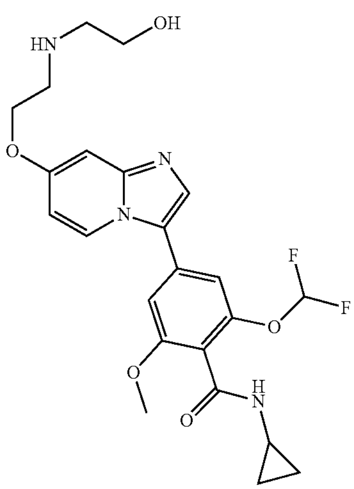 [SMILES: COc1cc(-c2cnc3cc(OCCNCCO)ccn23)cc(OC(F)F)c1C(=O)NC1CC1] | N-cyclopropyl-2-(difluoromethoxy)-4-[7-2-(2-hydroxyethylamino)ethoxy]imidazo[1,2-a]pyridin-3-yl]-6-methoxy-benzamide | Int 1 + CAS# 111-42-2 | A | 476.5 | 477.7 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 115 | 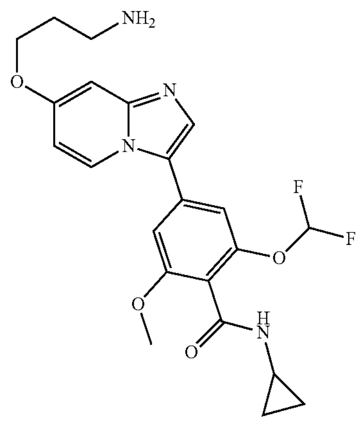 [SMILES: COc1cc(-c2cnc3cc(OCCCN)ccn23)cc(OC(F)F)c1C(=O)NC1CC1] | 4-[7-(3-aminopropoxy)imidazo[1,2-a]pyridin-3-yl]-N-cyclopropyl-2-(difluoromethoxy)-6-methoxy-benzamide | Int 1 + CAS# 156-87-6 | A | 446.4 | 447.7 |
| 116 | 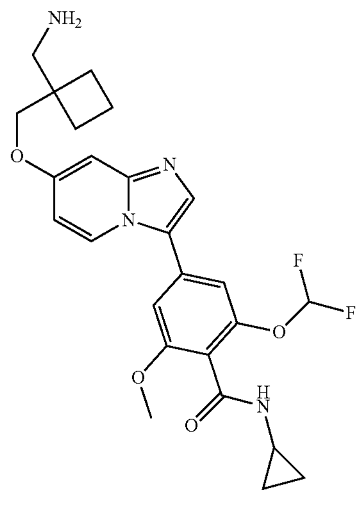 [SMILES: COc1cc(-c2cnc3cc(OCC4(CN)CCC4)ccn23)cc(OC(F)F)c1C(=O)NC1CC1] | 4-[7-[[1-(aminomethyl)cyclobutyl]methoxy]imidazo[1,2-a]pyridin-3-yl]-N-cyclopropyl-2-(difluoromethoxy)-6-methoxy-benzamide | Int 1 + CAS# 2041-56-7 | A | 486.5 | 487.2 |
| 117 | 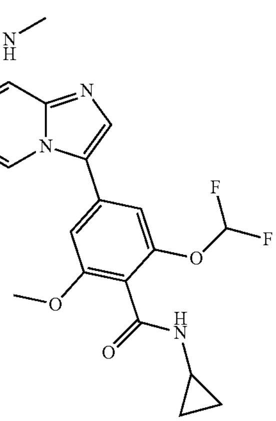 | N-cyclopropyl-2-(difluoromethoxy)-6-methoxy-4-[7-[2-(methylamino)ethoxy]imidazo[1,2-a]pyridin-3-yl]benzamide | Int 1 + CAS# 109-83-1 | A | 446.4 | 447.9 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 118 | 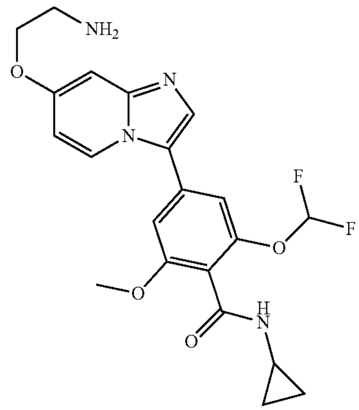 [SMILES: COc1cc(-c2cnc3cc(OCCN)ccn23)cc(OC(F)F)c1C(=O)NC1CC1] | 4-[7-(2-aminoethoxy)imidazo[1,2-a]pyridin-3-yl]-N-cyclopropyl-2-(difluoromethoxy)-6-methoxy-benzamide | Int 1 + CAS# 141-43-5 | A | 432.4 | 433.9 |
| 119 | 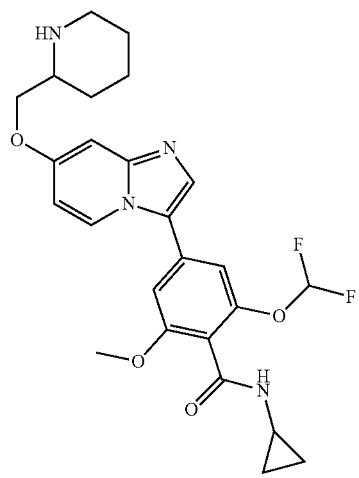 [SMILES: COc1cc(-c2cnc3cc(OCC4CCCCN4)ccn23)cc(OC(F)F)c1C(=O)NC1CC1] | N-cyclopropyl-2-(difluoromethoxy)-6-methoxy-4-[7-(2-piperidylmethoxy)imidazo[1,2-a]pyridin-3-yl]benzamide | Int 1 + CAS# 3433-37-2 | A | 486.5 | 487.8 |
| 120 | 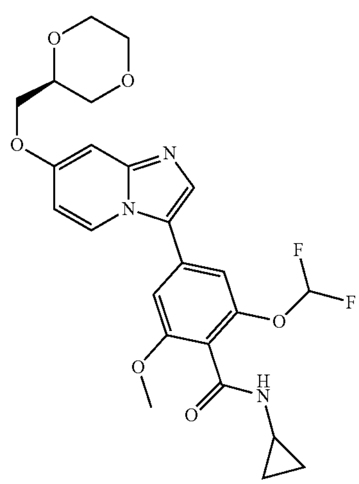 [SMILES: COc1cc(-c2cnc3cc(OC[C@@H]4COCCO4)ccn23)cc(OC(F)F)c1C(=O)NC1CC1] | N-cyclopropyl-2-(difluoromethoxy)-4-[7-[[(2S)-1,4-dioxan-2-yl]methoxy]imidazo[1,2-a]pyridin-3-yl]-6-methoxy-benzamide | Int 1 + CAS# 406913-88-0 | A | 489.5 | 490.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 121 | 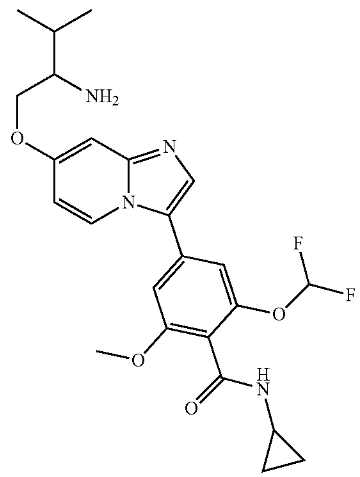 [SMILES: COc1cc(-c2cnc3cc(OCC(N)C(C)C)ccn23)cc(OC(F)F)c1C(=O)NC1CC1] | 4-[7-(2-amino-3-methyl-butoxy)imidazo[1,2-a]pyridin-3-yl]-N-cyclopropyl-2-(difluoromethoxy)-6-methoxy-benzamide | Int 1 + CAS# 16369-05-4 | A | 474.5 | 475.7 |
| 122 | 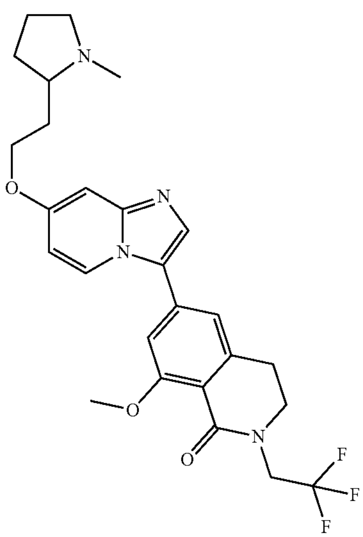 [SMILES: COc1cc(-c2cnc3cc(OCCC4CCCN4C)ccn23)cc2c1C(=O)N(CC(F)(F)F)CC2] | 8-methoxy-6-[7-[2-(1-methylpyrrolidin-2-yl)ethoxy]imidazo[1,2-a]pyridin-3-yl]-2-(2,2,2-trifluoroethyl)-3,4-dihydroisoquinolin-1-one | Int 2 + CAS# 67004-64-2 | Ex. 2.66 | 502.5 | 503.9 |
| 123 | 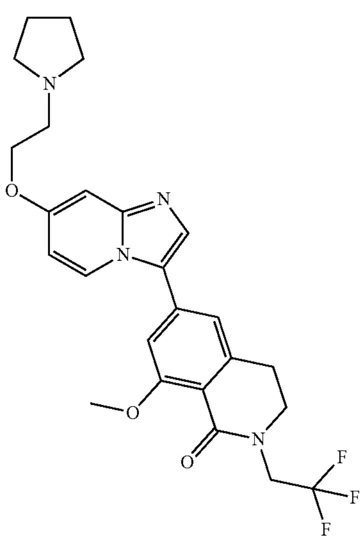 [SMILES: COc1cc(-c2cnc3cc(OCCN4CCCC4)ccn23)cc2c1C(=O)N(CC(F)(F)F)CC2] | 8-methoxy-6-[7-(2-pyrrolidin-1-ylethoxy)imidazo[1,2-a]pyridin-3-yl]-2-(2,2,2-trifluoroethyl)-3,4-dihydroisoquinolin-1-one | Int 2 + CAS# 2955-88-6 | A | 488.5 | 489.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 124 | 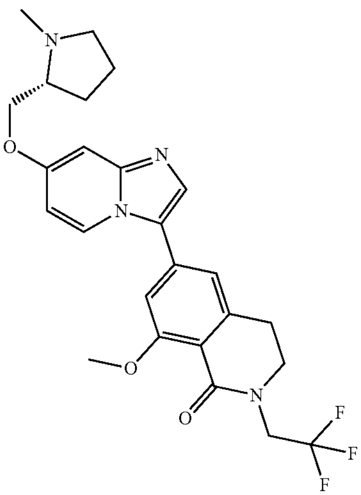 [SMILES: COc1cc(-c2cnc3cc(OC[C@H]4CCCN4C)ccn23)cc2c1C(=O)N(CC(F)(F)F)CC2] | 8-methoxy-6-[7-[[(2R)-1-methylpyrrolidin-2-yl]methoxy]imidazo[1,2-a]pyridin-3-yl]-2-(2,2,2-trifluoroethyl)-3,4-dihydroisoquinolin-1-one | Int 2 + CAS# 99494-01-6 | A | 488.5 | 489.6 |
| 125 | 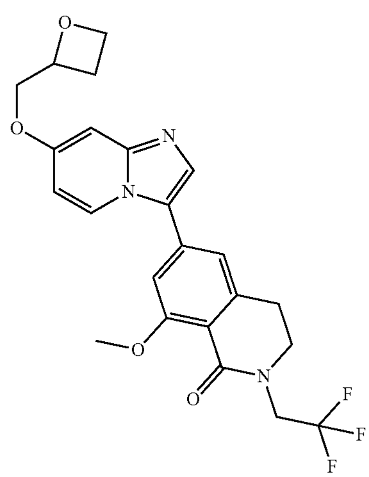 [SMILES: COc1cc(-c2cnc3cc(OCC4CCO4)ccn23)cc2c1C(=O)N(CC(F)(F)F)CC2] | 8-methoxy-6-[7-(oxetan-2-ylmethoxy)imidazo[1,2-a]pyridin-3-yl]-2-(2,2,2-trifluoroethyl)-3,4-dihydroisoquinolin-1-one | Int 2 + CAS# 61266-70-4 | A | 461.4 | 462.5 |
| 126 | 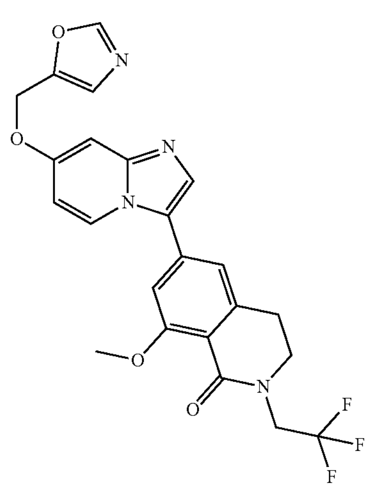 [SMILES: COc1cc(-c2cnc3cc(OCc4cnco4)ccn23)cc2c1C(=O)N(CC(F)(F)F)CC2] | 8-methoxy-6-[7-(oxazol-5-ylmethoxy)imidazo[1,2-a]pyridin-3-yl]-2-(2,2,2-trifluoroethyl)-3,4-dihydroisoquinolin-1-one | Int 2 + CAS# 127232-41-1 | A | 472.4 | 473.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 127 | 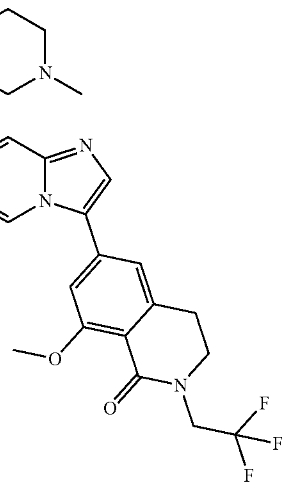 | 8-methoxy-6-[7-[(4-methylmorpholin-2-yl)methoxy]imidazo[1,2-a]pyridin-3-yl]-2-(2,2,2-trifluoroethyl)-3,4-dihydroisoquinolin-1-one | Int 2 + CAS# 40987-46-0 | A | 504.5 | 505.4 |
| 128 | 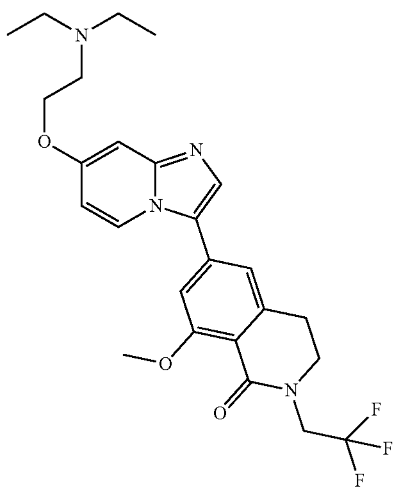 [SMILES: CCN(CC)CCOc1ccn2c(-c3cc4c(c(OC)c3)C(=O)N(CC(F)(F)F)CC4)cnc2c1] | 6-[7-[2-(diethylamino)ethoxy]imidazo[1,2-a]pyridin-3-yl]-8-methoxy-2-(2,2,2-trifluoroethyl)-3,4-dihydroisoquinolin-1-one | Int 2 + CAS# 100-37-8 | A | 490.5 | 489.5 |
| 129 | 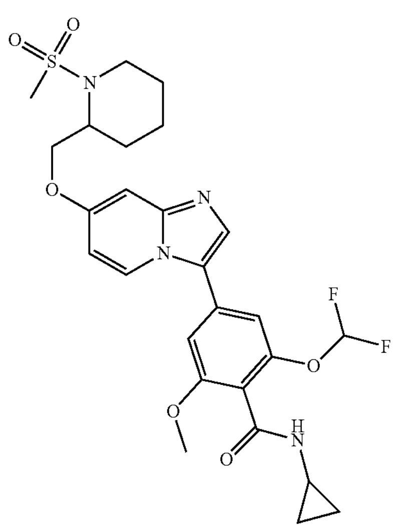 [SMILES: COc1cc(-c2cnc3cc(OCC4CCCCN4S(C)(=O)=O)ccn23)cc(OC(F)F)c1C(=O)NC1CC1] | N-cyclopropyl-2-(difluoromethoxy)-6-methoxy-4-[7-[(1-methylsulfonyl-2-piperidyl)methoxy]imidazo[1,2-a]pyridin-3-yl]benzamide | Cpd 119 | Ex. 2.67 | 564.6 | 565.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 130 | 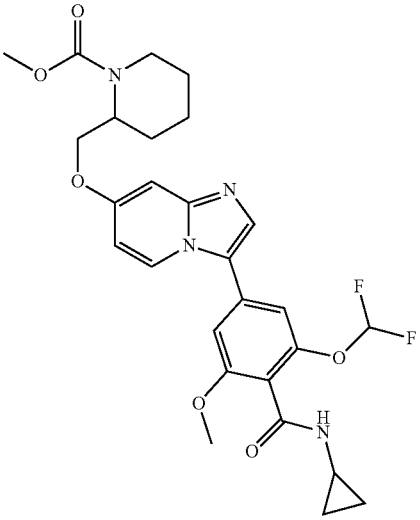 [SMILES: COC(=O)N1CCCCC1COc1ccn2c(-c3cc(OC)c(C(=O)NC4CC4)c(OC(F)F)c3)cnc2c1] | methyl 2-[[3-[4-(cyclopropylcarbamoyl)-3-(difluoromethoxy)-5-methoxy-phenyl]imidazo[1,2-a]pyridin-7-yl]oxymethyl]piperidine-1-carboxylate | Cpd 119 | Ex. 2.68 | 544.5 | 545.2 |
| 131 | 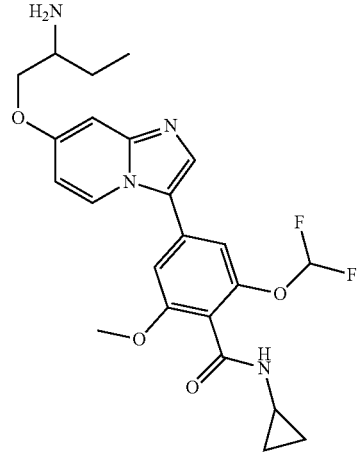 [SMILES: CCC(N)COc1ccn2c(-c3cc(OC)c(C(=O)NC4CC4)c(OC(F)F)c3)cnc2c1] | 4-[7-(2-aminobutoxy)imidazo[1,2-a]pyridin-3-yl]-N-cyclopropyl-2-(difluoromethoxy)-6-methoxy-benzamide | Int 1 + CAS# 96-20-8 | A | 460.5 | 461.3 |
| 132 | 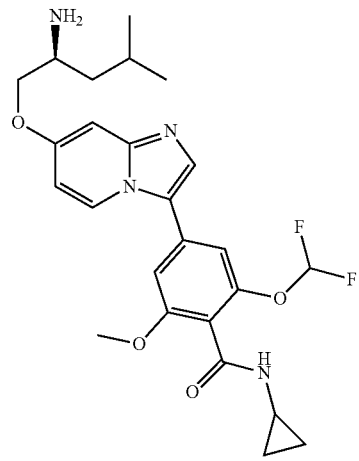 [SMILES: COc1cc(-c2cnc3cc(OC[C@@H](N)CC(C)C)ccn23)cc(OC(F)F)c1C(=O)NC1CC1] | 4-[7-[(2S)-2-amino-4-methyl-pentoxy]imidazo[1,2-a]pyridin-3-yl]-N-cyclopropyl-2-(difluoromethoxy)-6-methoxy-benzamide | Int 1 + CAS# 7533-40-6 | A | 488.5 | 489.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 133 | 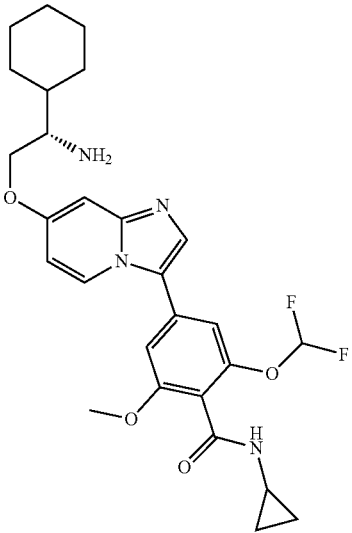 [SMILES: COc1cc(-c2cnc3cc(OC[C@@H](N)C4CCCCC4)ccn23)cc(OC(F)F)c1C(=O)NC1CC1] | 4-[7-[(2S)-2-amino-2-cyclohexyl-ethoxy]imidazo[1,2-a]pyridin-3-yl]-N-cyclopropyl-2-(difluoromethoxy)-6-methoxy-benzamide | Int 1 + CAS# 845714-30-9 | A | 514.6 | 515.6 |
| 134 | 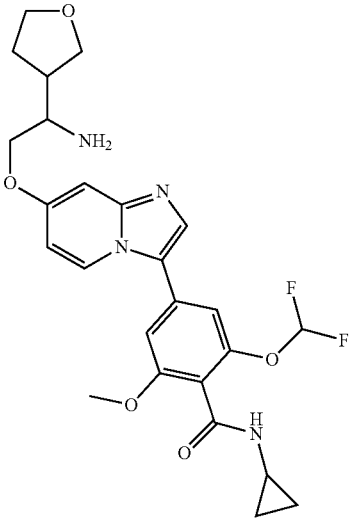 [SMILES: COc1cc(-c2cnc3cc(OCC(N)C4CCOC4)ccn23)cc(OC(F)F)c1C(=O)NC1CC1] | 4-[7-(2-amino-2-tetrahydrofuran-3-yl-ethoxy)imidazo[1,2-a]pyridin-3-yl]-N-cyclopropyl-2-(difluoromethoxy)-6-methoxy-benzamide | Int 1 + CAS# 889949-68-2 | A | 502.5 | 503.7 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 135 | 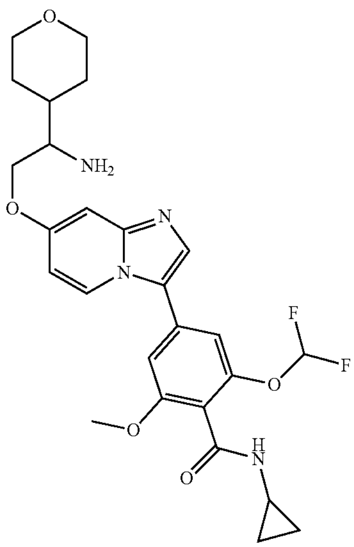 [SMILES: COc1cc(-c2cnc3cc(OCC(N)C4CCOCC4)ccn23)cc(OC(F)F)c1C(=O)NC1CC1] | 4-[7-(2-amino-2-tetrahydropyran-4-yl-ethoxy)imidazo[1,2-a]pyridin-3-yl]-N-cyclopropyl-2-(difluoromethoxy)-6-methoxy-benzamide | Int 1 + CAS# 1375472-26-6 | A | 516.5 | 517.7 |
| 136 | 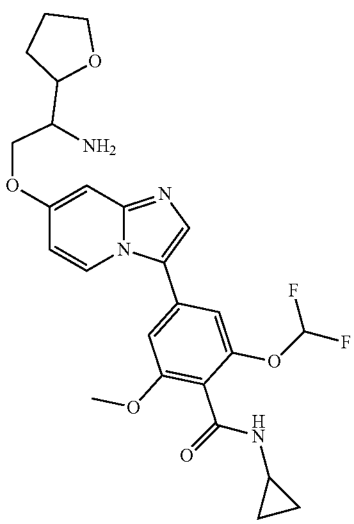 [SMILES: COc1cc(-c2cnc3cc(OCC(N)C4CCCO4)ccn23)cc(OC(F)F)c1C(=O)NC1CC1] | 4-[7-(2-amino-2-tetrahydrofuran-2-yl-ethoxy)imidazo[1,2-a]pyridin-3-yl]-N-cyclopropyl-2-(difluoromethoxy)-6-methoxy-benzamide | Int 1 + CAS# 1426427-02-2 | A | 502.5 | 503.5 |
| 137 | 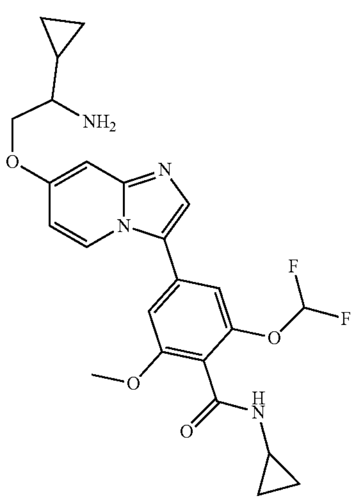 [SMILES: COc1cc(-c2cnc3cc(OCC(N)C4CC4)ccn23)cc(OC(F)F)c1C(=O)NC1CC1] | 4-[7-(2-amino-2-cyclopropyl-ethoxy)imidazo[1,2-a]pyridin-3-yl]-N-cyclopropyl-2-(difluoromethoxy)-6-methoxy-benzamide | Int 1 + CAS# 1306603-98-4 | A | 472.5 | 473.7 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 138 | 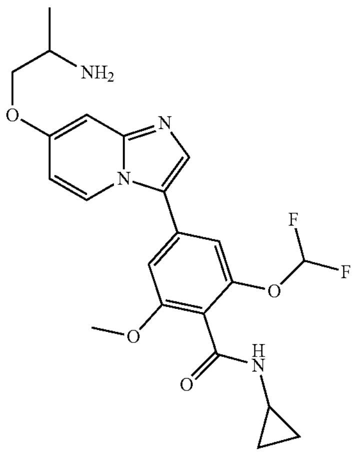 [SMILES: COc1cc(-c2cnc3cc(OCC(C)N)ccn23)cc(OC(F)F)c1C(=O)NC1CC1] | 4-[7-(2-aminopropoxy)imidazo[1,2-a]pyridin-3-yl]-N-cyclopropyl-2-(difluoromethoxy)-6-methoxy-benzamide | Int 1 + CAS# 6168-72-5 | A | 446.4 | 447.5 |
| 139 | 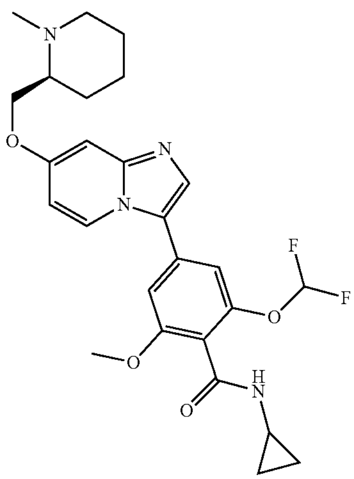 [SMILES: COc1cc(-c2cnc3cc(OC[C@@H]4CCCCN4C)ccn23)cc(OC(F)F)c1C(=O)NC1CC1] | N-cyclopropyl-2-(difluoromethoxy)-6-methoxy-4-[7-[[(2S)-1-methyl-2-piperidyl]methoxy]imidazo[1,2-a]pyridin-3-yl]benzamide | Int 1 + CAS# 136030-04-1 | A | 500.5 | 501.5 |
| 140 | 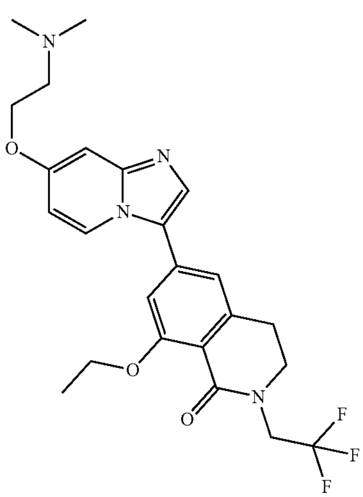 [SMILES: CCOc1cc(-c2cnc3cc(OCCN(C)C)ccn23)cc2c1C(=O)N(CC(F)(F)F)CC2] | 6-[7-[2-(dimethylamino)ethoxy]imidazo[1,2-a]pyridin-3-yl]-8-ethoxy-2-(2,2,2-trifluoroethyl)-3,4-dihydroisoquinolin-1-one | Int 3 + Int 9 | B | 476.5 | 477.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 141 | 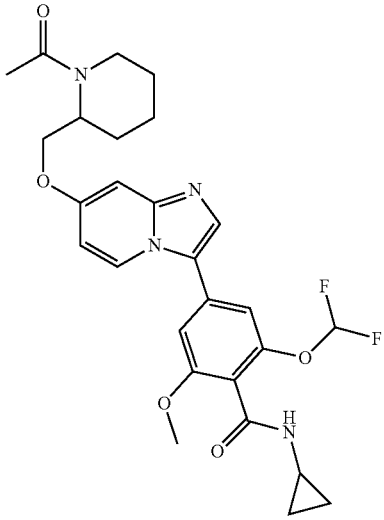 [SMILES: COc1cc(-c2cnc3cc(OCC4CCCCN4C(C)=O)ccn23)cc(OC(F)F)c1C(=O)NC1CC1] | 4-[7-[(1-acetyl-2-piperidyl)methoxy]imidazo[1,2-a]pyridin-3-yl]-N-cyclopropyl-2-(difluoromethoxy)-6-methoxy-benzamide | Cpd 119 | Ex. 2.69 | 528.5 | 529.2 |
| 142 | 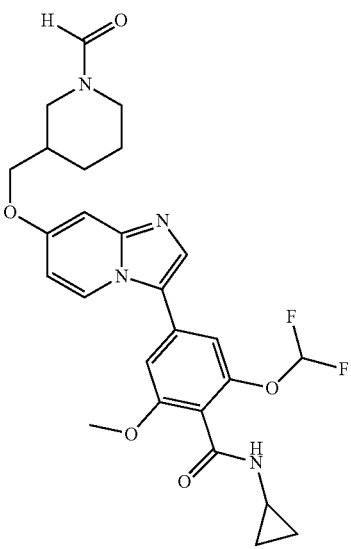 [SMILES: COc1cc(-c2cnc3cc(OCC4CCCN(C=O)C4)ccn23)cc(OC(F)F)c1C(=O)NC1CC1] | N-cyclopropyl-2-(difluoromethoxy)-4-[7-[(1-formyl-3-piperidyl)methoxy]imidazo[1,2-a]pyridin-3-yl]-6-methoxy-benzamide | Int 1 + CAS# 4606-65-9 | A | 514.5 | 515.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 143 | 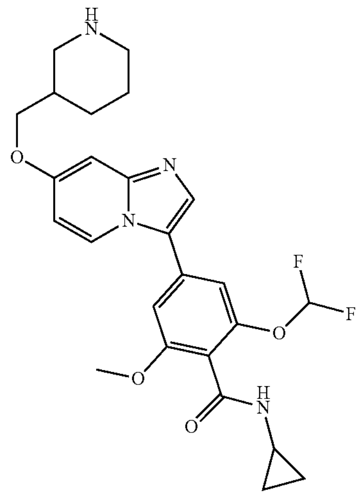 [SMILES: COc1cc(-c2cnc3cc(OCC4CCCNC4)ccn23)cc(OC(F)F)c1C(=O)NC1CC1] | N-cyclopropyl-2-(difluoromethoxy)-6-methoxy-4-[7-(3-piperidylmethoxy)imidazo[1,2-a]pyridin-3-yl]benzamide | Int 1 + CAS# 4606-65-9 | A | 486.5 | 487.4 |
| 144 | 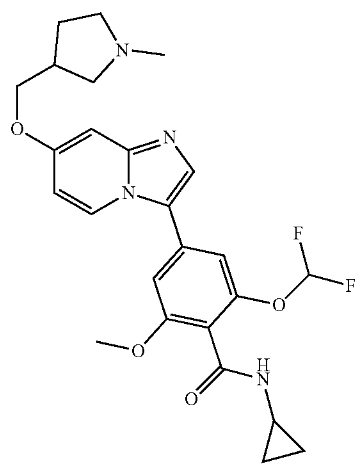 [SMILES: COc1cc(-c2cnc3cc(OCC4CCN(C)C4)ccn23)cc(OC(F)F)c1C(=O)NC1CC1] | N-cyclopropyl-2-(difluoromethoxy)-6-methoxy-4-[7-[(1-methylpyrrolidin-3-yl)methoxy]imidazo[1,2-a]pyridin-3-yl]benzamide | Int 1 + CAS# 5021-33-0 | A | 486.5 | 487.4 |
| 145 | 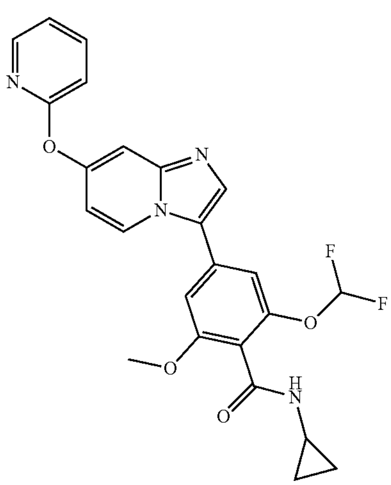 [SMILES: COc1cc(-c2cnc3cc(Oc4ccccn4)ccn23)cc(OC(F)F)c1C(=O)NC1CC1] | N-cyclopropyl-2-(difluoromethoxy)-6-methoxy-4-[7-(2-pyridyloxy)imidazo[1,2-a]pyridin-3-yl]benzamide | Int 10 + Int 11 | B | 466.4 | 467.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 146 | 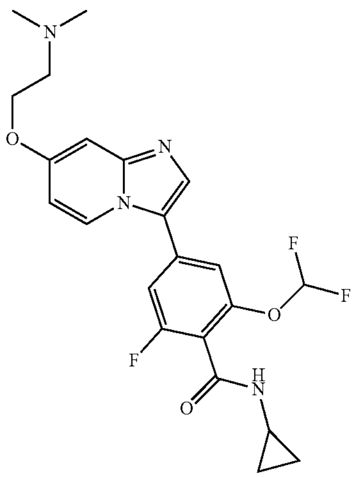 [SMILES: CN(C)CCOc1ccn2c(-c3cc(F)c(C(=O)NC4CC4)c(OC(F)F)c3)cnc2c1] | N-cyclopropyl-2-(difluoromethoxy)-4-[7-[2-(dimethylamino)ethoxy]imidazo[1,2-a]pyridin-3-yl]-6-fluoro-benzamide | Int 3 + Int 12 | B | 448.4 | 449.4 |
| 147 | 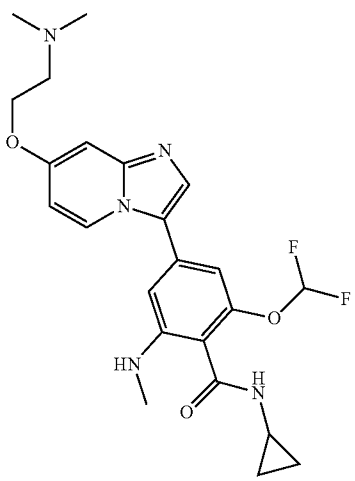 [SMILES: CNc1cc(-c2cnc3cc(OCCN(C)C)ccn23)cc(OC(F)F)c1C(=O)NC1CC1] | N-cyclopropyl-2-(difluoromethoxy)-4-[7-[2-(dimethylamino)ethoxy]imidazo[1,2-a]pyridin-3-yl]-6-(methylamino)benzamide | Int 3 + Int 13 | B | 459.5 | 460.4 |
| 148 | 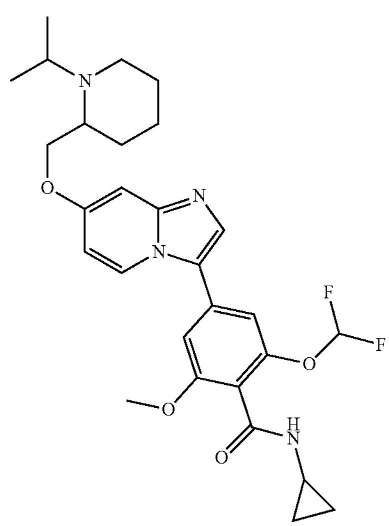 [SMILES: COc1cc(-c2cnc3cc(OCC4CCCCN4C(C)C)ccn23)cc(OC(F)F)c1C(=O)NC1CC1] | N-cyclopropyl-2-(difluoromethoxy)-4-[7-[(1-isopropyl-2-piperidyl)methoxy]imidazo[1,2-a]pyridin-3-yl]-6-methoxy-benzamide | Int 1 + Int 71 | A | 528.6 | 529.9 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 149 | 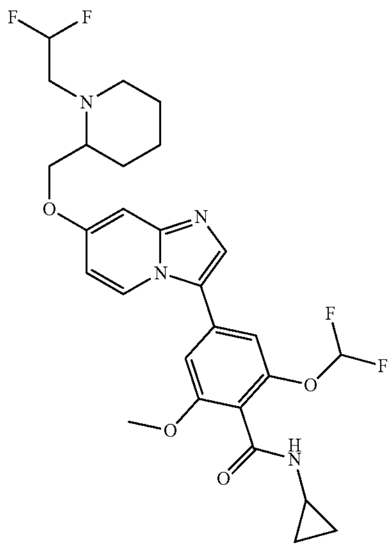 [SMILES: COc1cc(-c2cnc3cc(OCC4CCCCN4CC(F)F)ccn23)cc(OC(F)F)c1C(=O)NC1CC1] | N-cyclopropyl-4-[7-[[1-(2,2-difluoroethyl)-2-piperidyl]methoxy]imidazo[1,2-a]pyridin-3-yl]-2-(difluoromethoxy)-6-methoxy-benzamide | Int 1 + Int 72 | A | 550.5 | 551.8 |
| 150 | 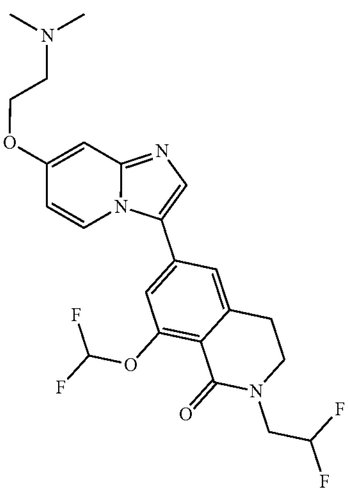 [SMILES: CN(C)CCOc1ccn2c(-c3cc4c(c(OC(F)F)c3)C(=O)N(CC(F)F)CC4)cnc2c1] | 2-(2,2-difluoroethyl)-8-(difluoromethoxy)-6-[7-[2-(dimethylamino)ethoxy]imidazo[1,2-a]pyridin-3-yl]-3,4-dihydroisoquinolin-1-one | Int 3 + Int 14 | Ex. 2.70 | 480.5 | 481.4 |
| 151 | 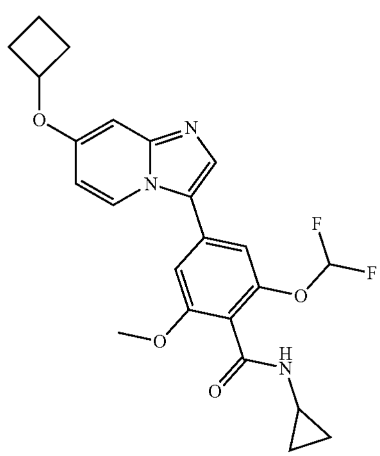 [SMILES: COc1cc(-c2cnc3cc(OC4CCC4)ccn23)cc(OC(F)F)c1C(=O)NC1CC1] | 4-[7-(cyclobutoxy)imidazo[1,2-a]pyridin-3-yl]-N-cyclopropyl-2-(difluoromethoxy)-6-methoxy-benzamide | Int 1 + CAS# 2919-23-5 | A | 443.4 | 444.7 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|------|-----------|------|----|----|----|----------|
| 152 | 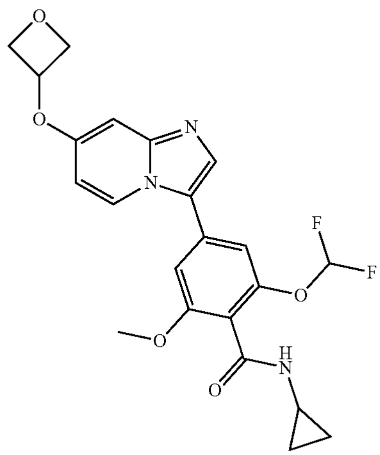 [SMILES: COc1cc(-c2cnc3cc(OC4COC4)ccn23)cc(OC(F)F)c1C(=O)NC1CC1] | N-cyclopropyl-2-(difluoromethoxy)-6-methoxy-4-[7-(oxetan-3-yloxy)imidazo[1,2-a]pyridin-3-yl]benzamide | Int 1 + CAS# 7748-36-9 | A | 445.4 | 446.7 |
| 153 | 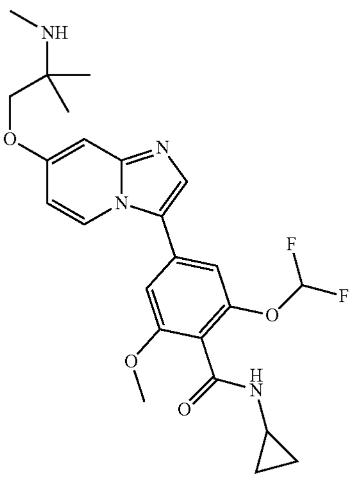 [SMILES: CNC(C)(C)COc1ccn2c(-c3cc(OC)c(C(=O)NC4CC4)c(OC(F)F)c3)cnc2c1] | N-cyclopropyl-2-(difluoromethoxy)-6-methoxy-4-[7-[2-methyl-2-(methylamino)propoxy]imidazo[1,2-a]pyridin-3-yl]benzamide | Int 1 + CAS# 27646-80-6 | Ex. 2.71 | 474.5 | 475.9 |
| 154 | 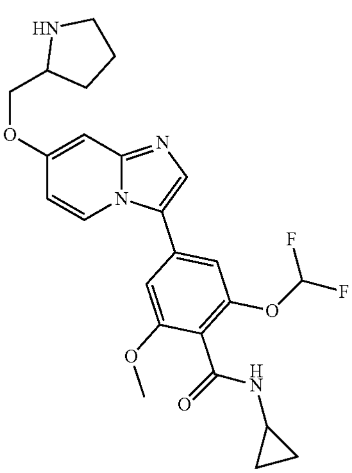 [SMILES: COc1cc(-c2cnc3cc(OCC4CCCN4)ccn23)cc(OC(F)F)c1C(=O)NC1CC1] | N-cyclopropyl-2-(difluoromethoxy)-6-methoxy-4-[7-(pyrrolidin-2-ylmethoxy)imidazo[1,2-a]pyridin-3-yl]benzamide | Int 1 + CAS# 498-63-5 | Ex. 2.72 | 472.5 | 473.7 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 155 | 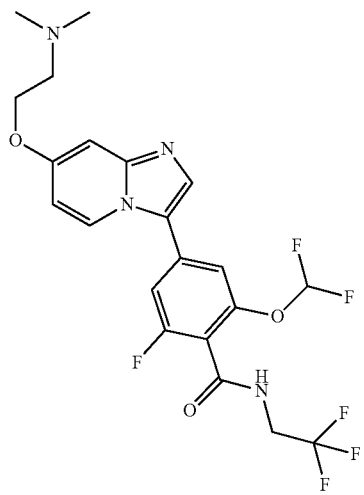 [SMILES: CN(C)CCOc1ccn2c(-c3cc(F)c(C(=O)NCC(F)(F)F)c(OC(F)F)c3)cnc2c1] | 2-(difluoromethoxy)-4-[7-[2-(dimethylamino)ethoxy]imidazo[1,2-a]pyridin-3-yl]-6-fluoro-N-(2,2,2-trifluoroethyl)benzamide | Int 3 + Int 15 | B | 490.4 | 491.3 |
| 156 | 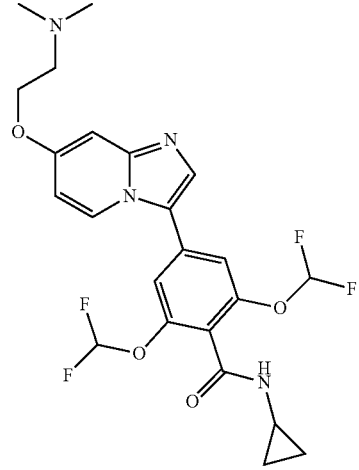 [SMILES: CN(C)CCOc1ccn2c(-c3cc(OC(F)F)c(C(=O)NC4CC4)c(OC(F)F)c3)cnc2c1] | N-cyclopropyl-2,6-bis(difluoromethoxy)-4-[7-[2-(dimethylamino)ethoxy]imidazo[1,2-a]pyridin-3-yl]benzamide | Int 3 + Int 16 | B | 496.5 | 497.4 |
| 157 | 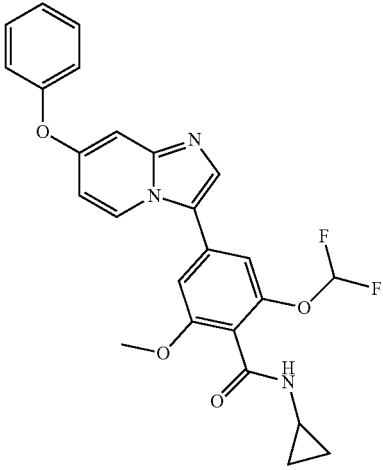 [SMILES: COc1cc(-c2cnc3cc(Oc4ccccc4)ccn23)cc(OC(F)F)c1C(=O)NC1CC1] | N-cyclopropyl-2-(difluoromethoxy)-6-methoxy-4-(7-phenoxyimidazo[1,2-a]pyridin-3-yl)benzamide | Int 17 + Int 11 | B | 465.4 | 466.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 158 | 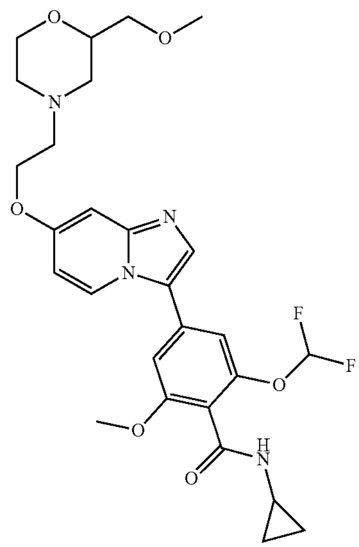 [SMILES: COCC1CN(CCOc2ccn3c(-c4cc(OC)c(C(=O)NC5CC5)c(OC(F)F)c4)cnc3c2)CCO1] | N-cyclopropyl-2-(difluoromethoxy)-6-methoxy-4-[7-[2-[2-(methoxymethyl)morpholin-4-yl]ethoxy]imidazo[1,2-a]pyridin-3-yl]benzamide | Int 18 + CAS# 156121-15-2 | I (without Et₃N) | 546.6 | 547.7 |
| 159 | 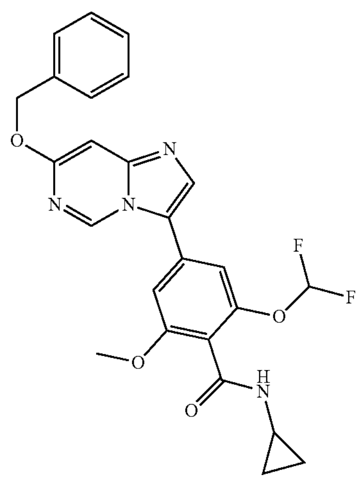 [SMILES: COc1cc(-c2cnc3cc(OCc4ccccc4)ncn23)cc(OC(F)F)c1C(=O)NC1CC1] | 4-(7-benzyloxyimidazo[1,2-c]pyrimidin-3-yl)-N-cyclopropyl-2-(difluoromethoxy)-6-methoxy-benzamide | Int 84 + Int 11 | Ex. 2.73 | 480.5 | 481.4 |
| 160 | 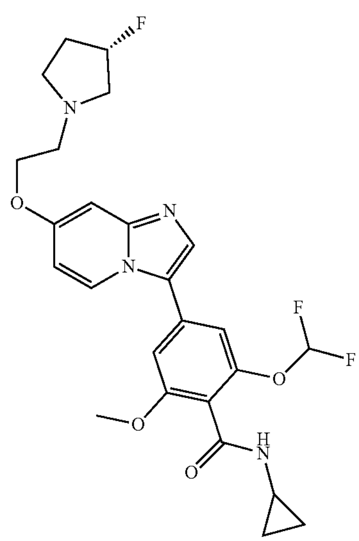 [SMILES: COc1cc(-c2cnc3cc(OCCN4CC[C@H](F)C4)ccn23)cc(OC(F)F)c1C(=O)NC1CC1] | N-cyclopropyl-2-(difluoromethoxy)-4-[7-[2-[(3S)-3-fluoropyrrolidin-1-yl]ethoxy]imidazo[1,2-a]pyridin-3-yl]-6-methoxy-benzamide | Int 1 + Int 63 | Ex. 2.74 | 504.5 | 505.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 161 | 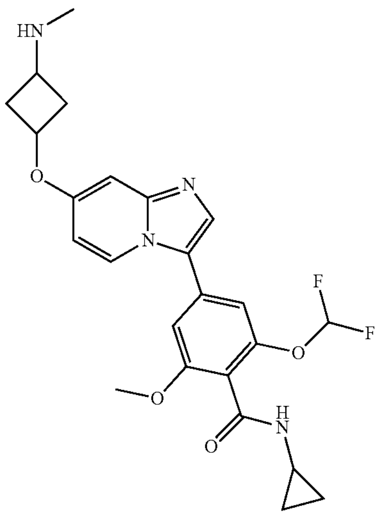 [SMILES: CNC1CC(Oc2ccn3c(-c4cc(OC)c(C(=O)NC5CC5)c(OC(F)F)c4)cnc3c2)C1] | N-cyclopropyl-2-(difluoromethoxy)-6-methoxy-4-[7-[3-(methylamino)cyclobutoxy]imidazo[1,2-a]pyridin-3-yl]benzamide | Int 1 + CAS# 1354952-94-5 | A | 472.5 | 473.6 |
| 162 | 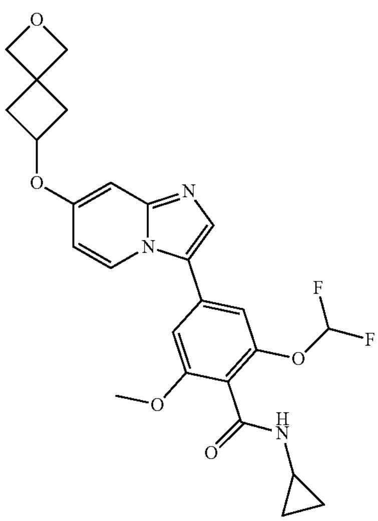 [SMILES: COc1cc(-c2cnc3cc(OC4CC5(COC5)C4)ccn23)cc(OC(F)F)c1C(=O)NC1CC1] | N-cyclopropyl-2-(difluoromethoxy)-6-methoxy-4-[7-(2-oxaspiro[3.3]heptan-6-yloxy)imidazo[1,2-a]pyridin-3-yl]benzamide | Int 1 + CAS# 1363381-08-1 | A | 485.5 | 486.5 |
| 163 | 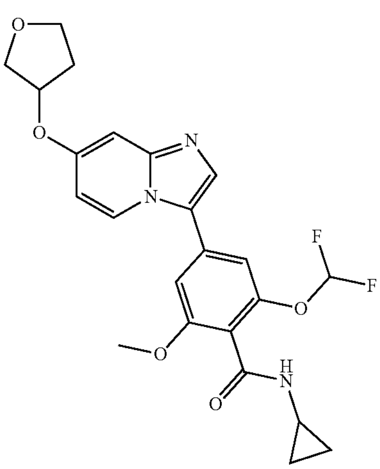 [SMILES: COc1cc(-c2cnc3cc(OC4CCOC4)ccn23)cc(OC(F)F)c1C(=O)NC1CC1] | N-cyclopropyl-2-(difluoromethoxy)-6-methoxy-4-(7-tetrahydrofuran-3-yloxyimidazo[1,2-a]pyridin-3-yl)benzamide | Int 1 + CAS# 453-20-3 | A | 459.4 | 460.8 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 164 | 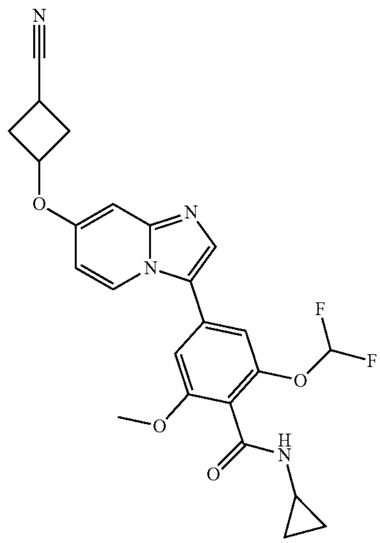 [SMILES: COc1cc(-c2cnc3cc(OC4CC(C#N)C4)ccn23)cc(OC(F)F)c1C(=O)NC1CC1] | 4-[7-(3-cyanocyclobutoxy)imidazo[1,2-a]pyridin-3-yl]-N-cyclopropyl-2-(difluoromethoxy)-6-methoxy-benzamide | Int 1 + CAS# 20249-17-6 | A | 468.5 | 469.7 |
| 165 | 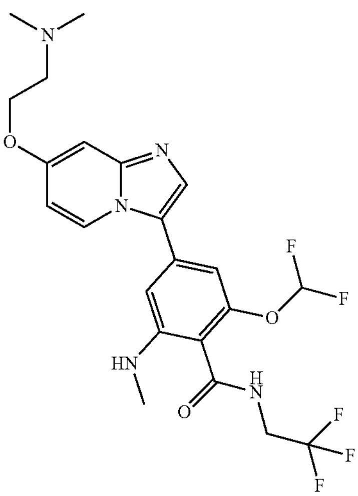 [SMILES: CNc1cc(-c2cnc3cc(OCCN(C)C)ccn23)cc(OC(F)F)c1C(=O)NCC(F)(F)F] | 2-(difluoromethoxy)-4-[7-[2-(dimethylamino)ethoxy]imidazo[1,2-a]pyridin-3-yl]-6-(methylamino)-N-(2,2,2-trifluoroethyl)benzamide | Cpd 155 | Ex. 2.75 | 501.4 | 502.2 |
| 166 | 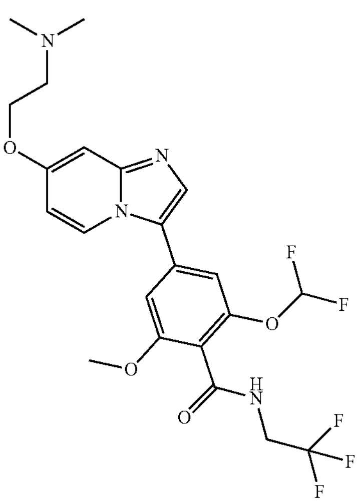 [SMILES: COc1cc(-c2cnc3cc(OCCN(C)C)ccn23)cc(OC(F)F)c1C(=O)NCC(F)(F)F] | 2-(difluoromethoxy)-4-[7-[2-(dimethylamino)ethoxy]imidazo[1,2-a]pyridin-3-yl]-6-methoxy-N-(2,2,2-trifluoroethyl)benzamide | Int 3 + Int 19 | B | 502.4 | 503.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 167 | 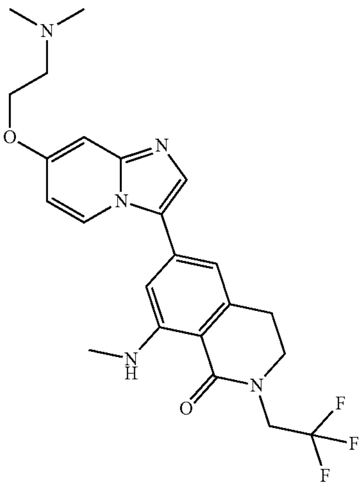 [SMILES: CNc1cc(-c2cnc3cc(OCCN(C)C)ccn23)cc2c1C(=O)N(CC(F)(F)F)CC2] | 6-[7-[2-(dimethylamino)ethoxy]imidazo[1,2-a]pyridin-3-yl]-8-(methylamino)-2-(2,2,2-trifluoroethyl)-3,4-dihydroisoquinolin-1-one | Int 3 + Int 20 | B | 461.5 | 462.4 |
| 168 | 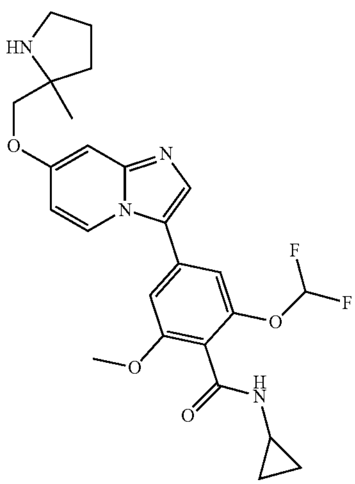 [SMILES: COc1cc(-c2cnc3cc(OCC4(C)CCCN4)ccn23)cc(OC(F)F)c1C(=O)NC1CC1] | N-cyclopropyl-2-(difluoromethoxy)-6-methoxy-4-[7-[(2-methyl pyrrolidin-2-yl)methoxy]imidazo[1,2-a]pyridin-3-yl]benzamide | Int 1 + CAS# 955029-45-5 | A | 486.5 | 487.3 |
| 169 | 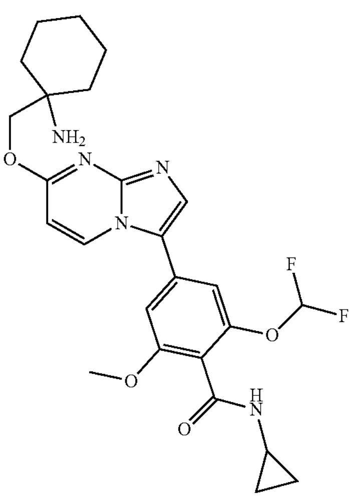 [SMILES: COc1cc(-c2cnc3nc(OCC4(N)CCCCC4)ccn23)cc(OC(F)F)c1C(=O)NC1CC1] | 4-[7-[(1-aminocyclohexyl)methoxy]imidazo[1,2-a]pyridin-3-yl]-N-cyclopropyl-2-(difluoromethoxy)-6-methoxy-benzamide | Int 1 + CAS# 4313-56-8 | A | 500.5 | 501.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 170 | 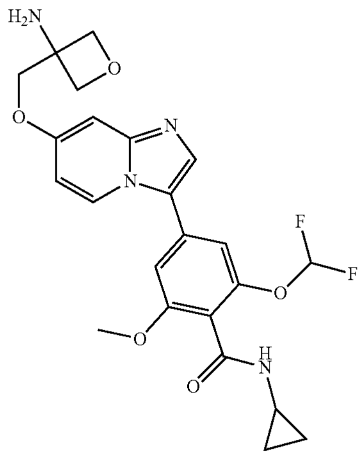 [SMILES: COc1cc(-c2cnc3cc(OCC4(N)COC4)ccn23)cc(OC(F)F)c1C(=O)NC1CC1] | 4-[7-[(3-aminooxetan-3-yl)methoxy]imidazo[1,2-a]pyridin-3-yl]-N-cyclopropyl-2-(difluoromethoxy)-6-methoxy-benzamide | Int 1 + CAS# 1305208-37-0 | A | 474.5 | 475.3 |
| 171 | 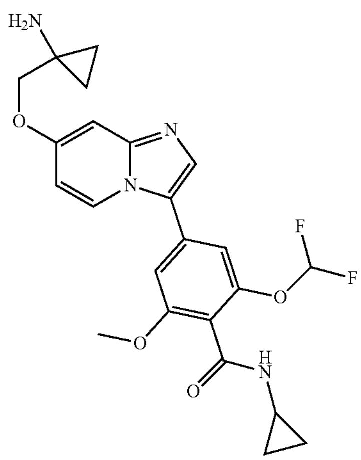 [SMILES: COc1cc(-c2cnc3cc(OCC4(N)CC4)ccn23)cc(OC(F)F)c1C(=O)NC1CC1] | 4-[7-[(1-aminocyclopropyl)methoxy]imidazo[1,2-a]pyridin-3-yl]-N-cyclopropyl-2-(difluoromethoxy)-6-methoxy-benzamide | Int 1 + CAS# 115652-52-3 | A | 458.5 | 459.3 |
| 172 | 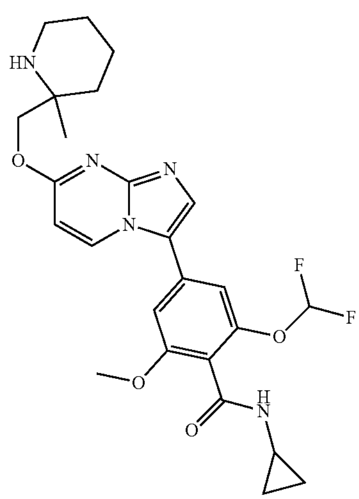 [SMILES: COc1cc(-c2cnc3nc(OCC4(C)CCCCN4)ccn23)cc(OC(F)F)c1C(=O)NC1CC1] | N-cyclopropyl-2-(difluoromethoxy)-6-methoxy-4-[7-[(2-methyl-2-piperidyl)methoxy]imidazo[1,2-a]pyridin-3-yl]benzamide | Int 1 + CAS# 1094071-26-7 | A | 500.5 | 501.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 173 | 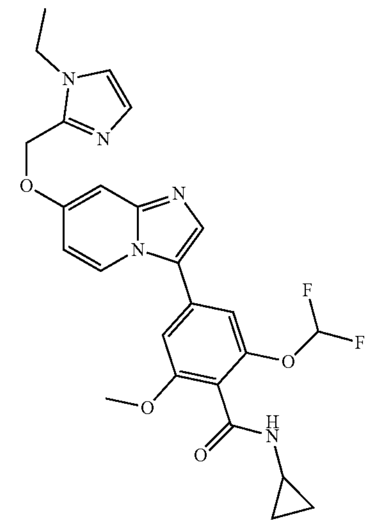 [SMILES: CCn1ccnc1COc1ccn2c(-c3cc(OC)c(C(=O)NC4CC4)c(OC(F)F)c3)cnc2c1] | N-cyclopropyl-2-(difluoromethoxy)-4-[7-[(1-ethylimidazol-2-yl)methoxy]imidazo[1,2-a]pyridin-3-yl]-6-methoxy-benzamide | Int 1 + CAS# 215872-62-1 | Ex. 2.76 | 497.5 | 498.3 |
| 174 | 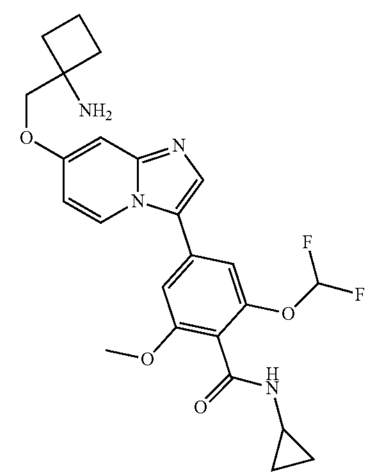 [SMILES: COc1cc(-c2cnc3cc(OCC4(N)CCC4)ccn23)cc(OC(F)F)c1C(=O)NC1CC1] | 4-[7-[(1-aminocyclobutyl)methoxy]imidazo[1,2-a]pyridin-3-yl]-N-cyclopropyl-2-(difluoromethoxy)-6-methoxy-benzamide | Int 1 + CAS# 180205-34-9 | A | 472.5 | 473.3 |
| 175 | 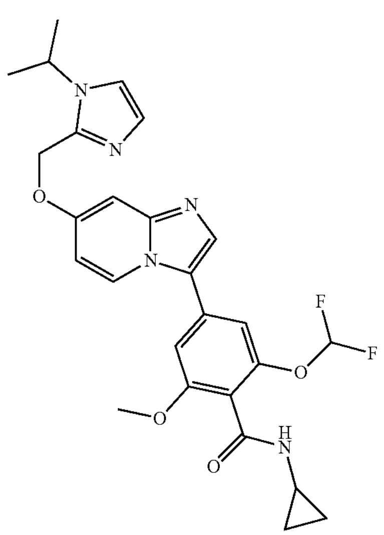 [SMILES: COc1cc(-c2cnc3cc(OCc4nccn4C(C)C)ccn23)cc(OC(F)F)c1C(=O)NC1CC1] | N-cyclopropyl-2-(difluoromethoxy)-4-[7-[(1-isopropylimidazol-2-yl)methoxy]imidazo[1,2-a]pyridin-3-yl]-6-methoxy-benzamide | Int 1 + CAS# 135205-82-2 | A | 511.5 | 512.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 176 | 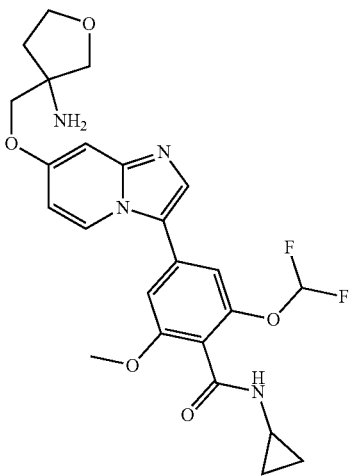 [SMILES: COc1cc(-c2cnc3cc(OCC4(N)CCOC4)ccn23)cc(OC(F)F)c1C(=O)NC1CC1] | 4-[7-[(3-amino tetrahydrofuran-3-yl)methoxy]imidazo[1,2-a]pyridin-3-yl]-N-cyclopropyl-2-(difluoromethoxy)-6-methoxy-benzamide | Int 1 + CAS# 1132878-81-9 | A | 488.5 | 489.3 |
| 177 | 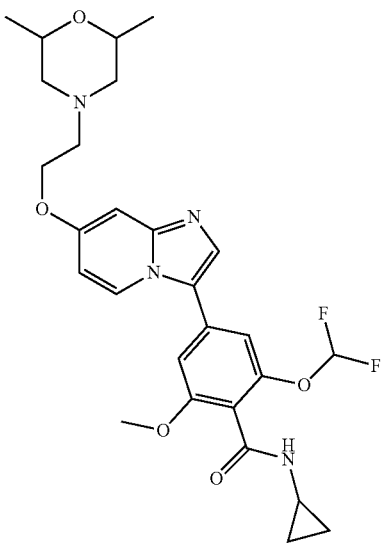 [SMILES: COc1cc(-c2cnc3cc(OCCN4CC(C)OC(C)C4)ccn23)cc(OC(F)F)c1C(=O)NC1CC1] | N-cyclopropyl-2-(difluoromethoxy)-4-[7-[2-(2,6-dimethylmorpholin-4-yl)ethoxy]imidazo[1,2-a]pyridin-3-yl]-6-methoxy-benzamide | Int 18 + CAS# 141-91-3 | I (without Et₃N) | 530.6 | 531.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 178 | 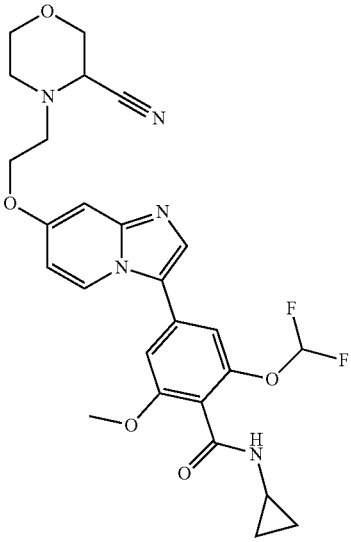 [SMILES: COc1cc(-c2cnc3cc(OCCN4CCOCC4C#N)ccn23)cc(OC(F)F)c1C(=O)NC1CC1] | 4-[7-[2-(3-cyanomorpholin-4-yl)ethoxy]imidazo[1,2-a]pyridin-3-yl]-N-cyclopropyl-2-(difluoromethoxy)-6-methoxy-benzamide | Int 18 + CAS# 97039-63-9 | I (without Et$_3$N) | 527.5 | 528.3 |
| 179 | 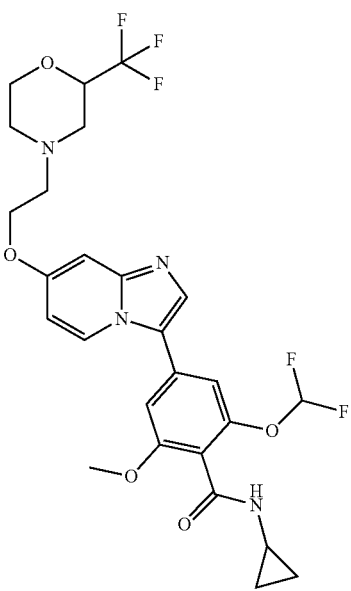 [SMILES: COc1cc(-c2cnc3cc(OCCN4CCOC(C(F)(F)F)C4)ccn23)cc(OC(F)F)c1C(=O)NC1CC1] | N-cyclopropyl-2-(difluoromethoxy)-6-methoxy-4-[7-[2-[2-(trifluoromethyl)morpholin-4-yl]ethoxy]imidazo[1,2-a]pyridin-3-yl]benzamide | Int 18 + CAS# 1196152-51-8 | I (with Et$_3$N) | 570.5 | 571.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|------|-----------|------|-----|-----|-----|----------|
| 180 | 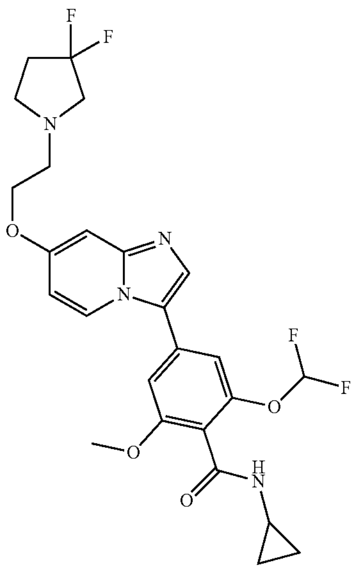 [SMILES: COc1cc(-c2cnc3cc(OCCN4CCC(F)(F)C4)ccn23)cc(OC(F)F)c1C(=O)NC1CC1] | N-cyclopropyl-2-(difluoromethoxy)-4-[7-[2-(3,3-difluoropyrrolidin-1-yl)ethoxy]imidazo[1,2-a]pyridin-3-yl]-6-methoxy-benzamide | Int 18 + CAS# 163457-23-6 | I (with Et$_3$N) | 522.5 | 523.3 |
| 181 | 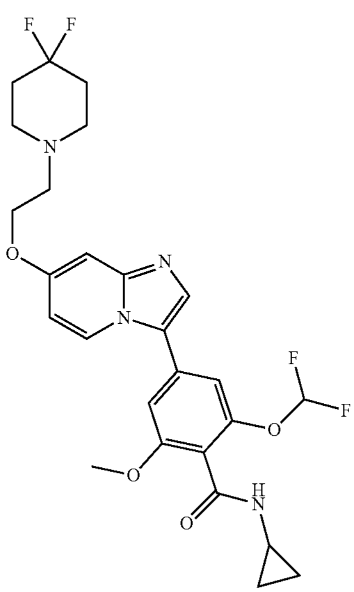 [SMILES: COc1cc(-c2cnc3cc(OCCN4CCC(F)(F)CC4)ccn23)cc(OC(F)F)c1C(=O)NC1CC1] | N-cyclopropyl-2-(difluoromethoxy)-4-[7-[2-(4,4-difluoro-1-piperidyl)ethoxy]imidazo[1,2-a]pyridin-3-yl]-6-methoxy-benzamide | Int 1 + Int 64 | Ex. 2.77 | 536.5 | 537.5 |

| Cpd# | Structure | Name | SM | Mtd | MW | MS Mes'd |
|---|---|---|---|---|---|---|
| 182 | 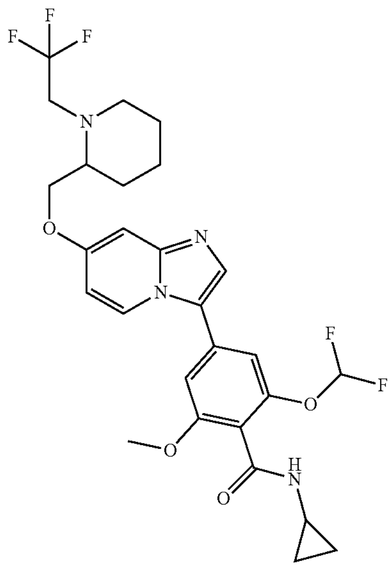 [SMILES: COc1cc(-c2cnc3cc(OCC4CCCCN4CC(F)(F)F)ccn23)cc(OC(F)F)c1C(=O)NC1CC1] | N-cyclopropyl-2-(difluoromethoxy)-6-methoxy-4-[7-[[1-(2,2,2-trifluoroethyl)-2-piperidyl]methoxy]imidazo[1,2-a]pyridin-3-yl]benzamide | Cpd 119 | Ex. 2.78 | 568.5 | 569.6 |
| 183 | 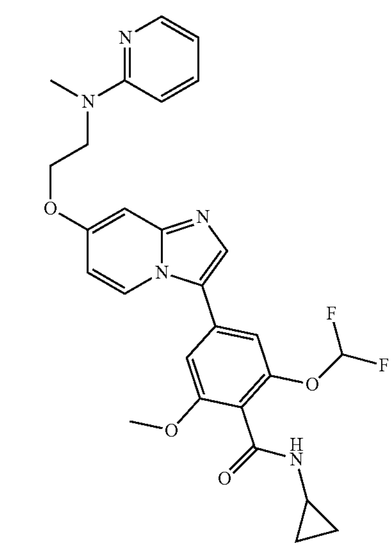 [SMILES: COc1cc(-c2cnc3cc(OCCN(C)c4ccccn4)ccn23)cc(OC(F)F)c1C(=O)NC1CC1] | N-cyclopropyl-2-(difluoromethoxy)-6-methoxy-4-[7-[2-[methyl(2-pyridyl)amino]ethoxy]imidazo[1,2-a]pyridin-3-yl]benzamide | Cpd 117 | Ex. 2.79 | 523.5 | 524.8 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 184 | 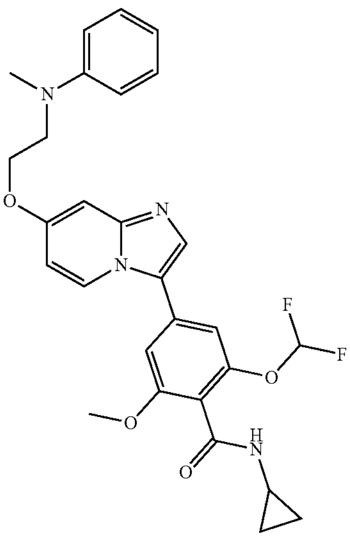 [SMILES: COc1cc(-c2cnc3cc(OCCN(C)c4ccccc4)ccn23)cc(OC(F)F)c1C(=O)NC1CC1] | N-cyclopropyl-2-(difluoromethoxy)-6-methoxy-4-[7-[2-(N-methylanilino)ethoxy]imidazo[1,2-a]pyridin-3-yl]benzamide | Cpd 117 | Ex. 2.80 | 522.5 | 523.6 |
| 185 | 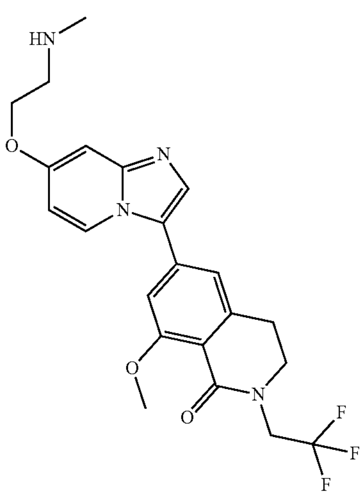 [SMILES: CNCCOc1ccn2c(-c3cc4c(c(OC)c3)C(=O)N(CC(F)(F)F)CC4)cnc2c1] | 8-methoxy-6-[7-[2-(methylamino)ethoxy]imidazo[1,2-a]pyridin-3-yl]-2-(2,2,2-trifluoroethyl)-3,4-dihydroisoquinolin-1-one | Int 2 + CAS# 109-83-1 | A | 448.4 | 449.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 186 | 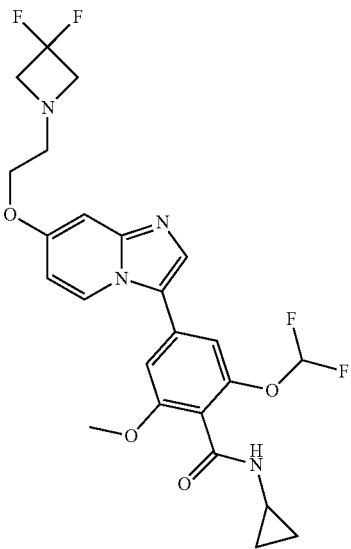 | N-cyclopropyl-4-[7-[2-(3,3-difluoro azetidin-1-yl) ethoxy]imidazo[1,2-a]pyridin-3-yl]-2-(difluoromethoxy)-6-methoxy-benzamide | Int 18 + CAS# 288315-03-7 | I (with Et₃N) | 508.5 | 509.8 |
| 187 | 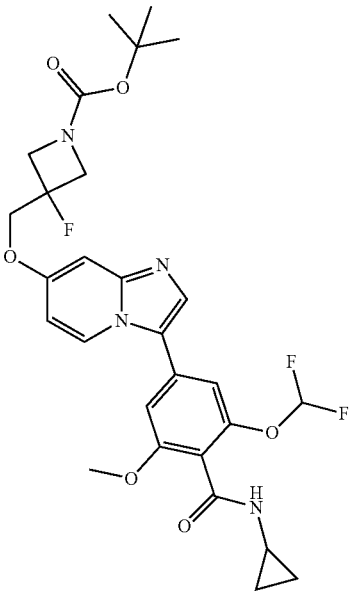 [SMILES: COc1cc(-c2cnc3cc(OCC4(F)CN(C(=O)OC(C)(C)C)C4)ccn23)cc(OC(F)F)c1C(=O)NC1CC1] | tert-butyl 3-[[3-[4-(cyclopropylcarbamoyl)-3-(difluoromethoxy)-5-methoxy-phenyl]imidazo[1,2-a]pyridin-7-yl]oxymethyl]-3-fluoro-azetidine-1-carboxylate | Int 1 + CAS# 1126650-66-5 | Ex. 2.81 | 576.6 | 577.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 188 | 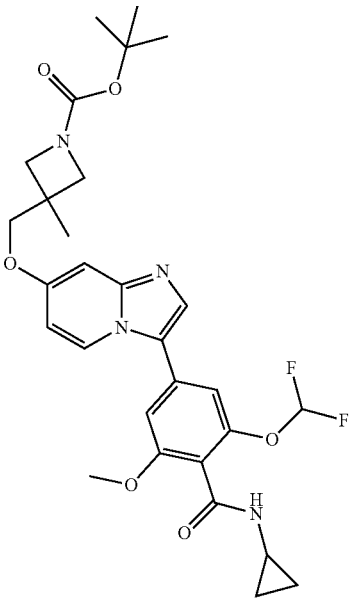 [SMILES: COc1cc(-c2cnc3cc(OCC4(C)CN(C(=O)OC(C)(C)C)C4)ccn23)cc(OC(F)F)c1C(=O)NC1CC1] | tert-butyl 3-[[3-[4-(cyclopropylcarbamoyl)-3-(difluoro methoxy)-5-methoxy-phenyl]imidazo[1,2-a]pyridin-7-yl]oxymethyl]-3-methyl-azetidine-1-carboxylate | Int 1 + CAS# 1363382-91-5 | Ex. 2.82 | 572.6 | 573.4 |
| 189 | 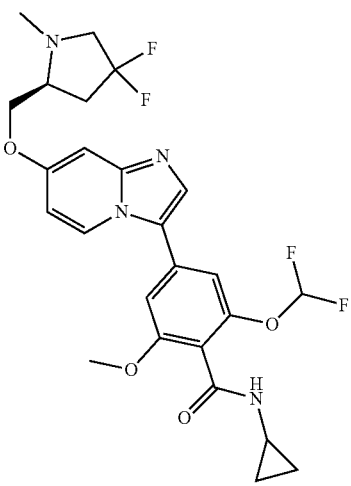 [SMILES: COc1cc(-c2cnc3cc(OC[C@@H]4CC(F)(F)CN4C)ccn23)cc(OC(F)F)c1C(=O)NC1CC1] | N-cyclopropyl-2-(difluoromethoxy)-4-[7-[[(2S)-4,4-difluoro-1-methyl-pyrrolidin-2-yl]methoxy]imidazo[1,2-a]pyridin-3-yl]-6-methoxy-benzamide | Int 1 + CAS# 1408057-44-2 | Ex. 2.83 | 522.5 | 523.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 190 | 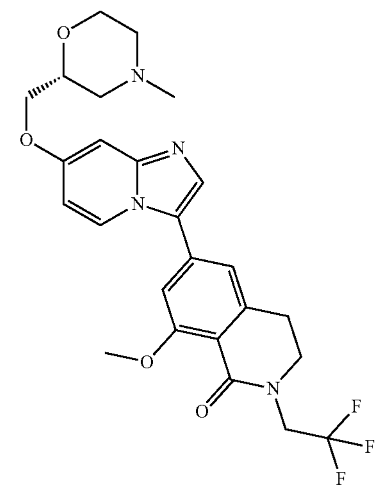 [SMILES: COc1cc(-c2cnc3cc(OC[C@H]4CN(C)CCO4)ccn23)cc2c1C(=O)N(CC(F)(F)F)CC2] | 8-methoxy-6-[7-[[(2R)-4-methyl morpholin-2-yl]methoxy]imidazo[1,2-a]pyridin-3-yl]-2-(2,2,2-trifluoroethyl)-3,4-dihydroisoquinolin-1-one | Int 2 + CAS# 1159598-35-2 | A | 504.5 | 505.5 |
| 191 | 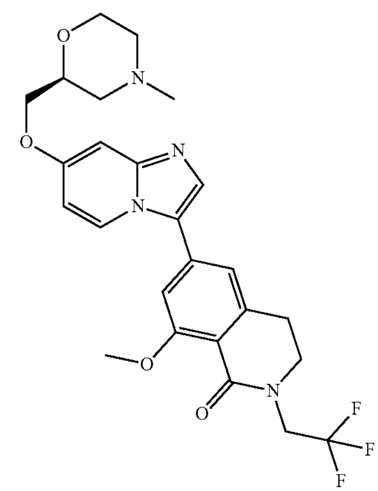 [SMILES: COc1cc(-c2cnc3cc(OC[C@@H]4CN(C)CCO4)ccn23)cc2c1C(=O)N(CC(F)(F)F)CC2] | 8-methoxy-6-[7-[[(2S)-4-methyl morpholin-2-yl]methoxy]imidazo[1,2-a]pyridin-3-yl]-2-(2,2,2-trifluoroethyl)-3,4-dihydroisoquinolin-1-one | Int 2 + CAS# 1159598-33-0 | A | 504.5 | 505.7 |
| 192 | 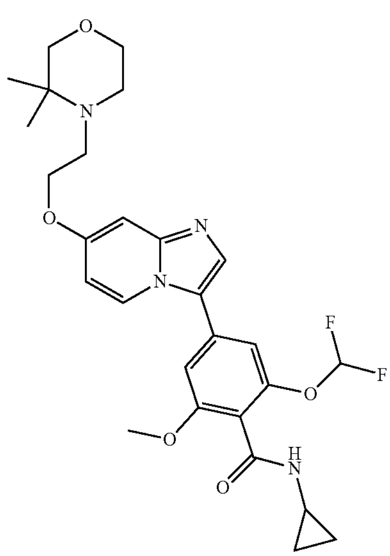 [SMILES: COc1cc(-c2cnc3cc(OCCN4CCOCC4(C)C)ccn23)cc(OC(F)F)c1C(=O)NC1CC1] | N-cyclopropyl-2-(difluoromethoxy)-4-[7-[2-(3,3-dimethylmorpholin-4-yl)ethoxy]imidazo[1,2-a]pyridin-3-yl]-6-methoxy-benzamide | Int 18 + CAS# 59229-63-9 | I (without Et₃N) | 530.6 | 531.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 193 | 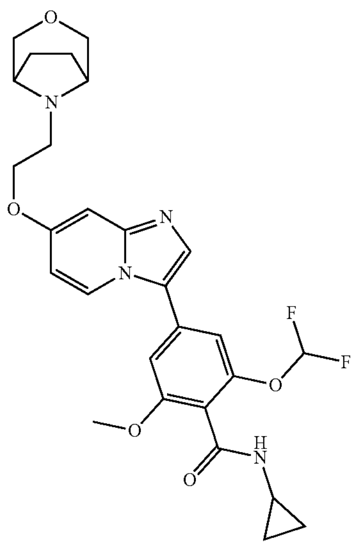 [SMILES: COc1cc(-c2cnc3cc(OCCN4C5CCC4COC5)ccn23)cc(OC(F)F)c1C(=O)NC1CC1] | N-cyclopropyl-2-(difluoromethoxy)-6-methoxy-4-[7-[2-(3-oxa-8-azabicyclo[3.2.1]octan-8-yl)ethoxy]imidazo[1,2-a]pyridin-3-yl]benzamide | Int 18 + CAS# 904316-92-3 | I (with Et$_3$N) | 528.5 | 529.4 |
| 194 | 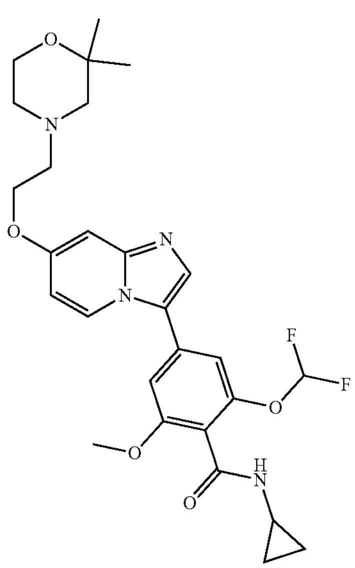 [SMILES: COc1cc(-c2cnc3cc(OCCN4CCOC(C)(C)C4)ccn23)cc(OC(F)F)c1C(=O)NC1CC1] | N-cyclopropyl-2-(difluoromethoxy)-4-[7-[2-(2,2-dimethylmorpholin-4-yl)ethoxy]imidazo[1,2-a]pyridin-3-yl]-6-methoxy-benzamide | Int 18 + CAS# 147688-58-2 | I (without Et$_3$N) | 530.6 | 531.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 195 | 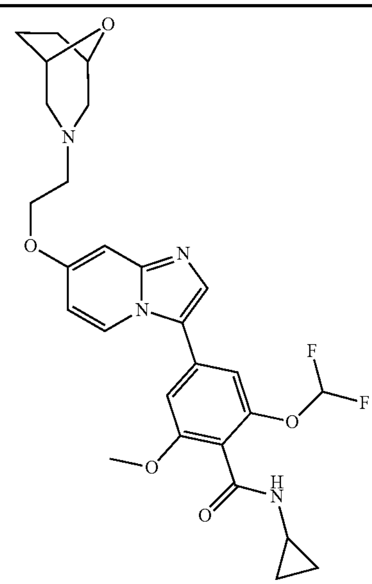 | N-cyclopropyl-2-(difluoromethoxy)-6-methoxy-4-[7-[2-(8-oxa-3-azabicyclo[3.2.1]octan-3-yl)ethoxy]imidazo[1,2-a]pyridin-3-yl]benzamide | Int 18 + CAS# 280-13-7 | I (without Et$_3$N) | 528.5 | 529.8 |
| 196 | 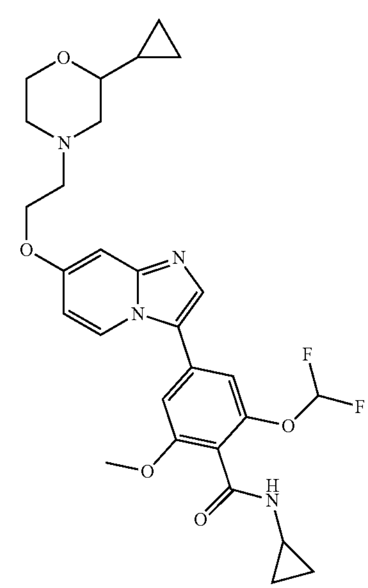 [SMILES: COc1cc(-c2cnc3cc(OCCN4CCOC(C5CC5)C4)ccn23)cc(OC(F)F)c1C(=O)NC1CC1] | N-cyclopropyl-4-[7-[2-(2-cyclopropylmorpholin-4-yl)ethoxy]imidazo[1,2-a]pyridin-3-yl]-2-(difluoromethoxy)-6-methoxy-benzamide | Int 18 + CAS# 1063734-79-1 | I (without Et$_3$N) | 542.6 | 543.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 197 | 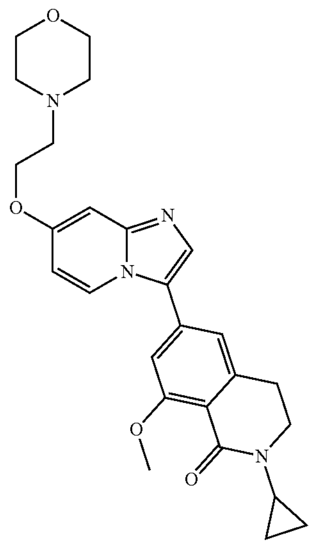 [SMILES: COc1cc(-c2cnc3cc(OCCN4CCOCC4)ccn23)cc2c1C(=O)N(C1CC1)CC2] | 2-cyclopropyl-8-methoxy-6-[7-(2-morpholinoethoxy)imidazo[1,2-a]pyridin-3-yl]-3,4-dihydroisoquinolin-1-one | Int 21 + CAS# 622-40-2 | Ex. 2.84 | 462.5 | 463.7 |
| 198 | 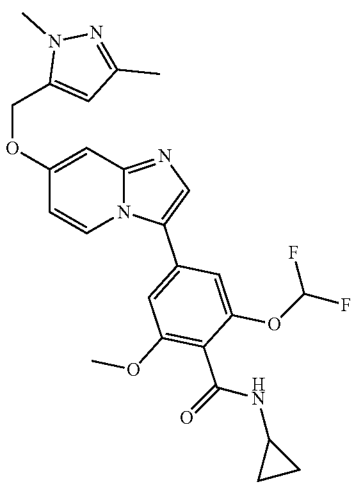 [SMILES: COc1cc(-c2cnc3cc(OCc4cc(C)nn4C)ccn23)cc(OC(F)F)c1C(=O)NC1CC1] | N-cyclopropyl-2-(difluoromethoxy)-4-[7-[(2,5-dimethylpyrazol-3-yl)methoxy]imidazo[1,2-a]pyridin-3-yl]-6-methoxy-benzamide | Int 1 + CAS# 57012-20-1 | A | 497.5 | 498.1 |
| 199 | 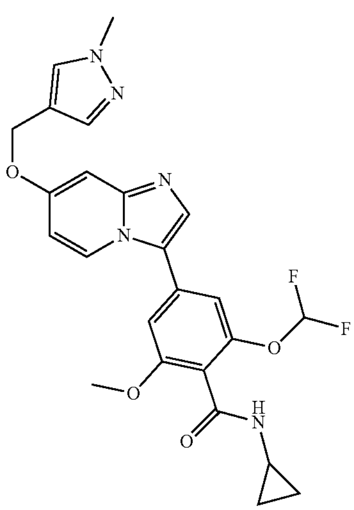 [SMILES: COc1cc(-c2cnc3cc(OCc4cnn(C)c4)ccn23)cc(OC(F)F)c1C(=O)NC1CC1] | N-cyclopropyl-2-(difluoromethoxy)-6-methoxy-4-[7-[(1-methylpyrazol-4-yl)methoxy]imidazo[1,2-a]pyridin-3-yl]benzamide | Int 1 + CAS# 112029-98-8 | A | 483.5 | 484.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|------|-----------|------|----|----|-----|----------|
| 200 | 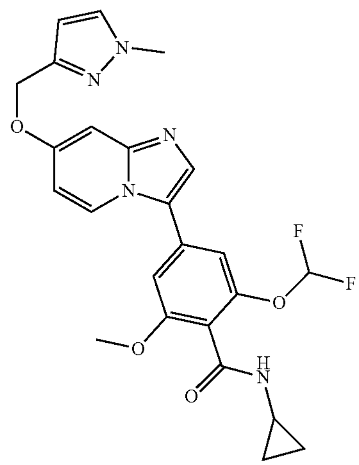 [SMILES: COc1cc(-c2cnc3cc(OCc4ccn(C)n4)ccn23)cc(OC(F)F)c1C(=O)NC1CC1] | N-cyclopropyl-2-(difluoromethoxy)-6-methoxy-4-[7-[(1-methylpyrazol-3-yl)methoxy]imidazo[1,2-a]pyridin-3-yl]benzamide | Int 1 + CAS# 84547-62-6 | A | 483.5 | 484.1 |
| 201 | 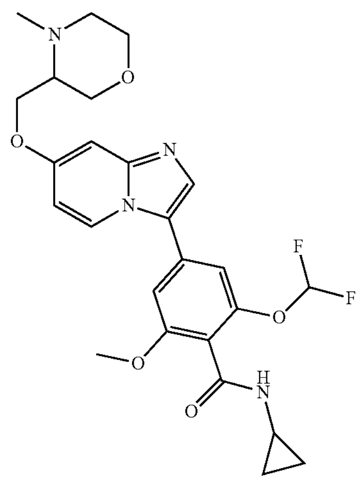 | N-cyclopropyl-2-(difluoromethoxy)-6-methoxy-4-[7-[(4-methylmorpholin-3-yl)methoxy]imidazo[1,2-a]pyridin-3-yl]benzamide | Int 1 + CAS# 1159598-86-3 | A | 502.5 | 503.1 |
| 202 | 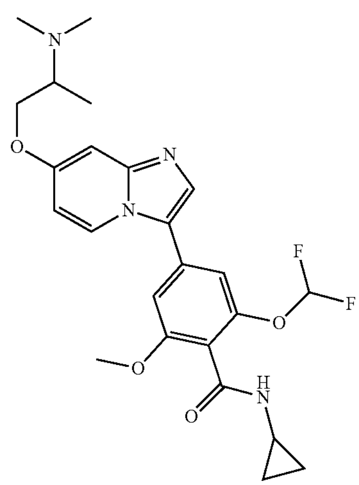 [SMILES: COc1cc(-c2cnc3cc(OCC(C)N(C)C)ccn23)cc(OC(F)F)c1C(=O)NC1CC1] | N-cyclopropyl-2-(difluoromethoxy)-4-[7-[2-(dimethylamino)propoxy]imidazo[1,2-a]pyridin-3-yl]-6-methoxy-benzamide | Int 1 + CAS# 15521-18-3 | A | 474.5 | 475.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 203 | 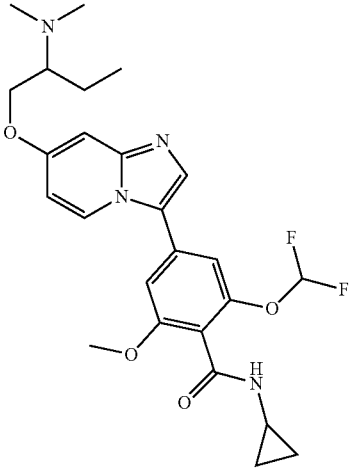 [SMILES: CCC(COc1ccn2c(-c3cc(OC)c(C(=O)NC4CC4)c(OC(F)F)c3)cnc2c1)N(C)C] | N-cyclopropyl-2-(difluoromethoxy)-4-[7-[2-(dimethylamino)butoxy imidazo[1,2-a]pyridin-3-yl]-6-methoxy-benzamide | Int 1 + CAS# 17199-17-6 | A | 488.5 | 489.1 |
| 204 | 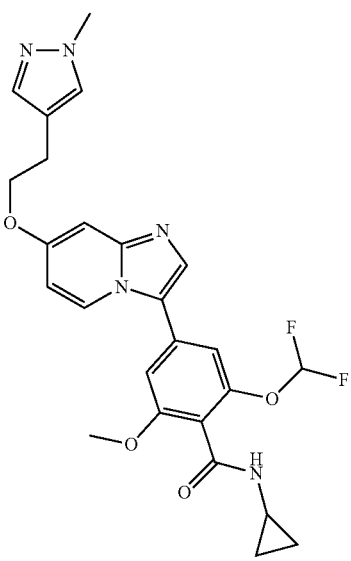 [SMILES: COc1cc(-c2cnc3cc(OCCc4cnn(C)c4)ccn23)cc(OC(F)F)c1C(=O)NC1CC1] | N-cyclopropyl-2-(difluoromethoxy)-6-methoxy-4-[7-[2-(1-methylpyrazol-4-yl)ethoxy]imidazo[1,2-a]pyridin-3-yl]benzamide | Int 1 + CAS# 176661-75-9 | A | 497.5 | 498.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 205 | 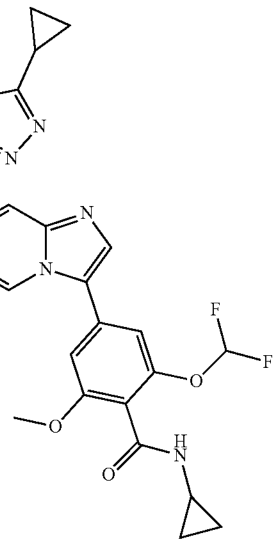 | N-cyclopropyl-4-[7-[(5-cyclopropyl-1,3,4-oxadiazol-2-yl)methoxy]imidazo[1,2-a]pyridin-3-yl]-2-(difluoromethoxy)-6-methoxy-benzamide | Int 1 + CAS# 1211144-22-7 | A | 511.5 | 512.1 |
| 206 | 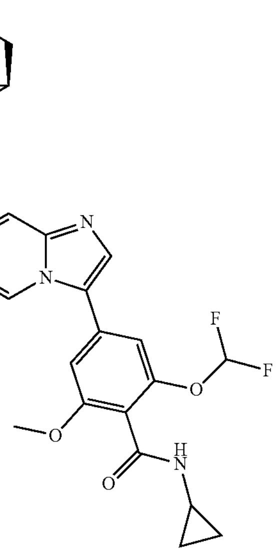 | N-cyclopropyl-2-(difluoromethoxy)-6-methoxy-4-[7-[2-[(1S,4S)-2-oxa-5-azabicyclo[2.2.1]heptan-5-yl]ethoxy]imidazo[1,2-a]pyridin-3-yl]benzamide | Int 18 + CAS# 547716-11-0 | I (without Et₃N) | 514.5 | 515.8 |
| 207 | 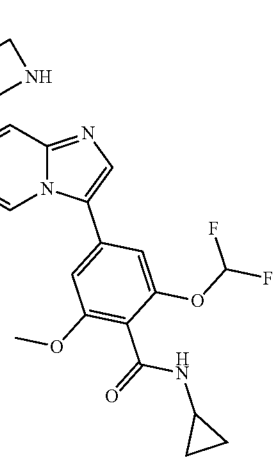 | N-cyclopropyl-2-(difluoromethoxy)-4-[7-[(3-fluoroazetidin-3-yl)methoxy]imidazo[1,2-a]pyridin-3-yl]-6-methoxy-benzamide | Cpd 187 | K | 476.4 | 477.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 208 | 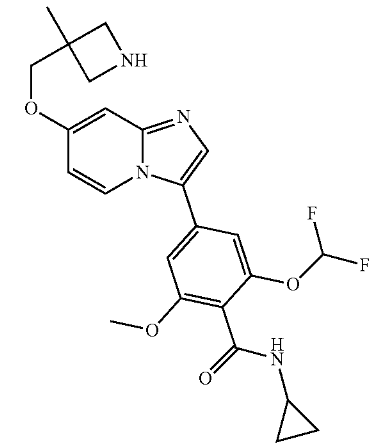 [SMILES: COc1cc(-c2cnc3cc(OCC4(C)CNC4)ccn23)cc(OC(F)F)c1C(=O)NC1CC1] | N-cyclopropyl-2-(difluoromethoxy)-6-methoxy-4-[7-[(3-methylazetidin-3-yl)methoxy]imidazo[1,2-a]pyridin-3-yl]benzamide | Cpd 188 | K | 472.5 | 473.1 |
| 209 | 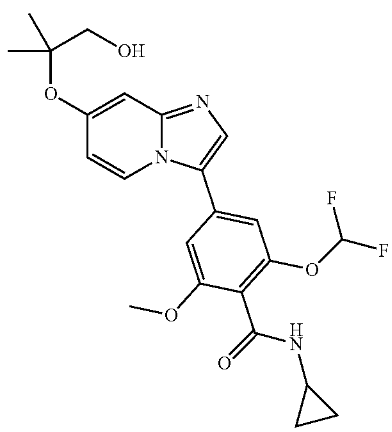 [SMILES: COc1cc(-c2cnc3cc(OC(C)(C)CO)ccn23)cc(OC(F)F)c1C(=O)NC1CC1] | N-cyclopropyl-2-(difluoromethoxy)-4-[7-(2-hydroxy-1,1-dimethyl-ethoxy)imidazo[1,2-a]pyridin-3-yl]-6-methoxy-benzamide | Int 73 | Ex. 2.85 | 461.5 | 462.6 |
| 210 | 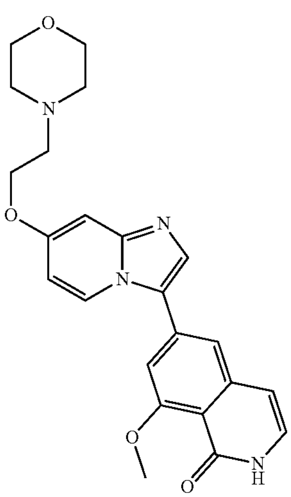 [SMILES: COc1cc(-c2cnc3cc(OCCN4CCOCC4)ccn23)cc2cc[nH]c(=O)c12] | 8-methoxy-6-[7-(2-morpholinoethoxy)imidazo[1,2-a]pyridin-3-yl]-2H-isoquinolin-1-one | Int 22 + CAS# 622-40-2 | A | 420.5 | 421.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 211 | 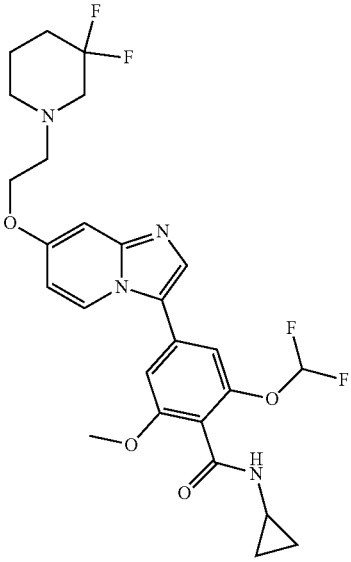 [SMILES: COc1cc(-c2cnc3cc(OCCN4CCCC(F)(F)C4)ccn23)cc(OC(F)F)c1C(=O)NC1CC1] | N-cyclopropyl-2-(difluoromethoxy)-4-[7-[2-(3,3-difluoro-1-piperidyl)ethoxy]imidazo[1,2-a]pyridin-3-yl]-6-methoxy-benzamide | Int 18 + CAS# 363179-66-2 | I (without Et₃N) | 536.5 | 537.6 |
| 212 | 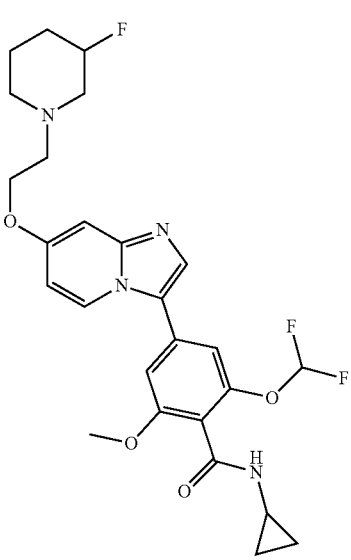 [SMILES: COc1cc(-c2cnc3cc(OCCN4CCCC(F)C4)ccn23)cc(OC(F)F)c1C(=O)NC1CC1] | N-cyclopropyl-2-(difluoromethoxy)-4-[7-[2-(3-fluoro-1-piperidyl)ethoxy]imidazo[1,2-a]pyridin-3-yl]-6-methoxy-benzamide | Int 18 + CAS# 116574-75-5 | I (without Et₃N) | 518.5 | 519.8 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 213 | 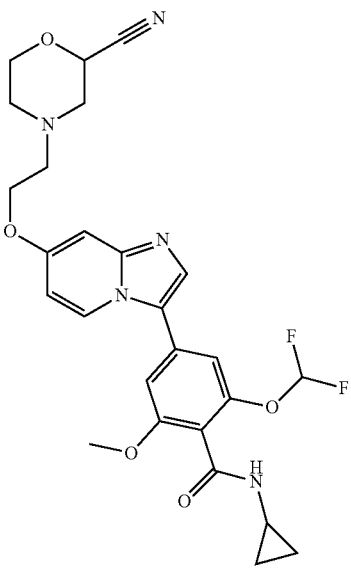 [SMILES: COc1cc(-c2cnc3cc(OCCN4CCOC(C#N)C4)ccn23)cc(OC(F)F)c1C(=O)NC1CC1] | 4-[7-[2-(2-cyanomorpholin-4-yl)ethoxy]imidazo[1,2-a]pyridin-3-yl]-N-cyclopropyl-2-(difluoromethoxy)-6-methoxy-benzamide | Int 18 + CAS# 135782-24-0 | I (without Et₃N) | 527.5 | 528.4 |
| 214 | 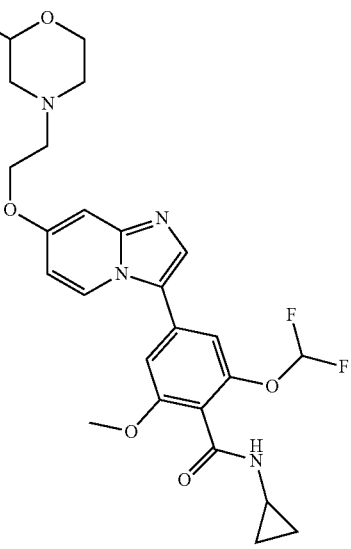 | N-cyclopropyl-2-(difluoromethoxy)-6-methoxy-4-[7-[2-(2-methylmorpholin-4-yl)ethoxy]imidazo[1,2-a]pyridin-3-yl]benzamide | Int 18 + CAS# 27550-90-9 | I (without Et₃N) | 516.5 | 517.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 215 | 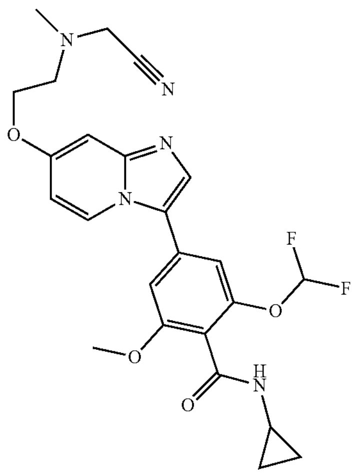 [SMILES: COc1cc(-c2cnc3cc(OCCN(C)CC#N)ccn23)cc(OC(F)F)c1C(=O)NC1CC1] | 4-[7-[2-[cyanomethyl(methyl)amino]ethoxy]imidazo[1,2-a]pyridin-3-yl]-N-cyclopropyl-2-(difluoromethoxy)-6-methoxy-benzamide | Int 18 + CAS# 5616-32-0 | I (without Et$_3$N) | 485.5 | 486.4 |
| 216 | 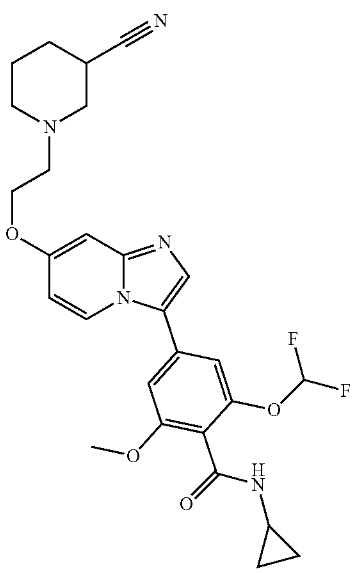 | 4-[7-[2-(3-cyano-1-piperidyl)ethoxy]imidazo[1,2-a]pyridin-3-yl]-N-cyclopropyl-2-(difluoromethoxy)-6-methoxy-benzamide | Int 18 + CAS# 828300-57-8 | I (without Et$_3$N) | 525.5 | 526.9 |
| 217 | 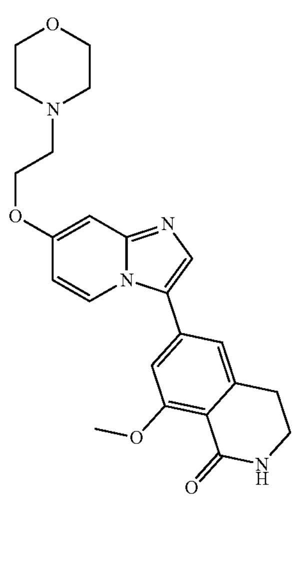 [SMILES: COc1cc(-c2cnc3cc(OCCN4CCOCC4)ccn23)cc2c1C(=O)NCC2] | 8-methoxy-6-[7-(2-morpholinoethoxy)imidazo[1,2-a]pyridin-3-yl]-3,4-dihydro-2H-isoquinolin-1-one | Int 23 + CAS# 622-40-2 | Ex. 2.86 | 422.5 | 423.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 218 | 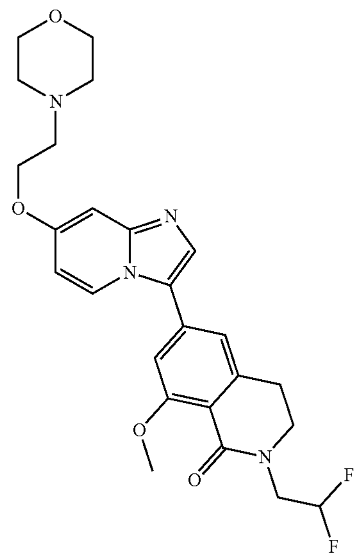 [SMILES: COc1cc(-c2cnc3cc(OCCN4CCOCC4)ccn23)cc2c1C(=O)N(CC(F)F)CC2] | 2-(2,2-difluoroethyl)-8-methoxy-6-[7-(2-morpholinoethoxy)imidazo[1,2-a]pyridin-3-yl]-3,4-dihydroisoquinolin-1-one | Int 24 + CAS# 622-40-2 | A | 486.5 | 485.3 |
| 219 | 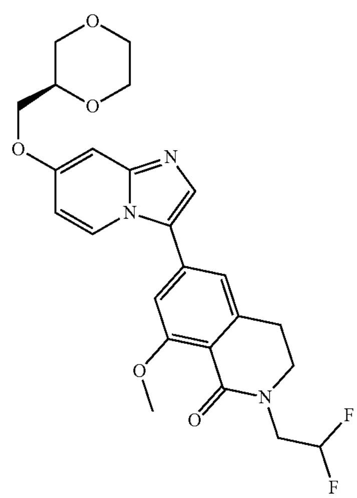 [SMILES: COc1cc(-c2cnc3cc(OC[C@H]4COCCO4)ccn23)cc2c1C(=O)N(CC(F)F)CC2] | 2-(2,2-difluoroethyl)-6-[7-[[(2R)-1,4-dioxan-2-yl]methoxy]imidazo[1,2-a]pyridin-3-yl]-8-methoxy-3,4-dihydroisoquinolin-1-one | Int 24 + CAS# 406913-93-7 | A | 473.5 | 474.4 |
| 220 | 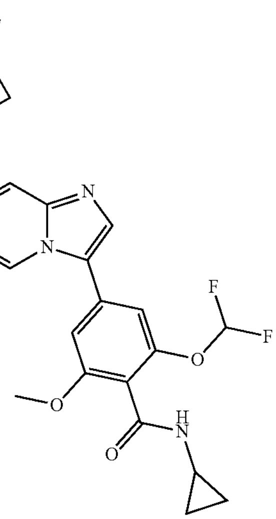 | N-cyclopropyl-2-(difluoromethoxy)-4-[7-[(1,3-dimethylazetidin-3-yl)methoxy]imidazo[1,2-a]pyridin-3-yl]-6-methoxy-benzamide | Cpd 208 | J | 486.5 | 487.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 221 | 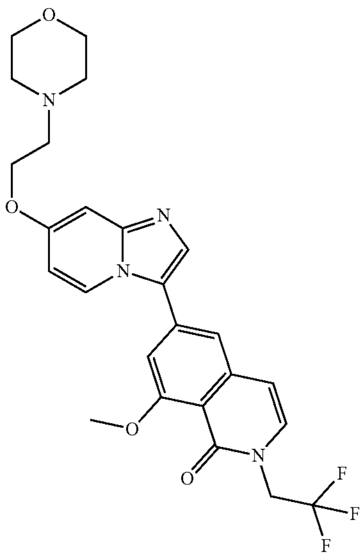 [SMILES: COc1cc(-c2cnc3cc(OCCN4CCOCC4)ccn23)cc2ccn(CC(F)(F)F)c(=O)c12] | 8-methoxy-6-[7-(2-morpholinoethoxy)imidazo[1,2-a]pyridin-3-yl]-2-(2,2,2-trifluoroethyl)isoquinolin-1-one | Int 25 + Int 26 | Ex. 2.87 | 502.5 | 503.9 |
| 222 | 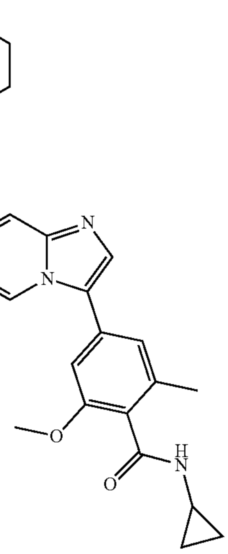 | N-cyclopropyl-2-methoxy-6-methyl-4-[7-(2-morpholinoethoxy)imidazo[1,2-a]pyridin-3-yl]benzamide | Int 27 + CAS# 622-40-2 | A | 450.5 | 451.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 223 | 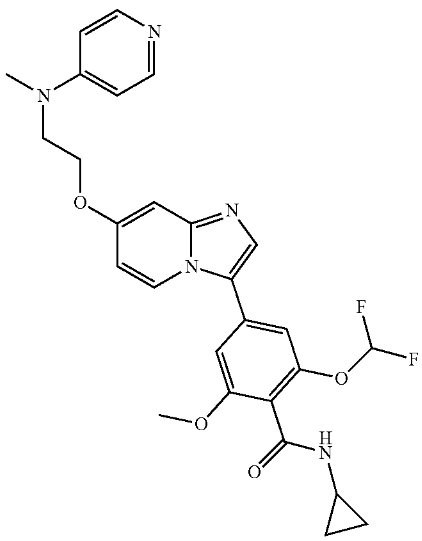 [SMILES: COc1cc(-c2cnc3cc(OCCN(C)c4ccncc4)ccn23)cc(OC(F)F)c1C(=O)NC1CC1] | N-cyclopropyl-2-(difluoromethoxy)-6-methoxy-4-[7-[2-[methyl(4-pyridyl)amino]ethoxy]imidazo[1,2-a]pyridin-3-yl]benzamide | Int 1 + Int 76 | A | 523.5 | 524.8 |
| 224 | 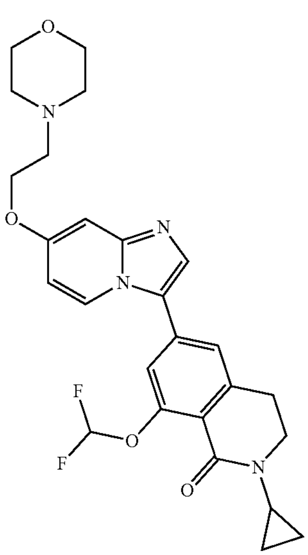 [SMILES: O=C1c2c(cc(-c3cnc4cc(OCCN5CCOCC5)ccn34)cc2OC(F)F)CCN1C1CC1] | 2-cyclopropyl-8-(difluoromethoxy)-6-[7-(2-morpholinoethoxy)imidazo[1,2-a]pyridin-3-yl]-3,4-dihydroisoquinolin-1-one | Int 25 + Int 28 | Ex. 2.88 | 498.5 | 499.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 225 | 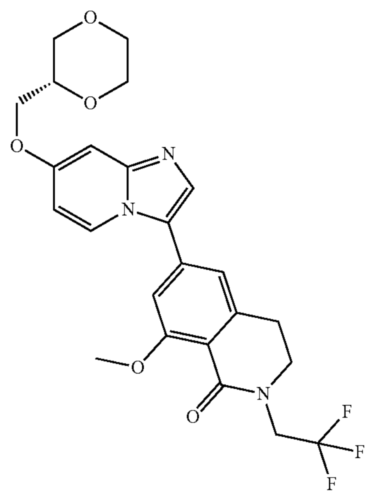 [SMILES: COc1cc(-c2cnc3cc(OC[C@@H]4COCCO4)ccn23)cc2c1C(=O)N(CC(F)(F)F)CC2] | 6-[7-[[(2S)-1,4-dioxan-2-yl]methoxy]imidazo[1,2-a]pyridin-3-yl]-8-methoxy-2-(2,2,2-trifluoroethyl)-3,4-dihydroisoquinolin-1-one | Int 2 + CAS# 406913-88-0 | A | 491.5 | 492.5 |
| 226 | 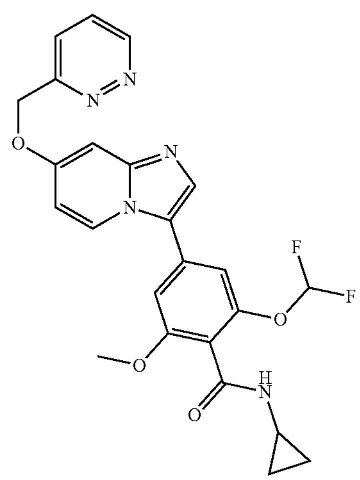 [SMILES: COc1cc(-c2cnc3cc(OCc4cccnn4)ccn23)cc(OC(F)F)c1C(=O)NC1CC1] | N-cyclopropyl-2-(difluoromethoxy)-6-methoxy-4-[7-(pyridazin-3-ylmethoxy)imidazo[1,2-a]pyridin-3-yl]benzamide | Int 1 + CAS# 37444-46-5 | A | 481.5 | 485.5 |
| 227 | 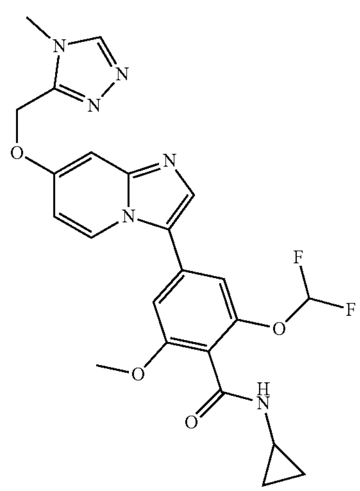 | N-cyclopropyl-2-(difluoromethoxy)-6-methoxy-4-[7-[(4-methyl-1,2,4-triazol-3-yl)methoxy]imidazo[1,2-a]pyridin-3-yl]benzamide | Int 1 + CAS# 59660-30-9 | A | 484.5 | 503.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 228 | 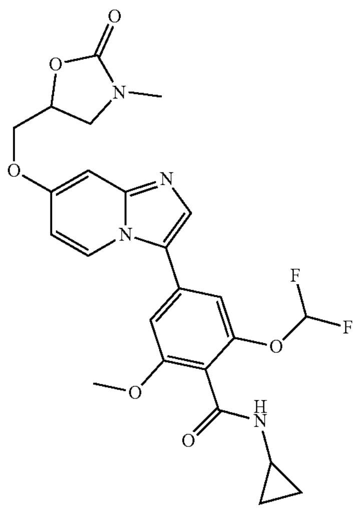 [SMILES: COc1cc(-c2cnc3cc(OCC4CN(C)C(=O)O4)ccn23)cc(OC(F)F)c1C(=O)NC1CC1] | N-cyclopropyl-2-(difluoromethoxy)-6-methoxy-4-[7-[(3-methyl-2-oxo-oxazolidin-5-yl)methoxy]imidazo[1,2-a]pyridin-3-yl]benzamide | Int 1 + CAS# 97899-29-1 | A | 502.5 | 503.4 |
| 229 | 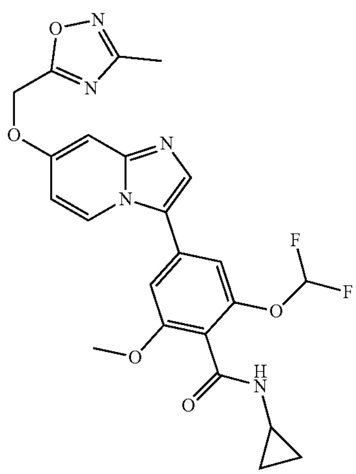 [SMILES: COc1cc(-c2cnc3cc(OCc4nc(C)no4)ccn23)cc(OC(F)F)c1C(=O)NC1CC1] | N-cyclopropyl-2-(difluoromethoxy)-6-methoxy-4-[7-[(3-methyl-1,2,4-oxadiazol-5-yl)methoxy]imidazo[1,2-a]pyridin-3-yl]benzamide | Int 1 + CAS# 112960-56-2 | A | 485.4 | 484.3 |
| 230 | 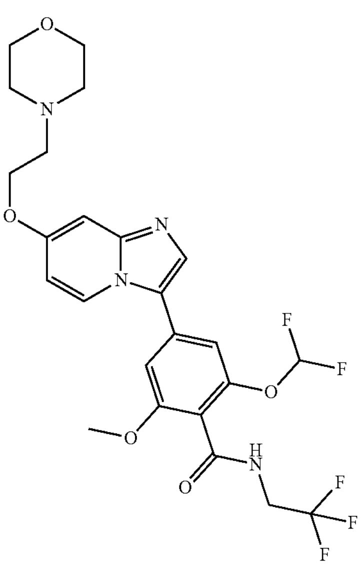 [SMILES: COc1cc(-c2cnc3cc(OCCN4CCOCC4)ccn23)cc(OC(F)F)c1C(=O)NCC(F)(F)F] | 2-(difluoromethoxy)-6-methoxy-4-[7-(2-morpholinoethoxy)imidazo[1,2-a]pyridin-3-yl]-N-(2,2,2-trifluoroethyl)benzamide | Int 25 + Int 19 | B | 544.5 | 545.7 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 231 | 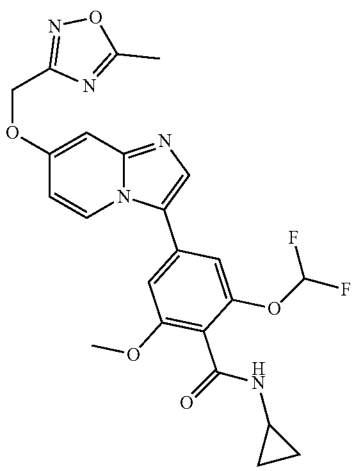 [SMILES: COc1cc(-c2cnc3cc(OCc4noc(C)n4)ccn23)cc(OC(F)F)c1C(=O)NC1CC1] | N-cyclopropyl-2-(difluoromethoxy)-6-methoxy-4-[7-[(5-methyl-1,2,4-oxadiazol-3-yl)methoxy]imidazo[1,2-a]pyridin-3-yl]benzamide | Int 1 + CAS# 25977-23-5 | A | 485.4 | 486.3 |
| 232 | 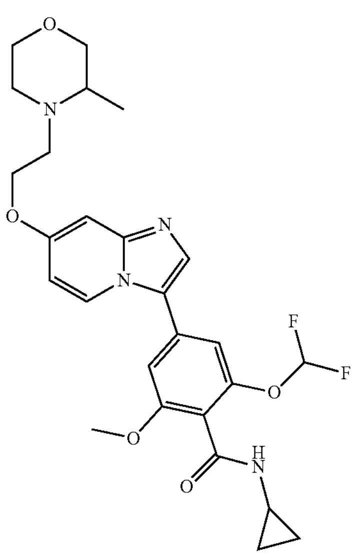 [SMILES: COc1cc(-c2cnc3cc(OCCN4CCOCC4C)ccn23)cc(OC(F)F)c1C(=O)NC1CC1] | N-cyclopropyl-2-(difluoromethoxy)-6-methoxy-4-[7-[2-(3-methylmorpholin-4-yl)ethoxy]imidazo[1,2-a]pyridin-3-yl]benzamide | Int 18 + CAS# 192661-47-5 | I (with Et$_3$N) | 516.5 | 518.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 233 | 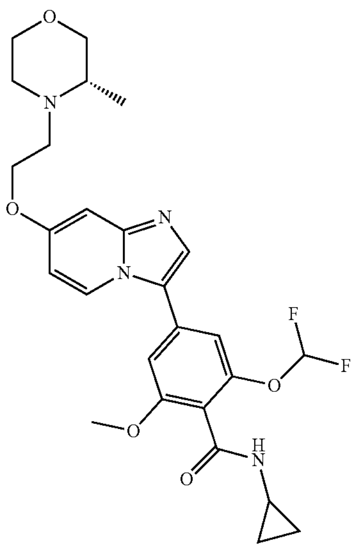 [SMILES: COc1cc(-c2cnc3cc(OCCN4CCOC[C@@H]4C)ccn23)cc(OC(F)F)c1C(=O)NC1CC1] | N-cyclopropyl-2-(difluoromethoxy)-6-methoxy-4-[7-[2-[(3S)-3-methylmorpholin-4-yl]ethoxy]imidazo[1,2-a]pyridin-3-yl]benzamide | Int 18 + CAS# 1022094-03-6 | I (with Et$_3$N) | 516.5 | 517.6 |
| 234 | 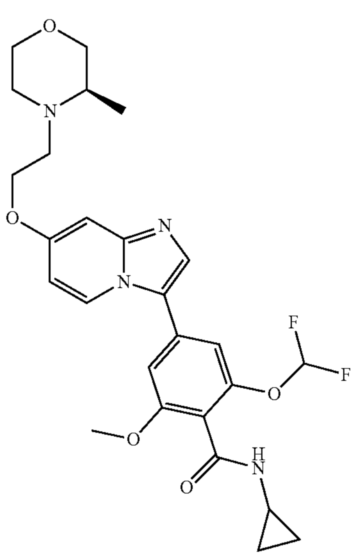 [SMILES: COc1cc(-c2cnc3cc(OCCN4CCOC[C@H]4C)ccn23)cc(OC(F)F)c1C(=O)NC1CC1] | N-cyclopropyl-2-(difluoromethoxy)-6-methoxy-4-[7-[2-[(3R)-3-methylmorpholin-4-yl]ethoxy]imidazo[1,2-a]pyridin-3-yl]benzamide | Int 18 + CAS# 953780-78-4 | I (with Et$_3$N) | 516.5 | 511.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 235 | 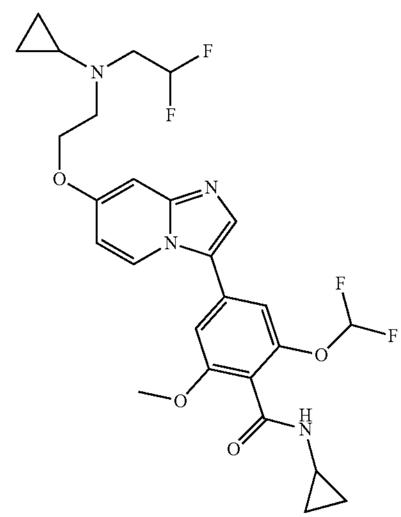 [SMILES: COc1cc(-c2cnc3cc(OCCN(CC(F)F)C4CC4)ccn23)cc(OC(F)F)c1C(=O)NC1CC1] | N-cyclopropyl-4-[7-[2-[cyclopropyl(2,2-difluoroethyl)amino]ethoxy]imidazo[1,2-a]pyridin-3-yl]-2-(difluoromethoxy)-6-methoxy-benzamide | Int 18 + CAS# 1010097-90-1 | I (with Et$_3$N) | 536.5 | 537.8 |
| 236 | 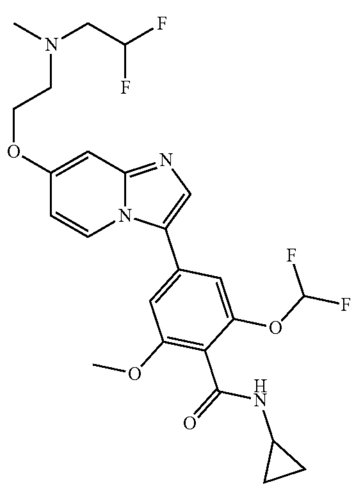 [SMILES: COc1cc(-c2cnc3cc(OCCN(C)CC(F)F)ccn23)cc(OC(F)F)c1C(=O)NC1CC1] | N-cyclopropyl-4-[7-[2-[2,2-difluoroethyl(methyl)amino]ethoxy]imidazo[1,2-a]pyridin-3-yl]-2-(difluoromethoxy)-6-methoxy-benzamide | Int 18 + CAS# 139364-36-6 | I (with Et$_3$N) | 510.5 | 511.7 |
| 237 | 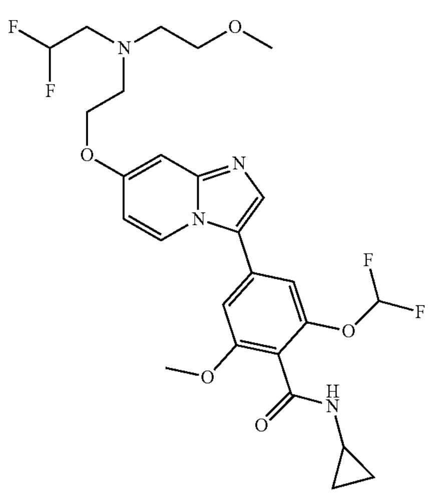 [SMILES: COCCN(CCOc1ccn2c(-c3cc(OC)c(C(=O)NC4CC4)c(OC(F)F)c3)cnc2c1)CC(F)F] | N-cyclopropyl-4-[7-[2-[2,2-difluoroethyl(2-methoxyethyl)amino]ethoxy]imidazo[1,2-a]pyridin-3-yl]-2-(difluoromethoxy)-6-methoxy-benzamide | Int 18 + CAS# 1240526-12-8 | I (with Et$_3$N) | 554.5 | 555.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 238 | 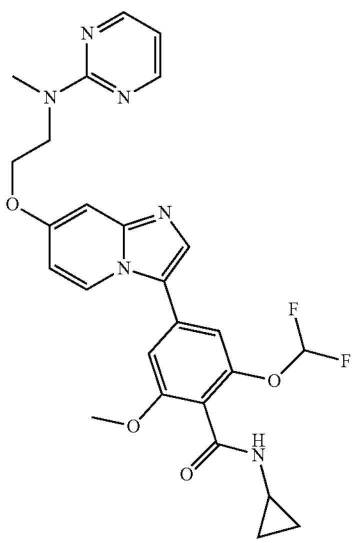 [SMILES: COc1cc(-c2cnc3cc(OCCN(C)c4ncccn4)ccn23)cc(OC(F)F)c1C(=O)NC1CC1] | N-cyclopropyl-2-(difluoromethoxy)-6-methoxy-4-[7-[2-[methyl(pyrimidin-2-yl)amino]ethoxy]imidazo[1,2-a]pyridin-3-yl]benzamide | Int 1 + Int 77 | A | 524.5 | 525.8 |
| 239 | 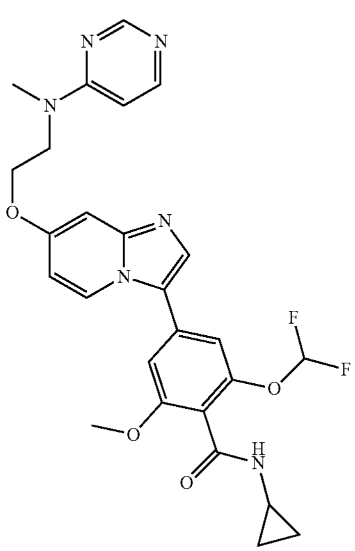 [SMILES: COc1cc(-c2cnc3cc(OCCN(C)c4ccncn4)ccn23)cc(OC(F)F)c1C(=O)NC1CC1] | N-cyclopropyl-2-(difluoromethoxy)-6-methoxy-4-[7-[2-[methyl(pyrimidin-4-yl)amino]ethoxy]imidazo[1,2-a]pyridin-3-yl]benzamide | Int 1 + Int 78 | A | 524.5 | 525.8 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 240 | 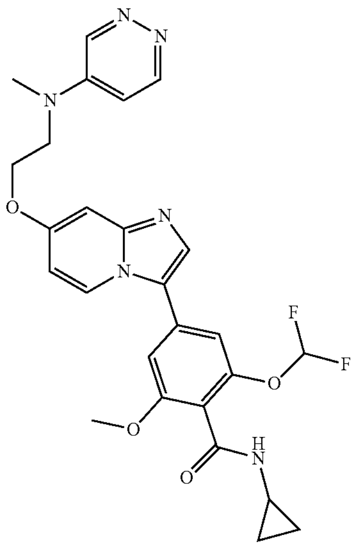 [SMILES: COc1cc(-c2cnc3cc(OCCN(C)c4ccnnc4)ccn23)cc(OC(F)F)c1C(=O)NC1CC1] | N-cyclopropyl-2-(difluoromethoxy)-6-methoxy-4-[7-[2-[methyl(pyridazin-4-yl)amino]ethoxy]imidazo[1,2-a]pyridin-3-yl]benzamide | Int 1 + Int 80 | A | 524.5 | 525.8 |
| 241 | 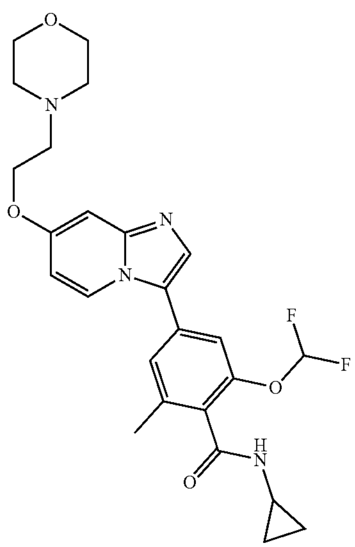 [SMILES: Cc1cc(-c2cnc3cc(OCCN4CCOCC4)ccn23)cc(OC(F)F)c1C(=O)NC1CC1] | N-cyclopropyl-2-(difluoromethoxy)-6-methyl-4-[7-(2-morpholinoethoxy)imidazo[1,2-a]pyridin-3-yl]benzamide | Int 25 + Int 29 | A | 486.5 | 487.3 |
| 242 | 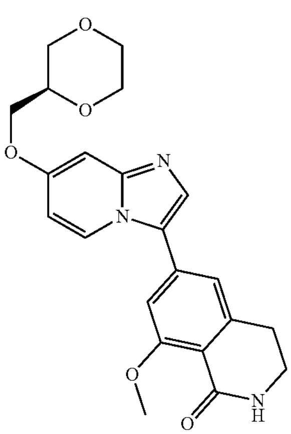 [SMILES: COc1cc(-c2cnc3cc(OC[C@H]4COCCO4)ccn23)cc2c1C(=O)NCC2] | 6-[7-[[(2R)-1,4-dioxan-2-yl]methoxy]imidazo[1,2-a]pyridin-3-yl]-8-methoxy-3,4-dihydro-2H-isoquinolin-1-one | Int 23 + CAS# 406913-93-7 | A | 409.4 | 410.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 243 | 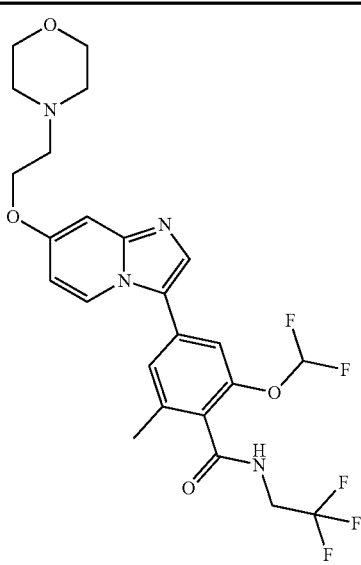 | 2-(difluoromethoxy)-6-methyl-4-[7-(2-morpholinoethoxy)imidazo[1,2-a]pyridin-3-yl]-N-(2,2,2-trifluoroethyl)benzamide | Int 30 + CAS# 622-40-2 | A | 528.5 | 529.3 |
| 244 | 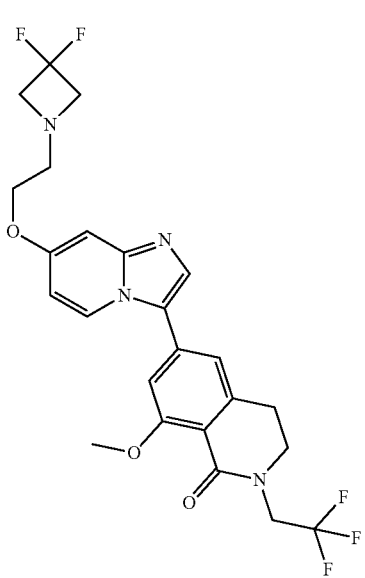 [SMILES: COc1cc(-c2cnc3cc(OCCN4CC(F)(F)C4)ccn23)cc2c1C(=O)N(CC(F)(F)F)CC2] | 6-[7-[2-(3,3-difluoroazetidin-1-yl)ethoxy]imidazo[1,2-a]pyridin-3-yl]-8-methoxy-2-(2,2,2-trifluoroethyl)-3,4-dihydroisoquinolin-1-one | Int 31 + CAS# 288315-03-7 | I (with Et$_3$N) | 510.5 | 511.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 245 | 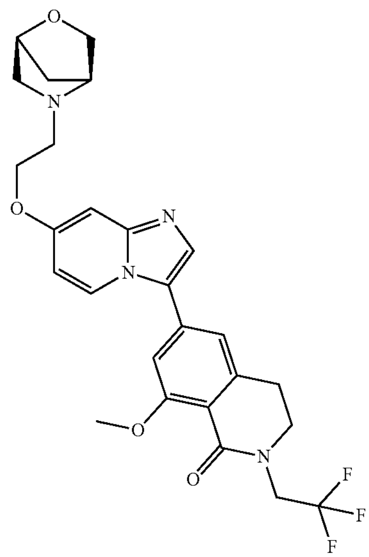 [SMILES: COc1cc(-c2cnc3cc(OCCN4C[C@@H]5C[C@H]4CO5)ccn23)cc2c1C(=O)N(CC(F)(F)F)CC2] | 8-methoxy-6-[7-[2-[(1S,4S)-2-oxa-5-azabicyclo[2.2.1]heptan-5-yl]ethoxy]imidazo[1,2-a]pyridin-3-yl]-2-(2,2,2-trifluoroethyl)-3,4-dihydroisoquinolin-1-one | Int 31 + CAS# 31560-06-2 | I (with Et₃N) | 516.5 | 517.3 |
| 246 | 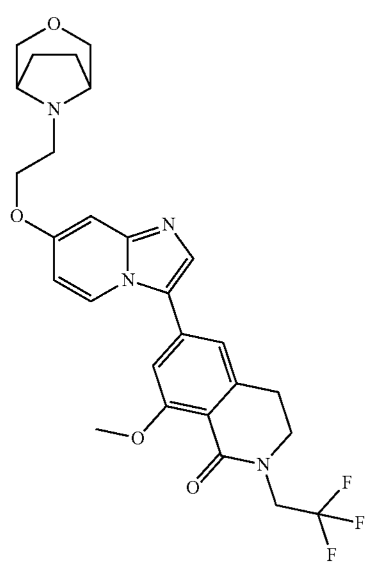 [SMILES: COc1cc(-c2cnc3cc(OCCN4C5CCC4COC5)ccn23)cc2c1C(=O)N(CC(F)(F)F)CC2] | 8-methoxy-6-[7-[2-(3-oxa-8-azabicyclo[3.2.1]octan-8-yl)ethoxy]imidazo[1,2-a]pyridin-3-yl]-2-(2,2,2-trifluoroethyl)-3,4-dihydroisoquinolin-1-one | Int 31 + CAS# 904316-92-3 | I (with Et₃N) | 530.5 | 531.5 |

US 12,264,156 B2

503                                                                                                                                      504

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|------|-----------|------|----|----|-----|----------|
| 247 | 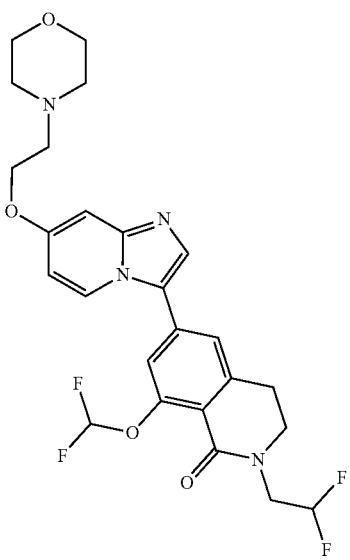 [SMILES: O=C1c2c(cc(-c3cnc4cc(OCCN5CCOCC5)ccn34)cc2OC(F)F)CCN1CC(F)F] | 2-(2,2-difluoro ethyl)-8-(difluoro methoxy)-6-[7-(2-morpholinoethoxy) imidazo[1,2-a]pyridin-3-yl]-3,4-dihydroisoquinolin-1-one | Int 32 + CAS# 622-40-2 | Ex. 2.89 | 522.5 | 523.3 |
| 248 | 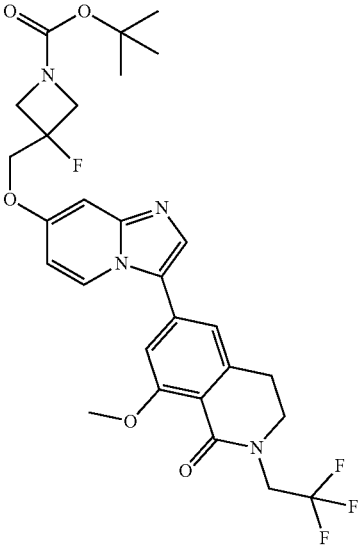 [SMILES: COc1cc(-c2cnc3cc(OCC4(F)CN(C(=O)OC(C)(C)C)C4)ccn23)cc2c1C(=O)N(CC(F)(F)F)CC2] | tert-butyl 3-fluoro-3-[[3-[8-methoxy-1-oxo-2-(2,2,2-trifluoroethyl)-3,4-dihydroisoquinolin-6-yl]imidazo[1,2-a]pyridin-7-yl]oxy methyl]azetidine-1-carboxylate | Int 2 + CAS# 1126650-66-5 | A | 578.6 | 579.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 249 | 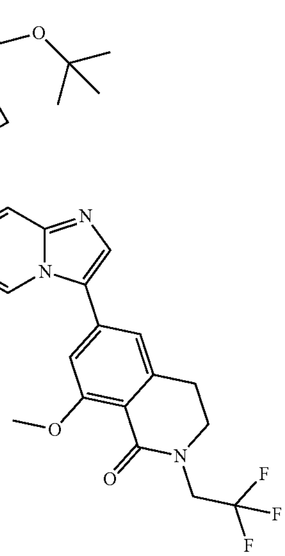 | tert-butyl 3-[[3-[8-methoxy-1-oxo-2-(2,2,2-trifluoro ethyl)-3,4-dihydro isoquinolin-6-yl] imidazo[1,2-a] pyridin-7-yl] oxymethyl]-3-methyl-azetidine-1-carboxylate | Int 2 + CAS# 1363382-91-5 | A | 574.6 | 575.4 |
| 250 | 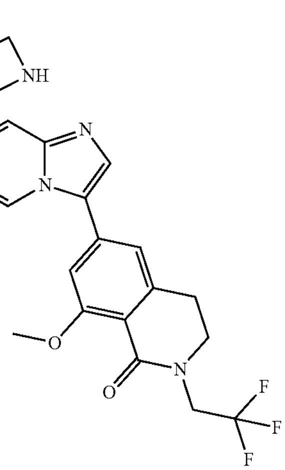 | 6-[7-[(3-fluoroazetidin-3-yl)methoxy]imidazo[1,2-a]pyridin-3-yl]-8-methoxy-2-(2,2,2-trifluoro ethyl)-3,4-dihydro isoquinolin-1-one | Cpd 248 | K | 478.4 | 479.5 |
| 251 | 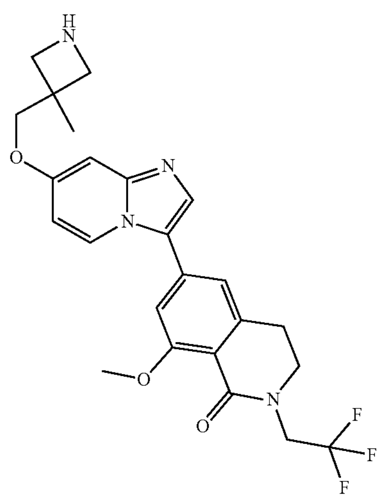 [SMILES: COc1cc(-c2cnc3cc(OCC4(C)CNC4)ccn23)cc2c1C(=O)N(CC(F)(F)F)CC2] | 8-methoxy-6-[7-[(3-methylazetidin-3-yl)methoxy]imidazo[1,2-a]pyridin-3-yl]-2-(2,2,2-trifluoroethyl)-3,4-dihydroisoquinolin-1-one | Cpd 249 | K | 474.5 | 475.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 252 | 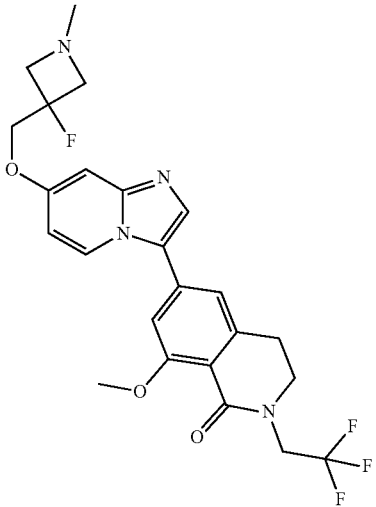 [SMILES: COc1cc(-c2cnc3cc(OCC4(C)CN(C)C4)ccn23)cc2c1C(=O)N(CC(F)(F)F)CC2] | 6-[7-[(3-fluoro-1-methyl-azetidin-3-yl)methoxy]imidazo[1,2-a]pyridin-3-yl]-8-methoxy-2-(2,2,2-trifluoro ethyl)-3,4-dihydro isoquinolin-1-one | Cpd 250 | J | 492.5 | 493.3 |
| 253 | 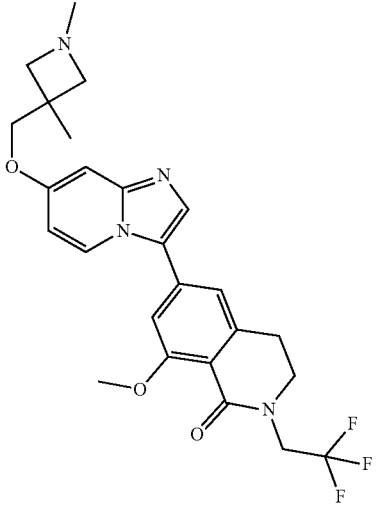 | 6-[7-[(1,3-dimethylazetidin-3-yl)methoxy] imidazo[1,2-a]pyridin-3-yl]-8-methoxy-2-(2,2,2-trifluoroethyl)-3,4-dihydroisoquinolin-1-one | Cpd 251 | J | 488.5 | 489.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 254 | 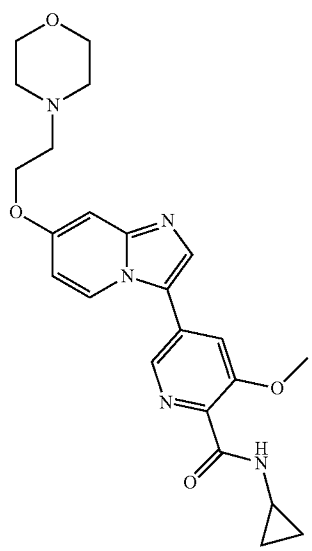 [SMILES: COc1cc(-c2cnc3cc(OCCN4CCOCC4)ccn23)cnc1C(=O)NC1CC1] | N-cyclopropyl-3-methoxy-5-[7-(2-morpholinoethoxy)imidazo[1,2-a]pyridin-3-yl]pyridine-2-carboxamide | Int 25 + Int 33 | B | 437.5 | 438.3 |
| 255 | 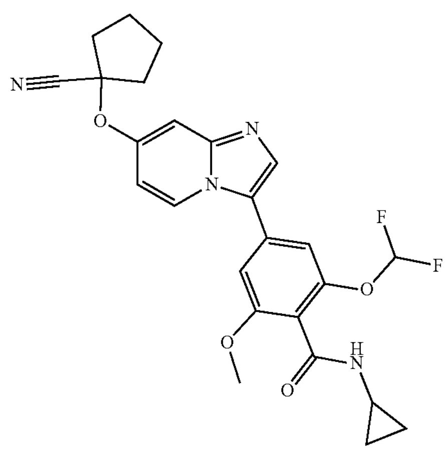 [SMILES: COc1cc(-c2cnc3cc(OC4(C#N)CCCC4)ccn23)cc(OC(F)F)c1C(=O)NC1CC1] | 4-[7-(1-cyanocyclopentoxy)imidazo[1,2-a]pyridin-3-yl]-N-cyclopropyl-2-(difluoromethoxy)-6-methoxy-benzamide | Int 81 + Int 11 | Ex. 2.90 | 482.5 | 483.2 |
| 256 | 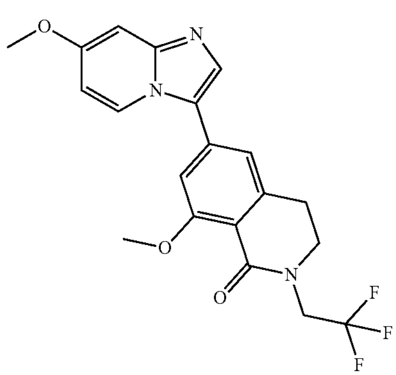 [SMILES: COc1ccn2c(-c3cc4c(c(OC)c3)C(=O)N(CC(F)(F)F)CC4)cnc2c1] | 8-methoxy-6-(7-methoxyimidazo[1,2-a]pyridin-3-yl)-2-(2,2,2-trifluoroethyl)-3,4-dihydroisoquinolin-1-one | Int 2 + CAS# 622-40-2 | Ex. 2.91 | 405.4 | 406.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 257 | 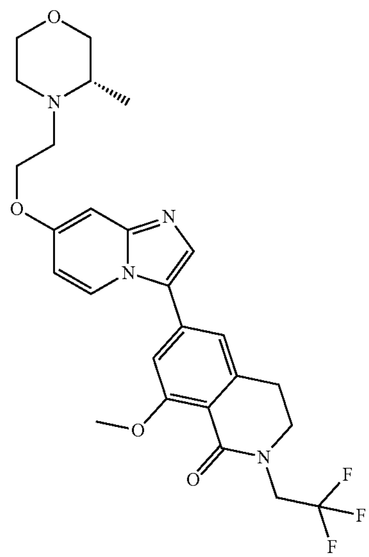 [SMILES: COc1cc(-c2cnc3cc(OCCN4CCOC[C@@H]4C)ccn23)cc2c1C(=O)N(CC(F)(F)F)CC2] | 8-methoxy-6-[7-[2-[(3S)-3-methylmorpholin-4-yl]ethoxy]imidazo[1,2-a]pyridin-3-yl]-2-(2,2,2-trifluoroethyl)-3,4-dihydroisoquinolin-1-one | Int 31 + CAS# 1022094-03-6 | I (with Et$_3$N) | 518.5 | 519.4 |
| 258 | 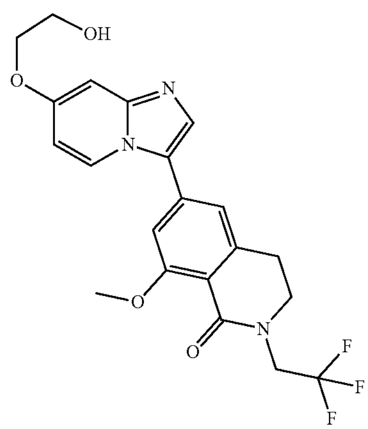 [SMILES: COc1cc(-c2cnc3cc(OCCO)ccn23)cc2c1C(=O)N(CC(F)(F)F)CC2] | 6-[7-(2-hydroxyethoxy)imidazo[1,2-a]pyridin-3-yl]-8-methoxy-2-(2,2,2-trifluoroethyl)-3,4-dihydroisoquinolin-1-one | Int 31 + CAS# 1022094-03-6 | I (with Et$_3$N) | 435.4 | 436.5 |
| 259 | 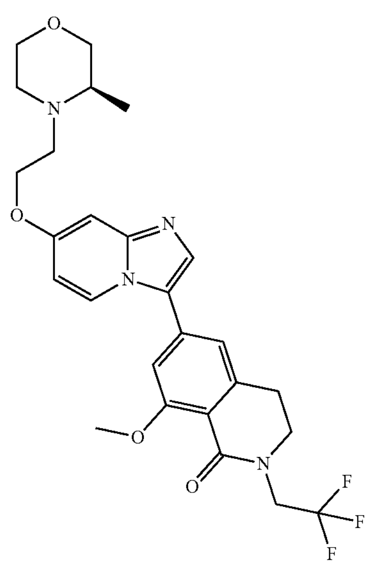 [SMILES: COc1cc(-c2cnc3cc(OCCN4CCOC[C@H]4C)ccn23)cc2c1C(=O)N(CC(F)(F)F)CC2] | 8-methoxy-6-[7-[2-[(3R)-3-methylmorpholin-4-yl]ethoxy]imidazo[1,2-a]pyridin-3-yl]-2-(2,2,2-trifluoroethyl)-3,4-dihydroisoquinolin-1-one | Int 31 + CAS# 953780-78-4 | I (with Et$_3$N) | 518.5 | 519.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 260 | 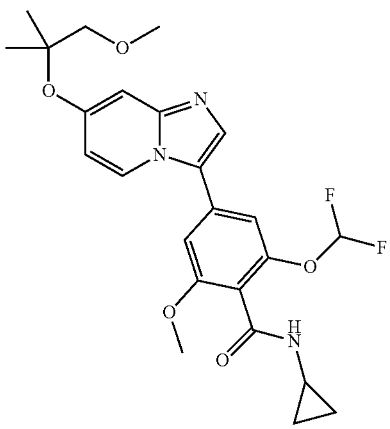 [SMILES: COCC(C)(C)Oc1ccn2c(-c3cc(OC)c(C(=O)NC4CC4)c(OC(F)F)c3)cnc2c1] | N-cyclopropyl-2-(difluoromethoxy)-6-methoxy-4-[7-(2-methoxy-1,1-dimethyl-ethoxy)imidazo[1,2-a]pyridin-3-yl]benzamide | Int 65 + Int 11 | Ex. 2.92 | 475.5 | 476.2 |
| 261 | 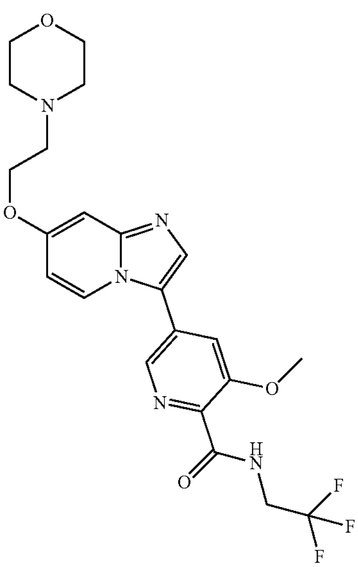 [SMILES: COc1cc(-c2cnc3cc(OCCN4CCOCC4)ccn23)cnc1C(=O)NCC(F)(F)F] | 3-methoxy-5-[7-(2-morpholinoethoxy)imidazo[1,2-a]pyridin-3-yl]-N-(2,2,2-trifluoroethyl)pyridine-2-carboxamide | Int 25 + Int 34 | B | 479.5 | 480.4 |
| 262 | 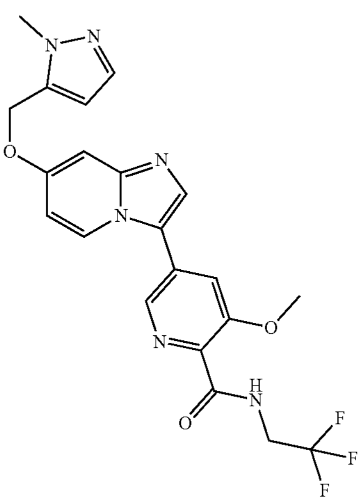 [SMILES: COc1cc(-c2cnc3cc(OCc4ccnn4C)ccn23)cnc1C(=O)NCC(F)(F)F] | 3-methoxy-5-[7-[(2-methylpyrazol-3-yl)methoxy]imidazo[1,2-a]pyridin-3-yl]-N-(2,2,2-trifluoroethyl)pyridine-2-carboxamide | Int 35 + CAS# 84547-61-5 | A | 460.4 | 461.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 263 | 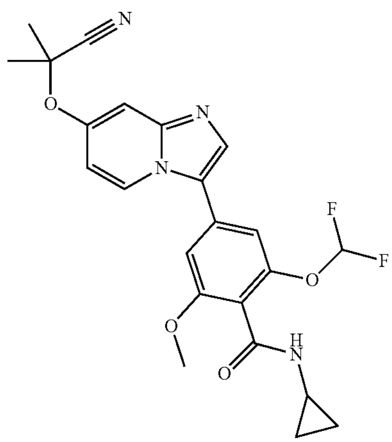 [SMILES: COc1cc(-c2cnc3cc(OC(C)(C)C#N)ccn23)cc(OC(F)F)c1C(=O)NC1CC1] | 4-[7-(1-cyano-1-methyl-ethoxy)imidazo[1,2-a]pyridin-3-yl]-N-cyclopropyl-2-(difluoromethoxy)-6-methoxy-benzamide | Int 68 + Int 11 | Ex. 2.93 | 456.4 | 457.2 |
| 264 | 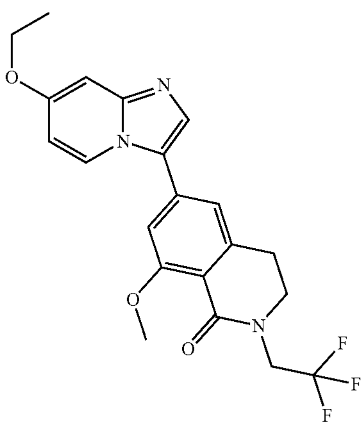 [SMILES: CCOc1ccn2c(-c3cc4c(c(OC)c3)C(=O)N(CC(F)(F)F)CC4)cnc2c1] | 6-(7-ethoxyimidazo[1,2-a]pyridin-3-yl)-8-methoxy-2-(2,2,2-trifluoroethyl)-3,4-dihydroisoquinolin-1-one | Int 2 + CAS# 406913-93-7 | Ex. 2.94 | 419.4 | 420.5 |
| 265 | 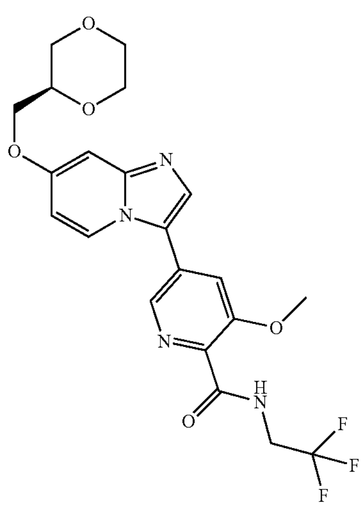 [SMILES: COc1cc(-c2cnc3cc(OC[C@H]4COCCO4)ccn23)cnc1C(=O)NCC(F)(F)F] | 5-[7-[[(2R)-1,4-dioxan-2-yl]methoxy]imidazo[1,2-a]pyridin-3-yl]-3-methoxy-N-(2,2,2-trifluoroethyl)pyridine-2-carboxamide | Int 36 + Int 34 | B | 466.4 | 467.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 266 | 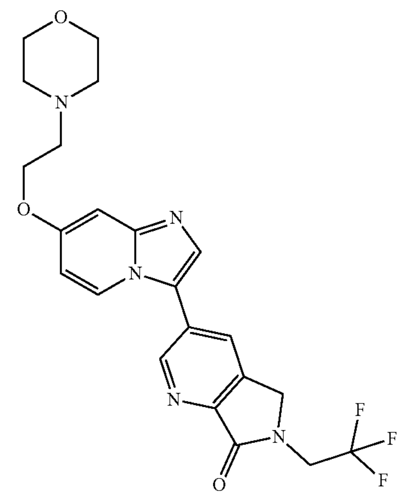 [SMILES: O=C1c2ncc(-c3cnc4cc(OCCN5CCOCC5)ccn34)cc2CN1CC(F)(F)F] | 3-[7-(2-morpholinoethoxy)imidazo[1,2-a]pyridin-3-yl]-6-(2,2,2-trifluoroethyl)-5H-pyrrolo[3,4-b]pyridin-7-one | Int 25 + Int 37 | Ex. 2.95 | 461.4 | 462.4 |
| 267 | 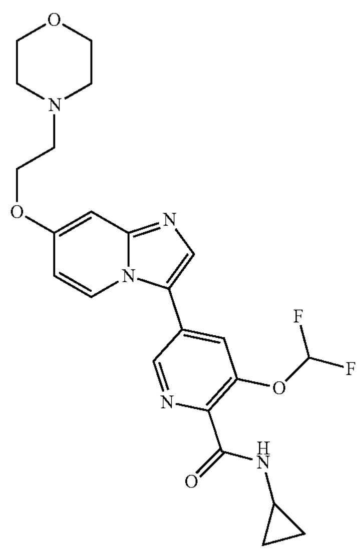 [SMILES: O=C(NC1CC1)c1ncc(-c2cnc3cc(OCCN4CCOCC4)ccn23)cc1OC(F)F] | N-cyclopropyl-3-(difluoromethoxy)-5-[7-(2-morpholinoethoxy)imidazo[1,2-a]pyridin-3-yl]pyridine-2-carboxamide | Int 25 + Int 38 | B | 473.5 | 474.3 |
| 268 | 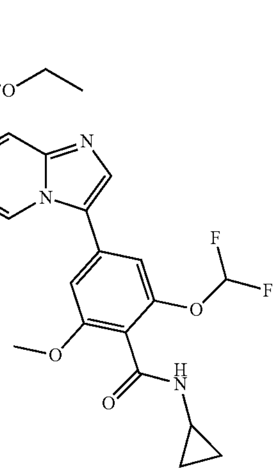 | ethyl 2-[3-[4-(cyclopropylcarbamoyl)-3-(difluoromethoxy)-5-methoxy-phenyl]imidazo[1,2-a]pyridin-7-yl]oxyacetate | Int 96 + CAS# 623-48-3 | Ex. 2.96 | 475.4 | 476.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 269 | 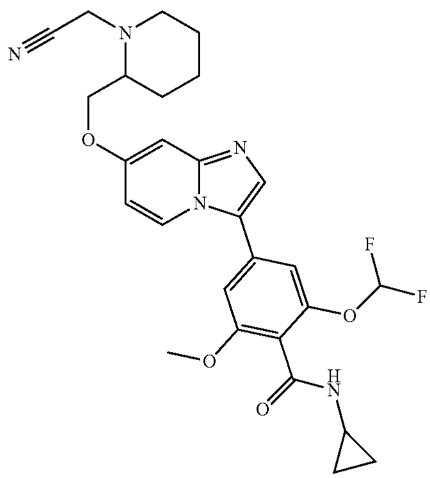 [SMILES: COc1cc(-c2cnc3cc(OCC4CCCCN4CC#N)ccn23)cc(OC(F)F)c1C(=O)NC1CC1] | 4-[7-[[1-(cyanomethyl)-2-piperidyl]methoxy]imidazo[1,2-a]pyridin-3-yl]-N-cyclopropyl-2-(difluoromethoxy)-6-methoxy-benzamide | Int 1 + CAS# 186790-31-8 | A | 525.5 | 526.4 |
| 270 | 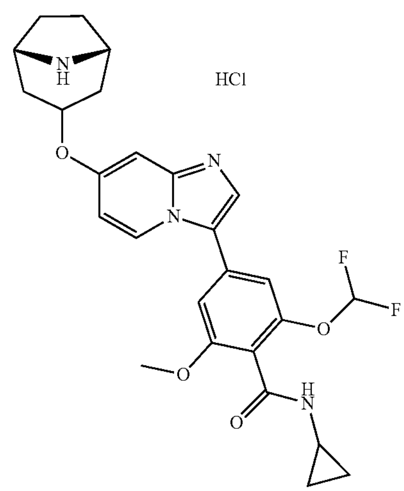 [SMILES: COc1cc(-c2cnc3cc(OC4C[C@H]5CC[C@@H](C4)N5)ccn23)cc(OC(F)F)c1C(=O)NC1CC1 ; Cl] | 4-[7-[[(1R,5S)-8-azabicyclo[3.2.1]octan-3-yl]oxy]imidazo[1,2-a]pyridin-3-yl]-N-cyclopropyl-2-(difluoromethoxy)-6-methoxy-benzamide hydrochloride salt | Int 1 + CAS# 478837-18-2 | A + K1 | 498.5 | 499.3 |
| 271 | 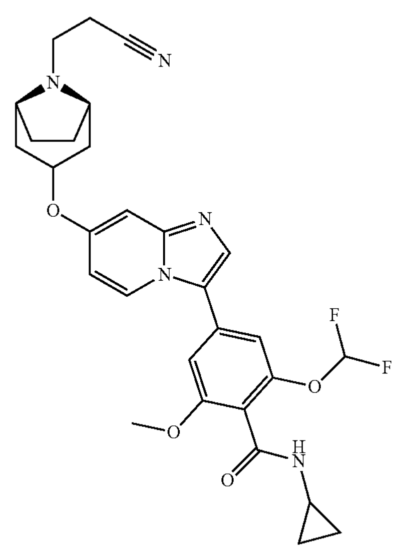 [SMILES: COc1cc(-c2cnc3cc(OC4C[C@H]5CC[C@@H](C4)N5CCC#N)ccn23)cc(OC(F)F)c1C(=O)NC1CC1] | 4-[7-[[(1S,5R)-8-(2-cyanoethyl)-8-azabicyclo[3.2.1]octan-3-yl]oxy]imidazo[1,2-a]pyridin-3-yl]-N-cyclopropyl-2-(difluoromethoxy)-6-methoxy-benzamide | Cpd 270 + CAS# 107-13-1 | L | 551.5 | 552.4 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 272 | 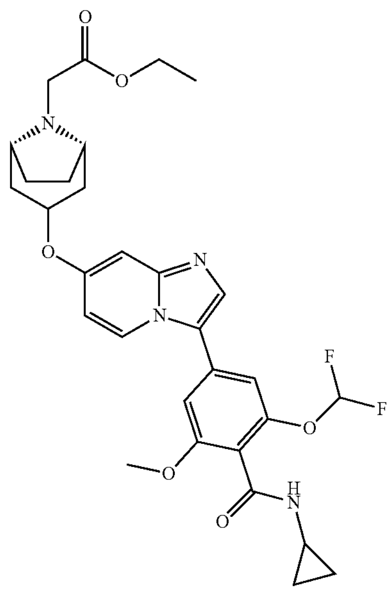 [SMILES: CCOC(=O)CN1[C@@H]2CC[C@H]1CC(Oc1ccn3c(-c4cc(OC)c(C(=O)NC5CC5)c(OC(F)F)c4)cnc3c1)C2] | ethyl 2-[(1R,5S)-3-[3-[4-(cyclopropylcarbamoyl)-3-(difluoromethoxy)-5-methoxy-phenyl]imidazo[1,2-a]pyridin-7-yl]oxy-8-azabicyclo[3.2.1]octan-8-yl]acetate | Cpd 270 + CAS# 105-36-2 | H | 584.6 | 585.5 |
| 273 | 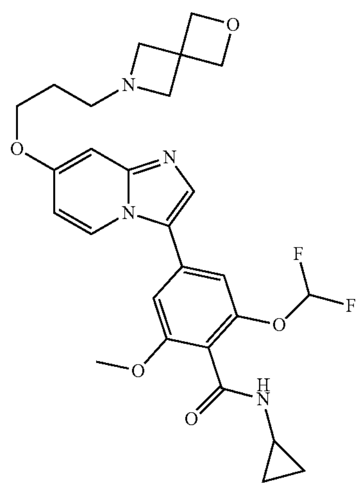 [SMILES: COc1cc(-c2cnc3cc(OCCCN4CC5(COC5)C4)ccn23)cc(OC(F)F)c1C(=O)NC1CC1] | N-cyclopropyl-2-(difluoromethoxy)-6-methoxy-4-[7-[3-(2-oxa-6-azaspiro[3.3]heptan-6-yl)propoxy]imidazo[1,2-a]pyridin-3-yl]benzamide | Int 1 + CAS# 1408284-92-3 | A | 528.5 | 529.4 |
| 274 | 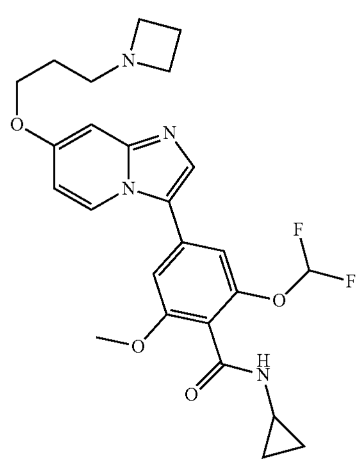 [SMILES: COc1cc(-c2cnc3cc(OCCCN4CCC4)ccn23)cc(OC(F)F)c1C(=O)NC1CC1] | 4-[7-[3-(azetidin-1-yl)propoxy]imidazo[1,2-a]pyridin-3-yl]-N-cyclopropyl-2-(difluoromethoxy)-6-methoxy-benzamide | Int 1 + CAS# 925903-31-7 | A | 486.5 | 487.8 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 275 | 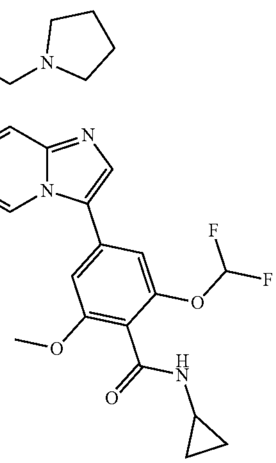 | N-cyclopropyl-2-(difluoromethoxy)-6-methoxy-4-[7-(3-pyrrolidin-1-ylpropoxy)imidazo[1,2-a]pyridin-3-yl]benzamide | Int 1 + CAS# 19748-66-4 | A | 500.5 | 501.9 |
| 276 | 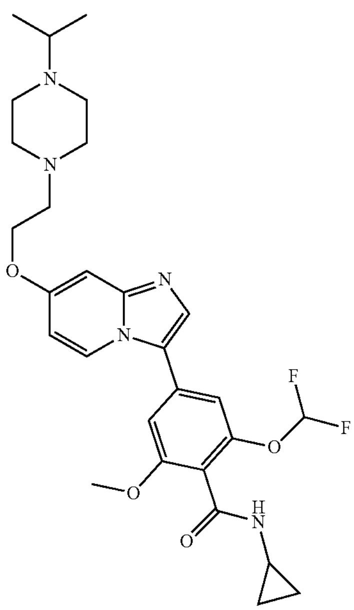 [SMILES: COc1cc(-c2cnc3cc(OCCN4CCN(C(C)C)CC4)ccn23)cc(OC(F)F)c1C(=O)NC1CC1] | N-cyclopropyl-2-(difluoromethoxy)-4-[7-[2-(4-isopropylpiperazin-1-yl)ethoxy]imidazo[1,2-a]pyridin-3-yl]-6-methoxy-benzamide | Int 1 + CAS# 103069-50-7 | A | 543.6 | 544.9 |
| 277 | 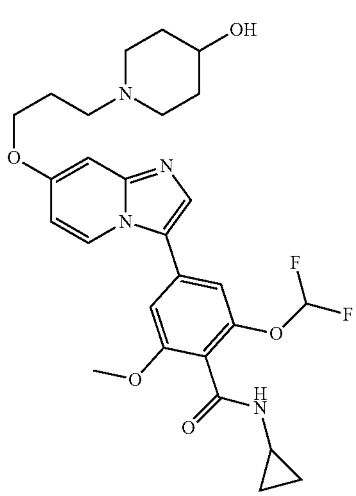 [SMILES: COc1cc(-c2cnc3cc(OCCCN4CCC(O)CC4)ccn23)cc(OC(F)F)c1C(=O)NC1CC1] | N-cyclopropyl-2-(difluoromethoxy)-4-[7-[3-(4-hydroxy-1-piperidyl)propoxy]imidazo[1,2-a]pyridin-3-yl]-6-methoxy-benzamide | Cpd 333 + CAS# 5382-16-1 | M | 530.5 | 531.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 278 | 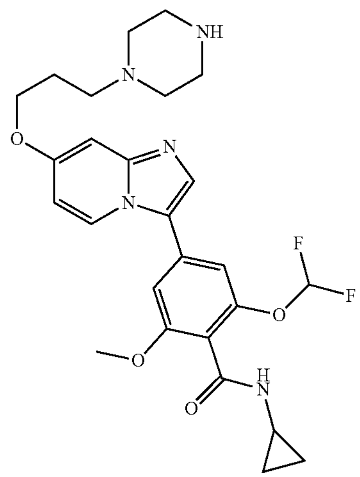 [SMILES: COc1cc(-c2cnc3cc(OCCCN4CCNCC4)ccn23)cc(OC(F)F)c1C(=O)NC1CC1] | N-cyclopropyl-2-(difluoromethoxy)-6-methoxy-4-[7-(3-piperazin-1-ylpropoxy)imidazo[1,2-a]pyridin-3-yl]benzamide | Int 1 + CAS# 5317-32-8 | A | 515.5 | 516.2 |
| 279 | 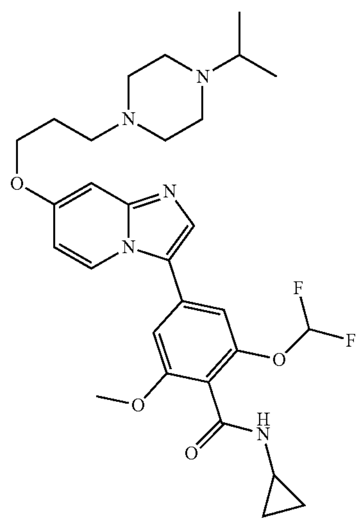 [SMILES: COc1cc(-c2cnc3cc(OCCCN4CCN(C(C)C)CC4)ccn23)cc(OC(F)F)c1C(=O)NC1CC1] | N-cyclopropyl-2-(difluoromethoxy)-4-[7-[3-(4-isopropylpiperazin-1-yl)propoxy]imidazo[1,2-a]pyridin-3-yl]-6-methoxy-benzamide | Int 1 + CAS# 5317-32-8 + CAS# 67-64-1 | A + J1 | 557.6 | 558.2 |
| 280 | 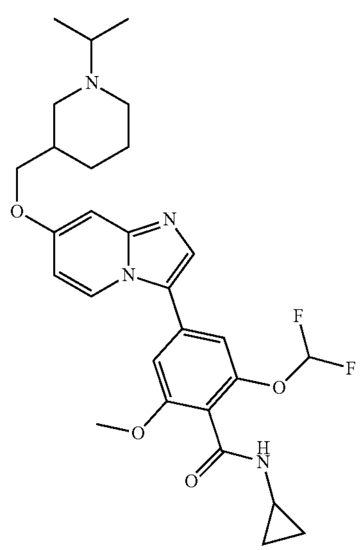 [SMILES: COc1cc(-c2cnc3cc(OCC4CCCN(C(C)C)C4)ccn23)cc(OC(F)F)c1C(=O)NC1CC1] | N-cyclopropyl-2-(difluoromethoxy)-4-[7-[(1-isopropyl-3-piperidyl)methoxy]imidazo[1,2-a]pyridin-3-yl]-6-methoxy-benzamide | Int 1 + CAS# 752970-45-9 | A | 528.5 | 529.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 281 | 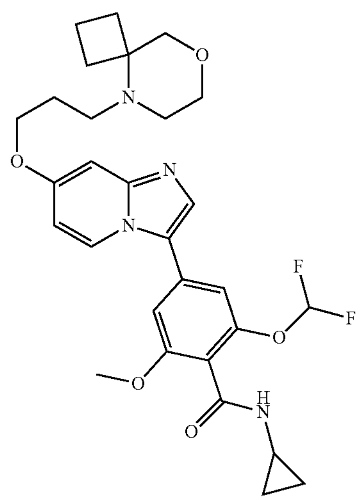 [SMILES: COc1cc(-c2cnc3cc(OCCCN4CCOCC45CCC5)ccn23)cc(OC(F)F)c1C(=O)NC1CC1] | N-cyclopropyl-2-(difluoromethoxy)-6-methoxy-4-[7-[3-(8-oxa-5-azaspiro[3.5]nonan-5-yl)propoxy]imidazo[1,2-a]pyridin-3-yl]benzamide | Cpd 333 + CAS# 602326-48-7 | M | 556.6 | 557.3 |
| 282 | 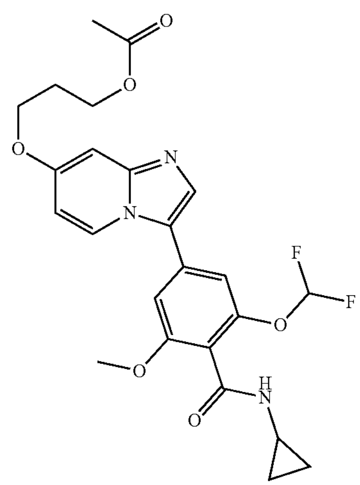 [SMILES: COc1cc(-c2cnc3cc(OCCCOC(C)=O)ccn23)cc(OC(F)F)c1C(=O)NC1CC1] | 3-[3-[4-(cyclopropylcarbamoyl)-3-(difluoromethoxy)-5-methoxy-phenyl]imidazo[1,2-a]pyridin-7-yl]oxypropyl acetate | Int 1 + CAS# 504-63-2 | A | 489.4 | 490.1 |
| 283 | 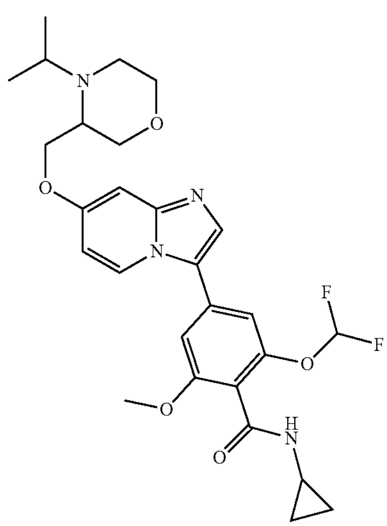 [SMILES: COc1cc(-c2cnc3cc(OCC4COCCN4C(C)C)ccn23)cc(OC(F)F)c1C(=O)NC1CC1] | N-cyclopropyl-2-(difluoromethoxy)-4-[7-[(4-isopropylmorpholin-3-yl)methoxy]imidazo[1,2-a]pyridin-3-yl]-6-methoxy-benzamide | Cpd 113 + CAS# 67-64-1 | J1 | 530.5 | 531.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 284 | 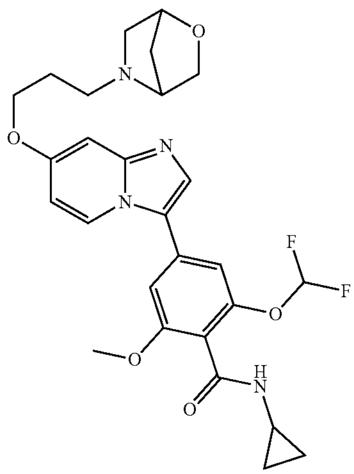 [SMILES: COc1cc(-c2cnc3cc(OCCCN4CC5CC4CO5)ccn23)cc(OC(F)F)c1C(=O)NC1CC1] | N-cyclopropyl-2-(difluoromethoxy)-6-methoxy-4-[7-[3-(2-oxa-5-azabicyclo[2.2.1]heptan-5-yl)propoxy]imidazo[1,2-a]pyridin-3-yl]benzamide | Cpd 333 + CAS# 909186-56-7 | M | 528.5 | 529.2 |
| 285 | 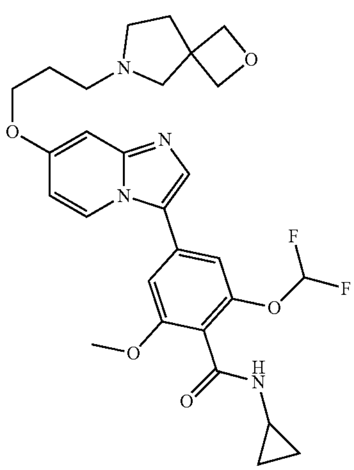 [SMILES: COc1cc(-c2cnc3cc(OCCCN4CCC5(COC5)C4)ccn23)cc(OC(F)F)c1C(=O)NC1CC1] | N-cyclopropyl-2-(difluoromethoxy)-6-methoxy-4-[7-[3-(2-oxa-7-azaspiro[3.4]octan-7-yl)propoxy]imidazo[1,2-a]pyridin-3-yl]benzamide | Cpd 333 + CAS# 220290-68-6 | M | 542.5 | 543.2 |
| 286 | 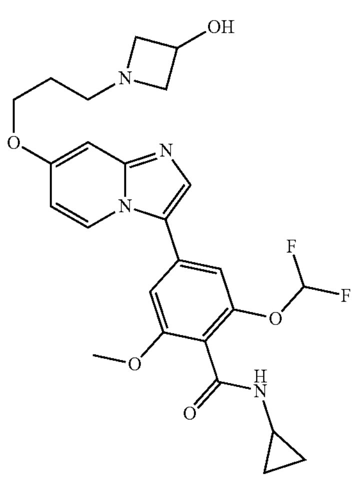 [SMILES: COc1cc(-c2cnc3cc(OCCCN4CC(O)C4)ccn23)cc(OC(F)F)c1C(=O)NC1CC1] | N-cyclopropyl-2-(difluoromethoxy)-4-[7-[3-(3-hydroxyazetidin-1-yl)propoxy]imidazo[1,2-a]pyridin-3-yl]-6-methoxy-benzamide | Cpd 333 + CAS# 45347-82-8 | M | 502.5 | 503.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 287 | 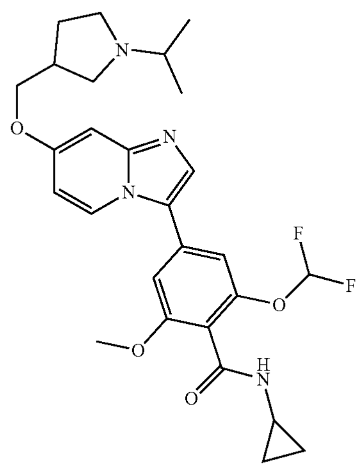 [SMILES: COc1cc(-c2cnc3cc(OCC4CCN(C(C)C)C4)ccn23)cc(OC(F)F)c1C(=O)NC1CC1] | N-cyclopropyl-2-(difluoromethoxy)-4-[7-[(1-isopropylpyrrolidin-3-yl)methoxy]imidazo[1,2-a]pyridin-3-yl]-6-methoxy-benzamide | Int 99 + CAS# 67-64-1 | J1 | 514.5 | 515.2 |
| 288 | 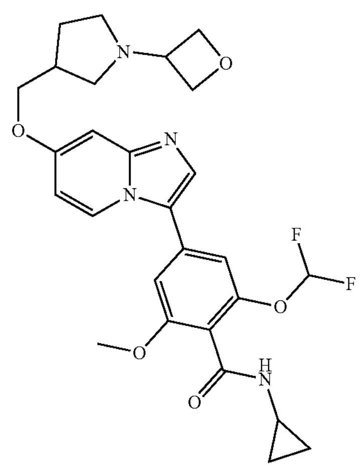 [SMILES: COc1cc(-c2cnc3cc(OCC4CCN(C5COC5)C4)ccn23)cc(OC(F)F)c1C(=O)NC1CC1] | N-cyclopropyl-2-(difluoromethoxy)-6-methoxy-4-[7-[[1-(oxetan-3-yl)pyrrolidin-3-yl]methoxy]imidazo[1,2-a]pyridin-3-yl]benzamide | Int 99 + CAS# 6704-31-0 | J1 | 528.5 | 529.1 |
| 289 | 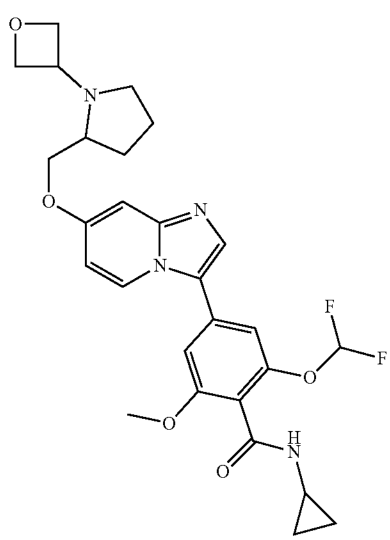 [SMILES: COc1cc(-c2cnc3cc(OCC4CCCN4C4COC4)ccn23)cc(OC(F)F)c1C(=O)NC1CC1] | N-cyclopropyl-2-(difluoromethoxy)-6-methoxy-4-[7-[[1-(oxetan-3-yl)pyrrolidin-2-yl]methoxy]imidazo[1,2-a]pyridin-3-yl]benzamide | Cpd 154 + CAS# 6704-31-0 | J1 | 528.5 | 529.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 290 | 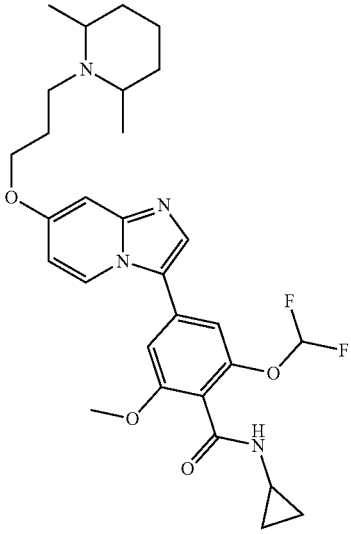 [SMILES: COc1cc(-c2cnc3cc(OCCCN4C(C)CCCC4C)ccn23)cc(OC(F)F)c1C(=O)NC1CC1] | N-cyclopropyl-2-(difluoromethoxy)-4-[7-[3-(2,6-dimethyl-1-piperidyl)propoxy]imidazo[1,2-a]pyridin-3-yl]-6-methoxy-benzamide | Cpd 333 + CAS# 504-03-0 | M | 542.6 | 543.2 |
| 291 | 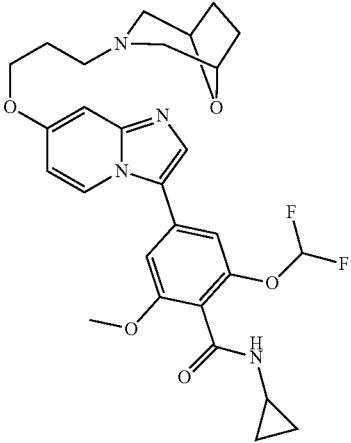 [SMILES: COc1cc(-c2cnc3cc(OCCCN4CC5CCC(C4)O5)ccn23)cc(OC(F)F)c1C(=O)NC1CC1] | N-cyclopropyl-2-(difluoromethoxy)-6-methoxy-4-[7-[3-(8-oxa-3-azabicyclo[3.2.1]octan-3-yl)propoxy]imidazo[1,2-a]pyridin-3-yl]benzamide | Cpd 333 + CAS# 280-13-7 | M | 542.5 | 543.2 |
| 292 | 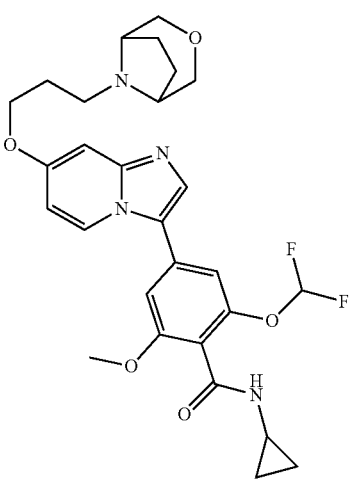 [SMILES: COc1cc(-c2cnc3cc(OCCCN4C5CCC4COC5)ccn23)cc(OC(F)F)c1C(=O)NC1CC1] | N-cyclopropyl-2-(difluoromethoxy)-6-methoxy-4-[7-[3-(3-oxa-8-azabicyclo[3.2.1]octan-8-yl)propoxy]imidazo[1,2-a]pyridin-3-yl]benzamide | Cpd 333 + CAS# 904316-92-3 | M | 542.5 | 543.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 293 | 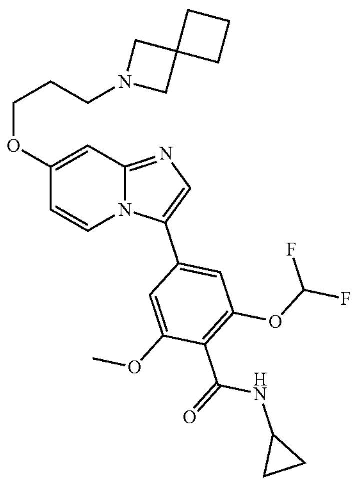 [SMILES: COc1cc(-c2cnc3cc(OCCCN4CC5(CCC5)C4)ccn23)cc(OC(F)F)c1C(=O)NC1CC1] | 4-[7-[3-(2-azaspiro[3.3]heptan-2-yl)propoxy]imidazo[1,2-a]pyridin-3-yl]-N-cyclopropyl-2-(difluoromethoxy)-6-methoxy-benzamide | Cpd 333 + CAS# 1045709-32-7 | M | 526.5 | 527.2 |
| 294 | 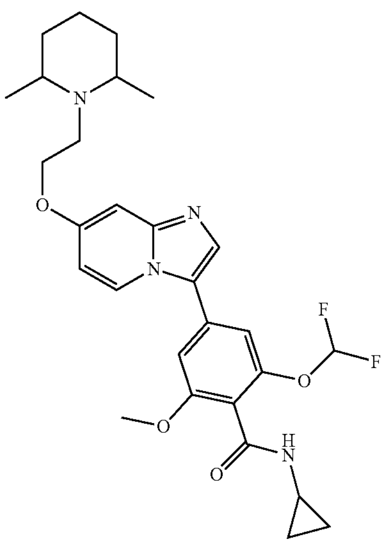 [SMILES: COc1cc(-c2cnc3cc(OCCN4C(C)CCCC4C)ccn23)cc(OC(F)F)c1C(=O)NC1CC1] | N-cyclopropyl-2-(difluoromethoxy)-4-[7-[2-(2,6-dimethyl-1-piperidyl)ethoxy]imidazo[1,2-a]pyridin-3-yl]-6-methoxy-benzamide | Int 1 + CAS# 23502-32-1 | A | 528.5 | 529.2 |
| 295 | 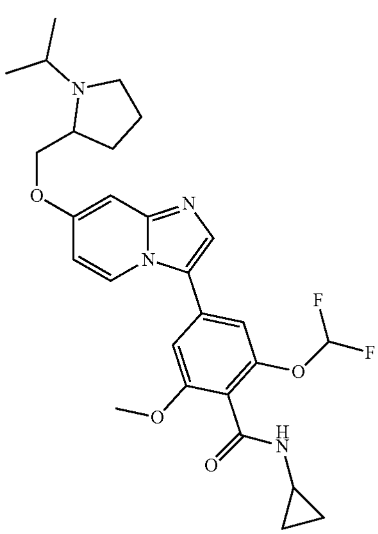 [SMILES: COc1cc(-c2cnc3cc(OCC4CCCN4C(C)C)ccn23)cc(OC(F)F)c1C(=O)NC1CC1] | N-cyclopropyl-2-(difluoromethoxy)-4-[7-[(1-isopropylpyrrolidin-2-yl)methoxy]imidazo[1,2-a]pyridin-3-yl]-6-methoxy-benzamide | Cpd 154 + CAS# 67-64-1 | J1 | 514.5 | 515.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 296 | 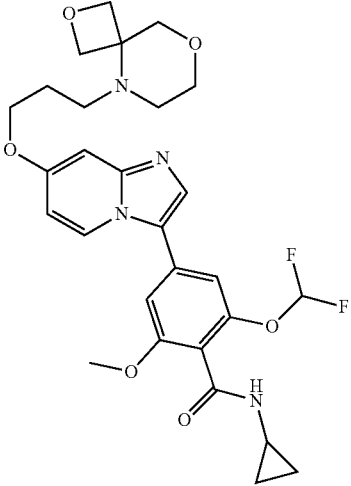 [SMILES: COc1cc(-c2cnc3cc(OCCCN4CCOCC45COC5)ccn23)cc(OC(F)F)c1C(=O)NC1CC1] | N-cyclopropyl-2-(difluoromethoxy)-4-[7-[3-(2,8-dioxa-5-azaspiro[3.5]nonan-5-yl)propoxy]imidazo[1,2-a]pyridin-3-yl]-6-methoxy-benzamide | Cpd 333 + CAS# 1240725-47-6 | M | 558.5 | 559.2 |
| 297 | 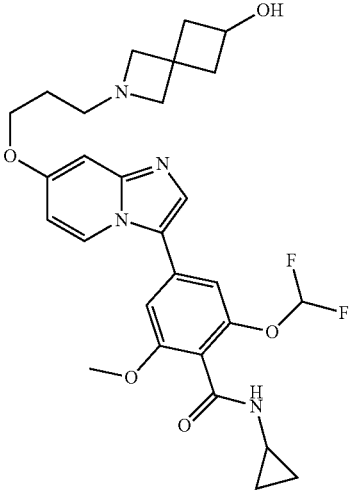 [SMILES: COc1cc(-c2cnc3cc(OCCCN4CC5(CC(O)C5)C4)ccn23)cc(OC(F)F)c1C(=O)NC1CC1] | N-cyclopropyl-2-(difluoromethoxy)-4-[7-[3-(6-hydroxy-2-azaspiro[3.3]heptan-2-yl)propoxy]imidazo[1,2-a]pyridin-3-yl]-6-methoxy-benzamide | Cpd 333 + CAS# 1630907-10-6 | M | 542.5 | 543.1 |
| 298 | 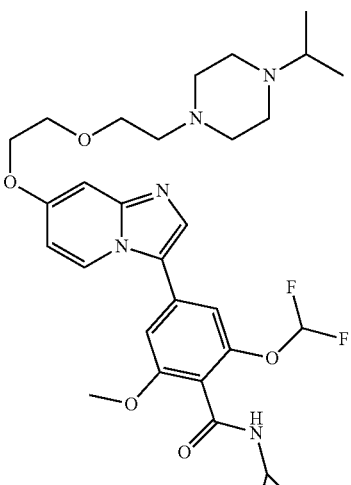 | N-cyclopropyl-2-(difluoromethoxy)-4-[7-[2-[2-(4-isopropylpiperazin-1-yl)ethoxy]ethoxy]imidazo[1,2-a]pyridin-3-yl]-6-methoxy-benzamide | Int 1 + Int 97 | A | 587.6 | 588.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 299 | 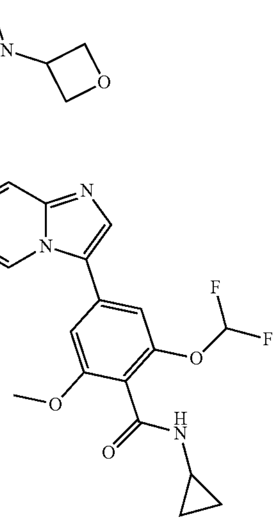 | N-cyclopropyl-2-(difluoromethoxy)-6-methoxy-4-[7-[2-[1-(oxetan-3-yl)pyrrolidin-2-yl]ethoxy]imidazo[1,2-a]pyridin-3-yl]benzamide | Int 100 + CAS# 6704-31-0 | J1 | 542.5 | 543.1 |
| 300 | 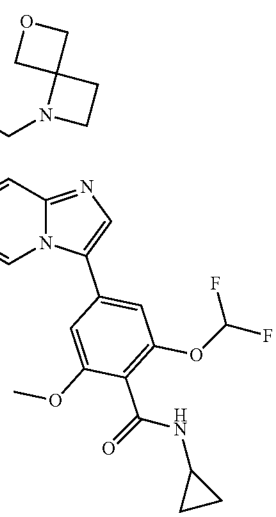 | N-cyclopropyl-2-(difluoromethoxy)-6-methoxy-4-[7-[3-(6-oxa-1-azaspiro[3.3]heptan-1-yl)propoxy]imidazo[1,2-a]pyridin-3-yl]benzamide | Cpd 333 + CAS# 1046153-00-7 | M | 528.5 | 529.1 |
| 301 | 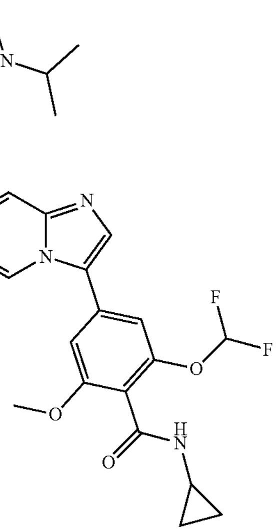 | N-cyclopropyl-2-(difluoromethoxy)-4-[7-[2-(1-isopropylpyrrolidin-2-yl)ethoxy]imidazo[1,2-a]pyridin-3-yl]-6-methoxy-benzamide | Int 100 + CAS# 67-64-1 | J1 | 528.5 | 529.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 302 | 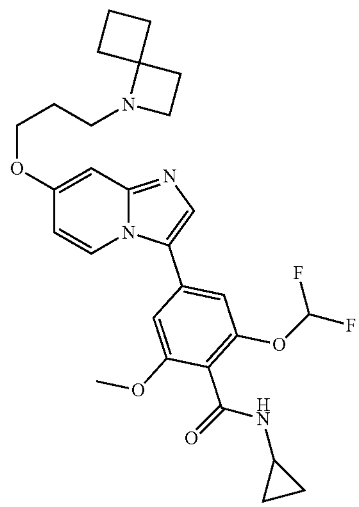 [SMILES: COc1cc(-c2cnc3cc(OCCCN4CCC45CCC5)ccn23)cc(OC(F)F)c1C(=O)NC1CC1] | 4-[7-[3-(1-azaspiro[3.3]heptan-1-yl)propoxy]imidazo[1,2-a]pyridin-3-yl]-N-cyclopropyl-2-(difluoromethoxy)-6-methoxy-benzamide | Cpd 333 + CAS# 51392-72-4 | M | 526.5 | 527.1 |
| 303 | 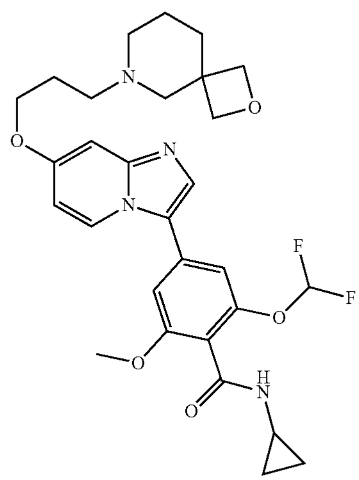 [SMILES: COc1cc(-c2cnc3cc(OCCCN4CCCC5(COC5)C4)ccn23)cc(OC(F)F)c1C(=O)NC1CC1] | N-cyclopropyl-2-(difluoromethoxy)-6-methoxy-4-[7-[3-(2-oxa-8-azaspiro[3.5]nonan-8-yl)propoxy]imidazo[1,2-a]pyridin-3-yl]benzamide | Cpd 333 + CAS# 1366396-42-0 | M | 556.6 | 557.1 |
| 304 | 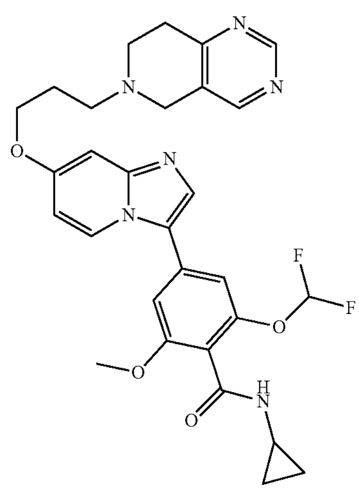 [SMILES: COc1cc(-c2cnc3cc(OCCCN4CCc5ncncc5C4)ccn23)cc(OC(F)F)c1C(=O)NC1CC1] | N-cyclopropyl-2-(difluoromethoxy)-4-[7-[3-(7,8-dihydro-5H-pyrido[4,3-d]pyrimidin-6-yl)propoxy]imidazo[1,2-a]pyridin-3-yl]-6-methoxy-benzamide | Cpd 333 + CAS# 192869-50-4 | M | 564.5 | 565.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 305 | 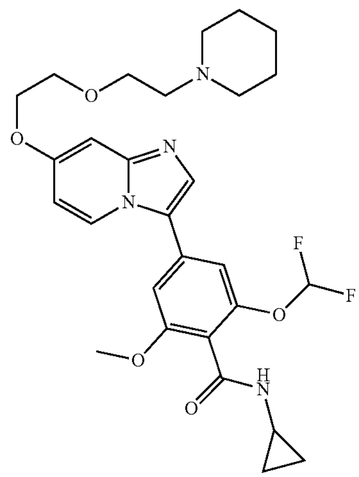 | N-cyclopropyl-2-(difluoromethoxy)-6-methoxy-4-[7-[2-[2-(1-piperidyl)ethoxy]ethoxy imidazo[1,2-a]pyridin-3-yl]benzamide | Int 1 + CAS# 3603-43-8 | A | 544.5 | 545.1 |
| 306 | 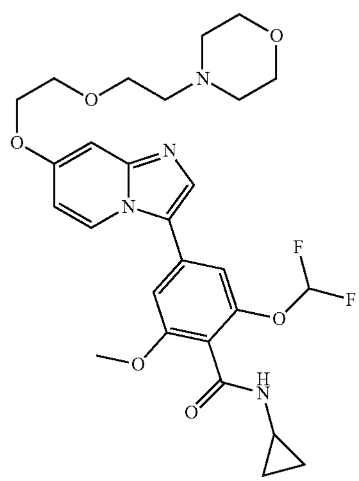 [SMILES: COc1cc(-c2cnc3cc(OCCOCCN4CCOCC4)ccn23)cc(OC(F)F)c1C(=O)NC1CC1] | N-cyclopropyl-2-(difluoromethoxy)-6-methoxy-4-[7-[2-[2-(2-morpholinoethoxy)ethoxy]imidazo[1,2-a]pyridin-3-yl]benzamide | Int 1 + CAS# 3603-45-0 | A | 546.5 | 547.1 |
| 307 | 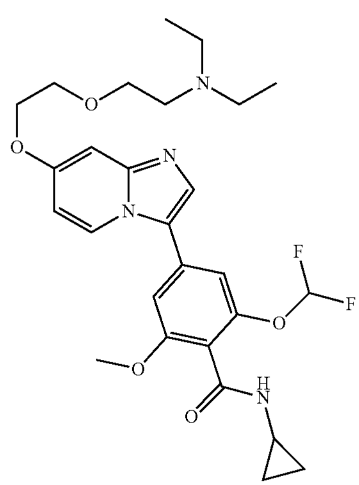 [SMILES: CCN(CC)CCOCCOc1ccn2c(-c3cc(OC)c(C(=O)NC4CC4)c(OC(F)F)c3)cnc2c1] | N-cyclopropyl-4-[7-[2-[2-(diethylamino)ethoxy]ethoxy]imidazo[1,2-a]pyridin-3-yl]-2-(difluoromethoxy)-6-methoxy-benzamide | Int 1 + CAS# 140-82-9 | A | 532.5 | 533.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 308 | 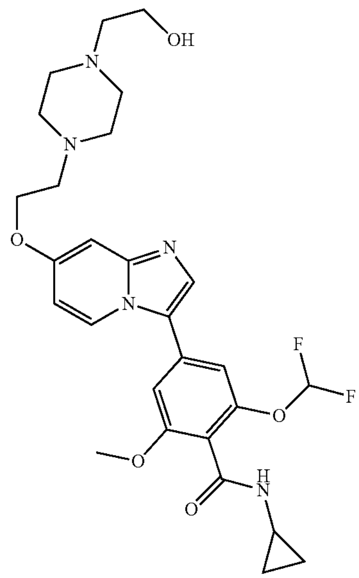 [SMILES: COc1cc(-c2cnc3cc(OCCN4CCN(CCO)CC4)ccn23)cc(OC(F)F)c1C(=O)NC1CC1] | N-cyclopropyl-2-(difluoromethoxy)-4-[7-[2-[4-(2-hydroxyethyl)piperazin-1-yl]ethoxy]imidazo[1,2-a]pyridin-3-yl]-6-methoxy-benzamide | Int 1 + CAS# 122-96-3 | A | 545.5 | 546.1 |
| 309 | 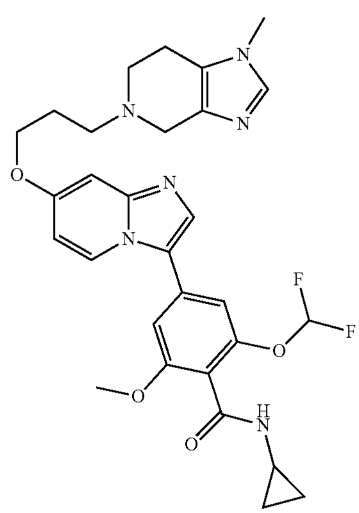 [SMILES: COc1cc(-c2cnc3cc(OCCCN4CCc5c(ncn5C)C4)ccn23)cc(OC(F)F)c1C(=O)NC1CC1] | N-cyclopropyl-2-(difluoromethoxy)-6-methoxy-4-[7-[3-(1-methyl-6,7-dihydro-4H-imidazo[4,5-c]pyridin-5-yl)propoxy]imidazo[1,2-a]pyridin-3-yl]benzamide | Cpd 333 + CAS# 87673-88-9 | M | 566.5 | 567.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 310 | 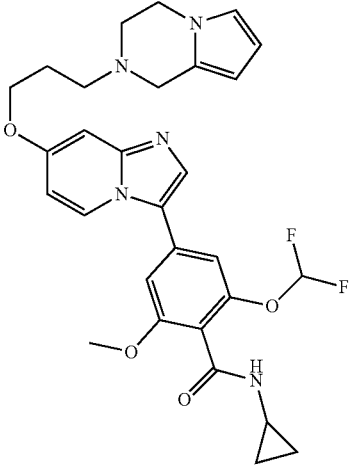 [SMILES: COc1cc(-c2cnc3cc(OCCCN4CCn5cccc5C4)ccn23)cc(OC(F)F)c1C(=O)NC1CC1] | N-cyclopropyl-2-(difluoromethoxy)-4-[7-[3-(3,4-dihydro-1H-pyrrolo[1,2-a]pyrazin-2-yl)propoxy]imidazo[1,2-a]pyridin-3-yl]-6-methoxy-benzamide | Cpd 333 + CAS# 71257-38-0 | M | 551.5 | 552.1 |
| 311 | 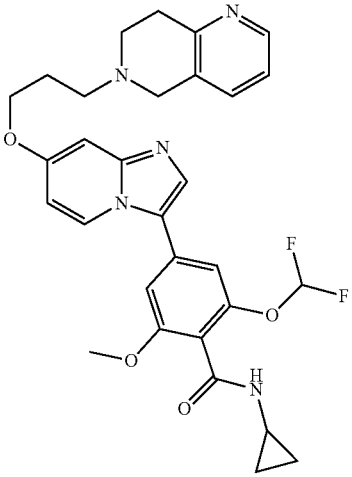 [SMILES: COc1cc(-c2cnc3cc(OCCCN4CCc5ncccc5C4)ccn23)cc(OC(F)F)c1C(=O)NC1CC1] | N-cyclopropyl-2-(difluoromethoxy)-4-[7-[3-(7,8-dihydro-5H-1,6-naphthyridin-6-yl)propoxy]imidazo[1,2-a]pyridin-3-yl]-6-methoxy-benzamide | Cpd 333 + CAS# 80957-68-2 | M | 563.5 | 564.1 |
| 312 | 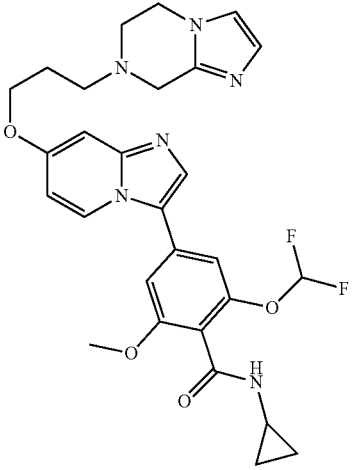 | N-cyclopropyl-2-(difluoromethoxy)-4-[7-[3-(6,8-dihydro-5H-imidazo[1,2-a]pyrazin-7-yl)propoxy]imidazo[1,2-a]pyridin-3-yl]-6-methoxy-benzamide | Cpd 333 + CAS# 91476-80-1 | M | 552.5 | 553.1 |

TABLE III-continued

Illustrative compounds of the invention.
SM = Starting Material, Mtd = Method, MS Mes'd = Measured mass

| Cpd# | Structure | Name | SM | Mtd | MW | MS Mes'd |
|---|---|---|---|---|---|---|
| 313 | 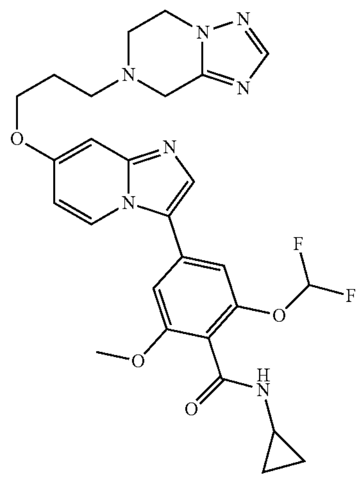 [SMILES: COc1cc(-c2cnc3cc(OCCCN4CCn5ncnc5C4)ccn23)cc(OC(F)F)c1C(=O)NC1CC1] | N-cyclopropyl-2-(difluoromethoxy)-4-[7-[3-(6,8-dihydro-5H-[1,2,4]triazolo[1,5-a]pyrazin-7-yl)propoxy]imidazo[1,2-a]pyridin-3-yl]-6-methoxy-benzamide | Cpd 333 + CAS# 874360-12-0 | M | 553.5 | 554.1 |
| 314 | 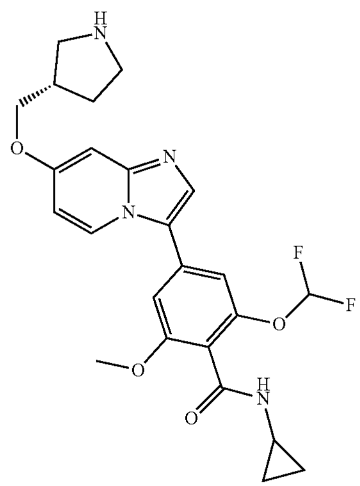 | N-cyclopropyl-2-(difluoromethoxy)-6-methoxy-4-[7-[[(3S)-pyrrolidin-3-yl]methoxy]imidazo[1,2-a]pyridin-3-yl]benzamide | Int 1 + CAS# 199174-24-8 | A + K1 | 472.4 | 473.1 |
| 315 | 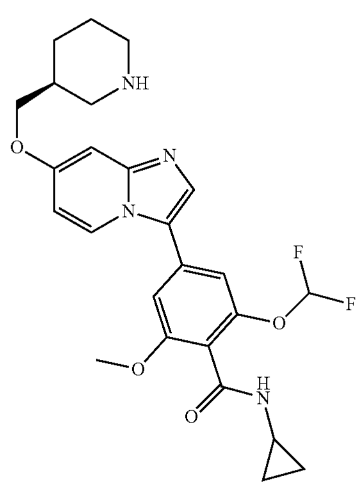 [SMILES: COc1cc(-c2cnc3cc(OC[C@H]4CCCNC4)ccn23)cc(OC(F)F)c1C(=O)NC1CC1] | N-cyclopropyl-2-(difluoromethoxy)-6-methoxy-4-[7-[[(3S)-3-piperidyl]methoxy]imidazo[1,2-a]pyridin-3-yl]benzamide | Int 1 + CAS# 140695-84-7 | A + K1 | 486.5 | 487.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 316 | 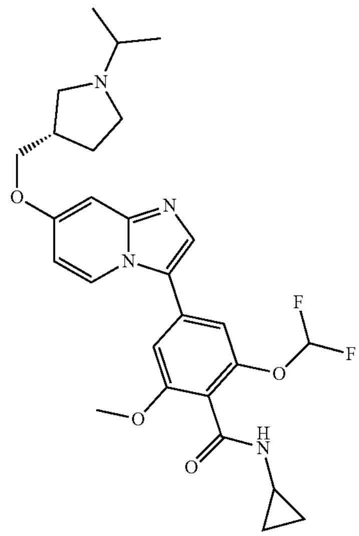 [SMILES: COc1cc(-c2cnc3cc(OC[C@H]4CCN(C(C)C)C4)ccn23)cc(OC(F)F)c1C(=O)NC1CC1] | N-cyclopropyl-2-(difluoromethoxy)-4-[7-[[(3S)-1-isopropylpyrrolidin-3-yl]methoxy]imidazo[1,2-a]pyridin-3-yl]-6-methoxy-benzamide | Cpd 314 + CAS# 67-64-1 | J1 | 514.5 | 515.1 |
| 317 | 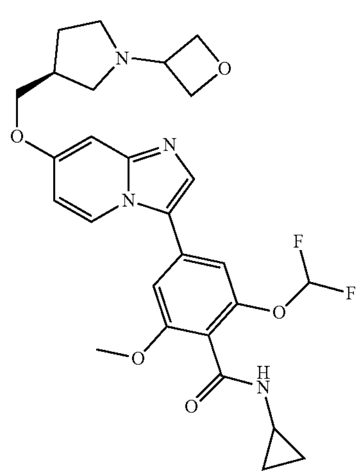 [SMILES: COc1cc(-c2cnc3cc(OC[C@H]4CCN(C5COC5)C4)ccn23)cc(OC(F)F)c1C(=O)NC1CC1] | N-cyclopropyl-2-(difluoromethoxy)-6-methoxy-4-[7-[[(3S)-1-(oxetan-3-yl)pyrrolidin-3-yl]methoxy]imidazo[1,2-a]pyridin-3-yl]benzamide | Cpd 314 + CAS# 6704-31-0 | J1 | 528.5 | 529.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|------|-----------|------|-----|-----|-----|----------|
| 318 | 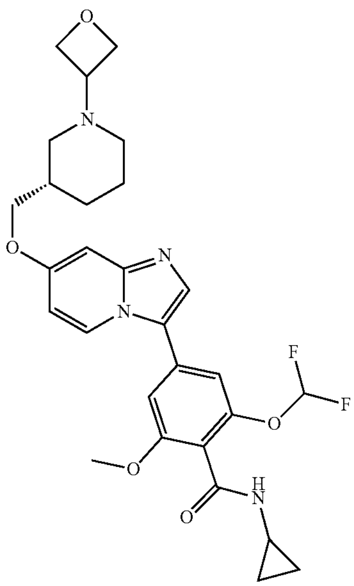 [SMILES: COc1cc(-c2cnc3cc(OC[C@H]4CCCN(C5COC5)C4)ccn23)cc(OC(F)F)c1C(=O)NC1CC1] | N-cyclopropyl-2-(difluoromethoxy)-6-methoxy-4-[7-[[(3S)-1-(oxetan-3-yl)-3-piperidyl]methoxy]imidazo[1,2-a]pyridin-3-yl]benzamide | Cpd 315 + CAS# 6704-31-0 | J1 | 542.5 | 543.1 |
| 319 | 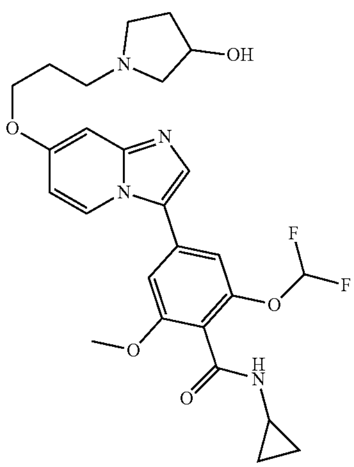 [SMILES: COc1cc(-c2cnc3cc(OCCCN4CCC(O)C4)ccn23)cc(OC(F)F)c1C(=O)NC1CC1] | N-cyclopropyl-2-(difluoromethoxy)-4-[7-[3-(3-hydroxypyrrolidin-1-yl)propoxy]imidazo[1,2-a]pyridin-3-yl]-6-methoxy-benzamide | Cpd 333 + CAS# 40499-83-0 | M | 516.5 | 517.1 |
| 320 | 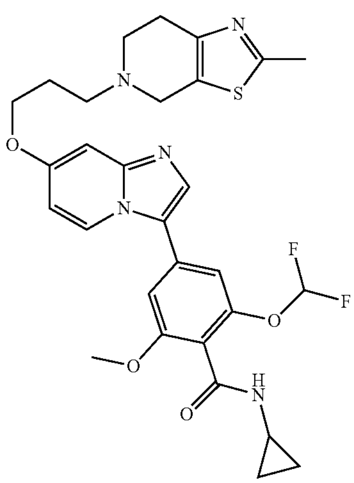 [SMILES: COc1cc(-c2cnc3cc(OCCCN4CCc5nc(C)sc5C4)ccn23)cc(OC(F)F)c1C(=O)NC1CC1] | N-cyclopropyl-2-(difluoromethoxy)-6-methoxy-4-[7-[3-(2-methyl-6,7-dihydro-4H-thiazolo[5,4-c]pyridin-5-yl)propoxy]imidazo[1,2-a]pyridin-3-yl]benzamide | Cpd 333 + CAS# 124458-27-1 | M | 583.6 | 584.0 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 321 | 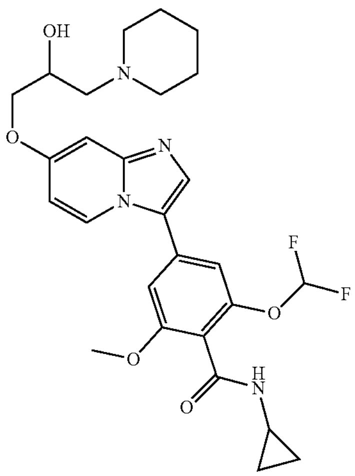 [SMILES: COc1cc(-c2cnc3cc(OCC(O)CN4CCCCC4)ccn23)cc(OC(F)F)c1C(=O)NC1CC1] | N-cyclopropyl-2-(difluoromethoxy)-4-[7-[2-hydroxy-3-(1-piperidyl)propoxy]imidazo[1,2-a]pyridin-3-yl]-6-methoxy-benzamide | Int 92 + CAS# 110-89-4 | 0 | 530.5 | 531.1 |
| 322 | 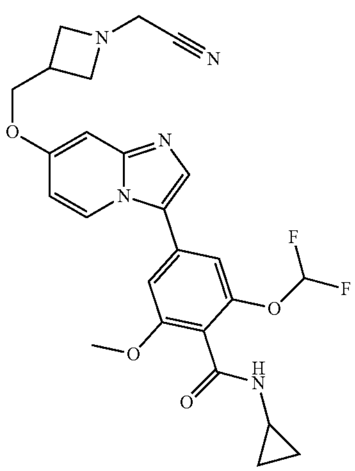 [SMILES: COc1cc(-c2cnc3cc(OCC4CN(CC#N)C4)ccn23)cc(OC(F)F)c1C(=O)NC1CC1] | 4-[7-[[1-(cyanomethyl)azetidin-3-yl]methoxy]imidazo[1,2-a]pyridin-3-yl]-N-cyclopropyl-2-(difluoromethoxy)-6-methoxy-benzamide | Int 1 | Ex. 2.104 | 497.4 | 498.0 |
| 323 | 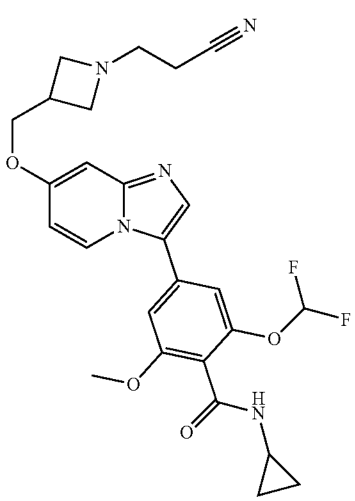 [SMILES: COc1cc(-c2cnc3cc(OCC4CN(CCC#N)C4)ccn23)cc(OC(F)F)c1C(=O)NC1CC1] | 4-[7-[[1-(2-cyanoethyl)azetidin-3-yl]methoxy]imidazo[1,2-a]pyridin-3-yl]-N-cyclopropyl-2-(difluoromethoxy)-6-methoxy-benzamide | Int 1 | Ex. 2.105 | 511.5 | 512.0 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 324 | 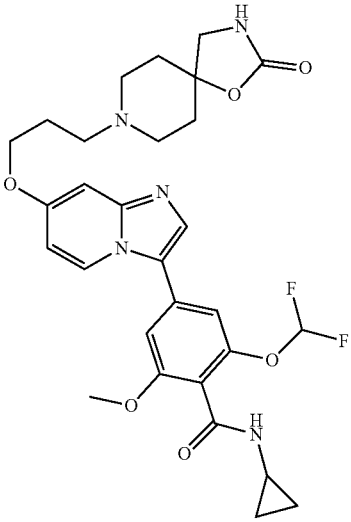 [SMILES: COc1cc(-c2cnc3cc(OCCCN4CCC5(CC4)CNC(=O)O5)ccn23)cc(OC(F)F)c1C(=O)NC1CC1] | N-cyclopropyl-2-(difluoromethoxy)-6-methoxy-4-[7-[3-(2-oxo-1-oxa-3,8-diazaspiro[4.5]decan-8-yl)propoxy]imidazo[1,2-a]pyridin-3-yl]benzamide | Cpd 333 + CAS# 5052-96-0 | M | 585.5 | 586.6 |
| 325 | 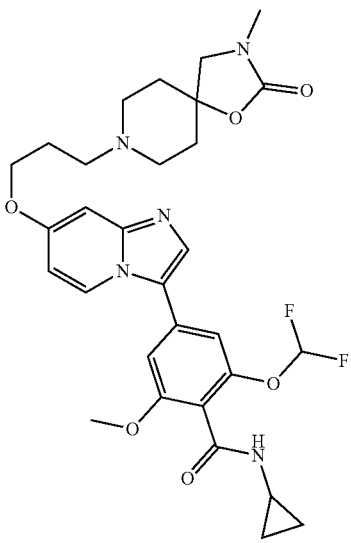 [SMILES: COc1cc(-c2cnc3cc(OCCCN4CCC5(CC4)CN(C)C(=O)O5)ccn23)cc(OC(F)F)c1C(=O)NC1CC1] | N-cyclopropyl-2-(difluoromethoxy)-6-methoxy-4-[7-[3-(3-methyl-2-oxo-1-oxa-3,8-diazaspiro[4.5]decan-8-yl)propoxy]imidazo[1,2-a]pyridin-3-yl]benzamide | Cpd 333 + CAS# 613675-34-6 | M | 599.6 | 600.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 326 | 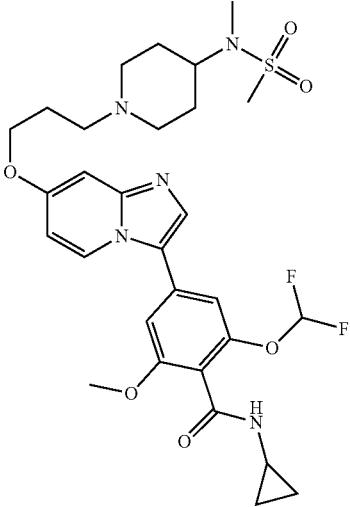 [SMILES: COc1cc(-c2cnc3cc(OCCCN4CCC(N(C)S(C)(=O)=O)CC4)ccn23)cc(OC(F)F)c1C(=O)NC1CC1] | N-cyclopropyl-2-(difluoromethoxy)-6-methoxy-4-[7-[3-[4-[methyl(methylsulfonyl)amino]-1-piperidyl]propoxy]imidazo[1,2-a]pyridin-3-yl]benzamide | Cpd 333 + CAS# 70724-74-2 | M | 621.6 | 622.1 |
| 327 | 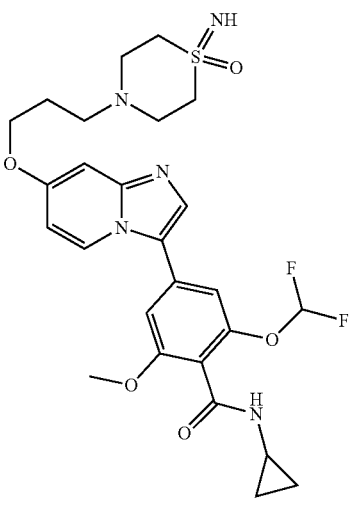 [SMILES: COc1cc(-c2cnc3cc(OCCCN4CCS(=N)(=O)CC4)ccn23)cc(OC(F)F)c1C(=O)NC1CC1] | N-cyclopropyl-2-(difluoromethoxy)-4-[7-[3-(1-imino-1-oxo-1,4-thiazinan-4-yl)propoxy]imidazo[1,2-a]pyridin-3-yl]-6-methoxy-benzamide | Cpd 333 + CAS# 1633667-60-3 | M | 563.6 | 564.0 |
| 328 | 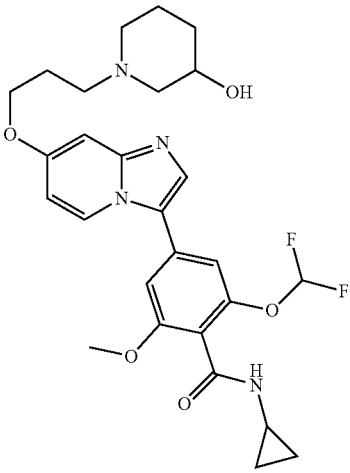 [SMILES: COc1cc(-c2cnc3cc(OCCCN4CCCC(O)C4)ccn23)cc(OC(F)F)c1C(=O)NC1CC1] | N-cyclopropyl-2-(difluoromethoxy)-4-[7-[3-(3-hydroxy-1-piperidyl)propoxy]imidazo[1,2-a]pyridin-3-yl]-6-methoxy-benzamide | Cpd 333 + CAS# 6859-99-0 | M | 530.5 | 531.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 329 | 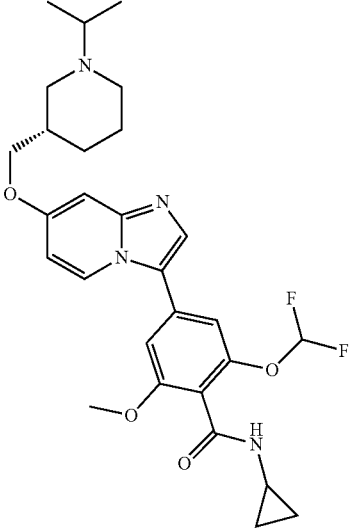 [SMILES: COc1cc(-c2cnc3cc(OC[C@H]4CCCN(C(C)C)C4)ccn23)cc(OC(F)F)c1C(=O)NC1CC1] | N-cyclopropyl-2-(difluoromethoxy)-4-[7-[[(3S)-1-isopropyl-3-piperidyl]methoxy]imidazo[1,2-a]pyridin-3-yl]-6-methoxy-benzamide | Cpd 315 + CAS# 67-64-1 | J1 | 528.5 | 529.2 |
| 330 | 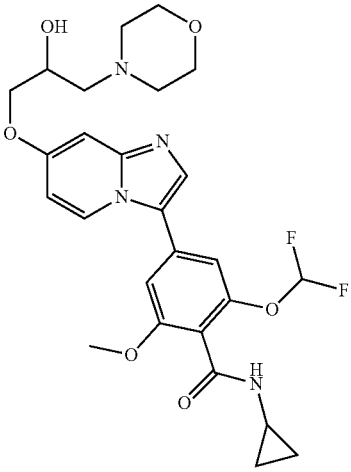 [SMILES: COc1cc(-c2cnc3cc(OCC(O)CN4CCOCC4)ccn23)cc(OC(F)F)c1C(=O)NC1CC1] | N-cyclopropyl-2-(difluoromethoxy)-4-[7-(2-hydroxy-3-morpholino-propoxy)imidazo[1,2-a]pyridin-3-yl]-6-methoxy-benzamide | Int 92 + CAS# 110-91-8 | 0 | 532.5 | 533.1 |
| 331 | 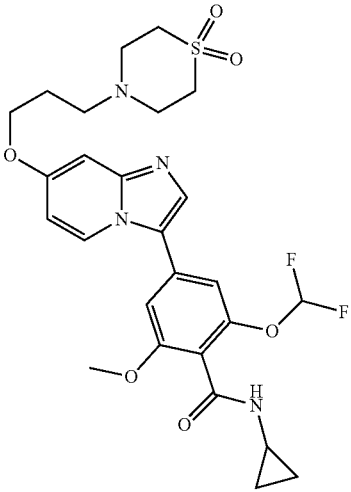 [SMILES: COc1cc(-c2cnc3cc(OCCCN4CCS(=O)(=O)CC4)ccn23)cc(OC(F)F)c1C(=O)NC1CC1] | N-cyclopropyl-2-(difluoromethoxy)-4-[7-[3-(1,1-dioxo-1,4-thiazinan-4-yl)propoxy]imidazo[1,2-a]pyridin-3-yl]-6-methoxy-benzamide | Cpd 333 + CAS# 39093-93-1 | M | 564.6 | 565.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 332 | 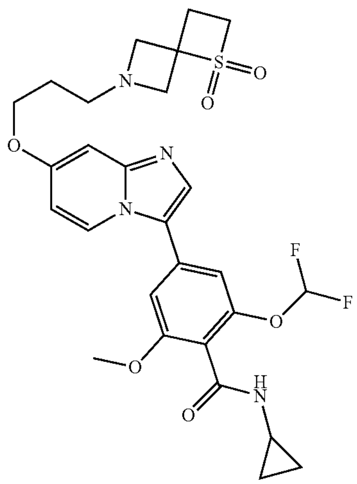 [SMILES: COc1cc(-c2cnc3cc(OCCCN4CC5(CCS5(=O)=O)C4)ccn23)cc(OC(F)F)c1C(=O)NC1CC1] | N-cyclopropyl-2-(difluoromethoxy)-4-[7-[3-(1,1-dioxo-1$\lambda^6$-thia-6-azaspiro[3.3]heptan-6-yl)propoxy]imidazo[1,2-a]pyridin-3-yl]-6-methoxy-benzamide | Cpd 333 + CAS# 1427358-97-1 | M | 576.6 | 577.1 |
| 333 | 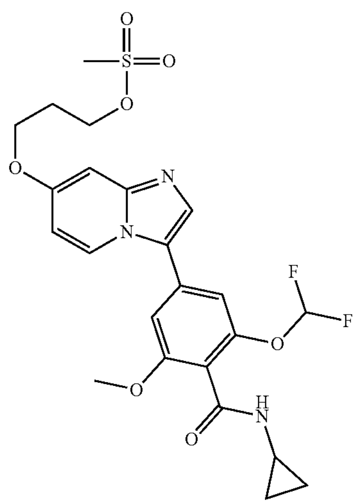 [SMILES: COc1cc(-c2cnc3cc(OCCCOS(C)(=O)=O)ccn23)cc(OC(F)F)c1C(=O)NC1CC1] | 3-[3-[4-(cyclopropylcarbamoyl)-3-(difluoromethoxy)-5-methoxy-phenyl]imidazo[1,2-a]pyridin-7-yl]oxypropyl methanesulfonate | Int 1 | Ex. 2.106 | 525.5 | 526.1 |
| 334 | 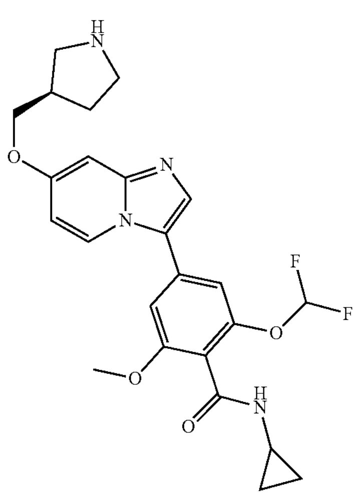 [SMILES: COc1cc(-c2cnc3cc(OC[C@@H]4CCNC4)ccn23)cc(OC(F)F)c1C(=O)NC1CC1] | N-cyclopropyl-2-(difluoromethoxy)-6-methoxy-4-[7-[[(3R)-pyrrolidin-3-yl]methoxy]imidazo[1,2-a]pyridin-3-yl]benzamide | Int 1 + CAS# 138108-72-2 | A + K1 | 472.4 | 473.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 335 | 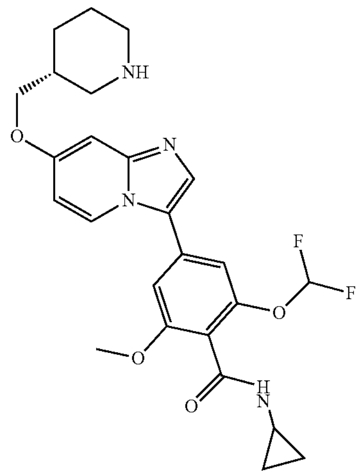 [SMILES: COc1cc(-c2cnc3cc(OC[C@@H]4CCCNC4)ccn23)cc(OC(F)F)c1C(=O)NC1CC1] | N-cyclopropyl-2-(difluoromethoxy)-6-methoxy-4-[7-[[(3R)-3-piperidyl]methoxy]imidazo[1,2-a]pyridin-3-yl]benzamide | Int 1 + CAS# 140695-85-8 | A + K1 | 486.5 | 487.1 |
| 336 | 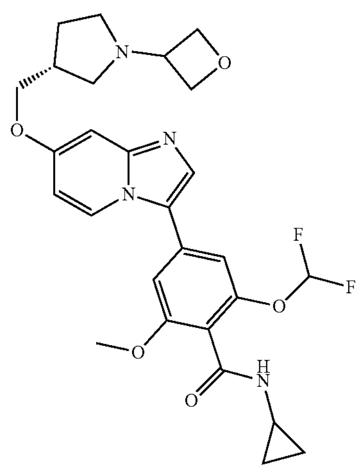 [SMILES: COc1cc(-c2cnc3cc(OC[C@@H]4CCN(C5COC5)C4)ccn23)cc(OC(F)F)c1C(=O)NC1CC1] | N-cyclopropyl-2-(difluoromethoxy)-6-methoxy-4-[7-[[(3R)-1-(oxetan-3-yl)pyrrolidin-3-yl]methoxy]imidazo[1,2-a]pyridin-3-yl]benzamide | Cpd 334 + CAS# 6704-31-0 | J1 | 528.5 | 529.1 |
| 337 | 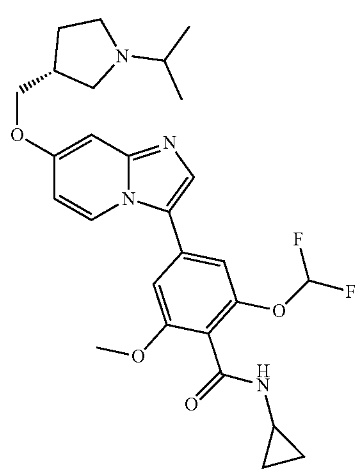 [SMILES: COc1cc(-c2cnc3cc(OC[C@@H]4CCN(C(C)C)C4)ccn23)cc(OC(F)F)c1C(=O)NC1CC1] | N-cyclopropyl-2-(difluoromethoxy)-4-[7-[[(3R)-1-isopropylpyrrolidin-3-yl]methoxy]imidazo[1,2-a]pyridin-3-yl]-6-methoxy-benzamide | Cpd 334 + CAS# 67-64-1 | J1 | 514.5 | 515.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 338 | 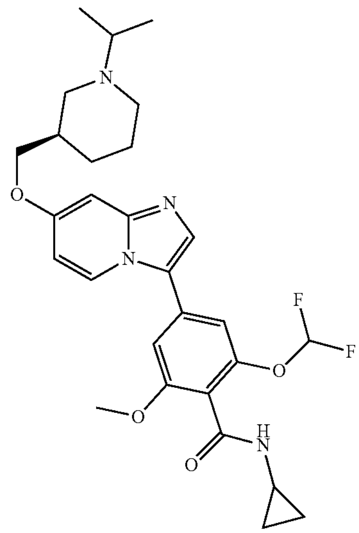 [SMILES: COc1cc(-c2cnc3cc(OC[C@@H]4CCCN(C(C)C)C4)ccn23)cc(OC(F)F)c1C(=O)NC1CC1] | N-cyclopropyl-2-(difluoromethoxy)-4-[7-[[(3R)-1-isopropyl-3-piperidyl]methoxy]imidazo[1,2-a]pyridin-3-yl]-6-methoxy-benzamide | Cpd 335 + CAS# 67-64-1 | J1 | 528.5 | 529.1 |
| 339 | 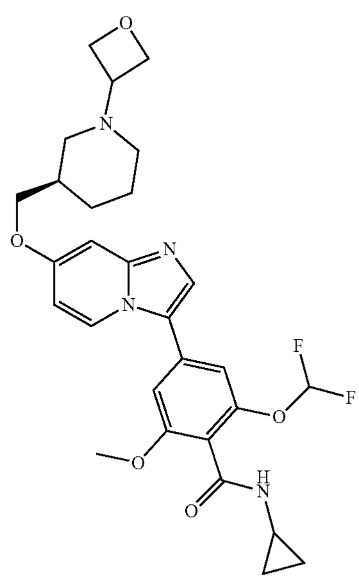 [SMILES: COc1cc(-c2cnc3cc(OC[C@@H]4CCCN(C5COC5)C4)ccn23)cc(OC(F)F)c1C(=O)NC1CC1] | N-cyclopropyl-2-(difluoromethoxy)-6-methoxy-4-[7-[[(3R)-1-(oxetan-3-yl)-3-piperidyl]methoxy]imidazo[1,2-a]pyridin-3-yl]benzamide | Cpd 335 + CAS# 6704-31-0 | J1 | 542.5 | 543.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 340 | 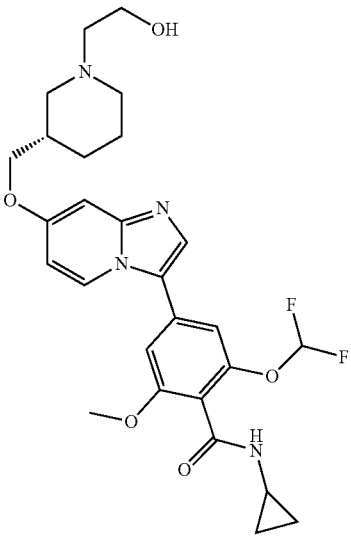 [SMILES: COc1cc(-c2cnc3cc(OC[C@H]4CCCN(CCO)C4)ccn23)cc(OC(F)F)c1C(=O)NC1CC1] | N-cyclopropyl-2-(difluoromethoxy)-4-[7-[[(3S)-1-(2-hydroxyethyl)-3-piperidyl]methoxy]imidazo[1,2-a]pyridin-3-yl]-6-methoxy-benzamide | Cpd 315 | Ex. 2.109 | 530.5 | 531.1 |
| 341 | 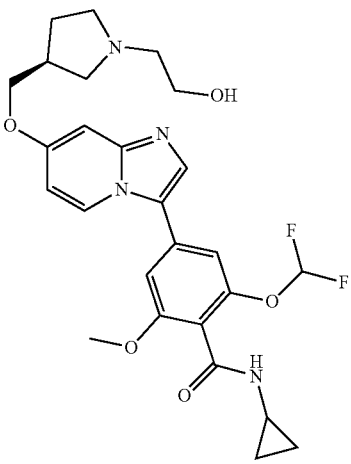 [SMILES: COc1cc(-c2cnc3cc(OC[C@H]4CCN(CCO)C4)ccn23)cc(OC(F)F)c1C(=O)NC1CC1] | N-cyclopropyl-2-(difluoromethoxy)-4-[7-[[(3S)-1-(2-hydroxyethyl)pyrrolidin-3-yl]methoxy]imidazo[1,2-a]pyridin-3-yl]-6-methoxy-benzamide | Cpd 314 | Ex. 2.110 | 516.5 | 517.1 |
| 342 | 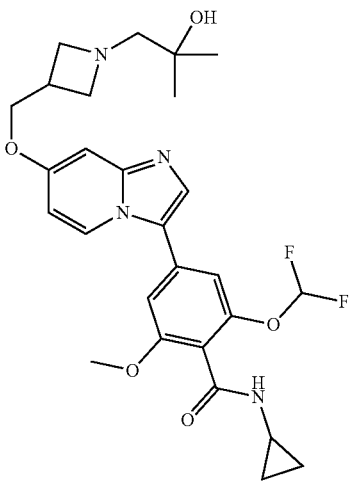 [SMILES: COc1cc(-c2cnc3cc(OCC4CN(CC(C)(C)O)C4)ccn23)cc(OC(F)F)c1C(=O)NC1CC1] | N-cyclopropyl-2-(difluoromethoxy)-4-[7-[[1-(2-hydroxy-2-methyl-propyl)azetidin-3-yl]methoxy]imidazo[1,2-a]pyridin-3-yl]-6-methoxy-benzamide | Int 93 + CAS# 558-30-5 | Ex. 2.111 | 530.5 | 531.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 343 | 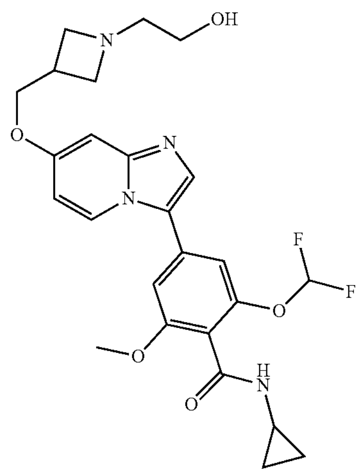 [SMILES: COc1cc(-c2cnc3cc(OCC4CN(CCO)C4)ccn23)cc(OC(F)F)c1C(=O)NC1CC1] | N-cyclopropyl-2-(difluoromethoxy)-4-[7-[[1-(2-hydroxyethyl)azetidin-3-yl]methoxy]imidazo[1,2-a]pyridin-3-yl]-6-methoxy-benzamide | Int 93 + CAS# 102191-92-4 | Ex. 2.112 | 502.5 | 503.1 |
| 344 | 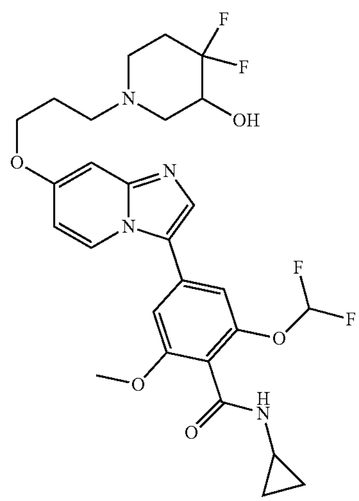 [SMILES: COc1cc(-c2cnc3cc(OCCCN4CCC(F)(F)C(O)C4)ccn23)cc(OC(F)F)c1C(=O)NC1CC1] | N-cyclopropyl-4-[7-[3-(4,4-difluoro-3-hydroxy-1-piperidyl)propoxy]imidazo[1,2-a]pyridin-3-yl]-2-(difluoromethoxy)-6-methoxy-benzamide | Cpd 333 + CAS# 1186688-54-9 | M | 566.5 | 567.1 |
| 345 | 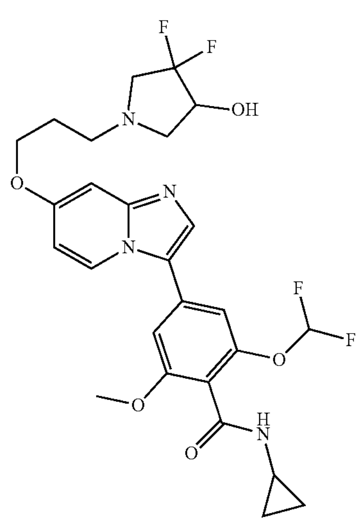 [SMILES: COc1cc(-c2cnc3cc(OCCCN4CC(O)C(F)(F)C4)ccn23)cc(OC(F)F)c1C(=O)NC1CC1] | N-cyclopropyl-4-[7-[3-(3,3-difluoro-4-hydroxy-pyrrolidin-1-yl)propoxy]imidazo[1,2-a]pyridin-3-yl]-2-(difluoromethoxy)-6-methoxy-benzamide | Cpd 333 + CAS# 1638764-82-5 | M | 552.5 | 553.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 346 | 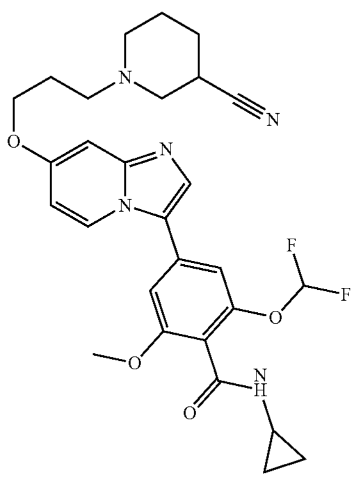 [SMILES: COc1cc(-c2cnc3cc(OCCCN4CCCC(C#N)C4)ccn23)cc(OC(F)F)c1C(=O)NC1CC1] | 4-[7-[3-(3-cyano-1-piperidyl)propoxy]imidazo[1,2-a]pyridin-3-yl]-N-cyclopropyl-2-(difluoromethoxy)-6-methoxy-benzamide | Cpd 333 + CAS# 7492-88-8 | M | 539.5 | 540.1 |
| 347 | 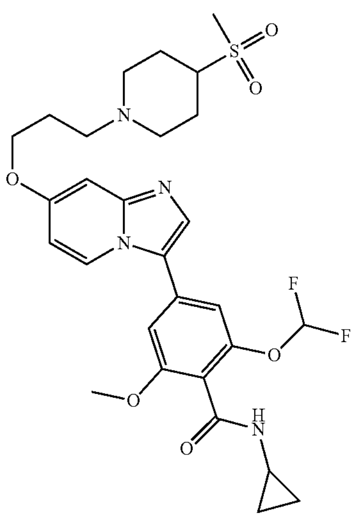 [SMILES: COc1cc(-c2cnc3cc(OCCCN4CCC(S(C)(=O)=O)CC4)ccn23)cc(OC(F)F)c1C(=O)NC1CC1] | N-cyclopropyl-2-(difluoromethoxy)-6-methoxy-4-[7-[3-(4-methylsulfonyl-1-piperidyl)propoxy]imidazo[1,2-a]pyridin-3-yl]benzamide | Cpd 333 + CAS# 290328-55-1 | M | 592.6 | 593.0 |
| 348 | 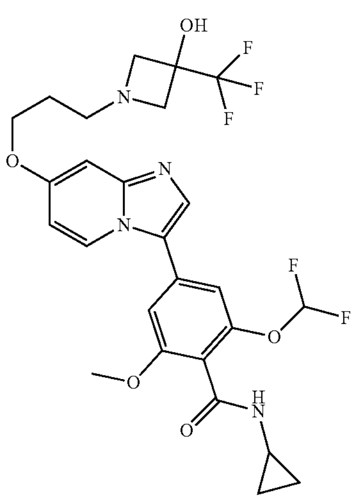 [SMILES: COc1cc(-c2cnc3cc(OCCCN4CC(O)(C(F)(F)F)C4)ccn23)cc(OC(F)F)c1C(=O)NC1CC1] | N-cyclopropyl-2-(difluoromethoxy)-4-[7-[3-[3-hydroxy-3-(trifluoromethyl)azetidin-1-yl]propoxy]imidazo[1,2-a]pyridin-3-yl]-6-methoxy-benzamide | Cpd 333 + CAS# 848192-96-1 | M | 570.5 | 571.0 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 349 | 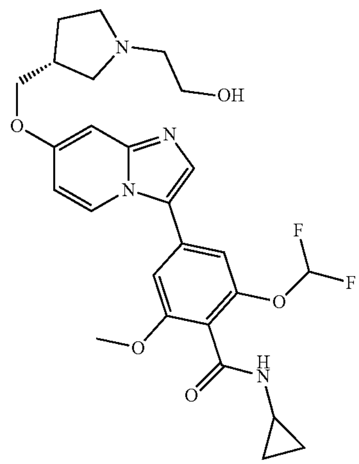 [SMILES: COc1cc(-c2cnc3cc(OC[C@@H]4CCN(CCO)C4)ccn23)cc(OC(F)F)c1C(=O)NC1CC1] | N-cyclopropyl-2-(difluoromethoxy)-4-[7-[[(3R)-1-(2-hydroxyethyl)pyrrolidin-3-yl]methoxy]imidazo[1,2-a]pyridin-3-yl]-6-methoxy-benzamide | Cpd 334 | Ex. 2.113 | 516.5 | 517.1 |
| 350 | 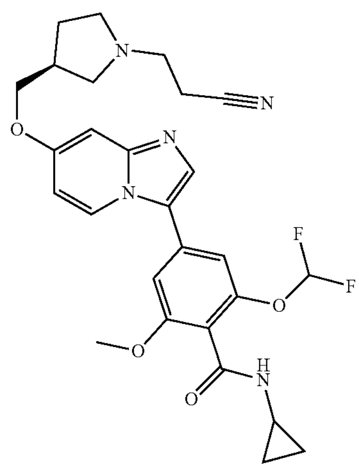 [SMILES: COc1cc(-c2cnc3cc(OC[C@H]4CCN(CCC#N)C4)ccn23)cc(OC(F)F)c1C(=O)NC1CC1] | 4-[7-[[(3S)-1-(2-cyanoethyl)pyrrolidin-3-yl]methoxy]imidazo[1,2-a]pyridin-3-yl]-N-cyclopropyl-2-(difluoromethoxy)-6-methoxy-benzamide | Cpd 314 + CAS# 107-13-1 | L | 525.5 | 526.1 |
| 351 | 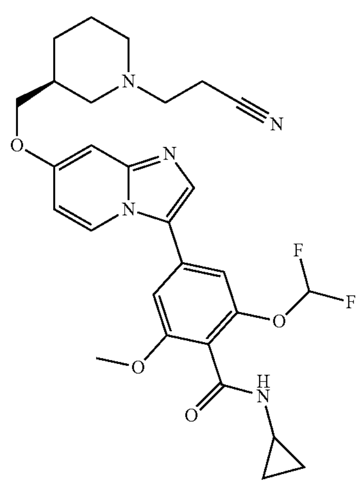 [SMILES: COc1cc(-c2cnc3cc(OC[C@H]4CCCN(CCC#N)C4)ccn23)cc(OC(F)F)c1C(=O)NC1CC1] | 4-[7-[[(3S)-1-(2-cyanoethyl)-3-piperidyl]methoxy]imidazo[1,2-a]pyridin-3-yl]-N-cyclopropyl-2-(difluoromethoxy)-6-methoxy-benzamide | Cpd 315 + CAS# 107-13-1 | L | 539.5 | 540.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 352 | 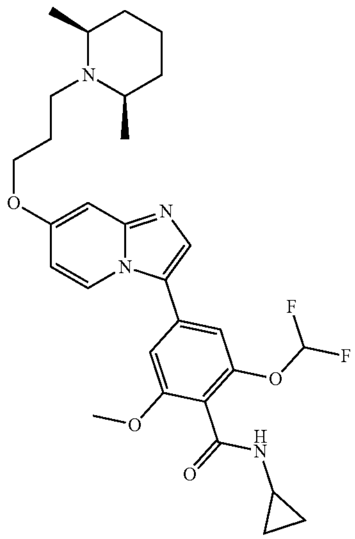 [SMILES: COc1cc(-c2cnc3cc(OCCCN4[C@H](C)CCC[C@@H]4C)ccn23)cc(OC(F)F)c1C(=O)NC1CC1] | N-cyclopropyl-2-(difluoromethoxy)-4-[7-[3-[(2R,6S)-2,6-dimethyl-1-piperidyl]propoxy]imidazo[1,2-a]pyridin-3-yl]-6-methoxy-benzamide | Cpd 333 + CAS# 766-17-6 | M | 542.6 | 543.1 |
| 353 | 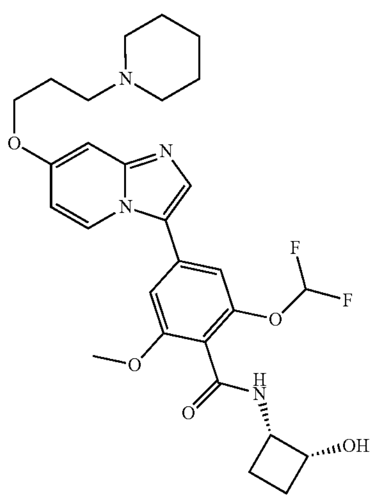 [SMILES: COc1cc(-c2cnc3cc(OCCCN4CCCCC4)ccn23)cc(OC(F)F)c1C(=O)N[C@H]1CC[C@H]1O] | 2-(difluoromethoxy)-6-methoxy-4-[7-[3-(1-piperidyl)propoxy]imidazo[1,2-a]pyridin-3-yl]-N-[(1S,2R)-2-hydroxycyclobutyl]benzamide/2-(difluoromethoxy)-N-[(1R,2S)-2-hydroxycyclobutyl]-6-methoxy-4-[7-[3-(1-piperidyl)propoxy]imidazo[1,2-a]pyridin-3-yl]benzamide mixture | Int 94 + CAS# 2070860-49-8 | N | 544.5 | 545.5 |

+

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 354 | 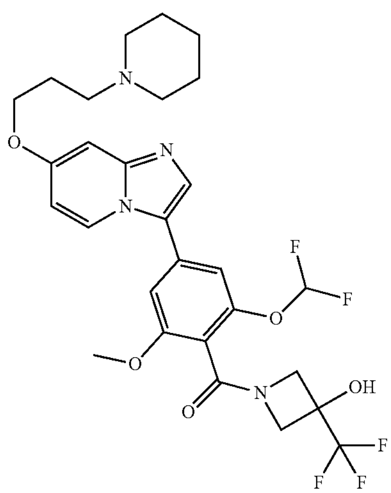 [SMILES: COc1cc(-c2cnc3cc(OCCCN4CCCCC4)ccn23)cc(OC(F)F)c1C(=O)N1CC(O)(C(F)(F)F)C1] | [2-(difluoromethoxy)-6-methoxy-4-[7-[3-(1-piperidyl)propoxy]imidazo[1,2-a]pyridin-3-yl]phenyl]-[3-hydroxy-3-(trifluoromethyl)azetidin-1-yl]methanone | Int 94 + CAS# 848192-96-1 | N | 598.5 | 599.5 |
| 355 | 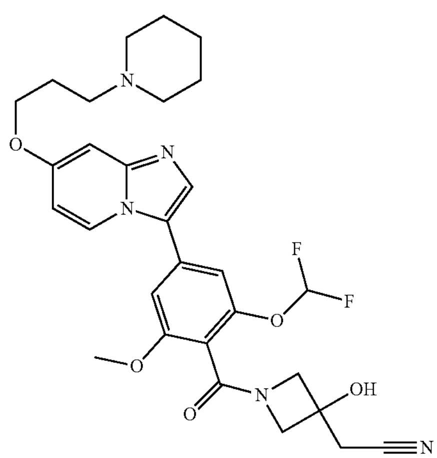 [SMILES: COc1cc(-c2cnc3cc(OCCCN4CCCCC4)ccn23)cc(OC(F)F)c1C(=O)N1CC(O)(CC#N)C1] | 2-[1-[2-(difluoromethoxy)-6-methoxy-4-[7-[3-(1-piperidyl)propoxy]imidazo[1,2-a]pyridin-3-yl]benzoyl]-3-hydroxy-azetidin-3-yl]acetonitrile | Int 94 + CAS# 1803604-94-5 | N | 569.5 | 570.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 356 | 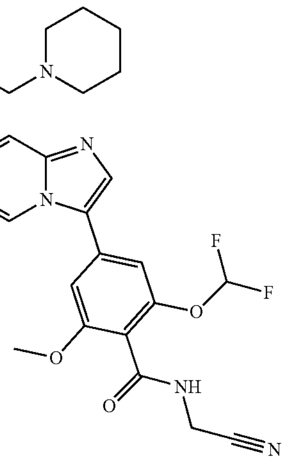 | N-(cyanomethyl)-2-(difluoromethoxy)-6-methoxy-4-[7-[3-(1-piperidyl)propoxy]imidazo[1,2-a]pyridin-3-yl]benzamide | Int 94 + CAS# 6011-14-9 | N | 513.5 | 514.5 |
| 357 | 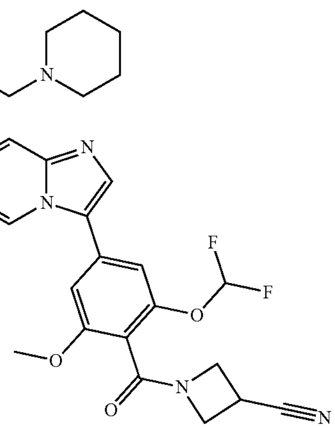 | 1-[2-(difluoromethoxy)-6-methoxy-4-[7-[3-(1-piperidyl)propoxy]imidazo[1,2-a]pyridin-3-yl]benzoyl]azetidine-3-carbonitrile | Int 94 + CAS# 345954-83-8 | N | 539.5 | 540.5 |
| 358 | 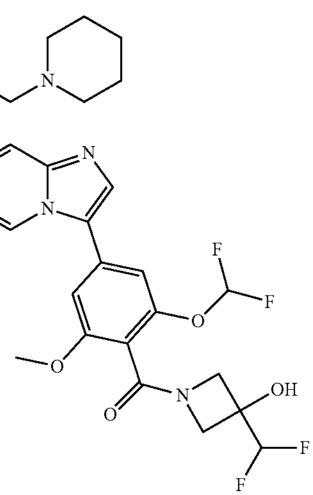 | [2-(difluoromethoxy)-6-methoxy-4-[7-[3-(1-piperidyl)propoxy]imidazo[1,2-a]pyridin-3-yl]phenyl]-[3-(difluoromethyl)-3-hydroxy-azetidin-1-yl]methanone | Int 94 + CAS# 72320-39-9 | N | 580.5 | 581.5 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 359 | | 2-(difluoromethoxy)-N-[(1R,2R)-2-hydroxycyclobutyl]-6-methoxy-4-[7-[3-(1-piperidyl)propoxy]imidazo[1,2-a]pyridin-3-yl]benzamide/2-(difluoromethoxy)-N-[(1S,2S)-2-hydroxycyclobutyl]-6-methoxy-4-[7-[3-(1-piperidyl)propoxy]imidazo[1,2-a]pyridin-3-yl]benzamide mixture | Int 94 + CAS# 72320-39-9 | N | 544.5 | 545.5 |
| 360 | 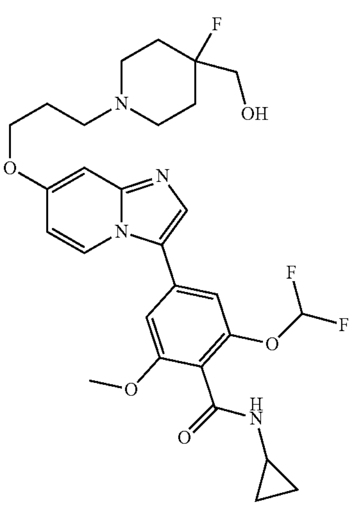 [SMILES: COc1cc(-c2cnc3cc(OCCCN4CCC(F)(CO)CC4)ccn23)cc(OC(F)F)c1C(=O)NC1CC1] | N-cyclopropyl-2-(difluoromethoxy)-4-[7-[3-[4-fluoro-4-(hydroxymethyl)-1-piperidyl]propoxy]imidazo[1,2-a]pyridin-3-yl]-6-methoxy-benzamide | Cpd 333 + CAS# 1254115-16-6 | M | 562.5 | 563.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 361 | 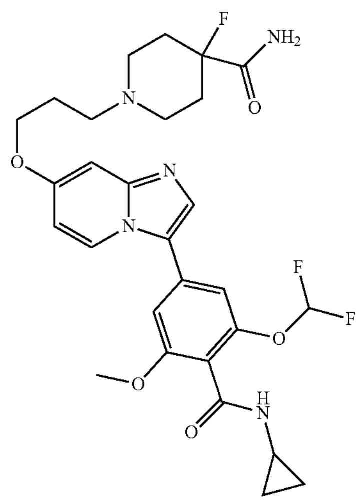 [SMILES: COc1cc(-c2cnc3cc(OCCCN4CCC(F)(C(N)=O)CC4)ccn23)cc(OC(F)F)c1C(=O)NC1CC1] | 1-[3-[3-[4-(cyclopropylcarbamoyl)-3-(difluoromethoxy)-5-methoxy-phenyl]imidazo[1,2-a]pyridin-7-yl]oxypropyl]-4-fluoro-piperidine-4-carboxamide | Cpd 363 | Ex. 2.114 | 575.5 | 576.1 |
| 362 | 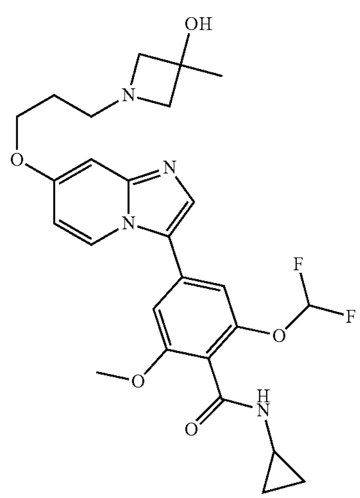 [SMILES: COc1cc(-c2cnc3cc(OCCCN4CC(C)(O)C4)ccn23)cc(OC(F)F)c1C(=O)NC1CC1] | N-cyclopropyl-2-(difluoromethoxy)-4-[7-[3-(3-hydroxy-3-methyl-azetidin-1-yl)propoxy]imidazo[1,2-a]pyridin-3-yl]-6-methoxy-benzamide | Cpd 333 + CAS# 124668-46-8 | M | 516.5 | 517.1 |
| 363 | 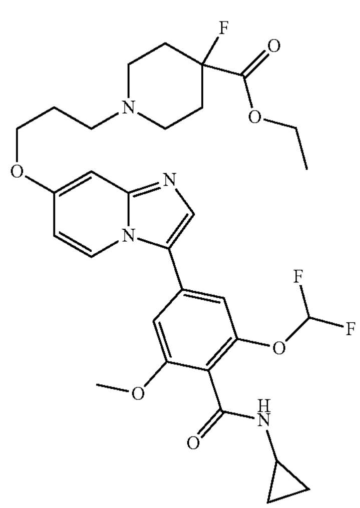 [SMILES: CCOC(=O)C1(F)CCN(CCCOc2ccn3c(-c4cc(OC)c(C(=O)NC5CC5)c(OC(F)F)c4)cnc3c2)CC1] | ethyl 1-[3-[3-[4-(cyclopropylcarbamoyl)-3-(difluoromethoxy)-5-methoxy-phenyl]imidazo[1,2-a]pyridin-7-yl]oxypropyl]-4-fluoro-piperidine-4-carboxylate | Cpd 333 + CAS# 845909-49-1 | Ex. 2.115 | 604.6 | 605.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 364 | 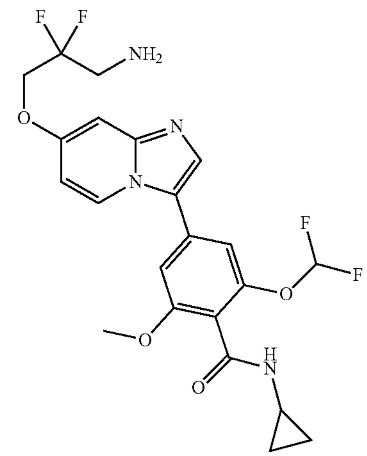 [SMILES: COc1cc(-c2cnc3cc(OCC(F)(F)CN)ccn23)cc(OC(F)F)c1C(=O)NC1CC1] | 4-[7-(3-amino-2,2-difluoro-propoxy)imidazo[1,2-a]pyridin-3-yl]-N-cyclopropyl-2-(difluoromethoxy)-6-methoxy-benzamide | Int 1 + CAS# 155310-11-5 | A | 482.4 | 483.0 |
| 365 | 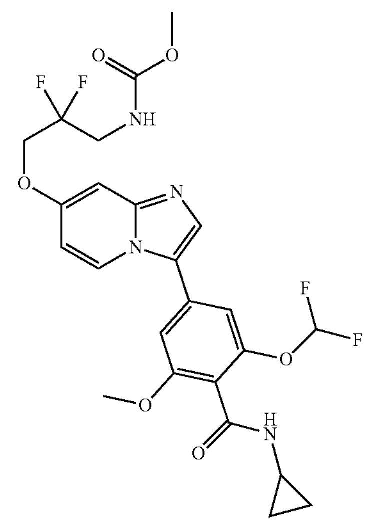 [SMILES: COC(=O)NCC(F)(F)COc1ccn2c(-c3cc(OC)c(C(=O)NC4CC4)c(OC(F)F)c3)cnc2c1] | methyl N-[3-[3-[4-(cyclopropylcarbamoyl)-3-(difluoromethoxy)-5-methoxy-phenyl]imidazo[1,2-a]pyridin-7-yl]oxy-2,2-difluoro-propyl]carbamate | Cpd 364 + CAS# 155310-11-5 | Ex. 2.116 | 540.4 | 541.1 |
| 366 | 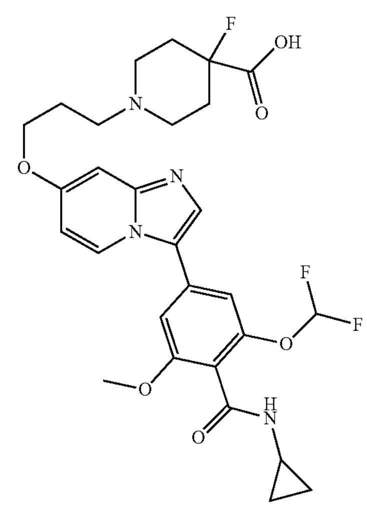 [SMILES: COc1cc(-c2cnc3cc(OCCCN4CCC(F)(C(=O)O)CC4)ccn23)cc(OC(F)F)c1C(=O)NC1CC1] | 1-[3-[3-[4-(cyclopropylcarbamoyl)-3-(difluoromethoxy)-5-methoxy-phenyl]imidazo[1,2-a]pyridin-7-yl]oxypropyl]-4-fluoro-piperidine-4-carboxylic acid | Cpd 363 | Ex. 2.117 | 576.5 | 577.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 367 | 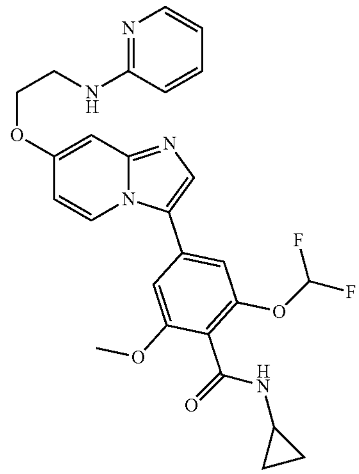 [SMILES: COc1cc(-c2cnc3cc(OCCNc4ccccn4)ccn23)cc(OC(F)F)c1C(=O)NC1CC1] | N-cyclopropyl-2-(difluoromethoxy)-6-methoxy-4-[7-[2-(2-pyridylamino)ethoxy]imidazo[1,2-a]pyridin-3-yl]benzamide | Int 1 + CAS# 89943-04-4 | A | 509.5 | 510.0 |
| 368 | 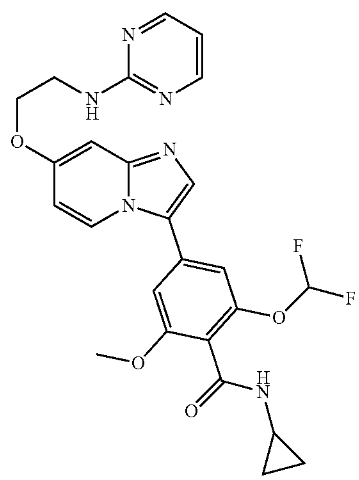 [SMILES: COc1cc(-c2cnc3cc(OCCNc4ncccn4)ccn23)cc(OC(F)F)c1C(=O)NC1CC1] | N-cyclopropyl-2-(difluoromethoxy)-6-methoxy-4-[7-[2-(pyrimidin-2-ylamino)ethoxy]imidazo[1,2-a]pyridin-3-yl]benzamide | Int 1 + CAS# 1640-87-5 | A | 510.4 | 511.0 |
| 369 | 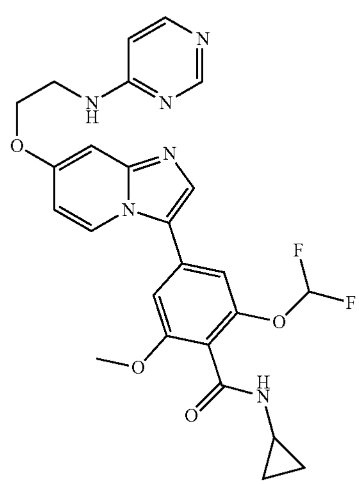 [SMILES: COc1cc(-c2cnc3cc(OCCNc4ccncn4)ccn23)cc(OC(F)F)c1C(=O)NC1CC1] | N-cyclopropyl-2-(difluoromethoxy)-6-methoxy-4-[7-[2-(pyrimidin-4-ylamino)ethoxy]imidazo[1,2-a]pyridin-3-yl]benzamide | Int 1 + CAS# 1640-87-5 | A | 510.4 | 511.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 370 | 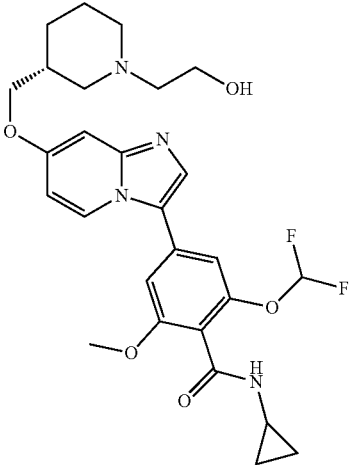 [SMILES: COc1cc(-c2cnc3cc(OC[C@@H]4CCCN(CCO)C4)ccn23)cc(OC(F)F)c1C(=O)NC1CC1] | N-cyclopropyl-2-(difluoromethoxy)-4-[7-[[(3R)-1-(2-hydroxyethyl)-3-piperidyl]methoxy]imidazo[1,2-a]pyridin-3-yl]-6-methoxy-benzamide | Cpd 335 + CAS# 102191-92-4 | Ex. 2.118 | 530.5 | 531.2 |
| 371 | 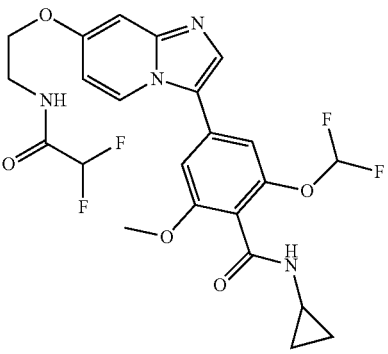 [SMILES: COc1cc(-c2cnc3cc(OCCNC(=O)C(F)F)ccn23)cc(OC(F)F)c1C(=O)NC1CC1] | N-cyclopropyl-4-[7-[2-[(2,2-difluoroacetyl)amino]ethoxy]imidazo[1,2-a]pyridin-3-yl]-2-(difluoromethoxy)-6-methoxy-benzamide | Int 1 + CAS# 141-43-5 + CAS# 381-73-7 | Ex. 2.119 | 510.4 | 511.1 |
| 372 | 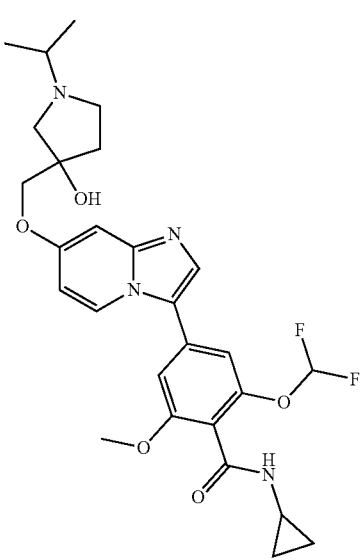 [SMILES: COc1cc(-c2cnc3cc(OCC4(O)CCN(C(C)C)C4)ccn23)cc(OC(F)F)c1C(=O)NC1CC1] | N-cyclopropyl-2-(difluoromethoxy)-4-[7-[(3-hydroxy-1-isopropyl-pyrrolidin-3-yl)methoxy]imidazo[1,2-a]pyridin-3-yl]-6-methoxy-benzamide | Int 96 + CAS# 301226-25-5 | Ex. 2.120 | 530.5 | 531.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 373 | | N-cyclopropyl-2-(difluoromethoxy)-4-[7-[[(3R,4S)-4-hydroxy-3-piperidyl]methoxy]imidazo[1,2-a]pyridin-3-yl]-6-methoxy-benzamide/ N-cyclopropyl-2-(difluoromethoxy)-4-[7-[[(3S,4R)-4-hydroxy-3-piperidyl]methoxy]imidazo[1,2-a]pyridin-3-yl]-6-methoxy-benzamide mixture | Int 1 + Int 95 | Ex. 2.121 | 502.5 | 503.1 |
| 374 | 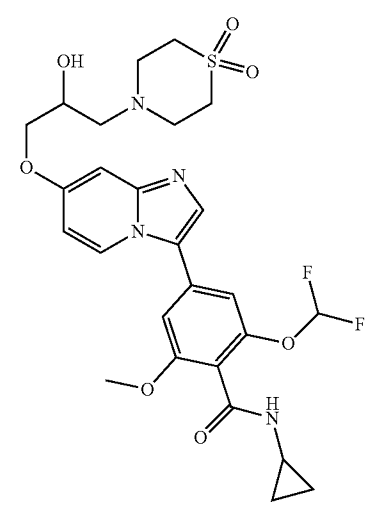 [SMILES: COc1cc(-c2cnc3cc(OCC(O)CN4CCS(=O)(=O)CC4)ccn23)cc(OC(F)F)c1C(=O)NC1CC1] | N-cyclopropyl-2-(difluoromethoxy)-4-[7-[3-(1,1-dioxo-1,4-thiazinan-4-yl)-2-hydroxy-propoxy]imidazo[1,2-a]pyridin-3-yl]-6-methoxy-benzamide | Int 92 + CAS# 39093-93-1 | O | 580.6 | 581.1 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 375 | 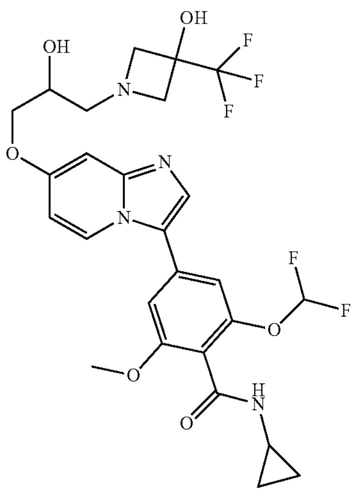 [SMILES: COc1cc(-c2cnc3cc(OCC(O)CN4CC(O)(C(F)(F)F)C4)ccn23)cc(OC(F)F)c1C(=O)NC1CC1] | N-cyclopropyl-2-(difluoromethoxy)-4-[7-[2-hydroxy-3-[3-hydroxy-3-(trifluoromethyl)azetidin-1-yl]propoxy]imidazo[1,2-a]pyridin-3-yl]-6-methoxy-benzamide | Int 92 + CAS# 848192-96-1 | O | 586.5 | 587.1 |
| 376 | 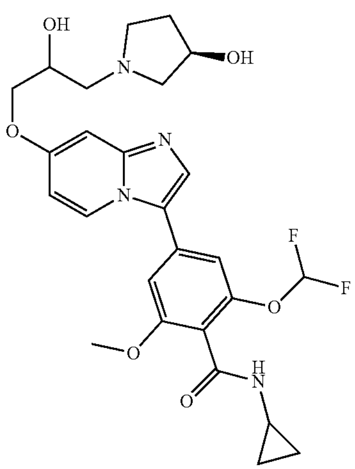 [SMILES: COc1cc(-c2cnc3cc(OCC(O)CN4CC[C@@H](O)C4)ccn23)cc(OC(F)F)c1C(=O)NC1CC1] | N-cyclopropyl-2-(difluoromethoxy)-4-[7-[2-hydroxy-3-[(3R)-3-hydroxypyrrolidin-1-yl]propoxy]imidazo[1,2-a]pyridin-3-yl]-6-methoxy-benzamide | Int 92 + CAS# 2799-21-5 | O | 532.5 | 533.1 |
| 377 | 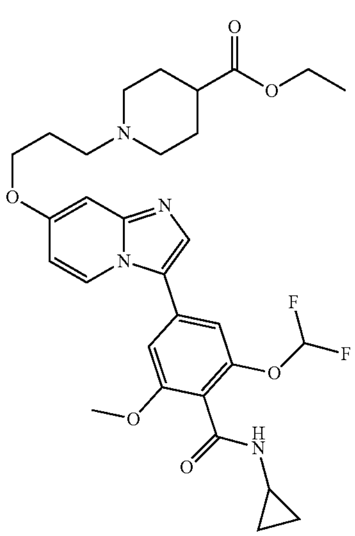 [SMILES: CCOC(=O)C1CCN(CCCOc2ccn3c(-c4cc(OC)c(C(=O)NC5CC5)c(OC(F)F)c4)cnc3c2)CC1] | ethyl 1-[3-[3-[4-(cyclopropylcarbamoyl)-3-(difluoromethoxy)-5-methoxy-phenyl]imidazo[1,2-a]pyridin-7-yl]oxypropyl]piperidine-4-carboxylate | Cpd 333 + CAS# 1126-09-6 | M | 586.6 | 587.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 378 | 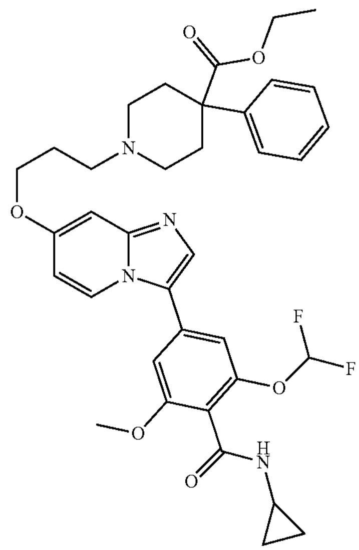 [SMILES: CCOC(=O)C1(c2ccccc2)CCN(CCCOc2ccn3c(-c4cc(OC)c(C(=O)NC5CC5)c(OC(F)F)c4)cnc3c2)CC1] | ethyl 1-[3-[3-[4-(cyclopropylcarbamoyl)-3-(difluoromethoxy)-5-methoxy-phenyl]imidazo[1,2-a]pyridin-7-yl]oxypropyl]-4-phenyl-piperidine-4-carboxylate | Cpd 333 + CAS# 77-17-8 | M | 662.7 | 663.2 |
| 379 | 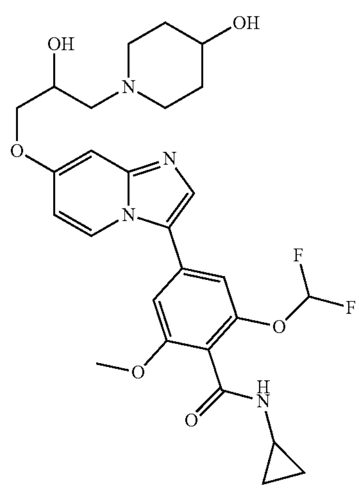 [SMILES: COc1cc(-c2cnc3cc(OCC(O)CN4CCC(O)CC4)ccn23)cc(OC(F)F)c1C(=O)NC1CC1] | N-cyclopropyl-2-(difluoromethoxy)-4-[7-[2-hydroxy-3-(4-hydroxy-1-piperidyl)propoxy]imidazo[1,2-a]pyridin-3-yl]-6-methoxy-benzamide | Int 92 + CAS# 5382-16-1 | O | 546.5 | 547.1 |
| 380 | 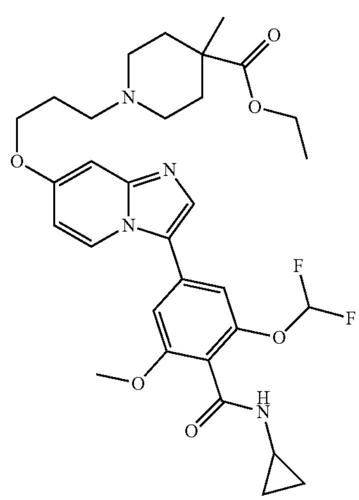 [SMILES: CCOC(=O)C1(C)CCN(CCCOc2ccn3c(-c4cc(OC)c(C(=O)NC5CC5)c(OC(F)F)c4)cnc3c2)CC1] | ethyl 1-[3-[3-[4-(cyclopropylcarbamoyl)-3-(difluoromethoxy)-5-methoxy-phenyl]imidazo[1,2-a]pyridin-7-yl]oxypropyl]-4-methyl-piperidine-4-carboxylate | Cpd 333 + CAS# 225240-71-1 | M | 600.6 | 601.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 381 | 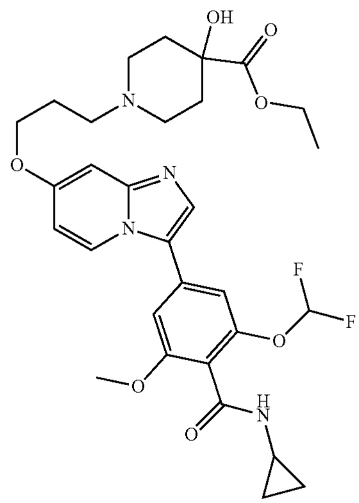 [SMILES: CCOC(=O)C1(O)CCN(CCCOc2ccn3c(-c4cc(OC)c(C(=O)NC5CC5)c(OC(F)F)c4)cnc3c2)CC1] | ethyl 1-[3-[3-[4-(cyclopropylcarbamoyl)-3-(difluoromethoxy)-5-methoxy-phenyl]imidazo[1,2-a]pyridin-7-yl]oxypropyl]-4-hydroxy-piperidine-4-carboxylate | Cpd 333 + CAS# 937063-36-0 | M | 602.6 | 603.2 |
| 382 | 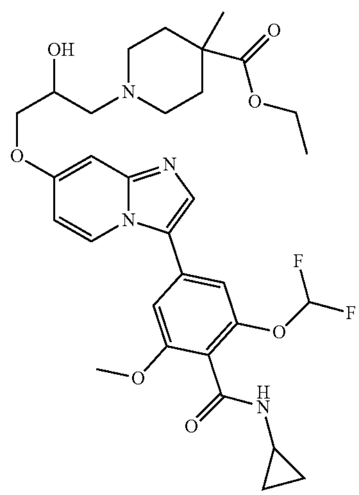 [SMILES: CCOC(=O)C1(C)CCN(CC(O)COc2ccn3c(-c4cc(OC)c(C(=O)NC5CC5)c(OC(F)F)c4)cnc3c2)CC1] | ethyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]-4-methyl-piperidine-4-carboxylate | Int 92 + CAS# 225240-71-1 | O | 616.6 | 617.2 |
| 383 | 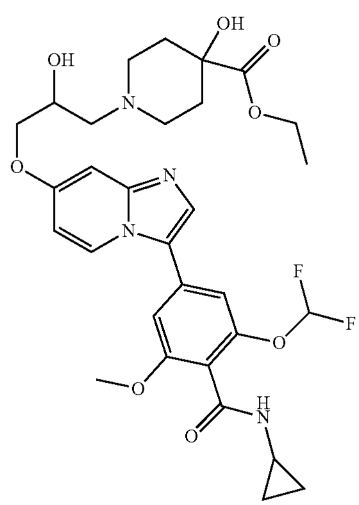 [SMILES: CCOC(=O)C1(O)CCN(CC(O)COc2ccn3c(-c4cc(OC)c(C(=O)NC5CC5)c(OC(F)F)c4)cnc3c2)CC1] | ethyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]-4-hydroxy-piperidine-4-carboxylate | Int 92 + CAS# 937063-36-0 | O | 618.6 | 619.2 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 384 | 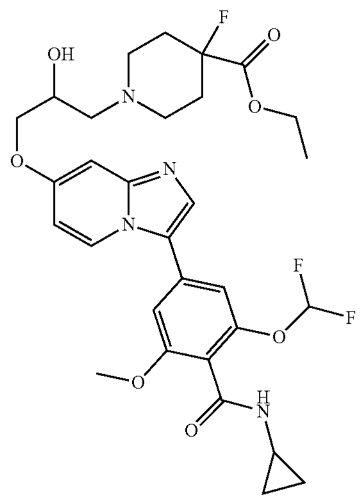 [SMILES: CCOC(=O)C1(F)CCN(CC(O)COc2ccn3c(-c4cc(OC)c(C(=O)NC5CC5)c(OC(F)F)c4)cnc3c2)CC1] | ethyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]-4-fluoro-piperidine-4-carboxylate | Int 92 + CAS# 845909-49-1 | O | 620.6 | 621.6 |
| 385 | 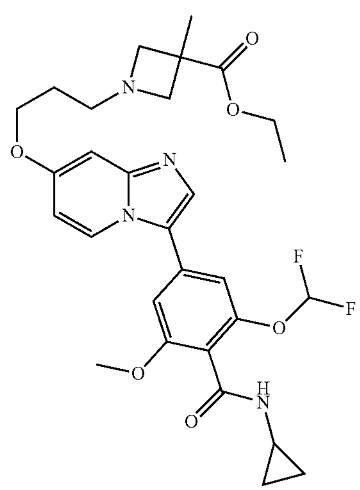 [SMILES: CCOC(=O)C1(C)CN(CCCOc2ccn3c(-c4cc(OC)c(C(=O)NC5CC5)c(OC(F)F)c4)cnc3c2)C1] | ethyl 1-[3-[3-[4-(cyclopropylcarbamoyl)-3-(difluoromethoxy)-5-methoxy-phenyl]imidazo[1,2-a]pyridin-7-yl]oxypropyl]-3-methyl-azetidine-3-carboxylate | Cpd 333 + CAS# 2126161-82-6 | M | 572.6 | 573.7 |
| 386 | first eluting | N-cyclopropyl-2-(difluoromethoxy)-4-[7-(2-hydroxy-3-morpholino-propoxy)imidazo[1,2-a]pyridin-3-yl]-6-methoxy-benzamide | Cpd 330 | Ex. 2.123 | 532.5 | 533.3 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 387 | 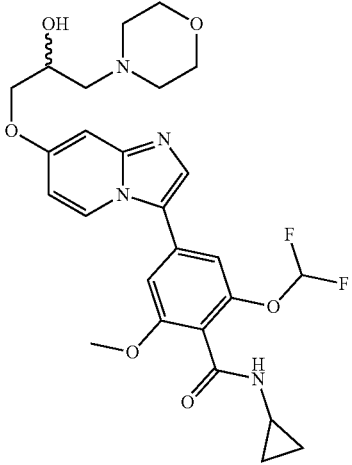 second eluting | N-cyclopropyl-2-(difluoromethoxy)-4-[7-(2-hydroxy-3-morpholino-propoxy)imidazo[1,2-a]pyridin-3-yl]-6-methoxy-benzamide | Cpd 330 | Ex. 2.123 | 532.5 | 533.3 |
| 388 | 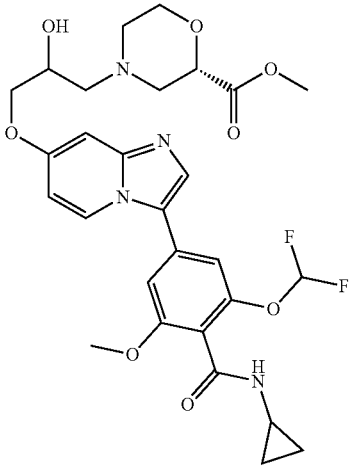 [SMILES: COC(=O)[C@@H]1CN(CC(O)COc2ccn3c(-c4cc(OC)c(C(=O)NC5CC5)c(OC(F)F)c4)cnc3c2)CCO1] | methyl (2S)-4-[3-[3-[4-(cyclopropylcarbamoyl)-3-(difluoromethoxy)-5-methoxy-phenyl]imidazo[1,2-a]pyridin-7-yl]oxy-2-hydroxy-propyl]morpholine-2-carboxylate | Int 92 + CAS# 1417789-45-7 | O | 590.5 | 591.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 389 | 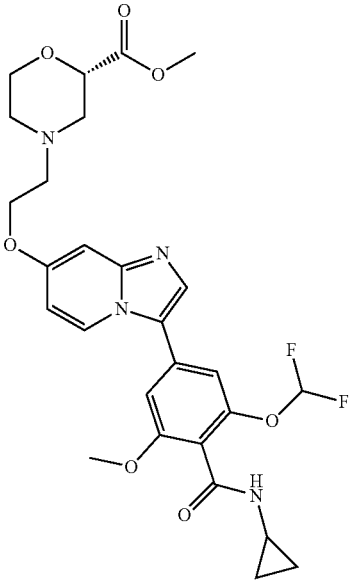 [SMILES: COC(=O)[C@@H]1CN(CCOc2ccn3c(-c4cc(OC)c(C(=O)NC5CC5)c(OC(F)F)c4)cnc3c2)CCO1] | methyl (2S)-4-[2-[3-[4-(cyclopropylcarbamoyl)-3-(difluoromethoxy)-5-methoxy-phenyl]imidazo[1,2-a]pyridin-7-yl]oxyethyl]morpholine-2-carboxylate | Int 98 + CAS# 1417789-45-7 | M | 560.5 | 561.6 |
| 390 | 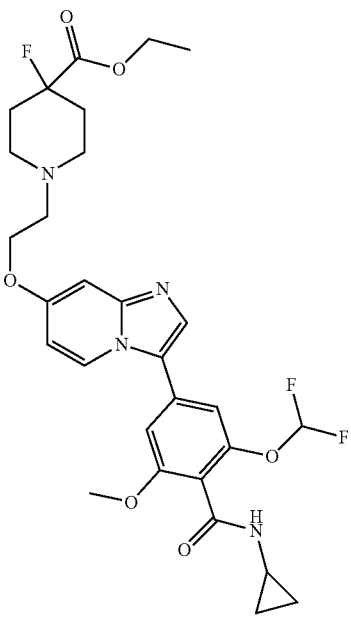 [SMILES: CCOC(=O)C1(F)CCN(CCOc2ccn3c(-c4cc(OC)c(C(=O)NC5CC5)c(OC(F)F)c4)cnc3c2)CC1] | ethyl 1-[2-[3-[4-(cyclopropylcarbamoyl)-3-(difluoromethoxy)-5-methoxy-phenyl]imidazo[1,2-a]pyridin-7-yl]oxyethyl]-4-fluoro-piperidine-4-carboxylate | Int 98 + CAS# 845909-49-1 | M | 590.6 | 591.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 391 | 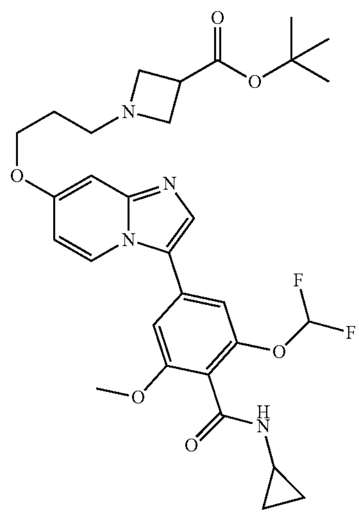 [SMILES: COc1cc(-c2cnc3cc(OCCCN4CC(C(=O)OC(C)(C)C)C4)ccn23)cc(OC(F)F)c1C(=O)NC1CC1] | tert-butyl 1-[3-[3-[4-(cyclopropylcarbamoyl)-3-(difluoromethoxy)-5-methoxy-phenyl]imidazo[1,2-a]pyridin-7-yl]oxypropyl]azetidine-3-carboxylate | Cpd 333 + CAS# 53871-08-2 | M | 586.6 | 587.7 |
| 392 | 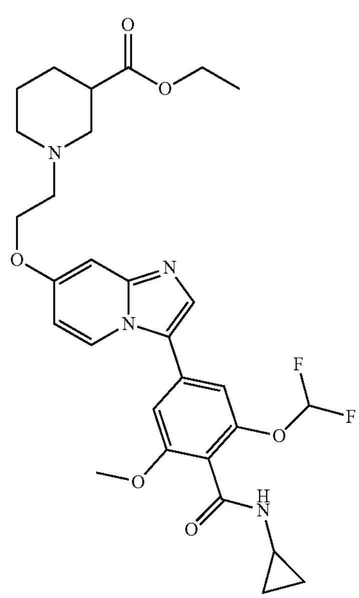 [SMILES: CCOC(=O)C1CCCN(CCOc2ccn3c(-c4cc(OC)c(C(=O)NC5CC5)c(OC(F)F)c4)cnc3c2)C1] | ethyl 1-[2-[3-[4-(cyclopropylcarbamoyl)-3-(difluoromethoxy)-5-methoxy-phenyl]imidazo[1,2-a]pyridin-7-yl]oxyethyl]piperidine-3-carboxylate | Int 98 + CAS# 5006-62-2 | M | 572.6 | 573.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 393 | 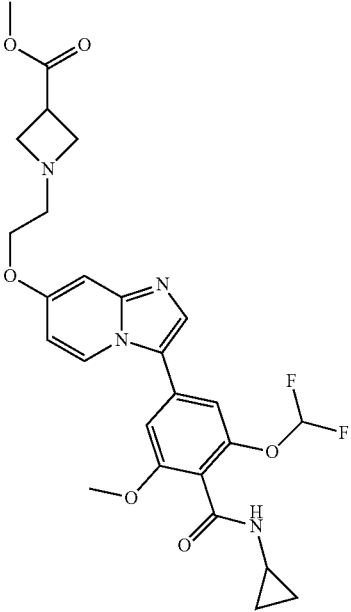 [SMILES: COC(=O)C1CN(CCOc2ccn3c(-c4cc(OC)c(C(=O)NC5CC5)c(OC(F)F)c4)cnc3c2)C1] | methyl 1-[2-[3-[4-(cyclopropylcarbamoyl)-3-(difluoromethoxy)-5-methoxy-phenyl]imidazo[1,2-a]pyridin-7-yl]oxyethyl]azetidine-3-carboxylate | Int 98 + CAS# 100202-39-9 | M | 530.5 | 531.6 |
| 394 | 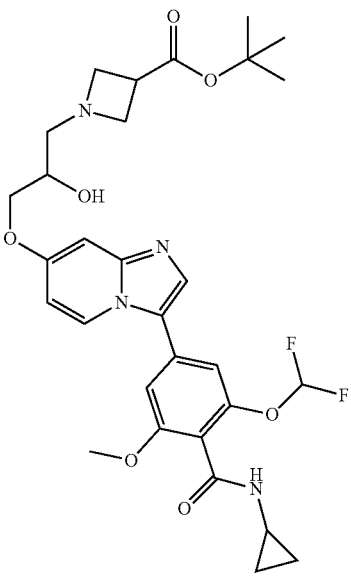 [SMILES: COc1cc(-c2cnc3cc(OCC(O)CN4CC(C(=O)OC(C)(C)C)C4)ccn23)cc(OC(F)F)c1C(=O)NC1CC1] | tert-butyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]azetidine-3-carboxylate | Int 92 + CAS# 53871-08-2 | O | 602.6 | 603.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 395 | 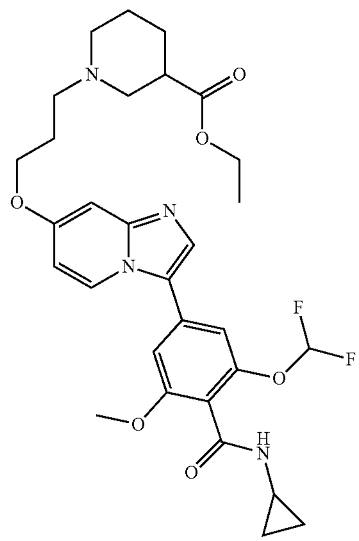 [SMILES: CCOC(=O)C1CCCN(CCCOc2ccn3c(-c4cc(OC)c(C(=O)NC5CC5)c(OC(F)F)c4)cnc3c2)C1] | ethyl 1-[3-[3-[4-(cyclopropylcarbamoyl)-3-(difluoromethoxy)-5-methoxy-phenyl]imidazo[1,2-a]pyridin-7-yl]oxypropyl]piperidine-3-carboxylate | Cpd 333 + CAS# 5006-62-2 | M | 586.6 | 587.6 |
| 396 | 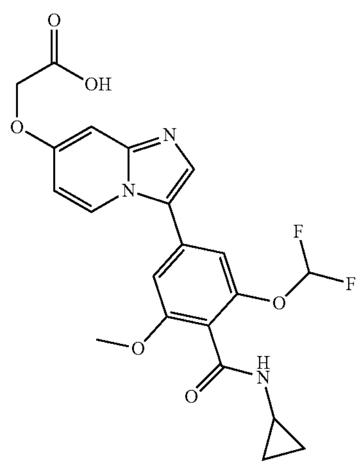 [SMILES: COc1cc(-c2cnc3cc(OCC(=O)O)ccn23)cc(OC(F)F)c1C(=O)NC1CC1] | 2-[3-[4-(cyclopropylcarbamoyl)-3-(difluoromethoxy)-5-methoxy-phenyl]imidazo[1,2-a]pyridin-7-yl]oxyacetic acid | Cpd 268 | Ex. 2.122 | 447.4 | 448.5 |
| 397 | 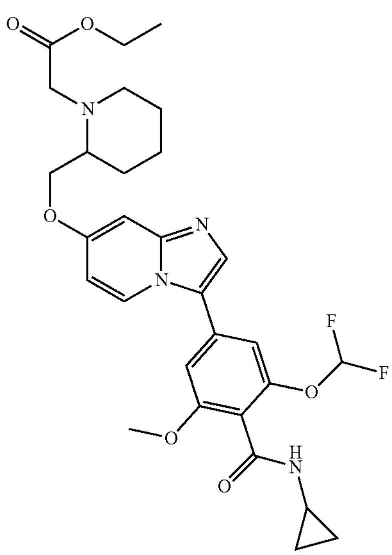 [SMILES: CCOC(=O)CN1CCCCC1COc1ccn2c(-c3cc(OC)c(C(=O)NC4CC4)c(OC(F)F)c3)cnc2c1] | ethyl 2-[2-[[3-[4-(cyclopropylcarbamoyl)-3-(difluoromethoxy)-5-methoxy-phenyl]imidazo[1,2-a]pyridin-7-yl]oxymethyl]-1-piperidyl]acetate | Int 1 + CAS# 3433-37-2 + CAS# 924-44-7 | Ex. 2.124 | 572.6 | 573.6 |

TABLE III-continued

Illustrative compounds of the invention.
SM = Starting Material, Mtd = Method, MS Mes'd = Mesured mass

| Cpd# | Structure | Name | SM | Mtd | MW | MS Mes'd |
|---|---|---|---|---|---|---|
| 398 | 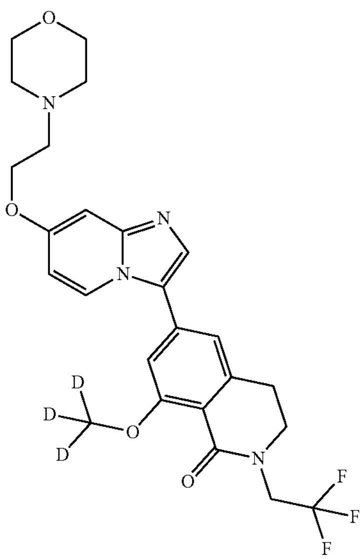 [SMILES: [2H]C([2H])([2H])Oc1cc(-c2cnc3cc(OCCN4CCOCC4)ccn23)cc2c1C(=O)N(CC(F)(F)F)CC2] | 6-[7-(2-morpholinoethoxy)imidazo[1,2-a]pyridin-3-yl]-8-(trideuteriomethoxy)-2-(2,2,2-trifluoroethyl)-3,4-dihydroisoquinolin-1-one | Int 25 + Int 91 | Ex. 2.125 | 507.5 | 508.2 |

TABLE IV

NMR data of illustrative compounds of the invention.

| Cpd# | NMR data |
|---|---|
| 6 | $^1$H NMR (300 MHz, CDCl3) δ 8.09 (d, 1H), 7.54 (s, 1H), 7.01-6.37 (m, 5H), 6.08 (s, 1H), 4.13 (t, 2H), 3.88 (s, 3H), 2.97-2.88 (m, 1H), 2.79 (t, 2H), 2.36 (s, 6H), 0.92-0.84 (m, 2H), 0.68-0.60 (m, 2H) |
| 10 | $^1$H NMR (400 MHz, DMSO-d$_6$) δ 8.46 (d, 1H), 8.33 (d, 1H), 7.70 (s, 1H), 7.42-7.02 (m, 3H), 6.99 (s, 1H), 6.70 (dd, 1H), 4.18 (t, 2H), 3.87 (s, 3H), 2.82-2.75 (m, 1H), 2.73-2.66 (m, 2H), 2.48-2.40 (m, 4H), 1.56-1.46 (m, 4H), 1.43-1.35 (m, 2H), 0.71-0.64 (m, 2H), 0.51-0.43 (m, 2H) |
| 16 | $^1$H NMR (400 MHz, DMSO-d$_6$) δ 8.48 (d, 1H), 8.34 (d, 1H), 8.17 (s, 2H), 7.70 (s, 1H), 7.42-7.03 (m, 3H), 6.99 (d, 1H), 6.70 (dd, 1H), 4.13 (t, 3H), 3.87 (s, 3H), 2.83-2.74 (m, 1H), 2.62-2.53 (m, 5H), 2.02-1.94 (m, 2H), 1.61-1.51 (m, 4H), 1.47-1.39 (m, 2H), 0.73-0.62 (m, 2H), 0.51-0.43 (m, 2H) |
| 18 | $^1$H NMR (400 MHz, CD$_3$OD) δ 8.52 (d, 1H), 7.68 (s, 1H), 7.22 (d, 1H), 7.17-7.12 (m, 1H), 6.99 (d, 1H), 6.79 (dd, 1H), 4.35 (q, 2H), 4.25 (t, 2H), 3.96 (s, 3H), 3.73 (t, 2H), 3.08 (t, 2H), 2.87 (t, 2H), 2.39 (s, 6H) |
| 20 | $^1$HNMR (400 MHz, CD$_3$OD) δ 8.52 (br s, 1H), 8.45 (d, 1H), 7.65 (s, 1H), 7.15 (d, 1H), 7.12-6.72 (m, 4H), 4.44 (t, 2H), 3.94 (s, 3H), 3.59 (t, 2H), 3.36-3.30 (m, 4H), 2.88-2.83 (m, 1H), 2.15-2.05 (m, 4H), 0.84-0.79 (m, 2H), 0.68-0.59 (m, 2H) |
| 86 | $^1$H NMR (400 MHz, CD$_3$OD) δ 8.50 (d, 1H), 7.67 (s, 1H), 7.21 (d, 1H), 7.12 (d, 1H), 6.96 (d, 1H), 6.76 (dd, 1H), 4.35 (q, 2H), 4.16-4.06 (m, 2H), 4.03-3.97 (m, 1H), 3.96 (s, 3H), 3.92 (dd, 1H), 3.89-3.61 (m, 6H), 3.58 (dd, 1H), 3.07 (t, 2H) |
| 88 | $^1$H NMR (400 MHz, DMSO-d$_6$) δ 8.58 (d, 1H), 7.77 (s, 1H), 7.17 (dd, 2H), 7.09 (d, 1H), 6.71 (dd, 1H), 4.35 (q, 2H), 4.22 (t, 2H), 3.88 (s, 3H), 3.67-3.56 (m, 6H), 2.99 (t, 2H), 2.75 (t, 2H), 2.55-2.45 (m, 4H) |
| 88 | $^1$H NMR (400 MHz, CD$_3$OD) δ 8.51 (d, 1H), 7.67 (s, 1H), 7.20 (d, 1H), 7.13 (d, 1H), 6.98 (d, 1H), 6.76 (dd, 1H), 4.34 (q, 2H), 4.26 (t, 2H), 3.94 (s, 3H), 3.76-3.70 (m, 6H), 3.06 (t, 2H), 2.88 (t, 2H), 2.63-2.61 (m, 4H) |
| 193 | $^1$H NMR (400 MHz, CD$_3$OD) δ 8.59 (d, 1H), 8.11 (s, 2H), 7.98 (s, 1H), 7.37 (d, 1H), 7.23 (d, 1H), 7.16 (dd, 1H), 7.12-6.73 (m, 2H), 4.71-4.64 (m, 2H), 4.15-4.12 (m, 2H), 4.09 (d, 2H), 3.93 (s, 3H), 3.80 (dd, 2H), 3.70-3.63 (m, 2H), 2.89-2.83 (m, 1H), 2.40-2.27 (m, 4H), 0.87-0.75 (m, 2H), 0.66-0.58 (m, 2H) |
| 217 | $^1$H NMR (400 MHz, CD$_3$OD) δ 8.49 (d, 1H), 7.65 (s, 1H), 7.18 (d, 1H), 7.13 (d, 1H), 6.97 (d, 1H), 6.76 (dd, 1H), 4.26 (t, 2H), 3.93 (s, 3H), 3.76-3.69 (m, 4H), 3.44 (dd, 2H), 3.00 (t, 2H), 2.88 (t, 2H), 2.66-2.59 (m, 4H) |
| 218 | $^1$H NMR (400 MHz, CD$_3$OD) δ 8.45 (d, 1H), 7.63 (s, 1H), 7.14 (d, 1H), 7.06 (d, 1H), 6.93 (d, 1H), 6.72 (dd, 1H), 6.08 (tt, 1H), 4.22 (t, 2H), 3.99-3.86 (m, 5H), 3.75-3.68 (m, 4H), 3.68-3.62 (m, 2H), 3.02 (t, 2H), 2.85 (t, 2H), 2.63-2.57 (m, 4H) |
| 219 | $^1$H NMR (400 MHz, CD$_3$OD) δ 8.45 (d, 1H), 7.64 (s, 1H), 7.15 (d, 1H), 7.07 (d, 1H), 6.92 (d, 1H), 6.72 (dd, 1H), 6.09 (tt, 1H), 4.12-3.52 (m, 16H), 3.03 (t, 2H) |

TABLE IV-continued

NMR data of illustrative compounds of the invention.

| Cpd# | NMR data |
|---|---|
| 225 | $^1$H NMR (400 MHz, CD$_3$OD) δ 8.51 (d, 1H), 7.68 (s, 1H), 7.22 (d, 1H), 7.14 (d, 1H), 6.98 (d, 1H), 6.77 (dd, 1H), 4.35 (q, 2H), 4.17-4.08 (m, 2H), 4.03-3.97 (m, 1H), 3.96 (s, 3H), 3.92 (dd, 1H), 3.89-3.62 (m, 6H), 3.58 (dd, 1H), 3.08 (t, 2H) |
| 242 | $^1$H NMR (400 MHz, CD$_3$OD) δ 8.50 (d, 1H), 7.66 (s, 1H), 7.17 (dd, 2H), 6.97 (d, 1H), 6.77 (dd, 1H), 4.14-3.54 (m, 12H), 3.46-3.41 (m, 2H), 3.01 (t, 2H) |
| 286 | $^1$H NMR (500 MHz, DMSO-d$_6$) δ 8.48-8.44 (m, 1H), 8.35-8.32 (m, 1H), 7.68 (s, 1H), 7.38-7.05 (m, 2H), 7.02-6.95 (m, 2H), 6.69 (d, 1H), 5.27-5.23 (m, 1H), 4.22-4.11 (m, 1H), 4.10-4.06 (m, 2H), 3.86 (s, 3H), 3.53-3.49 (m, 2H), 2.82-2.74 (m, 1H), 2.70-2.65 (m, 2H), 2.52-2.49 (m, 2H), 1.80-1.70 (m, 2H), 0.70-0.63 (m, 2H), 0.50-0.41 (m, 2H) |
| 321 | $^1$H NMR (600 MHz, , CDCl3) δ 8.14-8.10 (m, 1H), 7.58 (s, 1H), 6.99 (s, 1H), 6.95-6.91 (m, 2H), 6.78-6.50 (m, 2H), 6.08-6.03 (m, 1H), 4.23-4.15 (m, 1H), 4.09-4.03 (m, 2H), 3.92 (s, 3H), 2.98-2.93 (m, 1H), 2.75-2.65 (m, 2H), 2.61-2.51(m, 2H), 2.50-2.45 (m, 2H), 1.69-1.61 (m, 2H), 1.58-1.49 (m, 2H),1.31-1.25 (m, 1H), 0.94-0.87 (m, 3H), 0.69-0.62 (m, 2H) |
| 322 | $^1$H NMR (300 MHz, DMSO-d$_6$) δ 8.47 (d, 1H), 8.33 (d, 1H), 7.69 (s, 1H), 7.21 (t, 1H), 7.14-6.95 (m, 3H), 6.76-6.67 (m, 1H), 4.19 (d, 2H), 3.85 (s, 3H), 3.62 (s, 2H), 3.43 (t, 2H), 3.18 (t, 2H), 2.97-2.82 (m, 1H), 2.81-2.73 (m, 1H), 0.70-0.60 (m, 2H), 0.50-0.40 (m, 2H) |
| 323 | $^1$H NMR (300 MHz, DMSO-d$_6$) δ 8.46 (d, 1H), 8.33 (d, 1H), 7.68 (s, 1H), 7.21 (t, 1H), 7.14-6.95 (m, 3H), 6.70 (dd, 1H), 4.19 (d, 2H), 3.85 (s, 3H), 3.36 (t, 2H), 3.03 (t, 2H), 2.91-2.81 (m, 1H), 2.80-2.72 (m, 1H), 2.60 (m, 2H), 2.50 (m, 2H,), 0.70-0.60 (m, 2H), 0.48-0.42 (m, 2H) |
| 324 | $^1$H NMR (500 MHz, DMSO-d$_6$) 8.47 (d, 1H), 8.34 (d, 1H), 7.69 (s, 1H), 7.46 (s, 1H), 7.22 (t, 1H), 7.14 (d, 1H), 7.04-7.01 (m, 1H), 6.99 (s, 1H), 6.69 (dd, 1H), 4.12 (t, 2H), 3.86 (s, 3H), 3.22 (s, 2H), 2.82-2.72 (m, 1H), 2.49-2.40 (m, 6H), 1.96-1.87 (m, 2H), 1.83-1.68 (m, 4H), 0.71-0.64 (m, 2H), 0.48-0.43 (m, 2H) |
| 330 | $^1$H NMR (500 MHz, CDCl3) δ 8.11 (d, 1H), 7.57 (s, 1H), 6.99-6.93 (m, 2H), 6.91 (s, 1H), 6.69-6.64 (m, 1H), 6.63 (t, 1H), 6.03 (d, 1H), 4.25-4.15 (m, 1H), 4.12-4.00 (m, 2H), 3.90 (s, 3H), 3.82-3.72 (m, 4H), 2.99-2.87 (m, 1H), 2.77-2.69 (m, 2H), 2.66-2.55 (m, 2H), 2.55-2.46 (m, 2H), 0.92-0.84 (m, 3H), 0.68-0.64 (m, 2H) |
| 331 | $^1$H NMR (300 MHz, DMSO-d$_6$) δ 8.46 (d, 1H), 8.33 (d, 1H), 7.68 (s, 1H), 7.20 (t, 1H), 7.14-6.96 (m, 3H), 6.69 (dd, 1H), 4.12 (t, 2H), 3.85 (s, 3H), 3.12-3.02 (m, 4H), 2.93-2.85 (m, 4H), 2.81-2.73 (m, 1H), 2.62 (t, 2H), 1.97-1.79 (m, 2H), 0.72-0.62 (m, 2H), 0.50-0.39 (m, 2H) |
| 363 | $^1$H NMR (300 MHz, DMSO-d$_6$) δ 8.46 (d, 1H), 8.33 (d, 1H), 7.68 (s, 1H), 7.21 (t, 1H), 7.13 (d, 1H), 7.03 (d, 1H), 6.97 (s, 1H), 6.69 (dd, 1H), 4.22-4.06 (m, 4H), 3.85 (s, 3H), 2.84-2.71 (m, 3H), 2.46-2.42 (m, 2H), 2.24-1.99 (m, 3H), 1.98-1.79 (m, 5H), 1.20 (t, 3H), 0.71-0.60 (m, 2H), 0.50-0.41 (m, 2H) |
| 384 | $^1$H NMR (500 MHz, CDCl3) δ 8.11 (d, 1H), 7.58 (s, 1H), 6.99-6.93 (m, 2H), 6.91 (s, 1H), 6.82-6.45 (m, 2H), 6.02 (s, 1H), 4.27 (q, 2H), 4.24-4.03 (m, 1H), 4.13-4.00 (m, 2H), 3.94 (s, 1H), 3.02-2.91 (m, 2H), 2.87-2.79 (m, 1H), 2.74 (t, 1H), 2.67-2.60 (m, 2H), 2.47 (t, 1H), 2.32-2.08 (m, 1H), 2.03 (t, 2H), 1.35 (t, 3H), 0.92-0.87 (m, 3H), 0.66-0.62 (m, 2H) |

BIOLOGICAL EXAMPLES

Example 3. In Vitro Assays

3.1. Biochemical Assays

3.1.1. ADP-Glo™ Kinase Assay

3.1.1.1. Overview

The ADP-Glo™ kinase assay is a luminescent technology assay which measures the ADP formed from a kinase reaction. In this specific study, the kinase reactions consisted of the phosphorylation of the AMARA peptide substrate (SignalChem, Cat #A11-58) by SIK1 (Carna Biosciences, Cat #02-131), SIK2 (ThermoFisher Scientific, Cat #PV4792) or SIK3 (SignalChem, Cat #S12-11G-100). In a second step the kinase reactions are terminated and all the remaining ATP is depleted. In a final step the ADP is converted into ATP and this newly synthesized ATP is measured by using a luciferase/luciferin reaction. The generated light is measured using an Envision plate reader, wherein the luminescent signal obtained positively correlates with the kinase activity.

3.1.1.2. Protocol

The test compounds are prepared as a serial dilution of 10 point dose responses with 1/5 dilution steps in 100% DMSO starting from 2 mM highest concentration, diluted 1/20 in water and 1 μL is transferred to the assay plates (PerkinElmer Inc., Cat #6007290).

1% DMSO and 10 μM staurosporine final concentrations are used as negative and positive controls.

2 μL enzyme-substrate mixture is added to the assay plates.

The reaction is started by adding 2 μL diluted ATP on the assay plates. Plates are centrifuged for a few seconds at 1000 rpm and gently shaken for 2 min followed by an incubation at RT for 120 min.

The reactions are stopped and the unconsumed ATP is depleted by adding 5 μL ADP-Glo Reagent (Promega, Cat #V912B) to the reaction. The plates are centrifuged for a few seconds at 1000 rpm and incubated at RT for 40 min (ATP depletion).

The ADP is converted to ATP and luciferase and luciferin is introduced to detect ATP by adding 10 μL Kinase Detection Reagent (Promega, Cat #V913B+V914B) to the reaction. The plates are centrifuged for a few seconds at 1000 rpm and incubated at RT for 30 min (ADP detection).

Luminescence is measured on an Envision plate reader (PerkinElmer Inc.).

TABLE V

Conditions for human SIK kinase ADP-Glo ™ assays

| Kinase, [Kinase] | Substrate, [Substrate] | ATP | Assay buffer | Incubation time |
|---|---|---|---|---|
| SIK1 (Carna Biosciences, Cat# 02-131), 0.25 ng/μL | AMARA (SignalChem, Cat# A11-58), 45 μM | 5 μM ATP (Promega, Cat# V915B) | 25 mM Tris pH 7.5 0.01% Triton X-100 0.5 mM EGTA 2.5 mM DTT 5 mM MgCl$_2$ | 120 min |
| SIK2 (ThermoFisher Scientific, Cat# PV4792), 0.0625 ng/μL | AMARA (SignalChem, Cat# A11-58), 45 μM | 5 μM ATP (Promega, Cat# V915B) | 25 mM Tris pH 7.5 0.01% Triton X-100 0.5 mM EGTA 5 mM MgCl$_2$ 2.5 mM DTT | 120 min |
| SIK3 (SignalChem, Cat# S12-11G-100), 0.5 ng/μL | AMARA (SignalChem, Cat# A11-58), 45 μM | 5 μM ATP (Promega, Cat# V915B) | 25 mM Tris pH 7.5 0.01% Triton X-100 0.5 mM EGTA 5 mM MgCl$_2$ 2.5 mM DTT | 120 min |

3.1.1.3. Data Analysis and Results

Raw data are generated following the read-out performed on the TopCount, plotted to generate dose response curves to calculate percentage inhibition (PIN) and average IC$_{50}$ for each SIK homologue which are reported in the table below.

TABLE VI

ADP-Glo ™ SIK kinase assay IC$_{50}$ of illustrative compounds of the invention.

| Cpd# | SIK1 IC$_{50}$ | SIK2 IC$_{50}$ | SIK3 IC$_{50}$ |
|---|---|---|---|
| 1 | ** | ** | **** |
| 2 | * | *** | **** |
| 3 | *** | **** | **** |
| 4 | * | ** | *** |
| 5 | * | ** | *** |
| 6 | ** | **** | **** |
| 7 | * | *** | *** |
| 8 | *** | **** | **** |
| 9 | *** | **** | **** |
| 10 | *** | **** | **** |
| 11 | ** | *** | **** |
| 12 | * | ** | *** |
| 13 | *** | **** | **** |
| 14 | *** | **** | **** |
| 15 | * | *** | *** |
| 16 | *** | **** | **** |
| 17 | *** | **** | **** |
| 18 | * | **** | *** |
| 19 | *** | **** | **** |
| 20 | *** | **** | **** |
| 21 | *** | **** | **** |
| 22 | *** | **** | **** |
| 23 | ** | **** | **** |
| 24 | **** | **** | **** |
| 25 | **** | **** | **** |
| 26 | *** | **** | **** |
| 27 | **** | **** | **** |
| 28 | ** | **** | **** |
| 29 | ** | *** | *** |
| 30 | *** | **** | **** |
| 31 | * | * | * |
| 32 | *** | **** | **** |
| 33 | *** | **** | **** |
| 34 | *** | **** | **** |
| 35 | *** | **** | **** |
| 36 | *** | **** | **** |
| 37 | *** | **** | **** |
| 38 | *** | **** | **** |
| 39 | ** | **** | **** |
| 40 | * | **** | **** |
| 41 | ** | **** | **** |
| 42 | **** | **** | **** |
| 43 | *** | **** | **** |
| 44 | *** | **** | **** |
| 45 | ** | *** | **** |
| 46 | *** | **** | **** |
| 47 | *** | **** | **** |
| 48 | *** | **** | **** |
| 49 | **** | **** | **** |
| 50 | *** | **** | **** |
| 51 | * | *** | *** |
| 52 | **** | **** | **** |
| 53 | * | *** | *** |
| 54 | * | **** | *** |
| 55 | ** | **** | **** |
| 56 | * | ** | ** |
| 57 | *** | **** | **** |
| 58 | *** | *** | **** |
| 59 | **** | **** | **** |
| 60 | *** | **** | **** |
| 61 | **** | **** | **** |
| 62 | *** | *** | **** |
| 63 | **** | **** | **** |
| 64 | **** | **** | **** |
| 65 | **** | **** | **** |
| 66 | **** | **** | **** |
| 67 | * | **** | **** |
| 68 | **** | **** | **** |
| 69 | *** | **** | **** |
| 70 | *** | **** | **** |
| 71 | **** | **** | **** |
| 72 | *** | **** | **** |
| 73 | *** | **** | **** |
| 74 | *** | **** | **** |
| 75 | **** | **** | **** |
| 76 | *** | **** | **** |
| 77 | ** | *** | **** |
| 78 | ** | **** | **** |
| 79 | *** | **** | **** |
| 80 | *** | **** | **** |
| 81 | ** | **** | **** |
| 82 | *** | **** | **** |

TABLE VI-continued

ADP-Glo ™ SIK kinase assay $IC_{50}$ of illustrative compounds of the invention.

| Cpd# | SIK1 $IC_{50}$ | SIK2 $IC_{50}$ | SIK3 $IC_{50}$ |
|---|---|---|---|
| 83 | ** | **** | **** |
| 84 | ** | *** | **** |
| 85 | * | **** | **** |
| 86 | ** | *** | **** |
| 87 | *** | **** | **** |
| 88 | ** | **** | **** |
| 89 | *** | **** | **** |
| 90 | *** | **** | **** |
| 91 | *** | **** | **** |
| 92 | *** | **** | **** |
| 93 | *** | **** | **** |
| 94 | *** | *** | *** |
| 95 | *** | **** | **** |
| 96 | *** | **** | **** |
| 97 | *** | **** | **** |
| 98 | *** | **** | **** |
| 99 | **** | **** | **** |
| 100 | ** | *** | *** |
| 101 | *** | **** | **** |
| 102 | *** | **** | **** |
| 103 | *** | **** | **** |
| 104 | ** | **** | **** |
| 105 | *** | **** | **** |
| 106 | * | *** | *** |
| 107 | ** | **** | **** |
| 108 | **** | **** | **** |
| 109 | *** | **** | **** |
| 110 | ** | **** | **** |
| 111 | ** | **** | **** |
| 112 | *** | **** | **** |
| 113 | *** | **** | **** |
| 114 | *** | **** | **** |
| 115 | *** | **** | **** |
| 116 | *** | **** | **** |
| 117 | *** | **** | **** |
| 118 | *** | **** | **** |
| 119 | *** | **** | **** |
| 120 | *** | **** | **** |
| 121 | *** | **** | **** |
| 122 | ** | **** | **** |
| 123 | * | **** | **** |
| 124 | * | **** | **** |
| 125 | ** | **** | **** |
| 126 | ** | **** | **** |
| 127 | ** | **** | **** |
| 128 | ** | **** | **** |
| 129 | **** | **** | **** |
| 130 | **** | **** | **** |
| 131 | *** | **** | **** |
| 132 | *** | **** | **** |
| 133 | *** | **** | **** |
| 134 | *** | **** | **** |
| 135 | *** | **** | **** |
| 136 | *** | **** | **** |
| 137 | *** | **** | **** |
| 138 | ** | **** | **** |
| 139 | ** | **** | **** |
| 140 | * | *** | ** |
| 141 | **** | **** | **** |
| 142 | **** | **** | **** |
| 143 | **** | **** | **** |
| 144 | *** | **** | **** |
| 145 | ** | *** | *** |
| 146 | * | *** | *** |
| 147 | *** | **** | **** |
| 148 | ** | **** | **** |
| 149 | *** | *** | **** |
| 150 | ** | **** | **** |
| 151 | *** | **** | **** |
| 152 | *** | *** | **** |
| 153 | ** | **** | **** |
| 154 | *** | **** | **** |
| 155 | * | *** | *** |
| 156 | *** | **** | **** |
| 157 | ** | ** | **** |
| 158 | *** | **** | **** |
| 159 | ** | *** | **** |
| 160 | *** | **** | **** |
| 161 | *** | **** | **** |
| 162 | *** | *** | **** |
| 163 | *** | *** | **** |
| 164 | *** | **** | **** |
| 165 | ** | **** | **** |
| 166 | ** | **** | **** |
| 167 | * | **** | *** |
| 168 | ** | **** | **** |
| 169 | ** | *** | **** |
| 170 | *** | **** | **** |
| 171 | *** | **** | **** |
| 172 | ** | **** | **** |
| 173 | ** | **** | **** |
| 174 | ** | **** | **** |
| 175 | ** | **** | **** |
| 176 | *** | **** | **** |
| 177 | *** | **** | **** |
| 178 | *** | **** | **** |
| 179 | *** | **** | **** |
| 180 | *** | **** | **** |
| 181 | *** | **** | **** |
| 182 | *** | *** | **** |
| 183 | **** | **** | **** |
| 184 | **** | **** | **** |
| 185 | ** | **** | **** |
| 186 | *** | **** | **** |
| 187 | *** | **** | **** |
| 188 | *** | **** | **** |
| 189 | *** | **** | **** |
| 190 | ** | **** | **** |
| 191 | ** | **** | **** |
| 192 | *** | **** | **** |
| 193 | *** | **** | **** |
| 194 | *** | **** | **** |
| 195 | *** | **** | **** |
| 196 | *** | **** | **** |
| 197 | * | *** | *** |
| 198 | *** | **** | **** |
| 199 | *** | **** | **** |
| 200 | *** | **** | **** |
| 201 | *** | *** | **** |
| 202 | ** | **** | **** |
| 203 | ** | *** | **** |
| 204 | **** | **** | **** |
| 205 | **** | **** | **** |
| 206 | *** | **** | **** |
| 207 | *** | **** | **** |
| 208 | *** | **** | **** |
| 209 | * | * | *** |
| 210 | *** | **** | *** |
| 211 | **** | **** | **** |
| 212 | *** | **** | **** |
| 213 | *** | **** | **** |
| 214 | *** | **** | **** |
| 215 | *** | **** | **** |
| 216 | **** | **** | **** |
| 217 | *** | **** | **** |
| 218 | ** | **** | **** |
| 219 | ** | **** | **** |
| 220 | *** | **** | **** |
| 221 | * | *** | *** |
| 222 | * | ** | *** |
| 223 | **** | **** | **** |
| 224 | ** | **** | **** |
| 225 | ** | **** | **** |
| 226 | *** | **** | **** |
| 227 | ** | **** | **** |
| 228 | **** | **** | **** |
| 229 | *** | **** | **** |
| 230 | *** | **** | **** |

TABLE VI-continued

ADP-Glo ™ SIK kinase assay IC$_{50}$ of illustrative compounds of the invention.

| Cpd# | SIK1 IC$_{50}$ | SIK2 IC$_{50}$ | SIK3 IC$_{50}$ |
|---|---|---|---|
| 231 | *** | **** | **** |
| 232 | *** | **** | **** |
| 233 | *** | **** | **** |
| 234 | *** | **** | **** |
| 235 | **** | **** | **** |
| 236 | *** | **** | **** |
| 237 | *** | **** | **** |
| 238 | **** | **** | **** |
| 239 | **** | **** | **** |
| 240 | **** | **** | **** |
| 241 | ** | *** | **** |
| 242 | *** | **** | **** |
| 243 | * | *** | *** |
| 244 | ** | **** | **** |
| 245 | * | **** | **** |
| 246 | ** | **** | *** |
| 247 | ** | **** | **** |
| 248 | ** | **** | **** |
| 249 | ** | *** | **** |
| 250 | ** | **** | **** |
| 251 | ** | *** | **** |
| 252 | ** | **** | **** |
| 253 | * | *** | **** |
| 254 | * | ** | ** |
| 255 | * | ** | *** |
| 256 | ** | *** | *** |
| 257 | ** | *** | **** |
| 258 | ** | *** | **** |
| 259 | ** | *** | *** |
| 260 | * | * | *** |
| 261 | * | ** | ** |
| 262 | * | ** | *** |
| 263 | * | * | *** |
| 264 | ** | *** | **** |
| 265 | * | ** | ** |
| 266 | * | * | * |
| 267 | * | ** | ** |
| 268 | *** | *** | **** |
| 269 | *** | *** | **** |
| 270 | ** | *** | **** |
| 271 | ** | *** | **** |
| 272 | ** | *** | *** |
| 273 | *** | **** | **** |
| 274 | **** | **** | **** |
| 275 | *** | **** | **** |
| 276 | *** | **** | **** |
| 277 | *** | **** | **** |
| 278 | **** | **** | **** |
| 279 | **** | **** | **** |
| 280 | **** | **** | **** |
| 281 | **** | **** | **** |
| 282 | *** | **** | **** |
| 283 | *** | *** | **** |
| 284 | **** | **** | **** |
| 285 | *** | **** | **** |
| 286 | *** | **** | **** |
| 287 | *** | **** | **** |
| 288 | *** | **** | **** |
| 289 | *** | *** | **** |
| 290 | *** | **** | **** |
| 291 | *** | **** | **** |
| 292 | *** | **** | **** |
| 293 | *** | **** | **** |
| 294 | ** | **** | **** |
| 295 | * | **** | **** |
| 296 | *** | **** | **** |
| 297 | *** | **** | **** |
| 298 | *** | **** | **** |
| 299 | *** | **** | **** |
| 300 | *** | **** | **** |
| 301 | *** | **** | **** |
| 302 | *** | **** | **** |
| 303 | *** | **** | **** |
| 304 | *** | **** | **** |
| 305 | *** | **** | **** |
| 306 | *** | **** | **** |
| 307 | *** | **** | *** |
| 308 | *** | **** | **** |
| 309 | *** | **** | **** |
| 310 | *** | **** | **** |
| 311 | *** | **** | **** |
| 312 | *** | **** | **** |
| 313 | *** | **** | **** |
| 314 | *** | **** | **** |
| 315 | *** | **** | **** |
| 316 | *** | **** | **** |
| 317 | *** | **** | **** |
| 318 | **** | **** | **** |
| 319 | *** | **** | **** |
| 320 | *** | **** | **** |
| 321 | *** | **** | **** |
| 322 | *** | **** | **** |
| 323 | *** | **** | **** |
| 324 | *** | **** | **** |
| 325 | *** | **** | **** |
| 326 | *** | **** | **** |
| 327 | *** | **** | **** |
| 328 | *** | **** | **** |
| 329 | *** | **** | **** |
| 330 | *** | **** | **** |
| 331 | *** | **** | **** |
| 332 | *** | **** | **** |
| 333 | *** | **** | **** |
| 334 | *** | **** | **** |
| 335 | *** | **** | **** |
| 336 | *** | **** | **** |
| 337 | *** | **** | **** |
| 338 | *** | **** | **** |
| 339 | *** | **** | **** |
| 340 | *** | **** | **** |
| 341 | *** | **** | **** |
| 342 | *** | **** | **** |
| 343 | *** | **** | **** |
| 344 | *** | **** | **** |
| 345 | *** | **** | **** |
| 346 | *** | **** | **** |
| 347 | *** | **** | **** |
| 348 | *** | **** | **** |
| 349 | *** | **** | **** |
| 350 | *** | **** | **** |
| 351 | **** | **** | **** |
| 352 | **** | **** | **** |
| 353 | ** | **** | *** |
| 354 | *** | **** | **** |
| 355 | ** | *** | ** |
| 356 | *** | **** | **** |
| 357 | *** | **** | **** |
| 358 | *** | **** | **** |
| 359 | ** | **** | *** |
| 360 | *** | **** | **** |
| 361 | *** | **** | **** |
| 362 | *** | **** | **** |
| 363 | *** | **** | **** |
| 364 | *** | **** | **** |
| 365 | *** | **** | **** |
| 366 | *** | **** | **** |
| 367 | **** | **** | **** |
| 368 | **** | **** | **** |
| 369 | **** | **** | **** |
| 370 | *** | **** | **** |
| 371 | **** | **** | **** |
| 372 | *** | **** | **** |
| 373 | *** | **** | **** |
| 374 | *** | **** | **** |
| 375 | *** | **** | **** |
| 376 | *** | **** | **** |
| 377 | *** | **** | **** |
| 378 | *** | **** | **** |

TABLE VI-continued

ADP-Glo ™ SIK kinase assay IC$_{50}$ of illustrative compounds of the invention.

| Cpd# | SIK1 IC$_{50}$ | SIK2 IC$_{50}$ | SIK3 IC$_{50}$ |
|---|---|---|---|
| 379 | *** | **** | **** |
| 380 | *** | **** | **** |
| 381 | *** | **** | **** |
| 382 | *** | **** | **** |
| 383 | *** | **** | **** |
| 384 | *** | **** | **** |
| 385 | *** | **** | **** |
| 386 | *** | **** | **** |
| 387 | *** | **** | **** |
| 388 | *** | **** | **** |
| 389 | *** | **** | **** |
| 390 | *** | **** | **** |
| 391 | *** | **** | **** |
| 392 | *** | **** | **** |
| 393 | *** | **** | **** |
| 394 | *** | **** | **** |
| 395 | *** | **** | **** |
| 396 | ** | ** | *** |
| 397 | *** | *** | **** |

\* >500 nM
\*\* >100-500 nM
\*\*\* >10-100 nM
\*\*\*\* 0.01-10 nM
NA not measured

3.2. Cellular Assays

3.2.1. MdM Assay: LPS-Triggered TNFα/IL-10 (ELISA)

3.2.1.1. Overview

SIK inhibition inhibits TNFα and increases IL-10 release in LPS triggered monocyte-derived macrophages (MdM) and dendritic cells (MdDCs) (Clark et al. 2012; Sundberg et al. 2014; Ozanne et al. 2015). This assay evaluates illustrative compounds of the invention for their inhibition of LPS-induced TNFα and LPS triggered IL-10 secretion in monocyte-derived macrophages.

3.2.1.2. Protocols

PBMCs are isolated from human blood samples (buffy-coats). The buffy coat is aseptically transferred into a 50 mL Falcon tube, and diluted 1/2 in PBS. Falcon tubes are filled with 20 mL Lymphoprep™, on top of which 25 mL of the buffy coat is carefully added, tubes are centrifuged for 35 min at 400 g in temperature controlled centrifuge, without brake, at 25° C. PBMCs are aspirated from the white interface layer between sample and Lymphoprep™. PBMCs are washed five times in PBS. Cells are resuspended in RPMI 1640 complete medium supplemented with 10% FBS, 1% P/S, and cell density is determined using a hematologic analyzer (Sysmex XS-500i).

PBMCs are centrifuged at 300×g for 10 min and resuspended at a density of 1.0*10$^7$ cells/80 µL Miltenyi buffer (PBS, pH 7.4, 1% FBS, 2 mM EDTA).

3.2.1.2.1 Positive Labelling of CD14+ Monocytes

Starting from this point of the protocol all steps are performed on ice. 20 µL of CD14+ micro-beads are added per 1.0*10$^7$ cells, the tube is mixed and incubated for 15 min in the fridge at 4° C. Cell suspension volume is adjusted to total volume of 100 mL using Miltenyi buffer, mixed gently and subsequently centrifuged for 10 min at 300×g. Supernatant is discarded and cell pellet is resuspended in 12 mL of Miltenyi buffer.

3.2.1.2.2 Magnetic Cell Sorting

Four LS columns are placed in the MACS Separator (magnet) from Miltenyi Biotec, and are prewet by rinsing with 3 mL of MACS buffer per column. Three mL of cell suspension is added onto the column (max 1*10$^8$ of labelled cells/column), and columns are subsequently washed 3 times with 3 mL of Miltenyi buffer.

The columns are removed from the magnets, and 5 mL of Miltenyi buffer are added to the column to flush out the CD14+ fraction by pushing the plunger into the column. The flushed fractions are collected in a fresh 50 mL Falcon and volume is adjusted to 30 mL using Miltenyi buffer, cells are centrifuged for 10 min at 300×g. The obtained cell pellet is resuspended in 10 mL RPMI w/o FBS, and cell density is determined using a hematologic analyser (Sysmex XS-500i). 100 000 cells are seeded per well of a 96-well plate for differentiation to MdM in RPMI 1640 medium supplemented with 10% FBS, 1% P/S and 100 ng/mL rhM-CSF. On day 5 the medium is refreshed with 100 µL RPMI 1640 medium supplemented with 10% FBS, 1% P/S and 100 ng/mL rhM-CSF.

On day 10, MdMs are triggered and compound is added. A compound dilution plate is made in 100% DMSO by 3-fold dilution of 10 mM stock solution. An intermediate dilution plate (10× final concentration) is made by diluting the compound dilution plate 50-fold in RPMI medium.

Medium is carefully removed from cell plates using multichannel pipette, and replaced by 80 µL fresh medium. 10 µL of the 10× final concentration compound is added to the cells and incubated for 1 hour at 37° C. before addition of trigger. No trigger conditions/trigger conditions are spiked with equal final DMSO concentrations of 0.2% DMSO. 10 µL of 10×LPS (final conc. 200 ng/mL) solution are added to all wells except for the 'no trigger wells' where 10 µL medium is added. Supernatant is collected after 2 h (IL-10 determination) and after 20 h (TNFα determination) of LPS triggering.

3.2.1.2.3 TNFα ELISA

A Lumitrac 600 Greiner 384-well plate is coated with 40 µL of capture antibody (BD Pharmingen, Cat #551220) reaching a final concentration of 1 µg/mL in 1×PBS and stored overnight at 4° C.

The plate is then washed once with PBST (PBS+0.05% Tween20) and once with PBS followed by the addition of 100 µL of blocking buffer (1% Bovine Serum Albumin (BSA)–5% Sucrose) and plates are sealed and incubated for at least 4 h at RT. After washing the plate once with PBST and once with PBS, 40 µL of standard or sample are added (TNFα standard curve is prepared using a 1/2 serial dilution starting from 16000 µg/mL; dilutions are made in dilution buffer (PBS+1% BSA)). Plates are washed twice with PBST, and once with PBS, after which 35 µL of the detection antibody is added (final concentration 0.25 µg/mL diluted in dilution buffer) and plates are incubated for at least 2 h at RT. Plates are washed twice with PBST, and once with PBS, where after 35 µL of Strep-HRP conjugate (0.5 µg/mL final concentration diluted in dilution buffer) is added. Plates are incubated in the dark, at RT for at least 45 min but no longer than 1 hour. Plates are washed twice with PBST, and once with PBS. Thereafter, 50 µL of luminol substrate is added to each well (prepared according to manufacturer's instructions), and incubated for 5 min at RT protected from light. Chemiluminescence is measured on the Envision 2104.

3.2.1.2.1 IL-10 ELISA

An Immulon 2HB 96-well plate (Thermo Electron Co., Cat #3455) is coated with 40 µL of capture antibody (final concentration of 2 µg/mL diluted in Tris buffer (50 mM Tris; 150 mM NaCl; pH 9 (adjusted with HCl)) and stored overnight at 4° C. The next day the plate is washed three times with PBST, and subsequently 200 µL blocking buffer (1% BSA+5% sucrose in PBS-T) is added. After an incubation of 30 min at 37° C., the plate is washed three times with PBST, and 100 µL of standard or sample are added (IL-10 standard curve samples are prepared using a 1/2 serial dilution starting from 1000 µg/mL; dilutions are made in dilution buffer: PBS+1% BSA). After 1 hour incubation at 37° C., plates are washed three times with PBST, after which 100 µL of the detection antibody (BD Pharmingen, Cat #554499) is added (final concentration 0.25 µg/mL diluted in Tris buffer) and plates are incubated for at least 2 h at RT. Plates are washed three times with PBST, where after 100 µL of Strep-HRP conjugate (0.5 µg/mL final concentration diluted in dilution buffer) is added. Plates are incubated in the dark, at 37° C. for 30 min. Plates are washed three times with PBST. A substrate solution is made, for a total volume of 20 mL, 18 mL H$_2$O; 2 mL citrate acetate buffer; 200 µL TMB mix (tetramethil benzidine (TMB) 101 mg, DMSO 10 mL stored at 4° C.); 2.5 µL 30% H$_2$O$_2$ are mixed. 100 µL of substrate solution is added to each well and incubated until brilliant blue color develops. The reaction is stopped by adding 50 µL of 1 M H$_2$SO$_4$, after which absorbance is measured at 450 nm on the SpectraMax i3, Molecular Devices.

3.2.1.3. Data Analysis and Results

3.2.1.3.1 TNFα Inhibition Calculation

To measure the inhibition of LPS induced TNFα, percentage inhibition (PIN) values are calculated for all concentrations tested, compared to controls. Unstimulated samples (no trigger/vehicle (0.2% DMSO)) are used as negative control (100% inhibition). As a positive control (0% inhibition), the stimulated samples (trigger/vehicle)) are used.

$$PIN = \frac{(RLUp - RLU\text{test compound})}{RLUp - RLUn} \times 100$$

Wherein RLU=Relative Chemiluminescent Light Units (background subtracted) and p and n subscripts refer to the average of positive and negative controls, respectively.

PIN values are plotted in concentration-response and EC$_{50}$ values are derived using GraphPad Prism Software, applying 4-parameter nonlinear regression (sigmoidal) curve fitting. Because no clear bottom plateau is obtained, bottom of the curve is constrained to be equal to 0.

3.2.1.3.2 IL-10 Induction Calculation

IL-10 is induced upon SIK inhibition. To quantify these inductions fold changes (FC) compared to 'LPS only' are calculated for each concentration tested and the maximal FC is calculated (IL-10FCmax):

$$IL\text{-}10\ FC\text{max} = \frac{\text{max } ABS\text{test compound}}{ABS\text{trigger}}$$

wherein ABS=Absorbance measured at 450 nm.

The median maximal FC for test compounds across two or more assays is reported (IL-10FCmax median).

3.2.1.3.3 Results & Outcome

The data obtained when subjecting illustrative compounds of the invention are described in the table below.

TABLE VII

MdM TNFα inhibition and IL-10 induction of illustrative compounds of the invention.

| Cpd# | TNFα EC$_{50}$ (nM) | IL-10 FCmax median |
|---|---|---|
| 6 | *** | ++ |
| 8 | **** | NA |
| 9 | *** | NA |
| 10 | **** | ++ |
| 13 | **** | ++ |
| 14 | *** | ++ |
| 16 | **** | NA |
| 17 | **** | ++ |
| 18 | *** | ++ |
| 21 | **** | NA |
| 23 | *** | ++ |
| 33 | **** | NA |
| 35 | *** | NA |
| 37 | *** | ++ |
| 39 | *** | ++ |
| 40 | *** | ++ |
| 41 | ** | ++ |
| 44 | *** | + |
| 45 | *** | + |
| 48 | **** | NA |
| 50 | *** | NA |
| 54 | *** | ++ |
| 55 | *** | NA |
| 58 | ** | NA |
| 67 | ** | NA |
| 78 | *** | NA |
| 79 | *** | NA |
| 81 | *** | ++ |
| 83 | *** | ++ |
| 84 | *** | NA |
| 86 | *** | ++ |
| 88 | *** | ++ |
| 104 | ** | + |
| 107 | *** | + |
| 110 | *** | NA |
| 111 | *** | ++ |
| 117 | *** | ++ |
| 118 | *** | ++ |
| 122 | *** | ++ |
| 123 | *** | ++ |
| 124 | *** | ++ |
| 125 | *** | ++ |
| 126 | *** | + |
| 127 | *** | ++ |
| 128 | *** | ++ |
| 138 | ** | NA |
| 139 | *** | NA |
| 147 | *** | NA |
| 150 | *** | ++ |
| 156 | *** | ++ |
| 158 | **** | NA |
| 160 | *** | NA |
| 165 | *** | ++ |
| 166 | *** | ++ |
| 167 | * | + |
| 168 | *** | NA |

TABLE VII-continued

MdM TNFα inhibition and IL-10 induction of illustrative compounds of the invention.

| Cpd# | TNFα EC$_{50}$ (nM) | IL-10 FCmax median |
|---|---|---|
| 172 | ** | NA |
| 189 | *** | NA |
| 190 | *** | ++ |
| 191 | *** | ++ |
| 193 | *** | NA |
| 206 | *** | ++ |
| 209 | ** | NA |
| 217 | *** | NA |
| 218 | *** | ++ |
| 219 | ** | ++ |
| 220 | *** | ++ |
| 224 | *** | NA |
| 225 | *** | ++ |
| 227 | * | ++ |
| 230 | *** | NA |
| 233 | *** | ++ |
| 234 | *** | ++ |
| 242 | *** | NA |
| 244 | *** | NA |
| 245 | *** | NA |
| 248 | *** | NA |
| 252 | *** | ++ |
| 257 | *** | ++ |
| 259 | *** | NA |
| 273 | *** | NA |
| 274 | *** | NA |
| 275 | *** | NA |
| 276 | *** | NA |
| 278 | ** | ++ |
| 286 | ** | ++ |
| 305 | *** | NA |
| 321 | **** | ++ |
| 324 | *** | NA |
| 325 | **** | NA |
| 328 | **** | ++ |
| 330 | **** | ++ |
| 331 | *** | NA |
| 363 | **** | NA |
| 384 | **** | ++ |
| 386 | *** | NA |
| 387 | **** | NA |
| 390 | **** | NA |

\* >5000 nM
\*\* >1000-5000 nM
\*\*\* >100-1000 nM
\*\*\*\* 0.1-100 nM
+ ≤1.5
++ >1.5-4.5
+++ >4.5
NA not measured

3.2.2. Monocytes Assay: LPS-Triggered TNFα/IL-10 (ELISA)

3.2.2.1. Overview

SIK inhibition inhibits TNFα and increases IL-10 release in LPS triggered monocyte-derived macrophages (MdM) and dendritic cells (MdDCs) (Clark et al. 2012; Sundberg et al. 2014; Ozanne et al. 2015). This assay evaluates illustrative compounds of the invention for their inhibition of LPS-induced TNFα and LPS triggered IL-10 secretion in monocytes.

3.2.2.2. Protocols

PBMCs are isolated from human blood samples (buffy-coats). The buffy coat is aseptically transferred into a 50 mL Falcon tube, and diluted 1/2 in PBS. Falcon tubes are filled with 20 mL Lymphoprep™, on top of which 25 mL of the buffy coat is carefully added, tubes are centrifuged for 35 min at 400 g in temperature controlled centrifuge, without brake, at 25° C. PBMCs are aspirated from the white interface layer between sample and Lymphoprep™. PBMCs are washed five times in PBS. Cells are resuspended in RPMI 1640 complete medium supplemented with 10% FBS, 1% P/S, and cell density is determined using a hematologic analyzer (Sysmex XS-500i).

PBMCs are centrifuged at 300×g for 10 min and resuspended at a density of $1.0*10^7$ cells/80 µL Miltenyi buffer (PBS, pH 7.4, 1% FBS, 2 mM EDTA).

3.2.2.2.1 Positive Labelling of CD14+ Monocytes

Starting from this point of the protocol all steps are performed on ice. 20 µL of CD14+ micro-beads are added per $1.0*10^7$ cells, the tube is mixed and incubated for 15 min in the fridge at 4° C. Cell suspension volume is adjusted to total volume of 100 mL using Miltenyi buffer, mixed gently and subsequently centrifuged for 10 min at 300×g. Supernantant is discarded and cell pellet is resuspended in 12 mL of Miltenyi buffer.

3.2.2.2.2 Magnetic Cell Sorting

Four LS columns are placed in the MACS Separator (magnet) from Miltenyi Biotec, and are prewet by rinsing with 3 mL of MACS buffer per column. Three mL of cell suspension is added onto the column (max $1*10^8$ of labelled cells/column), and columns are subsequently washed 3 times with 3 mL of Miltenyi buffer.

The columns are removed from the magnets, and 5 mL of Miltenyi buffer are added to the column to flush out the CD14+ fraction by pushing the plunger into the column. The flushed fractions are collected in a fresh 50 mL Falcon and volume is adjusted to 30 mL using Miltenyi buffer, cells are centrifuged for 10 min at 300×g. The obtained cell pellet is resuspended in 10 mL RPMI w/o FBS, and cell density is determined using a hematologic analyser (Sysmex XS-500i). 100 000 cells are seeded in 80 µL per well of a 96-well plate in RPMI 1640 medium supplemented with 10% FBS, 1% P/S.

A compound dilution plate is made in 100% DMSO by 3-fold dilution of 10 mM stock solution. An intermediate dilution plate (10× final concentration) is made by diluting the compound dilution plate 50-fold in RPMI medium.

10 µL of the 10× final concentration compound is added to the cells and incubated for 1 h at 37° C. before addition of trigger. No trigger conditions/trigger conditions are spiked with equal final DMSO concentrations of 0.2% DMSO. 10 µL of 10×LPS (final conc. 200 ng/mL) solution are added to all wells except for the 'no trigger wells' where 10 µL medium is added. Supernatant is collected after 4 h of LPS triggering.

3.2.2.2.3 TNFα ELISA

A Lumitrac 600 Greiner 384-well plate is coated with 40 µL of capture antibody (BD Pharmingen, Cat #551220) reaching a final concentration of 1 µg/mL in 1×PBS and stored overnight at 4° C.

The plate is then washed once with PBST (PBS+0.05% Tween20) and once with PBS followed by the addition of 100 µL of blocking buffer (1% Bovine Serum Albumin (BSA)–5% Sucrose) and plates are sealed and incubated for at least 4 h at RT. After washing the plate once with PBST and once with PBS, 100 μL of of blocking buffer (1% BSA–5% Sucrose) is added and plates are sealed and incubated for at least 4 h at RT. Plates are washed twice with PBST, and once with PBS, after which 35 μL of the detection antibody is added (final concentration 0.25 μg/mL diluted in dilution buffer) and plates are incubated for at least 2 h at RT. Plates are washed twice with PBST, and once with PBS, whereafter 35 μL of Strep-HRP conjugate (0.5 μg/mL final concentration diluted in dilution buffer) is added. Plates are incubated in the dark, at RT for at least 45 min but no longer than 1 h. Plates are washed twice with PBST, and once with PBS. Thereafter, 50 μL of luminol substrate is added to each well (prepared according to manufacturer's instructions), and incubated for 5 min at RT protected from light. Chemiluminescence is measured on the Envision 2104.

3.2.2.2.4 IL-10 ELISA

A Lumitrac 600 Greiner 384-well plate is coated with 40 μL of capture antibody (final concentration of 1 μg/mL in 1×PBS) and stored overnight at 4° C. The next day the plate is washed three times with PBST (PBS+0.05% Tween20) and once with PBS followed by the addition of 100 μL of blocking buffer (1% BSA–5% Sucrose) and plates are sealed and incubated for at least 4 h at RT. After washing the plate once with PBST and once with PBS, 40 μL of standard or sample are added (IL-10 standard curve is prepared using a 1/2 serial dilution starting from 2000 μg/mL; dilutions are made in dilution buffer (PBS+1% BSA)). Plates are washed twice with PBST, and once with PBS, after which 35 μL of the detection antibody is added (final concentration 0.143 μg/mL diluted in dilution buffer) and plates are incubated for at least 2 h at RT. Plates are washed twice with PBST, and once with PBS, whereafter 35 μL of Strep-HRP conjugate (0.5 μg/mL final concentration diluted in dilution buffer) is added. Plates are incubated in the dark, at RT for at least 45 min but no longer than 1 h. Plates are washed twice with PBST, and once with PBS. Thereafter, 50 μL of luminol substrate is added to each well (prepared according to manufacturer's instructions), and incubated for 5 min at RT protected from light. Chemiluminescence is measured on the Envision 2104.

3.2.2.3. Data Analysis and Results

3.2.2.3.1 TNFα Inhibition Calculation

To measure the inhibition of LPS induced TNFα, percentage inhibition (PIN) values are calculated for all concentrations tested, compared to controls. Unstimulated samples (no trigger/vehicle (0.2% DMSO)) are used as negative control (100% inhibition). As a positive control (0% inhibition), the stimulated samples (trigger/vehicle)) are used.

$$PIN = \frac{(RLU_p - RLU_{test\ compound})}{RLU_p - RLU_n} \times 100$$

Wherein RLU=Relative Chemiluminescent Light Units (background subtracted) and p and n subscripts refer to the average of positive and negative controls, respectively.

PIN values are plotted in concentration-response and $EC_{50}$ values are derived using GraphPad Prism Software, applying 4-parameter nonlinear regression (sigmoidal) curve fitting. When no clear bottom plateau is obtained, bottom of the curve is constrained to be equal to 0.

3.2.2.3.2 IL-10 Induction Calculation

LPS-induced IL-10 is increased upon SIK inhibition. To quantify these increases, fold changes (FC) compared to 'LPS only' are calculated for each concentration tested and the maximal FC is calculated (IL-10 FCmax):

$$IL\text{-}10\ FCmax = \max \frac{(RLU_{test\ compound})}{RLU\ trigger}$$

The median maximal FC for test compounds across two or more runs is reported (IL-10FCmax median).

3.2.2.3.3 Results & Outcome

The data obtained when subjecting illustrative compounds of the invention are described in the table below.

TABLE VIII

Monocytes TNFα inhibition and IL-10 induction of illustrative compounds of the invention.

| Cpd# | TNFα $EC_{50}$ (nM) | IL-10 FCmax median |
|---|---|---|
| 6 | *** | +++ |
| 9 | **** | +++ |
| 86 | *** | +++ |
| 88 | *** | +++ |
| 193 | **** | +++ |
| 209 | *** | + |
| 218 | *** | +++ |
| 219 | *** | +++ |
| 220 | *** | +++ |
| 225 | *** | +++ |
| 227 | ** | ++ |
| 233 | *** | +++ |
| 234 | *** | +++ |
| 242 | *** | ++ |
| 244 | *** | +++ |
| 245 | NA | +++ |
| 248 | *** | +++ |
| 252 | *** | +++ |
| 257 | *** | +++ |
| 259 | *** | +++ |
| 268 | *** | +++ |
| 270 | ** | ++ |
| 271 | *** | ++ |
| 272 | **** | +++ |
| 273 | *** | ++ |
| 274 | *** | ++ |
| 275 | *** | +++ |
| 276 | *** | ++ |
| 277 | **** | +++ |
| 278 | *** | ++ |
| 279 | **** | +++ |
| 280 | **** | ++ |
| 281 | **** | +++ |
| 283 | *** | +++ |
| 284 | **** | ++ |
| 285 | *** | +++ |
| 286 | *** | ++ |
| 287 | **** | ++ |
| 288 | **** | +++ |
| 290 | **** | +++ |
| 291 | **** | +++ |
| 292 | **** | +++ |
| 293 | **** | +++ |
| 298 | *** | +++ |
| 299 | **** | +++ |

TABLE VIII-continued

Monocytes TNFα inhibition and IL-10 induction of illustrative compounds of the invention.

| Cpd# | TNFα EC$_{50}$ (nM) | IL-10 FCmax median |
|---|---|---|
| 300 | **** | +++ |
| 301 | **** | +++ |
| 302 | **** | +++ |
| 303 | **** | +++ |
| 305 | **** | +++ |
| 315 | *** | ++ |
| 316 | **** | +++ |
| 319 | *** | ++ |
| 321 | **** | +++ |
| 322 | **** | ++ |
| 323 | **** | +++ |
| 324 | *** | ++ |
| 325 | **** | ++ |
| 327 | *** | +++ |
| 328 | *** | +++ |
| 329 | **** | +++ |
| 330 | *** | +++ |
| 331 | **** | +++ |
| 334 | *** | ++ |
| 335 | *** | +++ |
| 337 | **** | +++ |
| 338 | **** | ++ |
| 344 | **** | ++ |
| 345 | **** | +++ |
| 348 | **** | ++ |
| 349 | *** | +++ |
| 354 | *** | +++ |
| 356 | *** | +++ |
| 358 | *** | +++ |
| 360 | **** | ++ |
| 361 | **** | ++ |
| 362 | *** | ++ |
| 363 | **** | +++ |
| 366 | ** | ++ |
| 370 | *** | ++ |
| 371 | *** | ++ |
| 374 | *** | +++ |
| 375 | *** | +++ |
| 377 | **** | ++ |
| 378 | **** | ++ |
| 379 | *** | ++ |
| 380 | **** | ++ |
| 381 | **** | ++ |
| 382 | **** | ++ |
| 383 | *** | ++ |
| 384 | **** | ++ |
| 385 | **** | +++ |
| 386 | *** | +++ |
| 387 | **** | +++ |
| 388 | *** | +++ |
| 390 | **** | +++ |
| 394 | **** | ++ |

\* >5000 nM
\*\* >1000-5000 nM
\*\*\* >100-1000 nM
\*\*\*\* 0.1-100 nM
+ ≤1.5
++ >1.5-4.5
+++ >4.5
NA not measured Example 4. In Vivo Assays 4.1. Inflammatory Bowel Disease 4.1.1. DSS Model (Mice)

The mouse chronic DSS-induced inflammatory bowel disease model (IBD) is a well validated disease model for inflammatory bowel disease (Wirtz et al. 2007; Sina et al. 2009).

To induce a chronic colitis, female BALB/c mice are fed with drinking water containing 400 dextran sodium sulfate (DSS) for 4 days, followed by 3 days of regular drinking water. This cycle is repeated until sacrifice on day 12 or 18. Animals are divided into several groups:
   a. intact water; vehicle alone, n=10),
   b. diseased (DSS; vehicle alone, n=10),
   c. sulfasalazine used as reference (DSS; 20 mg/kg/day, p.o., n=10) and
   d. the tested compound (DSS; e.g., 1, 3, 10, 30 mg/kg/day, p.o., n=10).

Clinical parameters are measured every other day. The disease activity index (DAI) is a composite measure combining the individual scores for weight loss, stool consistency and blood presence in stools. Mice are sacrificed according to the protocol introduced by Sina et al. (2009) (Sina et al. 2009). At sacrifice time, the complete colon is removed and rinsed with sterile PBS. Segments of the distal colon are dissected for histological analysis, gene expression and protein level measurement.

4.2. CIA Model 4.2.1. Materials

Completed Freund's adjuvant (CFA) and incomplete Freund's adjuvant (IFA) were purchased from Difco. Bovine collagen type II (CII), lipopolysaccharide (LPS), and Enbrel® (etanercept) were obtained from Chondrex (L'Isle d'Abeau, France); Sigma (P4252, L'Isle d'Abeau, France), Whyet (25 mg injectable syringe, France), respectively. All other reagents used were of reagent grade and all solvents were of analytical grade.

4.2.2. Animals

DBA1/J mice (male, 7-8 weeks old) were obtained from Charles River Laboratories (Écully, France). Mice were kept on a 12 h light/dark cycle. Temperature was maintained at 22° C., and food and water were provided ad libitum.

4.2.3. Collagen Induced Arthritis (CIA)

One day before the experiment, CII solution (2 mg/mL) was prepared with 0.05 M acetic acid and stored at 4° C. Just before the immunization, equal volumes of adjuvant (IFA) and CII were mixed by a homogenizer in a pre-cooled glass bottle in an ice water bath. Extra adjuvant and prolonged homogenization may be required if an emulsion is not formed. 0.2 mL of the emulsion was injected intradermally at the base of the tail of each mouse on day 1, a second booster intradermal injection (CII solution at 2 mg/mL in CFA 0.1 mL saline) was performed on day 9. This immunization method was modified from published methods (Jou et al. 2005; Sims et al. 2004).

4.2.4. Study Design

The therapeutic effects of the compounds were tested in the mouse CIA model. Mice were randomly divided into equal groups and each group contained 10 mice. All mice were immunized on day 1 and boosted on day 21. The negative control group was treated with vehicle (MC 0.5%) and the positive control group with Enbrel® (10 mg/kg, 3× week., sc). A compound of interest was typically tested at 3 doses per os (p.o.). At day 32, randomization between groups was performed with respect with clinical score and animals were therapeutically treated regarding their group until day 47. Body weight and clinical score, were recorded at least twice a week.

4.2.5 Clinical Assessment of Arthritis

Arthritis is scored according to the method of Khachigian 2006, Lin et al 2007 and Nishida et al. 2004 (Khachigian 2006; Lin et al. 2007; Nishida et al. 2004). The swelling of each of the four paws is ranked with the arthritic score as follows: 0-no symptoms; 1-mild, but definite redness and swelling of one type of joint such as the ankle or wrist, or apparent redness and swelling limited to individual digits, regardless of the number of affected digits; 2-moderate redness and swelling of two or more types of joints; 3-severe redness and swelling of the entire paw including digits; 4-maximally inflamed limb with involvement of multiple joints (maximum cumulative clinical arthritis score 16 per animal) (Nishida et al. 2004).

4.2.5.1. Change in Body Weight (%) after Onset of Arthritis

Clinically, body weight loss is associated with arthritis (Argilés & López-Soriano 1998; Rall & Roubenoff 2004; Shelton et al. 2005; Walsmith et al. 2004). Hence, changes in body weight after onset of arthritis can be used as a non-specific endpoint to evaluate the effect of therapeutics in the mouse model. The change in body weight (%) after onset of arthritis was calculated as follows:

$$\text{Mice: } \frac{\text{Body Weight}_{(week6)} - \text{Body Weight}_{(week5)}}{\text{Body Weight}_{(week5)}} \times 100\%$$

4.2.5.2. Radiology

X-ray photos were taken of the hind paws of each individual animal. A random blind identity number was assigned to each of the photos, and the severity of bone erosion was ranked by two independent scorers with the radiological Larsen's score system as follows: 0—normal with intact bony outlines and normal joint space; 1—slight abnormality with any one or two of the exterior metatarsal bones showing slight bone erosion; 2—definite early abnormality with any three to five of the exterior metatarsal bones showing bone erosion; 3—medium destructive abnormality with all the exterior metatarsal bones as well as any one or two of the interior metatarsal bones showing definite bone erosions; 4—severe destructive abnormality with all the metatarsal bones showing definite bone erosion and at least one of the inner metatarsal joints completely eroded leaving some bony joint outlines partly preserved; 5-mutilating abnormality without bony outlines. This scoring system is a modification from Salvemini et al., 2001; Bush et al., 2002; Sims et al., 2004; Jou et al., 2005 (Bush et al. 2002; Jou et al. 2005; Salvemini et al. 2001; Sims et al. 2004).

4.2.5.3. Steady State PK

At day 7, blood samples were collected at the retro-orbital sinus with lithium heparin as anti-coagulant at the following time points: predose, 1, 3 and 6 hrs. Whole blood samples were centrifuged and the resulting plasma samples were stored at −20° C. pending analysis. Plasma concentrations of each test compound were determined by an LC-MS/MS method in which the mass spectrometer was operated in positive electrospray mode.

4.2.6. Results

When tested in this protocol, the following data were obtained:

TABLE IX

| | CIA clinical score | | | | | | | | | | |
|---|---|---|---|---|---|---|---|---|---|---|---|
| Day | 32 | 33 | 35 | 36 | 39 | 40 | 41 | 42 | 43 | 46 | 47 |
| Disease vehicle | 2.7 | 2.9 | 4.1 | 4.3 | 6.4 | 6.2 | 6.5 | 7.0 | 7.0 | 8.1 | 8.0 |
| s.e.m. | 0.5 | 0.5 | 0.7 | 0.7 | 0.9 | 0.9 | 0.8 | 0.8 | 0.7 | 0.9 | 1.1 |
| P value | ns | ns | ns | ns | ns | ns | ns | ns | ns | ns | ns |
| Enbrel ® (10 mg/kg 3x/w) | 2.7 | 2.4 | 2.7 | 2.6 | 3.0 | 2.8 | 3.1 | 3.1 | 3.2 | 3.7 | 3.1 |
| s.e.m. | 0.52 | 0.56 | 0.73 | 0.70 | 0.68 | 0.59 | 0.77 | 0.74 | 0.74 | 0.84 | 0.7 |
| P value | ns | ns | ns | ns | ** | ** | ** | *** | *** | *** | *** |
| Cpd 88 (10 mg/kg b.i.d.) | 2.7 | 3.1 | 3.6 | 4.1 | 4.4 | 4.8 | 4.5 | 4.9 | 5.1 | 8.0 | 7.9 |
| s.e.m. | 0.5 | 0.5 | 0.6 | 0.6 | 0.6 | 0.8 | 0.7 | 0.7 | 0.5 | 0.7 | 0.8 |
| P value | ns | ns | ns | ns | ns | ns | ns | ns | ns | ns | ns |
| Cpd 88 (30 mg/kg b.i.d.) | 2.7 | 2.7 | 3.4 | 3.8 | 4.5 | 4.7 | 4.7 | 5.2 | 4.6 | 6.1 | 5.4 |
| s.e.m. | 0.6 | 0.7 | 0.8 | 0.6 | 0.5 | 0.7 | 0.7 | 0.7 | 0.7 | 0.8 | 0.6 |
| P value | ns | ns | ns | ns | ns | ns | ns | ns | ns | * | ns |
| Cpd 88 (60 mg/kg b.i.d.) | 2.7 | 2.7 | 3.1 | 2.8 | 3.3 | 3.0 | 2.7 | 2.8 | 2.3 | 2.8 | 2.5 |
| s.e.m. | 0.5 | 0.5 | 0.6 | 0.7 | 0.7 | 0.7 | 0.6 | 0.6 | 0.5 | 0.6 | 0.6 |
| P value | ns | ns | ns | ns | * | * |  | * | * | * | *** | ns: not significant
p-values:
*** (<0.001)
** (<0.01)
* (<0.05) vs disease vehicle group using ANOVA and Dunnett's test

4.3. Murine Model of Psoriatic-Like Epidermal Hyperplasia Induced by Topical Applications of Imiquimod, a TL1R7/8 Agonist

4.3.1. Materials

Aldara®500 imiquimod cream is obtained from MEDA.
Anti mouse IL 12/IL 23 p40 purified antibody (C17.8) (Cat #16 7123 85) is obtained from eBioscience (Frankfurt, Germany).

4.3.2. Animals

Balb/cJ mice (female, 18-20 g body weight) are obtained from Janvier Labs (Le Genest-Saint-Isle, France). Mice are kept on a 12 h light/dark cycle. Temperature is maintained at 22±2° C., food and water are provided ad libitum.

4.3.3. Study Design

The design of the study is adapted from Van der Fits L. et al. (van der Fits et al. 2009).

On the first day, the mice are shaved around the two ears under light anaesthesia.

30 mg of commercially available imiquimod cream (Aldara® 5% cream) are applied on both internal and external surfaces of each ear for 4 consecutive days, corresponding to a daily dose of 1.5 mg of the active compound. Control animals received the same quantity of vaseline.

From day 1 to day 5, mice are dosed with test compound, 10 or 30 mg/kg, p.o., b.i.d. in methyl cellulose 0.5%, before application of imiquimod (on day 5, the mice are dosed only once, 2 h before euthanasia).

In a positive reference group, the animals receive two intraperitoneal injections of anti mouse IL-12/IL-23 p40 antibody, 10 mg/kg, on day 1 and 3 days before day 1.

4.3.4. Assessment of Disease

The thickness of both ears is measured daily with a thickness gage (Mitutoyo, Absolute Digimatic, 547 321). Body weight is assessed at initiation of the experiment and at sacrifice. At day 5, 2 h after the last dosing, the mice are sacrificed. The pinnae of the ear are cut, excluding cartilage. The pinnae are weighed and then immersed in a vial containing 1 mL of RNAlater® solution to assess gene expression.

The results are expressed as mean±SEM and statistical analysis is performed using one way ANOVA followed by Dunnett's post hoc test versus imiquimod vehicle group.

4.3.5 Gene Expression Analysis

Ears are removed from the RNAlater® solution and put in Trizol® after disruption with 1.4 mm ceramic beads in a Precellys® device. Total RNA is then purified using NucleoSpin® RNA kit. cDNA is prepared and quantitative PCR is performed with gene-specific primers from Qiagen using SYBR Green technology in a ViiA7 real-time PCR system (Applied Biosystems). Expression levels of each gene (are calculated relative to the cyclophilin A housekeeping gene expression level. Data are expressed as mean±SEM of the relative quantity. The statistical test used is ANOVA analysis of variance with Dunnett's post-hoc test versus imiquimod vehicle group.

4.4. Murine Model of Psoriatic-Like Epidermal Hyperplasia Induced by Intradermal Injections of IL-23

4.4.1. Materials

Mouse recombinant IL-23, carrier free (Cat #14-8231) is provided by e-Bioscience (Frankfurt, Germany).

4.4.2. Animals

Balb/c mice (female, 18-20 g body weight) were obtained from Janvier Labs (Le Genest-Saint-Isle, France). Mice are kept on a 12 h light/dark cycle. Temperature was maintained at 22° C., food and water are provided ad libitum.

4.4.3. Study Design

The design of the study was adapted from Rizzo H L. et al. (Rizzo et al. 2011). On the first day (D1), the mice were shaved around the two ears. For 4 consecutive days (D1 to D4), the mice received a daily intradermal dose of mouse recombinant IL-23 (1 µg/20 µL in PBS/0.1% BSA) in the right pinna ear and 20 µL of PBS/0.1% BSA in the left pinna ear under anesthesia.

From D1 to D5, mice were dosed with test-compound or with vehicle, 1 h prior IL-23 injection.

4.4.4. Assessment of Disease

The thickness of both ears was measured daily with an automatic caliper. Body weight was assessed at initiation and at sacrifice. On fifth day, 2 h after the last dosing, the mice were sacrificed. The pinnae of the ear were cut, excluding cartilage. The pinnae, placed in a vial containing 1 mL of RNAlater® solution.

At D4, blood samples were also collected from the retro-orbital sinus for PK profiling just before dosing (T0) and 1 h, 3 h, 6 h post-dosing.

There were 8 mice per group. The results were expressed as mean±SEM and statistical analysis was performed using one-way ANOVA followed by Dunnett's post-hoc test versus IL-23 vehicle groups.

4.4.5 Gene Expression Analysis

Half ears were removed from RNAlater® solution and put in Trizol® after disruption with 1.4 mm ceramic beads in a Precellys® device. Total RNA was then purified using NucleoSpin® RNA kit. cDNA was prepared and quantitative PCR was performed with gene-specific primers from Qiagen using SYBR Green technology in a ViiA7 real-time PCR system (Applied Biosystems). Expression levels of each gene were calculated relative to the cyclophilin A housekeeping gene expression level. Data were expressed as mean±SEM of the relative quantity. The statistical test used was ANOVA analysis of variance with Dunnett's post-hoc test versus the IL-23 vehicle group.

4.4.6. Results

When subjected to this protocol, Cpd 88 dosed at 10 mg/kg p.o. b.i.d. showed a statistically significant decrease of the ear thickness compared to IL-23 vehicle group.

4.5. Murine Model of Systemic Lupus Erythematosus Induced by Epicutaneous Applications of Imiquimod

4.51. Materials

Aldara® 5% imiquimod cream is obtained from MEDA. Mouse anti-double-stranded DNA antibodies ELISA kits are obtained from Alpha Diagnostic International (Cat #5120). Mouse urinary albumin ELISA kits are obtained from Abcam (Cat #ab108792). Urine creatinine assay kits are obtained from Abnova (Cat #KA4344).

4.52. Animals

BALB/cJ mice (female, 18-20 g body weight) are obtained from Janvier Labs (Le Genest-Saint-Isle, France). Mice are kept on a 12 h light/dark cycle. Temperature is maintained at 22±2° C., food and water are provided ad libitum.

4.53. Study Design

The design of the study is adapted from Yokogawa M. et al. (Yokogawa et al. 2014).
On the first day (D1), the mice are shaved around the right ears.
The mice receive an epicutaneous application of 1.25 mg of imiquimod 3 times per week on the right pinna ear for 12 consecutive weeks (D1 to D86). The control group receives the same quantity of vaseline.
From D1 to D86, mice are dosed with test compound (30 mg/kg, p.o., q.d. in methylcellulose 0.5%) or with vehicle (10 mL/kg).

4.54. Assessment of Disease

The thickness of the ears is measured once a week with an automatic gage (Mitutoyo, Absolute Digimatic, 547-321).
Body weight is assessed at initiation and once a week until sacrifice. At necropsy, the spleen weight is also measured. The mice are sacrificed 2 h after the last dosing.
At different time points (e.g., on days D28, D56 and D84), the mice are individually placed in a metabolic cage to perform urinalysis and assess proteinuria (albumin to creatinine ratio).
Serums are collected at different time points (e.g., on D28, D56 and D86) to assess anti-double stranded-DNA IgG levels.
At D13, blood samples are also collected from the retroorbital sinus for PK profiling just before dosing (T0) and 1 h, 3 h, and 6 h post-dosing.
There are 8-19 mice per group. The results are expressed as mean±SEM and statistical analysis is performed using one-way ANOVA followed by Dunnett's post-hoc test versus imiquimod vehicle groups.

4.55 Quantification of Compound Levels in Plasma

Plasma concentrations of each test compound are determined by an LC-MS/MS method in which the mass spectrometer is operated in positive or negative electrospray mode.

4.5.5.1. Histopathology

In each glomerulus, 4 different readouts including mesangioproliferation, endocapillary proliferation, mesangial matrix expansion and segmental sclerosis are graded on a scale of 0 to 2 and then summed. For each kidney, about 50 glomeruli are scored and then averaged giving one glomerular lesion score (Yokogawa et al. 2014). Data are expressed as mean±SEM and statistical analysis is performed using the Kruskal-Wallis test followed by Dunn's post-hoc test versus imiquimod vehicle group.

4.5.5.2. Cellular Quantifications

For each cell type, immunohistochemical analysis is performed using image analysis (CaloPix software, TRIBVN Healthcare) on the whole tissue section at a magnification of ×20. Data are expressed as mean±SEM and statistical analysis is performed using one-way ANOVA followed by Dunnett's post-hoc test versus imiquimod vehicle group.

4.5.5.3. Gene Expression Analysis

At sacrifice, the second part of the left kidneys is placed in tubes containing 1.4 mm ceramic beads and disrupted in 1% DTT RLT lysis buffer (Qiagen, Cat #79216) with a Bertin Instruments Precellys® homogenizer. Total RNA is then purified with a QIAcube using an RNeasy® 96 QIAcube® HT Kit (Qiagen, Cat #74171). cDNA is prepared and quantitative PCR performed with gene-specific primers from Qiagen using SYBR Green technology in a ViiA 7 real-time PCR system (Applied Biosystems). Expression levels of each gene of interest (GOI=CD3, CD68, CD20, OAS1, Mx1, IFIT1, CXCL11 and Usp18) are calculated relative to the cyclophilin, GAPDH and R-actin housekeeping gene expression levels.

At sacrifice, one-third of the spleen is placed into tubes containing 1.4 mm ceramic beads and disrupted in Trizol® with a Bertin Instruments Precellys® homogenizer. Total RNA is extracted using a phenol/chloroform process and then purified with a QIAcube using an RNeasy® 96 QIAcube® HT Kit (Qiagen, Cat #74171). cDNA is prepared and quantitative PCR performed with gene-specific primers from Qiagen using SYBR Green technology in a ViiA 7 real-time PCR system (Applied Biosystems). Expression levels of each gene of interest are calculated relative to the cyclophilin, GAPDH and R-actin housekeeping gene expression levels.

4.6. Murine Model of Psoriatic Arthritis Induced by Overexpression of IL-23

4.6.1. Materials

Mouse IL-23 enhanced episomal expression vector (EEV) is obtained from System Biosciences (Cat #EEV651A-1). Mouse IL-23 Quantikine ELISA Kits are obtained from R&D Systems (Cat #M2300). ProSense® 680 and OsteoSense® 750EX are obtained from PerkinElmer (Cat #NEV10003 and NEV10053EX). RNAlater® is obtained from Ambion (Cat #AM7021). Imalgene® 1000 (Merial) and Rompun® 2% (Bayer) are obtained from Centravet (Cat #IMA004-6827812 and ROM001-6835444).

4.6.2. Animals

B10.RIII mice (male, 8-week old) are obtained from Charles River (Écully, France). Mice are kept on a 12 h light/dark cycle. Temperature is maintained at 22±2° C., food and water are provided ad libitum.

4.6.3. Study Design

The design of the study is adapted from Sherlock J P. et al. (Sherlock et al. 2012).

On the first day (D1), the mice undergo a hydrodynamic injection of Ringer or IL-23 EEV in Ringer into the tail vein.

As of D5, twice a week, the mice are scored for clinical symptoms until the end of the experiment.

On D5, blood is collected by puncture in the submandibular vein to assess the serum IL-23 concentration.

On D9, mice from all groups receive ProSense® 680 probe (0.8 nmol/10 g, i.p.). On D10, the mice are anesthetized. Granulocyte infiltration is then measured using in vivo molecular imaging (Bruker In-Vivo Xtreme imaging system).

On D11, randomization is performed according to ProSense® 680 molecular imaging and scoring.

As of D12, mice are dosed with test compound or with vehicle.

On D19, blood is sampled at time T0, T1 h, T3 h and T6 h after last dosing. Plasma is separated and kept at 20° C. until bioanalysis.

On D36, mice from all groups are sacrificed 2 h after last administration of compound.

Total blood is collected in a serum blood tube and mixed by gentle inversion 8-10 times. After clotting, blood samples are centrifuged 10 min at 1800×g. After centrifugation, serum is stored at −80° C.

4.6.4. Assessment of Disease

Body weight is assessed at initiation of the study, then twice a week and at sacrifice.

Twice weekly, clinical signs of inflammation are scored: 0 for normal paw; 1 if swelling of one digit; 2 if swelling of two or more digits; 3 if swelling of the entire paw. The scores of all limbs are summed up to produce a global score.

On D32, mice from all groups receive ProSense® 680 probe (0.8 nmol/10 g, i.p.) and OsteoSense® 750EX probe (0.8 nmol/10 g, i.p.). On D33, the mice are anesthetized and granulocyte infiltration and bone remodelling are measured using in vivo molecular imaging (Bruker In-Vivo Xtreme imaging system).

There are 10 mice per group. The results are expressed as mean±SEM and statistical analysis is performed using one-way ANOVA followed by Dunnett's post-hoc test versus diseased vehicle group for scoring and imaging analysis, versus sham vehicle group for body weight.

4.7. Murine Collagen-Antibody Induced Arthritis Model (CAIA)

4.7.1. Materials

ArthritoMabrm antibody cocktail for inducing arthritis and lipopolysaccharide (LPS) from *Escherichia Coli* serotype O55:B5 were purchased from MD Biosciences (OakdalMNnn., USA, Cat #CIA-MAB-50); PBS 1× (GIBCO, Cat #140190-086) was obtained from ThermoFisher Scientific, and Enbrel® (etanercept) was purchased from Chondrex (L'Isle d'Abeau, France, Cat #3771910).

4.7.2. Animals

Five to seven week old BALBc female mice were obtained from Janvier Labs (Le Genest-Saint-Isle, France). Mice were kept on a 12 h light/dark cycle. Temperature was maintained at 22° C., food and water were provided ad libitum.

4.7.3. Study Design

The therapeutic effects of the compounds of the invention were tested in the mouse CAIA model (MD Biosciences 2008; Nandakumar et al. 2003). At day 1 (D1), mice were randomly divided into equal groups containing 10 mice. All mice including vehicle, except the non-treated group, were immunized with ArthritoMabrm cocktail (100 mg/kg, i.v., 200 µL/mouse) and treatment with compound or vehicle started. Bodyweight and clinical score of each mouse was assessed every day except the weekend until the end of the study. At D4, all mice, except the non-treated group, received a challenge of LPS (2.5 mg/kg, i.p.). At D11, all mice were sacrificed and blood was sampled on serum tube. After centrifugation, serum was collected and frozen at −80° C. pending analysis (e.g., cytokine levels, gene expression, compound levels). For histology readouts, right and left hind paws were individually collected in vials (25 mL minimum) filled with 4% buffered formaldehyde for a minimum of 24 h to a maximum of 4 days at RT.

4.7.4. Clinical Assessment of Arthritis

Arthritis was scored according to the method of Khachigian 2006; Lin et al 2007 and Nishida et al. 2004 (Khachigian 2006; Lin et al. 2007; Nishida et al. 2004). The swelling of each of the four paws was ranked with the arthritic score as follows:

| Score | Definition |
|---|---|
| 0 | no symptoms |
| 1 | mild, but definite redness and swelling of one type of joint such as the ankle or wrist, or apparent redness and swelling limited to individual digits, regardless of the number of affected digits |
| 2 | moderate redness and swelling of two or more types of joints |
| 3 | severe redness and swelling of the entire paw including digits |
| 4 | maximally inflamed limb with involvement of multiple joints |

The final clinical score was the cumulative score of the four paws (maximum cumulative clinical arthritis score 16 per animal)(Nishida et al. 2004). A curve of cumulative clinical score was drawn for each group, and the area under the curve was calculated. The results were expressed as mean±SEM and statistical analysis was performed using one-way ANOVA followed by Dunnett's post-hoc test versus vehicle groups.

4.7.5. Results

When subjected to this protocol, Cpd 88 dosed at 60 mg/kg p.o. b.i.d. showed a statistically significant reduction of Area Under the Curve (AUC) of clinical score vs. vehicle group.

4.8. Murine therapeutic model of atopic dermatitis induced by topical application of MC903

4.8.1. Materials

Methylcellulose 0.5% (Cat #AX021233) is obtained from VWR. MC903 (calcipotriol, Cat #2700/50) is obtained from Tocris Bioscience (Bristol, UK). ProSense® 680 (Cat

NEV10003) is obtained from PerkinElmer (Massachusetts, USA). RNAlater® (Cat #AM7021) is obtained from Ambion (California, USA).

4.8.2. Animals

BALB/cN mice (female, 18-20 g body weight) or CD1/Swiss mice (female, 24-26 g body weight) are obtained from Janvier Labs (Le Genest-Saint-Isle, France). Mice are kept on a 12 h light/dark cycle. Temperature is maintained at 22±2° C., food and water are provided ad libitum.

4.8.3. Study Design

The design of the study is adapted from Li M. et al. (Li et al. 2006). On the first day (D1), the mice are anesthetized and shaved around the two ears. As of D1, either 20 µL EtOH or 2 nmol of MC903 (in 20 µL EtOH) are topically applied on each ear of the mice up to D9, D11 or D15 (except during the weekend).

From D5, the mice are dosed with test compound (15 or 30 mg/kg, p.o., b.i.d. in methylcellulose 0.5%) or dexamethasone (5 mg/kg, p.o., q.d. in methylcellulose 0.5%), or with vehicle, until D10, D12, or D16.

4.8.4. Quantification of Compound Levels in Plasma

Plasma concentrations of each test compound are determined by an LC-MS/MS method in which the mass spectrometer is operated in positive or negative electrospray mode.

4.8.5. Determination of Pharmacokinetic Parameters

Pharmacokinetic parameters are calculated using Phoenix® WinNonlin® (Pharsight®, USA).

4.8.6. Assessment of Disease

The thickness of each ear is measured immediately before first application of MC903 (baseline), three times a week, and at sacrifice using a thickness gauge (Mitutoyo, Absolute Digimatic, Cat #547-321).

Body weight is assessed at immediately before first application of EtOH (baseline), three times a week and at sacrifice.

On D8, D10 or D11, mice from all groups receive ProSense® 680 probe (0.8 nmol/10 g, i.p.). On the next day (D9, D11 or D12), the mice are anesthetized. Granulocyte infiltration is then measured using in vivo molecular imaging (Bruker In-Vivo Xtreme imaging system, excitation wavelength: 630 nm, emission wavelength: 700 nm, acquisition time: 5 seconds).

On D10, D12, or D16, 2 h after the last dosing, the mice are sacrificed, total blood is collected in EDTA-coated tubes and plasma is frozen for further measurements (including circulating compound).

The pinnae of the ears are collected. One ear is cut longitudinally into 2 halves. One half is fixed in formaldehyde buffer 3.7% for histology; the other one is immersed in RNAlater® to assess gene expression.

There are 8 mice per group. The results are expressed as mean±SEM and statistical analysis is performed using one-way ANOVA followed by Dunnett's post-hoc test versus MC903 vehicle groups (MC903 treated mice dosed with vehicle alone) for ear thickness and weight, and/or versus EtOH vehicle group (EtOH treated mice dosed with vehicle alone) for body weight.

4.8.7. Histology

After sacrifice, half ears are collected and fixed in 3.7% formaldehyde before embedding in paraffin. 4 µm thick sections are immunostained by immunohistochemistry with anti-CD3 antibody. The immunostained cell areas from a whole section per mouse are measured by image analysis (CaloPix software, TRIBVN Healthcare, France). Data are expressed as mean±SEM and statistical analysis is performed using one-way ANOVA followed by Dunnett's post-hoc test versus MC903 vehicle group.

4.8.8. Gene Expression Analysis

Ears are removed from RNAlater® solution and placed in Trizol® after disruption with 1.4 mm ceramic beads in a Bertin Instruments Precellys® homogenizer. Total RNA is then extracted using a phenol/chloroform protocol and purified with a QIAcube using an RNeasy® 96 QIAcube® HT Kit (Qiagen, Cat #74171). cDNA is prepared and quantitative PCR performed with gene-specific primers from Qiagen using SYBR Green technology in a ViiA 7 real-time PCR system (Applied Biosystems). Expression levels of each gene of interest (GOI=IL4, IL5, IL13, TSLP, IL33, ST2, IL25, IL31, IFNγ, IL6, IL10, LCN2, S100A8, and S100A9) are calculated relative to the housekeeping gene expression levels (HPRT, GAPDH and β-actin).

All qPCR data are expressed as mean±SEM of the normalized relative quantity (NRQ) calculated according to the following steps:

1—Calculate the geometric mean of NRQ for each group of animals $$NRQ_{sample} = \frac{2^{-Cq\ GOI}}{\text{Geometric mean}(2^{-Cq\ hPRT}, 2^{-Cq\ GADPH}, 2^{-Cq\ \beta\text{-}actin})}$$

2—Calculate NRQ-scaled compared to the MC903 vehicle group $$NRQscaled = \frac{NRQ_{sample}}{\text{Geometric mean}(NRQ_{samples\ MC903\ vehicle\ group})}$$

The statistical test used is ANOVA analysis of variance with Dunnett's post-hoc test versus the EtOH vehicle group and/or MC903 vehicle group.

4.9. Mouse LPS-Induced Endotoxic Shock

Injection of lipopolysaccharide (LPS) induces a rapid release of soluble tumour necrosis factor (TNFα) into the periphery. This model was used to assess prospective blockers of TNFα release in vivo.

4.9.1. Materials

Lipopolysaccharide (LPS) from *Escherichia Coli* serotype O111:B4 was obtained from Sigma Aldrich (Cat #L2630).

4.9.2. Animals

BALB/cAnNCrl mice (female, 18-20 g body weight) were obtained from Charles River (Calco, Italy). Mice were kept on a 12 h light/dark cycle. Temperature was maintained at 22±2° C., food and water were provided ad libitum.

4.9.3. Study Design

Mice were dosed once by oral (p.o.) or subcutaneous (sc) route with the tested compound in the appropriate vehicle.

At the Tmax of compound, 100 µg of LPS (in $H_2O$) was injected intraperitoneally to mice. A control group was included which comprises administering the vehicle without an LPS challenge.

Mice were sacrificed 90 min after LPS challenge and blood was collected in heparinised tubes. Plasma was obtained by centrifugation for 15 min, 2000×g at +4° C. and frozen at −80° C. before cytokine analysis.

4.9.4. Assessment of Disease

TNFα and IL-10 were quantified in plasma by AlphaLISA detection kits obtained from PerkinElmer (Massachusetts, USA), Cat4 AL505C and AL502C, respectively.

Statistics were performed with Prism 5.03 software (GraphPad) using an ANOVA analysis of variance with Dunnett's post-hoc test versus LPS group.

Active compounds were defined as showing a statistically significant decrease in TNFα with or without a statistically significant induction of IL-10

| Score | Definition |
|---|---|
| + | statistically significant inhibition of TNFα |
|   | statistically significant induction of IL-10 |
| − | no effect on the level of TNFα |
|   | no effect on the level of IL-10 |

| Compound | dose | TNFα | IL-10 |
|---|---|---|---|
| 6 | 3 mg/kg, p.o. | − | − |
|   | 10 mg/kg, p.o. | + | + |
| 18 | 3 mg/kg, p.o. | − | − |
|   | 10 mg/kg, p.o. | − | − |
| 86 | 3 mg/kg, p.o. | + | + |
|   | 10 mg/kg, p.o. | + | + |
| 225 | 3 mg/kg, p.o. | + | + |
|   | 10 mg/kg, p.o. | + | + |
| 88 | 3 mg/kg, p.o. | + | − |
|   | 10 mg/kg, p.o. | + | + |
|   | 30 mg/kg, p.o. | + | + |
| 16 | 3 mg/kg, p.o. | − | − |

4.10. MultiDrug Resistance-1a-Ablated (MDRa1) Model (Mice)

4.10.1. Principle of Assay

Mice deficient in Abcb1a (MDRa1) develop spontaneous colitis that can be accelerated by infection with *Helicobacter bilis*. This model is used to evaluate the ability of a compound to treat or prevent colitis (Maxwell et al. 2015).

4.10.2. Materials

Sterile PBS (Gibco, Cat #20012027) was obtained from ThermoFisher Scientific (Massachusetts, USA); *Brucella* Agar (Cat #211086) was obtained from Becton Dickinson (New Jersy, USA); *Brucella* Broth Base (Cat #B3051-500g) was obtained from Sigma Aldrich (Missouri, USA). Defibrinated sheep blood (Cat #SR0051) and Campygen (Cat #CN0025) were obtained from ThermoFisher Scientific (Massachusetts, USA). *H. bilis* ATCC 51360 was obtained from LGC Standards (Molsheim, France) and Combur testE (Cat #11896857) was obtained from Roche Diagnostics (Basel, Switzerland).

4.10.3. Animals

Seven to nine week old MDR1a (FVB.129P2-Abcblatm1Bor N7) female mice were obtained from Taconic (RensselaeNY.Y., USA) and seven to nine week old FVB female mice were obtained from Janvier Labs (Le Genest-Saint-Isle, France). Mice were kept on a 12 h light/dark cycle. Temperature was maintained at 22° C., food and water were provided ad libitum.

4.10.4. H. bilis Inoculum Preparation

Frozen vial of *H. bilis* was thawed, put in *Brucella* Broth and incubated in *Brucella* Agar slant containing 5% of defibrinated sheep blood under microaerophily at 37° C. for 4 to 5 days. At D1, just before administration, a part of *H. bilis* culture was diluted in PBS in order to obtain $10^7$ cfu/mouse and a second part was put in fresh *Brucella* Broth and incubated as previously for 7 days. At D8, just before administration, *H. bilis* culture was diluted in PBS in order to obtain $10^7$ cfu/mouse.

4.10.5 Study Design

After a 10 days acclimatization period, the disease activity index of each MDR1a mouse was determined in order to constitue homogene groups regarding the DAI score between groups. All mice (10 mice per group), except for the SHAM group (n=10), were then administered by oral route with an inoculum of *H. bilis* ($10^7$ cfu/mouse) and treatment started accordingly to the protocol for six weeks. Seven days after the start of treatment, a second administration of *H. bilis* was performed. During the whole treatment period, disease activity index was determined twice a week. Six weeks after the start of treatment, mice were sacrificed, blood was sampled and the complete colon was collected and rinsed with sterile PBS. Collected colons were measured and weighed in order to determine colon weight/length ratio, and histological analysis, gene expression, protein level measurement and/or FACs immunophenotyping analysis were performed on the samples. The results were expressed as mean±SEM and statistical analysis was performed using one-way ANOVA followed by Dunnett's post-hoc test versus vehicle groups.

4.10.6. Disease Activity Index (DAI) Determination

The DAI score of each mouse (sum of scores for weight loss, stool consistency and rectal bleeding) was monitored during the entire treatment period and a DAI score progression curve was obtained.

| DAI | Weight evolution | Stool consistency | Rectal bleeding* |
|---|---|---|---|
| 0 Point | No weight loss (vs D1) | Well molded stools | |

-continued

| DAI | Weight evolution | Stool consistency | Rectal bleeding* |
|---|---|---|---|
| 1 point | 1 to 5% | Semi-soft stools | |
| 2 points | 5 to 10% | Soft stools that do not stick to the anus | |
| 3 points | 10 to 20% | Semi-liquid stools not sticking to the anus | |
| 4 Points | >20% | Liquid stools remaining stuck to the anus | |

*A little piece of stool was deposited on a vial containing 1 mL of D-PBS and homogeneized, deposited on a test strip (Combur TestE), a color appears according to the blood intensity in the stool, a score was given according to this intensity, from 0 to 4 points.

4.11. Radiation Induced Fibrosis Mouse Model

4.11.1. Study Overview

Pneumonitis and lung fibrosis are the major radiation-induced complications following thoracic radiotherapy, which is one of the major treatment of lung and breast cancers, lymphomas and hematopoietic transplant conditioning. The objective of this model was to evaluate the effect of a compound of the invention in lung fibrosis induced by radiation in mice (Favaudon et al. 2014), in particular on lung functionality (Flexivent) and fibrosis marker (Collagen I).

4.11.2. Animals 7 weeks old (18-22 gr) female C57BL/6J mice from Charles River (Écully, France), batch number S1672) were maintained on 12 h light/dark cycle at 22° C. with ad libitum access to tap water and food.

4.11.3. Materials

The test compounds were dissolved/suspended in appropriate vehicle prior to using and kept light-free, under agitation at RT.

An aliquot of the formulation (~200 μL) was frozen at T0 (day of preparation) and all the formulations were checked (daily) for any change in aspect.

The dose volume administered was 10 mL/kg and the volume was adapted following mean (body weight (BW) of the group as follows: 200 μL if mean BW <22.5 g, 250 μL if mean BW ≥22.5 g; 300 μL if mean BW >27.5 g.

4.11.4. In Vivo Experimental Procedure

On day 1 of week 1, the animals were exposed at the thorax to a 17 Gray irradiation dose, under isoflurane anesthesia.

At the beginning of week 18 post radiation (D1), animals were randomized into 6 study groups (15 subjects per group): 1) sham (vehicle: methylcellulose (MC) 0.5%), 2) diseased (vehicle: methylcellulose (MC) 0.5%), 3) positive control (nintedanib dosed 60 mg/kg in 0.1% Natrosol™), and 4) 3 groups test compound (60 mg/kg in 0.5% Methylcellulose (MC)), and dosed p.o. b.i.d. until D23 (week 21).

Body weight was recorded once a week, and on D23, lung function measurement under anesthesia was realized by Flexivent (Devos et al. 2017) for all groups (6 successful measurement per group) before sacrifice.

Lungs were collected and fixed in 4% formaldehyde for 24 h before embedding in paraffin. 4 μm thick sections were immunostained with anti-collagen I antibody (LSBio, 2401 Fourth Avenue Suite 900, SeattWAsh. 98121, USA, Cat #LS-343921). The sections were deparaffinized and processed by heat antigen retrieval before incubation for one hour with the primary antibody. The anti-collagen I antibody was detected and amplified by ImmPress kit (Vector Laboratories, 3, Accent Park, Bakewell Road, Orton Southgate, Peterborough, PE2 6XS, United Kingdom, Cat #MP-7401). The immunostained sections were then scanned (Nanozoomer, Hamamatsu) before quantification by image analysis (CaloPix software, TRIBVN Healthcare). Data were expressed as percentage collagen I area per area of lung tissue.

Values of all mice from the same group were averaged. Data were expressed as mean±sem and were compared with a a one-way ANOVA on Log-transformed data and Dunnett's post-hoc test. Significance levels were defined as * ($p<0.05$),  ($p<0.01$), or * ($p<0.001$) versus irradiated control group.

4.11.5 Results

When subjected to this protocol, Cpd 88 dosed at 60 mg/kg p.o. b.i.d. showed a statistically significant reduction of ColI (collagen I) extent vs. vehicle group.

4.12. Bleomycin Induced Pulmonary Fibrosis in Mice

4.12.1. Study Overview

The aim of the study is to test the efficacy of a test compound at three different doses in a 14-day model of bleomycin induced pulmonary fibrosis in mice.

4.12.2. Animals

This study is carried out on C527BL/6N male mice, supplied by Charles River (Calco, Italy), which are acclimatized for at least 5 days in an environment maintained at 22° C., at 55% relative humidity, with 15-20 air changes per h under light cycles of 12 h. Mice pelleted food and water are provided ad libitum.

At least one day prior to start of experiment, all animals are allocated randomly into groups as indicated in the table below.

TABLE X

| | | | | | | |
|---|---|---|---|---|---|---|
| | | Study groups | | | | |
| Groups | Purpose | n | Dose | Treatment schedule Days (Frequency) | Route | Vehicle |
| 1 PBS + vehicle | control | 15 | — | D 0-D 14 (b.i.d.) | NA | NA |
| 2 BLM + vehicle | control | 15 | — | D 0-D 14 (b.i.d.) | p.o. | PEG/MC |

TABLE X-continued

Study groups

| Groups | Purpose | n | Dose | Treatment schedule Days (Frequency) | Route | Vehicle |
|---|---|---|---|---|---|---|
| 3<br>BLM + pirfenidone | control | 15 | 50 mg/kg | D 0-D 14 (b.i.d.) | p.o. | 0.1% Natrosol ™ |
| 4<br>BLM + test compound | active | 15 | 1 mg/kg | D 0-D 14 (b.i.d.) | p.o. | PEG400/MC 0.5% 20/80 (v/v) |
| 5<br>BLM + test compound | active | 15 | 3 mg/kg | D 0-D 14 (b.i.d.) | p.o. | PEG400/MC 0.5% 20/80 (v/v) |
| 6<br>BLM + test compound | active | 15 | 10 mg/kg | D 0-D 14 (b.i.d.) | p.o. | PEG400/MC 0.5% 20/80 (v/v) |
| 7<br>BLM + test compound satellite for PK | active | 10 | 10 mg/kg | D 0-D 7 (b.i.d.) | p.o. | PEG400/MC 0.5% 20/80 (v/v) |

4.12.3. Materials

The solvent for the test solutions is prepared by adding 0.5 g of hydroxyethylcellulose (Natrosol™) into 500 mL aqua distillate (0.1%) under continuous stirring without heating for 5 h on a magnetic stirrer.

To prepare a solution for intranasal (i.n.) challenge, 0.8 mg/mL stock solutions of bleomycin (Cat #BML-AP302-0010, Enzo Life Sciences, Inc., USA) are thawed and diluted in 330 µL of saline.

Prior to i.n. administration, mice are anesthetized i.p.

Fresh pirfenidone formulation is prepared daily in 0.1% Natrosol™ formulations to a final concentration of 5 mg/mL. Before dosing, animals are weighed and the pirfenidone amount administered is adjusted accordingly to individual weights corresponding to 10 mL/kg body weight, twice daily p.o., with 7.5 h intervals between two administrations.

Finally, test compound solutions are prepared by dissolving the suitable amount of said test compound in PEG 400 (20% of the final volume) then MC 0.5% (80% of the final volume) to reach final concentrations of 1 mg/mL, 0.3 mg/mL and 0.1 mg/mL, thus yielding compound for a doses of 10 mg/kg, 3 mg/kg and 1 mg/kg. Prior to dosing, animals are weighed and the amount administered adjusted accordingly to individual weights.

The application volume of the test doses corresponds to 10 mL/kg body weight, and the test compounds are administered p.o. twice daily, with 7.5 h interval between two administrations.

4.12.4. Study

Animals are examined clinically twice daily, and clinical signs and parameters are recorded. Animals are weighed daily starting from D0.

On day 14, 2 h post dosing with vehicle, pirfenidone or test compound, mice are sacrificed.

The lungs are excised and weighed individually. For all groups: the whole superior right lung lobe is placed into a Precellys® tube containing silica beads and immediately snap frozen in liquid nitrogen and subjected to gene expression analysis.

All remaining lungs are placed into marked bottles containing 10% buffered formalin for further histopathological evaluation.

4.13. Therapeutic Bleomycin Induced Pulmonary Fibrosis 21-Day Mice Model

The aim of the study is to test the efficacy of a test compound at three different doses in a 21-day model of bleomycin induced pulmonary fibrosis in mice.

4.13.1. Animals

This study is carried out on C57BL/6N male mice, supplied by Charles River (Calco, Italy), which are acclimatized for at least 5 days in an environment maintained at 22° C., at 55% relative humidity, with 15-20 air changes per hour under light cycles of 12 h. Mice pelleted food and water are provided ad libitum.

At least one day prior to start of experiment, all animals are allocated randomly into groups as indicated in the table below.

TABLE XI

Study groups

| Groups | Purpose | n | Dose | Treatment schedule Days (Frequency) | Route | Vehicle |
|---|---|---|---|---|---|---|
| 1<br>PBS + Vehicle | control | 15 | — | D 7-D 21 (b.i.d.) | NA | NA |
| 2<br>BLM + Vehicle | control | 15 | — | D 7-D 21 (b.i.d.) | p.o. | PEG/MC |
| 3<br>BLM + Nintedanib | control | 15 | 60 mg/kg | D 7-D 21 (q.d.) | p.o. | 0.1% Natrosol ™ |
| 4<br>BLM + test compound | active | 15 | 1 mg/kg | D 7-D 21 (b.i.d.) | p.o. | PEG400/MC 0.5% 20/80 (v/v) |
| 5<br>BLM + test compound | active | 15 | 3 mg/kg | D 7-D 21 (b.i.d.) | p.o. | PEG400/MC 0.5% 20/80 (v/v) |
| 6<br>BLM + test compound | active | 15 | 10 mg/kg | D 7-D 21 (b.i.d.) | p.o. | PEG400/MC 0.5% 20/80 (v/v) |

TABLE XI-continued

Study groups

| Groups | Purpose | n | Dose | Treatment schedule Days (Frequency) | Route | Vehicle |
|---|---|---|---|---|---|---|
| 7 BLM + test compound satellite for PK | active | 10 | 10 mg/kg | D 7-D 14 (b.i.d.) | p.o. | PEG400/MC 0.5% 20/80 (v/v) |

4.13.2. Materials

The solvent for the test solutions is prepared by adding 0.5 g of hydroxyethylcellulose (Natrosol™) into 500 mL aqua distillate (0.1%) under continuous stirring without heating for 5 h on a magnetic stirrer.

To prepare a solution for intranasal (i.n.) challenge, 0.8 mg/mL stock solutions of bleomycin (Cat4 BML-AP302-0010, Enzo Life Sciences, Inc., USA) are thawed and diluted in 330 µL of saline. Prior to i.n. administration, mice are anesthetized i.p.

Fresh nintedanib formulation is prepared daily in 0.1% Natrosol™ formulations to a final concentration of 5 mg/mL. Before dosing, animals are weighed and the nintedanib amount administered is adjusted accordingly to individual weights corresponding to 10 mL/kg body weight, once daily p.o.

Finally, test compound solutions are prepared by dissolving the suitable amount of said test compound in PEG 400 (20% of the final volume) then MC 0.5% (80% of the final volume) to reach final concentrations of 1 mg/mL, 0.3 mg/mL and 0.1 mg/mL, thus yielding compound for a doses of 10 mg/kg, 3 mg/kg and 1 mg/kg. Prior to dosing, animals are weighed and the amount administered adjusted accordingly to individual weights.

The application volume of the test doses corresponds to 10 mL/kg body weight, and is the test compounds are administered p.o. twice daily, with 7.5 h interval between two administrations.

4.13.3. Study

Animals are examined clinically twice daily. List of clinical signs and parameters are indicated in human endpoints table. Animals are weighed daily starting from D0.

On day 21, 2 h post dosing with vehicle, nintedanib or test compound, mice are sacrificed.

The lungs are excised and weighed individually. For all groups: the whole superior right lung lobe is placed into a Precellys® tube containing silica beads and immediately snap frozen in liquid nitrogen and subjected to gene expression analysis.

All remaining lungs are placed into marked bottles containing 10% buffered formalin for further histopathological evaluation.

4.13.4. Sample Analysis, Data Processing and Statistical Evaluation

Body weight data and lung weight data are processed using MS Excel. Statistical analysis and graphical presentation are performed using GraphPad Prism software. One-way ANOVA or Mann-Whitney test are employed for lung weights. Two-way ANOVA are employed for body weight changes.

Differences between groups were considered statistically significant when $p<0.05$.

For histopathological evaluation, whole lungs (except sampled superior right lung) are embedded in paraffin and stained with Mallory's trichrome.

Pulmonary histological changes are assessed using Matsuse modification of Ashcroft score (Ashcroft et al. 1988; Matsuse et al. 1999). Statistical analysis and graphical presentation is performed using GraphPad Prism software. A Mann-Whitney test is employed.

Differences between groups are considered statistically significant when $p<0.05$.

| Ashcroft Score | Definition |
|---|---|
| 1 | Normal lungs (no fibrosis) |
| 2 | Minimal fibrotic thickening of alveolar or bronchial walls (network of fine collagen fibrils) |
| 3 | Moderate fibrotic thickening of walls without obvious damage to lung architecture |
| 4 | Fibrosis with damage of pulmonary structure (coarse fibrous bands or small fibrous masses, intra-alveolar collagen fibrils) |
| 5 | Large fibrous area with severe distortion of lung structure |

4.13.5 PK Analysis—Group 7

4.13.5.1. Protocol

Animals in group 7 (n=10) are included for PK study only and are not subjected to clinical sign scoring.

These animals are induced with the disease at the start of treatment at day 0 (D0) and are sequentially sacrificed on D7 at 1 h, 3 h, 6 h, 8 h, 24 h after the first administration of test compound.

A blood sample (50 µL) is collected from the tail vein into Li-heparin anticoagulant tubes for each time point and kept on ice until separation. Within maximum 30 min after collection, blood samples are centrifuged at 2000×g for 10 min at 4° C. and the resulting plasma samples are aliquoted into polypropylene tubes (1×25 µL). The samples are stored frozen at −20° C. until analysis.

The lung tissue is collected at sacrifice after blood sampling for each animal, then weighed and placed into polypropylene tubes prior to freezing. The samples are stored frozen at −80° C. until analysis.

4.13.5.2. Plasma Concentration and Pharmacokinetic Analysis

Plasma and lung concentrations are measured via LC-MS/MS. Samples are prepared for LC-MS/MS analysis via protein precipitation. The plasma concentrations measured below the lower limit of quantification (LLOQ) are reported as below the limit of quantification (BLQ). The test compound concentrations in plasma are expressed in ng/mL.

Mean plasma concentrations are calculated. For mean calculation, the concentrations below the LLOQ are set to zero. Therefore, mean values may be BLQ. Standard deviation (SD), standard error of the mean (SE) and coefficient of variation (CV, %) are tabulated when at least three plasma concentration values are above the LLOQ.

Non-compartmental analysis on individual plasma concentrations is performed using Phoenix™ WinNonlin® 6.3 (Pharsight Corporation) to determine at least, the following pharmacokinetic parameters:

Maximum plasma concentration, Cmax ($\mu g/mL$) with the corresponding time, tmax (h), Area under the plasma concentration versus time curve up to the last quantifiable concentration $AUC_{0-t}$ or up to 24 h $AUC_{0-24\,h}$ ($\mu g \cdot h/mL$) (if compound is quantifiable up to 24 h postdose), and/or up to infinity $AUC_{0-\infty}$, ($\mu g \cdot h/mL$) is calculated according to the linear up/log down trapezoidal rule. Partial AUC may be calculated if deemed necessary. Concentrations below the limit of quantification (BLQ) are set to zero. No AUC is calculated if there are less than three quantifiable time points. AUC0-∞ is considered if % AUCextra <20%, Apparent terminal elimination half-life, t½ (h) is only reported if three or more time points, excluding tmax is used for linear regression, and if the adjusted $R^2 > 0.80$.

Normalized AUC and Cmax dose.

Mean pharmacokinetic parameters are calculated. Standard deviation (SD) and coefficient of variation (CV, %) are tabulated if at least three values are available.

4.14. T Cell Transfer Model (Mice)

4.14.1. Materials

DynaMag (Cat #12321D and 123203D) were obtained from Life Technologies Invitrogen (California, USA); DynabeadsFlowComp Mouse CD4+CD25-treg cells (Cat #11463D) were obtained from Life Technologies Invitrogen (California, USA), Fetal Bovine Serum (GIBCO), Cat #10270-106; RPMI (Gibco) Cat #32404-014 and D-PBS 1× without CaCl$_2$ without MgCl$_2$ (GIBCO), Cat #14190-086 were obtained ThermoFisher Scientific (Massachusetts, USA). Red Blood Cell (RBC) lysis buffer 10×, Cat #BLE420301 obtained from Ozyme (Montigny-le-Bretonneux, France). Cell strainer (70 µm grid), Cat #352350, obtained from Corning (New York, USA). Bovine Serum Albumin (BSA), Cat #A9647-50g and EDTA, Cat #EDS-100 g obtained from Sigma Aldrich (Missouri, USA) and Combur testE, Cat #11896857, obtained from Roche Diagnostics (Basel, Switzerland).

4.14.2. Animals

Five to seven week old BALBc/N female mice and five to seven week old SCID female mice were obtained from Janvier Labs (Le Genest-Saint-Isle, France). Mice were kept on a 12 h light/dark cycle. Temperature was maintained at 22° C., food and water were provided ad libitum.

4.14.3. Study Design

The therapeutic effects of the compounds were tested in the mouse T cell transfer model model (Lindebo Holm et al. 2012). After a 7-day acclimatization period, BALBc/N mice were sacrificed, spleens were removed, homogenized, rinsed with D-PBS and centrifuged. Cell pellets were resuspended in RBC lysis isolation buffer (D-PBS, EDTA, BSA, 1/1/1) and centrifuged, then resuspended in isolation buffer and processed following DynabeadsFlowComp Mouse CD4+CD25-treg cells Dynabeads kit protocol. The obtained cells were resuspended in RPMI and 0.2 mL were injected to SCID mice by intra-peritoneal injection. Sham group of mice received RPMI alone.

Fourteen days after cell injection, 100 µL of blood was sampled on each mouse under anesthesic conditions in order to determine CD4 level. Treatment start, two weeks after cell injection based on the level of disease activity index (DAI). Disease activity index was determined twice a week. Four to six weeks after the start of treatment, mice were sacrificed, blood was sampled and the complete colon was removed and rinsed with sterile PBS, it was measured and weighed in order to determine colon weight/length ratio. Segments of colon were dissected for histological analysis, gene expression, protein level measurement and/or totally sampled for immunophetntyping by FACs.

There were 12 mice per group. The results were expressed as mean±SEM and statistical analysis was performed using non parametric test Kruskal-Wallis with Dunn's Multiple comparison test versus vehicle groups.

4.14.4. Disease Activity Index (DAI) Determination

The DAI score of each mouse (sum of scores for weight loss, stool consistency and rectal bleeding) was monitored during the entire treatment period and a DAI score progression curve was obtained.

| DAI | Weight evolution | Stool consistency | Rectal bleeding* |
|---|---|---|---|
| 0 Point | No weight loss (vs D1) | Well molded stools | |
| 1 point | 1 to 5% | Semi-soft stools | |
| 2 points | 5 to 10% | Soft stools that do not stick to the anus | |
| 3 points | 10 to 20% | Semi-liquid stools not sticking to the anus | |
| 4 Points | >20% | Liquid stools remaining stuck to the anus | |

*A little piece of stool was deposited on a vial containing 1 mL of D-PBS and homogeneized, deposited on a test strip (Combur TestE), a color appears according to the blood intensity in the stool, a score was given according to this intensity, from 0 to 4 points.

4.14.5 Results

When subject to this protocol at 30 mg/kg p.o. b.i.d., illustrative Cpd 88 statistical significant reduction of AUC of DAI vs. vehicle group

4.15. Surgical Destabilization of the Medial Meniscus (DMM) Mouse Model of Osteoarthritis The experiment assesses disease-modifying osteoarthritis drug (DMOAD) effect by prophylactic treatment of compounds that inhibits the structural disease progression of OA and ideally also improves symptoms and/or function.

DMM surgery is performed in the right knees of 10-week old male C57BL/6 mice. For the prophylactic study, systemic (p.o.) treatment starts at the time of surgery. Mice are sacrificed 8 weeks after surgery, and another group are sacrificed 12 weeks after surgery. Knees are harvested for detailed histopathological assessment (Glasson et al. 2007). Thus, the DMM model uniquely captures the chronic progressive nature of OA and associated sensitization and pain-related behaviours. Knees are collected for histology, following standard methods (Miller et al. 2016).

4.16. Ovariectomized (OVX) Mouse Model

The OVX model is used widely for investigating problems related to postmenopausal bone loss, a primary risk factor for osteoporosis A cohort of C57B16 female mice of 12 weeks of age are subjected to sham surgery, or to OVX. Animals are kept for a period of 8 weeks, during which time hypogonadal bone loss is established. Then, at 20 weeks of age (8 weeks after sham or OVX surgery), the OVX mice are treated once daily over the course of 4 weeks (Dempster et al. 2013).

The following skeletal-directed endpoints are used at the completion of the 4 weeks treatment period: μ-CT of the femur and L5 vertebrae to assess bone mass and microarchitecture.

Final Remarks

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by OpenEye Scientific Software, Inc. and the Autonom Software tool sold by MDL, Inc. In the instance where the indicated chemical name and the depicted structure differ, the depicted structure will control.

REFERENCES

Argilés J M, López-Soriano F J. 1998. Catabolic proinflammatory cytokines. *Curr. Opin. Clin. Nutr. Metab. Care* 1, 245-251.

Ashcroft T, Simpson J M, Timbrell V. 1988. Simple method of estimating severity of pulmonary fibrosis on a numerical scale. *J. Clin. Pathol.* 41, 467-470.

Ashour Ahmed A et al. 2010. SIK2 is a centrosome kinase required for bipolar mitotic spindle formation that provides a potential target for therapy in ovarian cancer. *Cancer Cell* 18, 109-121.

Bundgaard H. 1985. *Design of prodrugs*, Elsevier.

Bush K A et al. 2002. Reduction of joint inflammation and bone erosion in rat adjuvant arthritis by treatment with interleukin-17 receptor IgG1 Fc fusion protein. *Arthritis Rheum.* 46, 802-805.

Charoenfuprasert S et al. 2011. Identification of salt-inducible kinase 3 as a novel tumor antigen associated with tumorigenesis of ovarian cancer. *Oncogene* 30, 3570-3584.

Clark K et al. 2012. Phosphorylation of CRTC3 by the salt-inducible kinases controls the interconversion of classically activated and regulatory macrophages. *Proc. Natl. Acad. Sci. U.S.A* 109, 16986-16991.

Darling N J et al. 2017. Inhibition of SIK2 and SIK3 during differentiation enhances the anti-inflammatory phenotype of macrophages. *Biochem. J.* 474, 521-537.

Dempster D W et al. 2013. Standardized nomenclature, symbols, and units for bone histomorphometry: a 2012 update of the report of the ASBMR Histomorphometry Nomenclature Committee. *J. Bone Miner. Res. Off. J. Am. Soc. Bone Miner. Res.* 28, 2-17.

Devos F C et al. 2017. Forced expiration measurements in mouse models of obstructive and restrictive lung diseases. *Respir. Res.* 18, 123.

Favaudon V et al. 2014. Ultrahigh dose-rate FLASH irradiation increases the differential response between normal and tumor tissue in mice. *Sci. Transl. Med.* 6, 245ra93.

van der Fits L et al. 2009. Imiquimod-induced psoriasis-like skin inflammation in mice is mediated via the IL-23/IL-17 axis. *J. Immunol.* 182, 5836-5845.

Glasson S S, Blanchet T J, Morris E A. 2007. The surgical destabilization of the medial meniscus (DMM) model of osteoarthritis in the 129/SvEv mouse. *Osteoarthritis Cartilage* 15, 1061-1069.

Jou I-M et al. 2005. Thrombospondin 1 as an effective gene therapeutic strategy in collagen-induced arthritis. *Arthritis Rheum.* 52, 339-344.

Katoh Y et al. 2004. Salt-inducible kinase (SIK) isoforms: their involvement in steroidogenesis and adipogenesis. *Mol. Cell. Endocrinol.* 217, 109-112.

Khachigian L M. 2006. Collagen antibody-induced arthritis. *Nat. Protoc.* 1, 2512-2516.

Kumagai A et al. 2011. A Potent Inhibitor of SIK2, 3, 3', 7-Trihydroxy-4'-Methoxyflavon (4'-O-Methylfisetin), Promotes Melanogenesis in B16F10 Melanoma Cells. *PLoS ONE* 6.

Li M et al. 2006. Topical vitamin D3 and low-calcemic analogs induce thymic stromal lymphopoietin in mouse keratinocytes and trigger an atopic dermatitis. *Proc. Natl. Acad. Sci. U.S.A* 103, 11736-11741.

Lin H—S et al. 2007. Anti-rheumatic activities of histone deacetylase (HDAC) inhibitors in vivo in collagen-induced arthritis in rodents. *Br. J. Pharmacol.* 150, 862-872.

Lindebo Holm T et al. 2012. Pharmacological Evaluation of the SCID T Cell Transfer Model of Colitis: As a Model of Crohn's Disease. *Int. J. Inflamm.* 2012, 412178.

Liu J Z et al. 2013. Dense genotyping of immune-related disease regions identifies nine new risk loci for primary sclerosing cholangitis. *Nat. Genet.* 45, 670-675.

Matsuse T et al. 1999. ICAM-1 mediates lung leukocyte recruitment but not pulmonary fibrosis in a murine model of bleomycin-induced lung injury. *Eur. Respir. J.* 13, 71-77.

Maxwell J R et al. 2015. Differential Roles for Interleukin-23 and Interleukin-17 in Intestinal Immunoregulation. *Immunity* 43, 739-750.

M D Biosciences Inc. 2008. Monoclonal Antibody Induced Arthritis: a shorter, more synchronized alternative to the classic CIA model. *BioTechniques* 44, 279-280.

Miller R E et al. 2016. Therapeutic effects of an anti-ADAMTS-5 antibody on joint damage and mechanical allodynia in a murine model of osteoarthritis. *Osteoarthritis Cartilage* 24, 299-306.

Nandakumar K S, Svensson L, Holmdahl R. 2003. Collagen Type II-Specific Monoclonal Antibody-Induced Arthritis in Mice. *Am. J. Pathol.* 163, 1827-1837.

Nishida K et al. 2004. Histone deacetylase inhibitor suppression of autoantibody-mediated arthritis in mice via regulation of p16INK4a and p21WAF1/Cip1 expression. *Arthritis Rheum.* 50, 3365-3376.

Nixon M et al. 2016. Skeletal muscle salt inducible kinase 1 promotes insulin resistance in obesity. *Mol. Metab.* 5, 34-46.

Ozanne J, Prescott A R, Clark K. 2015. The clinically approved drugs dasatinib and bosutinib induce anti-inflammatory macrophages by inhibiting the salt-inducible kinases. *Biochem. J.* 465, 271-279.

Rall L C, Roubenoff R. 2004. Rheumatoid cachexia: metabolic abnormalities, mechanisms and interventions. *Rheumatology* 43, 1219-1223.

Remington J P. 1985. Pharmaceutical Preparations and Their Manufacture. in Gennaro A R, (Ed.) *Remington's Pharmaceutical Sciences*. Mack Pub. Co., EastoPAPa. 18042.

Rizzo H L et al. 2011. IL-23-Mediated Psoriasis-Like Epidermal Hyperplasia Is Dependent on IL-17A. *J. Immunol.* 186, 1495-1502.

Salvemini D et al. 2001. Amelioration of joint disease in a rat model of collagen-induced arthritis by M40403, a superoxide dismutase mimetic. *Arthritis Rheum.* 44, 2909-2921.

Sasaki T et al. 2011. SIK2 Is a Key Regulator for Neuronal Survival after Ischemia via TORC1-CREB. *Neuron* 69, 106-119.

Shelton D L et al. 2005. Nerve growth factor mediates hyperalgesia and cachexia in auto-immune arthritis. *Pain* 116, 8-16.

Sherlock J P et al. 2012. IL-23 induces spondyloarthropathy by acting on ROR-γt+CD3+CD4-CD8-entheseal resident T cells. *Nat. Med.* 18, 1069-1076.

Sims N A et al. 2004. Targeting osteoclasts with zoledronic acid prevents bone destruction in collagen-induced arthritis. *Arthritis Rheum.* 50, 2338-2346.

Sina C et al. 2009. G Protein-Coupled Receptor 43 Is Essential for Neutrophil Recruitment during Intestinal Inflammation. *J. Immunol.* 183, 7514-7522.

Sundberg T B et al. 2014. Small-molecule screening identifies inhibition of salt-inducible kinases as a therapeutic strategy to enhance immunoregulatory functions of dendritic cells. *Proc. Natl. Acad. Sci. U.S.A.* 111, 12468-12473.

Walsmith J et al. 2004. Tumor necrosis factor-alpha production is associated with less body cell mass in women with rheumatoid arthritis. *J. Rheumatol.* 31, 23-29.

Wein M N et al. 2016. SIKs control osteocyte responses to parathyroid hormone. *Nat. Commun.* 7, 13176.

Wirtz S et al. 2007. Chemically induced mouse models of intestinal inflammation. *Nat. Protoc.* 2, 541-546.

Wuts PGM, Greene T W. 2006. *Greene's Protective Groups in Organic Synthesis* 4th ed., Wiley-Interscience.

Yao C et al. 2013. Prostaglandin E₂ promotes Th1 differentiation via synergistic amplification of IL-12 signalling by cAMP and PI3-kinase. *Nat. Commun.* 4, 1685.

Yokogawa M et al. 2014. Epicutaneous Application of Toll-like Receptor 7 Agonists Leads to Systemic Autoimmunity in Wild-Type Mice: A New Model of Systemic Lupus Erythematosus. *Arthritis Rheumatol.* 66, 694-706.

Yu J et al. 2013. Salt-inducible kinase 1 is involved in high glucose-induced mesangial cell proliferation mediated by the ALK5 signaling pathway. *Int. J. Mol. Med.* 32, 151-157.

The invention claimed is:

1. A compound according to Formula I:

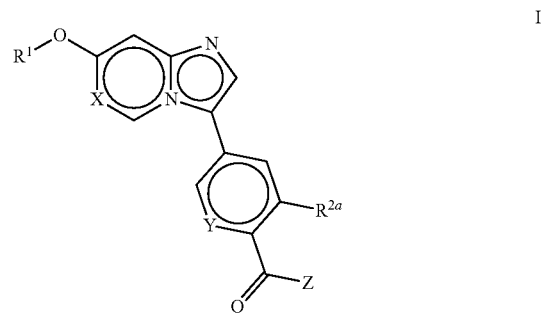

wherein,

X is N or CH;

Y is N or $CR^{2b}$;

Z is
- —$NHR^{3a}$,
- N-linked 4-7 membered heterocycloalkyl further having zero, one, or two additional heteroatoms independently selected from N, O, and S, optionally substituted with one or more independently selected $R^{15}$ groups, or
- —$NR^{3b}$—, wherein the N atom and $R^{2a}$ together with the atoms onto which they are attached form a fused 5-6 membered heterocycloalkenyl comprising one or two double bonds;

$R^1$ is
- $C_{1-8}$ alkyl optionally substituted with one or more independently selected $R^4$ groups,
- phenyl,
- $C_{3-8}$ monocyclic or bridged polycyclic cycloalkyl optionally substituted with one or more independently selected $R^5$ groups,
- 4-8 membered monocyclic, spirocyclic, or bridged polycyclic heterocycloalkyl having one, two, or three heteroatoms independently selected from N, O, and S, which heterocycloalkyl is optionally substituted with one or more independently selected $C_{1-4}$ alkyl optionally substituted with one or more independently selected —CN or C(=O)—$C_{1-4}$ alkoxy, or
- 5-6 membered monocyclic heteroaryl having one, two, or three heteroatoms independently selected from N, O, and S;

$R^{2a}$ and $R^{2b}$ are independently selected from
- halo,
- $C_{1-4}$ alkyl,
- $C_{1-4}$ alkoxy optionally substituted with one or more independently selected halo or $C_{1-4}$ alkoxy, and
- $NR^{6a}R^{6b}$;

$R^{3a}$ is
- $C_{1-6}$ alkyl optionally substituted with one or more independently selected halo or —CN, or $C_{3-7}$ cycloalkyl optionally substituted with one or more independently selected halo or —OH;

$R^{3b}$ is selected from H, $C_{3-7}$ cycloalkyl and $C_{1-6}$ alkyl optionally substituted with one or more independently selected halo or —CN;

each $R^4$ is independently selected from
- halo,
- —OH,
- —CN,
- phenyl,
- —C(=O)OH,
- —O—C(=O)—$C_{1-4}$ alkyl,
- —O—S(=O)$_2$—$C_{1-4}$ alkyl,
- $C_{1-4}$ alkoxy optionally substituted with one or more independently selected
  - —OH
  - $C_{1-4}$ alkoxy,
  - 4-8 membered monocyclic heterocycloalkyl having one, two, or three heteroatoms independently selected from N, O, and S, which heterocycloalkyl is optionally substituted with one or more independently selected $C_{1-4}$ alkyl, or
  - $NR^{7a}R^{7b}$, wherein each $R^{7a}$ and $R^{7b}$ is independently selected from H and $C_{1-4}$ alkyl,
- $C_{3-7}$ cycloalkyl optionally substituted with one or more independently selected halo, —C(=O)—$C_{1-4}$ alkoxy, —$NR^{8a}R^{8b}$, or $C_{1-4}$ alkyl optionally substituted with one or more independently selected —$NR^{9a}R^{9b}$,
- 5-6 membered monocyclic heterocycloalkyl comprising one or two N atoms fused to a 5-6 membered monocyclic heteroaryl having one, two, or three heteroatoms independently selected from N, O, and S, which heteroaryl is optionally substituted with one or more independently selected $C_{1-4}$ alkyl,
- 5-6 membered monocyclic heteroaryl having one, two, or three heteroatoms independently selected from N, O, and S, which heteroaryl is optionally substituted with one or more independently selected $C_{1-4}$ alkyl or $C_{3-7}$ cycloalkyl,
- 4-11 membered monocyclic, spirocyclic, or bridged polycyclic heterocycloalkyl having one, two, or three heteroatoms independently selected from N, O, and S, which heterocycloalkyl is optionally substituted with one or more independently selected $R^{10}$, —$NR^{11a}R^{11b}$,
- —C(=O)—$C_{1-4}$ alkoxy, and
- —C(=O)—$NR^{12a}R^{12b}$;

each R is selected from
- halo,
- —CN, and
- —$N^{13a}R^{13b}$;

each $R^{6a}$ and $R^{5b}$ is independently selected from H and $C_{1-4}$ alkyl;

each $R^{10}$ is selected from
- —OH,
- phenyl,
- =NH,
- halo,
- oxo,
- —CN,
- —C(=O)H,
- C(=O)NH$_2$,
- —C(=O)OH,
- $NR^{14a}R^{14b}$,
- $C_{1-4}$ alkyl optionally substituted with one or more independently selected halo, —CN, —OH, —C(=O)—$C_{1-4}$ alkoxy, or $C_{1-4}$ alkoxy,
- $C_{3-7}$ cycloalkyl,
- 4-6 membered monocyclic heterocycloalkyl having one, two, or three heteroatoms independently selected from N, O, and S,
- —C(=O)—$C_{1-4}$ alkyl,
- —S(=O)$_2$—$C_{1-4}$ alkyl, and
- —C(=O)—$C_{1-6}$ alkoxy;

each $R^{11a}$, $R^{11b}$ is independently selected from
- —H,
- phenyl,
- $C_{1-4}$ alkyl optionally substituted with one or more independently selected halo, —OH, —CN, or $C_{1-4}$ alkoxy,
- $C_{3-7}$ cycloalkyl,
- —C(=O)—$C_{1-4}$ alkoxy,
- —C(=O)—$C_{1-4}$ alkyl optionally substituted with one or more independently selected halo, and
- 5-6 membered monocyclic heteroaryl having one, two, or three heteroatoms independently selected from N, O, and S;

each $R^{8a}$, $R^{8b}$, $R^{9a}$, $R^{9b}$, $R^{12a}$, $R^{12b}$ $R^{13a}$, and $R^{13b}$ is independently selected from H and $C_{1-4}$ alkyl;

each $R^{14a}$ and $R^{14b}$ is independently selected from 1, $C_{1-4}$ alkyl, and —S(=O)$_2$—$C_{1-4}$ alkyl; and each $R^{15}$ is independently selected from —OH, —CN, and $C_{1-4}$ alkyl optionally substituted with one or more independently selected halo or —CN.

2. A compound or pharmaceutically acceptable salt thereof, according to claim 1, wherein Z is
- —$NHR^{3a}$, or
- —$NR^{3b}$—, wherein the N atom and $R^{2a}$ together with the atoms onto which they are attached form a fused 5-6 membered heterocycloalkenyl comprising one or two double bonds;

$R^1$ is
- $C_{1-8}$ alkyl optionally substituted with one or more independently selected $R^4$ groups,
- phenyl,
- $C_{3-8}$ monocyclic or bridged polycyclic cycloalkyl optionally substituted with one or more independently selected $R^5$ groups,
- 4-8 membered monocyclic or spirocyclic heterocycloalkyl having one, two, or three heteroatoms independently selected from N, O, and S, which heterocycloalkyl is optionally substituted with one or more independently selected $C_{1-4}$ alkyl, or
- 5-6 membered monocyclic heteroaryl having one, two, or three heteroatoms independently selected from N, O, and S;

$R^{3a}$ is
- $C_{1-6}$ alkyl optionally substituted with one or more independently selected halo or —CN, or
- $C_{3-7}$ cycloalkyl;

each $R^4$ is independently selected from
- halo,
- —OH,
- —CN,
- phenyl,
- $C_{1-4}$ alkoxy optionally substituted with one or more independently selected —OH, $C_{1-4}$ alkoxy, or —$NR^{7a}R^{7b}$, wherein each $R^{7a}$ and $R^{7b}$ is independently selected from H and $C_{1-4}$ alkyl, C$_{3-7}$ cycloalkyl optionally substituted with one or more independently selected halo, —C(=O)—C$_{1-4}$ alkoxy, —NR$^{8a}$R$^{8b}$, or C$_{1-4}$ alkyl optionally substituted with one or more independently selected —NR$^{9a}$R$^{9b}$, 5-6 membered monocyclic heteroaryl having one, two, or three heteroatoms independently selected from N, O, and S, which heteroaryl is optionally substituted with one or more independently selected C$_{1-4}$ alkyl or C$_{3-7}$ cycloalkyl, 4-8 membered monocyclic or bridged polycyclic heterocycloalkyl having one, two, or three heteroatoms independently selected from N, O, and S, which heterocycloalkyl is optionally substituted with one or more independently selected R$^{10}$, —NR$^{11a}$R$^{11b}$, and —C(=O)—NR$^{12a}$R$^{12b}$;

each R$^{10}$ is selected from halo, oxo,

—CN,

—C(=O)H,

—NR$^{14a}$R$^{14b}$,

C$_{1-4}$ alkyl optionally substituted with one or more independently selected halo or C$_{1-4}$ alkoxy, C$_{3-7}$ cycloalkyl, —C(=O)—(C$_{1-4}$ alkyl, —S(=O)—C$_{1-4}$ alkyl, and —C(=O)—C$_{1-6}$ alkoxy;

each R$^{11a}$, R$^{11b}$ is independently selected from

H, phenyl,

C$_{1-4}$ alkyl optionally substituted with one or more independently selected halo, —OH, —CN, or C$_{1-4}$ alkoxy, C$_{3-7}$ cycloalkyl, —C(=O)— C$_{1-4}$ alkyl, and 5-6 membered monocyclic heteroaryl having one, two, or three heteroatoms independently selected from N, O, and S; and each R$^{14a}$, and R$^{14b}$ is independently selected from H and C$_{1-4}$ alkyl.

3. A compound or pharmaceutically acceptable salt thereof, according to claim 1, wherein X is CH.

4. A compound or pharmaceutically acceptable salt thereof, according to claim 1, wherein Y is CR$^{2b}$ and R$^{2b}$ is C$_{1-4}$ alkoxy.

5. A compound or pharmaceutically acceptable salt thereof, according to claim 1, wherein R$^{2a}$ is —O—CH$_3$, substituted with one, two, or three independently selected halo.

6. A compound or pharmaceutically acceptable salt thereof, according to claim 1, wherein Z is —NR$^{3b}$—, wherein the N atom and R$^{2a}$ together with the atoms onto which they are attached form a fused 1,2,3,6-tetrahydropyridine.

7. A compound or pharmaceutically acceptable salt thereof, according to claim 1, wherein the compound is according to any one of Formulae IIIa-IIIc:

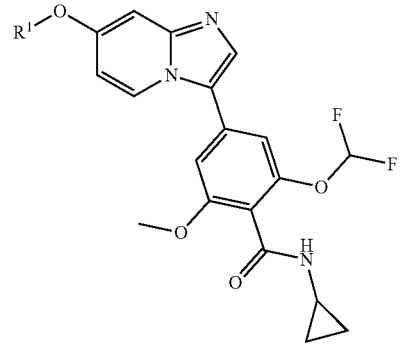

IIIa

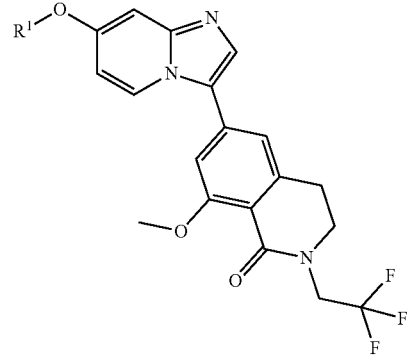

IIIb

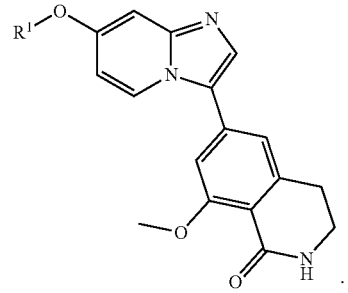

IIIc

8. A compound or pharmaceutically acceptable salt thereof, according to claim 1, wherein R$^1$ is —CH$_3$ or —CH$_2$CH$_3$, each of which is substituted with one R$^4$ group.

9. A compound or pharmaceutically acceptable salt thereof, according to claim 1, wherein the compound is according to any one of Formulae IVa-IVf:

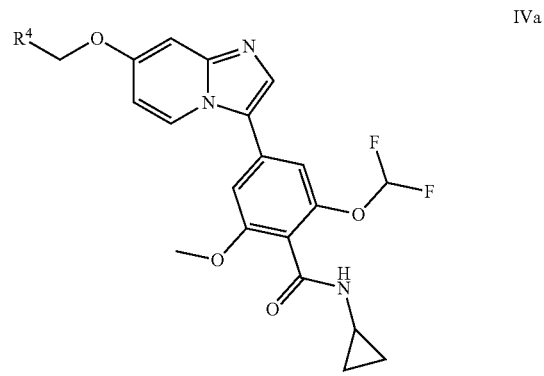

IVa

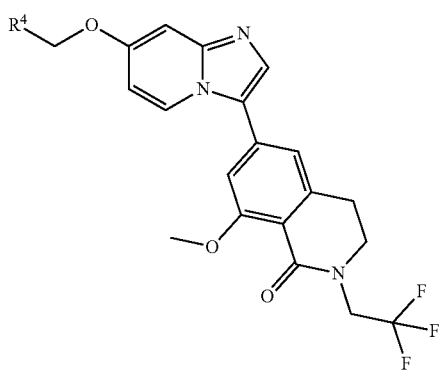

IVb

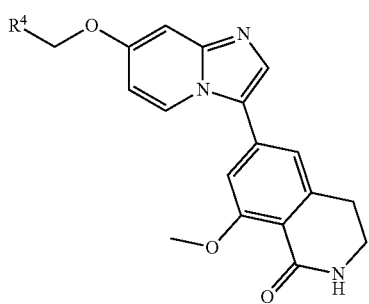

IVc

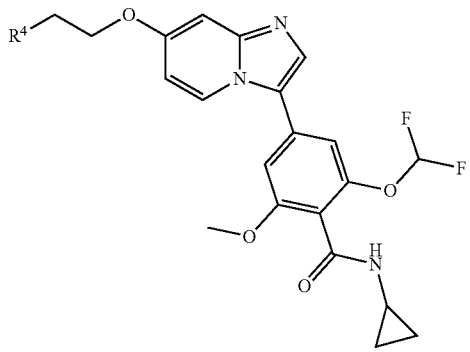

IVd

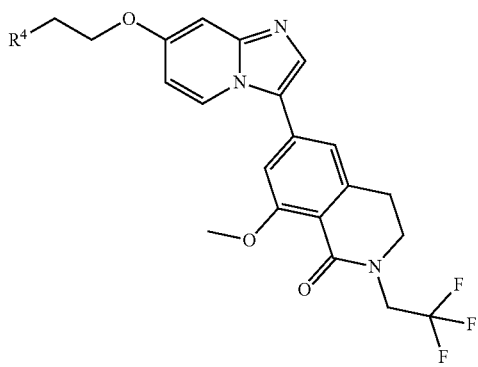

IVe

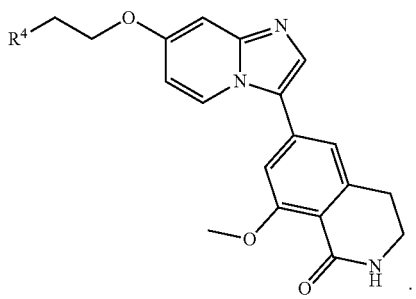

IVf

10. A compound or pharmaceutically acceptable salt thereof, according to claim 1, wherein $R^4$ is —NH—CH$_3$, —N(CH$_3$)$_2$, —NH—CH$_2$CH$_3$, —N(CH$_2$CH$_3$)$_2$, —N(CH(CH$_3$)$_2$)$_2$, or —N(CH$_3$)—CH$_2$CHF$_2$.

11. A compound or pharmaceutically acceptable salt thereof, according to claim 1, wherein $R^4$ is azetidinyl, oxetanyl, pyrrolidinyl, tetrahydrofuranyl, piperidinyl, tetrahydropyranyl, morpholinyl, dioxanyl, 2-oxa-5-azabicyclo[2.2.1]heptanyl, 3-oxa-8-azabicyclo[3.2.1]octanyl, or 8-oxa-3-azabicyclo[3.2.1]octanyl.

12. A compound or pharmaceutically acceptable salt thereof, according to claim 1, wherein $R^4$ is morpholinyl.

13. A compound or pharmaceutically acceptable salt thereof, according to claim 1, wherein $R^4$ is dioxanyl.

14. A pharmaceutical composition comprising a pharmaceutically acceptable carrier and a pharmaceutically effective amount of a compound or pharmaceutically acceptable salt thereof according to claim 1.

15. A method for treatment of inflammatory diseases, fibrotic diseases, diseases involving impairment of cartilage turnover, diseases involving impairment of bone turnover, systemic lupus erythematosus, cancer, psoriasis, and/or inflammatory bowel diseases, comprising administering an effective amount of the compound or pharmaceutically acceptable salt thereof, according to claim 1.

16. A method for treatment of inflammatory diseases, fibrotic diseases, diseases involving impairment of cartilage turnover, diseases involving impairment of bone turnover, systemic lupus erythematosus, cancer, psoriasis, and/or inflammatory bowel diseases, comprising administering a pharmaceutical composition according to claim 14.

17. The compound of claim 1, wherein the compound is
N-cyclopropyl-2-(difluoromethoxy)-6-methoxy-4-(7-tetrahydropyran-4-yloxyimidazo[1,2-a]pyridin-3-yl)benzamide,
N-cyclopropyl-2-(difluoromethoxy)-6-methoxy-4-[7-[(1-methyl-3-piperidyl)oxy]imidazo[1,2-a]pyridin-3-yl]benzamide,
N-cyclopropyl-2-(difluoromethoxy)-6-methoxy-4-[7-(2-methoxy-2-methyl-propoxy)imidazo[1,2-a]pyridin-3-yl]benzamide,
2,6-dimethoxy-4-(7-tetrahydropyran-4-yloxyimidazo[1,2-a]pyridin-3-yl)-N-(2,2,2-trifluoroethyl)benzamide,
2,6-dimethoxy-4-[7-[(1-methyl-3-piperidyl)oxy]imidazo[1,2-a]pyridin-3-yl]-N-(2,2,2-trifluoroethyl)benzamide,
N-cyclopropyl-2-(difluoromethoxy)-4-[7-[2-(dimethylamino)ethoxy]imidazo[1,2-a]pyridin-3-yl]-6-methoxybenzamide,
N-cyclopropyl-2-(difluoromethoxy)-6-methoxy-4-[7-[(1-methyl-4-piperidyl)oxy]imidazo[1,2-a]pyridin-3-yl]benzamide, N-cyclopropyl-2-(difluoromethoxy)-6-methoxy-4-[7-(2-morpholinoethoxy)imidazo[1,2-a]pyridin-3-yl]benzamide,
N-cyclopropyl-2-(difluoromethoxy)-6-methoxy-4-[7-[2-(4-methylpiperazin-1-yl)ethoxy]imidazo[1,2-a]pyridin-3-yl]benzamide,
N-cyclopropyl-2-(difluoromethoxy)-6-methoxy-4-[7-[2-(1-piperidyl)ethoxy]imidazo[1,2-a]pyridin-3-yl]benzamide,
N-cyclopropyl-2-(difluoromethoxy)-6-methoxy-4-[7-(2-methyl-2-morpholino-propoxy)imidazo[1,2-a]pyridin-3-yl]benzamide,
N-cyclopropyl-2-(difluoromethoxy)-6-methoxy-4-[7-(1-methyl-2-morpholino-ethoxy)imidazo[1,2-a]pyridin-3-yl]benzamide,
N-cyclopropyl-2-(difluoromethoxy)-4-[7-[3-(dimethylamino)propoxy]imidazo[1,2-a]pyridin-3-yl]-6-methoxy-benzamide,
N-cyclopropyl-2-(difluoromethoxy)-6-methoxy-4-[7-[(1-methylazetidin-3-yl)methoxy]imidazo[1,2-a]pyridin-3-yl]benzamide,
N-cyclopropyl-2-(difluoromethoxy)-6-methoxy-4-[7-(1-methylpyrrolidin-3-yl)oxyimidazo[1,2-a]pyridin-3-yl]benzamide,
N-cyclopropyl-2-(difluoromethoxy)-6-methoxy-4-[7-[3-(1-piperidyl)propoxy]imidazo[1,2-a]pyridin-3-yl]benzamide,
N-cyclopropyl-2-(difluoromethoxy)-6-methoxy-4-[7-[2-(1-methylpyrrolidin-2-yl)ethoxy]imidazo[1,2-a]pyridin-3-yl]benzamide,
6-[7-[2-(dimethylamino)ethoxy]imidazo[1,2-a]pyridin-3-yl]-8-methoxy-2-(2,2,2-trifluoroethyl)-3,4-dihydroisoquinolin-1-one,
N-cyclopropyl-2-(difluoromethoxy)-6-methoxy-4-[7-[(3-methylimidazol-4-yl)methoxy]imidazo[1,2-a]pyridin-3-yl]benzamide,
N-cyclopropyl-2-(difluoromethoxy)-6-methoxy-4-[7-(2-pyrrolidin-1-ylethoxy)imidazo[1,2-a]pyridin-3-yl]benzamide,
N-cyclopropyl-2-(difluoromethoxy)-6-methoxy-4-[7-(3-morpholinopropoxy)imidazo[1,2-a]pyridin-3-yl]benzamide,
N-cyclopropyl-2-(difluoromethoxy)-4-[7-[2-(1,1-dioxo-1,4-thiazinan-4-yl)ethoxy]imidazo[1,2-a]pyridin-3-yl]-6-methoxy-benzamide,
N-cyclopropyl-2-(difluoromethoxy)-6-methoxy-4-[7-[(1-methyl-2-piperidyl)methoxy]imidazo[1,2-a]pyridin-3-yl]benzamide,
N-cyclopropyl-2-(difluoromethoxy)-6-methoxy-4-[7-[2-(1-methyl-2-piperidyl)ethoxy]imidazo[1,2-a]pyridin-3-yl]benzamide,
N-cyclopropyl-2-(difluoromethoxy)-6-methoxy-4-[7-[(1-methyl-4-piperidyl)methoxy]imidazo[1,2-a]pyridin-3-yl]benzamide,
N-cyclopropyl-2-(difluoromethoxy)-6-methoxy-4-[7-[(1-methyl-5-oxo-pyrrolidin-3-yl)methoxy]imidazo[1,2-a]pyridin-3-yl]benzamide,
4-[7-(2-acetamidoethoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-[(1-methylpyrrolidin-2-yl)methoxy]imidazo[1,2-a]pyridin-3-yl]benzamide,
N-cyclopropyl-2-(difluoromethoxy)-6-methoxy-4-[7-(1-methylazetidin-3-yl)oxyimidazo[1,2-a]pyridin-3-yl]benzamide,
N-cyclopropyl-2-(difluoromethoxy)-4-[7-(2-hydroxyethoxy)imidazo[1,2-a]pyridin-3-yl]-6-methoxy-benzamide,
4-[7-(2-cyanoethoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(oxazol-2-ylmethoxy)imidazo[1,2-a]pyridin-3-yl]benzamide,
N-cyclopropyl-2-(difluoromethoxy)-6-methoxy-4-[7-(oxazol-5-ylmethoxy)imidazo[1,2-a]pyridin-3-yl]benzamide,
4-[7-(2-cyano-2-methyl-propoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(oxetan-2-ylmethoxy)imidazo[1,2-a]pyridin-3-yl]benzamide,
N-cyclopropyl-2-(difluoromethoxy)-4-[7-(2-fluoroethoxy)imidazo[1,2-a]pyridin-3-yl]-6-methoxy-benzamide,
N-cyclopropyl-2-(difluoromethoxy)-4-[7-[2-(ethylamino)ethoxy]imidazo[1,2-a]pyridin-3-yl]-6-methoxy-benzamide,
N-cyclopropyl-2-(difluoromethoxy)-6-methoxy-4-[7-[2-(2-methoxyethoxy)ethoxy]imidazo[1,2-a]pyridin-3-yl]benzamide,
8-methoxy-6-[7-[(1-methylazetidin-3-yl)methoxy]imidazo[1,2-a]pyridin-3-yl]-2-(2,2,2-trifluoroethyl)-3,4-dihydroisoquinolin-1-one,
8-methoxy-6-[7-[2-(1-piperidyl)ethoxy]imidazo[1,2-a]pyridin-3-yl]-2-(2,2,2-trifluoroethyl)-3,4-dihydroisoquinolin-1-one,
6-[7-[2-(1,1-dioxo-1,4-thiazinan-4-yl)ethoxy]imidazo[1,2-a]pyridin-3-yl]-8-methoxy-2-(2,2,2-trifluoroethyl)-3,4-dihydroisoquinolin-1-one,
N-cyclopropyl-4-[7-[(2,2-difluorocyclopropyl)methoxy]imidazo[1,2-a]pyridin-3-yl]-2-(difluoromethoxy)-6-methoxy-benzamide,
N-cyclopropyl-2-(difluoromethoxy)-6-methoxy-4-[7-(3-pyridylmethoxy)imidazo[1,2-a]pyridin-3-yl]benzamide,
N-cyclopropyl-2-(difluoromethoxy)-6-methoxy-4-[7-[(2-methylpyrazol-3-yl)methoxy]imidazo[1,2-a]pyridin-3-yl]benzamide,
N-cyclopropyl-2-(difluoromethoxy)-6-methoxy-4-[7-(2,2,2-trifluoro-1-methyl-ethoxy)imidazo[1,2-a]pyridin-3-yl]benzamide,
N-cyclopropyl-2-(difluoromethoxy)-6-methoxy-4-[7-(thiazol-4-ylmethoxy)imidazo[1,2-a]pyridin-3-yl]benzamide,
N-cyclopropyl-2-(difluoromethoxy)-6-methoxy-4-[7-(thiazol-2-ylmethoxy)imidazo[1,2-a]pyridin-3-yl]benzamide,
N-cyclopropyl-2-(difluoromethoxy)-6-methoxy-4-[7-(tetrahydropyran-2-ylmethoxy)imidazo[1,2-a]pyridin-3-yl]benzamide,
N-cyclopropyl-2-(difluoromethoxy)-6-methoxy-4-[7-(tetrahydropyran-4-ylmethoxy)imidazo[1,2-a]pyridin-3-yl]benzamide,
N-cyclopropyl-2-(difluoromethoxy)-4-[7-[[(2R)-1,4-dioxan-2-yl]methoxy]imidazo[1,2-a]pyridin-3-yl]-6-methoxy-benzamide,
N-cyclopropyl-4-[7-[2-(dimethylamino)ethoxy]imidazo[1,2-a]pyridin-3-yl]-2-fluoro-6-methoxy-benzamide,
N-cyclopropyl-4-[7-[(3,3-difluorocyclobutyl)methoxy]imidazo[1,2-a]pyridin-3-yl]-2-(difluoromethoxy)-6-methoxy-benzamide, 6-[7-[2-(dimethylamino)ethoxy]imidazo[1,2-a]pyridin-3-yl]-2-ethyl-8-methoxy-3,4-dihydroisoquinolin-1-one,
2-(2,2-difluoroethyl)-6-[7-[2-(dimethylamino)ethoxy]imidazo[1,2-a]pyridin-3-yl]-8-methoxy-3,4-dihydroisoquinolin-1-one,
8-methoxy-6-[7-(3-morpholinopropoxy)imidazo[1,2-a]pyridin-3-yl]-2-(2,2,2-trifluoroethyl)-3,4-dihydroisoquinolin-1-one,
N-cyclopropyl-4-[7-[2-(dimethylamino)ethoxy]imidazo[1,2-a]pyridin-3-yl]-2-(2-ethoxyethoxy)-6-methoxy-benzamide,
methyl 1-[[3-[4-(cyclopropylcarbamoyl)-3-(difluoromethoxy)-5-methoxy-phenyl]imidazo[1,2-a]pyridin-7-yl]oxymethyl]cyclopropanecarboxylate,
N-cyclopropyl-2-(difluoromethoxy)-6-methoxy-4-(7-norbornan-2-yloxyimidazo[1,2-a]pyridin-3-yl)benzamide,
N-cyclopropyl-2-(difluoromethoxy)-6-methoxy-4-[7-(tetrahydropyran-3-ylmethoxy)imidazo[1,2-a]pyridin-3-yl]benzamide,
N-cyclopropyl-2-(difluoromethoxy)-6-methoxy-4-[7-(oxazol-4-ylmethoxy)imidazo[1,2-a]pyridin-3-yl]benzamide,
4-[7-(cyclopentylmethoxy)imidazo[1,2-a]pyridin-3-yl]-N-cyclopropyl-2-(difluoromethoxy)-6-methoxy-benzamide,
N-cyclopropyl-4-[7-(3,3-difluorocyclopentoxy)imidazo[1,2-a]pyridin-3-yl]-2-(difluoromethoxy)-6-methoxy-benzamide,
N-cyclopropyl-2-(difluoromethoxy)-6-methoxy-4-[7-[2-(2-oxopyrrolidin-1-yl)ethoxy]imidazo[1,2-a]pyridin-3-yl]benzamide,
N-cyclopropyl-2-(difluoromethoxy)-6-methoxy-4-[7-(2-tetrahydropyran-4-ylethoxy)imidazo[1,2-a]pyridin-3-yl]benzamide,
N-cyclopropyl-2-(difluoromethoxy)-4-[7-[2-[2-(dimethylamino)ethoxy]ethoxy]imidazo[1,2-a]pyridin-3-yl]-6-methoxy-benzamide,
N-cyclopropyl-2-(difluoromethoxy)-4-[7-(2,2-dimethylpropoxy)imidazo[1,2-a]pyridin-3-yl]-6-methoxy-benzamide,
2-[6-[7-[2-(dimethylamino)ethoxy]imidazo[1,2-a]pyridin-3-yl]-8-methoxy-1-oxo-3,4-dihydroisoquinolin-2-yl]acetonitrile,
4-(7-benzyloxyimidazo[1,2-a]pyridin-3-yl)-N-cyclopropyl-2-(difluoromethoxy)-6-methoxy-benzamide,
4-[7-(cyclohexylmethoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(2-methoxyethoxy)imidazo[1,2-a]pyridin-3-yl]benzamide,
4-[7-(cyclobutylmethoxy)imidazo[1,2-a]pyridin-3-yl]-N-cyclopropyl-2-(difluoromethoxy)-6-methoxy-benzamide,
N-cyclopropyl-2-(difluoromethoxy)-4-[7-(2-ethoxyethoxy)imidazo[1,2-a]pyridin-3-yl]-6-methoxy-benzamide,
N-cyclopropyl-2-(difluoromethoxy)-4-[7-[2-(2-hydroxyethoxy)ethoxy]imidazo[1,2-a]pyridin-3-yl]-6-methoxy-benzamide,
N-cyclopropyl-2-(difluoromethoxy)-4-[7-(3-hydroxy-2,2-dimethyl-propoxy)imidazo[1,2-a]pyridin-3-yl]-6-methoxy-benzamide,
N-cyclopropyl-4-[7-[(3,3-difluorocyclopentyl)methoxy]imidazo[1,2-a]pyridin-3-yl]-2-(difluoromethoxy)-6-methoxy-benzamide,
N-cyclopropyl-4-[7-[2-(3,3-difluorocyclobutyl)ethoxy]imidazo[1,2-a]pyridin-3-yl]-2-(difluoromethoxy)-6-methoxy-benzamide,
N-cyclopropyl-4-[7-(4,4-difluorocyclohexoxy)imidazo[1,2-a]pyridin-3-yl]-2-(difluoromethoxy)-6-methoxy-benzamide,
N-cyclopropyl-2-(difluoromethoxy)-4-[7-[2-(diisopropylamino)ethoxy]imidazo[1,2-a]pyridin-3-yl]-6-methoxy-benzamide,
N-cyclopropyl-2-(difluoromethoxy)-6-methoxy-4-[7-[[(2S)-1-methylpyrrolidin-2-yl]methoxy]imidazo[1,2-a]pyridin-3-yl]benzamide,
N-cyclopropyl-4-[7-[[(2R)-1-(2,2-difluoroethyl)pyrrolidin-2-yl]methoxy]imidazo[1,2-a]pyridin-3-yl]-2-(difluoromethoxy)-6-methoxy-benzamide,
N-cyclopropyl-2-(difluoromethoxy)-6-methoxy-4-[7-[[(2R)-1-methylpyrrolidin-2-yl]methoxy]imidazo[1,2-a]pyridin-3-yl]benzamide,
N-cyclopropyl-2-(difluoromethoxy)-6-methoxy-4-[7-[(4-methylmorpholin-2-yl)methoxy]imidazo[1,2-a]pyridin-3-yl]benzamide,
N-cyclopropyl-2-(difluoromethoxy)-4-[7-[(1-ethyl-2-piperidyl)methoxy]imidazo[1,2-a]pyridin-3-yl]-6-methoxy-benzamide,
8-methoxy-6-[7-[(2-methylpyrazol-3-yl)methoxy]imidazo[1,2-a]pyridin-3-yl]-2-(2,2,2-trifluoroethyl)-3,4-dihydroisoquinolin-1-one,
8-methoxy-6-[7-[(3-methylimidazol-4-yl)methoxy]imidazo[1,2-a]pyridin-3-yl]-2-(2,2,2-trifluoroethyl)-3,4-dihydroisoquinolin-1-one,
6-[7-[[(2R)-1,4-dioxan-2-yl]methoxy]imidazo[1,2-a]pyridin-3-yl]-8-methoxy-2-(2,2,2-trifluoroethyl)-3,4-dihydroisoquinolin-1-one,
tert-butyl 2-[[3-[4-(cyclopropylcarbamoyl)-3-(difluoromethoxy)-5-methoxy-phenyl]imidazo[1,2-a]pyridin-7-yl]oxymethyl]azetidine-1-carboxylate,
8-methoxy-6-[7-(2-morpholinoethoxy)imidazo[1,2-a]pyridin-3-yl]-2-(2,2,2-trifluoroethyl)-3,4-dihydroisoquinolin-1-one,
N-cyclopropyl-2-(difluoromethoxy)-6-methoxy-4-[7-[(3-methyloxetan-3-yl)methoxy]imidazo[1,2-a]pyridin-3-yl]benzamide,
N-cyclopropyl-4-[7-(2,2-difluoroethoxy)imidazo[1,2-a]pyridin-3-yl]-2-(difluoromethoxy)-6-methoxy-benzamide,
N-cyclopropyl-2-(difluoromethoxy)-6-methoxy-4-[7-(2,2,2-trifluoroethoxy)imidazo[1,2-a]pyridin-3-yl]benzamide,
N-cyclopropyl-2-(difluoromethoxy)-6-methoxy-4-[7-(tetrahydrofuran-3-ylmethoxy)imidazo[1,2-a]pyridin-3-yl]benzamide,
N-cyclopropyl-2-(difluoromethoxy)-6-methoxy-4-[7-(tetrahydrofuran-2-ylmethoxy)imidazo[1,2-a]pyridin-3-yl]benzamide,
N-cyclopropyl-2-(difluoromethoxy)-6-methoxy-4-[7-(pyrimidin-2-ylmethoxy)imidazo[1,2-a]pyridin-3-yl]benzamide,
N-cyclopropyl-2-(difluoromethoxy)-6-methoxy-4-[7-(thiazol-5-ylmethoxy)imidazo[1,2-a]pyridin-3-yl]benzamide,
N-cyclopropyl-4-[7-(cyclopropylmethoxy)imidazo[1,2-a]pyridin-3-yl]-2-(difluoromethoxy)-6-methoxy-benzamide,
N-cyclopropyl-2-(difluoromethoxy)-6-methoxy-4-[7-[(1-methylcyclopropyl)methoxy]imidazo[1,2-a]pyridin-3-yl]benzamide, N-cyclopropyl-2-(difluoromethoxy)-4-[7-(1,4-dioxan-2-ylmethoxy)imidazo[1,2-a]pyridin-3-yl]-6-methoxy-benzamide, N-cyclopropyl-2-(difluoromethoxy)-6-methoxy-4-[7-[(5-oxopyrrolidin-2-yl)methoxy]imidazo[1,2-a]pyridin-3-yl]benzamide, N-cyclopropyl-2-(difluoromethoxy)-4-[7-[2-(dimethylamino)-2-oxo-ethoxy]imidazo[1,2-a]pyridin-3-yl]-6-methoxy-benzamide, N-cyclopropyl-2-(difluoromethoxy)-6-methoxy-4-[7-[(1-methylimidazol-4-yl)methoxy]imidazo[1,2-a]pyridin-3-yl]benzamide, N-cyclopropyl-2-(difluoromethoxy)-6-methoxy-4-[7-[(5-oxopyrrolidin-3-yl)methoxy]imidazo[1,2-a]pyridin-3-yl]benzamide, N-cyclopropyl-2-(difluoromethoxy)-6-methoxy-4-[7-(4-pyridylmethoxy)imidazo[1,2-a]pyridin-3-yl]benzamide, 4-[7-(2-amino-2-methyl-propoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(2-pyridylmethoxy)imidazo[1,2-a]pyridin-3-yl]benzamide, N-cyclopropyl-2-(difluoromethoxy)-4-[7-[2-(dimethylamino)-2-methyl-propoxy]imidazo[1,2-a]pyridin-3-yl]-6-methoxy-benzamide, N-cyclopropyl-4-[7-[2-(diethylamino)ethoxy]imidazo[1,2-a]pyridin-3-yl]-2-(difluoromethoxy)-6-methoxy-benzamide, 4-[7-[(3-aminocyclobutyl)methoxy]imidazo[1,2-a]pyridin-3-yl]-N-cyclopropyl-2-(difluoromethoxy)-6-methoxy-benzamide, 4-[7-(azetidin-2-ylmethoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[(1-methylimidazol-2-yl)methoxy]imidazo[1,2-a]pyridin-3-yl]benzamide, N-cyclopropyl-2-(difluoromethoxy)-6-methoxy-4-[7-[[(2R)-1-methyl-2-piperidyl]methoxy]imidazo[1,2-a]pyridin-3-yl]benzamide, 4-[7-[2-(azetidin-1-yl)ethoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(morpholin-3-ylmethoxy)imidazo[1,2-a]pyridin-3-yl]benzamide, N-cyclopropyl-2-(difluoromethoxy)-4-[7-[2-(2-hydroxyethylamino)ethoxy]imidazo[1,2-a]pyridin-3-yl]-6-methoxy-benzamide, 4-[7-(3-aminopropoxy)imidazo[1,2-a]pyridin-3-yl]-N-cyclopropyl-2-(difluoromethoxy)-6-methoxy-benzamide, 4-[7-[[1-(aminomethyl)cyclobutyl]methoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[2-(methylamino)ethoxy]imidazo[1,2-a]pyridin-3-yl]benzamide, 4-[7-(2-aminoethoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(2-piperidylmethoxy)imidazo[1,2-a]pyridin-3-yl]benzamide, N-cyclopropyl-2-(difluoromethoxy)-4-[7-[[(2S)-1,4-dioxan-2-yl]methoxy]imidazo[1,2-a]pyridin-3-yl]-6-methoxy-benzamide, 4-[7-(2-amino-3-methyl-butoxy)imidazo[1,2-a]pyridin-3-yl]-N-cyclopropyl-2-(difluoromethoxy)-6-methoxy-benzamide, 8-methoxy-6-[7-[2-(1-methylpyrrolidin-2-yl)ethoxy]imidazo[1,2-a]pyridin-3-yl]-2-(2,2,2-trifluoroethyl)-3,4-dihydroisoquinolin-1-one, 8-methoxy-6-[7-[2-(pyrrolidin-1-ylethoxy)imidazo[1,2-a]pyridin-3-yl]-2-(2,2,2-trifluoroethyl)-3,4-dihydroisoquinolin-1-one, 8-methoxy-6-[7-[[(2R)-1-methylpyrrolidin-2-yl]methoxy]imidazo[1,2-a]pyridin-3-yl]-2-(2,2,2-trifluoroethyl)-3,4-dihydroisoquinolin-1-one, 8-methoxy-6-[7-(oxetan-2-ylmethoxy)imidazo[1,2-a]pyridin-3-yl]-2-(2,2,2-trifluoroethyl)-3,4-dihydroisoquinolin-1-one, 8-methoxy-6-[7-(oxazol-5-ylmethoxy)imidazo[1,2-a]pyridin-3-yl]-2-(2,2,2-trifluoroethyl)-3,4-dihydroisoquinolin-1-one, 8-methoxy-6-[7-[(4-methylmorpholin-2-yl)methoxy]imidazo[1,2-a]pyridin-3-yl]-2-(2,2,2-trifluoroethyl)-3,4-dihydroisoquinolin-1-one, 6-[7-[2-(diethylamino)ethoxy]imidazo[1,2-a]pyridin-3-yl]-8-methoxy-2-(2,2,2-trifluoroethyl)-3,4-dihydroisoquinolin-1-one, N-cyclopropyl-2-(difluoromethoxy)-6-methoxy-4-[7-[(1-methylsulfonyl-2-piperidyl)methoxy]imidazo[1,2-a]pyridin-3-yl]benzamide, methyl 2-[[3-[4-(cyclopropylcarbamoyl)-3-(difluoromethoxy)-5-methoxy-phenyl]imidazo[1,2-a]pyridin-7-yl]oxymethyl]piperidine-1-carboxylate, 4-[7-(2-aminobutoxy)imidazo[1,2-a]pyridin-3-yl]-N-cyclopropyl-2-(difluoromethoxy)-6-methoxy-benzamide, 4-[7-[(2S)-2-amino-4-methyl-pentoxy]imidazo[1,2-a]pyridin-3-yl]-N-cyclopropyl-2-(difluoromethoxy)-6-methoxy-benzamide, 4-[7-[(2S)-2-amino-2-cyclohexyl-ethoxy]imidazo[1,2-a]pyridin-3-yl]-N-cyclopropyl-2-(difluoromethoxy)-6-methoxy-benzamide, 4-[7-(2-amino-2-tetrahydrofuran-3-yl-ethoxy)imidazo[1,2-a]pyridin-3-yl]-N-cyclopropyl-2-(difluoromethoxy)-6-methoxy-benzamide, 4-[7-(2-amino-2-tetrahydropyran-4-yl-ethoxy)imidazo[1,2-a]pyridin-3-yl]-N-cyclopropyl-2-(difluoromethoxy)-6-methoxy-benzamide, 4-[7-(2-amino-2-tetrahydrofuran-2-yl-ethoxy)imidazo[1,2-a]pyridin-3-yl]-N-cyclopropyl-2-(difluoromethoxy)-6-methoxy-benzamide, 4-[7-(2-amino-2-cyclopropyl-ethoxy)imidazo[1,2-a]pyridin-3-yl]-N-cyclopropyl-2-(difluoromethoxy)-6-methoxy-benzamide, 4-[7-(2-aminopropoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[[(2S)-1-methyl-2-piperidyl]methoxy]imidazo[1,2-a]pyridin-3-yl]benzamide, 6-[7-[2-(dimethylamino)ethoxy]imidazo[1,2-a]pyridin-3-yl]-8-ethoxy-2-(2,2,2-trifluoroethyl)-3,4-dihydroisoquinolin-1-one, 4-[7-[(1-acetyl-2-piperidyl)methoxy]imidazo[1,2-a]pyridin-3-yl]-N-cyclopropyl-2-(difluoromethoxy)-6-methoxy-benzamide, N-cyclopropyl-2-(difluoromethoxy)-4-[7-[(1-formyl-3-piperidyl)methoxy]imidazo[1,2-a]pyridin-3-yl]-6-methoxy-benzamide, N-cyclopropyl-2-(difluoromethoxy)-6-methoxy-4-[7-(3-piperidylmethoxy)imidazo[1,2-a]pyridin-3-yl]benzamide, N-cyclopropyl-2-(difluoromethoxy)-6-methoxy-4-[7-[(1-methylpyrrolidin-3-yl)methoxy]imidazo[1,2-a]pyridin-3-yl]benzamide, N-cyclopropyl-2-(difluoromethoxy)-6-methoxy-4-[7-(2-pyridyloxy)imidazo[1,2-a]pyridin-3-yl]benzamide, N-cyclopropyl-2-(difluoromethoxy)-4-[7-[2-(dimethylamino)ethoxy]imidazo[1,2-a]pyridin-3-yl]-6-fluoro-benzamide, N-cyclopropyl-2-(difluoromethoxy)-4-[7-[2-(dimethylamino)ethoxy]imidazo[1,2-a]pyridin-3-yl]-6-(methylamino)benzamide, N-cyclopropyl-2-(difluoromethoxy)-4-[7-[(1-isopropyl-2-piperidyl)methoxy]imidazo[1,2-a]pyridin-3-yl]-6-methoxy-benzamide, N-cyclopropyl-4-[7-[[1-(2,2-difluoroethyl)-2-piperidyl]methoxy]imidazo[1,2-a]pyridin-3-yl]-2-(difluoromethoxy)-6-methoxy-benzamide, 2-(2,2-difluoroethyl)-8-(difluoromethoxy)-6-[7-[2-(dimethylamino)ethoxy]imidazo[1,2-a]pyridin-3-yl]-3,4-dihydroisoquinolin-1-one, 4-[7-(cyclobutoxy)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(oxetan-3-yloxy)imidazo[1,2-a]pyridin-3-yl]benzamide, N-cyclopropyl-2-(difluoromethoxy)-6-methoxy-4-[7-[2-methyl-2-(methylamino)propoxy]imidazo[1,2-a]pyridin-3-yl]benzamide, N-cyclopropyl-2-(difluoromethoxy)-6-methoxy-4-[7-(pyrrolidin-2-ylmethoxy)imidazo[1,2-a]pyridin-3-yl]benzamide, 2-(difluoromethoxy)-4-[7-[2-(dimethylamino)ethoxy]imidazo[1,2-a]pyridin-3-yl]-6-fluoro-N-(2,2,2-trifluoroethyl)benzamide, N-cyclopropyl-2,6-bis(difluoromethoxy)-4-[7-[2-(dimethylamino)ethoxy]imidazo[1,2-a]pyridin-3-yl]benzamide, N-cyclopropyl-2-(difluoromethoxy)-6-methoxy-4-(7-phenoxyimidazo[1,2-a]pyridin-3-yl)benzamide, N-cyclopropyl-2-(difluoromethoxy)-6-methoxy-4-[7-[2-[2-(methoxymethyl)morpholin-4-yl]ethoxy]imidazo[1,2-a]pyridin-3-yl]benzamide, 4-(7-benzyloxyimidazo[1,2-c]pyrimidin-3-yl)-N-cyclopropyl-2-(difluoromethoxy)-6-methoxy-benzamide, N-cyclopropyl-2-(difluoromethoxy)-4-[7-[2-[(3S)-3-fluoropyrrolidin-1-yl]ethoxy]imidazo[1,2-a]pyridin-3-yl]-6-methoxy-benzamide, N-cyclopropyl-2-(difluoromethoxy)-6-methoxy-4-[7-[3-(methylamino)cyclobutoxy]imidazo[1,2-a]pyridin-3-yl]benzamide, N-cyclopropyl-2-(difluoromethoxy)-6-methoxy-4-[7-(2-oxaspiro[3.3]heptan-6-yloxy)imidazo[1,2-a]pyridin-3-yl]benzamide, N-cyclopropyl-2-(difluoromethoxy)-6-methoxy-4-(7-tetrahydrofuran-3-yloxyimidazo[1,2-a]pyridin-3-yl)benzamide, 4-[7-(3-cyanocyclobutoxy)imidazo[1,2-a]pyridin-3-yl]-N-cyclopropyl-2-(difluoromethoxy)-6-methoxy-benzamide, 2-(difluoromethoxy)-4-[7-[2-(dimethylamino)ethoxy]imidazo[1,2-a]pyridin-3-yl]-6-(methylamino)-N-(2,2,2-trifluoroethyl)benzamide, 2-(difluoromethoxy)-4-[7-[2-(dimethylamino)ethoxy]imidazo[1,2-a]pyridin-3-yl]-6-methoxy-N-(2,2,2-trifluoroethyl)benzamide, 6-[7-[2-(dimethylamino)ethoxy]imidazo[1,2-a]pyridin-3-yl]-8-(methylamino)-2-(2,2,2-trifluoroethyl)-3,4-dihydroisoquinolin-1-one, N-cyclopropyl-2-(difluoromethoxy)-6-methoxy-4-[7-[(2-methylpyrrolidin-2-yl)methoxy]imidazo[1,2-a]pyridin-3-yl]benzamide, 4-[7-[(1-aminocyclohexyl)methoxy]imidazo[1,2-a]pyridin-3-yl]-N-cyclopropyl-2-(difluoromethoxy)-6-methoxy-benzamide, 4-[7-[(3-aminooxetan-3-yl)methoxy]imidazo[1,2-a]pyridin-3-yl]-N-cyclopropyl-2-(difluoromethoxy)-6-methoxy-benzamide, 4-[7-[(1-aminocyclopropyl)methoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[(2-methyl-2-piperidyl)methoxy]imidazo[1,2-a]pyridin-3-yl]benzamide, N-cyclopropyl-2-(difluoromethoxy)-4-[7-[(1-ethylimidazol-2-yl)methoxy]imidazo[1,2-a]pyridin-3-yl]-6-methoxy-benzamide, 4-[7-[(1-aminocyclobutyl)methoxy]imidazo[1,2-a]pyridin-3-yl]-N-cyclopropyl-2-(difluoromethoxy)-6-methoxy-benzamide, N-cyclopropyl-2-(difluoromethoxy)-4-[7-[(1-isopropylimidazol-2-yl)methoxy]imidazo[1,2-a]pyridin-3-yl]-6-methoxy-benzamide, 4-[7-[(3-aminotetrahydrofuran-3-yl)methoxy]imidazo[1,2-a]pyridin-3-yl]-N-cyclopropyl-2-(difluoromethoxy)-6-methoxy-benzamide, N-cyclopropyl-2-(difluoromethoxy)-4-[7-[2-(2,6-dimethylmorpholin-4-yl)ethoxy]imidazo[1,2-a]pyridin-3-yl]-6-methoxy-benzamide, 4-[7-[2-(3-cyanomorpholin-4-yl)ethoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[2-[2-(trifluoromethyl)morpholin-4-yl]ethoxy]imidazo[1,2-a]pyridin-3-yl]benzamide, N-cyclopropyl-2-(difluoromethoxy)-4-[7-[2-(3,3-difluoropyrrolidin-1-yl)ethoxy]imidazo[1,2-a]pyridin-3-yl]-6-methoxy-benzamide, N-cyclopropyl-2-(difluoromethoxy)-4-[7-[2-(4,4-difluoro-1-piperidyl)ethoxy]imidazo[1,2-a]pyridin-3-yl]-6-methoxy-benzamide, N-cyclopropyl-2-(difluoromethoxy)-6-methoxy-4-[7-[[1-(2,2,2-trifluoroethyl)-2-piperidyl]methoxy]imidazo[1,2-a]pyridin-3-yl]benzamide, N-cyclopropyl-2-(difluoromethoxy)-6-methoxy-4-[7-[2-[methyl(2-pyridyl)amino]ethoxy]imidazo[1,2-a]pyridin-3-yl]benzamide, N-cyclopropyl-2-(difluoromethoxy)-6-methoxy-4-[7-[2-(N-methylanilino)ethoxy]imidazo[1,2-a]pyridin-3-yl]benzamide, 8-methoxy-6-[7-[2-(methylamino)ethoxy]imidazo[1,2-a]pyridin-3-yl]-2-(2,2,2-trifluoroethyl)-3,4-dihydroisoquinolin-1-one, N-cyclopropyl-4-[7-[2-(3,3-difluoroazetidin-1-yl)ethoxy]imidazo[1,2-a]pyridin-3-yl]-2-(difluoromethoxy)-6-methoxy-benzamide, tert-butyl 3-[[3-[4-(cyclopropylcarbamoyl)-3-(difluoromethoxy)-5-methoxy-phenyl]imidazo[1,2-a]pyridin-7-yl]oxymethyl]-3-fluoro-azetidine-1-carboxylate, tert-butyl 3-[[3-[4-(cyclopropylcarbamoyl)-3-(difluoromethoxy)-5-methoxy-phenyl]imidazo[1,2-a]pyridin-7-yl]oxymethyl]-3-methyl-azetidine-1-carboxylate, N-cyclopropyl-2-(difluoromethoxy)-4-[7-[[(2S)-4,4-difluoro-1-methyl-pyrrolidin-2-yl]methoxy]imidazo[1,2-a]pyridin-3-yl]-6-methoxy-benzamide, 8-methoxy-6-[7-[[(2R)-4-methylmorpholin-2-yl]methoxy]imidazo[1,2-a]pyridin-3-yl]-2-(2,2,2-trifluoroethyl)-3,4-dihydroisoquinolin-1-one, 8-methoxy-6-[7-[[(2S)-4-methylmorpholin-2-yl]methoxy]imidazo[1,2-a]pyridin-3-yl]-2-(2,2,2-trifluoroethyl)-3,4-dihydroisoquinolin-1-one, N-cyclopropyl-2-(difluoromethoxy)-4-[7-[2-(3,3-dimethylmorpholin-4-yl)ethoxy]imidazo[1,2-a]pyridin-3-yl]-6-methoxy-benzamide, N-cyclopropyl-2-(difluoromethoxy)-6-methoxy-4-[7-[2-(3-oxa-8-azabicyclo[3.2.1]octan-8-yl)ethoxy]imidazo[1,2-a]pyridin-3-yl]benzamide, N-cyclopropyl-2-(difluoromethoxy)-4-[7-[2-(2,2-dimethylmorpholin-4-yl)ethoxy]imidazo[1,2-a]pyridin-3-yl]-6-methoxy-benzamide, N-cyclopropyl-2-(difluoromethoxy)-6-methoxy-4-[7-[2-(8-oxa-3-azabicyclo[3.2.1]octan-3-yl)ethoxy]imidazo[1,2-a]pyridin-3-yl]benzamide, N-cyclopropyl-4-[7-[2-(2-cyclopropylmorpholin-4-yl)ethoxy]imidazo[1,2-a]pyridin-3-yl]-2-(difluoromethoxy)-6-methoxy-benzamide, 2-cyclopropyl-8-methoxy-6-[7-(2-morpholinoethoxy)imidazo[1,2-a]pyridin-3-yl]-3,4-dihydroisoquinolin-1-one, N-cyclopropyl-2-(difluoromethoxy)-4-[7-[(2,5-dimethylpyrazol-3-yl)methoxy]imidazo[1,2-a]pyridin-3-yl]-6-methoxy-benzamide, N-cyclopropyl-2-(difluoromethoxy)-6-methoxy-4-[7-[(1-methylpyrazol-4-yl)methoxy]imidazo[1,2-a]pyridin-3-yl]benzamide, N-cyclopropyl-2-(difluoromethoxy)-6-methoxy-4-[7-[(1-methylpyrazol-3-yl)methoxy]imidazo[1,2-a]pyridin-3-yl]benzamide, N-cyclopropyl-2-(difluoromethoxy)-6-methoxy-4-[7-[(4-methylmorpholin-3-yl)methoxy]imidazo[1,2-a]pyridin-3-yl]benzamide, N-cyclopropyl-2-(difluoromethoxy)-4-[7-[2-(dimethylamino)propoxy]imidazo[1,2-a]pyridin-3-yl]-6-methoxy-benzamide, N-cyclopropyl-2-(difluoromethoxy)-4-[7-[2-(dimethylamino)butoxy]imidazo[1,2-a]pyridin-3-yl]-6-methoxy-benzamide, N-cyclopropyl-2-(difluoromethoxy)-6-methoxy-4-[7-[2-(1-methylpyrazol-4-yl)ethoxy]imidazo[1,2-a]pyridin-3-yl]benzamide, N-cyclopropyl-4-[7-[(5-cyclopropyl-1,3,4-oxadiazol-2-yl)methoxy]imidazo[1,2-a]pyridin-3-yl]-2-(difluoromethoxy)-6-methoxy-benzamide, N-cyclopropyl-2-(difluoromethoxy)-6-methoxy-4-[7-[2-[(1S,4S)-2-oxa-5-azabicyclo[2.2.1]heptan-5-yl]ethoxy]imidazo[1,2-a]pyridin-3-yl]benzamide, N-cyclopropyl-2-(difluoromethoxy)-4-[7-[(3-fluoroazetidin-3-yl)methoxy]imidazo[1,2-a]pyridin-3-yl]-6-methoxy-benzamide, N-cyclopropyl-2-(difluoromethoxy)-6-methoxy-4-[7-[(3-methylazetidin-3-yl)methoxy]imidazo[1,2-a]pyridin-3-yl]benzamide, N-cyclopropyl-2-(difluoromethoxy)-4-[7-(2-hydroxy-1,1-dimethyl-ethoxy)imidazo[1,2-a]pyridin-3-yl]-6-methoxy-benzamide, 8-methoxy-6-[7-(2-morpholinoethoxy)imidazo[1,2-a]pyridin-3-yl]-2H-isoquinolin-1-one, N-cyclopropyl-2-(difluoromethoxy)-4-[7-[2-(3,3-difluoro-1-piperidyl)ethoxy]imidazo[1,2-a]pyridin-3-yl]-6-methoxy-benzamide, N-cyclopropyl-2-(difluoromethoxy)-4-[7-[2-(3-fluoro-1-piperidyl)ethoxy]imidazo[1,2-a]pyridin-3-yl]-6-methoxy-benzamide, 4-[7-[2-(2-cyanomorpholin-4-yl)ethoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[2-(2-methylmorpholin-4-yl)ethoxy]imidazo[1,2-a]pyridin-3-yl]benzamide, 4-[7-[2-[cyanomethyl(methyl)amino]ethoxy]imidazo[1,2-a]pyridin-3-yl]-N-cyclopropyl-2-(difluoromethoxy)-6-methoxy-benzamide, 4-[7-[2-(3-cyano-1-piperidyl)ethoxy]imidazo[1,2-a]pyridin-3-yl]-N-cyclopropyl-2-(difluoromethoxy)-6-methoxy-benzamide, 8-methoxy-6-[7-(2-morpholinoethoxy)imidazo[1,2-a]pyridin-3-yl]-3,4-dihydro-2H-isoquinolin-1-one, 2-(2,2-difluoroethyl)-8-methoxy-6-[7-(2-morpholinoethoxy)imidazo[1,2-a]pyridin-3-yl]-3,4-dihydroisoquinolin-1-one, 2-(2,2-difluoroethyl)-6-[7-[[(2R)-1,4-dioxan-2-yl]methoxy]imidazo[1,2-a]pyridin-3-yl]-8-methoxy-3,4-dihydroisoquinolin-1-one, N-cyclopropyl-2-(difluoromethoxy)-4-[7-[(1,3-dimethylazetidin-3-yl)methoxy]imidazo[1,2-a]pyridin-3-yl]-6-methoxy-benzamide, 8-methoxy-6-[7-(2-morpholinoethoxy)imidazo[1,2-a]pyridin-3-yl]-2-(2,2,2-trifluoroethyl)isoquinolin-1-one, N-cyclopropyl-2-methoxy-6-methyl-4-[7-(2-morpholinoethoxy)imidazo[1,2-a]pyridin-3-yl]benzamide, N-cyclopropyl-2-(difluoromethoxy)-6-methoxy-4-[7-[2-[methyl(4-pyridyl)amino]ethoxy]imidazo[1,2-a]pyridin-3-yl]benzamide, 2-cyclopropyl-8-(difluoromethoxy)-6-[7-(2-morpholinoethoxy)imidazo[1,2-a]pyridin-3-yl]-3,4-dihydroisoquinolin-1-one, 6-[7-[[(2S)-1,4-dioxan-2-yl]methoxy]imidazo[1,2-a]pyridin-3-yl]-8-methoxy-2-(2,2,2-trifluoroethyl)-3,4-dihydroisoquinolin-1-one, N-cyclopropyl-2-(difluoromethoxy)-6-methoxy-4-[7-(pyridazin-3-ylmethoxy)imidazo[1,2-a]pyridin-3-yl]benzamide, N-cyclopropyl-2-(difluoromethoxy)-6-methoxy-4-[7-[(4-methyl-1,2,4-triazol-3-yl)methoxy]imidazo[1,2-a]pyridin-3-yl]benzamide, N-cyclopropyl-2-(difluoromethoxy)-6-methoxy-4-[7-[(3-methyl-2-oxo-oxazolidin-5-yl)methoxy]imidazo[1,2-a]pyridin-3-yl]benzamide, N-cyclopropyl-2-(difluoromethoxy)-6-methoxy-4-[7-[(3-methyl-1,2,4-oxadiazol-5-yl)methoxy]imidazo[1,2-a]pyridin-3-yl]benzamide, 2-(difluoromethoxy)-6-methoxy-4-[7-(2-morpholinoethoxy)imidazo[1,2-a]pyridin-3-yl]-N-(2,2,2-trifluoroethyl)benzamide, N-cyclopropyl-2-(difluoromethoxy)-6-methoxy-4-[7-[(5-methyl-1,2,4-oxadiazol-3-yl)methoxy]imidazo[1,2-a]pyridin-3-yl]benzamide, N-cyclopropyl-2-(difluoromethoxy)-6-methoxy-4-[7-[2-(3-methylmorpholin-4-yl)ethoxy]imidazo[1,2-a]pyridin-3-yl]benzamide,
N-cyclopropyl-2-(difluoromethoxy)-6-methoxy-4-[7-[2-[(3S)-3-methylmorpholin-4-yl]ethoxy]imidazo[1,2-a]pyridin-3-yl]benzamide,
N-cyclopropyl-2-(difluoromethoxy)-6-methoxy-4-[7-[2-[(3R)-3-methylmorpholin-4-yl]ethoxy]imidazo[1,2-a]pyridin-3-yl]benzamide,
N-cyclopropyl-4-[7-[2-[cyclopropyl(2,2-difluoroethyl)amino]ethoxy]imidazo[1,2-a]pyridin-3-yl]-2-(difluoromethoxy)-6-methoxy-benzamide,
N-cyclopropyl-4-[7-[2-[2,2-difluoroethyl(methyl)amino]ethoxy]imidazo[1,2-a]pyridin-3-yl]-2-(difluoromethoxy)-6-methoxy-benzamide,
N-cyclopropyl-4-[7-[2-[2,2-difluoroethyl(2-methoxyethyl)amino]ethoxy]imidazo[1,2-a]pyridin-3-yl]-2-(difluoromethoxy)-6-methoxy-benzamide,
N-cyclopropyl-2-(difluoromethoxy)-6-methoxy-4-[7-[2-[methyl(pyrimidin-2-yl)amino]ethoxy]imidazo[1,2-a]pyridin-3-yl]benzamide,
N-cyclopropyl-2-(difluoromethoxy)-6-methoxy-4-[7-[2-[methyl(pyrimidin-4-yl)amino]ethoxy]imidazo[1,2-a]pyridin-3-yl]benzamide,
N-cyclopropyl-2-(difluoromethoxy)-6-methoxy-4-[7-[2-[methyl(pyridazin-4-yl)amino]ethoxy]imidazo[1,2-a]pyridin-3-yl]benzamide,
N-cyclopropyl-2-(difluoromethoxy)-6-methyl-4-[7-(2-morpholinoethoxy)imidazo[1,2-a]pyridin-3-yl]benzamide,
6-[7-[[(2R)-1,4-dioxan-2-yl]methoxy]imidazo[1,2-a]pyridin-3-yl]-8-methoxy-3,4-dihydro-2H-isoquinolin-1-one,
2-(difluoromethoxy)-6-methyl-4-[7-(2-morpholinoethoxy)imidazo[1,2-a]pyridin-3-yl]-N-(2,2,2-trifluoroethyl)benzamide,
6-[7-[2-(3,3-difluoroazetidin-1-yl)ethoxy]imidazo[1,2-a]pyridin-3-yl]-8-methoxy-2-(2,2,2-trifluoroethyl)-3,4-dihydroisoquinolin-1-one,
8-methoxy-6-[7-[2-[(1S,4S)-2-oxa-5-azabicyclo[2.2.1]heptan-5-yl]ethoxy]imidazo[1,2-a]pyridin-3-yl]-2-(2,2,2-trifluoroethyl)-3,4-dihydroisoquinolin-1-one,
8-methoxy-6-[7-[2-(3-oxa-8-azabicyclo[3.2.1]octan-8-yl)ethoxy]imidazo[1,2-a]pyridin-3-yl]-2-(2,2,2-trifluoroethyl)-3,4-dihydroisoquinolin-1-one,
2-(2,2-difluoroethyl)-8-(difluoromethoxy)-6-[7-(2-morpholinoethoxy)imidazo[1,2-a]pyridin-3-yl]-3,4-dihydroisoquinolin-1-one,
tert-butyl 3-fluoro-3-[[3-[8-methoxy-1-oxo-2-(2,2,2-trifluoroethyl)-3,4-dihydroisoquinolin-6-yl]imidazo[1,2-a]pyridin-7-yl]oxymethyl]azetidine-1-carboxylate,
tert-butyl 3-[[3-[8-methoxy-1-oxo-2-(2,2,2-trifluoroethyl)-3,4-dihydroisoquinolin-6-yl]imidazo[1,2-a]pyridin-7-yl]oxymethyl]-3-methyl-azetidine-1-carboxylate,
6-[7-[(3-fluoroazetidin-3-yl)methoxy]imidazo[1,2-a]pyridin-3-yl]-8-methoxy-2-(2,2,2-trifluoroethyl)-3,4-dihydroisoquinolin-1-one,
8-methoxy-6-[7-[(3-methylazetidin-3-yl)methoxy]imidazo[1,2-a]pyridin-3-yl]-2-(2,2,2-trifluoroethyl)-3,4-dihydroisoquinolin-1-one,
6-[7-[(3-fluoro-1-methyl-azetidin-3-yl)methoxy]imidazo[1,2-a]pyridin-3-yl]-8-methoxy-2-(2,2,2-trifluoroethyl)-3,4-dihydroisoquinolin-1-one,
6-[7-[(1,3-dimethylazetidin-3-yl)methoxy]imidazo[1,2-a]pyridin-3-yl]-8-methoxy-2-(2,2,2-trifluoroethyl)-3,4-dihydroisoquinolin-1-one,
N-cyclopropyl-3-methoxy-5-[7-(2-morpholinoethoxy)imidazo[1,2-a]pyridin-3-yl]pyridine-2-carboxamide,
4-[7-(1-cyanocyclopentoxy)imidazo[1,2-a]pyridin-3-yl]-N-cyclopropyl-2-(difluoromethoxy)-6-methoxy-benzamide,
8-methoxy-6-(7-methoxyimidazo[1,2-a]pyridin-3-yl)-2-(2,2,2-trifluoroethyl)-3,4-dihydroisoquinolin-1-one,
8-methoxy-6-[7-[2-[(3S)-3-methylmorpholin-4-yl]ethoxy]imidazo[1,2-a]pyridin-3-yl]-2-(2,2,2-trifluoroethyl)-3,4-dihydroisoquinolin-1-one,
6-[7-(2-hydroxyethoxy)imidazo[1,2-a]pyridin-3-yl]-8-methoxy-2-(2,2,2-trifluoroethyl)-3,4-dihydroisoquinolin-1-one,
8-methoxy-6-[7-[2-[(3R)-3-methylmorpholin-4-yl]ethoxy]imidazo[1,2-a]pyridin-3-yl]-2-(2,2,2-trifluoroethyl)-3,4-dihydroisoquinolin-1-one,
N-cyclopropyl-2-(difluoromethoxy)-6-methoxy-4-[7-(2-methoxy-1,1-dimethyl-ethoxy)imidazo[1,2-a]pyridin-3-yl]benzamide,
3-methoxy-5-[7-(2-morpholinoethoxy)imidazo[1,2-a]pyridin-3-yl]-N-(2,2,2-trifluoroethyl)pyridine-2-carboxamide,
3-methoxy-5-[7-[(2-methylpyrazol-3-yl)methoxy]imidazo[1,2-a]pyridin-3-yl]-N-(2,2,2-trifluoroethyl)pyridine-2-carboxamide,
4-[7-(1-cyano-1-methyl-ethoxy)imidazo[1,2-a]pyridin-3-yl]-N-cyclopropyl-2-(difluoromethoxy)-6-methoxy-benzamide,
6-(7-ethoxyimidazo[1,2-a]pyridin-3-yl)-8-methoxy-2-(2,2,2-trifluoroethyl)-3,4-dihydroisoquinolin-1-one,
5-[7-[[(2R)-1,4-dioxan-2-yl]methoxy]imidazo[1,2-a]pyridin-3-yl]-3-methoxy-N-(2,2,2-trifluoroethyl)pyridine-2-carboxamide,
3-[7-(2-morpholinoethoxy)imidazo[1,2-a]pyridin-3-yl]-6-(2,2,2-trifluoroethyl)-5H-pyrrolo[3,4-b]pyridin-7-one,
N-cyclopropyl-3-(difluoromethoxy)-5-[7-(2-morpholinoethoxy)imidazo[1,2-a]pyridin-3-yl]pyridine-2-carboxamide,
ethyl 2-[3-[4-(cyclopropylcarbamoyl)-3-(difluoromethoxy)-5-methoxy-phenyl]imidazo[1,2-a]pyridin-7-yl]oxyacetate,
4-[7-[[1-(cyanomethyl)-2-piperidyl]methoxy]imidazo[1,2-a]pyridin-3-yl]-N-cyclopropyl-2-(difluoromethoxy)-6-methoxy-benzamide,
4-[7-[[(1R,5S)-8-azabicyclo[3.2.1]octan-3-yl]oxy]imidazo[1,2-a]pyridin-3-yl]-N-cyclopropyl-2-(difluoromethoxy)-6-methoxy-benzamide,
4-[7-[[(1S,5R)-8-(2-cyanoethyl)-8-azabicyclo[3.2.1]octan-3-yl]oxy]imidazo[1,2-a]pyridin-3-yl]-N-cyclopropyl-2-(difluoromethoxy)-6-methoxy-benzamide,
ethyl 2-[(1R,5S)-3-[3-[4-(cyclopropylcarbamoyl)-3-(difluoromethoxy)-5-methoxy-phenyl]imidazo[1,2-a]pyridin-7-yl]oxy-8-azabicyclo[3.2.1]octan-8-yl]acetate,
N-cyclopropyl-2-(difluoromethoxy)-6-methoxy-4-[7-[3-(2-oxa-6-azaspiro[3.3]heptan-6-yl)propoxy]imidazo[1,2-a]pyridin-3-yl]benzamide,
4-[7-[3-(azetidin-1-yl)propoxy]imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(3-pyrrolidin-1-ylpropoxy)imidazo[1,2-a]pyridin-3-yl]benzamide,
N-cyclopropyl-2-(difluoromethoxy)-4-[7-[2-(4-isopropylpiperazin-1-yl)ethoxy]imidazo[1,2-a]pyridin-3-yl]-6-methoxy-benzamide, N-cyclopropyl-2-(difluoromethoxy)-4-[7-[3-(4-hydroxy-1-piperidyl)propoxy]imidazo[1,2-a]pyridin-3-yl]-6-methoxy-benzamide, N-cyclopropyl-2-(difluoromethoxy)-6-methoxy-4-[7-(3-piperazin-1-ylpropoxy)imidazo[1,2-a]pyridin-3-yl]benzamide, N-cyclopropyl-2-(difluoromethoxy)-4-[7-[3-(4-isopropylpiperazin-1-yl)propoxy]imidazo[1,2-a]pyridin-3-yl]-6-methoxy-benzamide, N-cyclopropyl-2-(difluoromethoxy)-4-[7-[(1-isopropyl-3-piperidyl)methoxy]imidazo[1,2-a]pyridin-3-yl]-6-methoxy-benzamide, N-cyclopropyl-2-(difluoromethoxy)-6-methoxy-4-[7-[3-(8-oxa-5-azaspiro[3.5]nonan-5-yl)propoxy]imidazo[1,2-a]pyridin-3-yl]benzamide, 3-[3-[4-(cyclopropylcarbamoyl)-3-(difluoromethoxy)-5-methoxy-phenyl]imidazo[1,2-a]pyridin-7-yl]oxypropyl acetate, N-cyclopropyl-2-(difluoromethoxy)-4-[7-[(4-isopropylmorpholin-3-yl)methoxy]imidazo[1,2-a]pyridin-3-yl]-6-methoxy-benzamide, N-cyclopropyl-2-(difluoromethoxy)-6-methoxy-4-[7-[3-(2-oxa-5-azabicyclo[2.2.1]heptan-5-yl)propoxy]imidazo[1,2-a]pyridin-3-yl]benzamide, N-cyclopropyl-2-(difluoromethoxy)-6-methoxy-4-[7-[3-(2-oxa-7-azaspiro[3.4]octan-7-yl)propoxy]imidazo[1,2-a]pyridin-3-yl]benzamide, N-cyclopropyl-2-(difluoromethoxy)-4-[7-[3-(3-hydroxyazetidin-1-yl)propoxy]imidazo[1,2-a]pyridin-3-yl]-6-methoxy-benzamide, N-cyclopropyl-2-(difluoromethoxy)-4-[7-[(1-isopropylpyrrolidin-3-yl)methoxy]imidazo[1,2-a]pyridin-3-yl]-6-methoxy-benzamide, N-cyclopropyl-2-(difluoromethoxy)-6-methoxy-4-[7-[[1-(oxetan-3-yl)pyrrolidin-3-yl]methoxy]imidazo[1,2-a]pyridin-3-yl]benzamide, N-cyclopropyl-2-(difluoromethoxy)-6-methoxy-4-[7-[[1-(oxetan-3-yl)pyrrolidin-2-yl]methoxy]imidazo[1,2-a]pyridin-3-yl]benzamide, N-cyclopropyl-2-(difluoromethoxy)-4-[7-[3-(2,6-dimethyl-1-piperidyl)propoxy]imidazo[1,2-a]pyridin-3-yl]-6-methoxy-benzamide, N-cyclopropyl-2-(difluoromethoxy)-6-methoxy-4-[7-[3-(8-oxa-3-azabicyclo[3.2.1]octan-3-yl)propoxy]imidazo[1,2-a]pyridin-3-yl]benzamide, N-cyclopropyl-2-(difluoromethoxy)-6-methoxy-4-[7-[3-(3-oxa-8-azabicyclo[3.2.1]octan-8-yl)propoxy]imidazo[1,2-a]pyridin-3-yl]benzamide, 4-[7-[3-(2-azaspiro[3.3]heptan-2-yl)propoxy]imidazo[1,2-a]pyridin-3-yl]-N-cyclopropyl-2-(difluoromethoxy)-6-methoxy-benzamide, N-cyclopropyl-2-(difluoromethoxy)-4-[7-[2-(2,6-dimethyl-1-piperidyl)ethoxy]imidazo[1,2-a]pyridin-3-yl]-6-methoxy-benzamide, N-cyclopropyl-2-(difluoromethoxy)-4-[7-[(1-isopropylpyrrolidin-2-yl)methoxy]imidazo[1,2-a]pyridin-3-yl]-6-methoxy-benzamide, N-cyclopropyl-2-(difluoromethoxy)-4-[7-[3-(2,8-dioxa-5-azaspiro[3.5]nonan-5-yl)propoxy]imidazo[1,2-a]pyridin-3-yl]-6-methoxy-benzamide, N-cyclopropyl-2-(difluoromethoxy)-4-[7-[3-(6-hydroxy-2-azaspiro[3.3]heptan-2-yl)propoxy]imidazo[1,2-a]pyridin-3-yl]-6-methoxy-benzamide, N-cyclopropyl-2-(difluoromethoxy)-4-[7-[2-[2-(4-isopropylpiperazin-1-yl)ethoxy]ethoxy]imidazo[1,2-a]pyridin-3-yl]-6-methoxy-benzamide, N-cyclopropyl-2-(difluoromethoxy)-6-methoxy-4-[7-[2-[1-(oxetan-3-yl)pyrrolidin-2-yl]ethoxy]imidazo[1,2-a]pyridin-3-yl]benzamide, N-cyclopropyl-2-(difluoromethoxy)-6-methoxy-4-[7-[3-(6-oxa-1-azaspiro[3.3]heptan-1-yl)propoxy]imidazo[1,2-a]pyridin-3-yl]benzamide, N-cyclopropyl-2-(difluoromethoxy)-4-[7-[2-(1-isopropylpyrrolidin-2-yl)ethoxy]imidazo[1,2-a]pyridin-3-yl]-6-methoxy-benzamide, 4-[7-[3-(1-azaspiro[3.3]heptan-1-yl)propoxy]imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-[3-(2-oxa-8-azaspiro[3.5]nonan-8-yl)propoxy]imidazo[1,2-a]pyridin-3-yl]benzamide, N-cyclopropyl-2-(difluoromethoxy)-4-[7-[3-(7,8-dihydro-5H-pyrido[4,3-d]pyrimidin-6-yl)propoxy]imidazo[1,2-a]pyridin-3-yl]-6-methoxy-benzamide, N-cyclopropyl-2-(difluoromethoxy)-6-methoxy-4-[7-[2-[2-(1-piperidyl)ethoxy]ethoxy]imidazo[1,2-a]pyridin-3-yl]benzamide, N-cyclopropyl-2-(difluoromethoxy)-6-methoxy-4-[7-[2-(2-morpholinoethoxy)ethoxy]imidazo[1,2-a]pyridin-3-yl]benzamide, N-cyclopropyl-4-[7-[2-[2-(diethylamino)ethoxy]ethoxy]imidazo[1,2-a]pyridin-3-yl]-2-(difluoromethoxy)-6-methoxy-benzamide, N-cyclopropyl-2-(difluoromethoxy)-4-[7-[2-[4-(2-hydroxyethyl)piperazin-1-yl]ethoxy]imidazo[1,2-a]pyridin-3-yl]-6-methoxy-benzamide, N-cyclopropyl-2-(difluoromethoxy)-6-methoxy-4-[7-[3-(1-methyl-6,7-dihydro-4H-imidazo[4,5-c]pyridin-5-yl)propoxy]imidazo[1,2-a]pyridin-3-yl]benzamide, N-cyclopropyl-2-(difluoromethoxy)-4-[7-[3-(3,4-dihydro-1H-pyrrolo[1,2-a]pyrazin-2-yl)propoxy]imidazo[1,2-a]pyridin-3-yl]-6-methoxy-benzamide, N-cyclopropyl-2-(difluoromethoxy)-4-[7-[3-(7,8-dihydro-5H-1,6-naphthyridin-6-yl)propoxy]imidazo[1,2-a]pyridin-3-yl]-6-methoxy-benzamide, N-cyclopropyl-2-(difluoromethoxy)-4-[7-[3-(6,8-dihydro-5H-imidazo[1,2-a]pyrazin-7-yl)propoxy]imidazo[1,2-a]pyridin-3-yl]-6-methoxy-benzamide, N-cyclopropyl-2-(difluoromethoxy)-4-[7-[3-(6,8-dihydro-5H-[1,2,4]triazolo[1,5-a]pyrazin-7-yl)propoxy]imidazo[1,2-a]pyridin-3-yl]-6-methoxy-benzamide, N-cyclopropyl-2-(difluoromethoxy)-6-methoxy-4-[7-[[(3S)-pyrrolidin-3-yl]methoxy]imidazo[1,2-a]pyridin-3-yl]benzamide, N-cyclopropyl-2-(difluoromethoxy)-6-methoxy-4-[7-[[(3S)-3-piperidyl]methoxy]imidazo[1,2-a]pyridin-3-yl]benzamide, N-cyclopropyl-2-(difluoromethoxy)-4-[7-[[(3S)-1-isopropylpyrrolidin-3-yl]methoxy]imidazo[1,2-a]pyridin-3-yl]-6-methoxy-benzamide, N-cyclopropyl-2-(difluoromethoxy)-6-methoxy-4-[7-[[(3S)-1-(oxetan-3-yl)pyrrolidin-3-yl]methoxy]imidazo[1,2-a]pyridin-3-yl]benzamide, N-cyclopropyl-2-(difluoromethoxy)-6-methoxy-4-[7-[[(3S)-1-(oxetan-3-yl)-3-piperidyl]methoxy]imidazo[1,2-a]pyridin-3-yl]benzamide, N-cyclopropyl-2-(difluoromethoxy)-4-[7-[3-(3-hydroxypyrrolidin-1-yl)propoxy]imidazo[1,2-a]pyridin-3-yl]-6-methoxy-benzamide, N-cyclopropyl-2-(difluoromethoxy)-6-methoxy-4-[7-[3-(2-methyl-6,7-dihydro-4H-thiazolo[5,4-c]pyridin-5-yl)propoxy]imidazo[1,2-a]pyridin-3-yl]benzamide, N-cyclopropyl-2-(difluoromethoxy)-4-[7-[2-hydroxy-3-(1-piperidyl)propoxy]imidazo[1,2-a]pyridin-3-yl]-6-methoxy-benzamide,
4-[7-[[1-(cyanomethyl)azetidin-3-yl]methoxy]imidazo[1,2-a]pyridin-3-yl]-N-cyclopropyl-2-(difluoromethoxy)-6-methoxy-benzamide,
4-[7-[[1-(2-cyanoethyl)azetidin-3-yl]methoxy]imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-[3-(2-oxo-1-oxa-3, 8-diazaspiro[4.5]decan-8-yl)propoxy]imidazo[1,2-a]pyridin-3-yl]benzamide,
N-cyclopropyl-2-(difluoromethoxy)-6-methoxy-4-[7-[3-(3-methyl-2-oxo-1-oxa-3,8-diazaspiro[4.5]decan-8-yl)propoxy]imidazo[1,2-a]pyridin-3-yl]benzamide,
N-cyclopropyl-2-(difluoromethoxy)-6-methoxy-4-[7-[3-[4-[methyl(methylsulfonyl)amino]-1-piperidyl]propoxy]imidazo[1,2-a]pyridin-3-yl]benzamide,
N-cyclopropyl-2-(difluoromethoxy)-4-[7-[3-(1-imino-1-oxo-1,4-thiazinan-4-yl)propoxy]imidazo[1,2-a]pyridin-3-yl]-6-methoxy-benzamide,
N-cyclopropyl-2-(difluoromethoxy)-4-[7-[3-(3-hydroxy-1-piperidyl)propoxy]imidazo[1,2-a]pyridin-3-yl]-6-methoxy-benzamide,
N-cyclopropyl-2-(difluoromethoxy)-4-[7-[[(3S)-1-isopropyl-3-piperidyl]methoxy]imidazo[1,2-a]pyridin-3-yl]-6-methoxy-benzamide,
N-cyclopropyl-2-(difluoromethoxy)-4-[7-(2-hydroxy-3-morpholino-propoxy)imidazo[1,2-a]pyridin-3-yl]-6-methoxy-benzamide,
N-cyclopropyl-2-(difluoromethoxy)-4-[7-[3-(1,1-dioxo-1,4-thiazinan-4-yl)propoxy]imidazo[1,2-a]pyridin-3-yl]-6-methoxy-benzamide,
N-cyclopropyl-2-(difluoromethoxy)-4-[7-[3-(1,1-dioxo-1Â»^{6}-thia-6-azaspiro[3.3]heptan-6-yl)propoxy]imidazo[1,2-a]pyridin-3-yl]-6-methoxy-benzamide,
3-[3-[4-(cyclopropylcarbamoyl)-3-(difluoromethoxy)-5-methoxy-phenyl]imidazo[1,2-a]pyridin-7-yl]oxypropyl methanesulfonate,
N-cyclopropyl-2-(difluoromethoxy)-6-methoxy-4-[7-[[(3R)-pyrrolidin-3-yl]methoxy]imidazo[1,2-a]pyridin-3-yl]benzamide,
N-cyclopropyl-2-(difluoromethoxy)-6-methoxy-4-[7-[[(3R)-3-piperidyl]methoxy]imidazo[1,2-a]pyridin-3-yl]benzamide,
N-cyclopropyl-2-(difluoromethoxy)-6-methoxy-4-[7-[[(3R)-1-(oxetan-3-yl)pyrrolidin-3-yl]methoxy]imidazo[1,2-a]pyridin-3-yl]benzamide,
N-cyclopropyl-2-(difluoromethoxy)-4-[7-[[(3R)-1-isopropylpyrrolidin-3-yl]methoxy]imidazo[1,2-a]pyridin-3-yl]-6-methoxy-benzamide,
N-cyclopropyl-2-(difluoromethoxy)-4-[7-[[(3R)-1-isopropyl-3-piperidyl]methoxy]imidazo[1,2-a]pyridin-3-yl]-6-methoxy-benzamide,
N-cyclopropyl-2-(difluoromethoxy)-6-methoxy-4-[7-[[(3R)-1-(oxetan-3-yl)-3-piperidyl]methoxy]imidazo[1,2-a]pyridin-3-yl]benzamide,
N-cyclopropyl-2-(difluoromethoxy)-4-[7-[[(3S)-1-(2-hydroxyethyl)-3-piperidyl]methoxy]imidazo[1,2-a]pyridin-3-yl]-6-methoxy-benzamide,
N-cyclopropyl-2-(difluoromethoxy)-4-[7-[[(3S)-1-(2-hydroxyethyl)pyrrolidin-3-yl]methoxy]imidazo[1,2-a]pyridin-3-yl]-6-methoxy-benzamide,
N-cyclopropyl-2-(difluoromethoxy)-4-[7-[[1-(2-hydroxy-2-methyl-propyl)azetidin-3-yl]methoxy]imidazo[1,2-a]pyridin-3-yl]-6-methoxy-benzamide,
N-cyclopropyl-2-(difluoromethoxy)-4-[7-[[1-(2-hydroxyethyl)azetidin-3-yl]methoxy]imidazo[1,2-a]pyridin-3-yl]-6-methoxy-benzamide,
N-cyclopropyl-4-[7-[3-(4,4-difluoro-3-hydroxy-1-piperidyl)propoxy]imidazo[1,2-a]pyridin-3-yl]-2-(difluoromethoxy)-6-methoxy-benzamide,
N-cyclopropyl-4-[7-[3-(3,3-difluoro-4-hydroxy-pyrrolidin-1-yl)propoxy]imidazo[1,2-a]pyridin-3-yl]-2-(difluoromethoxy)-6-methoxy-benzamide,
4-[7-[3-(3-cyano-1-piperidyl)propoxy]imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-[3-(4-methylsulfonyl-1-piperidyl)propoxy]imidazo[1,2-a]pyridin-3-yl]benzamide,
N-cyclopropyl-2-(difluoromethoxy)-4-[7-[3-[3-hydroxy-3-(trifluoromethyl)azetidin-1-yl]propoxy]imidazo[1,2-a]pyridin-3-yl]-6-methoxy-benzamide,
N-cyclopropyl-2-(difluoromethoxy)-4-[7-[[(3R)-1-(2-hydroxyethyl)pyrrolidin-3-yl]methoxy]imidazo[1,2-a]pyridin-3-yl]-6-methoxy-benzamide,
4-[7-[[(3S)-1-(2-cyanoethyl)pyrrolidin-3-yl]methoxy]imidazo[1,2-a]pyridin-3-yl]-N-cyclopropyl-2-(difluoromethoxy)-6-methoxy-benzamide,
4-[7-[[(3S)-1-(2-cyanoethyl)-3-piperidyl]methoxy]imidazo[1,2-a]pyridin-3-yl]-N-cyclopropyl-2-(difluoromethoxy)-6-methoxy-benzamide,
N-cyclopropyl-2-(difluoromethoxy)-4-[7-[3-[(2R,6S)-2,6-dimethyl-1-piperidyl]propoxy]imidazo[1,2-a]pyridin-3-yl]-6-methoxy-benzamide,
2-(difluoromethoxy)-N-[(1S,2R)-2-hydroxycyclobutyl]-6-methoxy-4-[7-[3-(1-piperidyl)propoxy]imidazo[1,2-a]pyridin-3-yl]benzamide,
2-(difluoromethoxy)-N-[(1R,2S)-2-hydroxycyclobutyl]-6-methoxy-4-[7-[3-(1-piperidyl)propoxy]imidazo[1,2-a]pyridin-3-yl]benzamide,
[2-(difluoromethoxy)-6-methoxy-4-[7-[3-(1-piperidyl)propoxy]imidazo[1,2-a]pyridin-3-yl]phenyl]-[3-hydroxy-3-(trifluoromethyl)azetidin-1-yl]methanone,
2-[1-[2-(difluoromethoxy)-6-methoxy-4-[7-[3-(1-piperidyl)propoxy]imidazo[1,2-a]pyridin-3-yl]benzoyl]-3-hydroxy-azetidin-3-yl]acetonitrile,
N-(cyanomethyl)-2-(difluoromethoxy)-6-methoxy-4-[7-[3-(1-piperidyl)propoxy]imidazo[1,2-a]pyridin-3-yl]benzamide,
1-[2-(difluoromethoxy)-6-methoxy-4-[7-[3-(1-piperidyl)propoxy]imidazo[1,2-a]pyridin-3-yl]benzoyl]azetidine-3-carbonitrile,
[2-(difluoromethoxy)-6-methoxy-4-[7-[3-(1-piperidyl)propoxy]imidazo[1,2-a]pyridin-3-yl]phenyl]-[3-(difluoromethyl)-3-hydroxy-azetidin-1-yl]methanone,
2-(difluoromethoxy)-N-[(1R,2R)-2-hydroxycyclobutyl]-6-methoxy-4-[7-[3-(1-piperidyl)propoxy]imidazo[1,2-a]pyridin-3-yl]benzamide,
2-(difluoromethoxy)-N-[(1S,2S)-2-hydroxycyclobutyl]-6-methoxy-4-[7-[3-(1-piperidyl)propoxy]imidazo[1,2-a]pyridin-3-yl]benzamide,
N-cyclopropyl-2-(difluoromethoxy)-4-[7-[3-[4-fluoro-4-(hydroxymethyl)-1-piperidyl]propoxy]imidazo[1,2-a]pyridin-3-yl]-6-methoxy-benzamide,
1-[3-[3-[4-(cyclopropylcarbamoyl)-3-(difluoromethoxy)-5-methoxy-phenyl]imidazo[1,2-a]pyridin-7-yl]oxypropyl]-4-fluoro-piperidine-4-carboxamide,
N-cyclopropyl-2-(difluoromethoxy)-4-[7-[3-(3-hydroxy-3-methyl-azetidin-1-yl)propoxy]imidazo[1,2-a]pyridin-3-yl]-6-methoxy-benzamide, ethyl 1-[3-[3-[4-(cyclopropylcarbamoyl)-3-(difluoromethoxy)-5-methoxy-phenyl]imidazo[1,2-a]pyridin-7-yl]oxypropyl]-4-fluoro-piperidine-4-carboxylate,
4-[7-(3-amino-2,2-difluoro-propoxy)imidazo[1,2-a]pyridin-3-yl]-N-cyclopropyl-2-(difluoromethoxy)-6-methoxy-benzamide,
methyl N-[3-[3-[4-(cyclopropylcarbamoyl)-3-(difluoromethoxy)-5-methoxy-phenyl]imidazo[1,2-a]pyridin-7-yl]oxy-2,2-difluoro-propyl]carbamate,
1-[3-[3-[4-(cyclopropylcarbamoyl)-3-(difluoromethoxy)-5-methoxy-phenyl]imidazo[1,2-a]pyridin-7-yl]oxypropyl]-4-fluoro-piperidine-4-carboxylic acid,
N-cyclopropyl-2-(difluoromethoxy)-6-methoxy-4-[7-[2-(2-pyridylamino)ethoxy]imidazo[1,2-a]pyridin-3-yl]benzamide,
N-cyclopropyl-2-(difluoromethoxy)-6-methoxy-4-[7-[2-(pyrimidin-2-ylamino)ethoxy]imidazo[1,2-a]pyridin-3-yl]benzamide,
N-cyclopropyl-2-(difluoromethoxy)-6-methoxy-4-[7-[2-(pyrimidin-4-ylamino)ethoxy]imidazo[1,2-a]pyridin-3-yl]benzamide,
N-cyclopropyl-2-(difluoromethoxy)-4-[7-[[(3R)-1-(2-hydroxyethyl)-3-piperidyl]methoxy]imidazo[1,2-a]pyridin-3-yl]-6-methoxy-benzamide,
N-cyclopropyl-4-[7-[2-[(2,2-difluoroacetyl)amino]ethoxy]imidazo[1,2-a]pyridin-3-yl]-2-(difluoromethoxy)-6-methoxy-benzamide,
N-cyclopropyl-2-(difluoromethoxy)-4-[7-[(3-hydroxy-1-isopropyl-pyrrolidin-3-yl)methoxy]imidazo[1,2-a]pyridin-3-yl]-6-methoxy-benzamide,
N-cyclopropyl-2-(difluoromethoxy)-4-[7-[[(3R,4S)-4-hydroxy-3-piperidyl]methoxy]imidazo[1,2-a]pyridin-3-yl]-6-methoxy-benzamide,
N-cyclopropyl-2-(difluoromethoxy)-4-[7-[[(3S,4R)-4-hydroxy-3-piperidyl]methoxy]imidazo[1,2-a]pyridin-3-yl]-6-methoxy-benzamide,
N-cyclopropyl-2-(difluoromethoxy)-4-[7-[3-(1,1-dioxo-1,4-thiazinan-4-yl)-2-hydroxy-propoxy]imidazo[1,2-a]pyridin-3-yl]-6-methoxy-benzamide,
N-cyclopropyl-2-(difluoromethoxy)-4-[7-[2-hydroxy-3-[3-hydroxy-3-(trifluoromethyl)azetidin-1-yl]propoxy]imidazo[1,2-a]pyridin-3-yl]-6-methoxy-benzamide,
N-cyclopropyl-2-(difluoromethoxy)-4-[7-[2-hydroxy-3-[(3R)-3-hydroxypyrrolidin-1-yl]propoxy]imidazo[1,2-a]pyridin-3-yl]-6-methoxy-benzamide,
ethyl 1-[3-[3-[4-(cyclopropylcarbamoyl)-3-(difluoromethoxy)-5-methoxy-phenyl]imidazo[1,2-a]pyridin-7-yl]oxypropyl]piperidine-4-carboxylate,
ethyl 1-[3-[3-[4-(cyclopropylcarbamoyl)-3-(difluoromethoxy)-5-methoxy-phenyl]imidazo[1,2-a]pyridin-7-yl]oxypropyl]-4-phenyl-piperidine-4-carboxylate,
N-cyclopropyl-2-(difluoromethoxy)-4-[7-[2-hydroxy-3-(4-hydroxy-1-piperidyl)propoxy]imidazo[1,2-a]pyridin-3-yl]-6-methoxy-benzamide,
ethyl 1-[3-[3-[4-(cyclopropylcarbamoyl)-3-(difluoromethoxy)-5-methoxy-phenyl]imidazo[1,2-a]pyridin-7-yl]oxypropyl]-4-methyl-piperidine-4-carboxylate,
ethyl 1-[3-[3-[4-(cyclopropylcarbamoyl)-3-(difluoromethoxy)-5-methoxy-phenyl]imidazo[1,2-a]pyridin-7-yl]oxypropyl]-4-hydroxy-piperidine-4-carboxylate,
ethyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]-4-methyl-piperidine-4-carboxylate,
ethyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]-4-hydroxy-piperidine-4-carboxylate,
ethyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]-4-fluoro-piperidine-4-carboxylate,
ethyl 1-[3-[3-[4-(cyclopropylcarbamoyl)-3-(difluoromethoxy)-5-methoxy-phenyl]imidazo[1,2-a]pyridin-7-yl]oxypropyl]-3-methyl-azetidine-3-carboxylate,
methyl (2S)-4-[3-[3-[4-(cyclopropylcarbamoyl)-3-(difluoromethoxy)-5-methoxy-phenyl]imidazo[1,2-a]pyridin-7-yl]oxy-2-hydroxy-propyl]morpholine-2-carboxylate,
methyl (2S)-4-[2-[3-[4-(cyclopropylcarbamoyl)-3-(difluoromethoxy)-5-methoxy-phenyl]imidazo[1,2-a]pyridin-7-yl]oxyethyl]morpholine-2-carboxylate,
ethyl 1-[2-[3-[4-(cyclopropylcarbamoyl)-3-(difluoromethoxy)-5-methoxy-phenyl]imidazo[1,2-a]pyridin-7-yl]oxyethyl]-4-fluoro-piperidine-4-carboxylate,
tert-butyl 1-[3-[3-[4-(cyclopropylcarbamoyl)-3-(difluoromethoxy)-5-methoxy-phenyl]imidazo[1,2-a]pyridin-7-yl]oxypropyl]azetidine-3-carboxylate,
ethyl 1-[2-[3-[4-(cyclopropylcarbamoyl)-3-(difluoromethoxy)-5-methoxy-phenyl]imidazo[1,2-a]pyridin-7-yl]oxyethyl]piperidine-3-carboxylate,
methyl 1-[2-[3-[4-(cyclopropylcarbamoyl)-3-(difluoromethoxy)-5-methoxy-phenyl]imidazo[1,2-a]pyridin-7-yl]oxyethyl]azetidine-3-carboxylate,
tert-butyl 1-[3-[3-[4-(cyclopropylcarbamoyl)-3-(difluoromethoxy)-5-methoxy-phenyl]imidazo[1,2-a]pyridin-7-yl]oxy-2-hydroxy-propyl]azetidine-3-carboxylate,
ethyl 1-[3-[3-[4-(cyclopropylcarbamoyl)-3-(difluoromethoxy)-5-methoxy-phenyl]imidazo[1,2-a]pyridin-7-yl]oxypropyl]piperidine-3-carboxylate,
2-[3-[4-(cyclopropylcarbamoyl)-3-(difluoromethoxy)-5-methoxy-phenyl]imidazo[1,2-a]pyridin-7-yl]oxyacetic acid, or
ethyl 2-[2-[[3-[4-(cyclopropylcarbamoyl)-3-(difluoromethoxy)-5-methoxy-phenyl]imidazo[1,2-a]pyridin-7-yl]oxymethyl]-1-piperidyl]acetate.

18. A pharmaceutical composition comprising a pharmaceutically acceptable carrier and a pharmaceutically effective amount of a compound or pharmaceutically acceptable salt thereof according to claim 17.

19. A method for treatment of inflammatory diseases, fibrotic diseases, diseases involving impairment of cartilage turnover, diseases involving impairment of bone turnover, systemic lupus erythematosus, cancer, psoriasis, and/or inflammatory bowel diseases, comprising administering an effective amount of the compound or pharmaceutically acceptable salt thereof, according to claim 17.

20. A method for treatment of inflammatory diseases, fibrotic diseases, diseases involving impairment of cartilage turnover, diseases involving impairment of bone turnover, systemic lupus erythematosus, cancer, psoriasis, and/or inflammatory bowel diseases, comprising administering a pharmaceutical composition according to claim 18.

\* \* \* \* \*